United States Patent
Diller et al.

(10) Patent No.: US 11,161,864 B2
(45) Date of Patent: Nov. 2, 2021

(54) STING AGONISTS

(71) Applicant: Venenum Biodesign, LLC, Hamilton, NJ (US)

(72) Inventors: David J. Diller, East Windsor, NJ (US); Axel Metzger, Jackson, NJ (US); David E. Kaelin, Jr., Helmetta, NJ (US); Steven Paget, Hillsborough, NJ (US); Chia-Yu Huang, West Windsor, NJ (US); Brian F. Mcguinness, Plainsboro, NJ (US); Audrey Julie Hospital, Robbinsville, NJ (US); William Ronald Solvibile, Jr., Cranbury, NJ (US)

(73) Assignee: VENENUM BIODESIGN, LLC, Hamilton, NJ (US)

( * ) Notice: Subject to any disclaimer, the term of this patent is extended or adjusted under 35 U.S.C. 154(b) by 0 days.

(21) Appl. No.: 16/662,980

(22) Filed: Oct. 24, 2019

(65) Prior Publication Data

US 2020/0131209 A1    Apr. 30, 2020

Related U.S. Application Data

(60) Provisional application No. 62/785,711, filed on Dec. 28, 2018, provisional application No. 62/751,769, filed on Oct. 29, 2018.

(51) Int. Cl.
| | | |
|---|---|---|
| *C07F 9/6587* | (2006.01) | |
| *A61P 35/00* | (2006.01) | |
| *A61P 31/22* | (2006.01) | |
| *A61K 45/06* | (2006.01) | |

(52) U.S. Cl.
CPC ............ *C07F 9/6587* (2013.01); *A61P 31/22* (2018.01); *A61P 35/00* (2018.01); *A61K 45/06* (2013.01)

(58) Field of Classification Search
CPC .................................................... C07F 9/6587
See application file for complete search history.

(56) References Cited

U.S. PATENT DOCUMENTS

| | | | |
|---|---|---|---|
| 9,724,408 B2 | 8/2017 | Dubensky, Jr. et al. | |
| 2016/0068560 A1 | 3/2016 | Patel et al. | |
| 2017/0158724 A1 | 6/2017 | Adams et al. | |
| 2018/0162899 A1 | 6/2018 | Bignan et al. | |
| 2018/0258132 A1 | 9/2018 | Adams et al. | |

FOREIGN PATENT DOCUMENTS

| | | |
|---|---|---|
| WO | 2014/093936 A1 | 6/2014 |
| WO | 2014/189805 A1 | 11/2014 |
| WO | 2015/077354 A1 | 5/2015 |
| WO | 2015/185565 A1 | 12/2015 |
| WO | 2016/096174 A1 | 6/2016 |
| WO | 2016/096577 A1 | 6/2016 |
| WO | 2016/145102 A1 | 9/2016 |
| WO | 2017/027645 A1 | 2/2017 |
| WO | 2017/027646 A1 | 2/2017 |
| WO | 2017/075477 A1 | 5/2017 |
| WO | 2017/093933 A1 | 6/2017 |
| WO | 2017/123657 A1 | 7/2017 |
| WO | 2017/123669 A1 | 7/2017 |
| WO | 2017/161349 A1 | 9/2017 |
| WO | 2018/009648 A1 | 1/2018 |
| WO | 2018/009652 A1 | 1/2018 |
| WO | 2018/045204 A1 | 3/2018 |
| WO | 2018/060323 A1 | 4/2018 |
| WO | 2018/065360 A1 | 4/2018 |
| WO | 2018/098203 A1 | 5/2018 |
| WO | 2018/100558 A2 | 6/2018 |
| WO | 2018/118664 A1 | 6/2018 |
| WO | 2018/118665 A1 | 6/2018 |
| WO | 2018/138684 A1 | 8/2018 |
| WO | 2018/138685 A2 | 8/2018 |
| WO | 2018/156625 A1 | 8/2018 |
| WO | 2018/198076 A1 | 11/2018 |
| WO | 2018/198084 A1 | 11/2018 |
| WO | 2018/208667 A1 | 11/2018 |
| WO | 2019/023459 A1 | 1/2019 |
| WO | 2019/046496 A1 | 3/2019 |
| WO | 2019/046498 A1 | 3/2019 |
| WO | 2019/046500 A1 | 3/2019 |
| WO | 2019/046511 A1 | 3/2019 |
| WO | 2019/074887 A1 | 4/2019 |
| WO | 2019/079261 A1 | 4/2019 |
| WO | 2019/092660 A1 | 5/2019 |

(Continued)

OTHER PUBLICATIONS

Bhat N and Fitzgerald Ka. "Recognition of Cytosolic DNA by cGAS and other STING-dependent sensors". Eur Immunol. Mar. 2014; 44(3):634-40.

(Continued)

*Primary Examiner* — Brian E McDowell
(74) *Attorney, Agent, or Firm* — Heslin Rothenberg Farley & Mesiti, P.C.

(57) ABSTRACT

The present invention provides compounds of Formula I':

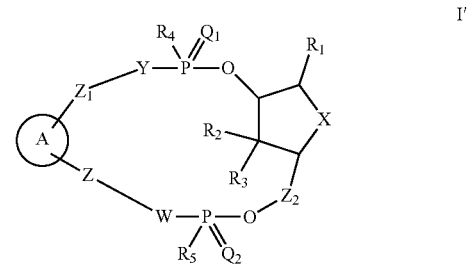

wherein (A), W, X, Y, Z, $Z_1$, $Z_2$, $R_1$, $R_2$, $R_3$, $R_4$ and $R_5$ are as defined herein, or a stereoisomer, tautomer, pharmaceutically acceptable salt, prodrug ester or solvate form thereof, wherein all of the variables are as defined herein. These compounds are effective at modulating the STING protein and thus can be used as medicaments for treating or preventing disorders affected by the agonism of STING.

18 Claims, 13 Drawing Sheets

(56) References Cited

FOREIGN PATENT DOCUMENTS

| WO | 2019/118839 A1 | 6/2019 |
|---|---|---|
| WO | 2019/123338 A1 | 6/2019 |
| WO | 2019/123339 A1 | 6/2019 |
| WO | 2019/123340 A1 | 6/2019 |
| WO | 2019/160884 A1 | 8/2019 |

OTHER PUBLICATIONS

Bundgaard, H., (C) Means to enhance penetration: (1) Prodrugs as a means to improve the delivery of peptide drugs. Adv. Drug Deliv. Rev., 8:1-38 (1992).

Bundgaard, H., Chapter 5, "Design and Application of Prodrugs," A Textbook of Drug Design and Development, pp. 113-191, Krosgaard-Larsen, P. et al., eds., Harwood Academic Publishers (1991).

Cerón S. et al., The STING agonist 5,6-dimethylxanthenone-4-acetic acid (DMXAA) stimulates an antiviral state and protects mice against herpes simplex virus induced neurological disease. Virology, 2019:529:23-28.

Chen H, et al. "Activation of STAT6 by STING Is Critical for Antiviral Innate Immunity" Cell. 2011, vol. 14: 436-446.

Corrales, L. et al. "Direct activation of STING in the tumor microenvironment leads to potent and systemic tumor regression and immunity" Cell Reports, 2015, vol. 11: 1-13.

Danilchanka, O. and Mekalanos, JJ. "Cyclic Dinucleotides and the Innate Immune Response" Cell. 2013. vol. 154: 962-970.

Huynh K, Partch CL. Current Protocols in Protein Science: Analysis of protein stability and ligand interactions by thermal shift assay. .2015;79:28.9.1-28.9.14.

Kakeya, N. et al., Studies on Prodrugs of Cephalosporins. I. Synthesis and Biological Properties of Glycyloxybenzoyloxymethol and Glycylaminobenzoyloxymethyl Esters of 7beta-[2-)2-Aminothiazol-4-yl)-(Z)-2-methoxyiminoacetamido]-3-methyl-3-cephem-4-carboxylic Acid. Chem. Pharm. Bull., 32:692-698 (1984).

Konno, H. et al. "Cyclic dinucleotides trigger ULK1 (ATG1) phosphorylation of STING to prevent sustained innate immune signaling" Cell, 2013, vol. 155: 688-698.

Liu S, et al. "Phosphorylation of innate immune adaptor proteins MAVS, STING, and TRIF induces IRF3 activation" Science. 2015: 347(6227) aaa2630.

Nielsen, N.M. and Bundgaard, H et al., Glycolamide esters as biolabile prodrugs of carboxylic acid agents: Synthesis, stability, bioconversion, and physicochemical properties. J. Pharm. Sci., 77:285 (1988).

Ouyang S, et al. Structural and Functional Analysis of STING Sheds New Light on Cyclic di-GMP Mediated Immune Signaling Mechanism. Immunity. 2012;36(6):10 1016/j.immuni.2012.03.019. doi:10.1016/j.immuni.2012.03.019.

Rader, K., et al. In vivo characterization of site-directed mutations in the promoter of the herpes simplex virus type 1 latency-associated transcripts. J. Gen. Virol. 1993;74 (Pt 9):1859-1869.

Rautio, J. (editor) Prodrugs and Targeted Delivery (Methods and Principles in Medicinal Chemistry, vol. 47, Wiley-VCH, 2011.

Sun, L. et al. "Cyclic GMP-AMP Synthase Is a Cytosolic DNA Sensor That Activates the Type-I Interferon Pathway" Science, 2013, vol. 339(6121).

Wang, H., et al., HSV-1 strain McKrae is more neuroinvasive than HSV-1 KOS after corneal or vaginal inoculation in mice. Virus Res. 2013;173:436-440.

Widder, K., Green, R. eds., Drug and Enzyme Targeting. Methods in Enzymology, 112:309-396, Academic Press (1985).

Yi, G, et al. "Single Nucleotide Polymorphisms of Human STING Can Affect Innate Immune Response to Cyclic Dinucleotides." PLoS ONE. 2013; 8(10):e77846.

Zhang X, et al. "Cyclic GMP-AMP Containing Mixed Phosphodiester Linkages Is An Endogenous High-Affinity Ligand for STING" Molecular Cell, 2013, vol. 51: 226-235.

Zhong B, et al. "The Adaptor Protein MITA Links Virus-Sensing Receptors to IRF3 Transcription Factor Activation". Immunity. 2008. vol. 29: 538-550.

Human IFN-β Secretion Assay in THP1 Dual (HAQ) Human Cells

Biochemical Analysis of STING Pathway Activation in THP1 Dual (HAQ) Human Cells

Western Blot Analysis of Example 1C that Demonstrates Activity is STING Dependent Activation of Type I and II Interferons and Interferon Stimulated (ISG) Genes in Human PBMCs by Example 1C IFN-β Secretion by Human Peripheral Blood Mononuclear Cells STING Pathway Activation in Primary Human Bladder Epithelial Cells CT-26 Tumor Bearing Mice Treated with Example 1C: Normalized Tumor Volumes MC-38 Tumor Bearing Mice Treated with Example 1C and Anti-PD-1

MB49-luc Tumor Bearing Mice Treated with Example 1C

Pseudo-Survival of MB49-luc Tumor Bearing Mice Treated with Example 1C

MB49-luc Mouse Tumor BLI on Day 14

MB49-luc Mouse Bladder Weights at the Experimental End Points

MB49-luc Mouse Pseudo-survival Curves

STING AGONISTS

CROSS REFERENCES TO RELATED APPLICATIONS

This application claims the benefit of U.S. Provisional Application Ser. Nos. 62/751,769 and 62/785,711, filed on Oct. 29, 2018 and Dec. 28, 2018, respectively. The entirety of each application is incorporated herein by reference.

FIELD OF THE INVENTION

The present invention provides novel compounds which are STING (Stimulator of Interferon Genes) agonists and are useful in preventing or treating disorders affected by modulating the STING protein. This invention also relates to pharmaceutical compositions containing these compounds and methods of using the same.

BACKGROUND OF THE INVENTION

STING (stimulator of interferon genes), also known as TMEM173, MITA, MPYS, and ERIS, is a transmembrane receptor located inside the cell and a key sensor of cytosolic nucleic acids (Zhong B, et al. "The Adaptor Protein MITA Links Virus-Sensing Receptors to IRF3 Transcription Factor Activation". Immunity. 2008. vol. 29: 538-550). Recent studies have revealed the biology of STING and its role in mobilizing an innate immune response resulting in robust antitumor activity in mouse models.

Activation of the STING pathway results in production of Type I interferons (mainly IFN-α and IFN-β) induced through the IRF3 (interferon regulatory factor 3) pathway. Activation of IRF3 is thought to be mediated by TBK1 (TANK-binding kinase 1) which recruits and phosphorylates IRF3 thus forming an IRF3 homodimer capable of entering the nucleus to transcribe type I interferon and other genes (Liu S, et al. "Phosphorylation of innate immune adaptor proteins MAVS, STING, and TRIF induces IRF3 activation" Science. 2015: 2630-2637). TBK1 also activates the nuclear factor kappa-light-chain-enhancer of activated B cells pathway which leads to production of pro-inflammatory cytokines (IL-1α, IL-1β, IL-2, IL-6, TNF-α, etc.), via the oncogenic transcription factor NF-κB.

In addition, STING activates STAT6 (signal transducer and activator of transcription 6) to induce (Th2-type), increase (IL-12) or decrease (IL-10) production of various cytokines, including the chemokines CCL2, CCL20, and CCL26 (Chen H, et al. "Activation of STAT6 by STING Is Critical for Antiviral Innate Immunity" Cell. 2011, vol. 14: 433-446). Direct phosphorylation of STING on Ser366 upon activation has also been reported to occur through TBK1 or ULK1 (Corrales, L. et al "Direct activation of STING in the tumor microenvironment leads to potent and systemic tumor regression and immunity" Cell Reports, 2015, vol. 11: 1-13; Konno, H. et al. "Cyclic dinucleotides trigger ULK1 (ATG1) phosphorylation of STING to prevent sustained innate immune signaling" Cell, 2013, vol. 155: 688-698).

Single nucleotide polymorphisms in the STING gene result in variants of human STING protein that can affect the binding and immune response elicited by cyclic dinucleotides. (Yi G, Brendel V P, Shu C, Li P, Palanathan S, Cheng Kao C. "Single Nucleotide Polymorphisms of Human STING Can Affect Innate Immune Response to Cyclic Dinucleotides." Li K, ed. *PLoS ONE*. 2013; 8(10):e77846. doi:10.1371/journal.pone.0077846.). According to Yi et al, the three most prevalent variants are STING-WT, STING (R71H-G230A-R293Q), also referred to as STING(HAQ), and STING(R232H).

The natural ligand that binds to and activates STING, (2',3')cyclic guanosine monophosphate-adenosine monophosphate (2',3'-cGAMP), and the enzyme responsible for its synthesis (cGAS, also known as C6orf150 or MB21D1) have been elucidated, providing an opportunity to modulate this pathway. cGAMP is a high affinity ligand for STING produced in mammalian cells that serves as an endogenous second messenger to activate the STING pathway. It is a cyclic dinucleotide with a unique 2',3' linkage produced by cGAS in the presence of exogenous double-stranded DNA (e.g. that released by invading bacteria, viruses or protozoa) or of self-DNA in mammals (Wu et al., 2013; Sun, L. et al. "Cyclic GMP-AMP Synthase Is a Cytosolic DNA Sensor That Activates the Type I Interferon Pathway" Science, 2013, vol. 339: 786-791; Bhat N and Fitzgerald K A. "Recognition of Cytosolic DNA by cGAS and other STING-dependent sensors". Eur Immunol. 2014 March; 44(3):634-40). STING activation can also occur through binding of exogenous (3',3) cyclic dinucleotides (c-di-GMP, c-di-AMP and 3',3'-cGAMP) that are released by invading bacteria (Zhang X, et al. "Cyclic GMP-AMP Containing Mixed Phosphodiester Linkages Is An Endogenous High-Affinity Ligand for STING" Molecular Cell, 2013, vol. 51: 226-235; Danilchanka, O and Mekalanos, J J. "Cyclic Dinucleotides and the Innate Immune Response" Cell. 2013. vol. 154: 962-970).

Activation of the STING pathway triggers an immune response that results in generation of specific killer T-cells that can shrink tumors and provide long lasting immunity so they do not recur. The striking antitumor activity obtained with STING agonists in preclinical models has generated a high level of excitement for this target, and small molecule compounds that can modulate the STING pathway have potential to treat both cancer and reduce autoimmune diseases.

The potential therapeutic benefits of enhancing both innate and adaptive immunity make STING an attractive therapeutic target that demonstrates impressive activity by itself and can also be combined with other immunotherapies.

SUMMARY OF THE INVENTION

It has been found that cyclic mononucleotide compounds in accordance with the present invention are STING agonists which modulate the STING protein in assays. Most STING agonists to date have been cyclic dinucleotides. In the present invention, novel cyclic mononucleotide chemotypes have been demonstrated to be effective STING agonists. Moreover, a compound(s) of the present invention has been shown to regress tumors in mice and to provide protection against further challenges by the same type of tumor.

Accordingly, the present invention provides novel cyclic mononucleotide analogues which are STING agonists and are useful as selective immunotherapies, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of disorders, diseases, syndromes, or conditions affected by the agonism of STING comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a disorder, disease, syndrome, or condition affected by the agonism of STING.

Other features and advantages of the invention will be apparent from the following detailed description and claims.

DETAILED DESCRIPTION

Definitions

Figure 1:
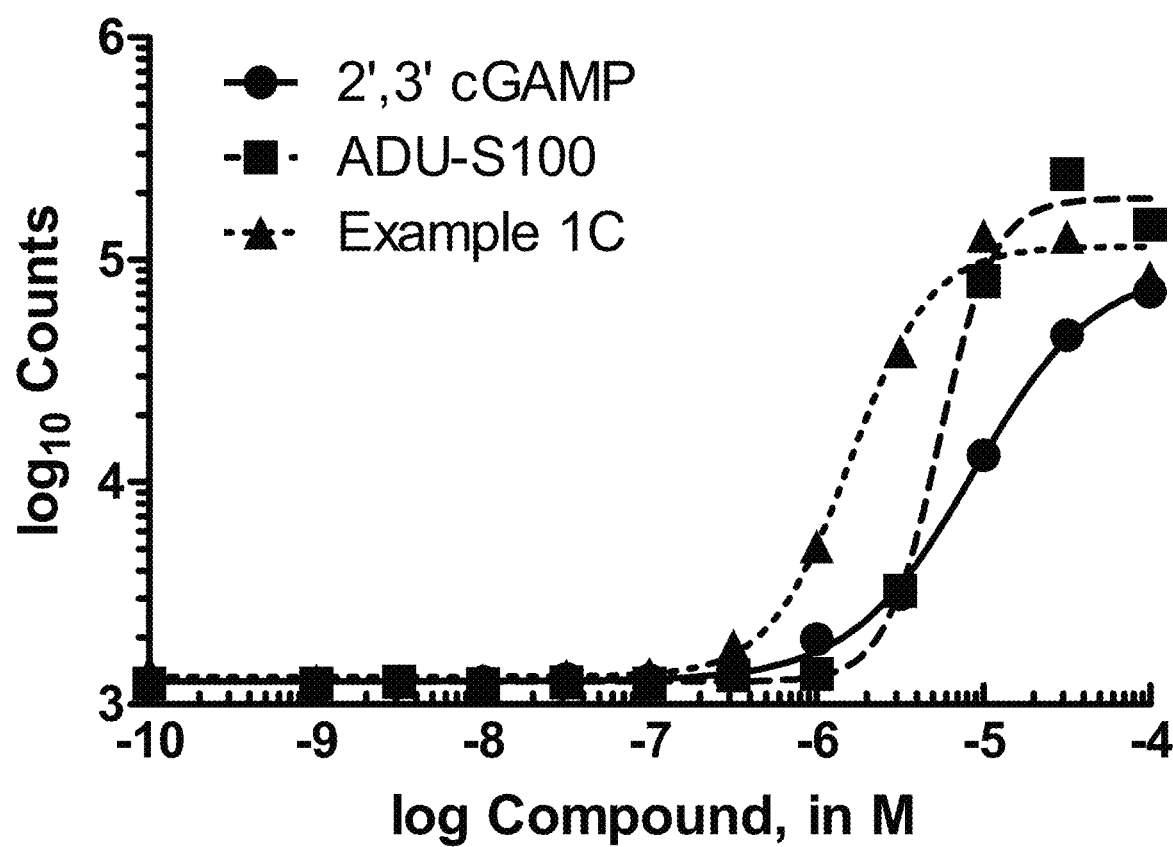
FIG. 1 is a graph which shows the effectiveness of Example 1C in activating the STING pathway.

The term "about" as used herein means plus or minus 50% of the numerical value of the number with which it is being used. Therefore, about 50% means in the range of 25%-75% on a logarithmic scale.

The term "activate" as used herein means to make active; cause to function or act.

The term "adjuvant therapy" means a treatment added to a curative treatment to prevent recurrence of clinical cancer from microscopic residual disease; the additional therapy given to enhance or extend primary therapy's effect, as in chemotherapy's addition to a surgical regimen.

The term "affected by" as used herein means influenced, acted upon, or touched by an external factor.

The term "agonist" as used herein means a chemical substance capable of activating a receptor or protein to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "antigen" as used herein means any substance that causes the body to raise an immune response against that substance. Antigens include toxins, chemicals, bacteria, viruses, or other substances that come from outside the body.

The term "antigen presenting cell" or "APC" as used herein means highly specialized immune cells that can process antigens and display their peptide fragments on the cell surface together with other co-stimulatory proteins required for activating naïve T cells. The main antigen presenting cells are dendritic cells (DCs), macrophages and B cells. APCs boost an immune response by presenting antigens on their surfaces to other cells of the immune system.

The term "binding" and its various grammatical forms means a lasting attraction between chemical substances. Binding specificity: involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "biotherapeutic agent" as used herein means microorganisms with therapeutic properties.

The terms "cancer" or "malignancy" as used herein refer to diseases in which abnormal cells divide without control and can invade nearby tissues. Cancer cells also can spread to other parts of the body through the blood and lymph systems. Central nervous system cancers are cancers that begin in the tissues of the brain and spinal cord.

The term "cell" is used herein to refer to the structural and functional unit of living organisms and is the smallest unit of an organism classified as living.

The term "cell line" as used herein, means a permanently established cell culture developed from a single cell and therefore consisting of a population of cells with a uniform genetic and functional makeup that will proliferate indefinitely in culture.

The term "chemotherapeutic agent" as used herein means chemicals useful in the treatment or control of a disease.

The term "chemotherapy" as used herein means a course of treatment with one or more chemotherapeutic agent.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "chemotype" means a chemical distinct entity.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_{18}$, $SR_{18}$, (=S), $-NR_{18}R_{19}$, $-N(alkyl)_3^+$, $-NR_{18}SO_2$, $-NR_{18}SO_2R_{20}$, $-SO_2R_{20}$, $-SO_2NR_{18}R_{19}$, $-SO_2NR_{18}C(=O)R_{19}$, $SO_3H$, $-PO(OH)_2$, $-C(=O)R_{18}$, $-CO_2R_{18}$, $-C(=O)NR_{18}R_{19}$, $-C(=O)(C_1$-$C_4$ alkylene)$NR_{18}R_{19}$, $-C(=O)NR_{18}(SO_2)R_{19}$, $-CO_2(C_1$-$C_4$ alkylene)$NR_{18}R_{19}$, $-NR_{18}C(=O)R_{19}$, $-NR_{18}CO_2R_{19}$, $-NR_{18}(C_1$-$C_4$ alkylene)$CO_2R_9$, $=N-OH$, $=N-O$-alkyl, wherein $R_{18}$ and $R_{19}$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_{20}$ is selected from same groups as $R_{18}$ and $R_{19}$ but is not hydrogen. Each group $R_{18}$ and $R_{19}$ when other than hydrogen, and each $R_{20}$ group optionally has up to three further substituents attached at any available carbon or nitrogen atom of $R_{18}$, $R_{19}$, and/or $R_{20}$, said substituent(s) being the same or different and are independently selected from the group consisting of ($C_1$-$C_6$)alkyl, ($C_2$-$C_6$)alkenyl, hydroxy, halogen, cyano, nitro, $CF_3$, $O(C_1$-$C_6$ alkyl), $OCF_3$, $C(=O)H$, $C(=O)(C_1$-$C_6$ alkyl), $CO_2H$, $CO_2(C_1$-$C_6$ alkyl), $NHCO_2(C_1$-$C_6$ alkyl), $-S(C_1$-$C_6$ alkyl), $-NH_2$, $NH(C_1$-$C_6$ alkyl), $N(C_1$-$C_6$ alkyl)$_2$, $N(CH_3)_3^+$, $SO_2(C_1$-$C_6$ alkyl), $C(=O)(C_1$-$C_4$ alkylene)$NH_2$, $C(=O)(C_1$-$C_4$ alkylene)$NH$(alkyl), $C(=O)(C_1$-$C_4$ alkylene)$N(C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Halo-$C_1$-$C_6$-alkyl" or "Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_4$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

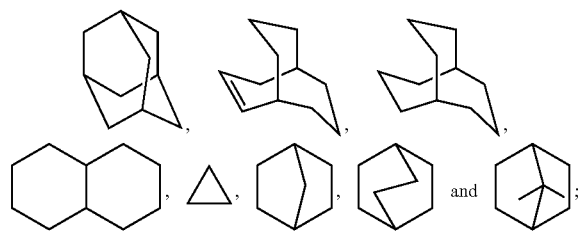

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, $C(=O)NH_2$ and $CO_2CH_3$.

As used herein, the term "heterocycle," "heterocyclo", "heterocyclyl" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$, $C(=O)NH_2$ and $CO_2CH_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" or "heterocyclyl" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Exemplary heterocyclo groups include

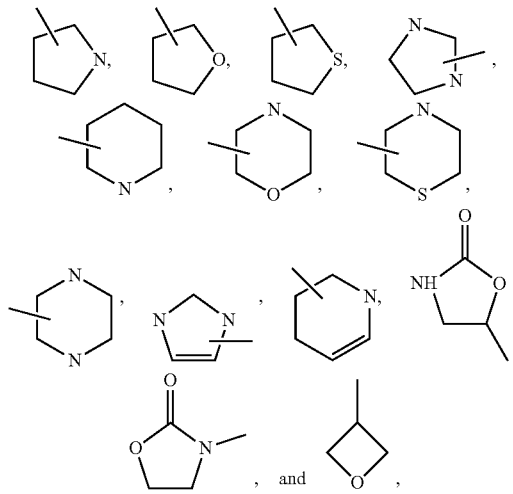

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$, $C(=O)NH_2$, $CH_2OCH_3$ and $CO_2CH_3$. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Exemplary heteroaryl groups include

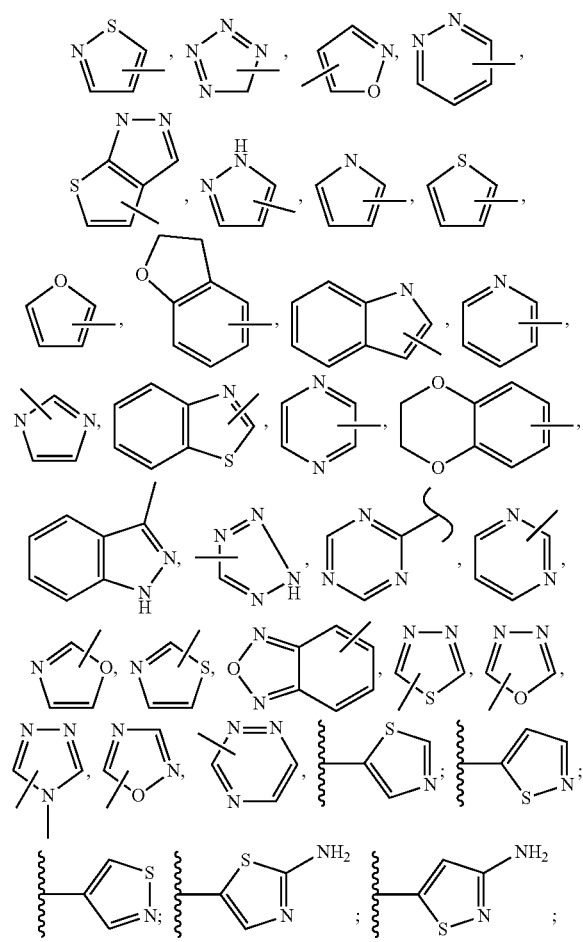

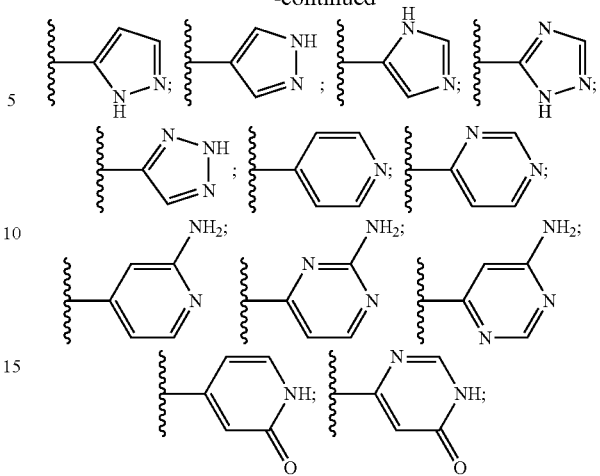

and the like.

The designation "〰" or "§-" or "-§-" attached to a ring or other group refers to a free bond or linking group.

The term "chiral" is used to describe asymmetric molecules that are nonsuperposable since they are mirror images of each other and therefore have the property of chirality.

The term "chirality" refers to the geometric property of a molecule (or spatial arrangement of points or atoms) of being non-superposable on its mirror image.

The term "chirality center" or "chiral center" refers to an asymmetric central atom bonded to a set of atoms in a spatial arrangement so that it has a nonsuperimposable mirror image.

The term "compatible" as used herein means that the components of a therapy comprising a composition are capable of being combined with each other in a manner such that there is no interaction that would substantially reduce the efficacy of the composition under ordinary use conditions.

The term "composition" as used herein means a mixture of ingredients, or a material formed of two or more substances.

The term "compound," as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof. The compounds as used herein include stereoisomers and tautomers.

The term "controlled release" as used herein means a drug-containing formulation in which the manner and profile of drug release from the formulation are regulated. This means immediate as well as non-immediate release formulations, with non-immediate release formulations including, but not limited to, sustained release and delayed release formulations.

The term "cytokine" as used herein means small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells.

The term "cytotoxic agent" as used herein means a substance that kills cells, including cancer cells. It may stop cancer cells from dividing and growing and may cause tumors to shrink in size.

The term "delayed release" is used herein in its conventional sense to refer to a drug formulation in which there is a time delay between administration of the formulation and the release of the drug therefrom. "Delayed release" may or may not involve gradual release of drug over an extended period of time, and thus may or may not be "sustained release."

The term "expression" encompasses the biosynthesis of mRNA, polypeptide biosynthesis, polypeptide activation, e.g., by post-translational modification, or an activation of expression by changing the subcellular location or by recruitment to chromatin.

The term "immune checkpoint inhibitor" as used herein means a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1, CTLA-4/B7-1/B7-2, TIGIT, LAG-3, and LIM-3. Some immune checkpoint inhibitors are used to treat cancer.

The term "immune response" as used herein means any functional expression of a subject's immune system against foreign or self-antigens, whether beneficial or harmful to the subject.

The term "immunogenic agent" as used herein means a substance that elicits an immune response.

The term "immunomodulators" as used herein means a chemical agent that modifies the immune response or the functioning of the immune system.

The term "immunotherapy" as used herein means a type of therapy that uses substances to stimulate or suppress the immune system to help the body fight cancer, infection, and other diseases. Some types of immunotherapy only target certain cells of the immune system. Others affect the immune system in a general way. Types of immunotherapy include cytokines, vaccines, bacillus Calmette-Guerin (BCG), and some monoclonal antibodies. Types of immunotherapy used to treat cancer include nonspecific immune stimulation, T-cell transfer therapy, and immune checkpoint inhibitors.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of an amount, rate, action function, or process by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "isomers" as used herein refers to two or more molecules that have the same molecular formula but differ in arrangement and configuration of the atoms. Isomers may differ in the connectivities of the atoms (structural isomers), or they may have the same atomic connectivities but differ in the arrangement or configuration of the atoms in space (stereoisomers). Stereoisomers may include, but are not limited to, E/Z double bond isomers, enantiomers, and diastereomers. Enantiomers are non-superimposable mirror images. A mixture of equal parts of the optical forms of a compound is known as a racemic mixture or racemate. Diastereomers are stereoisomers that are not mirror images.

The term "half maximal effective concentration" ("EC50") is a measure of the concentration of an agent that provokes a response halfway between the baseline and maximal response.

The term "half maximal inhibitory concentration" ("IC50") is a measure of the effectiveness of a compound in inhibiting biological or biochemical function.

The term "modulate" as used herein means to regulate, alter, adapt, or adjust to a certain measure or proportion.

The term "outcome" or "clinical outcome" as used herein means a specific result or effect that can be measured.

The term "overall survival" as used herein means the length of time from either the date of diagnosis or the start of treatment for a disease, such as cancer, that patients diagnosed with the disease are still alive.

As used herein, the term "patient" encompasses all mammalian species.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The term "progression-free survival" as used herein means the length of time during and after the treatment of a disease, such as cancer, that a patient lives with the disease but it does not get worse.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

The term "relapse-free survival" as used herein in cancer means the length of time after primary treatment for a cancer ends that the patient survives without any signs or symptoms of that cancer.

The term "regress" and its various grammatical forms" means to decrease the size of a tumor or the extent of cancer in the body.

The term "selective immunotherapy" means therapies that enlist and strengthen the power of a patient's immune system to attack their tumors. Tumors employ multiple strategies to escape from anti-tumor immunity, some of which result from the selection of cancer cells with immunosuppressive activity by the process of cancer immunoediting. Apart from this selective process, anti-tumor immune responses can also be inhibited in multiple different ways which vary from patient to patient. A rapidly emerging immunotherapy approach is called adoptive cell transfer (ACT): collecting and using patients' own immune cells to treat their cancer. Chimeric antigen receptor T-cell (CAR-T cell) therapy is a type of treatment in which a patient's T cells are changed in the laboratory so they will attack cancer cells. T cells are taken from a patient's blood. Then the gene for a synthetic receptor that binds to a certain protein on the patient's cancer cells (chimeric antigen receptor (CAR)) is added in the laboratory. Once the collected T cells have been engineered to express the antigen-specific CAR, they are "expanded" in the laboratory into the hundreds of millions. The final step is the infusion of the CAR T cells into the patient (which is preceded by a "lymphodepleting" chemotherapy regimen). If all goes as planned, the engineered cells further multiply in the patient's body and, with guidance from their engineered receptor, recognize and kill cancer cells that harbor the antigen on their surfaces.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

The terms "Stable compound" and "stable structure" are meant to indicate a compound that is sufficiently robust to survive isolation from a reaction mixture, and formulation into an efficacious therapeutic agent.

The term "STING agonist" or "STING Protein Agonist" denotes an agonist which binds to STING and activates the STING pathway promoting IKK-related kinase TANK-binding kinase 1 (TBK1) signaling and activates nuclear factor-kappa B (NF-kB) and interferon regulatory factor 3 (IRF3) in immune cells in the tumor microenvironment.

The term "substantially pure" as used herein means being substantially separated from substances with which it may be associated in living systems. It means a purity of at least 75%, at least 80%, at least 85%, at least 90%, at least 95% or at least 99% as determined by an analytical protocol.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period.

The term "target" as used herein means a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

The term "tumor" as used herein means a diseases involving abnormal cell growth in numbers (proliferation) or in size with the potential to invade or spread to other parts of the body (metastasis).

The term "tumor burden" as used herein means the number of cancer cells, the size of a tumor, or the amount of cancer in the body. Also called tumor load.

The term "tumor debulking" as used herein means surgical removal of as much of a solid tumor as possible.

The term "transfection" means the introduction of foreign DNA into eukaryotic or prokaryotic cells. Transfection typically involves opening transient holes in cells to allow the entry of extracellular molecules, typically supercoiled plasmid DNA, but also siRNA, among others. There are various methods of transfecting cells.

The term "wild-type" as used herein means the typical form of an organism, strain, gene, protein, nucleic acid, or characteristic as it occurs in nature. Wild-type means the most common phenotype in the natural population.

As used herein, the term "subject" refers to any human or nonhuman organism that could potentially benefit from treatment with a STING agonist. Exemplary subjects include human beings of any age with risk factors for a disorder, disease, syndrome, or condition affected by the agonism of STING, or patients that have already experienced one episode of a disorder, disease, syndrome, or condition affected by the agonism of STING.

As used herein, "treating" or "treatment" refers to obtaining desired pharmacological and/or physiological effect and covers the treatment of a disease-state in a mammal, for example in a human. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate STING and/or to prevent or treat the disorders listed herein. When applied to a combination, the term refers to combined amounts of the active ingredients that result in the preventive or therapeutic effect, whether administered in combination, serially, or simultaneously. In some embodiments as defined herein, the therapeutically effective amount of the compound elicits the desired biological response in a subject. Such response includes alleviation of the symptoms of the disease or disorder being treated. The therapeutically effective amount of the compound of the invention in such a therapeutic method is from about 0.0005 mg/day to about 1000 mg/day or from about 0.01 mg/day to about 100 mg/day.

Compounds

A first embodiment of the invention is a compound of Formula I':

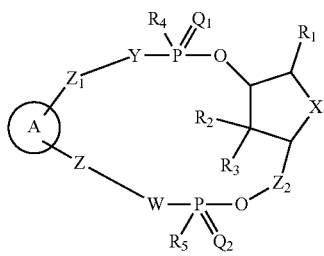

or a stereoisomer, tautomer, pharmaceutically acceptable salt, solvate or prodrug thereof, wherein:

W is absent or independently selected from O, S or —$NR_6$;

X is $CH_2$, O or S;

Y is absent or independently selected from O, S or —$NR_7$;

$Q_1$ and $Q_2$ are each independently O or S;

(A) is a 5- to 6-membered monocyclic heteroaryl or a 7- to 12-membered bicyclic heteroaryl; both of which are optionally substituted with $R_{10}$ and $R_{11}$ and wherein the 7- to 12-membered bicyclic heteroaryl contains at least two N atoms;

Z is independently selected from $C_1$-$C_6$ alkyl, halo-C1-$C_6$-alkyl and $C_3$-$C_6$ cycloalkyl;

$Z_1$ is independently selected from $C_1$-$C_6$ alkyl, halo-C1-$C_6$-alkyl and $C_3$-$C_6$ cycloalkyl;

$Z_2$ is independently selected from $C_1$-$C_4$ alkyl and halo-$C_1$-$C_4$-alkyl;

$R_1$ is a 5- to 6-membered monocyclic heteroaryl or a 7- to 10-membered bicyclic heteroaryl; both of which are optionally substituted with $R_{12}$ and $R_{13}$ and wherein the 7- to 10-membered bicyclic heteroaryl contains at least two N atoms;

$R_2$ is independently selected from H, halo, $C_1$-$C_4$ alkyl, C1-$C_4$ alkoxy, halo-$C_1$-$C_4$ alkyl, halo-$C_1$-$C_4$ alkoxy, CN, —$NR_8R_9$, $C_3$-$C_4$ cycloalkyl and OH;

$R_3$ is independently selected from H, halo, $C_1$-$C_4$ alkyl, $C_1$-$C_4$ alkoxy, halo-$C_1$-$C_4$ alkyl, halo-$C_1$-$C_4$ alkoxy, CN, and OH;

or $R_2$ and $R_3$ can be taken together with the carbon to which they are attached to form a $C_3$-$C_4$ cycloalkyl ring;

$R_4$ is selected from OH, SH, $C_1$-$C_6$ alkoxy-carbonyl-oxy-$C_1$-$C_6$ alkoxy, $C_1$-$C_6$ alkoxy-carbonyl-oxy-$C_1$-$C_6$ alkylthio, and $BH_3$;

$R_5$ is selected from OH, SH, $C_1$-$C_6$ alkoxy-carbonyl-oxy-$C_1$-$C_6$ alkoxy, $C_1$-$C_6$ alkoxy-carbonyl-oxy-$C_1$-$C_6$ alkylthio, and $BH_3$;

$R_6$ is independently selected from H, $C_1$-$C_4$ alkyl, $C_2$-$C_3$ alkenyl, $C_2$-$C_3$ alkynyl, $C_3$-$C_6$ cycloalkyl and $C_1$-$C_4$ alkoxy;

$R_7$ is independently selected from H, $C_1$-$C_4$ alkyl, $C_2$-$C_3$ alkenyl, $C_2$-$C_3$ alkynyl, $C_3$-$C_6$ cycloalkyl and $C_1$-$C_4$ alkoxy;

$R_8$ is independently selected from H, $C_1$-$C_4$ alkyl, $C_1$-$C_4$ alkoxy, halo-$C_1$-$C_4$-alkyl, —C(=O)$R_{15}$ and —$SO_2R_{15}$;

$R_9$ is independently selected from H, $C_1$-$C_4$ alkyl, $C_1$-$C_4$ alkoxy, and halo-C1-$C_4$-alkyl;

$R_{10}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, —C(=O)$NR_{14}R_{15}$, a $C_6$-$C_{10}$ aryl, a 5- to 10-membered heteroaryl, a 4- to 6-membered heterocycloalkyl, a $C_3$-$C_6$ cycloalkyl, $SR_{18}$ and OH; wherein the $C_1$-$C_4$ alkyl, $C_1$-$C_4$ alkoxy, halo-$C_1$-$C_4$ alkyl, halo-$C_1$-$C_4$ alkoxy, $C_6$-$C_{10}$ aryl, the 5- to 10-membered heteroaryl and the $C_3$-$C_6$ cycloalkyl are each optionally substituted with OH, 1 to 3 halo, CN, —$NR_{14}R_{15}$, —C(=O)$NR_{14}R_{15}$, $C_1$-$C_4$ alkyl, $C_1$-$C_4$ alkoxy, halo-$C_1$-$C_4$ alkyl and halo-$C_1$-$C_4$ alkoxy;

$R_{11}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, —C(=O)$NR_{14}R_{15}$, a $C_6$-$C_{10}$ aryl, a 5- to 10-membered heteroaryl, a 4- to 6-membered heterocycloalkyl, a $C_3$-$C_6$ cycloalkyl, $SR_{18}$ and OH; wherein the $C_1$-$C_4$ alkyl, $C_1$-$C_4$ alkoxy, halo-$C_1$-$C_4$ alkyl, halo-$C_1$-$C_4$ alkoxy, $C_6$-$C_{10}$ aryl, the 5- to 10-membered heteroaryl and the $C_3$-$C_6$ cycloalkyl are optionally substituted with OH, 1 to 3 halo, CN, —$NR_{14}R_{15}$, —C(=O)$NR_{14}R_{15}$, $C_1$-$C_4$ alkyl, $C_1$-$C_4$ alkoxy, halo-$C_1$-$C_4$ alkyl and halo-$C_1$-$C_4$ alkoxy;

$R_{12}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{16}R_{17}$, —$NR_{16}$C(=O)$R_{17}$, a $C_6$-$C_{10}$ aryl, a 5- to 10-membered heteroaryl and OH;

$R_{13}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{16}R_{17}$, —$NR_{16}$C(=O)$R_{17}$, a $C_6$-$C_{10}$ aryl, a 5- to 10-membered heteroaryl and OH;

$R_{14}$, at each occurrence, is independently selected from H, $C_1$-$C_4$ alkyl, $C_1$-$C_4$ alkoxy, halo-$C_1$-$C_4$-alkyl, —C(=O)$R_{15}$ and —$SO_2R_{15}$;

$R_{15}$, at each occurrence, is independently selected from H, $C_1$-$C_4$ alkyl, $C_1$-$C_4$ alkoxy, halo-C1-$C_4$-alkyl, a $C_6$-$C_{10}$ aryl and a 5- to 10-membered heteroaryl;

$R_{16}$, at each occurrence, is independently selected from H, $C_1$-$C_4$ alkyl, $C_1$-$C_4$ alkoxy, halo-$C_1$-$C_4$-alkyl, —C(=O)$R_{17}$ and —$SO_2R_{17}$;

$R_{17}$, at each occurrence, is independently selected from H, $C_1$-$C_4$ alkyl, $C_1$-$C_4$ alkoxy, halo-C1-$C_4$-alkyl, a $C_6$-$C_{10}$ aryl, and a 5- to 10-membered heteroaryl; and $R_{18}$ is selected from H and $C_1$-$C_4$ alkyl.

In a second embodiment, the present invention provides cyclic mononucleotides compounds, stereoisomers, tautomers, salts, solvates or prodrugs thereof, of Formula I having the structure:

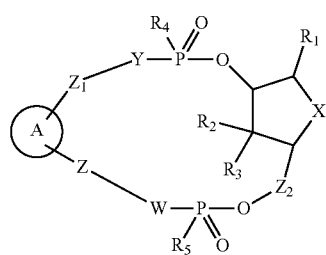

or a stereoisomer, tautomer, pharmaceutically acceptable salt, solvate or prodrug thereof, wherein:

W is absent or independently selected from O, S or —$NR_6$;

X is $CH_2$, O or S;

Y is absent or independently selected from O, S or —$NR_7$;

(A) is a 5- to 6-membered monocyclic heteroaryl or a 7- to 12-membered bicyclic heteroaryl; both of which are optionally substituted with $R_{10}$ and $R_{11}$ and wherein the 7- to 12-membered bicyclic heteroaryl contains at least two N atoms;

Z is independently selected from $C_1$-$C_6$ alkyl, halo-$C_1$-$C_6$-alkyl and $C_3$-$C_4$ cycloalkyl;

$Z_1$ is independently selected from $C_1$-$C_6$ alkyl, halo-$C_1$-$C_6$-alkyl and $C_3$-$C_4$ cycloalkyl;

$Z_2$ is independently selected from $C_1$-$C_4$ alkyl and halo-$C_1$-$C_4$-alkyl;

$R_1$ is a 5- to 6-membered monocyclic heteroaryl or a 7- to 10-membered bicyclic heteroaryl; both of which are optionally substituted with $R_{12}$ and $R_{13}$ and wherein the 7- to 10-membered bicyclic heteroaryl contains at least two N atoms;

$R_2$ is independently selected from H, halo, $C_1$-$C_4$ alkyl, $C_1$-$C_4$ alkoxy, halo-$C_1$-$C_4$ alkyl, halo-$C_1$-$C_4$ alkoxy, CN, —$NR_8R_9$, $C_3$-$C_4$ cycloalkyl and OH;

$R_3$ is independently selected from H, halo, $C_1$-$C_4$ alkyl, $C1$-$C_4$ alkoxy, halo-$C_1$-$C_4$ alkyl, halo-$C_1$-$C_4$ alkoxy, CN, and OH;

or $R_2$ and $R_3$ can be taken together with the carbon to which they are attached to form a $C_3$-$C_4$ cycloalkyl ring;

$R_4$ is selected from OH, SH, $C_1$-$C_6$ alkoxy-carbonyl-oxy-$C_1$-$C_6$ alkoxy, $C_1$-$C_6$ alkoxy-carbonyl-oxy-$C_1$-$C_6$ alkylthio, and $BH_3$;

$R_5$ is selected from OH, SH, $C_1$-$C_6$ alkoxy-carbonyl-oxy-$C_1$-$C_6$ alkoxy, $C_1$-$C_6$ alkoxy-carbonyl-oxy-$C_1$-$C_6$ alkylthio, and $BH_3$;

$R_6$ is independently selected from H, $C_1$-$C_4$ alkyl, $C_2$-$C_3$ alkenyl, $C_2$-$C_3$ alkynyl, $C_3$-$C_6$ cycloalkyl and $C_1$-$C_4$ alkoxy;

$R_7$ is independently selected from H, $C_1$-$C_4$ alkyl, $C_2$-$C_3$ alkenyl, $C_2$-$C_3$ alkynyl, $C_3$-$C_6$ cycloalkyl and $C_1$-$C_4$ alkoxy;

$R_8$ is independently selected from H, $C_1$-$C_4$ alkyl, $C_1$-$C_4$ alkoxy, halo-$C1$-$C_4$-alkyl, —C(=O)$R_{15}$ and —$SO_2R_{15}$;

$R_9$ is independently selected from H, $C_1$-$C_4$ alkyl, $C_1$-$C_4$ alkoxy, and halo-$C_1$-$C_4$-alkyl;

$R_{10}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, C(=O)$NR_{14}R_{15}$, a $C_6$-$C_{10}$ aryl, a 5- to 10-membered heteroaryl and OH;

$R_{11}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, C(=O)$NR_{14}R_{15}$, —$NR_{14}R_{15}$, —$NR_{14}$C(=O)$R_5$, a $C_6$-$C_{10}$ aryl, a 5- to 10-membered heteroaryl; and OH;

$R_{12}$ is independently selected from H, =O, halo, $C_1$-$C_4$ alkyl, $C1$-$C_4$ alkoxy, halo-$C_1$-$C_4$ alkyl, halo-$C_1$-$C_4$ alkoxy, CN, —$NR_{16}R_{17}$, —$NR_{16}$C(=O)$R_{17}$, a $C_6$-$C_{10}$ aryl, a 5- to 10-membered heteroaryl and OH;

$R_{13}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{16}R_{17}$, —$NR_{16}$C(=O)$R_{17}$, a $C_6$-$C_{10}$ aryl, a 5- to 10-membered heteroaryl and OH;

$R_{14}$, at each occurrence, is independently selected from H, $C_1$-$C_4$ alkyl, $C_1$-$C_4$ alkoxy, halo-$C_1$-$C_4$-alkyl, —C(=O)$R_5$ and —$SO_2R_{15}$;

$R_{15}$, at each occurrence, is independently selected from H, $C_1$-$C_4$ alkyl, $C_1$-$C_4$ alkoxy, halo-$C_1$-$C_4$-alkyl, a $C_6$-$C_{10}$ aryl and a 5- to 10-membered heteroaryl;

$R_{16}$, at each occurrence, is independently selected from H, $C_1$-$C_4$ alkyl, $C_1$-$C_4$ alkoxy, halo-$C_1$-$C_4$-alkyl, —C(=O)$R_{17}$ and —$SO_2R_{17}$; and $R_{17}$, at each occurrence, is independently selected from H, $C_1$-$C_4$ alkyl, $C_1$-$C_4$ alkoxy, halo-$C_1$-$C_4$-alkyl, a $C_6$-$C_{10}$ aryl, and a 5- to 10-membered heteroaryl.

In another embodiment, the present invention provides compounds of Formula I' or I, stereoisomers, tautomers, salts, solvates or prodrugs thereof, wherein X is O.

In yet another embodiment, the present invention provides compounds of Formula I' or I, stereoisomers, tautomers, salts, solvates or prodrugs thereof, wherein W is O, S or —$NR_6$.

In still yet another embodiment, the present invention provides compounds of Formula I' or I, stereoisomers, tautomers, salts, solvates or prodrugs thereof, wherein Y is O, S or —$NR_7$.

In one embodiment, the present invention provides compounds of Formula I' or I, stereoisomers, tautomers, salts, solvates or prodrugs thereof, wherein W is O, S or —$NR_6$ and Y is O, S or —$NR_7$.

In one embodiment, the present invention provides compounds of Formula I' or I, stereoisomers, tautomers, salts, solvates or prodrugs thereof, wherein $R_4$ and $R_5$ are the same moiety.

In one embodiment, the present invention provides compounds of Formula I' or I, stereoisomers, tautomers, salts, solvates or prodrugs thereof, wherein W is O or —$NR_6$.

In yet another embodiment, the present invention provides compounds of Formula I' or I, stereoisomers, tautomers, salts, solvates or prodrugs thereof, wherein Y is O or —$NR_7$.

In yet another embodiment, the present invention provides compounds of Formula I' or I, stereoisomers, tautomers, salts, solvates or prodrugs thereof, wherein W is O or —$NR_6$ and Y is O or —$NR_7$.

In yet another embodiment, the present invention provides compounds of Formula I' or I, stereoisomers, tautomers, salts, solvates or prodrugs thereof, wherein W and Y are O.

In still yet another embodiment, the present invention provides compounds of Formula I' or I, stereoisomers, tautomers, salts, solvates or prodrugs thereof, wherein $Z_2$ is $C_1$-$C_4$ alkyl.

In one embodiment, the present invention provides compounds of Formula I' or I, stereoisomers, tautomers, salts, solvates or prodrugs thereof, wherein $R_3$ is H.

In another embodiment, the present invention provides compounds of Formula I' or I, stereoisomers, tautomers, salts, solvates or prodrugs thereof, wherein W and Y are O; $Z_2$ is $C_1$-$C_4$ alkyl; and $R_3$ is H.

In yet another embodiment, the present invention provides compounds of Formula I' or I, stereoisomers, tautomers, salts, solvates or prodrugs thereof, wherein (A) is a 7- to 10-membered bicyclic heteroaryl ring containing at least three N atoms; which is optionally substituted with $R_{10}$ and $R_{11}$.

In yet another embodiment, the present invention provides compounds of Formula I' or I, stereoisomers, tautomers, salts, solvates or prodrugs thereof, wherein (A) is selected from purinyl, dihydropurinyl, dihydroimidazopyridazinyl, dihydropyrrolopyrimidinyl, imidazopyridinyl, imidazopyrazinyl, pyrrolopyrimidinyl, triazolyl, imidazolyl, pyrrolyl, and pyridyl; all of which are optionally substituted with $R_{10}$ and $R_{11}$.

In yet another embodiment, the present invention provides compounds of Formula I' or I, stereoisomers, tautomers, salts, solvates or prodrugs thereof, wherein (A) is selected from purinyl, dihydropurinyl, dihydroimidazopyridazinyl, dihydropyrrolopyrimidinyl, imidazopyridinyl, imidazopyrazinyl, and pyrrolopyrimidinyl; all of which are optionally substituted with $R_{10}$ and $R_{11}$.

In still yet another embodiment, the present invention provides compounds of Formula I' or I, stereoisomers, tautomers, salts, solvates or prodrugs thereof, wherein:

(A) is selected from

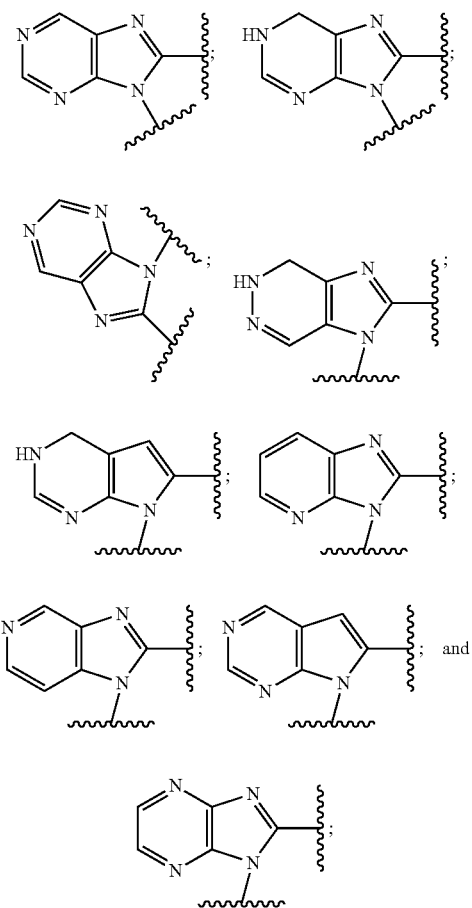

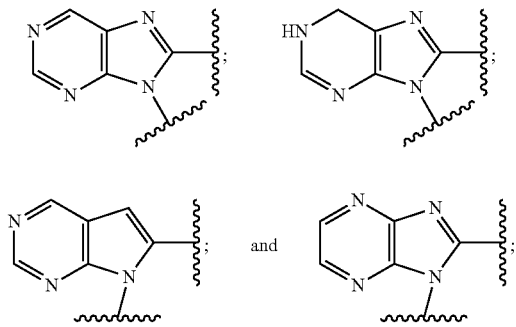

all of which are optionally substituted with $R_{10}$ and $R_{11}$.

In one embodiment, the present invention provides compounds of Formula I' or I, stereoisomers, tautomers, salts, solvates or prodrugs thereof, wherein:

(A) is selected from

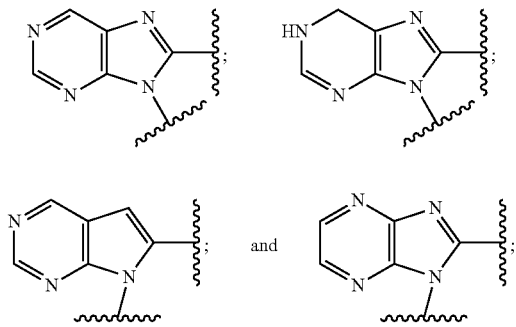

all of which are optionally substituted with $R_{10}$ and $R_{11}$.

In another embodiment, the present invention provides compounds of Formula I' or I, stereoisomers, tautomers, salts, solvates or prodrugs thereof, wherein:

(A) is selected from

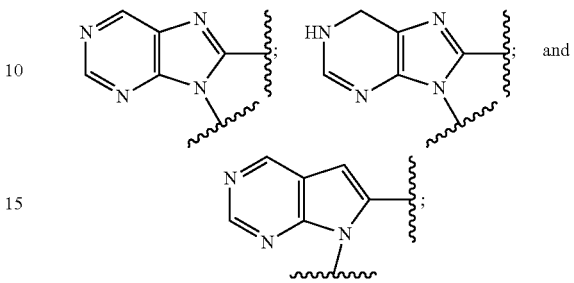

all of which are optionally substituted with $R_{10}$ and $R_{11}$.

In yet another embodiment, the present invention provides compounds of Formula I' or I, stereoisomers, tautomers, salts, solvates or prodrugs thereof, wherein:

(A) is selected from

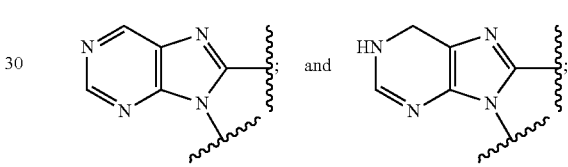

all of which are optionally substituted with $R_{10}$ and $R_{11}$.

In yet another embodiment, the present invention provides compounds of Formula I' or I, stereoisomers, tautomers, salts, solvates or prodrugs thereof, wherein $R_1$ is a 7- to 10-membered bicyclic heteroaryl containing at least three N atoms, which is optionally substituted with $R_{12}$ and $R_{13}$.

In still yet another embodiment, the present invention provides compounds of Formula I' or I, stereoisomers, tautomers, salts, solvates or prodrugs thereof, wherein $R_1$ is selected from dihydropurinyl, purinyl, pyrrolopyrimidinyl, dihydrotriazolopyrimidinyl, triazolopyrimidinyl, dihydroimidazopyridazinyl, and dihydropyrrolopyrimidinyl; all of which are optionally substituted with $R_{12}$ and $R_{13}$.

In one embodiment, the present invention provides compounds of Formula I' or I, stereoisomers, tautomers, salts, solvates or prodrugs thereof, wherein:

$R_1$ is selected from

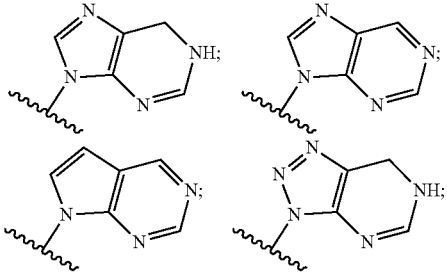

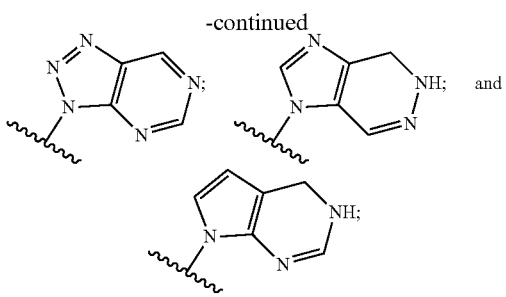

all of which are optionally substituted with $R_{12}$ and $R_{13}$.

In yet another embodiment, the present invention provides compounds of Formula I' or I, stereoisomers, tautomers, salts, solvates or prodrugs thereof, wherein:

$R_1$ is selected from

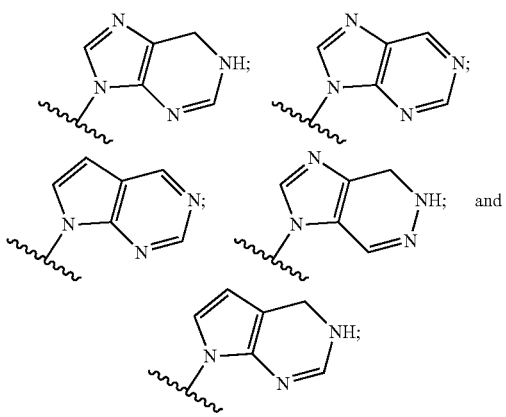

all of which are optionally substituted with $R_{12}$ and $R_{13}$.

In still yet another embodiment, the present invention provides compounds of Formula I' or I, stereoisomers, tautomers, salts, solvates or prodrugs thereof, wherein:

$R_1$ is selected from

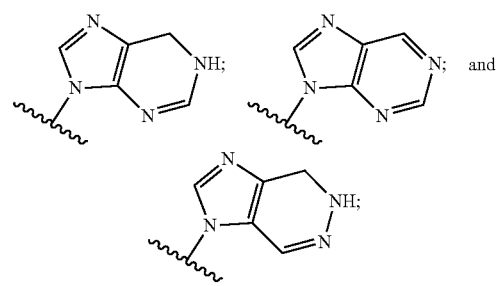

all of which are optionally substituted with $R_{12}$ and $R_{13}$.

In a third embodiment, the present invention provides compounds, stereoisomers, tautomers, salts, solvates or prodrugs thereof, wherein:

W is O or —$NR_6$;
Y is O or —$NR_7$;

Ⓐ is a 7- to 10-membered bicyclic heteroaryl ring containing at least three N atoms; which is optionally substituted with $R_{10}$ and $R_{11}$;

Z is independently selected from $C_1$-$C_6$ alkyl and halo-$C_1$-$C_6$-alkyl;

$Z_1$ is independently selected from $C_1$-$C_6$ alkyl and halo-$C_1$-$C_6$-alkyl;

$Z_2$ is independently selected from $C_1$-$C_4$ alkyl and halo-$C_1$-$C_4$-alkyl;

$R_1$ is a 7- to 10-membered bicyclic heteroaryl containing at least three N atoms, which is optionally substituted with $R_{12}$ and $R_{13}$;

$R_2$ is independently selected from H, halo, $C_1$-$C_4$ alkyl, $C_1$-$C_4$ alkoxy, halo-$C_1$-$C_4$ alkyl, halo-$C_1$-$C_4$ alkoxy, —$NR_8R_9$ and OH;

$R_3$ is independently selected from H, halo, $C_1$-$C_4$ alkyl, C1-$C_4$ alkoxy, halo-$C_1$-$C_4$ alkyl, halo-$C_1$-$C_4$ alkoxy, and OH;

$R_4$ is selected from OH, SH, C1-$C_6$ alkoxy-carbonyl-oxy-$C_1$-$C_6$ alkoxy, and $BH_3$;

$R_5$ is selected from OH, SH, $C_1$-$C_6$ alkoxy-carbonyl-oxy-$C_1$-$C_6$ alkoxy, and $BH_3$;

$R_6$ is independently selected from H, $C_1$-$C_4$ alkyl, $C_2$-$C_3$ alkenyl, $C_3$-$C_6$ cycloalkyl and $C_1$-$C_4$ alkoxy;

$R_7$ is independently selected from H, $C_1$-$C_4$ alkyl, $C_2$-$C_3$ alkenyl, $C_3$-$C_6$ cycloalkyl and $C_1$-$C_4$ alkoxy;

$R_8$ is independently selected from H, $C_1$-$C_4$ alkyl, and halo-$C_1$-$C_4$-alkyl;

$R_9$ is independently selected from H, $C_1$-$C_4$ alkyl, and halo-C1-$C_4$-alkyl;

$R_{10}$ is independently selected from H, =O, halo, $C_1$-$C_4$ alkyl, C1-$C_4$ alkoxy, halo-$C_1$-$C_4$ alkyl, halo-$C_1$-$C_4$ alkoxy, —$NR_{14}R_{15}$, —$NR_{14}C(=O)R_{15}$, $C(O)NHR_9$ and OH;

$R_{11}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, —$NR_{14}R_{15}$, —$NR_{14}C(=O)R_{15}$, $C(O)NHR_9$ and OH;

$R_{12}$ is independently selected from H, =O, halo, $C_1$-$C_4$ alkyl, C1-$C_4$ alkoxy, halo-$C_1$-$C_4$ alkyl, halo-$C_1$-$C_4$ alkoxy, —$NR_{16}R_{17}$, —$NR_{16}C(=O)R_{17}$ and OH;

$R_{13}$ is independently selected from H, =O, halo, $C_1$-$C_4$ alkyl, $C_1$-$C_4$ alkoxy, halo-$C_1$-$C_4$ alkyl, halo-$C_1$-$C_4$ alkoxy, —$NR_{16}R_{17}$, —$NR_{16}C(=O)R_{17}$ and OH;

$R_{14}$, at each occurrence, is independently selected from H, $C_1$-$C_4$ alkyl, and halo-$C_1$-$C_4$-alkyl;

$R_{15}$, at each occurrence, is independently selected from H, $C_1$-$C_4$ alkyl, and halo-$C_1$-$C_4$-alkyl;

$R_{16}$, at each occurrence, is independently selected from H, $C_1$-$C_4$ alkyl, and halo-$C_1$-$C_4$-alkyl; and $R_{17}$, at each occurrence, is independently selected from H, $C_1$-$C_4$ alkyl, and halo-$C_1$-$C_4$-alkyl, and the definitions for the remaining variables are as defined in the first or second embodiment.

In a fourth embodiment, the present invention provides compounds of Formula I' or I, stereoisomers, tautomers, salts, solvates or prodrugs thereof, wherein:

W is O or —$NR_6$;
Y is O or —$NR_7$;

Ⓐ is selected from purinyl, dihydropurinyl, dihydroimidazopyridazinyl, dihydropyrrolopyrimidinyl, imidazopyridinyl, imidazopyrazinyl, and pyrrolopyrimidinyl; all of which are optionally substituted with $R_{10}$ and $R_{11}$;

Z is independently selected from $C_1$-$C_6$ alkyl and halo-$C_1$-$C_6$-alkyl;

$Z_1$ is independently selected from $C_1$-$C_6$ alkyl and halo-$C_1$-$C_6$-alkyl;

$Z_2$ is independently selected from $C_1$-$C_4$ alkyl and halo-$C_1$-$C_4$-alkyl;

$R_1$ is selected from dihydropurinyl, purinyl, pyrrolopyrimidinyl, dihydrotriazolopyrimidinyl, triazolopyrimidinyl, dihydroimidazopyridazinyl, and dihydropyrrolopyrimidinyl; all of which are optionally substituted with $R_{12}$ and $R_{13}$;

$R_2$ is independently selected from H, halo, $C_1$-$C_4$ alkyl, $C_1$-$C_4$ alkoxy, halo-$C_1$-$C_4$ alkyl, —$NR_8R_9$ and OH;

$R_3$ is independently selected from H, halo, $C_1$-$C_4$ alkyl, $C_1$-$C_4$ alkoxy, halo-$C_1$-$C_4$ alkyl, and OH;

$R_4$ is selected from OH, SH, and $C_1$-$C_6$ alkoxy-carbonyl-oxy-$C_1$-$C_6$ alkoxy;

$R_5$ is selected from OH, SH, and $C_1$-$C_6$ alkoxy-carbonyl-oxy-$C_1$-$C_6$ alkoxy;

$R_6$ is independently selected from H, $C_1$-$C_4$ alkyl, $C_3$-$C_6$ cycloalkyl and $C_1$-$C_4$ alkoxy;

$R_7$ is independently selected from H, $C_1$-$C_4$ alkyl, $C_3$-$C_6$ cycloalkyl and $C_1$-$C_4$ alkoxy;

$R_8$ is independently selected from H, $C_1$-$C_4$ alkyl, and halo-$C_1$-$C_4$-alkyl;

$R_9$ is independently selected from H, $C_1$-$C_4$ alkyl, and halo-$C_1$-$C_4$-alkyl;

$R_{10}$ is independently selected from H, =O, halo, $C_1$-$C_4$ alkyl, $C_1$-$C_4$ alkoxy, halo-$C_1$-$C_4$ alkyl, —$NR_{14}R_{15}$, —$NR_{14}C(=O)R_{15}$, $C(O)NHR_9$ and OH;

$R_{11}$ is independently selected from H, =O, halo, $C_1$-$C_4$ alkyl, $C_1$-$C_4$ alkoxy, halo-$C_1$-$C_4$ alkyl, —$NR_{14}R_{15}$, —$NR_{14}C(=O)R_{15}$, $C(O)NHR_9$ and OH;

$R_{12}$ is independently selected from H, =O, halo, $C_1$-$C_4$ alkyl, $C_1$-$C_4$ alkoxy, halo-$C_1$-$C_4$ alkyl, —$NR_{16}R_{17}$, —$NR_{16}C(=O)R_{17}$ and OH;

$R_{13}$ is independently selected from H, =O, halo, $C_1$-$C_4$ alkyl, $C_1$-$C_4$ alkoxy, halo-$C_1$-$C_4$ alkyl, —$NR_{16}R_{17}$, —$NR_{16}C(=O)R_{17}$ and OH;

$R_{14}$, at each occurrence, is independently selected from H, $C_1$-$C_4$ alkyl, and halo-$C_1$-$C_4$-alkyl;

$R_{15}$, at each occurrence, is independently selected from H, $C_1$-$C_4$ alkyl, and halo-$C_1$-$C_4$-alkyl;

$R_{16}$, at each occurrence, is independently selected from H, $C_1$-$C_4$ alkyl, and halo-$C_1$-$C_4$-alkyl; and $R_{17}$, at each occurrence, is independently selected from H, $C_1$-$C_4$ alkyl, and halo-$C_1$-$C_4$-alkyl, and the definitions for the remaining variables are as defined in the first or second embodiment.

In a fifth embodiment, the present invention provides compounds of Formula I' or I, stereoisomers, tautomers, salts, solvates or prodrugs thereof, wherein:

W is O or —$NR_6$;

Y is O or —$NR_7$;

(A) is selected from

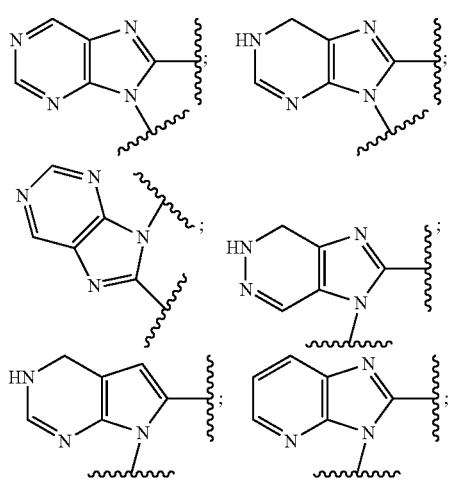

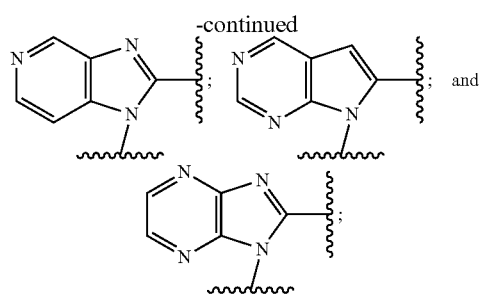

all of which are optionally substituted with $R_{10}$ and $R_{11}$;

Z is independently selected from $C_1$-$C_6$ alkyl and halo-$C_1$-$C_6$-alkyl;

$Z_1$ is independently selected from $C_1$-$C_6$ alkyl and halo-$C_1$-$C_6$-alkyl;

$Z_2$ is independently selected from $C_1$-$C_4$ alkyl and halo-$C_1$-$C_4$-alkyl;

$R_1$ is selected from

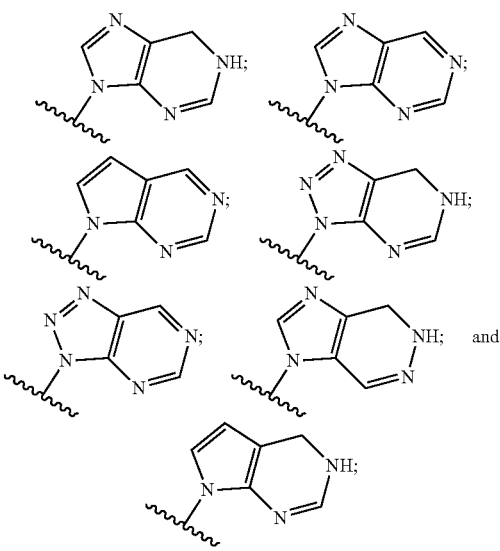

all of which are optionally substituted with $R_{12}$ and $R_{13}$;

$R_2$ is independently selected from H, halo, $C_1$-$C_4$ alkyl, $C_1$-$C_4$ alkoxy, —$NR_8R_9$ and OH;

$R_3$ is independently selected from H, halo, $C_1$-$C_4$ alkyl, $C_1$-$C_4$ alkoxy, and OH;

$R_4$ is selected from OH, SH, and $C_1$-$C_6$ alkoxy-carbonyl-oxy-$C_1$-$C_6$ alkoxy;

$R_5$ is selected from OH, SH, and $C_1$-$C_6$ alkoxy-carbonyl-oxy-$C_1$-$C_6$ alkoxy;

$R_6$ is independently selected from H, $C_1$-$C_4$ alkyl, $C_3$-$C_6$ cycloalkyl and $C_1$-$C_4$ alkoxy;

$R_7$ is independently selected from H, $C_1$-$C_4$ alkyl, $C_3$-$C_6$ cycloalkyl and $C_1$-$C_4$ alkoxy;

$R_8$ is independently selected from H, $C_1$-$C_4$ alkyl, and halo-$C_1$-$C_4$-alkyl;

$R_9$ is independently selected from H, $C_1$-$C_4$ alkyl, and halo-$C_1$-$C_4$-alkyl;

$R_{10}$ is independently selected from H, =O, halo, $C_1$-$C_4$ alkyl, $C_1$-$C_4$ alkoxy, halo-$C_1$-$C_4$ alkyl, —$NR_{14}R_{15}$, $C(O)NHR_9$ and OH;

$R_{11}$ is independently selected from H, =O, halo, $C_1$-$C_4$ alkyl, $C_1$-$C_4$ alkoxy, halo-$C_1$-$C_4$ alkyl, —$NR_{14}R_{15}$, $C(O)NHR_9$ and OH;

$R_{12}$ is independently selected from H, =O, halo, $C_1$-$C_4$ alkyl, $C_1$-$C_4$ alkoxy, —$NR_{16}R_{17}$, —$NR_{16}C$(=O)$R_{17}$ and OH;

$R_{13}$ is independently selected from H, =O, halo, $C_1$-$C_4$ alkyl, $C_1$-$C_4$ alkoxy, —$NR_{16}R_{17}$, —$NR_{16}C$(=O)$R_{17}$ and OH;

$R_{14}$, at each occurrence, is independently selected from H, $C_1$-$C_4$ alkyl, and halo-$C_1$-$C_4$-alkyl;

$R_{15}$, at each occurrence, is independently selected from H, $C_1$-$C_4$ alkyl, and halo-$C_1$-$C_4$-alkyl;

$R_{16}$, at each occurrence, is independently selected from H, $C_1$-$C_4$ alkyl, and halo-$C_1$-$C_4$-alkyl; and $R_{17}$, at each occurrence, is independently selected from H, $C_1$-$C_4$ alkyl, and halo-$C_1$-$C_4$-alkyl, and the definitions for the remaining variables are as defined in the first and second embodiment.

In a sixth embodiment, the present invention provides compounds of Formula I' or I, stereoisomers, tautomers, salts, solvates or prodrugs thereof, wherein:

W is O or —$NR_6$;
Y is O or —$NR_7$;
(A) is selected from

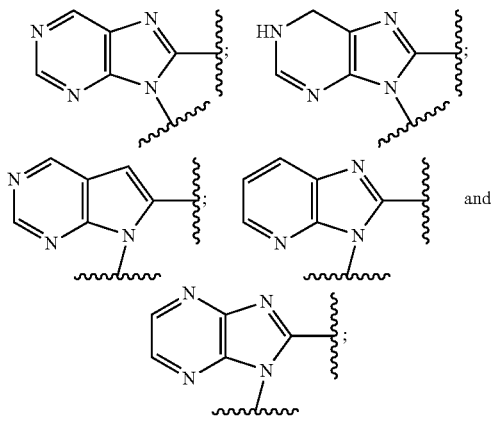

all of which are optionally substituted with $R_{10}$ and $R_{11}$;

Z is independently selected from $C_1$-$C_6$ alkyl and halo-$C_1$-$C_6$-alkyl;

$Z_1$ is independently selected from $C_1$-$C_6$ alkyl and halo-$C_1$-$C_6$-alkyl;

$Z_2$ is independently selected from $C_1$-$C_4$ alkyl and halo-$C_1$-$C_4$-alkyl;

$R_1$ is selected from

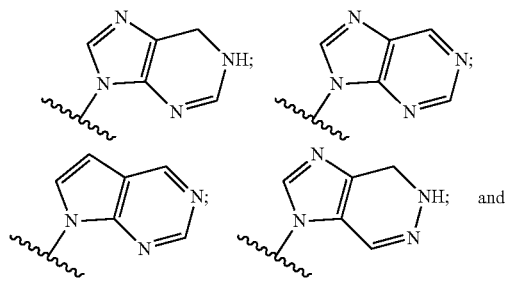

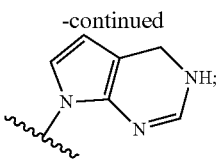

all of which are optionally substituted with $R_{12}$ and $R_{13}$;

$R_2$ is independently selected from H, halo, $C_1$-$C_4$ alkoxy, —$NR_8R_9$ and OH;

$R_3$ is independently selected from H, halo, $C_1$-$C_4$ alkoxy, and OH;

$R_4$ is selected from OH, SH, and $C_1$-$C_6$ alkoxy-carbonyl-oxy-$C_1$-$C_6$ alkoxy;

$R_5$ is selected from OH, SH, and $C_1$-$C_6$ alkoxy-carbonyl-oxy-$C_1$-$C_6$ alkoxy;

$R_6$ is independently selected from H, $C_1$-$C_4$ alkyl, $C_3$-$C_6$ cycloalkyl and $C_1$-$C_4$ alkoxy;

$R_7$ is independently selected from H, $C_1$-$C_4$ alkyl, $C_3$-$C_6$ cycloalkyl and $C_1$-$C_4$ alkoxy;

$R_8$ is independently selected from H, $C_1$-$C_4$ alkyl, and halo-$C_1$-$C_4$-alkyl;

$R_9$ is independently selected from H, $C_1$-$C_4$ alkyl, and halo-$C_1$-$C_4$-alkyl;

$R_{10}$ is independently selected from H, =O, halo, $C_1$-$C_4$ alkyl, $C_1$-$C_4$ alkoxy, —$NR_{14}R_{15}$, C(O)$NHR_9$ and OH;

$R_{11}$ is independently selected from H, =O, halo, $C_1$-$C_4$ alkyl, $C_1$-$C_4$ alkoxy, —$NR_{14}R_{15}$, C(O)$NHR_9$ and OH;

$R_{12}$ is independently selected from H, =O, halo, $C_1$-$C_4$ alkyl, —$NR_{16}R_{17}$, —$NR_{16}C$(=O)$R_{17}$ and OH;

$R_{13}$ is independently selected from H, =O, halo, $C_1$-$C_4$ alkyl, —$NR_{16}R_{17}$, —$NR_{16}C$(=O)$R_{17}$ and OH;

$R_{14}$, at each occurrence, is independently selected from H, $C_1$-$C_4$ alkyl, and halo-$C_1$-$C_4$-alkyl;

$R_{15}$, at each occurrence, is independently selected from H, $C_1$-$C_4$ alkyl, and halo-$C_1$-$C_4$-alkyl;

$R_{16}$, at each occurrence, is independently selected from H, $C_1$-$C_4$ alkyl, and halo-$C_1$-$C_4$-alkyl; and $R_{17}$, at each occurrence, is independently selected from H, $C_1$-$C_4$ alkyl, and halo-$C_1$-$C_4$-alkyl, and the definitions for the remaining variables are as defined in the first or second embodiment.

In a seventh embodiment, the present invention provides compounds of Formula I' or I, stereoisomers, tautomers, salts, solvates or prodrugs thereof, wherein:

W is O or —$NR_6$;
Y is O or —$NR_7$;
(A) is selected from

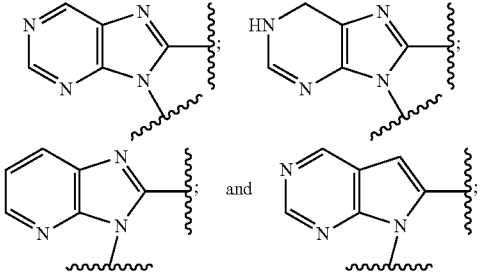

all of which are optionally substituted with $R_{10}$ and $R_{11}$;

Z is independently selected from $C_1$-$C_6$ alkyl and halo-$C_1$-$C_6$-alkyl;

$Z_1$ is $C_1$-$C_6$ alkyl;
$Z_2$ is $C_1$-$C_4$ alkyl;
$R_1$ is selected from

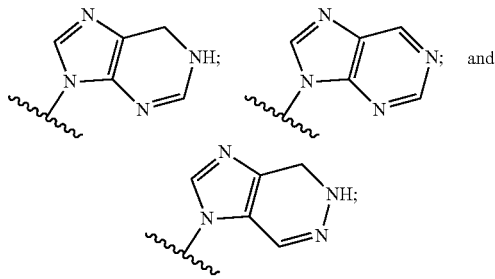

all of which are optionally substituted with $R_{12}$ and $R_{13}$;
$R_2$ is independently selected from H, halo, $C_1$-$C_4$ alkoxy, —$NR_8R_9$ and OH;
$R_3$ is independently selected from H, halo, and OH;
$R_4$ is selected from OH and SH;
$R_5$ is selected from OH and SH;
$R_6$ is independently selected from H, $C_1$-$C_4$ alkyl and $C_3$-$C_6$ cycloalkyl;
$R_7$ is independently selected from H, $C_1$-$C_4$ alkyl and $C_3$-$C_6$ cycloalkyl;
$R_8$ is independently selected from H, $C_1$-$C_4$ alkyl, and halo-$C_1$-$C_4$-alkyl;
$R_9$ is independently selected from H, $C_1$-$C_4$ alkyl, and halo-$C_1$-$C_4$-alkyl;
$R_{10}$ is independently selected from H, =O, halo, $C_1$-$C_4$ alkyl, —$NR_{14}R_{15}$, $C(O)NHR_9$ and OH;
$R_{11}$ is independently selected from H, =O, halo, $C_1$-$C_4$ alkyl, —$NR_{14}R_{15}$, $C(O)NHR_9$ and OH;
$R_{12}$ is independently selected from H, =O, halo, $C_1$-$C_4$ alkyl, —$NR_{16}R_{17}$, and —$NR_{16}C(=O)R_{17}$;
$R_{13}$ is independently selected from H, =O, halo, $C_1$-$C_4$ alkyl, —$NR_{16}R_{17}$, and —$NR_{16}C(=O)R_{17}$;
$R_{14}$, at each occurrence, is independently selected from H, $C_1$-$C_4$ alkyl, and halo-$C_1$-$C_4$-alkyl;
$R_{15}$, at each occurrence, is independently selected from H, $C_1$-$C_4$ alkyl, and halo-$C_1$-$C_4$-alkyl;
$R_{16}$, at each occurrence, is independently selected from H, $C_1$-$C_4$ alkyl, and halo-$C_1$-$C_4$-alkyl; and
$R_{17}$, at each occurrence, is independently selected from H, $C_1$-$C_4$ alkyl, and halo-$C_1$-$C_4$-alkyl, and the definitions for the other remaining variables are as defined in the first or second embodiment.

In an eighth embodiment, the present invention provides compounds of Formula I' or I, stereoisomers, tautomers, salts, solvates or prodrugs thereof, wherein:
W is O or —$NR_6$;
Y is O or —$NR_7$;
Ⓐ is selected from

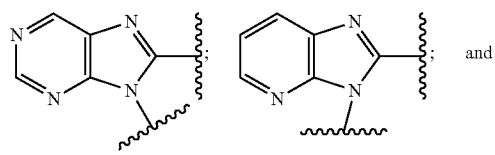

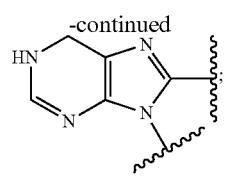

all of which are optionally substituted with $R_{10}$ and $R_{11}$;
Z is independently selected from $C_1$-$C_6$ alkyl;
$Z_1$ is independently selected from $C_1$-$C_3$ alkyl;
$Z_2$ is independently selected from $C_1$-$C_2$ alkyl;
$R_1$ is selected from

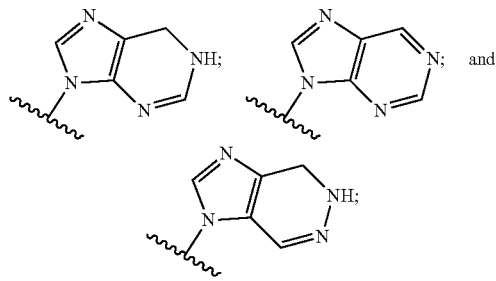

all of which are optionally substituted with $R_{12}$ and $R_{13}$;
$R_2$ is independently selected from H, halo, $C_1$-$C_4$ alkoxy, —$NR_8R_9$ and OH;
$R_3$ is independently selected from H and halo;
$R_4$ is selected from OH and SH;
$R_5$ is selected from OH and SH;
$R_6$ is independently selected from H and $C_1$-$C_4$ alkyl;
$R_7$ is independently selected from H and $C_1$-$C_4$ alkyl;
$R_8$ is independently selected from H and $C_1$-$C_4$ alkyl;
$R_9$ is independently selected from H and $C_1$-$C_4$ alkyl;
$R_{10}$ is independently selected from H, =O, halo, $C_1$-$C_4$ alkyl, $C(O)NHR_9$ and —$NR_{14}R_{15}$;
$R_{11}$ is independently selected from H, =O, halo, $C_1$-$C_4$ alkyl, $C(O)NHR_9$ and —$NR_{14}R_{15}$;
$R_{12}$ is independently selected from H, =O, halo, —$NR_{16}R_{17}$, and —$NR_{16}C(=O)R_{17}$;
$R_{13}$ is independently selected from H, =O, halo and —$NR_{16}R_{17}$;
$R_{14}$, at each occurrence, is independently selected from H and $C_1$-$C_4$ alkyl;
$R_{15}$, at each occurrence, is independently selected from H and $C_1$-$C_4$ alkyl;
$R_{16}$, at each occurrence, is independently selected from H and $C_1$-$C_4$ alkyl; and
$R_{17}$, at each occurrence, is independently selected from H and $C_1$-$C_4$ alkyl, and the definitions for the remaining variables are as defined in the first or second embodiment.

In a ninth embodiment, the present invention provides compounds of Formula I' or I, stereoisomers, tautomers, pharmaceutically acceptable salts, solvates or prodrugs thereof, wherein the compound is represented by any one of the following formulae:

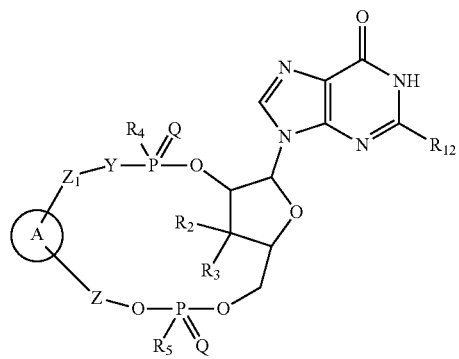

II

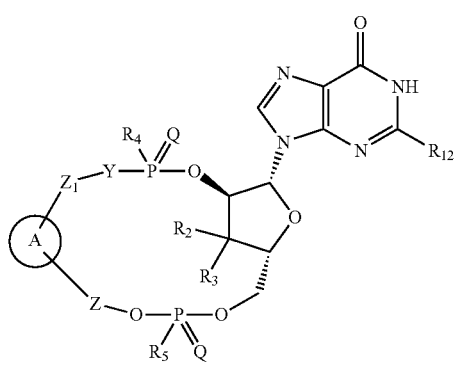

IIA

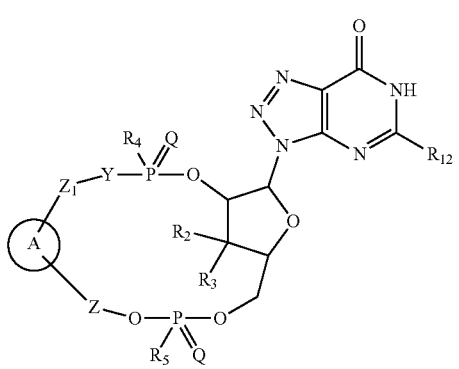

III

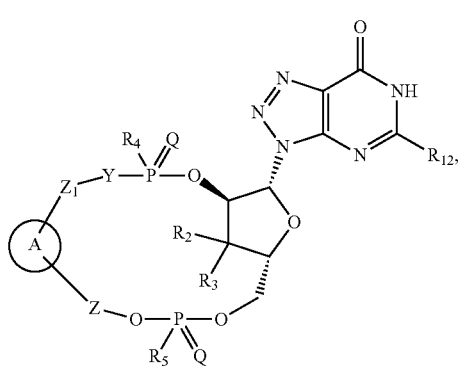

IIIA wherein:

Q is O or S;

Y is O or NH;

Z is independently selected from $C_1$-$C_6$ alkyl and halo-$C_1$-$C_6$-alkyl;

$Z_1$ is independently selected from $C_1$-$C_6$ alkyl and halo-$C_1$-$C_6$-alkyl;

Ⓐ is selected from

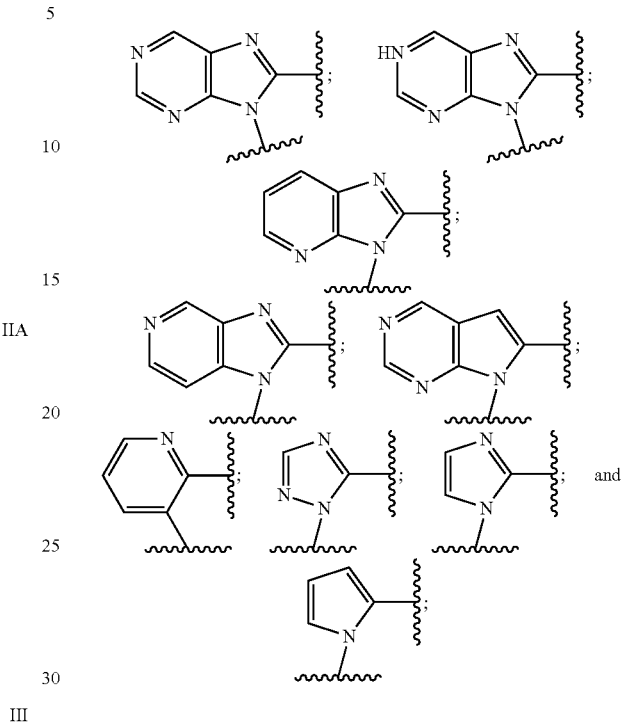

all of which are optionally substituted with $R_{10}$ and $R_{11}$ $R_2$ is selected from H, halo, $C_1$-$C_4$ alkyl, $C_1$-$C_4$ alkoxy, —$NR_8R_9$, and OH;

$R_3$ is selected from H, halo, $C_1$-$C_4$ alkyl, $C_1$-$C_4$ alkoxy, —$NR_8R_9$, and OH;

$R_4$ is selected from SH, OH and $BH_3$;

$R_5$ is selected from SH, OH and $BH_3$;

$R_8$ is independently selected from H and $C_1$-$C_4$ alkyl;

$R_9$ is independently selected from H and $C_1$-$C_4$ alkyl;

$R_{10}$ is H, =O, halo, CN, —$NR_{14}R_{15}$, —C(=O)$NR_{14}R_{15}$, $C_1$-$C_4$ alkyl, $C_3$-$C_6$ cycloalkyl, 5- or 6-membered monocyclic heteroaryl having one to two heteroatoms independently selected from N, O and S, wherein the $C_1$-$C_4$ alkyl, $C_3$-$C_6$ cycloalkyl and 5- or 6-membered monocyclic heteroaryl are each optionally substituted with halo, —$NR_{14}R_{15}$, $C_1$-$C_4$ alkyl, halo-$C_1$-$C_4$ alkyl and $C_1$-$C_4$ alkoxy;

$R_{11}$ is H;

$R_{12}$ is H or $NH_2$;

$R_{14}$ is selected from H and $C_1$-$C_4$ alkyl;

$R_{15}$ is selected from H and $C_1$-$C_4$ alkyl, and the definitions for the other variables are as defined in the first and second embodiment.

In a tenth embodiment, the present invention provides compounds of Formula I or I', stereoisomers, tautomers, pharmaceutically acceptable salts, solvates or prodrugs thereof, wherein the 5- or 6-membered monocyclic heteroaryl of $R_{10}$ or $R_{11}$ of any of the above is selected from

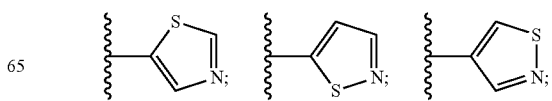

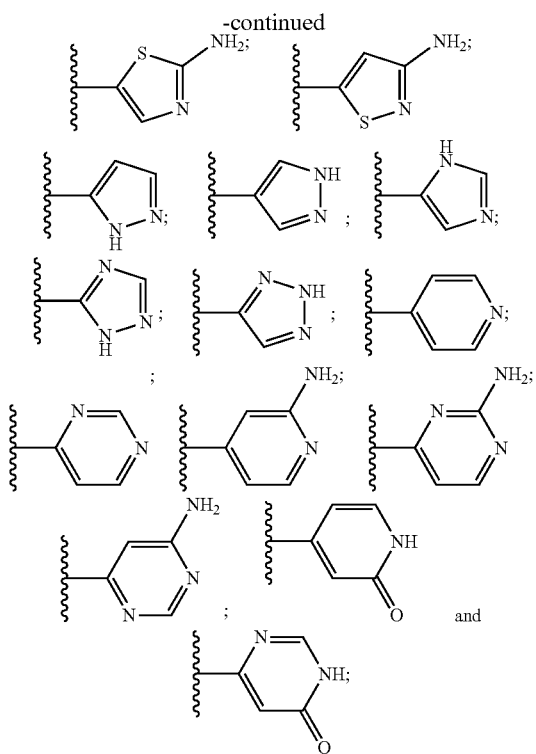

In an eleventh embodiment, the present invention provides compounds of Formula I' or I, stereoisomers, tautomers, salts, solvates or prodrugs thereof, wherein:

$Z_1$ is selected from —CH$_2$— and —CH(CH$_3$)—,

Z is selected from —CH$_2$CH$_2$—, —CH(CH$_3$)CH$_2$—, —CH$_2$CH(CH$_3$)—, —CH$_2$CH$_2$CH$_2$—, —CH$_2$CF$_2$CH$_2$—, —CH$_2$CH(CH$_3$)CH$_2$—, and cyclobutyl, $R_2$ is selected from H, F, OH, —OCH$_3$ and —NH$_2$, $R_3$ is selected from H and F;

$R_4$ is selected from SH and OH, $R_5$ is selected from SH, OH and BH$_3$;

$R_{10}$ is selected from H, —NH$_2$, —Cl, —C(=O)NH$_2$, —CH$_2$—O—CH$_3$, —CN, —CH$_3$, cyclopropyl, thiazolyl, pyridyl, and 2-aminothiazol-5-yl;

$R_{11}$ is H, and the definitions for the remaining variables are as defined in the ninth embodiment.

In a twelfth embodiment, the present invention provides compounds of Formula I' or I, stereoisomers, tautomers, pharmaceutically acceptable salts, solvates or prodrugs thereof, wherein the compound is represented by any one of the following formulae:

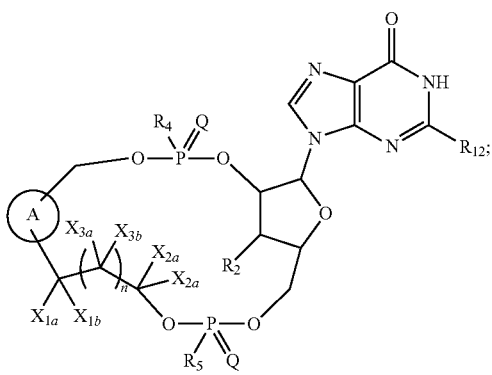

IV

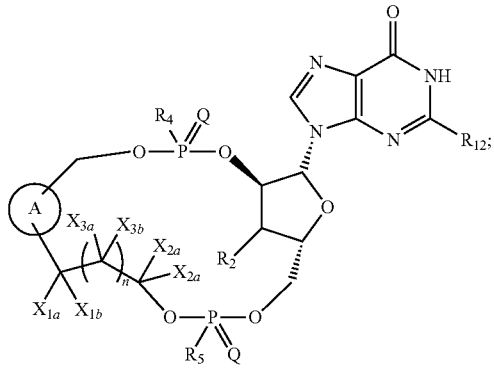

IVA

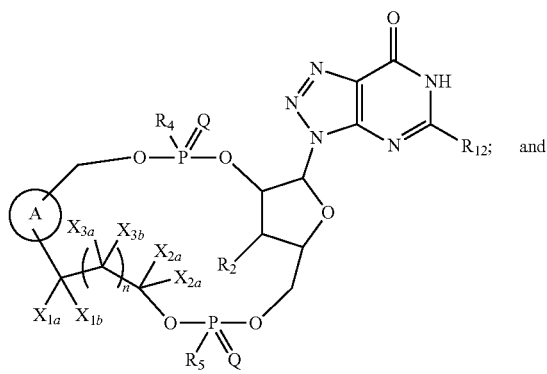

V

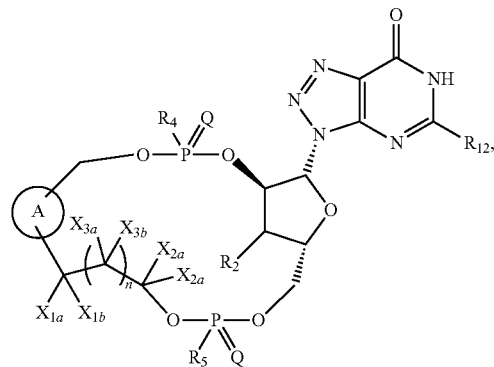

VA wherein:

$X_{1a}$ and $X_{1b}$ are each independently selected from H, halo and C$_{1-4}$ alkyl;

$X_{2a}$ and $X_{2b}$ are each independently selected from H, halo and C$_{1-4}$ alkyl;

$X_{3a}$ and $X_{3b}$ are each independently selected from H, halo, and C$_{1-4}$ alkyl;

Ring A is selected from

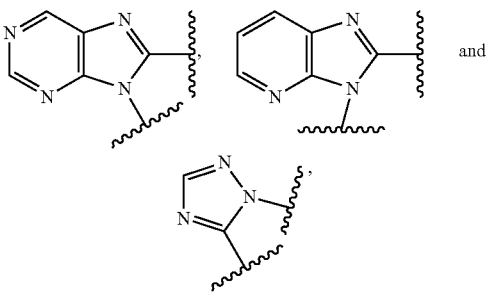

each of which is optionally substituted with $R_{10}$ and $R_{11}$;

$R_2$ is selected from H, halo, $C_1$-$C_4$ alkoxy and OH;
$R_{10}$ is selected from H, halo, —C(=O)NH$_2$, —CN, $C_1$-$C_4$ alkyl, —NH$_2$, and 5- to 6-membered monocyclic heteroaryl having one to two heteroatoms independently selected from N, O and S;
$R_{11}$ is H;
$R_{12}$ is H or —NH$_2$; and
n is 0 or 1, and the definitions for the other variables are as defined in the ninth embodiment.

In a thirteenth embodiment, the present invention provides compounds of Formula I' or I, stereoisomers, tautomers, pharmaceutically acceptable salts, solvates or prodrugs thereof, wherein:
$X_{1a}$ and $X_{1b}$ are both H;
$X_{2a}$ and $X_{2b}$ are each independently selected form H, halo and $C_{1-4}$ alkyl; and
n is 0, and the definitions for the remaining variables are as defined in the twelfth embodiment.

In a fourteenth embodiment, the present invention provides compounds of Formula I' or I, stereoisomers, tautomers, pharmaceutically acceptable salts, solvates or prodrugs thereof, wherein:
$R_{10}$ is selected from H, $C_1$, —C(=O)NH$_2$, —CN, —CH$_3$, —NH$_2$, pyridyl, and thiazolyl;
$X_{1a}$ and $X_{1b}$ are both H;
$X_{2a}$ and $X_{2b}$ are independently selected from H, F and methyl;
$R_4$ and $R_5$ are independently selected from —OH and SH;
$R_2$ is selected from H, F, —OCH$_3$ and OH; and
(i) n is 0; or
(ii) n is 1; and $X_{3a}$ and $X_{3b}$ are F, and the definitions for the remaining variables are as defined in the twelfth embodiment.

In a fifteenth embodiment, the present invention provides a compound selected from any one of the compounds listed in Table 1, or a stereoisomer, tautomer, pharmaceutically acceptable salt, solvate or prodrug thereof.

TABLE 1

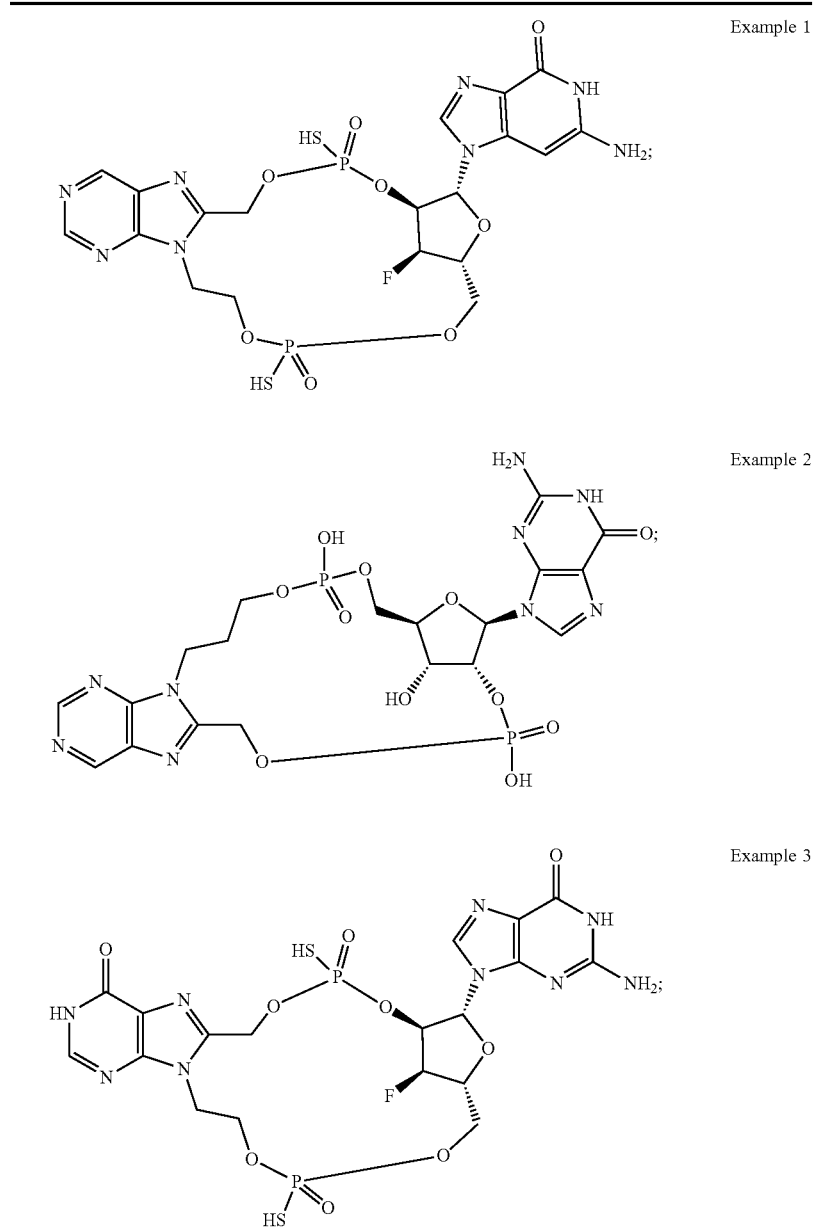

TABLE 1-continued
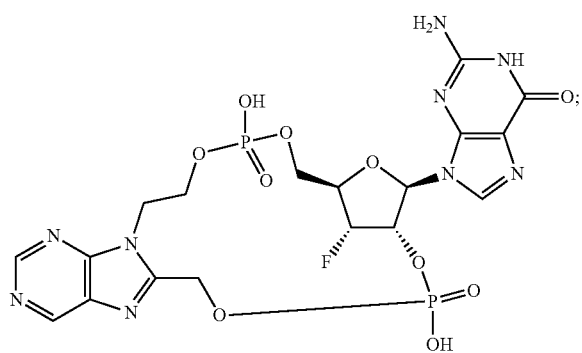 [SMILES: Nc1nc2c(ncn2[C@@H]2O[C@@H]3COP(=O)(O)OCCn4c(nc5cncnc54)COP(=O)(O)O[C@@H]2[C@@H]3F)c(=O)[nH]1]
Example 4
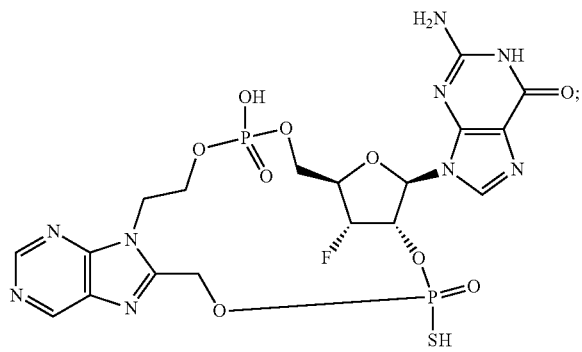 [SMILES: Nc1nc2c(ncn2[C@@H]2O[C@@H]3COP(=O)(O)OCCn4c(nc5cncnc54)COP(=O)(S)O[C@@H]2[C@@H]3F)c(=O)[nH]1]
Example 5
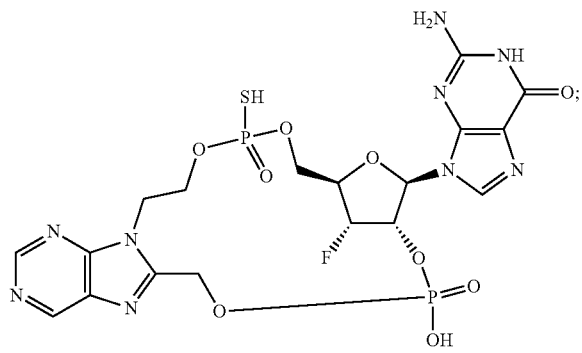 [SMILES: Nc1nc2c(ncn2[C@@H]2O[C@@H]3COP(=O)(S)OCCn4c(nc5cncnc54)COP(=O)(O)O[C@@H]2[C@@H]3F)c(=O)[nH]1]
Example 6
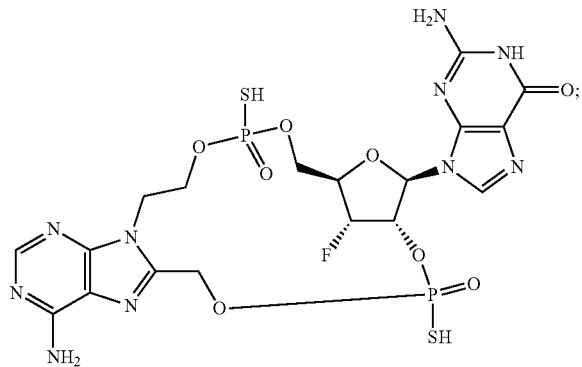 [SMILES: Nc1nc2c(ncn2[C@@H]2O[C@@H]3COP(=O)(S)OCCn4c(nc5c(N)ncnc54)COP(=O)(S)O[C@@H]2[C@@H]3F)c(=O)[nH]1]
Example 7

TABLE 1-continued
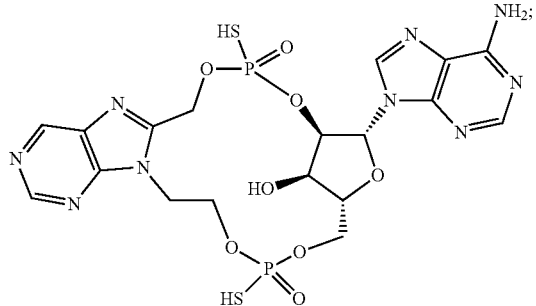 [SMILES: Nc1ncnc2c1ncn2[C@@H]1O[C@@H]2COP(=O)(S)OCCn3c(nc4cncnc43)COP(=O)(S)O[C@@H]1[C@@H]2O] Example 8
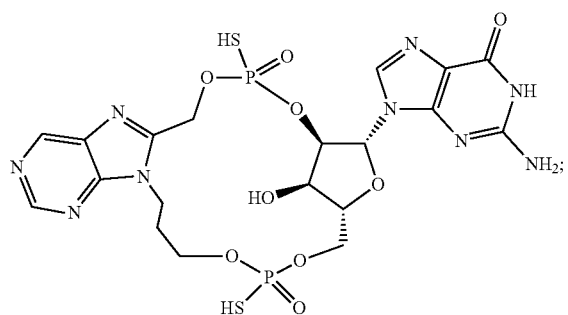 [SMILES: Nc1nc2c(ncn2[C@@H]2O[C@@H]3COP(=O)(S)OCCCn4c(nc5cncnc54)COP(=O)(S)O[C@@H]2[C@@H]3O)c(=O)[nH]1] Example 9
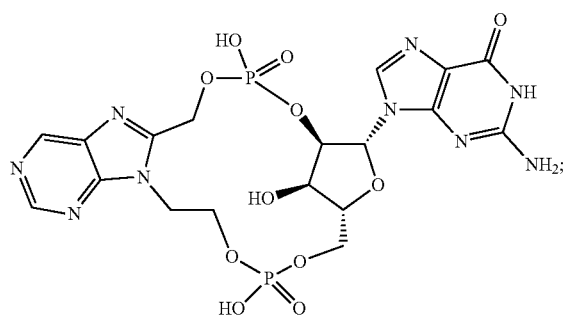 [SMILES: Nc1nc2c(ncn2[C@@H]2O[C@@H]3COP(=O)(O)OCCn4c(nc5cncnc54)COP(=O)(O)O[C@@H]2[C@@H]3O)c(=O)[nH]1] Example 10
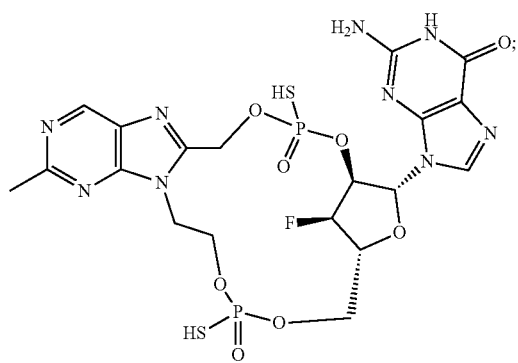 [SMILES: Cc1ncc2nc3n(c2n1)CCOP(=O)(S)OC[C@H]1O[C@@H](n2cnc4c(=O)[nH]c(N)nc42)[C@H](OP(=O)(S)OC3)[C@@H]1F] Example 11

TABLE 1-continued
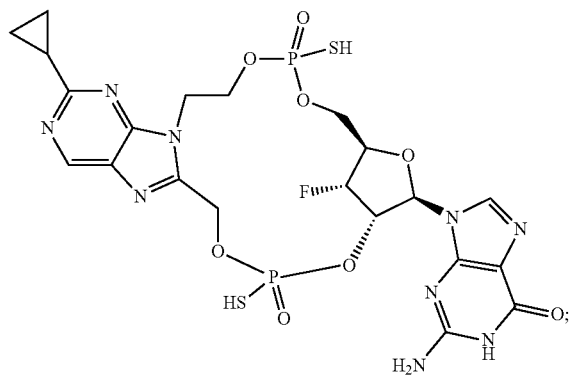 [SMILES: Nc1nc2c(ncn2[C@@H]2O[C@@H]3COP(=O)(S)OCCn4c(nc5cnc(C6CC6)nc54)COP(=O)(S)O[C@@H]2[C@@H]3F)c(=O)[nH]1]
Example 12
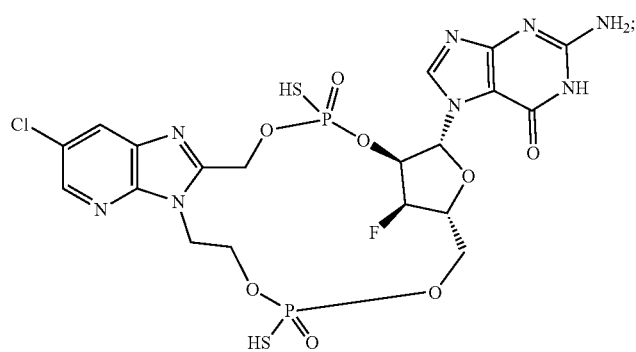 [SMILES: Nc1nc2ncn([C@@H]3O[C@@H]4COP(=O)(S)OCCn5c(nc6cc(Cl)cnc65)COP(=O)(S)O[C@@H]3[C@@H]4F)c2c(=O)[nH]1]
Example 13
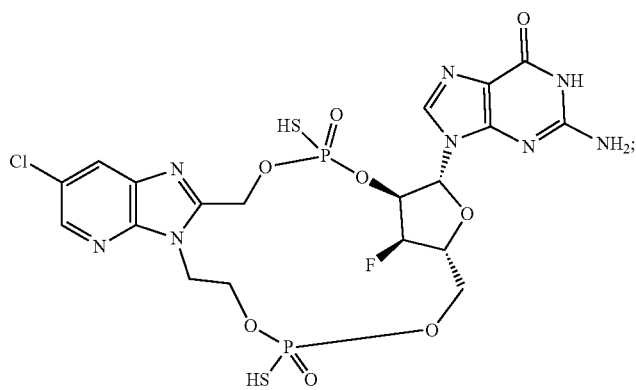 [SMILES: Nc1nc2c(ncn2[C@@H]2O[C@@H]3COP(=O)(S)OCCn4c(nc5cc(Cl)cnc54)COP(=O)(S)O[C@@H]2[C@@H]3F)c(=O)[nH]1]
Example 14
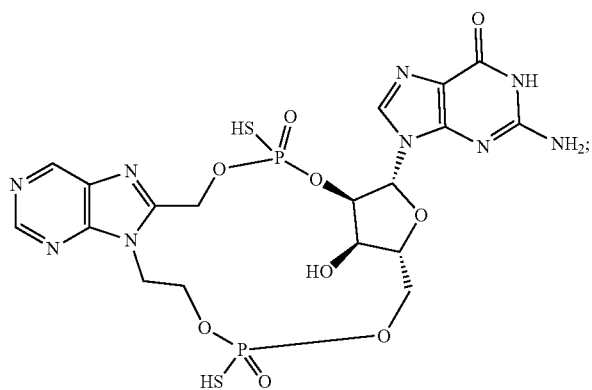 [SMILES: Nc1nc2c(ncn2[C@@H]2O[C@@H]3COP(=O)(S)OCCn4c(nc5cncnc54)COP(=O)(S)O[C@@H]2[C@@H]3O)c(=O)[nH]1]
Example 15

TABLE 1-continued
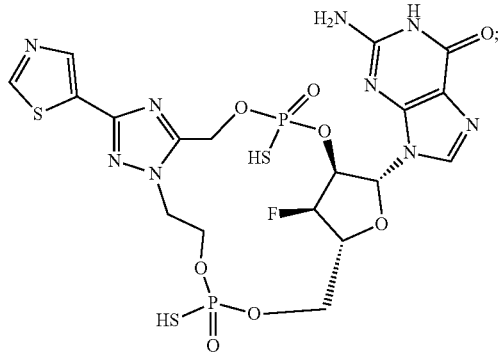 [SMILES: Nc1nc2c(ncn2[C@@H]2O[C@@H]3COP(=O)(S)OCCn4nc(-c5cncs5)nc4COP(=O)(S)O[C@@H]2[C@@H]3F)c(=O)[nH]1]
Example 16
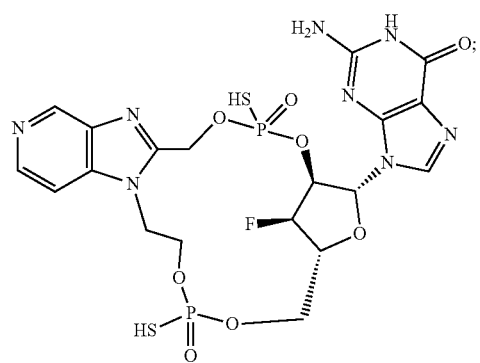 [SMILES: Nc1nc2c(ncn2[C@@H]2O[C@@H]3COP(=O)(S)OCCn4c(nc5cnccc54)COP(=O)(S)O[C@@H]2[C@@H]3F)c(=O)[nH]1]
Example 17
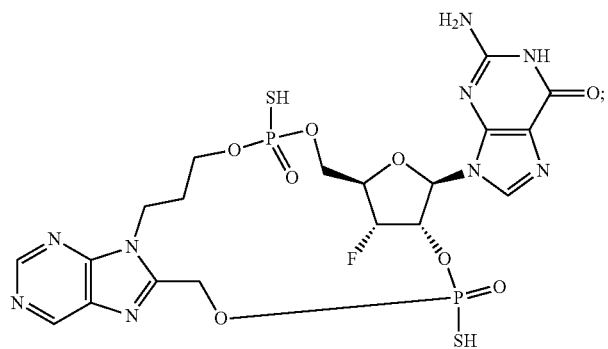 [SMILES: Nc1nc2c(ncn2[C@@H]2O[C@@H]3COP(=O)(S)OCCCn4c(nc5cncnc54)COP(=O)(S)O[C@@H]2[C@@H]3F)c(=O)[nH]1]
Example 18
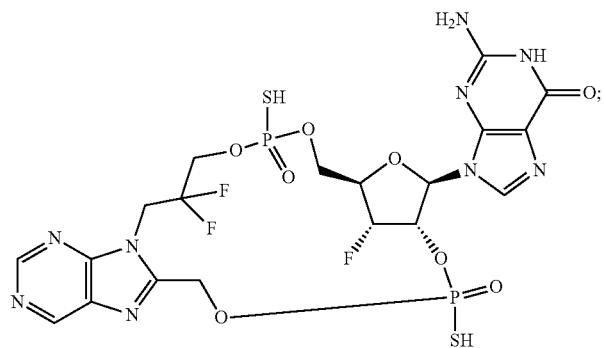 [SMILES: Nc1nc2c(ncn2[C@@H]2O[C@@H]3COP(=O)(S)OCC(F)(F)Cn4c(nc5cncnc54)COP(=O)(S)O[C@@H]2[C@@H]3F)c(=O)[nH]1]
Example 19

TABLE 1-continued
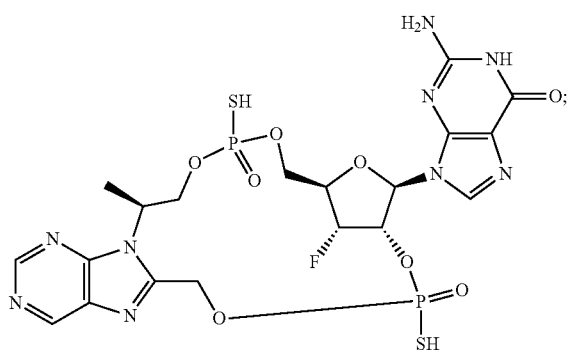 [SMILES: C[C@H]1COP(=O)(S)OC[C@H]2O[C@@H](n3cnc4c(=O)[nH]c(N)nc43)[C@H](OP(=O)(S)OCc3nc4cncnc4n31)[C@@H]2F]
Example 20
Example 21
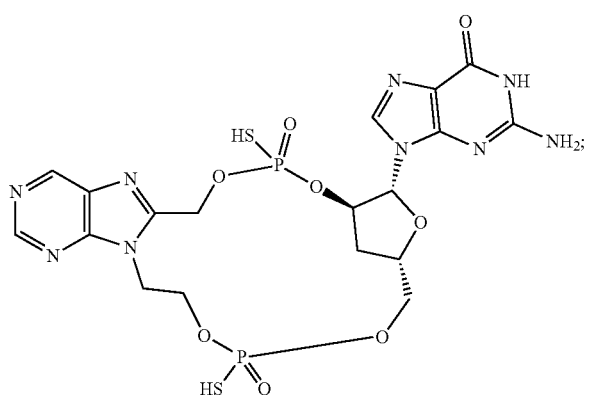 [SMILES: Nc1nc2c(ncn2[C@@H]2O[C@@H]3COP(=O)(S)OCCn4c(nc5cncnc54)COP(=O)(S)O[C@@H]2C3)c(=O)[nH]1]
Example 22
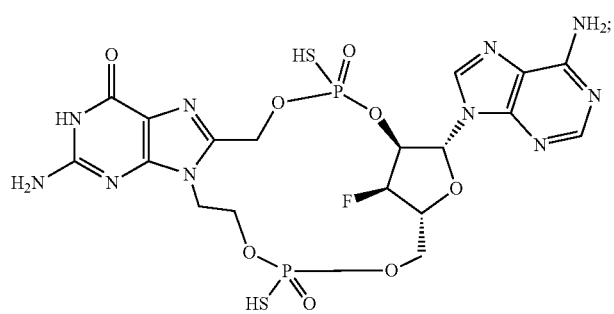 [SMILES: Nc1nc2c(nc3n2CCOP(=O)(S)OC[C@H]2O[C@@H](n4cnc5c(N)ncnc54)[C@H](OP(=O)(S)OC3)[C@@H]2F)c(=O)[nH]1]
Example 23

TABLE 1-continued
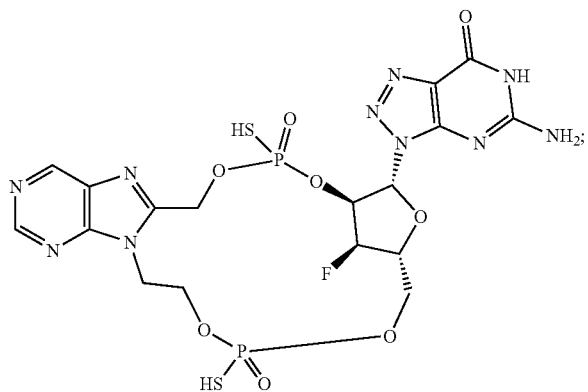 [SMILES: Nc1nc2c(nnn2[C@@H]2O[C@@H]3COP(=O)(S)OCCn4c(nc5cncnc54)COP(=O)(S)O[C@@H]2[C@@H]3F)c(=O)[nH]1]
Example 24
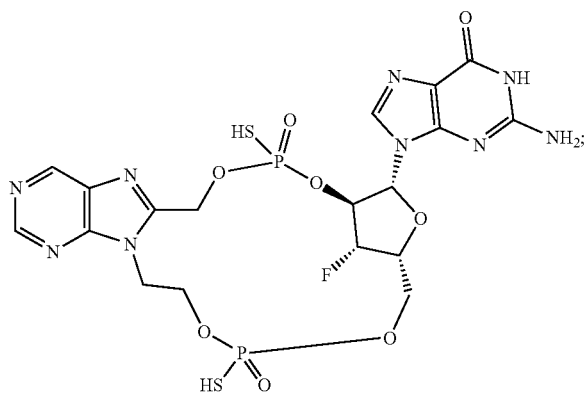 [SMILES: Nc1nc2c(ncn2[C@@H]2O[C@@H]3COP(=O)(S)OCCn4c(nc5cncnc54)COP(=O)(S)O[C@@H]2[C@H]3F)c(=O)[nH]1]
Example 25
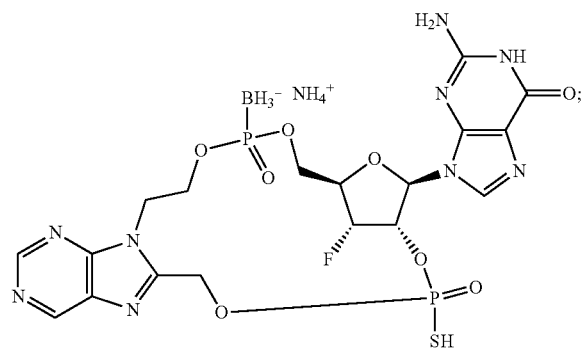
Example 26
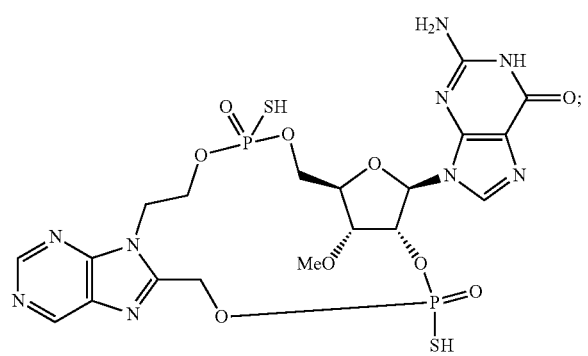 [SMILES: CO[C@H]1[C@H]2OP(=O)(S)OCc3nc4cncnc4n3CCOP(=O)(S)OC[C@H]1O[C@H]2n1cnc2c(=O)[nH]c(N)nc21]
Example 27

TABLE 1-continued
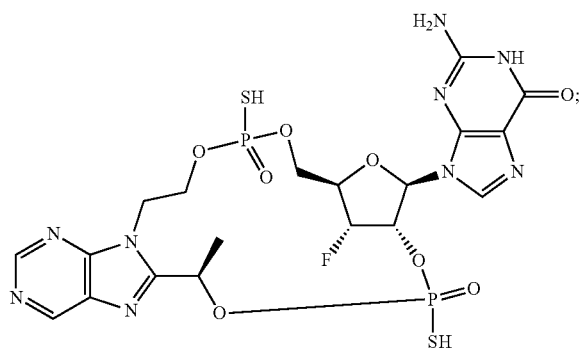 [SMILES: C[C@H]1OP(=O)(S)O[C@@H]2[C@H](F)[C@@H](COP(=O)(S)OCCn3c1nc1cncnc13)O[C@H]2n1cnc2c(=O)[nH]c(N)nc21]
Example 28
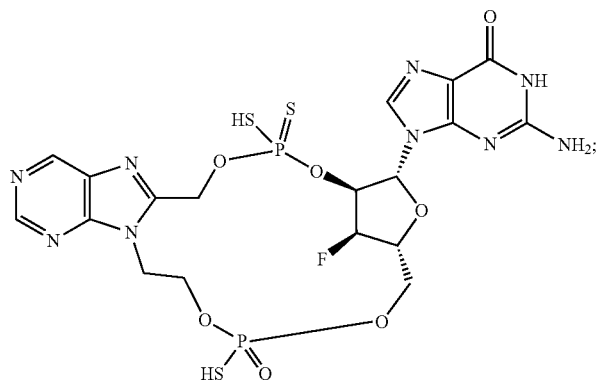 [SMILES: Nc1nc2c(ncn2[C@@H]2O[C@@H]3COP(=O)(S)OCCn4c(nc5cncnc54)COP(=S)(S)O[C@@H]2[C@@H]3F)c(=O)[nH]1]
Example 29
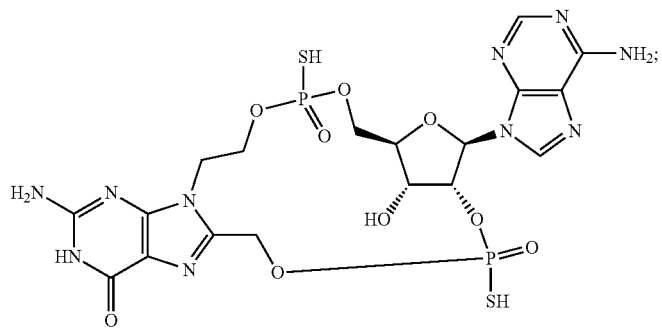 [SMILES: Nc1nc2c(nc3n2CCOP(=O)(S)OC[C@H]2O[C@@H](n4cnc5c(N)ncnc54)[C@H](OP(=O)(S)OC3)[C@@H]2O)c(=O)[nH]1]
Example 30
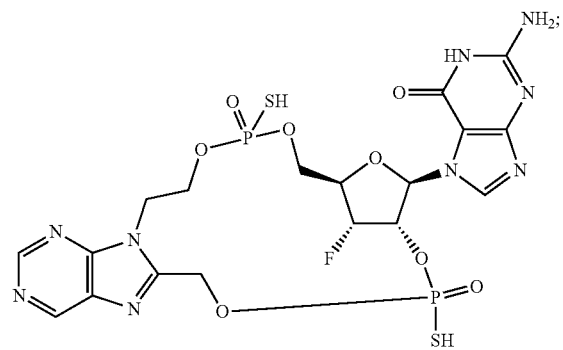 [SMILES: Nc1nc2ncn([C@@H]3O[C@@H]4COP(=O)(S)OCCn5c(nc6cncnc65)COP(=O)(S)O[C@@H]3[C@@H]4F)c2c(=O)[nH]1]
Example 31

TABLE 1-continued
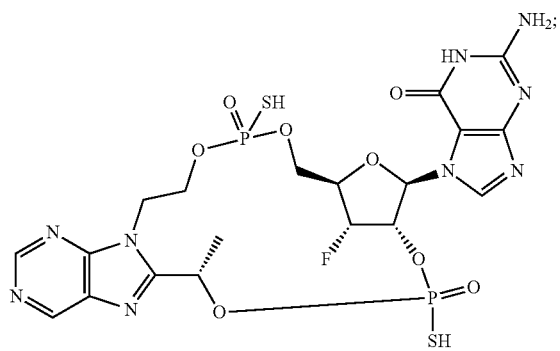 [SMILES: C[C@@H]1OP(=O)(S)O[C@@H]2[C@H](F)[C@@H](COP(=O)(S)OCCn3c1nc1cncnc13)O[C@H]2n1cnc2nc(N)[nH]c(=O)c21]
Example 32
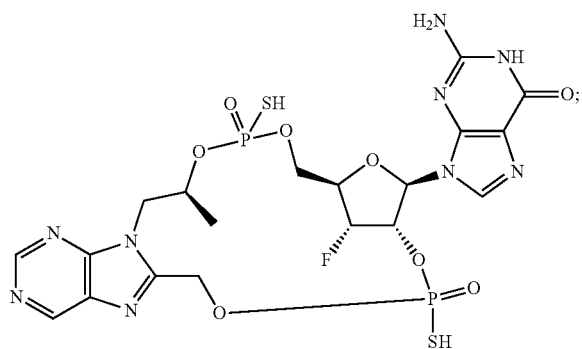 [SMILES: C[C@H]1Cn2c(nc3cncnc32)COP(=O)(S)O[C@@H]2[C@H](F)[C@@H](COP(=O)(S)O1)O[C@H]2n1cnc2c(=O)[nH]c(N)nc21]
Example 33
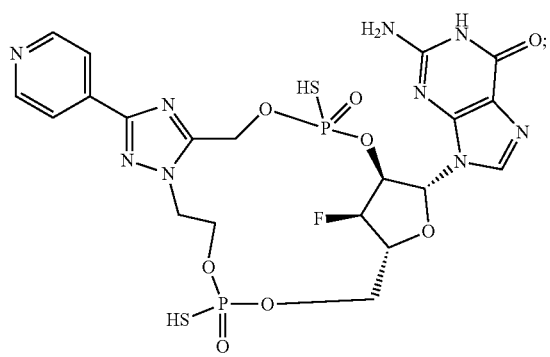 [SMILES: Nc1nc2c(ncn2[C@@H]2O[C@@H]3COP(=O)(S)OCCn4nc(-c5ccncc5)nc4COP(=O)(S)O[C@@H]2[C@@H]3F)c(=O)[nH]1]
Example 34
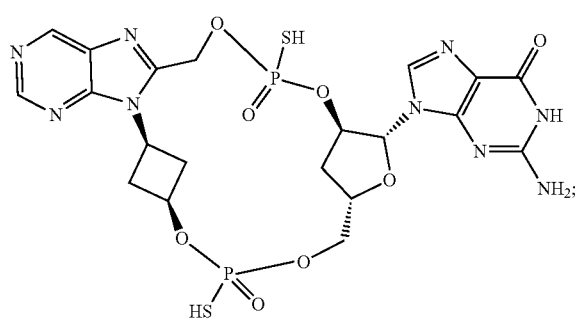 [SMILES: Nc1nc2c(ncn2[C@@H]2O[C@@H]3COP(=O)(S)O[C@H]4C[C@H](C4)n4c(nc5cncnc54)COP(=O)(S)O[C@@H]2C3)c(=O)[nH]1]
Example 35

TABLE 1-continued
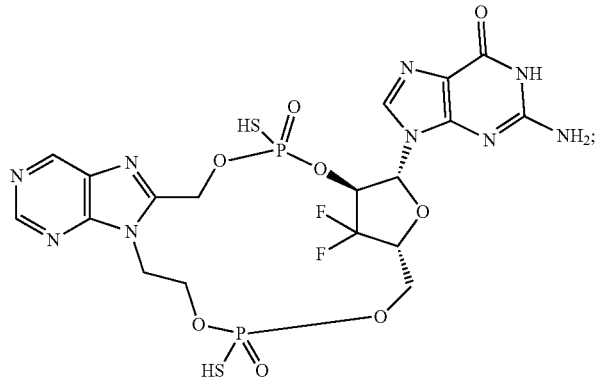 [SMILES: Nc1nc2c(ncn2[C@@H]2O[C@@H]3COP(=O)(S)OCCn4c(nc5cncnc54)COP(=O)(S)O[C@@H]2C3(F)F)c(=O)[nH]1]
Example 36
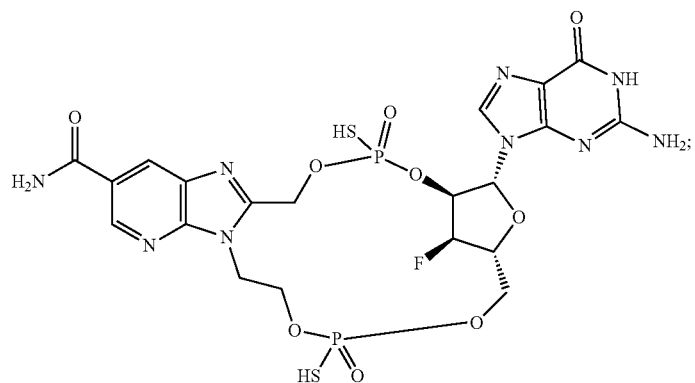 [SMILES: NC(=O)c1cnc2c(c1)nc1n2CCOP(=O)(S)OC[C@H]2O[C@@H](n3cnc4c(=O)[nH]c(N)nc43)[C@H](OP(=O)(S)OC1)[C@@H]2F]
Example 37
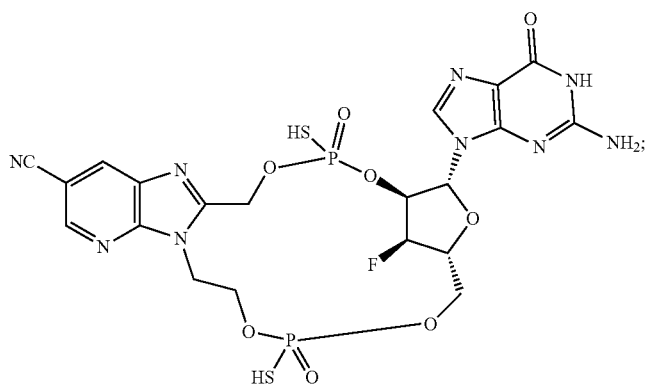 [SMILES: N#Cc1cnc2c(c1)nc1n2CCOP(=O)(S)OC[C@H]2O[C@@H](n3cnc4c(=O)[nH]c(N)nc43)[C@H](OP(=O)(S)OC1)[C@@H]2F]
Example 38
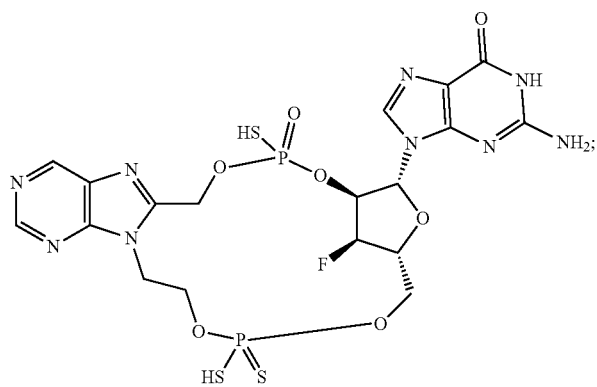 [SMILES: Nc1nc2c(ncn2[C@@H]2O[C@@H]3COP(=S)(S)OCCn4c(nc5cncnc54)COP(=O)(S)O[C@@H]2[C@@H]3F)c(=O)[nH]1]
Example 39

TABLE 1-continued
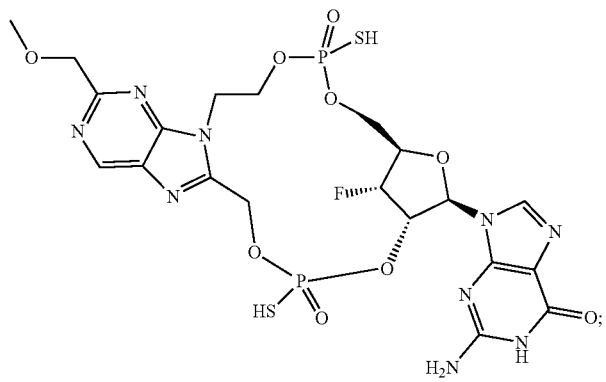 [SMILES: COCc1ncc2nc3n(c2n1)CCOP(=O)(S)OC[C@H]1O[C@@H](n2cnc4c(=O)[nH]c(N)nc42)[C@H](OP(=O)(S)OC3)[C@@H]1F]
Example 40
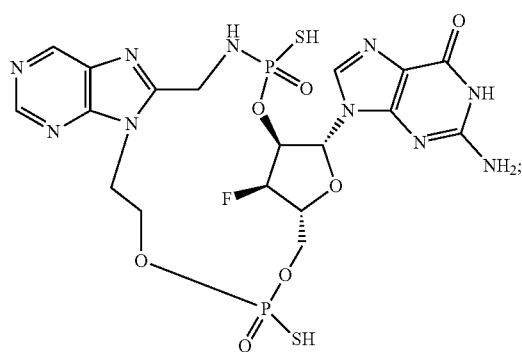 [SMILES: Nc1nc2c(ncn2[C@@H]2O[C@@H]3COP(=O)(S)OCCn4c(nc5cncnc54)CNP(=O)(S)O[C@@H]2[C@@H]3F)c(=O)[nH]1]
Example 41
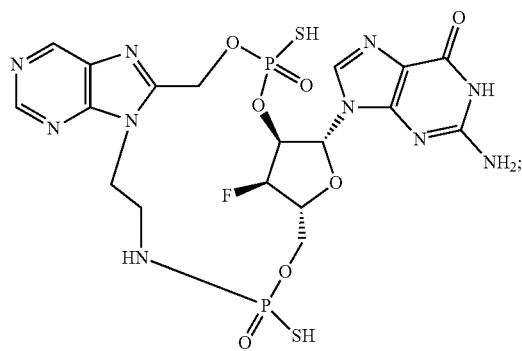 [SMILES: Nc1nc2c(ncn2[C@@H]2O[C@@H]3COP(=O)(S)NCCn4c(nc5cncnc54)COP(=O)(S)O[C@@H]2[C@@H]3F)c(=O)[nH]1]
Example 42
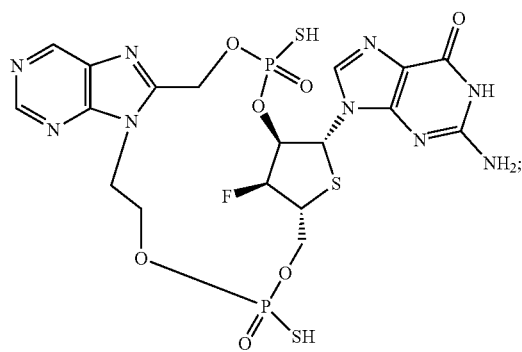 [SMILES: Nc1nc2c(ncn2[C@@H]2S[C@@H]3COP(=O)(S)OCCn4c(nc5cncnc54)COP(=O)(S)O[C@@H]2[C@@H]3F)c(=O)[nH]1]
Example 43

TABLE 1-continued
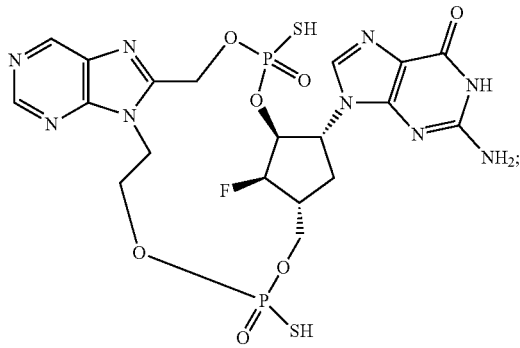 [SMILES: Nc1nc2c(ncn2[C@@H]2C[C@@H]3COP(=O)(S)OCCn4c(nc5cncnc54)COP(=O)(S)O[C@@H]2[C@@H]3F)c(=O)[nH]1]
Example 44
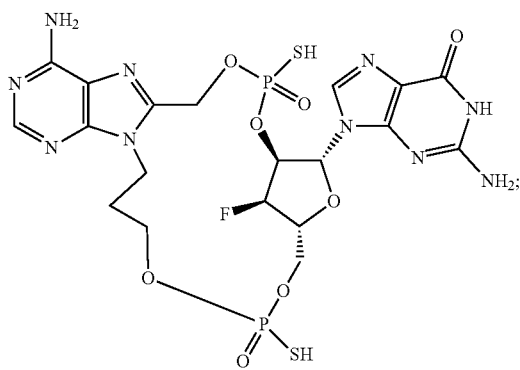 [SMILES: Nc1nc2c(ncn2[C@@H]2O[C@@H]3COP(=O)(S)OCCCn4c(nc5c(N)ncnc54)COP(=O)(S)O[C@@H]2[C@@H]3F)c(=O)[nH]1]
Example 45
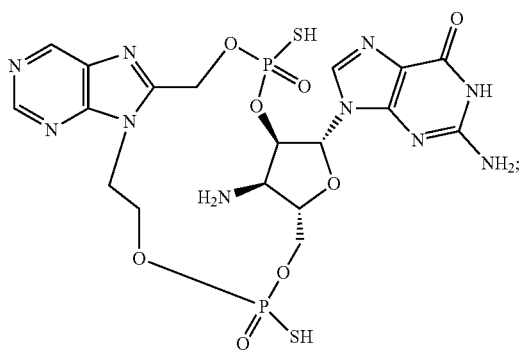 [SMILES: Nc1nc2c(ncn2[C@@H]2O[C@@H]3COP(=O)(S)OCCn4c(nc5cncnc54)COP(=O)(S)O[C@@H]2[C@@H]3N)c(=O)[nH]1]
Example 46
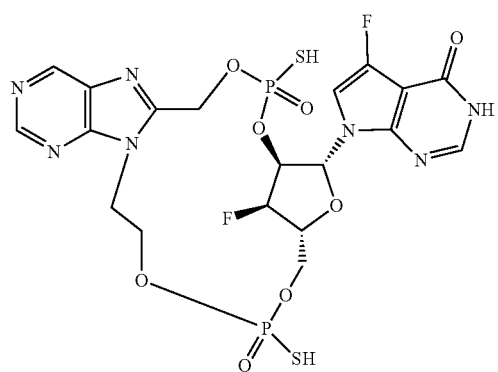 [SMILES: O=c1[nH]cnc2c1c(F)cn2[C@@H]1O[C@@H]2COP(=O)(S)OCCn3c(nc4cncnc43)COP(=O)(S)O[C@@H]1[C@@H]2F]
Example 47

TABLE 1-continued
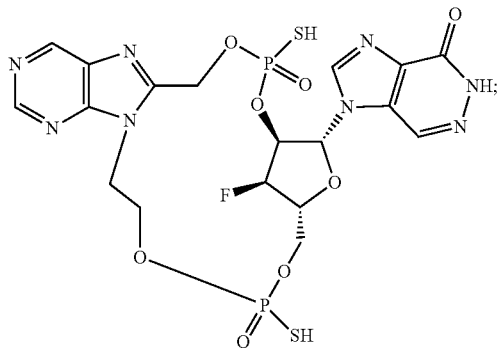 [SMILES: O=c1[nH]ncc2c1ncn2[C@@H]1O[C@@H]2COP(=O)(S)OCCn3c(nc4cncnc43)COP(=O)(S)O[C@@H]1[C@@H]2F]
Example 48
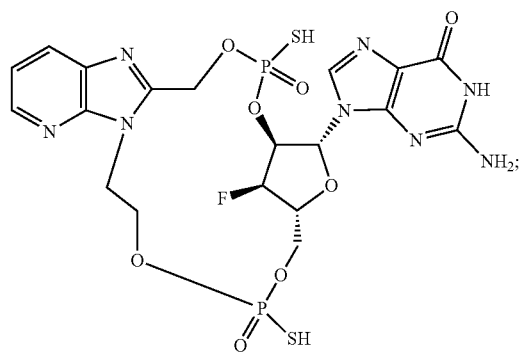 [SMILES: Nc1nc2c(ncn2[C@@H]2O[C@@H]3COP(=O)(S)OCCn4c(nc5cccnc54)COP(=O)(S)O[C@@H]2[C@@H]3F)c(=O)[nH]1]
Example 49
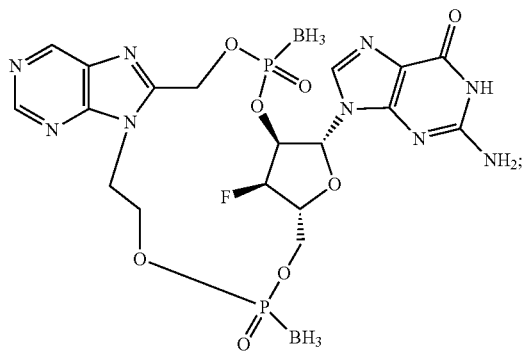
Example 50
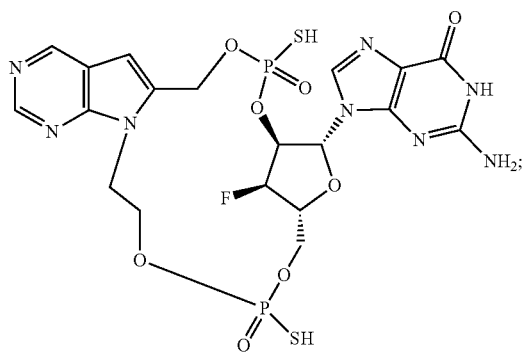 [SMILES: Nc1nc2c(ncn2[C@@H]2O[C@@H]3COP(=O)(S)OCCn4c(cc5cncnc54)COP(=O)(S)O[C@@H]2[C@@H]3F)c(=O)[nH]1]
Example 51

TABLE 1-continued
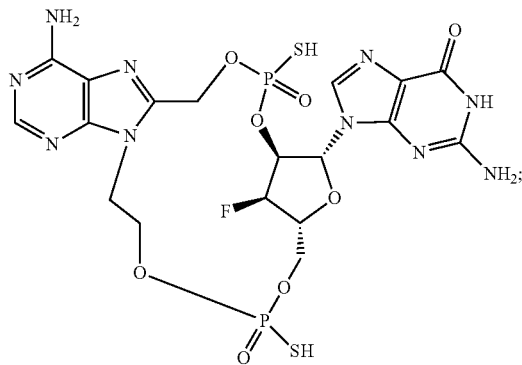
Example 52
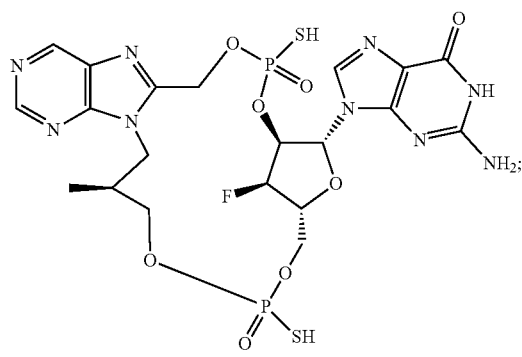 [SMILES: C[C@@H]1COP(=O)(S)OC[C@H]2O[C@@H](n3cnc4c(=O)[nH]c(N)nc43)[C@H](OP(=O)(S)OCc3nc4cncnc4n3C1)[C@@H]2F]
Example 53
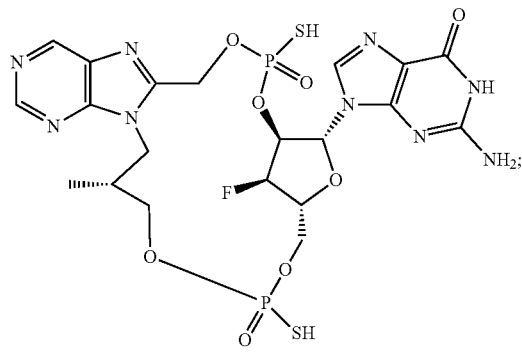 [SMILES: C[C@H]1COP(=O)(S)OC[C@H]2O[C@@H](n3cnc4c(=O)[nH]c(N)nc43)[C@H](OP(=O)(S)OCc3nc4cncnc4n3C1)[C@@H]2F]
Example 54
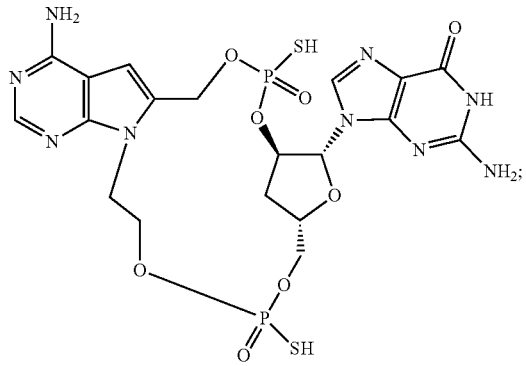 [SMILES: Nc1nc2c(ncn2[C@@H]2O[C@@H]3COP(=O)(S)OCCn4c(cc5c(N)ncnc54)COP(=O)(S)O[C@@H]2C3)c(=O)[nH]1]
Example 55

TABLE 1-continued
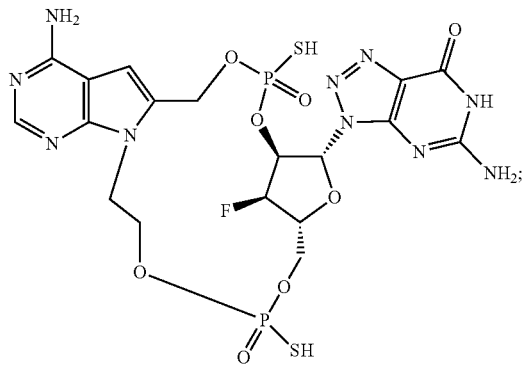 [SMILES: Nc1nc2c(nnn2[C@@H]2O[C@@H]3COP(=O)(S)OCCn4c(cc5c(N)ncnc54)COP(=O)(S)O[C@@H]2[C@@H]3F)c(=O)[nH]1]
Example 56
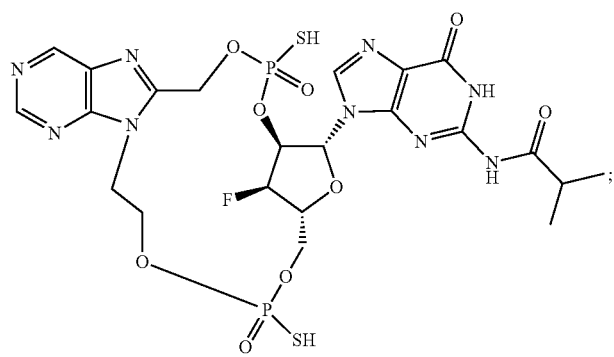 [SMILES: CC(C)C(=O)Nc1nc2c(ncn2[C@@H]2O[C@@H]3COP(=O)(S)OCCn4c(nc5cncnc54)COP(=O)(S)O[C@@H]2[C@@H]3F)c(=O)[nH]1]
Example 57
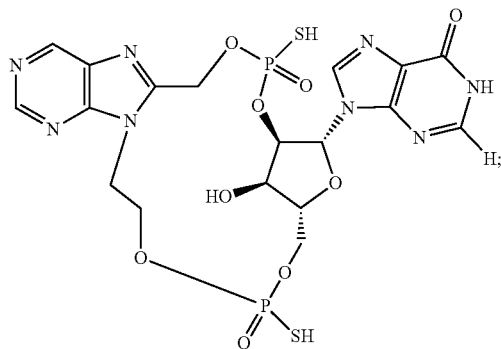
Example 58
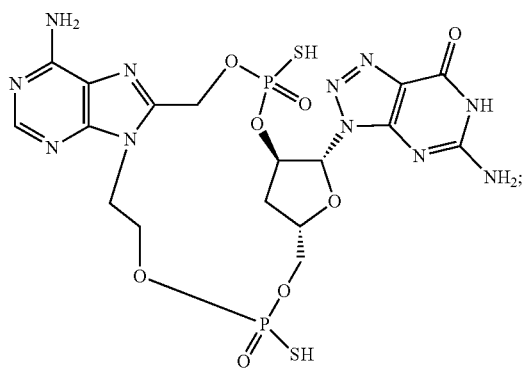 [SMILES: Nc1nc2c(nnn2[C@@H]2O[C@@H]3COP(=O)(S)OCCn4c(nc5c(N)ncnc54)COP(=O)(S)O[C@@H]2C3)c(=O)[nH]1]
Example 59

TABLE 1-continued
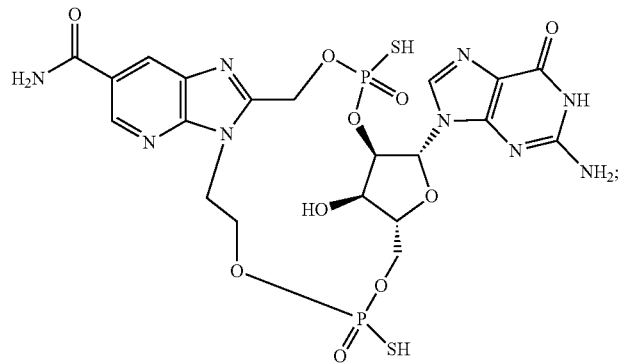
Example 60
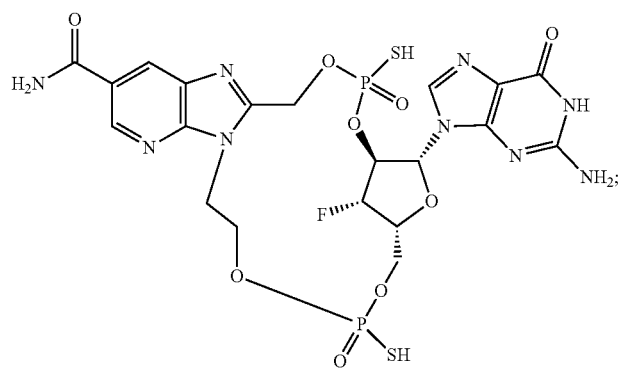 [SMILES: NC(=O)c1cnc2c(c1)nc1n2CCOP(=O)(S)OC[C@H]2O[C@@H](n3cnc4c(=O)[nH]c(N)nc43)[C@H](OP(=O)(S)OC1)[C@H]2F]
Example 61
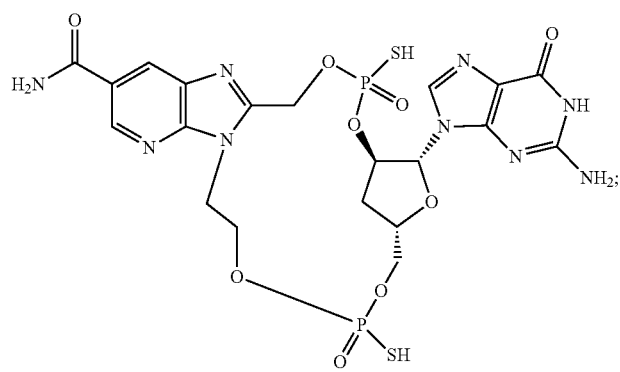 [SMILES: NC(=O)c1cnc2c(c1)nc1n2CCOP(=O)(S)OC[C@@H]2C[C@@H](OP(=O)(S)OC1)[C@H](n1cnc3c(=O)[nH]c(N)nc31)O2]
Example 62
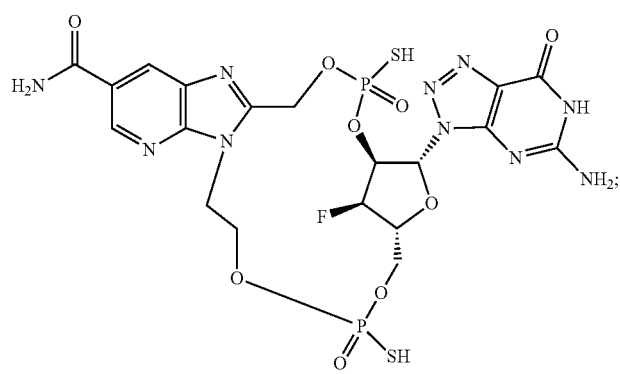 [SMILES: NC(=O)c1cnc2c(c1)nc1n2CCOP(=O)(S)OC[C@H]2O[C@@H](n3nnc4c(=O)[nH]c(N)nc43)[C@H](OP(=O)(S)OC1)[C@@H]2F]
Example 63

TABLE 1-continued
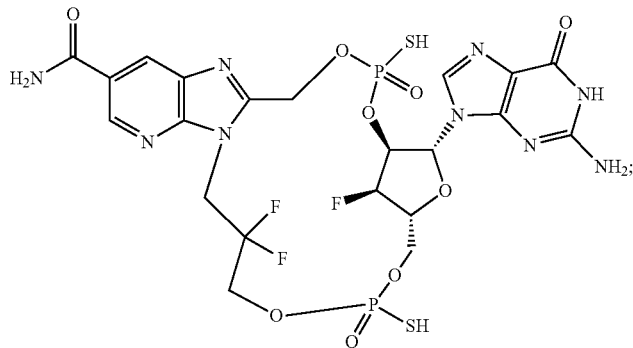 [SMILES: NC(=O)c1cnc2c(c1)nc1n2CC(F)(F)COP(=O)(S)OC[C@H]2O[C@@H](n3cnc4c(=O)[nH]c(N)nc43)[C@H](OP(=O)(S)OC1)[C@@H]2F]
Example 64
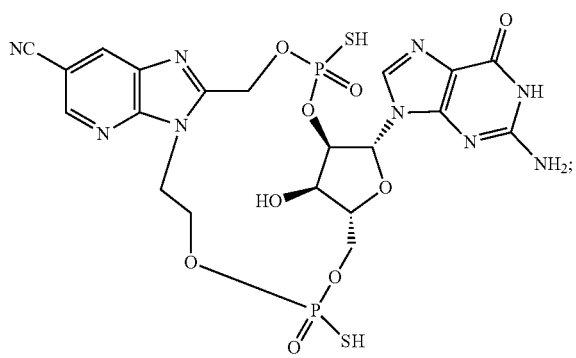 [SMILES: N#Cc1cnc2c(c1)nc1n2CCOP(=O)(S)OC[C@H]2O[C@@H](n3cnc4c(=O)[nH]c(N)nc43)[C@H](OP(=O)(S)OC1)[C@@H]2O]
Example 65
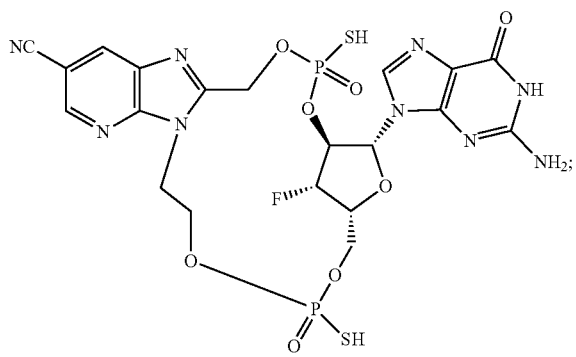 [SMILES: N#Cc1cnc2c(c1)nc1n2CCOP(=O)(S)OC[C@H]2O[C@@H](n3cnc4c(=O)[nH]c(N)nc43)[C@H](OP(=O)(S)OC1)[C@H]2F]
Example 66
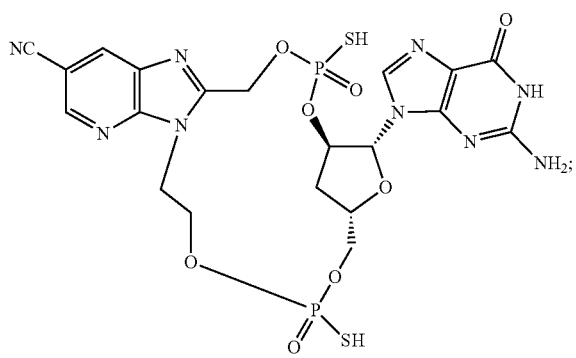 [SMILES: N#Cc1cnc2c(c1)nc1n2CCOP(=O)(S)OC[C@@H]2C[C@@H](OP(=O)(S)OC1)[C@H](n1cnc3c(=O)[nH]c(N)nc31)O2]
Example 67

TABLE 1-continued
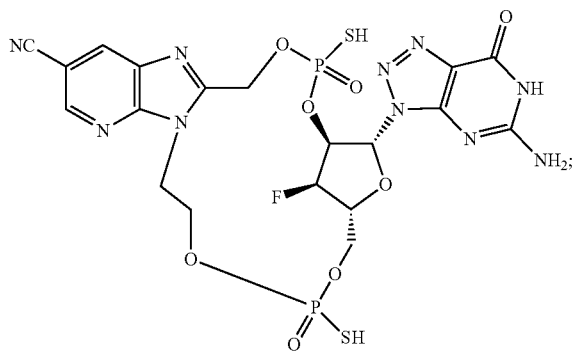 [SMILES: N#Cc1cnc2c(c1)nc1n2CCOP(=O)(S)OC[C@H]2O[C@@H](n3nnc4c(=O)[nH]c(N)nc43)[C@H](OP(=O)(S)OC1)[C@@H]2F]
Example 68
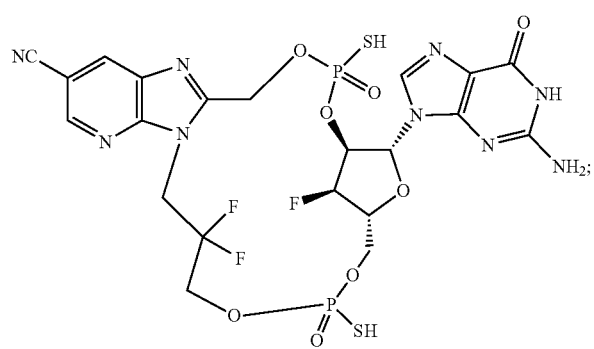 [SMILES: N#Cc1cnc2c(c1)nc1n2CC(F)(F)COP(=O)(S)OC[C@H]2O[C@@H](n3cnc4c(=O)[nH]c(N)nc43)[C@H](OP(=O)(S)OC1)[C@@H]2F]
Example 69
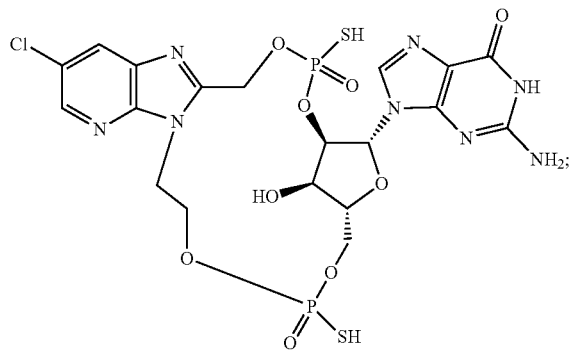 [SMILES: Nc1nc2c(ncn2[C@@H]2O[C@@H]3COP(=O)(S)OCCn4c(nc5cc(Cl)cnc54)COP(=O)(S)O[C@@H]2[C@@H]3O)c(=O)[nH]1]
Example 70
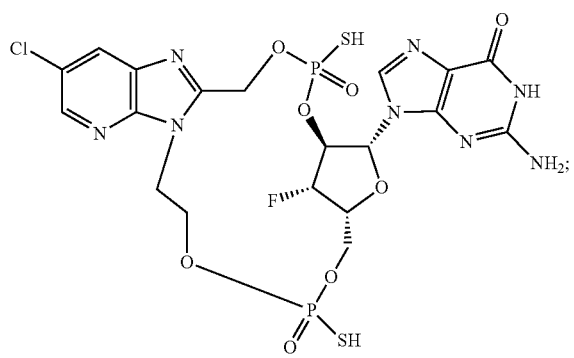 [SMILES: Nc1nc2c(ncn2[C@@H]2O[C@@H]3COP(=O)(S)OCCn4c(nc5cc(Cl)cnc54)COP(=O)(S)O[C@@H]2[C@H]3F)c(=O)[nH]1]
Example 71

TABLE 1-continued
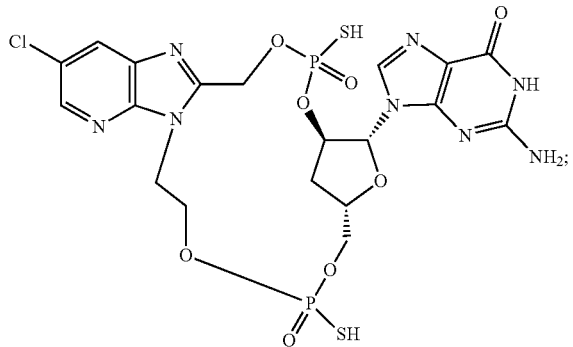 [SMILES: Nc1nc2c(ncn2[C@@H]2O[C@@H]3COP(=O)(S)OCCn4c(nc5cc(Cl)cnc54)COP(=O)(S)O[C@@H]2C3)c(=O)[nH]1]
Example 72
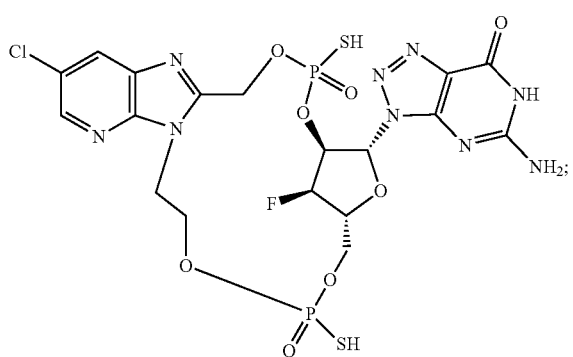 [SMILES: Nc1nc2c(nnn2[C@@H]2O[C@@H]3COP(=O)(S)OCCn4c(nc5cc(Cl)cnc54)COP(=O)(S)O[C@@H]2[C@@H]3F)c(=O)[nH]1]
Example 73
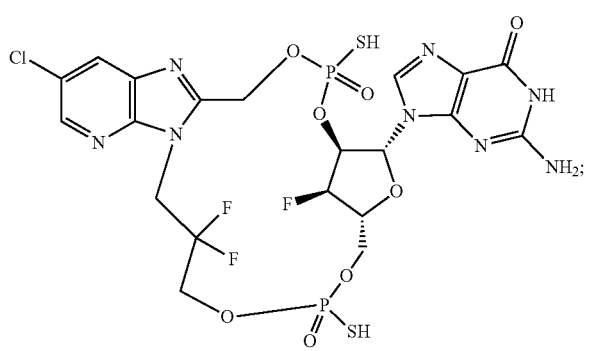 [SMILES: Nc1nc2c(ncn2[C@@H]2O[C@@H]3COP(=O)(S)OCC(F)(F)Cn4c(nc5cc(Cl)cnc54)COP(=O)(S)O[C@@H]2[C@@H]3F)c(=O)[nH]1]
Example 74
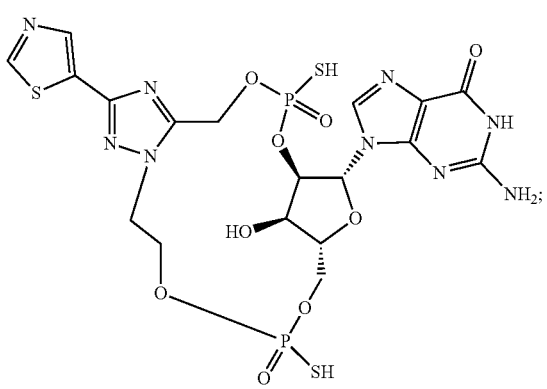 [SMILES: Nc1nc2c(ncn2[C@@H]2O[C@@H]3COP(=O)(S)OCCn4nc(-c5cncs5)nc4COP(=O)(S)O[C@@H]2[C@@H]3O)c(=O)[nH]1]
Example 75

TABLE 1-continued
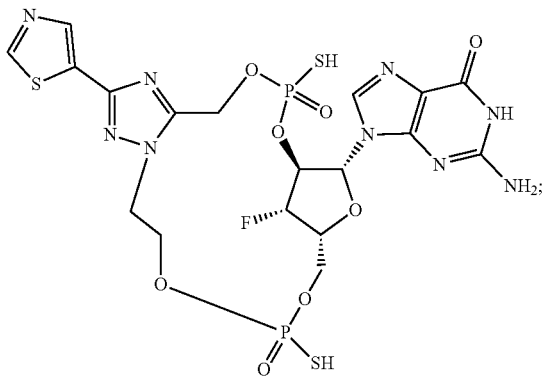 [SMILES: Nc1nc2c(ncn2[C@@H]2O[C@@H]3COP(=O)(S)OCCn4nc(-c5cncs5)nc4COP(=O)(S)O[C@@H]2[C@H]3F)c(=O)[nH]1]
Example 76
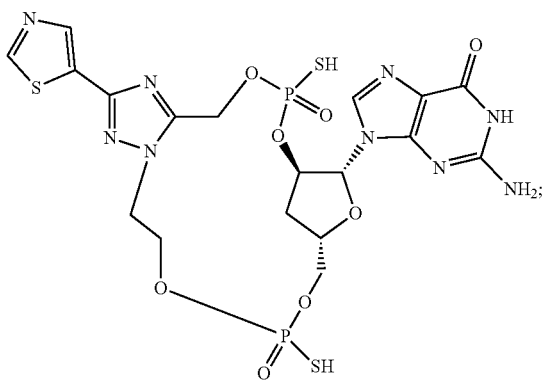 [SMILES: Nc1nc2c(ncn2[C@@H]2O[C@@H]3COP(=O)(S)OCCn4nc(-c5cncs5)nc4COP(=O)(S)O[C@@H]2C3)c(=O)[nH]1]
Example 77
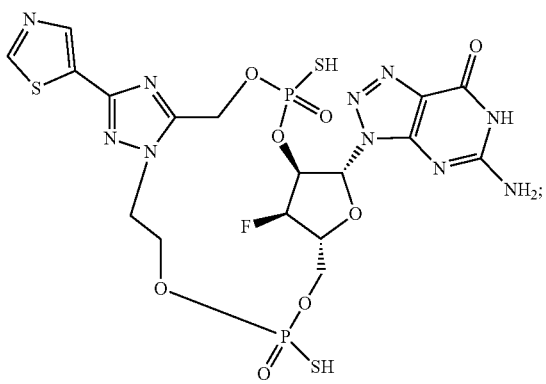 [SMILES: Nc1nc2c(nnn2[C@@H]2O[C@@H]3COP(=O)(S)OCCn4nc(-c5cncs5)nc4COP(=O)(S)O[C@@H]2[C@@H]3F)c(=O)[nH]1]
Example 78
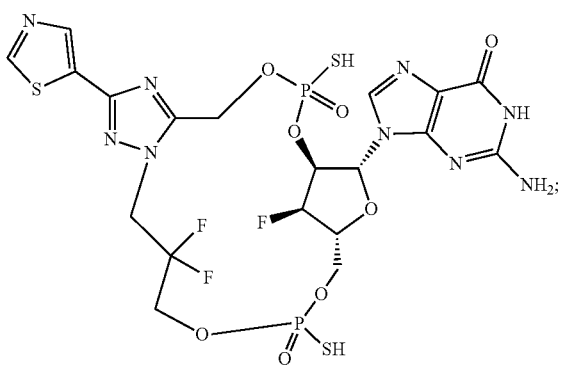 [SMILES: Nc1nc2c(ncn2[C@@H]2O[C@@H]3COP(=O)(S)OCC(F)(F)Cn4nc(-c5cncs5)nc4COP(=O)(S)O[C@@H]2[C@@H]3F)c(=O)[nH]1]
Example 79

TABLE 1-continued
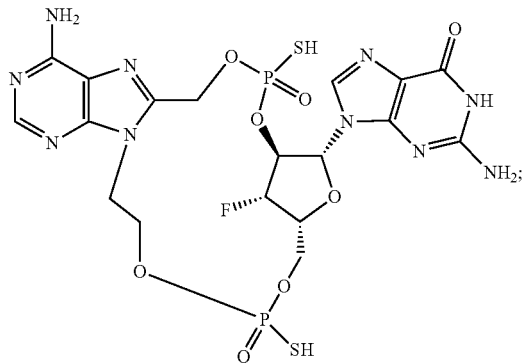 [SMILES: Nc1nc2c(ncn2[C@@H]2O[C@@H]3COP(=O)(S)OCCn4c(nc5c(N)ncnc54)COP(=O)(S)O[C@@H]2[C@H]3F)c(=O)[nH]1]
Example 80
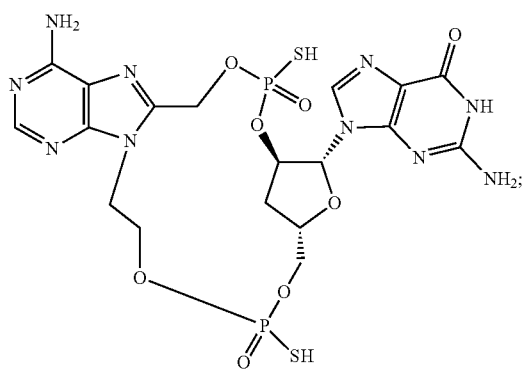
Example 81
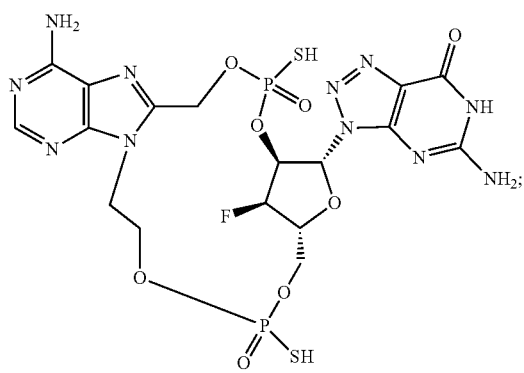 [SMILES: Nc1nc2c(nnn2[C@@H]2O[C@@H]3COP(=O)(S)OCCn4c(nc5c(N)ncnc54)COP(=O)(S)O[C@@H]2[C@@H]3F)c(=O)[nH]1]
Example 82
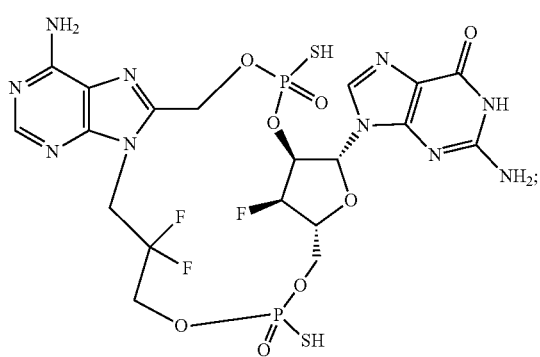 [SMILES: Nc1nc2c(ncn2[C@@H]2O[C@@H]3COP(=O)(S)OCC(F)(F)Cn4c(nc5c(N)ncnc54)COP(=O)(S)O[C@@H]2[C@@H]3F)c(=O)[nH]1]
Example 83

TABLE 1-continued
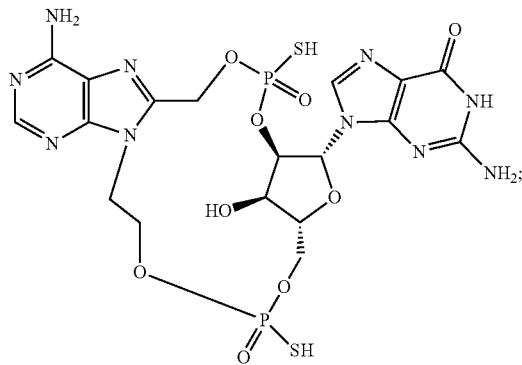 [SMILES: Nc1nc2c(ncn2[C@@H]2O[C@@H]3COP(=O)(S)OCCn4c(nc5c(N)ncnc54)COP(=O)(S)O[C@@H]2[C@@H]3O)c(=O)[nH]1]
Example 84
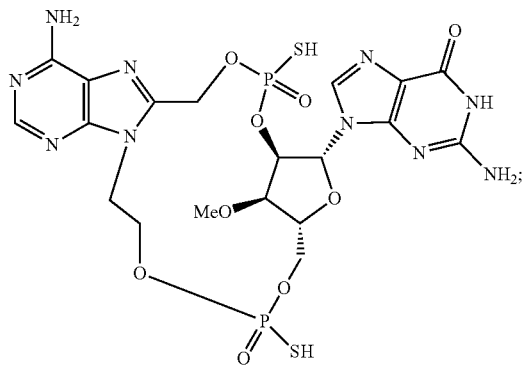 [SMILES: CO[C@H]1[C@H]2OP(=O)(S)OCc3nc4c(N)ncnc4n3CCOP(=O)(S)OC[C@H]1O[C@H]2n1cnc2c(=O)[nH]c(N)nc21]
Example 85
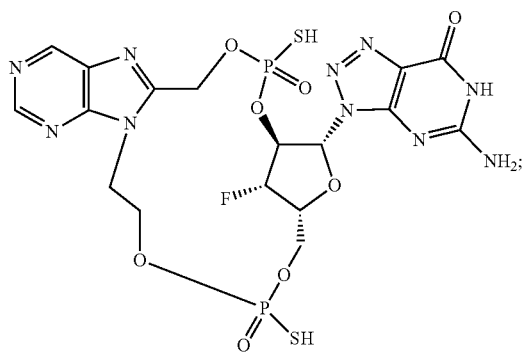 [SMILES: Nc1nc2c(nnn2[C@@H]2O[C@@H]3COP(=O)(S)OCCn4c(nc5cncnc54)COP(=O)(S)O[C@@H]2[C@H]3F)c(=O)[nH]1]
Example 86
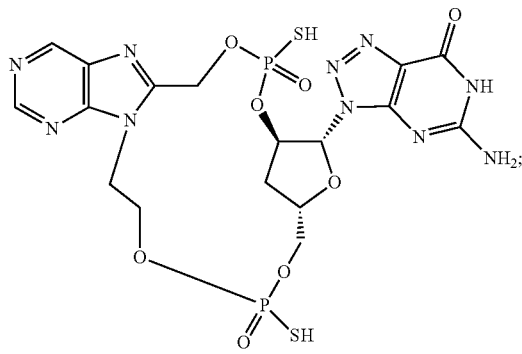 [SMILES: Nc1nc2c(nnn2[C@@H]2O[C@@H]3COP(=O)(S)OCCn4c(nc5cncnc54)COP(=O)(S)O[C@@H]2C3)c(=O)[nH]1]
Example 87

TABLE 1-continued
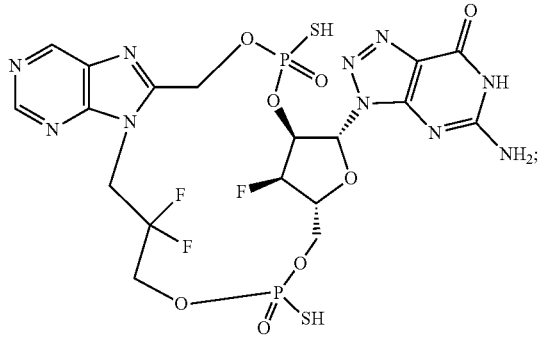 [SMILES: Nc1nc2c(nnn2[C@@H]2O[C@@H]3COP(=O)(S)OCC(F)(F)Cn4c(nc5cncnc54)COP(=O)(S)O[C@@H]2[C@@H]3F)c(=O)[nH]1]
Example 88
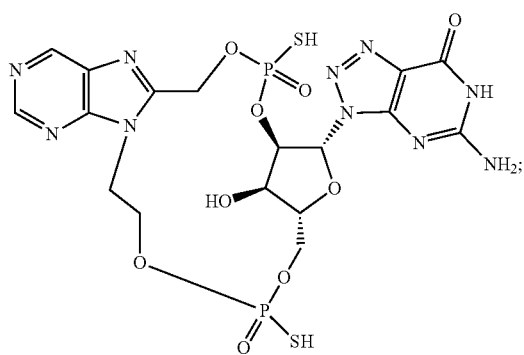 [SMILES: Nc1nc2c(nnn2[C@@H]2O[C@@H]3COP(=O)(S)OCCn4c(nc5cncnc54)COP(=O)(S)O[C@@H]2[C@@H]3O)c(=O)[nH]1]
Example 89
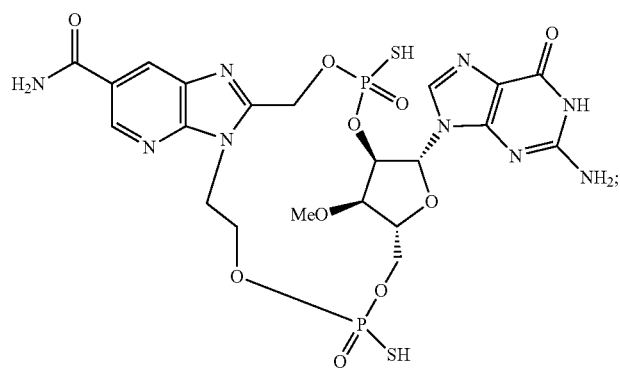 [SMILES: CO[C@H]1[C@H]2OP(=O)(S)OCc3nc4cc(C(N)=O)cnc4n3CCOP(=O)(S)OC[C@H]1O[C@H]2n1cnc2c(=O)[nH]c(N)nc21]
Example 90
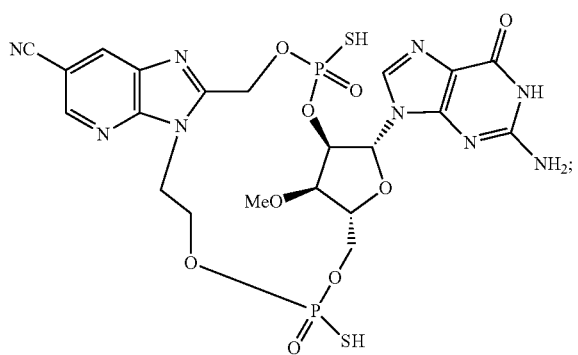 [SMILES: CO[C@H]1[C@H]2OP(=O)(S)OCc3nc4cc(C#N)cnc4n3CCOP(=O)(S)OC[C@H]1O[C@H]2n1cnc2c(=O)[nH]c(N)nc21]
Example 91

TABLE 1-continued
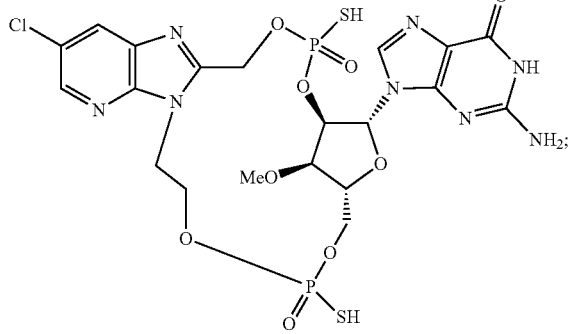
Example 92
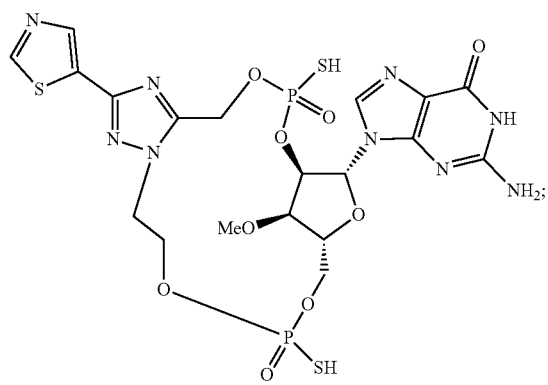 [SMILES: CO[C@H]1[C@H]2OP(=O)(S)OCc3nc(-c4cncs4)nn3CCOP(=O)(S)OC[C@H]1O[C@H]2n1cnc2c(=O)[nH]c(N)nc21]
Example 93
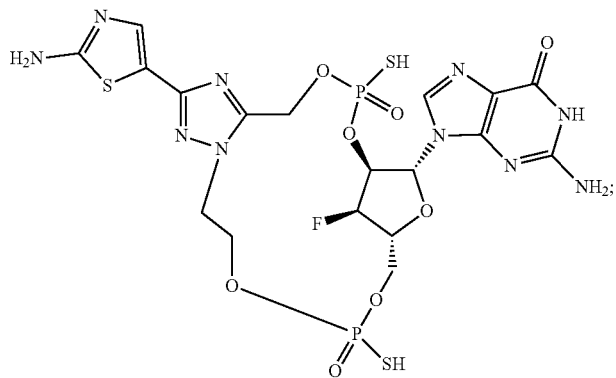 [SMILES: Nc1nc2c(ncn2[C@@H]2O[C@@H]3COP(=O)(S)OCCn4nc(-c5cnc(N)s5)nc4COP(=O)(S)O[C@@H]2[C@@H]3F)c(=O)[nH]1]
Example 94
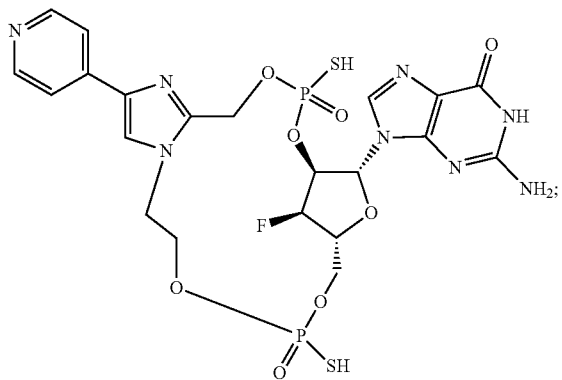 [SMILES: Nc1nc2c(ncn2[C@@H]2O[C@@H]3COP(=O)(S)OCCn4cc(-c5ccncc5)nc4COP(=O)(S)O[C@@H]2[C@@H]3F)c(=O)[nH]1]
Example 95

TABLE 1-continued
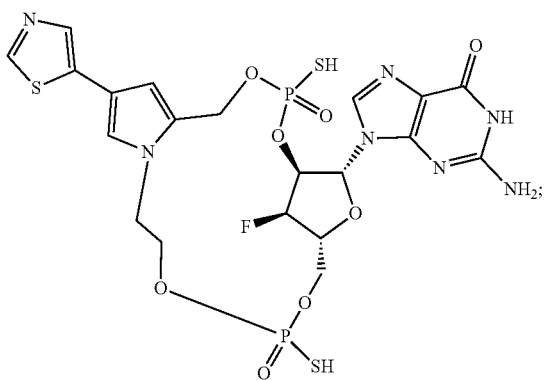 [SMILES: Nc1nc2c(ncn2[C@@H]2O[C@@H]3COP(=O)(S)OCCn4cc(-c5cncs5)cc4COP(=O)(S)O[C@@H]2[C@@H]3F)c(=O)[nH]1]
Example 96
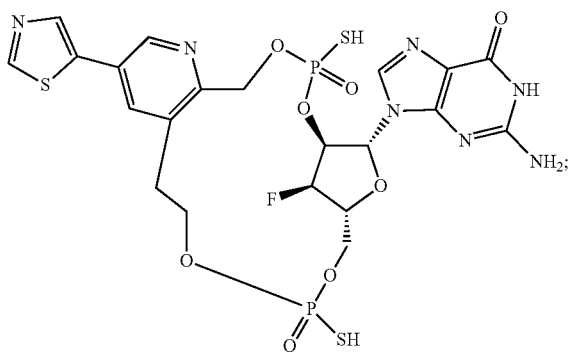 [SMILES: Nc1nc2c(ncn2[C@@H]2O[C@@H]3COP(=O)(S)OCCc4cc(-c5cncs5)cnc4COP(=O)(S)O[C@@H]2[C@@H]3F)c(=O)[nH]1]
Example 97
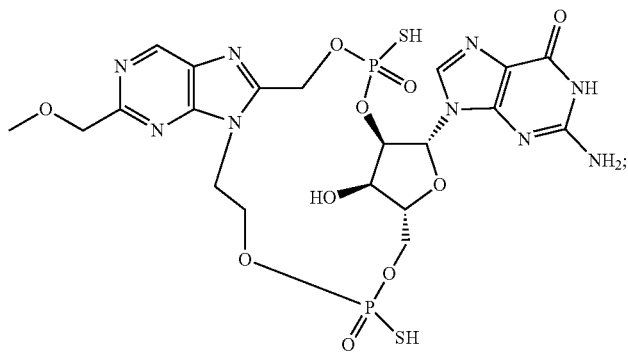 [SMILES: COCc1ncc2nc3n(c2n1)CCOP(=O)(S)OC[C@H]1O[C@@H](n2cnc4c(=O)[nH]c(N)nc42)[C@H](OP(=O)(S)OC3)[C@@H]1O]
Example 98
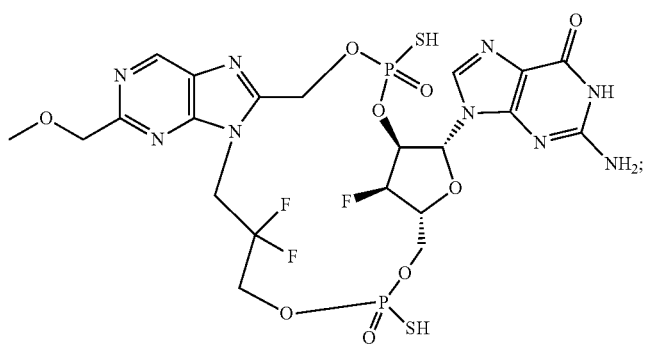 [SMILES: COCc1ncc2nc3n(c2n1)CC(F)(F)COP(=O)(S)OC[C@H]1O[C@@H](n2cnc4c(=O)[nH]c(N)nc42)[C@H](OP(=O)(S)OC3)[C@@H]1F]
Example 99

TABLE 1-continued

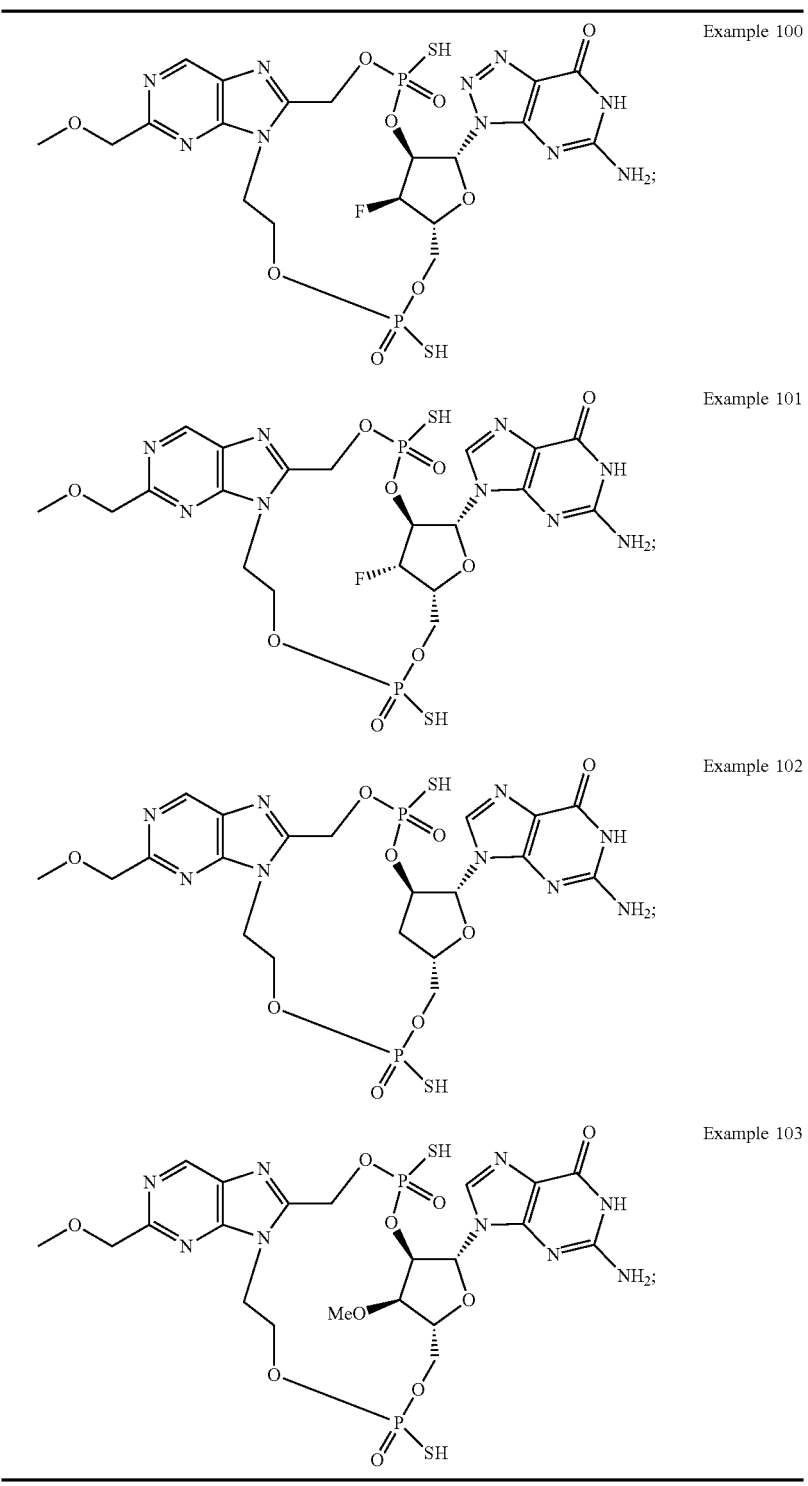

Example 100

Example 101

Example 102

Example 103

In a specific embodiment, the compounds disclosed in Table 1 include all possible diasteromers.

The compounds, stereoisomers, tautomers, salts, solvates or prodrugs of the invention have $IC_{50}$ values in the human, wild-type and variants thereof, STING SPA binding assay (described hereinafter) of for example, about 100 μM or less, about 50 μM or less, about 25 μM or less, or about 10 μM or less. Activity data for compounds, stereoisomers, tautomers, salts, solvates or prodrugs of the present invention are presented in Tables 6 and 8.

In some embodiments, the present invention provides a pharmaceutical composition, which includes a pharmaceutically acceptable carrier and a therapeutically effective amount of a compound of Formula I or Formula I'. Specifically, the compound is selected from one of the examples of Table 1 and diastereomers of all the exemplary compounds, e.g. diasteromers A-D disclosed herein. For example, 1A, 1B, 1C and 1D are different diastereomers of exemplary compound 1. More specifically, the compound is selected from one of the examples 1C, 1D, 6B, 11C, 7C, 14C, 15A, 15D, 16C, 19D, 22D, 24C, 25D, 27C, 29B, 33D, 37A, 37B, 38C and 39. Even more specifically, the compound is selected from one of the examples 1C, 11C, 7C, 16C, 24C, 27C, 37A, 37B, 38C and 39, or stereoisomers, tautomers, pharmaceutically acceptable salts, prodrugs, or solvates thereof, alone or in combination with another therapeutic agent.

In some embodiments, the present invention provides a pharmaceutical composition which further includes another therapeutic agent(s). According to some embodiments, the present invention provides a pharmaceutical composition, wherein the additional therapeutic agent(s) are an anti-cancer agent, an anti-viral compound, an antigen, an adjuvant, a lipid, a liposome, a peptide, a cytotoxic agent, a chemotherapeutic agent, an immunomodulatory cell line, a checkpoint inhibitor, a biotherapeutic agent, an immunogenic agent, and cells transfected with genes encoding immune stimulating cytokines or a combination thereof. Preferably, the additional therapeutic agents include, without limitation, VEGF, VEGFR, EGFR, Her2/neu, other growth factor receptors, CD20, CD40, CD-40L, CTLA-4, OX-40, 4-1BB, ICOS, IL-2, IFNa2, GM-CSF, another STING agonists, a TREX-1 antagonist, a CTLA-4 pathway antagonist, a LAG-3 pathway antagonist, a PD-1 pathway antagonist, a PD-L1 antibody, a vascular endothelial growth factor (VEGF) receptor inhibitor, a topoisomerase II inhibitor, a smoothen inhibitor, an alkylating agent, an anti-tumor antibiotic, an anti-metabolite, a retinoid, and an anti-cancer vaccine.

In some embodiments, the present invention provides a pharmaceutical composition which is utilized in combination with radiation therapy.

In some embodiments, the present invention provides a method for the treatment or prophylaxis of a disorder, disease, syndrome, or condition, wherein said disorder, disease, syndrome, or condition is affected by the agonism of STING, which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrugs thereof.

In some additional embodiments, the present invention provides a method for the treatment or prophylaxis of a disorder, disease, syndrome, or condition, wherein said disorder, disease, syndrome, or condition is affected by the agonism of STING, which includes the step of administering to a subject (for example, a human) in need of such treatment or prophylaxis a therapeutic amount of at least one of the compounds of the present invention or stereoisomers, tautomers, pharmaceutically acceptable salts, solvates, or prodrugs thereof, wherein the therapeutic amount is effective to treat said disorder, disease, syndrome, or condition.

In one embodiment, the therapeutic amount is effective:
a) to bind to a human STING protein in an in vitro assay; or
b) to increase STING activity within a murine or human cell compared to such activity in a control cell; or
c) to activate a STING pathway within a murine or human cell; or
d) to induce one or more interferon responsive genes, or one or more NF-κB dependent pro-inflammatory cytokines; or
e) to induce secretion of murine or human IFNα, IFN-β or both; or
f) to decrease tumor burden compared to an untreated control, increase overall survival compared to an untreated control, increase progression-free survival compared to an untreated control, or increase relapse-free survival compared to an untreated control.

In one embodiment, the one or more interferon response genes are selected from the group consisting of IFN-β, CXCL10, IFIT1, IFIT3, and ISG15.

In one embodiment, the one or more NF-κB dependent pro-inflammatory cytokines is selected from the group consisting of IL-6 and TNFα.

In another embodiment, the therapeutic amount is effective to:
(a) bind to a human WT STING protein in an in vitro assay, wherein IC50 of the compound ranges from about 0.1 nM to about 1,000,000 nM (1 mM), about 1 nM to about 100,000 nM, or about 1 nM to about 1000 nM, inclusive; or
(b) increase STING activity by at least about 0.1% to about 100% compared to such activity in a control cell; or
(c) activate a STING pathway within a murine or human cell, wherein EC50 of the compound ranges from about 0.1 nM to about 1,000,000 nM (1 mM), about 1 nM to about 100,000 nM, or about 1 nM to about 1000 nM, inclusive; or
(d) induce one or more interferon responsive genes selected from the group consisting of IFN-β, CXCL10, IFIT1, IFIT3, and ISG15; or to induce one or more NF-κB dependent pro-inflammatory cytokines selected from the group consisting of IL-6 and TNFα; or both; or
(f) induce secretion of murine or human IFNα, IFN-β or both, wherein EC50 of the compound ranges from bout 0.1 nM to about 1,000,000 nM (1 mM), about 1 nM to about 100,000 nM, or about 1 nM to about 1000 nM, inclusive; or
(g) decrease tumor burden, to increase overall survival, progression free survival or relapse free survival compared to an untreated control.

In another embodiment, the therapeutic amount is effective to:
(a) bind to a human WT STING protein in an in vitro assay, wherein IC50 of the compound ranges from about 1 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, about 200,000 nM, about 300,000 nM, about 400,000 nM, about 500,000 nM, about 600,000 nM, about 700,000 nM, about 800,000 nM, about 900,000 nM, about 1,000,000 nM (1 mM), inclusive, and the like; or
(b) increase STING activity by at least about 0.01%, about 0.05%, about 0.1%, about 0.5%, about 1.0%, about 5.0%, about 10%, about 20%, about 30%, about 40%, about 50%, about 60%, about 70%, about 80%, about 90%, or about 100% compared to such activity in a control cell; or
(c) activate a STING pathway within a murine or human cell, wherein EC50 of the compound ranges from about 1 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, about 200,000 nM, about 300,000 nM, about 400,000 nM, about 500,000 nM, about 600,000 nM, about 700,000 nM, about 800,000 nM, about 900,000 nM, about 1,000,000 nM (1 mM), inclusive, and the like; or (d) induce one or more interferon responsive genes selected from the group consisting of IFN-β, CXCL10, IFIT1, IFIT3, and ISG15; or to induce one or more NF-κB dependent pro-inflammatory cytokines selected from the group consisting of IL-6 and TNFα; or both; or (e) induce secretion of murine or human IFNα, IFN-β or both, wherein EC50 of the compound ranges from about 1 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, about 200,000 nM, about 300,000 nM, about 400,000 nM, about 500,000 nM, about 600,000 nM, about 700,000 nM, about 800,000 nM, about 900,000 nM, about 1,000,000 nM (1 mM), inclusive, and the like; or (f) decrease tumor burden, to increase overall survival, progression free survival or relapse free survival compared to an untreated control.

In another embodiment, the therapeutic amount is effective to:

(a) bind to a human WT STING protein in an in vitro assay, wherein IC50 of the compound ranges from about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, inclusive, and the like; or (b) increase STING activity by at least 10%, 20%, 30%, 40%, 50%, 60%, 70%, 80%, 90%, or 100% compared to such activity in a control cell; or (c) activate a STING pathway within a murine or human cell, wherein EC50 of the compound ranges from about 300 nM, about 400 nM, about 500 nM, about 600 nM, about 700 nM, about 800 nM, about 900 nM, about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, inclusive, and the like; or (d) induce one or more interferon responsive genes selected from the group consisting of IFN-β, CXCL10, IFIT1, IFIT3, and ISG15; or to induce one or more NF-κB dependent pro-inflammatory cytokines selected from the group consisting of IL-6 and TNF; α or both; or (e) induce secretion of murine or human IFNα, IFN-β or both, wherein EC50 of the compound ranges from about 1000 nM, about 2000 nM, about 3000 nM, about 4000 nM, about 5000 nM, about 6000 nM, about 7000 nM, about 8000 nM, about 9000 nM, about 10,000 nM, about 20,000 nM, about 30,000 nM, about 40,000 nM, about 50,000 nM, about 60,000 nM, about 70,000 nM, about 80,000 nM, about 90,000 nM, about 100,000 nM, about 200,000 nM, inclusive and the like; or (f) decrease tumor burden, to increase overall survival, progression free survival or relapse free survival compared to an untreated control.

In some embodiments, the present invention provides a method for the treatment or prophylaxis of a disorder, disease, syndrome, or condition, wherein said disorder, disease, syndrome, or condition is affected by the agonism of STING, and wherein the disorder, disease, syndrome or condition is cancer or a viral infection. For example, the present invention provides a method for the treatment or prophylaxis of a disorder, disease, syndrome, or condition, wherein said disorder, disease, syndrome, or condition is affected by the agonism of STING, and wherein the disorder, disease, syndrome or condition is cancer. Exemplary cancers include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease; brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer; or combinations thereof. In another example, the present invention provides a method for the treatment or prophylaxis of a disorder, disease, syndrome, or condition, wherein said disorder, disease, syndrome, or condition is affected by the agonism of STING, and wherein the disorder, disease, syndrome or condition is a viral infection. Exemplary viral infections include, but are not limited to, Hepatitis A, Hepatitis B, Hepatitis C, Hepatitis D, Human papillomavirus, Human T-cell lymphotropic virus, Coronaviruses, Rubella, Mumps, Coxsackie virus A, Coxsackie virus B, Human enteroviruses, Poliovirus, Viral encephalitides viruses, Human herpesviruses including Cytomegalovirus, Epstein-Barr viruses, Human herpesviruses, Herpes B virus, Herpes simplex viruses, Varicella zoster virus, Human immunodeficiency viruses, Reoviruses, Rhinoviruses, Adenoviruses, Filoviruses, including Marburg virus and Ebola virus, Arenaviruses including lymphocytic choriomeningitis virus, Lassa virus, Junin virus, and Machupo Virus, Rabies virus, Arboviruses including West Nile virus, Dengue viruses, Colorado tick fever virus, Sinbis virus, Togaviraidae, Flaviviridae, Bunyaviridae, Reoviridae, and Rhabdoviridae, Poxviruses, Yellow fever virus, Hantaviruses, Measles virus, Human parainfluenza viruses, Influenza viruses, Respiratory syncytial viruses, Rotaviruses, Polyomaviruses, Coltiviruses, Calciviruses, and Parvoviruses.

In some embodiments, the present invention provides methods for the treatment of a disorder, disease, syndrome, or condition affected by the agonism of STING, which includes the steps of administering to a patient (for example, a human) in need thereof a therapeutically effective amount of a compound of Formula I or Formula I', or stereoisomers, tautomers, pharmaceutically acceptable salts, prodrugs, or solvates thereof, wherein the disorder, disease, syndrome, or condition is selected from cancer or a viral infection. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts thereof.

In some embodiments, the present invention provides methods for the treatment of a disease, syndrome, or condition affected by the agonism of STING, which includes the steps of administering to a patient (for example, a human) in need thereof a therapeutically effective amount of a compound of Formula I or Formula I', stereoisomers, tautomers, pharmaceutically acceptable salts, prodrugs, or solvates thereof, wherein the disorder, disease, syndrome, or condition is cancer. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C, and 39, stereoisomers, tautomers or pharmaceutically acceptable salts thereof.

In some embodiments, the present invention provides methods for the treatment of a disorder, disease, syndrome, or condition affected by the agonism of STING, which includes the steps of administering to a patient (for example, a human) in need thereof a therapeutically effective amount of a compound of Formula I or Formula I', stereoisomers, tautomers, pharmaceutically acceptable salts, prodrugs, or solvates thereof, wherein the disorder, disease, syndrome, or condition is selected from the group consisting of melanoma, colon cancer, colorectal cancer, breast cancer, prostate cancer, lung cancer, bladder cancer and fibrosarcoma. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts thereof.

In some embodiments, the present invention provides methods for the treatment of a disorder, disease, syndrome, or condition affected by the agonism of STING, which includes the steps of administering to a patient (for example, a human) in need thereof a therapeutically effective amount of a compound of Formula I or Formula I', stereoisomers, tautomers, pharmaceutically acceptable salts, prodrugs, or solvates thereof, wherein the disorder, disease, syndrome, or condition is a viral infection. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts thereof.

In some embodiments, the present invention provides methods for the treatment of a disorder, disease, syndrome, or condition affected by the agonism of STING, which includes the steps of administering to a patient (for example, a human) in need thereof a therapeutically effective amount of a compound of Formula I or Formula I', stereoisomers, tautomers, pharmaceutically acceptable salts, prodrugs, or solvates thereof, wherein the disorder, disease, syndrome, condition is a viral infection selected from the group consisting of Hepatitis A, Hepatitis B, Hepatitis C, Hepatitis D, Human papillomavirus, Human T-cell lymphotropic virus, Human coronavirus OC43 A-D, Human cornonavirus 229E, SARS-Human coronavirus, MERS-Human coronavirus, Rubella virus, Mumps virus, Coxsackie virus A, Coxsackie virus B, Human enterovirus A-L, Rhinovirus A-C, Poliovirus, Viral encephalitis, Cytomegalovirus, Epstein-Barr virus, Human herpesviruses, Herpes B virus, Herpes simplex virus I-II, Varicella zoster virus, Marburg virus, Ebola virus, lymphocytic choriomeningitis virus, Lassa virus, Junin virus, Machupo Virus, Rabies virus, West Nile virus, Dengue viruses, Colorado tick fever virus, Sinbis virus, Yellow fever virus, Hantavirus, Measles virus, Human parainfluenza virus 1-4, Influenza virus A-D, Respiratory syncytial virus, Rotavirus A-I, BK and JC polymavirus, Norovirus, Parvovirus B19 and human bocavirus 1. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts thereof.

In some embodiments, the present invention provides methods for the treatment of a disorder, disease, syndrome, or condition affected by the agonism of STING, which includes the steps of administering to a patient (for example, a human) in need thereof a therapeutically effective amount of a compound of Formula I or Formula I', stereoisomers, tautomers, pharmaceutically acceptable salts, prodrugs, or solvates thereof, wherein the disorder, disease, syndrome, or condition is Hepatitis viruses A through D, Human papillomavirus, Human herpesviruses, Influenza viruses, Epstein-Barr viruses, Human immunodeficiency viruses, Respiratory syncytial viruses, Rotaviruses, Rhinoviruses melanoma, colon cancer, colorectal cancer, breast cancer, prostate cancer, lung cancer, bladder cancer, or fibrosarcoma. Specifically, the compound is selected from one of the examples of Table 1, or stereoisomers, tautomers, pharmaceutically acceptable salts, prodrugs, or solvates thereof. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts thereof.

In yet another embodiment, the present invention provides uses a compound of Formula I or Formula I' or a stereoisomer, a tautomer, a pharmaceutically acceptable salt, prodrugs, or solvates thereof for the preparation of a medicament for treating a disorder, disease, syndrome, or condition selected from the group consisting of Hepatitis viruses A through D, Human papillomavirus, Human herpesviruses, Influenza viruses, Epstein-Barr viruses, Human immunodeficiency viruses, Respiratory syncytial viruses, Rotaviruses, Rhinoviruses, melanoma, colon cancer, colorectal cancer, breast cancer, prostate cancer, lung cancer, bladder cancer, and fibrosarcoma, in a subject in need thereof. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts.

In still yet another embodiment, the present invention provides uses a compound of Formula I or Formula I', stereoisomers, tautomers, pharmaceutically acceptable salts, prodrugs, or solvates thereof, in a method for treating a disorder, disease, syndrome, or condition selected from the group consisting of Hepatitis viruses A through D, Human papillomavirus, Human herpesviruses, Influenza viruses, Epstein-Barr viruses, Human immunodeficiency viruses, Respiratory syncytial viruses, Rotaviruses, Rhinoviruses, melanoma, colon cancer, colorectal cancer, breast cancer, prostate cancer, lung cancer, bladder cancer, and fibrosarcoma, in a subject in need thereof. Specifically, the compound is selected from one of the examples of Table 1. More specifically, the compound is selected from one of the examples 1C, 1D, 6B, 7C, 11C, 14C, 15A, 15D, 16C, 19D, 22D, 24C, 25D, 27C, 29B, 33D, 37A, 37B, 38C and 39. Even more specifically, the compound is selected from one of the examples 1C, 7C, 11C, 16C, 24C, 27C, 37A, 37B, 38C and 39, stereoisomers, tautomers or pharmaceutically acceptable salts.

Other Embodiments of the Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the present invention provides a compound of the present invention or stereoisomers, tautomers, pharmaceutically acceptable salts, solvates, or prodrugs thereof, for use in therapy for the treatment or prophylaxis of a disorder, disease, syndrome, or condition affected by the agonism of STING.

In some embodiments, the present invention also provides the use of a compound of the present invention or stereoisomers, tautomers, pharmaceutically acceptable salts, solvates, or prodrugs thereof, for the manufacture of a medicament for the treatment or prophylaxis of a disorder, disease, syndrome, or condition affected by the agonism of STING.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of the present invention may have one or more asymmetric centers. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). Unless otherwise indicated, all chiral (enantiomeric and diastereomeric) and racemic forms of compounds of the present invention are included in the present invention. It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated.

Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The described compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. Notwithstanding the foregoing, a phosphorothioate linkage is inherently chiral. One of ordinary skill in the art would understand that phosphorthioates of the present invention may each exist in R or S forms. Thus, Rp or Sp forms are possible in compounds containing one phosphorthioate moiety and Rp,Rp; Sp,Sp; and Rp,Sp forms are possible in compounds containing two phosphorthioate moieties. In cases where a phosphorthioate moiety is present in a given compound, there is a preferred Rp or Sp configuration for each phosphorus atom. For example, the diastereomeric phosphorthioates are resolved prior to any type of in vitro or in vivo testing. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced.

Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R_{10}$, then said group may optionally be substituted with up to three $R_{10}$ groups, and at each occurrence $R_{10}$ is selected independently from the definition of $R_{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of Formula I or Formula I' may have prodrug forms. Any compound that will be converted in vivo to provide the bioactive agent (i.e., a compound of formula I or Formula I') is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Exemplary methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

Compounds of the present invention were prepared using the synthetic schemes described herein. The schemes set forth below utilize various transformations such as alkylations, reductions, oxidations, displacements, and hydrogen phosphate/S-hydrogen phosphorthioate bond forming reactions. During the chemical syntheses, various protecting groups may be employed and subsequently removed in order to generate the compounds of the present invention. Exemplary protecting groups and conditions for their removal are described in Greene's *Protecting Groups in Organic Synthesis* P. G. M. Nuts, T. W. Greene, Fourth Edition, Wiley, New York, 2006.

Alcohol protecting groups may include, but are not limited to, DMTr (4,4'-dimethoxytriphenylmethyl), TBS (tert-butyldimethylsilyl) and Ac (acetyl). Deprotection conditions vary depending on the protecting groups. For example, if the alcohol is protected as its TBS ether, deprotection can be effected by the use of fluoride. If the alcohol is protected as its DMTr ether, mild acid can be employed for its removal.

Protecting groups for weakly nucleophilic amines generally employed in the current invention can include benzoyl or isobutyryl. These can be removed by the action of a nucleophilic amine, for example, dimethylamine in ethanol.

In the schemes set forth below, the syntheses of compounds sometimes require the formation of a new P—O bond with concomitant oxidation or oxidative sulfurization from P(III) to P(V). This can be accomplished by addition of an alcohol to an activated P(III) intermediate followed by treatment with either iodine/H$_2$O or tert-butylhydroperoxide to give the H-phosphate. Alternatively, the coupled product can be treated with (E)-N,N-dimethyl-N'-(3-thioxo-3H-1,2,4-dithiazol-5-yl)formimidamide, 3H-benzo[c][1,2]dithiol-3-one, or a similar reagent to effect oxidative sulfurization and deliver the corresponding S-hydrogen phosphorothioate.

Specific synthetic transformations not covered in the schemes below are described in detail in the experimental section. It is apparent to those skilled in the art that the order of steps might be adjusted depending on the compound to be produced.

Compounds of Formula I or Formula I' of this invention can be obtained in accordance with the Schemes set forth below.

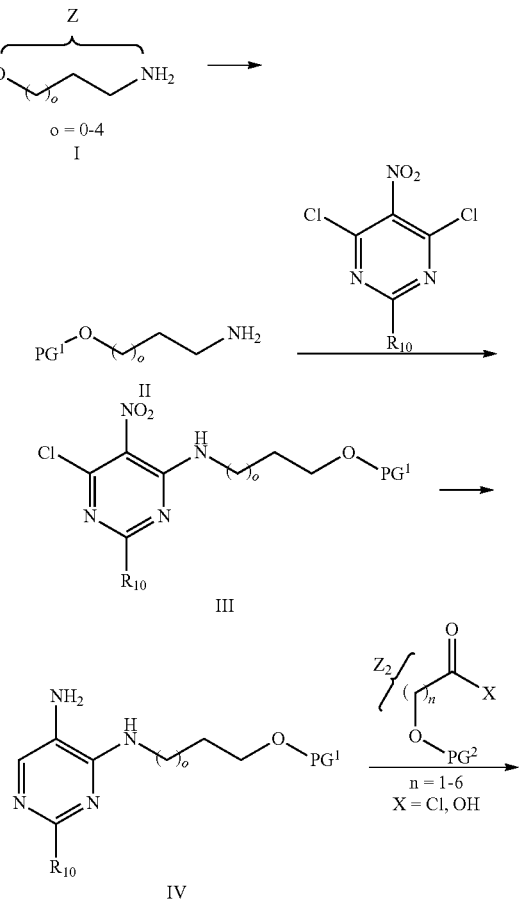

Scheme 1

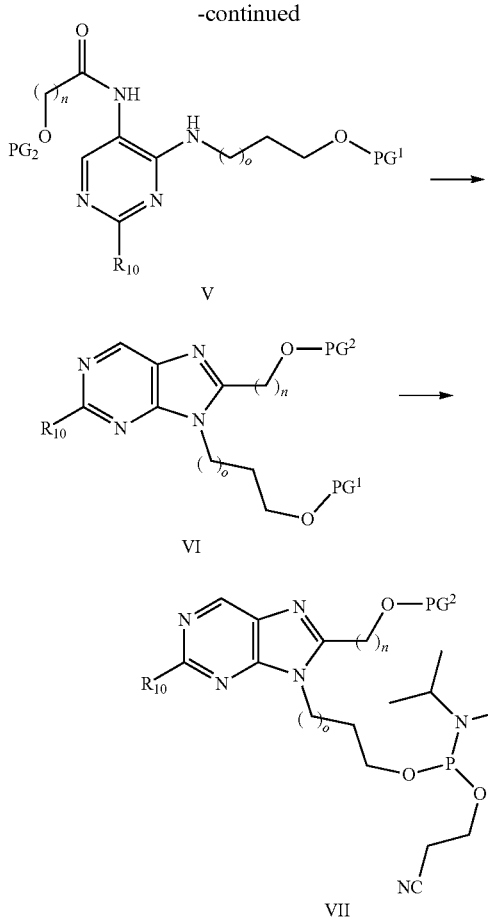

V

VI

VII

Scheme 1 depicts the synthesis of Intermediate VII starting from an amino alcohol of the structure (I) containing at least two carbon atoms separating the —OH and —NH$_2$ moieties. The alcohol functionality can be optionally protected with any appropriate group (PG$^1$), so long as the amino functionality is left unmasked, to give Intermediate II. The amine can then be added, via an S$_N$Ar reaction, to any suitably electrophilic aromatic moiety containing an appropriate leaving group (e.g. Cl or F) as well as a substituent that can be converted to an amine to give Intermediate III. Removal of any blocking/directing groups in conjunction with reduction of any activating substituents (e.g. —NO$_2$) can be effected in a stepwise or sequential fashion to give Intermediate IV. Intermediate V can be prepared from Intermediate IV by coupling of a protected (PG$^2$) alkoxy carboxylic acid, using standard reagents for activation such as EDCI, or activated carboxylic acid derivative (e.g. an acid chloride) in which the alkoxy and carbonyl functionalities are separated by at least one carbon atom (n≥1). PG$^1$ and PG$^2$ can be selected from a variety of standard protecting groups with the condition that either one can be selectively removed in the presence of the other. Intermediate V can be converted to Intermediate VI using a variety of dehydrative cyclization conditions (e.g. N,O-bis(trimethylsilyl)acetamide with heating). In case of R$_{10}$=halo (e.g. Cl) intermediate VI can be further transformed via Suzuki-, Stille-, and Negishi-type couplings to generate Intermediate VI derivatives wherein R$_2$=aryl, heteroaryl, and alkyl. Metal-mediated aryl-heteroatom cross coupling reactions can also be utilized to introduce oxygen or nitrogen functionality at R$_2$.

The protecting group (PG$^1$) can then be removed, and then the resulting free alcohol can be reacted with an activated P(III) reagent such as 3-((chloro(diisopropylamino)phosphino)oxy)propanenitrile or 3-((bis(diisopropylamino)phosphino)oxy)propanenitrile to give Intermediate VII.

Scheme 2

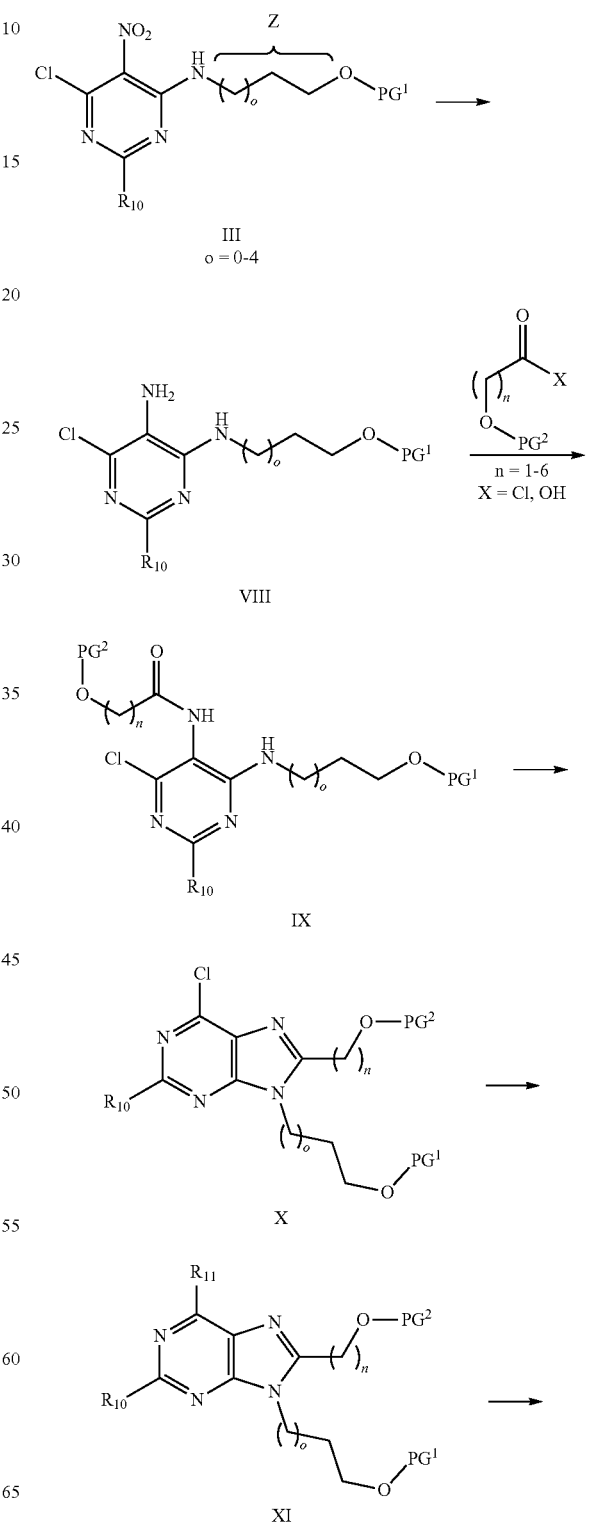

III
o = 0-4

VIII

IX

X

XI

-continued

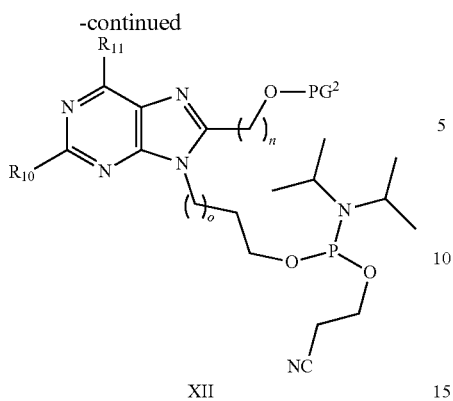

XII

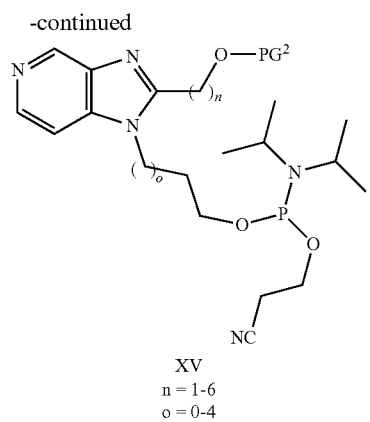

XV
n = 1-6
o = 0-4

As shown in Scheme 2, the chloro substituent of Intermediate III can be retained by chemoselective reduction of the nitro group to give Intermediate VIII. Acylation and cyclization as depicted in Scheme 1 gives Intermediates IX and X, respectively. The aryl chloride in Intermediate X can be displaced by $S_NAr$ reaction with oxygen, nitrogen, or sulfur nucleophiles to give Intermediate XI wherein $R_{11}$=—$OR_{14}$, —$NR_{14}R_{15}$, or —$SR_{14}$, and wherein $R_{14}$ and $R_{15}$ are as defined herein. Metal-mediated aryl-heteroatom cross coupling reactions can also be utilized to introduce oxygen or nitrogen functionality at $R_{11}$. Finally, Suzuki-, Stille-, and Negishi-type couplings can be used to generate Intermediate XI derivatives wherein $R_{11}$=aryl, heteroaryl, and alkyl. All aforementioned transformations to introduce $R_{11}$ can be followed by further derivatization reactions (e.g. alkylation, reductive amination, acylation, sulfonylation, etc.) to introduce additional functionality to this new substituent. After appropriate protection of the $R_{11}$ group of Intermediate XI, as needed, the phosphoramidite Intermediate XII can be prepared using the methods discussed in Scheme 1.

Additional compounds of Formula I or Formula I' of this invention can be obtained in accordance with the Schemes set forth below.

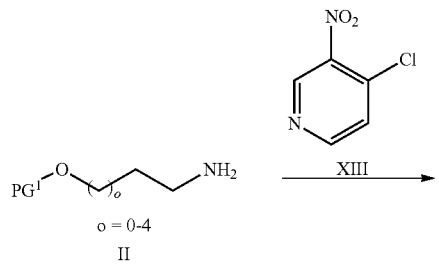

XIII

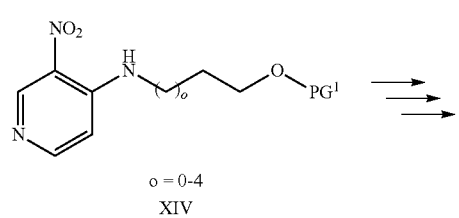

o = 0-4
XIV

Scheme 3 depicts the synthesis of Intermediate XV starting from an amino alcohol of the structure (II) described in detail for Scheme 1 and 4-chloro-3-nitropyridine XIII. Following the reaction sequence aforementioned in accordance to Scheme 1 Intermediate XV can be synthesized.

Scheme 4

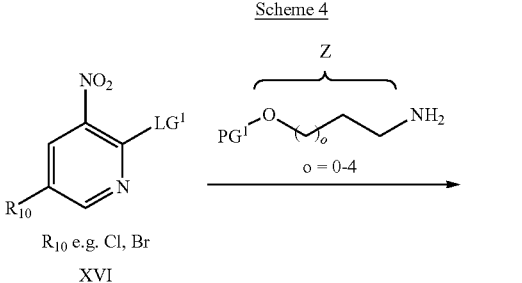

$R_{10}$ e.g. Cl, Br
XVI

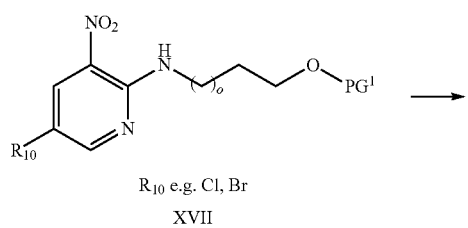

$R_{10}$ e.g. Cl, Br
XVII

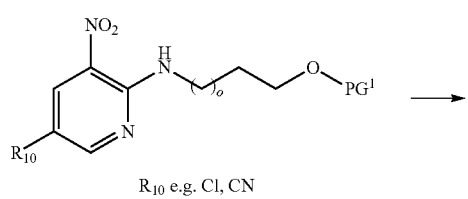

$R_{10}$ e.g. Cl, CN
XVIII

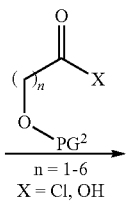

n = 1-6
X = Cl, OH

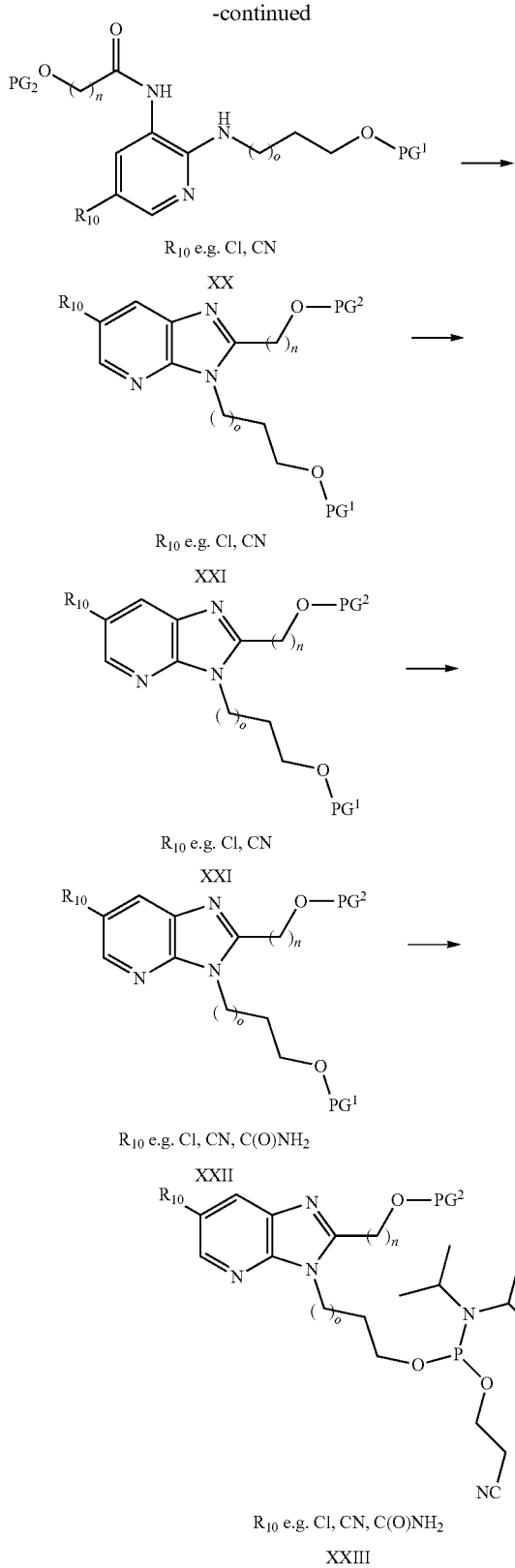

reaction with an O-protected amino-alcohol to give Intermediate XVII. If desired, transition metal-catalyzed cyanation can introduce a nitrile at this step to give intermediate XVIII that can be transformed further into various functional groups (e.g. amido or carboxylic acid). Subsequent reduction of the nitro-group gives Intermediate XIX. Acylation and cyclization as depicted in Scheme 1 gives Intermediates XX and XXI, respectively. Suzuki-, Stille-, and Negishi-type couplings can be used to generate Intermediate XXII derivatives wherein $R_{10}$=aryl, heteroaryl, and alkyl. All aforementioned manipulations to transform $R_{10}$ can be followed by further derivatization reactions (e.g. alkylation, reductive amination, acylation, sulfonylation, etc.) to introduce additional functionality to this new substituent. Following the reaction sequence aforementioned in accordance to Scheme 1 Intermediate XXIII can be synthesized.

Additional compounds of Formula I or Formula I' of this invention are accessible by incorporation of bis-heteroaryl moieties as depicted in Scheme 5.

Scheme 5

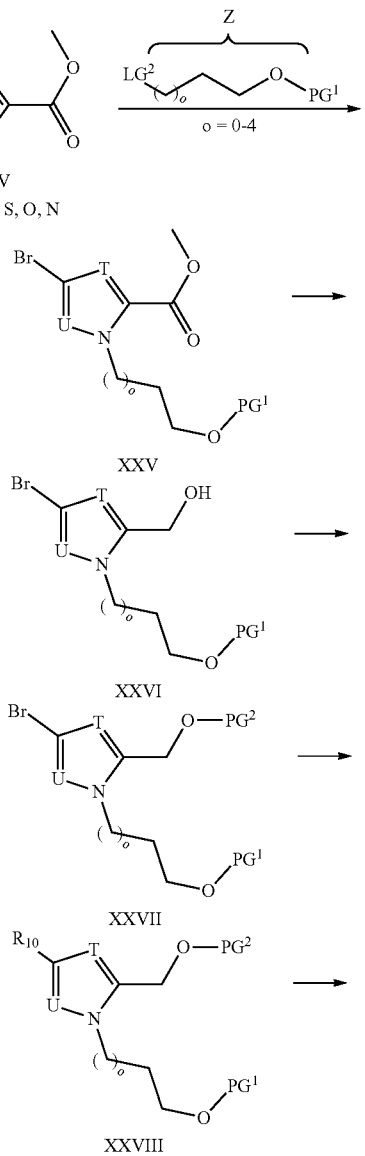

One possible synthesis of substituted imidazo-pyridines is represented in Scheme 4. Starting from an appropriately substituted pyridine XVI (e.g. $R_2$=Cl or Br), a leaving group $LG^1$ (e.g. Cl or Tosyl), can be displaced via a $S_NAr$ -continued

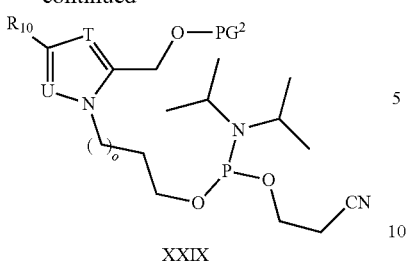

XXIX

One possible synthesis of bis-heteroaryl Intermediate XXIX starts from a 5-membered aromatic heterocycle containing at least one nitrogen suitable for attachment of an alkyl group. Additional attachments (e.g. halogen or carboxylic acid) can be introduced by someone skilled in the art or are commercially available (e.g. Intermediate XXIV with T, U=N). A substituted alkyl linker containing at least two carbon atoms separating a leaving group $LG^2$ and an alcohol functionality protected with any appropriate protecting group ($PG^1$) can be introduced via $S_N1$ reaction to generate Intermediate XXV. Subsequent reduction of the ester can be effected in various ways (e.g. $LiBH_4$) to give Intermediate XXVI. An additional protecting group $PG^2$ to generate Intermediate XXVII can be selected from a variety of standard protecting groups with the condition that either one can be selectively removed in the presence of the other. Suzuki-, Stille-, and Negishi-type couplings can then be used to generate Intermediate XXVIII derivatives wherein $R_{10}$=aryl, heteroaryl, and alkyl. All aforementioned transformations to incorporate $R_{10}$ can be followed by further derivatization reactions (e.g. alkylation, reductive amination, acylation, sulfonylation, etc.) to introduce additional functionality to this new substituent. Following the reaction sequence aforementioned in accordance to Scheme 1 Intermediate XXIX can be synthesized.

Scheme 6

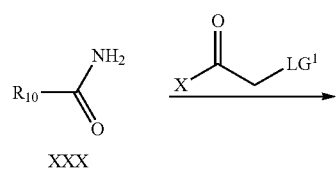

XXX

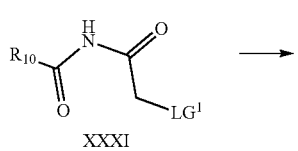

XXXI

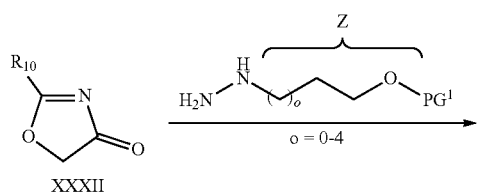

XXXII

-continued

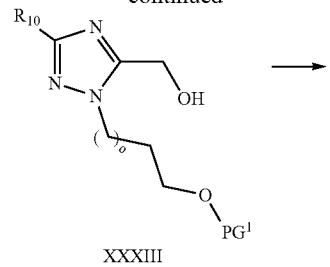

XXXIII

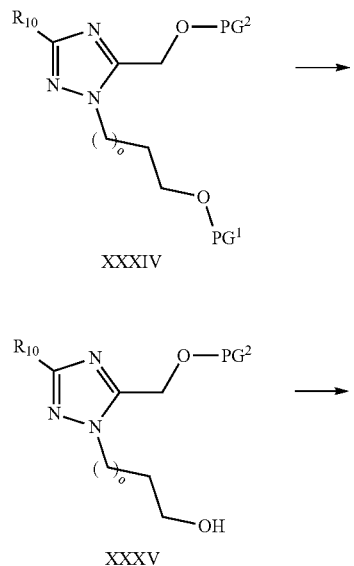

XXXIV

XXXV

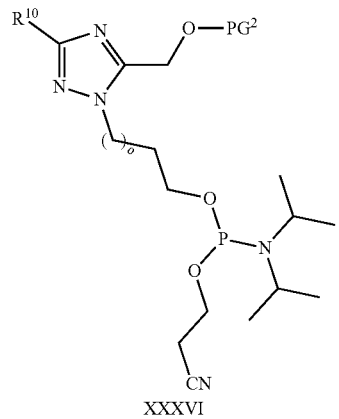

XXXVI

An alternative method to synthesize suitable bis-heteroaryl Intermediates starts from a 5- to 6-membered monocyclic heteroaryl or a 7- to 10-membered bicyclic heteroaryl substituted carboxamide which are commercially available or can be prepared by someone skilled in the art e.g. from the corresponding carboxylic acid. Intermediate XXXI can be prepared from XXX by coupling with an activated carboxylic acid derivative (e.g. an acid chloride or acid bromide) containing a suitable leaving group (e.g. Cl or Br). Treatment of Intermediate XXXI with a base (e.g. sodium hydride) does result in cyclic Intermediate XXXII which can be transformed to intermediate XXXIII by nucleophilic attack from an appropriate hydrazine derivative containing a protected hydroxyl group with at least two carbon atoms separating the —OPG¹ and hydrazine moieties. After appropriate protection of the free hydroxyl group of resulting Intermediate XXXIII, the phosphoramidite Intermediate XXXVI can be prepared using the methods discussed in Scheme 1.

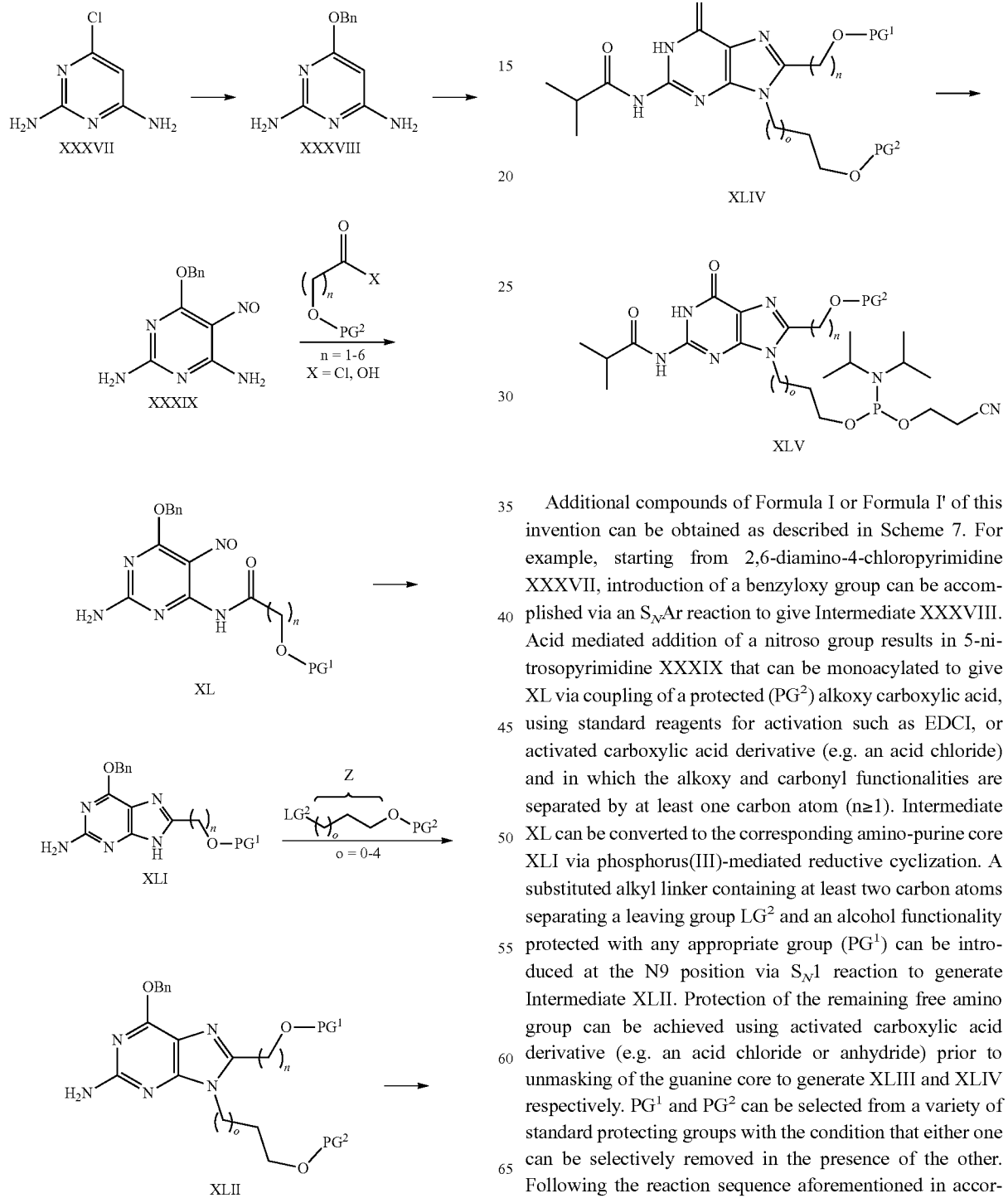

Additional compounds of Formula I or Formula I' of this invention can be obtained as described in Scheme 7. For example, starting from 2,6-diamino-4-chloropyrimidine XXXVII, introduction of a benzyloxy group can be accomplished via an $S_NAr$ reaction to give Intermediate XXXVIII. Acid mediated addition of a nitroso group results in 5-nitrosopyrimidine XXXIX that can be monoacylated to give XL via coupling of a protected (PG²) alkoxy carboxylic acid, using standard reagents for activation such as EDCI, or activated carboxylic acid derivative (e.g. an acid chloride) and in which the alkoxy and carbonyl functionalities are separated by at least one carbon atom (n≥1). Intermediate XL can be converted to the corresponding amino-purine core XLI via phosphorus(III)-mediated reductive cyclization. A substituted alkyl linker containing at least two carbon atoms separating a leaving group LG² and an alcohol functionality protected with any appropriate group (PG¹) can be introduced at the N9 position via $S_N1$ reaction to generate Intermediate XLII. Protection of the remaining free amino group can be achieved using activated carboxylic acid derivative (e.g. an acid chloride or anhydride) prior to unmasking of the guanine core to generate XLIII and XLIV respectively. PG¹ and PG² can be selected from a variety of standard protecting groups with the condition that either one can be selectively removed in the presence of the other. Following the reaction sequence aforementioned in accordance to Scheme 1 Intermediate XLV can be synthesized.

Scheme 8

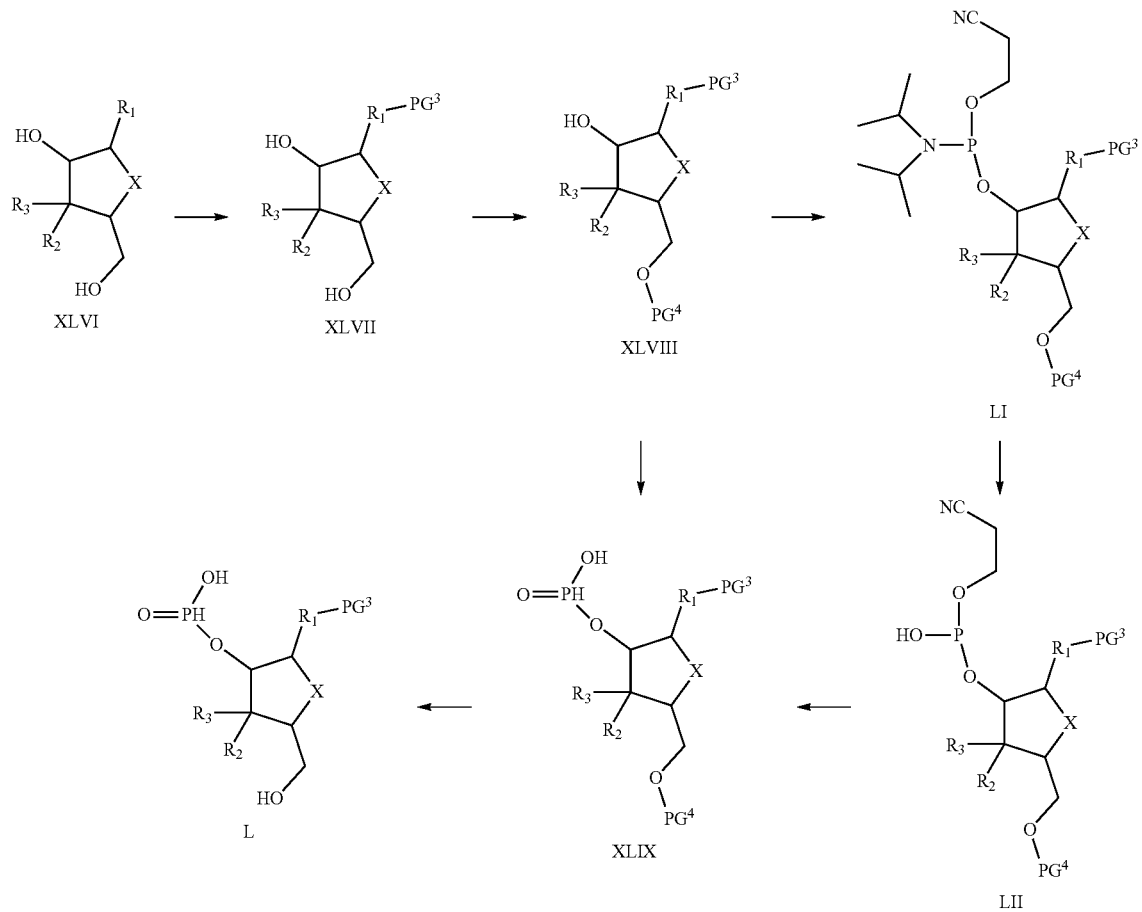

Scheme 8 depicts methods for the preparation of an intermediate possessing an H-phosphonate-containing 5-membered ring attached to a heteroaryl. Methods for the preparation of Intermediate XLVI wherein $R_2$ or $R_3$ are not —OH are abundant in the literature, and several are also commercially available. The regioselective preparation of Intermediate XLVI in which $R_2$ or $R_3$ is a protected hydroxyl is also known in the literature. The starting materials needed for Scheme 8 can be prepared using one of these literature methods or they can be purchased. The $R_2$ and/or $R_3$ groups can first be protected, as needed, with any number of common protecting groups. Depending on the protecting group reagent employed, the free hydroxyl groups of Intermediate XLVI can be transiently protected, if necessary, with a trimethylsilyl group by the action of TMSCl and a base. After protection of $R_1$, the trimethylsilyl group can be removed during the reaction workup to give Intermediate XLVII. The primary alcohol of this intermediate can be selectively protected ($PG^4$) in the presence of the more crowded secondary alcohol, particularly when a bulky protecting group such as trityl or dimethoxytrityl is used to generate XLVIII. The requisite H-phosphonate Intermediate XLIX can be prepared via a number of different routes. One simple method involves treatment of Intermediate XLVIII with diphenyl phosphite followed by mild basic hydrolysis of the phosphorus adduct to provide the H-phosphonate XLIX directly. Removal of $PG^4$ gives coupling partner L.

Also shown in Scheme 8 is an alternative synthesis of an H-phosphonate-containing 5-membered ring using O-cyanoethyl-protected phosphoramidites of the structure LI of which several are commercially available. Phosphoramidites LI are also accessible from the corresponding alcohol XLVIII employing N,N-diisopropylmethylphosphonamidic chloride and a base or using 2-cyanoethyl N,N,N',N'-tetraisopropylphosphoramidite in the presence of a weak acid such as pyridinium trifluoroacetate. The N,N-diisopropyl group of LI can be replaced by an —OH in the presence of $H_2O$ and a weak acid, such as pyridinium trifluoroacetate to give Intermediate LII. The cyanoethyl group of this intermediate can then be removed by the action of a non-nucleophilic amine base, such as tert-butylamine to give Intermediate XLIX. Removal of $PG^4$ utilizing appropriate conditions for the protecting group generates coupling partner L.

Scheme 9

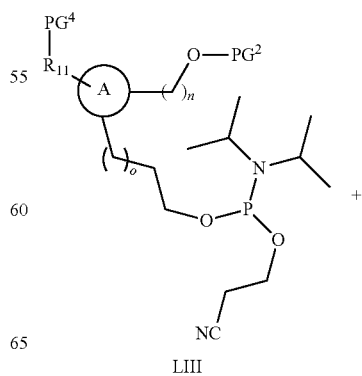

LIII

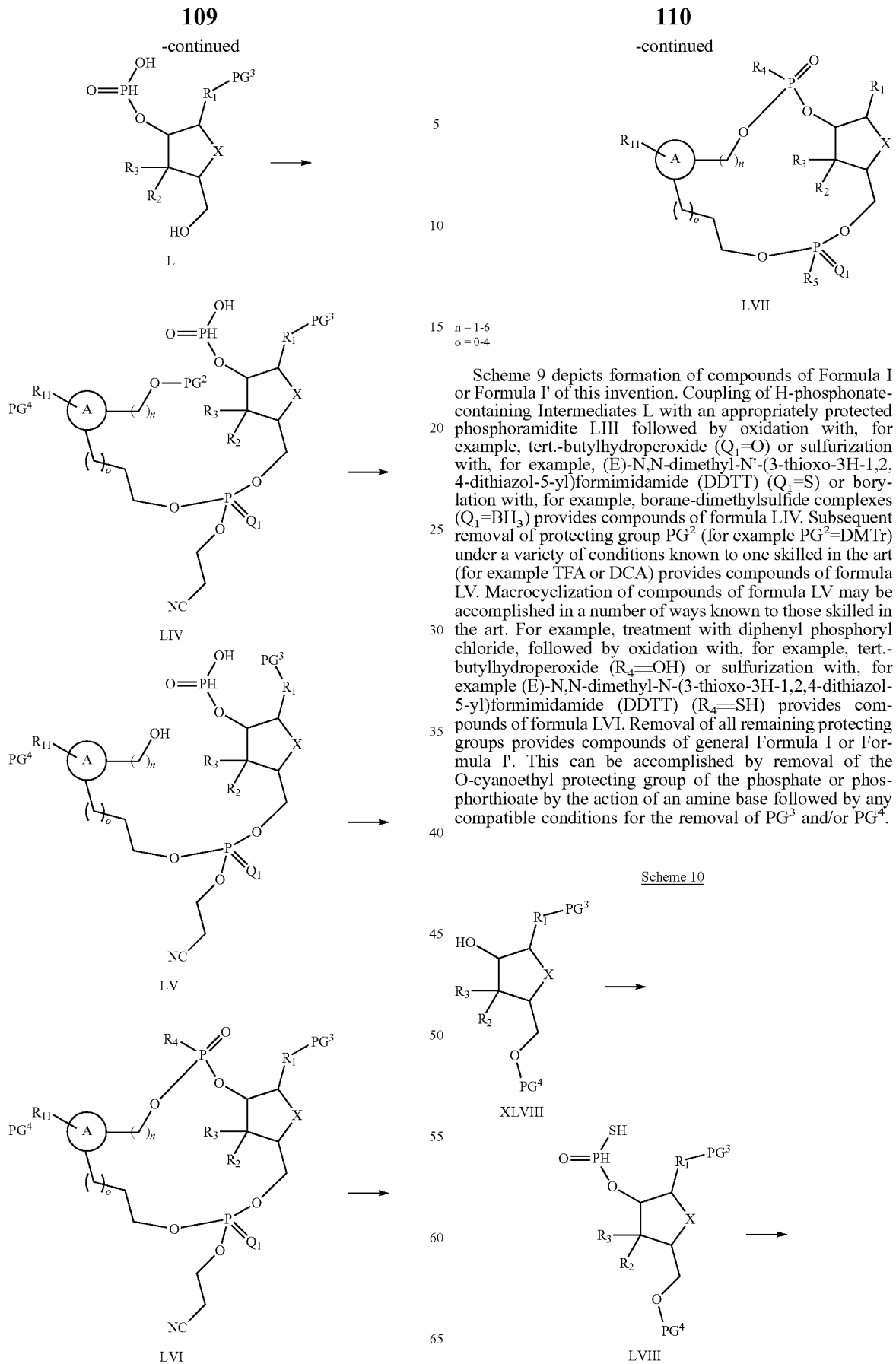

n = 1-6
o = 0-4

Scheme 9 depicts formation of compounds of Formula I or Formula I' of this invention. Coupling of H-phosphonate-containing Intermediates L with an appropriately protected phosphoramidite LIII followed by oxidation with, for example, tert.-butylhydroperoxide ($Q_1$=O) or sulfurization with, for example, (E)-N,N-dimethyl-N'-(3-thioxo-3H-1,2,4-dithiazol-5-yl)formimidamide (DDTT) ($Q_1$=S) or borylation with, for example, borane-dimethylsulfide complexes ($Q_1$=$BH_3$) provides compounds of formula LIV. Subsequent removal of protecting group $PG^2$ (for example $PG^2$=DMTr) under a variety of conditions known to one skilled in the art (for example TFA or DCA) provides compounds of formula LV. Macrocyclization of compounds of formula LV may be accomplished in a number of ways known to those skilled in the art. For example, treatment with diphenyl phosphoryl chloride, followed by oxidation with, for example, tert.-butylhydroperoxide ($R_4$=OH) or sulfurization with, for example (E)-N,N-dimethyl-N-(3-thioxo-3H-1,2,4-dithiazol-5-yl)formimidamide (DDTT) ($R_4$=SH) provides compounds of formula LVI. Removal of all remaining protecting groups provides compounds of general Formula I or Formula I'. This can be accomplished by removal of the O-cyanoethyl protecting group of the phosphate or phosphorthioate by the action of an amine base followed by any compatible conditions for the removal of $PG^3$ and/or $PG^4$.

Scheme 10

Scheme 10 depicts the preparation of H-thiophosphonates used in the synthesis of certain phosphorodithioates of the invention. Alcohol XLVIII can be reacted with a P(III) electrophile, such as diphenylphosphite, followed by treatment of the intermediate with a sulfide nucleophile, such as lithium sulfide, to give LVIII. The protecting group (PG⁴) can be removed using appropriate conditions to give LIX. LIX can then be substituted for L in Scheme 9 and the remainder of the chemistry depicted in the scheme can be carried out to give LVII wherein the "northern" phosphate group is a phosphorodithioate.

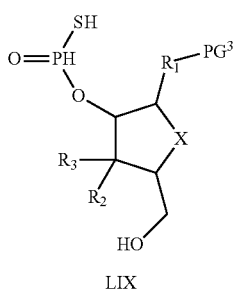

LIX

Scheme 11

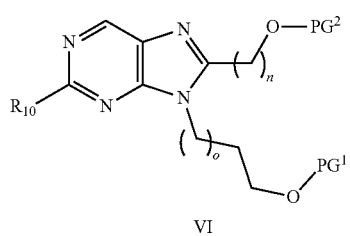

VI

↓

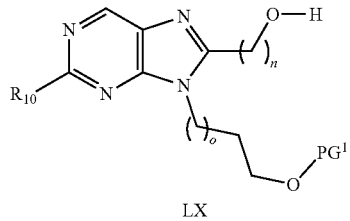 + 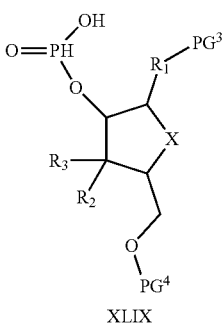

LX      XLIX

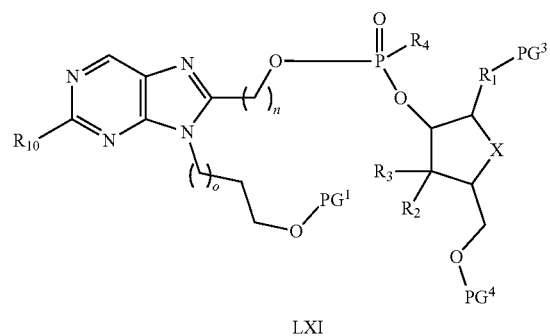

LXI

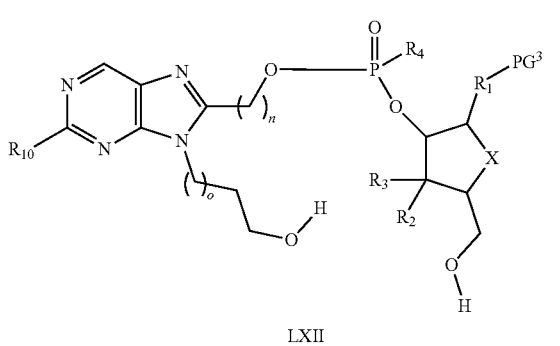 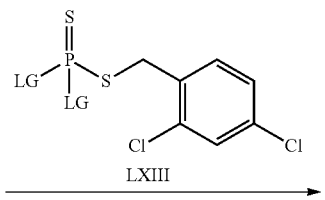

LXII     LXIII

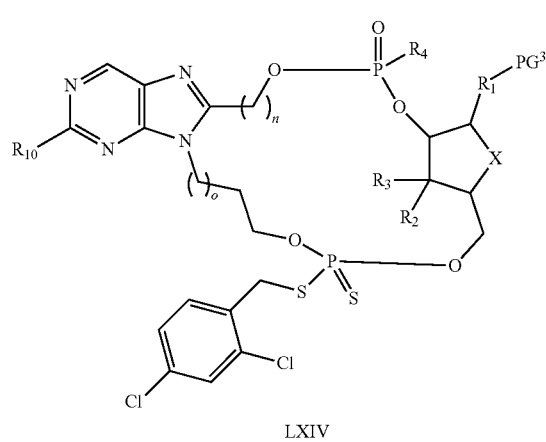

LXIV n = 1-6
o = 0-4

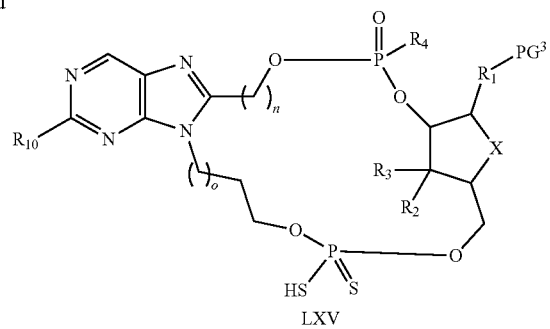

LXV

Scheme 11 depicts a method for the preparation of a compound of the invention wherein the "southern" phosphate or thiophosphate has been replaced with a phosphorodithioate. $PG^2$ can be selectively removed from VI to give LX using appropriate conditions previously described. LX can be coupled with XLIX by activation of the H-phosphonate of XLIX with a reagent such as diphenylphosphoryl chloride followed by reaction with LX and then oxidation or oxidative sulfurization of the resulting P(III) intermediate to give LXI. Both protecting groups ($PG^1$ and $PG^4$) can be selectively removed in the presence of any other protecting groups to give diol LXII. LXII can be cyclized by the action of an appropriately substituted reagent LXIII containing two appropriate leaving groups (LG) to give LXIV. LXIV can then be treated with a suitable thiol nucleophile to unmask the phosphorodithioate functionality to give LXV. Global deprotection of LXV can then provide the final phosphorodithioate targets of the invention.

EXAMPLES

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise.

Abbreviations as used herein, are defined as follows: Ac=acetyl; AcCl=acetyl chloride; $Ac_2O$=acetic anhydride; ACN=acetonitrile; AcOH=acetic acid; AIBN=Azobisisobutyronitrile; app=apparent; aq.=aqueous, Avi=peptide sequence allowing biotinylation by the enzyme BirA; BLI=bioluminescence imaging; Bn=benzyl; brine=saturated aqueous sodium chloride; BSA (chemistry)=N,O-bis(trimethylsilyl)acetamide; BSA (biology)=bovine serum albumin; br=broad; t-BuOH=tert-butyl alcohol; $Bu_2SnO$=Dibutyltin(IV) oxide; Bz=benzoyl; comp=complex multiplet (non-magnetically equivalent overlapping signals); d=doublet; DBU=1,8-Diazabicyclo[5.4.0]undec-7-ene; DCA=dichloroacetic acid; DCM=dichloromethane; dd=doublet of doublets; ddd=doublet of doublets of doublets; DDTT=(E)-N,N-dimethyl-N'-(3-thioxo-3H-1,2,4-dithiazol-5-yl)formimidamide; dq=doublet of quartets; dt=doublet of triplets; $(DHQ)_2$Pyr=Hydroquinine 2,5-diphenyl-4,6-pyrimidinediyl diether; DIEA=diisopropylethylamine; DMA=dimethylacetamide; DMAP=4-N,N-dimethylaminopyridine; DIEA=N,N-diisopropylethylamine; DMOCP=2-chloro-5,5-dimethyl-1,3,2-dioxaphosphorinane 2-oxide; DMSO=dimethylsulfoxide; DMTr=4,4'-dimethoxytriphenylmethyl; DMTrCl=4,4'-dimethoxytriphenylmethyl chloride; EA=EtOAc=ethyl acetate; EtOH=ethanol; $Et_3N$=triethylamine; eq=Equivalents; GAPDH=Glyceraldehyde 3-phosphate dehydrogenase; HCl=hydrochloric acid; HEK=human embryonic kidney cell line; hept=heptet; HIS=polyhistidine-tag; HPLC=high performance liquid chromatography; hr=hour; hrs=hours; LCMS=liquid chromatography-mass spectrometry; m=multiplet; $MeNH_2$=methylamine; MeOH=methanol; MeONa=sodium methoxide; min=minutes; MPLC=medium pressure liquid chromatography; MS=molecular sieves; NaOAc=sodium acetate; MPLC=medium pressure liquid chromatography; NP-MPLC=normal phase medium pressure liquid chromatography; PBS=phosphate buffered saline; PBMC=human peripheral blood mononuclear cells; PE=petroleum ether; PG=protecting group; PVDF Membrane=polyvinylidene difluoride membrane; PVT=polyvinyltoluene; prep. RP-HPLC=preparative reverse phase HPLC; Py=pyridine; Py.TFA=pyridinium trifluoroacetate; quant=quantitative yield; q=quartet; RAW=murine macrophage cancer cell line; RP=reverse phase; RT=room temperature; s=singlet; sat.=saturated, SDS-PAGE=sodium dodecyl sulfate polyacrylamide gel electrophoresis; SEAP=secreted alkaline phosphatase; SPA=scintillation proximity assay; SUMO=small ubiquitin-like modifier tag; t=tertiary; TBAF=tetrabutylammonium fluoride; TBDPS=tert-butyldiphenylsilyl; TBDPSCl=tert-butyldiphenylsilyl chloride; TBSCl=tert-butyldimethylsilyl chloride; TBS=tert-butyldimethylsilyl; TEA=triethylamine; TES=triethylsilane, TFA=trifluoroacetic acid; THF=tetrahydrofuran; THP1=Tohoku-Hospital Pediatrics-1 human monocytic cell line derived from an acute monocytic leukemia patient; TMSCl=chlorotrimethylsilane; TMSOTf=Trimethylsilyl trifluoromethanesulfonate; $T_R$=retention time (minutes); and Tris=tris(hydroxymethyl)aminomethane.

Names of compounds as used herein, were generated as follows: Names for linear intermediates were created using Chemdraw (CambridgeSoft) version 12.0.2. These names were generated using the "Convert Structure to Name" functionality found in the "Structure" menu. Names for all macrocyclic intermediates and final compounds were generated using MarvinSketch (Chemaxon Ltd.) version 18.22. These names were generated by using the "Preferred IUPAC Name" option in the "Generate Name . . . " utility found in the "Structure" menu.

Compounds were analyzed on an Acquity Ultra Performance Liquid Chromatography system employing an Acquity UPLC BEH C18, 1.7 μm, 2.1×50 mm column. Detection was via an Aquity Ultra Performance LC PDA detector and an Acquity SQD single quadrupole mass spectrometer using $H_2O+0.1\%$ formic acid (A) and $ACN+0.1\%$ formic acid (B) as eluents. Unless specified elsewhere, Method A was used for all LCMS analyses.

Method A—Gradient: 0-0.1 min—Isocratic—10% B; 0.1-1.3 min—Linear gradient 10%-90% B; 1.3-1.8 min—Isocratic 90% B. Flow rate: 0.6 mL/min.

Method B—Gradient: 0-0.1 min—Isocratic—1% B; 0.1-1.3 min—Linear gradient 1%-50% B; 1.3-1.8 min—Isocratic 50% B. Flow rate: 0.6 mL/min.

Method C—Gradient: 0-0.1 min—Isocratic—0.5% B; 0.1-1.3 min—Linear gradient 0.5%-50% B; 1.3-1.8 min—Isocratic 50% B. Flow rate: 0.6 mL/min.

Method D—Gradient: 0-0.1 min—Isocratic—100% A; 0.1-1.5 min—Linear gradient 0%-20% B; 1.5-2.0 min—Isocratic 20% B. Flow rate: 0.6 mL/min.

Method E—Gradient: 0-0.1 min—Isocratic—40% B; 0.1-1.3 min—Linear gradient 40%-95% B; 1.3-1.8 min—Isocratic 95% B. Flow rate: 0.6 mL/min.

NMR Spectroscopy Method: $^1$H NMR (400 MHz); $^{19}$F NMR (376 MHz), run in decoupled mode; and $^{31}$P NMR (162 MHz), run in decoupled mode; Spectroscopy was conducted on a Bruker 400 MHz Avance II FTNMR Spectrometer. $^1$H NMR chemical shifts (δ) are reported in parts per million (ppm) and referenced to the residual C—H signal from the deuterated solvent indicated.

Intermediate 1

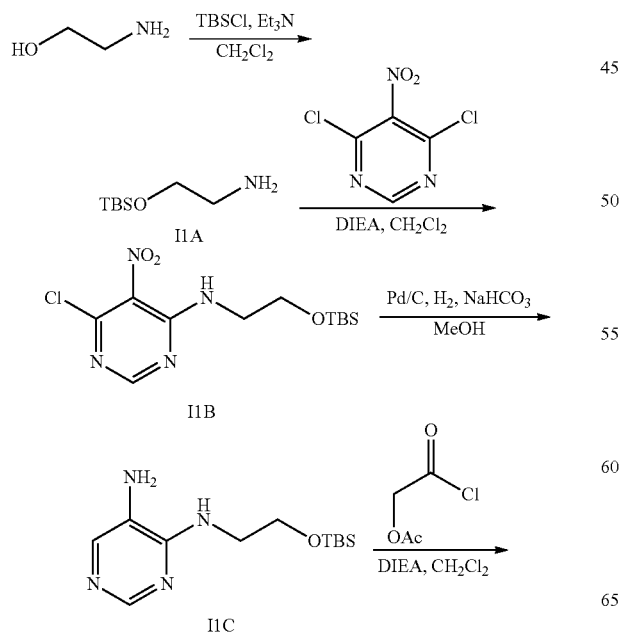

2-((tert-Butyldimethylsilyl)oxy)ethanamine (I1A)

To a solution of 2-aminoethanol (2.50 g, 40.9 mmol) in DCM (50 mL) was added $Et_3N$ (6.30 mL, 45.20 mmol) followed by a solution of TBSCl (6.20 g, 41.1 mmol) in DCM (20 mL) at RT over 10 minutes. The reaction mixture was stirred at RT for 4 hrs, whereupon it was diluted with DCM and washed with saturated, aq. $NaHCO_3$, then brine. The organic layer was dried ($Na_2SO_4$) and then concentrated under reduced pressure to give I1A (6.86 g, 96%) as a clear, colorless oil. ¹H NMR (CDCl₃) δ 3.60 (t, J=5.3 Hz, 2H), 2.74 (t, J=5.3 Hz, 2H), 0.88 (s, 9H), 0.05 (s, 6H).

N-(2-((tert-Butyldimethylsilyl)oxy)ethyl)-6-chloro-5-nitropyrimidin-4-amine (I1B)

To a solution of 4,6-dichloro-5-nitropyrimidine (7.59 g, 39.1 mmol) in DCM (150 mL) cooled to −78° C. was added DIEA (6.00 mL, 43.1 mmol) followed by I1A (6.86 g, 39.1 mmol) as a solution in DCM (50 mL) over 1 hr. The reaction mixture was stirred at −78° C. for 5 hrs, then at RT overnight. The resulting solution was diluted with DCM, and then washed with sat. aq. NaHCO₃, water, and brine. The organic layer was dried (MgSO₄) and then concentrated under reduced pressure. The residue was purified by silica gel chromatography (0-10% MeOH/DCM) to give I1B (9.92 g, 76%) as a pale yellow oil. LCMS m/z 333.1 (M+H)⁺. ¹H NMR (CDCl₃) δ 8.36 (s, 1H), 7.88 (br s, 1H), 3.81-3.78 (m, 2H), 3.74-3.70 (m, 2H), 0.89 (s, 9H), 0.06 (s, 6H).

N4-(2-((tert-Butyldimethylsilyl)oxy)ethyl)pyrimidine-4,5-diamine (I1C)

A mixture of I1B (1.00 g, 3.00 mmol), 10% Pd/C (200 mg), and NaHCO₃ (505 mg, 6.01 mmol) in MeOH (50 mL) was hydrogenated at 50 psi H₂ overnight using a Parr shaker. The reaction mixture was filtered through a pad of Celite® and the filtrate was concentrated under reduced pressure. The residue was partitioned between EtOAc and H₂O. The organic layer was removed and washed with sat. aq. NH₄Cl, H₂O, and then brine. The organic layer was dried (MgSO₄) and then concentrated under reduced pressure. The residue was purified by silica gel chromatography (0-10% MeOH/DCM) to give I1C (722 mg, 90%) as a light tan solid. LCMS m/z 269.2 (M+H)⁺. ¹H NMR (CDCl₃) δ 8.20 (s, 1H), 7.67 (s, 1H), 5.45 (br s, 1H), 3.75 (t, J=5.0 Hz, 2H), 3.55 (t, J=5.0 Hz, 2H), 3.23 (br s, 2H), 0.83 (s, 9H), −0.01 (s, 6H).

2-((4-((2-((tert-Butyldimethylsilyl)oxy)ethyl)amino)pyrimidin-5-yl)amino)-2-oxoethyl acetate (I1D)

To a solution of I1C (722 mg, 2.69 mmol) in DCM (15 mL) was added DIEA (609 μL, 3.50 mmol), and the resulting mixture was cooled to 0° C. 2-Chloro-2-oxoethyl acetate (304 μL, 2.83 mmol) was added in a dropwise fashion. The resulting mixture was stirred at 0° C. for 1 hr, then allowed to warm to RT and stirred overnight. The reaction mixture was diluted with DCM, and washed with sat. aq. NaHCO₃, H₂O, and brine. The organic layer was dried (MgSO₄), and then concentrated under reduced pressure to give I1D (901 mg, 91%) as a pale yellow oil. LCMS m/z 369.3 (M+H)⁺. ¹H NMR (CDCl₃) δ 8.43 (s, 1H), 8.30 (br s, 1H), 8.05 (s, 1H), 5.73 (br t, J=5.0 Hz, 1H), 4.68 (s, 2H), 3.74 (t, J=5.5 Hz, 2H), 3.57 (dt, J=5.5, 5.0 Hz, 2H), 2.15 (s, 3H), 0.85 (s, 9H), 0.02 (s, 6H).

(9-(2-((tert-Butyldimethylsilyl)oxy)ethyl)-9H-purin-8-yl)methyl acetate (I1E)

A mixture of I1D (901 mg, 2.45 mmol) and BSA (10 mL) was heated at 90° C. for 4 hrs, and then cooled to RT. The reaction mixture was diluted with DCM, and washed with sat. aq. NaHCO₃, H₂O, and brine. The organic layer was dried over MgSO₄, and then filtered. To the filtrate was added silica gel (10 g), and then the mixture was concentrated under reduced pressure. The preadsorbed material was purified by silica gel chromatography (0-1.5% MeOH/DCM) to give I1E (740 mg, 86%) as a pale yellow solid. LCMS m/z 351.2 (M+H)⁺. ¹H NMR (CDCl₃) δ 8.89 (s, 1H), 8.75 (s, 1H), 5.28 (s, 2H), 4.31 (t, J=5.1 Hz, 2H), 3.78 (t, J=5.1 Hz, 2H), 1.96 (s, 3H), 0.54 (s, 9H), −0.37 (s, 6H).

(9-(2-((tert-Butyldimethylsilyl)oxy)ethyl)-9H-purin-8-yl)methanol (I1F)

A mixture of I1E (1.20 g, 3.42 mmol) and K₂CO₃ (47.0 mg, 0.340 mmol) in MeOH (60 mL) was stirred at RT overnight, and then concentrated under reduced pressure. The residue was partitioned between EtOAc and H₂O. The organic layer was removed and the aqueous layer was extracted with EtOAc (2×). The combined organic layers were washed with brine, dried (MgSO₄), and then concentrated under reduced pressure to give I1F (1.01 g, 95%) of sufficient purity for subsequent transformations. LCMS m/z 308.2 (M+H)⁺. ¹H NMR (CDCl₃) δ 9.01 (s, 1H), 8.89 (s, 1H), 4.99 (s, 2H), 4.75 (br s, 1H), 4.47 (t, J=5.0 Hz, 2H), 3.98 (t, J=5.0 Hz, 2H), 0.70 (s, 9H), −0.20 (s, 6H).

8-((Bis(4-methoxyphenyl)(phenyl)methoxy)methyl)-9-(2-((tert-butyldimethylsilyl)oxy)ethyl)-9H-purine (I1G)

A mixture of I1F (1.01 g, 3.27 mmol) and DMTrCl (1.33 g, 3.93 mmol) in pyridine (11 mL) was stirred at RT overnight. The resulting mixture was concentrated under reduced pressure, and then the residue was redissolved in DCM (20 mL). Silica gel (5 g) was added, and the mixture was concentrated to dryness under reduced pressure. The residue was purified by silica gel chromatography (0-10% MeOH/DCM) to give I1G (2.05 g, quant) as a white solid. LCMS m/z 610.3 (M+H)⁺. ¹H NMR (CDCl₃) δ 9.06 (s, 1H), 8.92 (s, 1H), 7.48-7.14 (comp, 9H), 6.83 (d, J=8.8 Hz, 4H), 4.50 (s, 2H), 4.35 (t, J=5.4 Hz, 2H), 3.78-3.75 (comp, 8H), 0.57 (s, 9H), −0.39 (s, 6H).

2-(8-((Bis(4-methoxyphenyl)(phenyl)methoxy)methyl)-9H-purin-9-yl)ethanol (I1H)

To a solution of I1G (2.10 g, 3.44 mmol) in THF (20 mL) cooled to −5° C. was added TBAF/THF (1 M, 4.40 mL, 4.40 mmol) in a slow, dropwise fashion. The reaction mixture was stirred at 0° C. for 1.5 hrs, whereupon silica gel (5 g) was added. The resulting mixture was concentrated under reduced pressure, and then purified by silica gel chromatography (0-10% MeOH/DCM) to give I1H (1.29 g, 77%) as a white solid. LCMS m/z 497.3 (M+H)⁺. ¹H NMR (CDCl₃) δ 9.09 (s, 1H), 8.92 (s, 1H), 7.47-7.23 (comp, 9H), 6.85 (d, J=9.0 Hz, 4H), 4.49 (s, 2H), 4.26 (t, J=4.8 Hz, 2H), 3.88 (dt, J=5.6, 4.8 Hz, 2H), 3.78 (s, 6H), 3.38 (br t, J=5.6 Hz, 1H).

2-(8-((Bis(4-methoxyphenyl)(phenyl)methoxy)methyl)-9H-purin-9-yl)ethyl (2-cyanoethyl) diisopropylphosphoramidite (Intermediate 1)

To a solution of I1H (1.29 g, 2.60 mmol) in ACN (13 mL) was added DIEA (1.36 mL, 7.81 mmol) followed by dropwise addition of neat 3-((chloro(diisopropylamino)phosphino)oxy)propanenitrile (0.78 mL, 3.12 mmol). The reaction mixture was stirred at RT for 2 hrs, and then quenched by the addition of 5% aq. NaHCO₃ (1 mL). The resulting mixture was stirred for 10 min, and then partially concentrated under reduced pressure. The remaining solution was purified directly by RP-MPLC (5-100% ACN/H₂O containing 0.04% NH₄HCO₃) to give Intermediate 1 (1.40 g, 77%) as a white foam. LCMS m/z 614.3 (M+H+OH-N,N-diisopropylamino)⁺. ¹H NMR (CDCl₃) δ 9.05 (s, 1H), 8.92 (s, 1H), 7.47-7.19 (comp, 5H), 7.37 (d, J=9.0 Hz, 4H), 6.83 (d, J=9.0 Hz, 4H), 4.55 (d, J=11.8 Hz, 1H), 4.50 (d, J=11.8 Hz, 1H), 4.47-4.44 (comp, 2H), 3.86-3.72 (comp, 2H), 3.76 (s, 6H), 3.48-3.43 (comp, 2H), 3.33-3.24 (comp, 2H), 2.38 (t, J=6.3 Hz, 2H), 1.01 (d, J=6.8 Hz, 6H), 0.84 (d, J=6.8 Hz, 6H). $^{31}$P NMR (CDCl$_3$) δ 148.1.

Intermediate 2

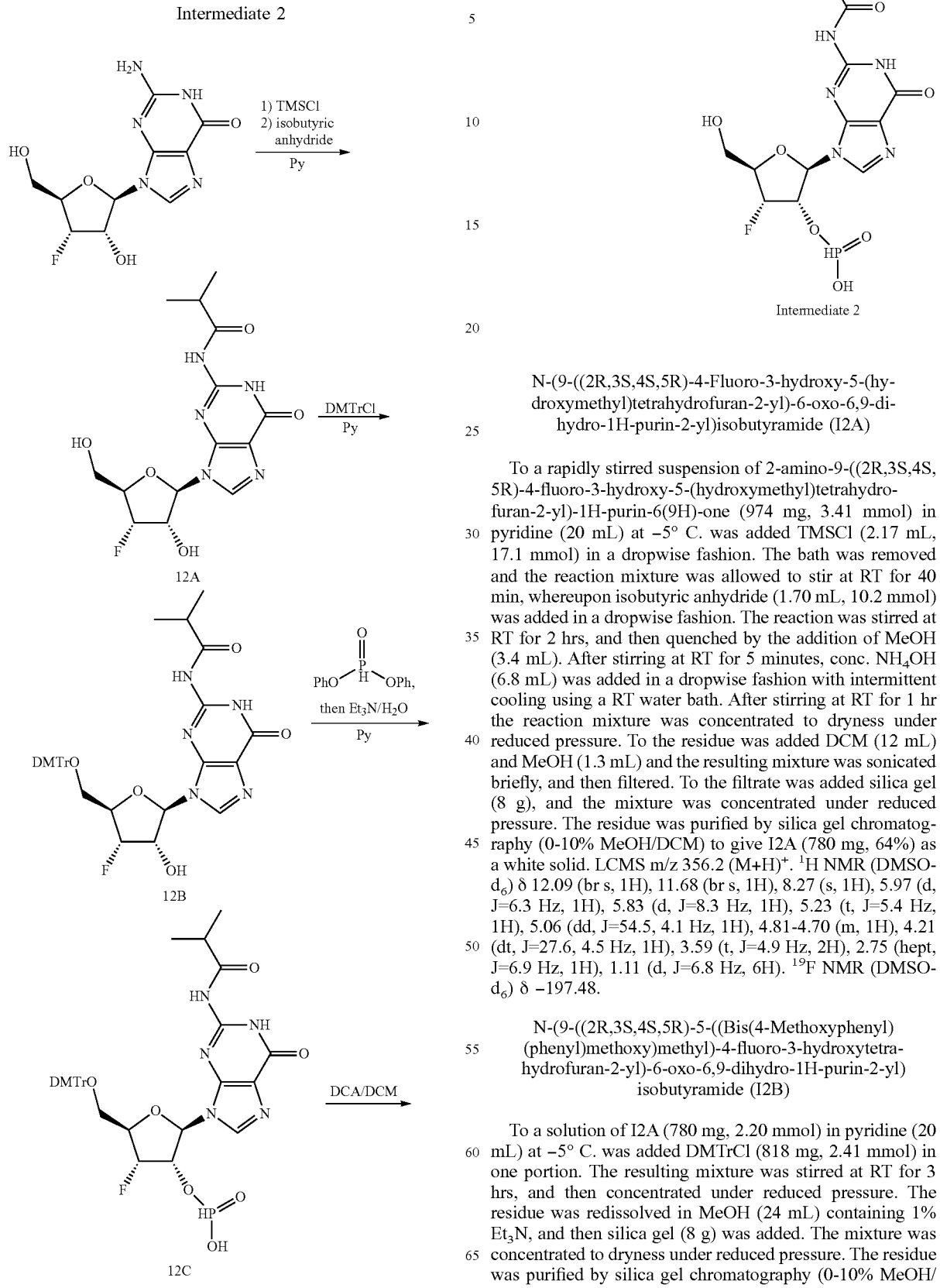

Intermediate 2

N-(9-((2R,3S,4S,5R)-4-Fluoro-3-hydroxy-5-(hydroxymethyl)tetrahydrofuran-2-yl)-6-oxo-6,9-dihydro-1H-purin-2-yl)isobutyramide (I2A)

To a rapidly stirred suspension of 2-amino-9-((2R,3S,4S,5R)-4-fluoro-3-hydroxy-5-(hydroxymethyl)tetrahydrofuran-2-yl)-1H-purin-6(9H)-one (974 mg, 3.41 mmol) in pyridine (20 mL) at −5° C. was added TMSCl (2.17 mL, 17.1 mmol) in a dropwise fashion. The bath was removed and the reaction mixture was allowed to stir at RT for 40 min, whereupon isobutyric anhydride (1.70 mL, 10.2 mmol) was added in a dropwise fashion. The reaction was stirred at RT for 2 hrs, and then quenched by the addition of MeOH (3.4 mL). After stirring at RT for 5 minutes, conc. NH$_4$OH (6.8 mL) was added in a dropwise fashion with intermittent cooling using a RT water bath. After stirring at RT for 1 hr the reaction mixture was concentrated to dryness under reduced pressure. To the residue was added DCM (12 mL) and MeOH (1.3 mL) and the resulting mixture was sonicated briefly, and then filtered. To the filtrate was added silica gel (8 g), and the mixture was concentrated under reduced pressure. The residue was purified by silica gel chromatography (0-10% MeOH/DCM) to give I2A (780 mg, 64%) as a white solid. LCMS m/z 356.2 (M+H)$^+$. $^1$H NMR (DMSO-d$_6$) δ 12.09 (br s, 1H), 11.68 (br s, 1H), 8.27 (s, 1H), 5.97 (d, J=6.3 Hz, 1H), 5.83 (d, J=8.3 Hz, 1H), 5.23 (t, J=5.4 Hz, 1H), 5.06 (dd, J=54.5, 4.1 Hz, 1H), 4.81-4.70 (m, 1H), 4.21 (dt, J=27.6, 4.5 Hz, 1H), 3.59 (t, J=4.9 Hz, 2H), 2.75 (hept, J=6.9 Hz, 1H), 1.11 (d, J=6.8 Hz, 6H). $^{19}$F NMR (DMSO-d$_6$) δ −197.48.

N-(9-((2R,3S,4S,5R)-5-((Bis(4-Methoxyphenyl)(phenyl)methoxy)methyl)-4-fluoro-3-hydroxytetrahydrofuran-2-yl)-6-oxo-6,9-dihydro-1H-purin-2-yl)isobutyramide (I2B)

To a solution of I2A (780 mg, 2.20 mmol) in pyridine (20 mL) at −5° C. was added DMTrCl (818 mg, 2.41 mmol) in one portion. The resulting mixture was stirred at RT for 3 hrs, and then concentrated under reduced pressure. The residue was redissolved in MeOH (24 mL) containing 1% Et$_3$N, and then silica gel (8 g) was added. The mixture was concentrated to dryness under reduced pressure. The residue was purified by silica gel chromatography (0-10% MeOH/DCM containing 1% Et$_3$N) to give I2B (1.20 g, 83%) as a white solid. LCMS m/z 658.4 (M+H)+. $^1$H NMR (DMSO-$d_6$) δ 12.06 (br s, 1H), 11.59 (br s, 1H), 8.12 (s, 1H), 7.32 (d, J=7.0 Hz, 1H), 7.26-7.19 (comp, 7H), 6.82 (d, J=8.3 Hz, 2H), 6.80 (d, J=8.5 Hz, 2H), 6.06 (d, J=6.0 Hz, 1H), 5.85 (d, J=7.3 Hz, 1H), 5.13 (dd, J=54.0, 3.0 Hz, 1H), 4.94 (dq, J=22.6, 6.5 Hz, 1H), 4.27 (br dt, J=26.4, 3.6 Hz, 1H), 3.71 (s, 6H), 3.39 (dd, J=10.6, 5.7 Hz, 1H), 3.19 (dd, J=10.8, 3.8 Hz, 1H), 2.73 (hept, J=6.8 Hz, 1H), 1.12 (d, J=6.8 Hz, 6H). $^{19}$F NMR (DMSO-$d_6$) δ −198.0.

(2R,3S,4R,5R)-5-((Bis(4-methoxyphenyl)(phenyl)methoxy)methyl)-4-fluoro-2-(2-isobutyramido-6-oxo-1H-purin-9(6H)-yl)tetrahydrofuran-3-yl hydrogen phosphonate (I2C)

To a solution of I2B (1.20 g, 1.82 mmol) in pyridine (10 mL) was added diphenyl phosphite (1.05 mL, 5.48 mmol). The reaction mixture was stirred at RT for 20 min, and then cooled in an ice/acetone bath, whereupon $Et_3N$ (1.8 mL) and $H_2O$ (1.8 mL) were added. The bath was removed and the reaction mixture was stirred at RT for 40 min, and concentrated under reduced pressure. The residue was redissolved in MeOH (15 mL) containing 1% $Et_3N$, and then silica gel (5 g) was added. The mixture was concentrated under reduced pressure, and then the residue was purified by silica gel chromatography (0-7% MeOH/DCM containing 1% $Et_3N$). Concentration of appropriate fractions gave a product that contained inorganic phosphate and $Et_3N$ salts. This was partitioned between DCM (70 mL) and 5% aq. $NaHCO_3$ (20 mL). The organic layer was removed, dried ($Na_2SO_4$), and then concentrated to give I2C (1.50 g, >quant) that was slightly contaminated with $Et_3N$ salts. This material was used "as is" in subsequent transformations. LCMS m/z 722.3 (M+H)+. $^1$H NMR ($CD_3OD$) δ 8.13 (s, 1H), 7.44-7.42 (m, 2H), 7.33-7.17 (comp, 7H), 6.86-6.79 (comp, 4H), 6.79 (dd, J=632.0 Hz, 1.3 Hz, 1H), 6.19 (d, J=6.8 Hz, 1H), 5.84-5.74 (m, 1H), 5.41 (ddd, J=77.6, 4.5, 2.3 Hz, 1H), 4.49 (app dt, J=24.9, 2.3 Hz, 1H), 3.80 (s, 3H), 3.79 (s, 3H), 3.56-3.51 (m, 1H), 3.38-3.34 (m, 1H), 2.63 (hept, J=6.8 Hz, 1H), 1.23 (d, J=7.0 Hz, 3H), 1.20 (d, J=7.0 Hz, 3H). $^{19}$F NMR ($CD_3OD$) δ −200.22. $^{31}$P NMR ($CD_3OD$) δ 2.81.

(2R,3S,4R,5R)-4-Fluoro-5-(hydroxymethyl)-2-(2-isobutyramido-6-oxo-1H-purin-9(6H)-yl)tetrahydrofuran-3-yl hydrogen phosphonate (Intermediate 2)

To a suspension of I2C (1.32 g, 1.83 mmol) in DCM (10 mL) was added $H_2O$ (329 mg, 18.3 mmol) followed by a solution of DCA (1.36 mL, 16.5 mmol) in DCM (15 mL). The reaction mixture was stirred and sonicated occasionally for 20 min at RT, and then TES (15 mL) was added. After stirring and sonicating for an additional 1.5 hrs, pyridine (3 mL) was added. The mixture was concentrated under reduced pressure, and the residue was purified by RP-MPLC (C18 column, 0-30% $ACN/H_2O$ containing 0.04% $NH_4HCO_3$) to give Intermediate 2 (410 mg, 53%) as a white solid. LCMS (Method C, $T_R$=0.93 min) m/z 418.2 (M−H)−. $^1$H NMR ($CD_3OD$) δ 8.35 (s, 1H), 6.74 (dd, J=631.7, 1.3 Hz, 1H), 6.20 (d, J=6.8 Hz, 1H), 5.43-5.25 (comp, 2H), 4.46-4.40 (m, 1H), 3.85 (d, J=3.5 Hz, 2H), 2.77 (hept, J=6.8 Hz, 1H), 1.27 (d, J=7.0 Hz, 6H). $^{19}$F NMR ($CD_3OD$) δ −200.82. $^{31}$P NMR ($CD_3OD$) δ2.42.

Example 1

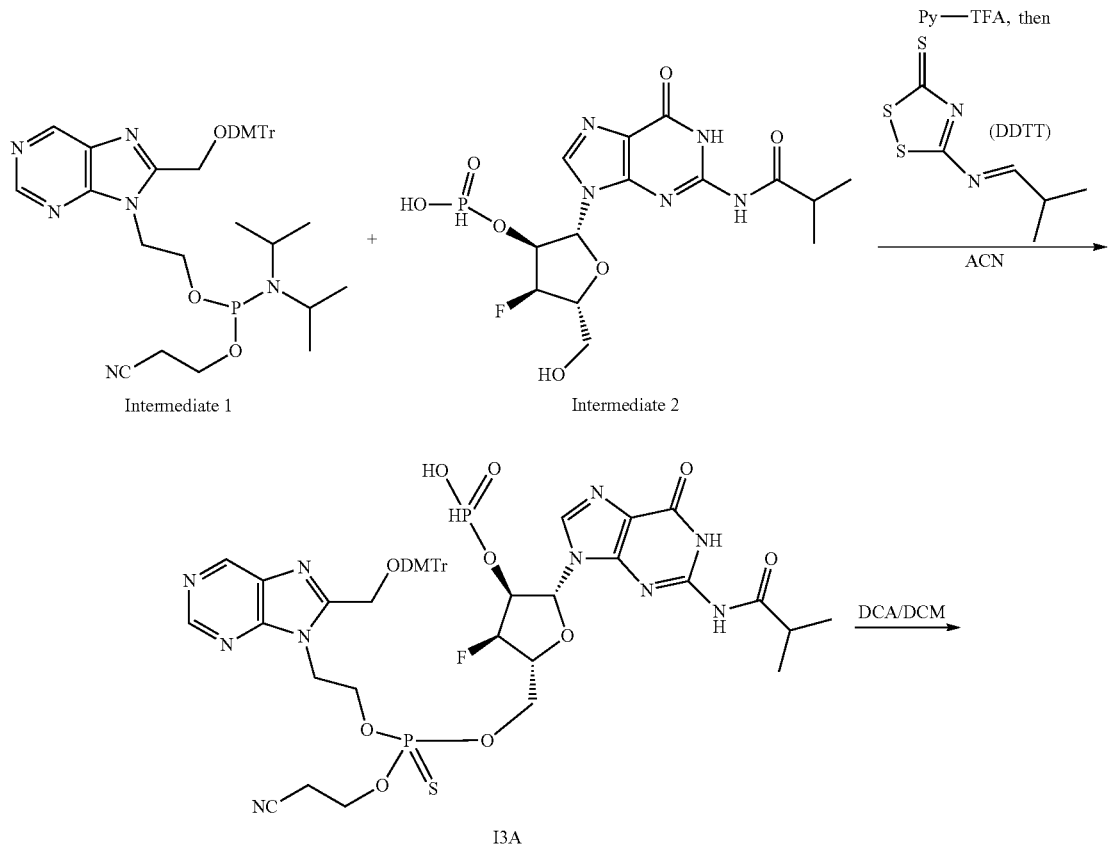

I3A

-continued

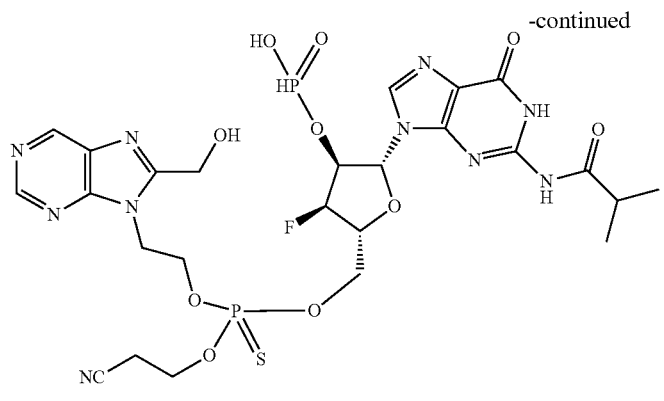

I3B

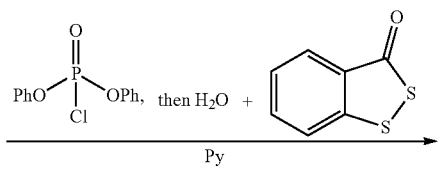

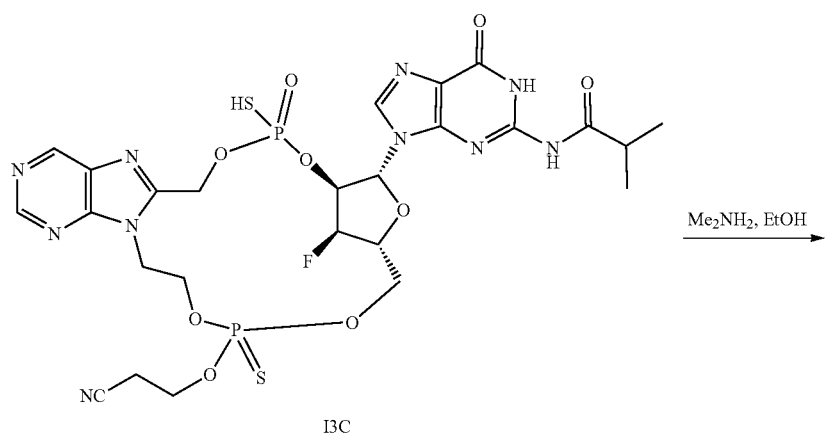

I3C

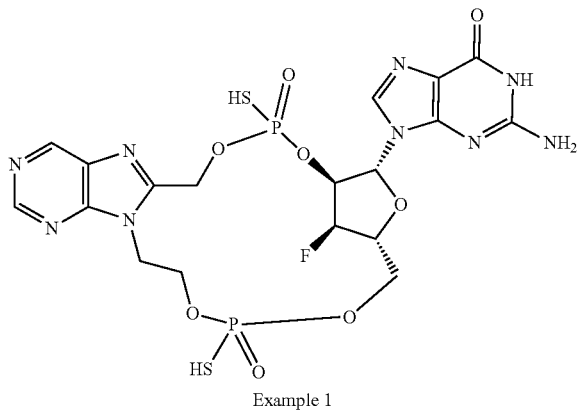

Example 1

(2R,3S,4R,5R)-5-((((2-(8-((Bis(4-methoxyphenyl)(phenyl)methoxy)methyl)-9H-purin-9-yl)ethoxy)(2-cyanoethoxy)phosphorothioyl)oxy)methyl)-4-fluoro-2-(2-isobutyramido-6-oxo-1H-purin-9(6H)-yl)tetrahydrofuran-3-yl hydrogen phosphonate (I3A)

Coupling-Oxidative Sulfurization (Coupling Method A)

A suspension of Intermediate 1 (810 mg, 1.16 mmol) and crushed, freshly activated 3A MS (200 mg) in ACN (6 mL) was stirred with occasional sonication for 45 minutes under $N_2$. In the meantime, a suspension of Intermediate 2 (406 mg, 0.970 mmol), Py.TFA (374 mg, 1.94 mmol), and crushed, freshly activated 3 Å MS (200 mg) in ACN (4 mL) was stirred with occasional sonication for 45 min under $N_2$. The supernatant containing Intermediate 1 was added to the suspension of Intermediate 2 in a dropwise fashion, via syringe. The flask and residual MS that contained Intermediate 1 was washed with ACN (2 mL) and the supernatant was again added to the mixture containing Intermediate 2. The resulting mixture was stirred at RT for 45 min, whereupon DDTT (219 mg, 1.07 mmol) was added in one portion. The reaction mixture was stirred at RT for 1 hr, and then filtered to remove the sieves. The filtrate was concentrated under reduced pressure, and the residue was purified by RP-MPLC (C18, 10-100% ACN/$H_2O$ containing 0.04% $NH_4HCO_3$) to give I3A (462 mg, 46% of a 1.0:1.2 mixture of diastereomers by $^{31}P$ NMR) as a pale yellow solid. LCMS m/z 1045.1 (M−H)⁻. $^{19}F$ NMR (CD$_3$OD) δ −202.16, −202.45. $^{31}P$ NMR (CD$_3$OD) δ P=S$_{major}$ 68.05, P=S$_{minor}$ 67.69, P=O$_{major/minor}$ 2.55.

(2R,3S,4R,5R)-5-((((2-Cyanoethoxy)(2-(8-(hydroxymethyl)-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I3B)

To a rapidly stirred mixture of I3A (462 mg, 0.440 mmol, 1.0:1.2 mixture of diastereomers) and H₂O (80.0 mg, 4.44 mmol) in DCM (7 mL) was added DCA (512 mg, 3.97 mmol) in DCM (7 mL). After 15 min at RT, Et₃SiH (12.3 mL) was introduced and the reaction mixture was stirred for 1 hr. Pyridine (1.4 mL) and MeOH (1.4 mL) were added, and then the reaction mixture was concentrated under reduced pressure. The residue was dissolved in MeOH (7 mL), and silica gel (4 g) was added. The mixture was concentrated to dryness, and purified by silica gel chromatography (0-100% MeOH/DCM) to give I3B (288 mg, 88% of a 1.0:1.1 mixture of diastereomers by $^{31}$P NMR) as a white solid. LCMS m/z 743.1 (M−H)⁻. $^{19}$F NMR (CD₃OD) δ −201.64, −201.75. $^{31}$P NMR (CD₃OD) δ P=S$_{major}$ 68.18, P=S$_{minor}$ 67.89, P=O$_{major/minor}$ 2.55.

N-{9-[(1S,21R,23R,24R)-18-(2-Cyanoethoxy)-24-fluoro-3-oxo-3-sulfanyl-18-sulfanylidene-2,4,17,19,22-pentaoxa-7,10,12,14-tetraaza-3lambda5,18lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (I3C)

Cyclization-Oxidative Sulfurization (Cyclization Method A)

To dry pyridine (25 mL) cooled to −30° C. was added diphenyl phosphoryl chloride (746 μL, 3.60 mmol). After 5 min, a solution of I3B (134 mg, 0.180 mmol) in pyridine (7 mL) was added in a dropwise fashion over 20 min while maintaining the bath temperature between −35 and −30° C. After stirring at −30° C. for 40 min, H₂O (162 mg, 9.00 mmol) and 3H-benzo[c][1,2]dithiol-3-one (45 mg, 0.27 mmol) were added in rapid succession. The −30° C. bath was replaced with a RT bath and the reaction mixture was stirred at this temperature for 1 hr. The reaction mixture was cooled to 0° C., then quenched by adding a solution of sodium thiosulfate (112 mg) in H₂O (30 mL) in a dropwise fashion. The bath was removed and the mixture was stirred at RT for 5 min, partially concentrated (to ca. 5 mL) under reduced pressure, then purified using RP-MPLC (C18, 0-50% ACN/H₂O containing 0.04% NH₄HCO₃) to give I3C (112 mg, 82% of a 1.0:1.4:2.3:3.0 mixture of diastereomers by $^{31}$P NMR) as a white solid. LCMS (Method C) m/z 757.1 (M−H)⁻. $^{19}$F NMR (CD₃OD) δ −196.82 (minor), −197.44 (minor), −198.73 (major), −199.48 (major). $^{31}$P NMR (CD₃OD) δ 69.01 (minor), 67.89 (major), 65.51 (minor), 65.27 (major), 60.69 (minor), 60.14 (minor), 57.54 (major), 56.54 (major).

(1S,21R,23R,24R)-23-(2-Amino-6-oxo-6,9-dihydro-1H-purin-9-yl)-24-fluoro-3,18-disulfanyl-2,4,17,19,22-pentaoxa-7,10,12,14-tetraaza-3lambda5,18lambda5-diphosphatetracyclo[19.2.1.06,14.08,13]tetracosa-6,8(13),9,11-tetraene-3,18-dione (Example 1)

A solution of I3C (112 mg, 0.150 mmol, 1.0:1.4:2.3:3.0 mixture of diastereomers) in MeNH₂/EtOH (33%, 10 mL) was stirred at RT for 5 hrs, and then concentrated under reduced pressure. The residue was purified by RP-HPLC (Sunfire Prep C18, 5 μm, 19×100 mm column eluting with 0-30% ACN/H₂O containing 0.04% NH₄HCO₃, Flow rate=7 mL/min) to give 4 pure diastereomers (Diastereomer A: T$_R$=8.1 min, 11.9 mg; Diastereomer B: T$_R$=9.7 min, 6.4 mg; Diastereomer C: T$_R$=11.2 min, 22.0 mg; Diastereomer D: T$_R$=11.8 min, 7.4 mg; Total: 47.7 mg, 51%) of Example 1. Example 1A (Diastereomer A): LCMS (Method D, T$_R$=1.17 min) m/z 634.0 (M−H)⁻. $^1$H NMR (CD₃OD) δ 9.06 (s, 1H), 8.97 (s, 1H), 8.15 (s, 1H), 6.12 (d, J=8.3 Hz, 1H), 5.65 (dd, J=53.2, 3.5 Hz, 1H), 5.50 (dd, J=12.8, 7.3 Hz, 1H), 5.41-5.28 (m, 1H), 5.07-4.54 (comp, 5H), 4.42-4.35 (m, 2H), 4.08 (app dt, J=11.3, 2.5 Hz, 1H). $^{19}$F NMR (CD₃OD) δ −199.75. $^{31}$P NMR (CD₃OD) δ 57.20, 57.05. Example 1B (Diastereomer B): LCMS (Method D, T$_R$=1.12 min) m/z 634.0 (M−H)⁻. $^1$H NMR (CD₃OD) δ 9.06 (s, 1H), 8.97 (s, 1H), 8.33 (s, 1H), 6.10 (d, J=8.3 Hz, 1H), 5.80-5.68 (m, 1H), 5.50 (dd, J=12.8, 7.3 Hz, 1H), 5.23-4.41 (comp, 8H), 4.01-3.97 (m, 1H) $^{19}$F NMR (CD₃OD) δ −198.64. $^{31}$P NMR (CD₃OD) δ 60.53, 57.40. Example 1C (Diastereomer C): LCMS (Method D, T$_R$=1.20 min) m/z 634.0 (M−H)⁻. $^1$H NMR (CD₃OD) δ 9.10 (s, 1H), 8.98 (s, 1H), 7.90 (s, 1H), 6.09 (d, J=8.5 Hz, 1H), 5.60 (dd, J=53.2, 3.8 Hz, 1H), 5.53 (dd, J=12.8, 7.8 Hz, 1H), 5.40-5.28 (comp, 6H), 4.34-4.30 (m, 1H), 4.40-4.01 (m, 1H). $^{19}$F NMR (CD₃OD) δ −199.24. $^{31}$P NMR (CD₃OD) δ 57.05, 56.14. Example 1D (Diastereomer D): LCMS (Method D, T$_R$=1.24 min) m/z 634.0 (M−H)⁻. $^1$H NMR (CD₃OD) δ 9.06 (s, 1H), 8.97 (s, 1H), 8.17 (s, 1H), 6.12 (d, J=8.3 Hz, 1H), 5.72-5.59 (m, 1H), 5.48 (dd, J=13.1, 7.8 Hz, 1H), 5.32-4.44 (comp, 7H), 4.36 (ddd, J=11.3, 8.3, 2.3 Hz, 1H), 4.12-4.10 (m, 1H). $^{19}$F NMR (CD₃OD) δ −197.59. $^{31}$P NMR (CD₃OD) δ 60.29, 58.08.

Intermediate 4

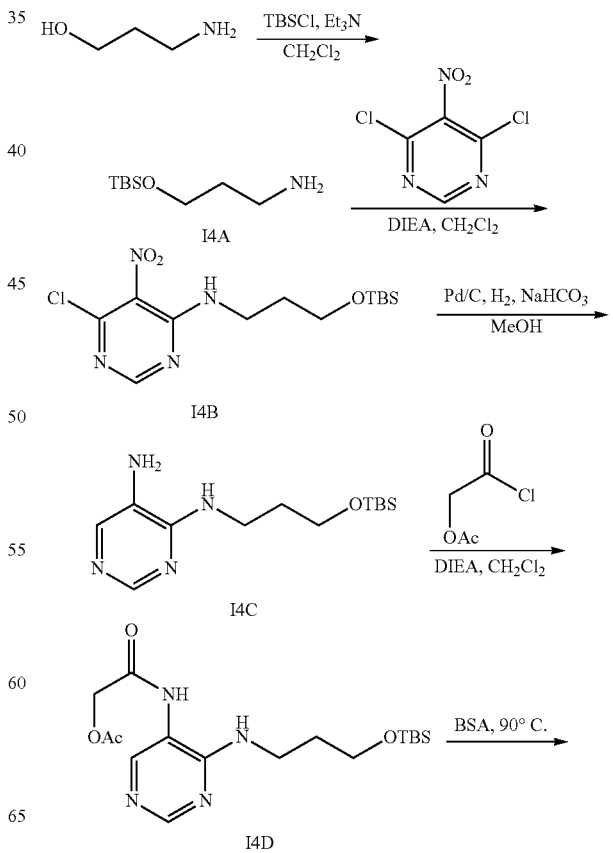

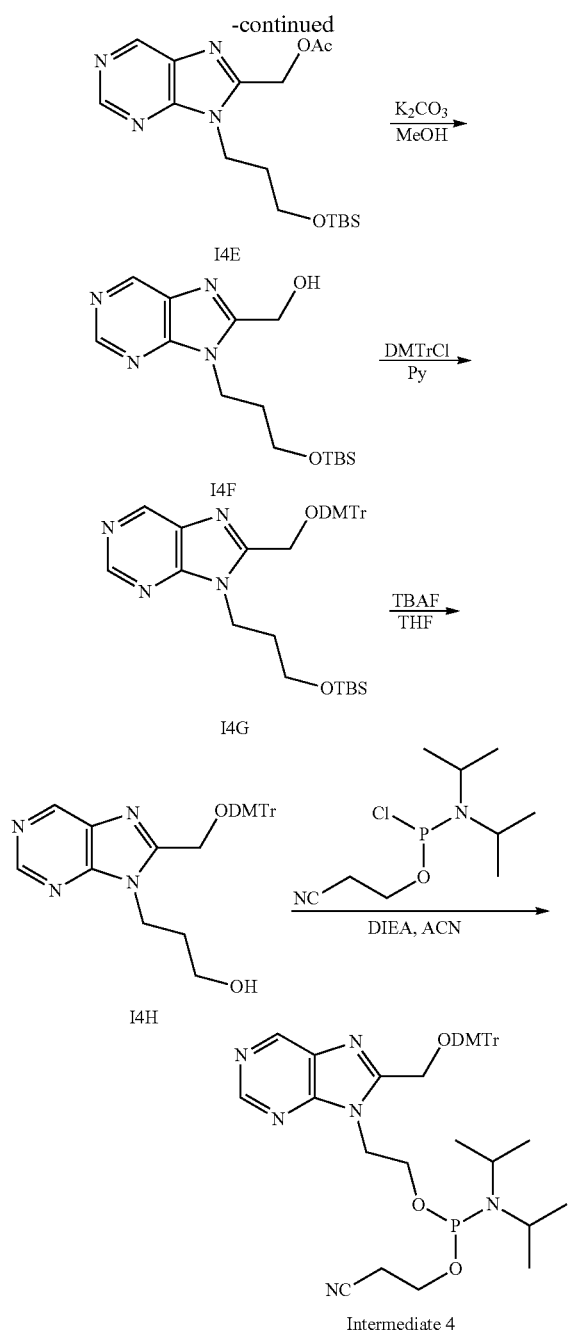

Intermediate 4

3-((tert-Butyldimethylsilyl)oxy)propan-1-amine (I4A)

To a solution of 3-aminopropanol (5.00 g, 66.6 mmol) in DCM (100 mL) was added triethylamine (10.2 mL, 73.2 mmol) followed by a solution of TBSCl (10.0 g, 66.3 mmol) in DCM (20 mL) over 5 min. The reaction mixture was stirred at RT overnight, whereupon it was washed with sat. aq.NaHCO$_3$, and brine. The organic layer was dried (Na$_2$SO$_4$) and concentrated under reduced pressure to give I4A (12.7 g, quant) as a clear, colorless oil. $^1$H NMR (CDCl$_3$) δ 3.67 (t, J=6.0 Hz, 2H), 2.77 (t, J=6.8 Hz, 2H), 1.64 (app p, J=6.5 Hz, 2H), 0.86 (s, 9H), 0.02 (s, 6H).

N-(3-((tert-Butyldimethylsilyl)oxy)propyl)-6-chloro-5-nitropyrimidin-4-amine (I4B)

To a solution of 4,6-dichloro-5-nitropyrimidine (13.1 g, 67.3 mmol) in DCM (350 mL) cooled to −78° C. was added triethylamine (9.40 mL, 67.4 mmol) followed by dropwise addition of a solution of I4A (12.7 g, 67.3 mmol) in DCM (20 mL) over 30 min. The reaction mixture was allowed to warm slowly to RT, and then stirred overnight. The mixture was washed with sat. aq.NaHCO$_3$, and then brine. The organic layer was dried (Na$_2$SO$_4$), then concentrated under reduced pressure. The residue was purified by silica gel chromatography (0-100% EtOAc/Hexane) to give I4B (14.1 g, 61%) as a pale yellow solid. LCMS m/z 347.2 (M+H)$^+$. $^1$H NMR (CDCl$_3$) δ 8.36 (s, 1H), 7.83 (br s, 1H), 3.76 (t, J=5.5 Hz, 2H), 3.72 (app dt, J=6.3, 5.5 Hz, 2H), 1.85 (app p, J=5.8 Hz, 2H), 0.89 (s, 9H), 0.07 (s, 6H).

N-4-(3-((tert-Butyldimethylsilyl)oxy)propyl)pyrimidine-4,5-diamine (I4C)

A mixture of I4B (3.00 g, 8.65 mmol), 10% Pd/C (470 mg), and NaHCO$_3$ (1.83 g, 17.3 mmol) in MeOH (100 mL) was hydrogenated at 50 psi H$_2$ for 3 hrs using a Parr shaker. The reaction mixture was filtered through a pad of Celite® and the filtrate was concentrated under reduced pressure. The residue was partitioned between DCM and H$_2$O. The organic layer was removed and washed with H$_2$O (3×), and then washed with brine. The organic layer was dried (Na$_2$SO$_4$) and concentrated under reduced pressure. The residue was purified by silica gel chromatography (0-10% MeOH/DCM) to give I4C (1.89 g, 77%) as a light tan solid. LCMS m/z 283.9 (M+H)$^+$. $^1$H NMR (CDCl$_3$) δ 8.27 (s, 1H), 7.71 (s, 1H), 5.42 (br s, 1H), 3.79 (t, J=5.5 Hz, 2H), 3.59 (dd, J=11.5, 6.3 Hz, 2H), 2.93 (br s, 2H), 1.86 (app dt, J=12.3, 5.8 Hz, 2H), 0.89 (s, 9H), 0.07 (s, 6H).

2-((4-((3-((tert-Butyldimethylsilyl)oxy)propyl)amino)pyrimidin-5-yl)amino)-2-oxoethyl acetate (I4D)

To a solution of I4C (1.89 g, 6.69 mmol) in DCM (50 mL) cooled to 0° C. was added DIEA (1.52 mL, 8.67 mmol) then 2-chloro-2-oxoethyl acetate (0.760 mL, 7.03 mmol) was added in a dropwise fashion. The resulting mixture was stirred at 0° C. for 15 min, then allowed to warm to RT and stirred for 4 hrs. The reaction mixture was diluted with DCM, and washed with sat. aq.NaHCO$_3$ and brine. The organic layer was dried (Na$_2$SO$_4$), and then concentrated under reduced pressure. The residue was purified by silica gel chromatography (0-8% MeOH/DCM) to give I4D (1.61 g, 63%) as a pale yellow oil. $^1$H NMR (CDCl$_3$) δ 8.51 (s, 1H), 8.03 (s, 1H), 7.39 (br s, 1H), 5.39 (br s, 1H), 4.69 (s, 2H), 3.71 (t, J=6.0 Hz, 2H), 3.58 (app q, J=6.4 Hz, 2H), 2.22 (s, 3H), 1.83 (app p, J=6.4 Hz, 2H), 0.87 (s, 9H), 0.03 (s, 6H).

(9-(3-((tert-Butyldimethylsilyl)oxy)propyl)-9H-purin-8-yl)methyl acetate (I4E)

A mixture of I4D (4.58 g, 12.0 mmol) and BSA (30 mL) was heated at 90° C. for 2 hrs, and then cooled to RT. The reaction mixture was diluted with EtOAc and washed with H$_2$O. The organic layer was washed with brine, then dried (MgSO$_4$) and concentrated under reduced pressure. The residue was purified by silica gel chromatography (0-5% MeOH/DCM) to give I4E (3.85 g, 88%) as an orange oil.

LCMS m/z (M+H)⁺ 365.2. ¹H NMR (CDCl₃) δ 9.08 (s, 1H), 8.95 (s, 1H), 5.41 (s, 2H), 4.42 (t, J=7.2 Hz, 2H), 3.63 (t, J=5.5 Hz, 2H), 2.15 (s, 3H), 2.11-2.04 (m, 2H), 0.86 (s, 9H), 0.02 (s, 6H).

(9-(3-((tert-Butyldimethylsilyl)oxy)propyl)-9H-purin-8-yl)methanol (I4F)

A mixture of I4E (3.85 g, 10.6 mmol) and K₂CO₃ (146 mg, 1.06 mmol) in MeOH (100 mL) was stirred at RT overnight, and then concentrated under reduced pressure. The residue was partitioned between EtOAc and H₂O. The organic phase was removed and the aqueous layer was extracted with EtOAc (1×). The combined organic layers were washed with brine, dried (MgSO₄), and concentrated to give I4F (3.25 g, 96%) as a pale yellow solid. LCMS m/z (M+H)⁺ 323.4. ¹H NMR (CDCl₃) δ 9.03 (s, 1H), 8.92 (s, 1H), 4.97 (br d, J=4.8 Hz, 2H), 4.42 (t, J=6.8 Hz, 2H), 3.98 (br m, 1H), 3.62 (t, J=5.3 Hz, 2H), 2.12 (dt, J=6.5, 5.8 Hz, 2H), 0.87 (s, 9H), 0.03 (s, 6H).

8-((Bis(4-methoxyphenyl)(phenyl)methoxy)methyl)-9-(3-((tert-butyldimethylsilyl)oxy)propyl)-9H-purine (I4G)

A mixture of I4F (0.500 g, 1.55 mmol) and DMTrCl (0.680 g, 2.02 mmol) in pyridine (12 mL) was stirred at RT overnight. The reaction was quenched with sat. aq. NaHCO₃ and H₂O then extracted twice with EtOAc. The organics were combined, washed with brine, dried (Na₂SO₄) and concentrated under reduced pressure. The residue was purified by silica gel chromatography (0-100% EtOAc/Hexane) to give I4G (0.63 g, 65%) as a white solid. LCMS m/z (M+H)⁺ 625.3. ¹H NMR (CDCl₃) δ 9.04 (s, 1H), 8.92 (s, 1H), 7.48-7.46 (m, 2H), 7.39-7.36 (m, 4H), 7.31-7.27 (m, 2H), 7.23-7.19 (m, 1H), 6.84-6.81 (m, 4H), 4.46 (s, 2H), 4.31 (t, J=7.3 Hz, 2H), 3.76 (s, 6H), 3.50 (t, J=6.0 Hz, 2H), 1.92 (dt, J=7.2, 6.0 Hz, 2H), 0.78 (s, 9H), -0.09 (s, 6H).

3-(8-((Bis(4-methoxyphenyl)(phenyl)methoxy)methyl)-9H-purin-9-yl)propan-1-ol (I4H)

To a solution of 14G (0.890 g, 1.42 mmol) in THF (28 mL) cooled to -5° C. was added TBAF/THF (1 M, 1.85 mL, 1.85 mmol) in a slow, dropwise fashion. The reaction mixture was stirred at -5° C. for 0.5 hr, then warmed to RT and stirred for 2 hrs. The reaction was quenched with sat. aq. NH₄Cl and H₂O then extracted twice with EtOAc. The organic layers were combined, washed with brine, dried (Na₂SO₄) and concentrated under reduced pressure. The residue was purified by silica gel chromatography (0-7% MeOH/DCM) to give 14H (0.57 g, 78%) as a white solid. LCMS m/z (M+H)⁺ 511.3. ¹H NMR (CDCl₃) δ 9.10 (s, 1H), 8.93 (s, 1H), 7.48-7.46 (m, 2H), 7.41-7.37 (m, 4H), 7.33-7.29 (m, 2H), 7.25-7.21 (m, 1H), 6.87-6.83 (m, 4H), 4.44 (s, 2H), 4.26 (t, J=6.0 Hz, 2H), 3.78 (s, 6H), 3.67 (t, J=7.0 Hz, 1H), 3.37 (dt, J=6.4, 5.8 Hz, 2H), 1.82 (dt, J=6.0, 5.8 Hz, 2H).

3-(8-((Bis(4-methoxyphenyl)(phenyl)methoxy)methyl)-9H-purin-9-yl)propyl (2-cyanoethyl) diisopropylphosphoramidite (Intermediate 4)

To a solution of I4H (0.570 g, 1.11 mmol) in ACN (4 mL) was added DIEA (0.58 mL, 3.32 mmol) followed by dropwise addition of neat 3-((chloro(diisopropylamino)phosphino)oxy)propanenitrile (0.41 mL, 1.66 mmol). The reaction mixture was stirred at RT for 2 hrs, and then quenched by the addition of sat. aq. NaHCO₃ (1 mL) and H₂O (1 mL). The resulting mixture was purified directly by RP-MPLC (0-100% ACN/H₂O) to give Intermediate 4 (0.56 g, 71%) as a white foam. LCMS m/z (M+H+OH-N,N-diisopropylamino)⁺628.3. ¹H NMR (CD₃CN) δ 8.96 (s, 1H), 8.85 (s, 1H), 7.51-7.46 (m, 2H), 7.40-7.37 (m, 4H), 7.36-7.31 (m, 2H), 7.27-7.23 (m, 1H), 6.90-6.86 (m, 4H), 4.42 (s, 2H), 4.30-4.23 (comp, 2H), 3.75 (s, 6H), 3.69-3.64 (comp, 2H), 3.58-3.43 (comp, 4H), 2.57 (app t, J=6.0 Hz, 2H), 2.00 (app hept, J=6.8 Hz, 2H), 1.11 (d, J=6.8 Hz, 6H), 1.03 (d, J=6.8 Hz, 6H).

Intermediate 5

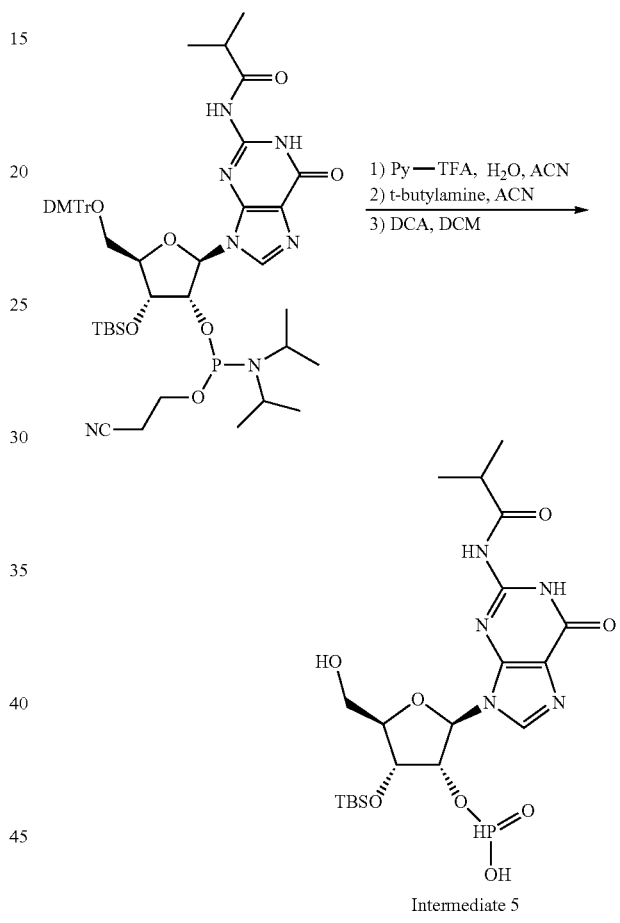

Intermediate 5

(2R,3R,4R,5R)-4-((tert-Butyldimethylsilyl)oxy)-5-(hydroxymethyl)-2-(2-isobutyramido-6-oxo-1H-purin-9(6H)-yl)tetrahydrofuran-3-yl hydrogen phosphonate (Intermediate 5)

To a solution of (2R,3R,4R,5R)-5-((bis(4-methoxyphenyl)(phenyl)methoxy)methyl)-4-((tert-butyldimethylsilyl)oxy)-2-(2-isobutyramido-6-oxo-1H-purin-9(6H)-yl)tetrahydrofuran-3-yl (2-cyanoethyl) diisopropylphosphoramidite (2.74 g, 2.82 mmol) in ACN (14 mL) was added H₂O (137 mg, 7.61 mmol) followed by Py.TFA (655 mg, 3.39 mmol). The reaction mixture was stirred at RT for 1 hr, and then t-butylamine (14.0 mL, 133 mmol) was rapidly introduced. The resulting mixture was stirred at RT for 3 hrs, and then concentrated under reduced pressure. The residue was redissolved in DCM (35 mL), then H₂O (508 mg, 28.2 mmol) and 6% DCA in DCM (35 mL) were added. The resulting bright orange solution was stirred at RT for 2 hrs, and then Et₃SiH (10 mL) was added. The reaction mixture was stirred at RT for 1.5 hrs, then a 1:1 mixture of pyridine:MeOH (10 mL) was added. The solvents were removed under reduced pressure and the residue was purified by silica gel chromatography (0-30% MeOH/DCM) to give Intermediate 5 (1.20 g, 80%) as a white solid. LCMS m/z (M+H)$^+$532.2. $^1$H NMR (CDCl$_3$+drop of CD$_3$OD) δ 8.01 (s, 1H), 6.67 (d, J=636.5 Hz, 1H), 5.90 (d, J=6.0 Hz, 1H), 5.06-5.01 (m, 1H), 4.32 (dd, J=4.8, 3.0 Hz, 1H), 4.09-4.07 (m, 1H), 3.82 (dd, J=12.6, 6.2 Hz, 1H), 3.66 (dd, J=12.6, 2.3 Hz, 1H), 2.62 (hept, J=6.8 Hz, 1H), 1.23 (s, 9H), 1.17 (d, J=6.8 Hz, 3H), 1.16 (d, J=6.8 Hz, 3H), 0.07 (s, 3H), 0.05 (s, 3H).

Example 2

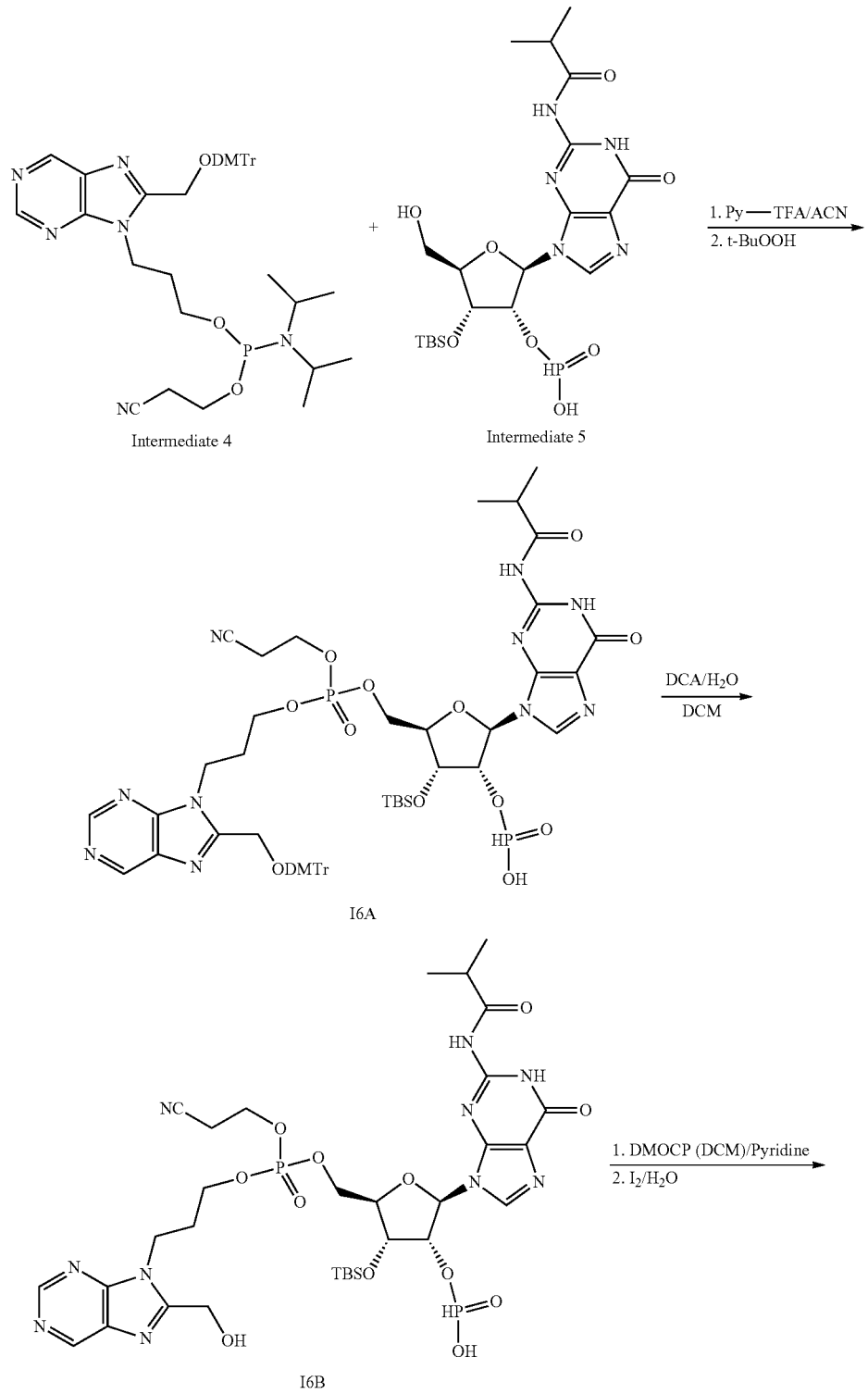

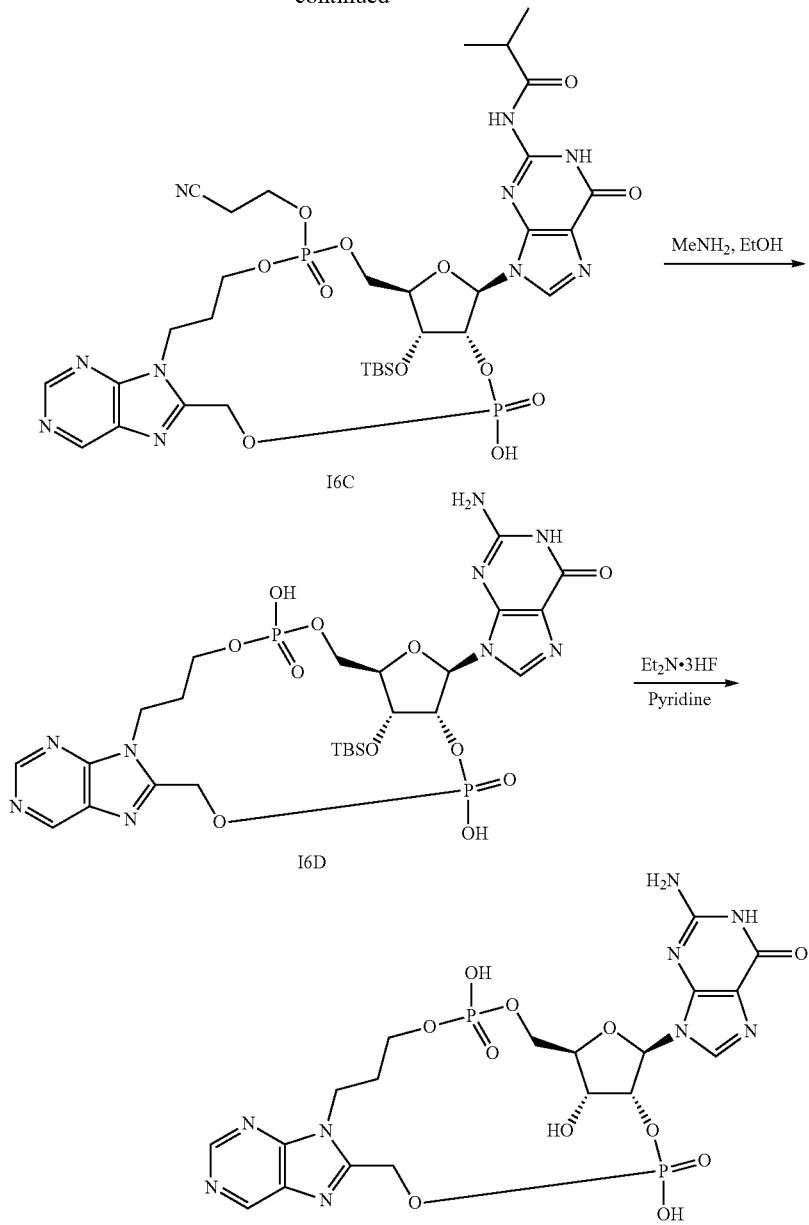

Example 2

(2R,3R,4R,5R)-5-(((((3-(8-((Bis(4-methoxyphenyl)
(phenyl)methoxy)methyl)-9H-purin-9-yl)propoxy)
(2-cyanoethoxy)phosphoryl)oxy)methyl)-4-((tert-
butyldimethylsilyl)oxy)-2-(2-isobutyramido-6-oxo-
1H-purin-9(6H)-yl)tetrahydrofuran-3-yl hydrogen
phosphonate (I6A)

Coupling-Oxidation (Coupling Method B)

A suspension of Intermediate 4 (0.540 g, 0.760 mmol) and crushed, freshly activated 3 Å MS (275 mg) in ACN (3.6 mL) was stirred for 2 hrs under $N_2$. In the meantime, a suspension of Intermediate 5 (0.250 g, 0.470 mmol), Py.TFA (0.140 g, 0.710 mmol), and crushed, freshly activated 3 Å MS (275 mg) in ACN (2 mL) was stirred for 2 hrs under $N_2$. The supernatant containing Intermediate 4 (2.2 mL) was added to the suspension of Intermediate 5 in a dropwise fashion, via syringe over 10 min. The resulting mixture was stirred at RT for 1 hr. The remaining supernatant containing Intermediate 4 (1.4 mL) was then added over 5 min. The resulting mixture was stirred at RT for 45 min, whereupon t-BuOOH in decane (5.5 M, 0.30 mL, 1.65 mmol) was added dropwise, very slowly, at a rate of 1 drop/10 seconds. The reaction mixture was stirred at RT for 15 min then stored in the freezer overnight. The mixture was removed from the freezer and placed in an ice/acetone bath (ca −5° C.). $NaHCO_3$ (0.12 g, 1.02 mmol) in $H_2O$ (2 mL) was added dropwise over 35 min. The mixture was stirred in the bath for 5 min, and then filtered. The solids were washed with ACN and $H_2O$ containing 0.04% $NH_4HCO_3$. The combined filtrates were concentrated under reduced pressure, and the residue was purified by RP-MPLC (C18, 0-50% ACN/$H_2O$ containing 0.04% $NH_4HCO_3$) to give I6A (0.30 g, 54% of a ca. 1:1 mixture of diastereomers) as a white solid. LCMS m/z (M–H)⁻ 1155.1. ³¹P NMR (CD₃CN) δ 2.36, 2.28, –2.12, –2.18.

(2R,3R,4R,5R)-4-((tert-Butyldimethylsilyl)oxy)-5-((((2-cyanoethoxy) (3-(8-(hydroxymethyl)-9H-purin-9-yl)propoxy)phosphoryl)oxy)methyl)-2-(2-isobutyramido-6-oxo-1H-purin-9(6H)-yl) tetrahydrofuran-3-yl hydrogen phosphonate (I6B)

To a rapidly stirred mixture of I6A (0.290 g, 0.250 mmol, and H₂O (46 mg, 2.53 mmol) in DCM (5 mL) was added a 6% solution of DCA in DCM (5 mL). After 2 hrs at RT, Et₃SiH (3.0 mL) was introduced and the reaction mixture was stirred for 1 hr. Pyridine (2 mL) and MeOH (2 mL) were added and the mixture was stirred for 5 min, and then concentrated under reduced pressure. The residue was purified by silica gel chromatography (0-50% MeOH/DCM) to give I6B (0.15 g, 71% of a ca. 1:1 mixture of diastereomers) as a white solid. LCMS m/z (M–H)⁻ 853.0. ³¹P NMR (CD₃OD) δ 2.67, 2.63, –2.00, –2.02.

N-{9-[(1R,22R,24R,25R)-25-[(tert-Butyldimethylsilyl)oxy]-19-(2-cyanoethoxy)-3-hydroxy-3,19-dioxo-2,4,18,20,23-pentaoxa-7,10,12,14-tetraaza-3lambda5,19lambda5-diphosphatetracyclo[20.2.1.0⁶,¹⁴.0⁸,¹³]pentacosa-6,8,10,12-tetraen-24-yl]-6-oxo-6,9-dihydro-1H-purin-2-yl}-2-methylpropanamide (I6C)

Cyclization-Oxidation (Cyclization Method B)

I6B was co-evaporated with pyridine three times. To a solution of 16B in pyridine (5 mL) was added DMOCP (12 mg, 0.067 mmol) in DCM (0.1 mL). The mixture was stirred for 45 min at RT. Iodine (21 mg, 0.089 mmol) was added followed by H₂O (3 drops) and the mixture was stirred for 15 min. A solution of NaHSO₃ (150 mg) dissolved in H₂O (150 mL) was added dropwise until the solution turned colorless. The mixture was concentrated and the residue was purified by RP-MPLC (C18, 0-50% ACN/H₂O containing 0.04% NH₄HCO₃) to give I6C (24 mg, 41%) as a white solid. LCMS m/z (M–H)⁻ 851.3. ³¹P NMR (CD₃CN) δ –0.91, –1.79, –2.15, –2.65.

(1R,22R,24R,25R)-24-(2-Amino-6-oxo-1H-purin-9-yl)-25-[(tert-butyldimethylsilyl)oxy]-3,19-dihydroxy-2,4,18,20,23-pentaoxa-7,10,12,14-tetraaza-3lambda5,19lambda5-diphosphatetracyclo[20.2.1.0⁶,¹⁴.0⁸,¹³]pentacosa-6,8,10,12-tetraene-3,19-dione (I6D)

A solution of I6C (24 mg, 0.028 mmol) in 33% MeNH₂/EtOH (2 mL) was stirred at RT for 2 hrs, then concentrated under reduced pressure to give crude I6D.

(1R,22R,24R,25R)-24-(2-Amino-6-oxo-6,9-dihydro-1H-purin-9-yl)-3,19,25-trihydroxy-2,4,18,20,23-pentaoxa-710,122,14-tetraaza-3lambda5,19lambda5-diphosphatetracyclo[20.2.1.0⁶,¹⁴.0⁸,¹³]pentacosa-6,8(13),9,11-tetraene-3,19-dione (Example 2)

To the crude I6D from the previous step was added pyridine (1 mL) and the mixture was concentrated. In a plastic vial, Et₃N·HF (0.092 mL, 0.56 mmol) was added to I6D in pyridine (3 mL). The mixture was heated at 50° C. for 2 hrs, and then concentrated under reduced pressure. The residue was dissolved in 2% aq. NaHCO₃ and purified by RP-MPLC (C18, 0-10% ACN/H₂O containing 0.04% NH₄HCO₃). The resulting semi-pure material was dissolved in MeOH and adsorbed onto Celite®, then purified by silica gel chromatography (0-100% MeOH/DCM) to give Example 2 (6 mg, 35%) as a white solid. LCMS (Method D, T_R=0.75 min) m/z 613.9 (M–H)⁻. ¹H NMR (D₂O) δ 8.91 (s, 1H), 8.79 (s, 1H), 7.84 (s, 1H), 5.90 (d, J=7.5 Hz, 1H), 4.98 (dd, J=12.8, 4.5 Hz, 1H), 4.85-4.79 (m, 1H), 4.75-4.60 (comp, 2H), 4.45 (d, J=4.8 Hz, 1H), 4.17-3.97 (comp, 4H), 3.93-3.90 (comp, 2H), 2.06-1.96 (m, 1H), 1.91-1.80 (m, 1H). ³¹P NMR (D₂O) δ 1.05, –1.76.

Intermediate 7

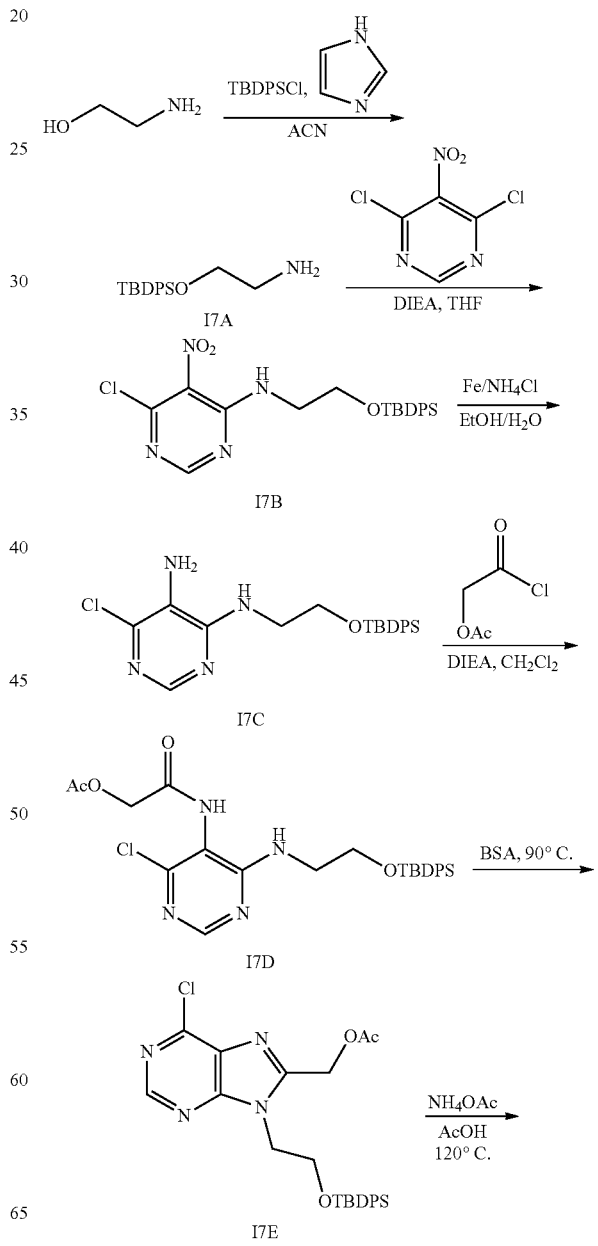

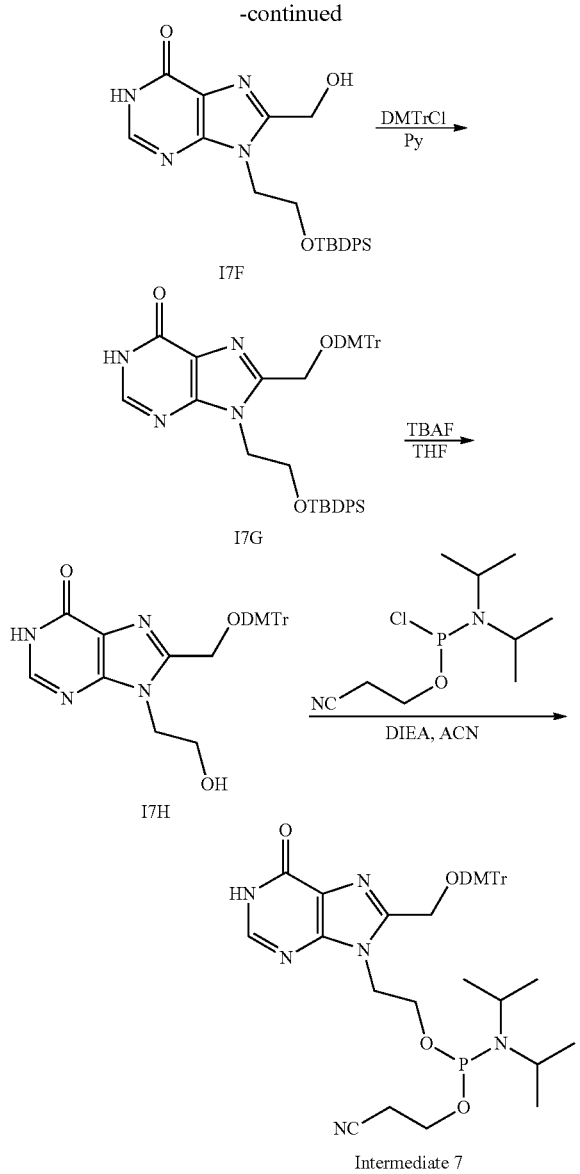

Intermediate 7

2-((tert-Butyldiphenylsilyl)oxy)ethanamine (I7A)

To a solution of 2-aminoethanol (3.00 g, 49.1 mmol) in ACN (100 mL) was added imidazole (6.68 g, 98.2 mmol) followed by a solution of TBDPSCl (16.6 mL, 63.8 mmol) in ACN (100 mL) at RT over 10 min. The reaction mixture was stirred at RT for 4 hrs, whereupon it was quenched with sat. aq. NaHCO$_3$ and extracted three times with EtOAc. The combined organic layers were washed with brine, dried (Na$_2$SO$_4$) and then concentrated under reduced pressure. The residue was purified by silica gel chromatography (0-100% EtOAc/Hexane) to give I7A (12.3 g, 84%) as a yellow oil. LCMS m/z 301.3 (M+H)$^+$. $^1$H NMR (CDCl$_3$) δ 7.69-7.64 (m, 4H), 7.44-7.34 (m, 6H), 3.66 (t, J=5.2 Hz, 2H), 2.79 (t, J=5.2 Hz, 2H), 1.10 (s, 9H).

N-(2-((tert-Butyldiphenylsilyl)oxy)ethyl)-6-chloro-5-nitropyrimidin-4-amine (I7B)

To a solution of 4,6-dichloro-5-nitropyrimidine (8.00 g, 41.2 mmol) in THF (200 mL) cooled to −78° C. was added dropwise a solution of I7A and DIEA (8.6 mL, 49.5 mmol) in THF (10 mL). The reaction mixture was stirred at −78° C. for 1 hr. The resulting solution was quenched at −78° C. by addition of a sat. aq. NaHCO$_3$ solution and the resulting mixture was allowed to warm to RT. This was then extracted with EtOAc (3×) and the combined organic layers were washed with brine, dried (Na$_2$SO$_4$) and concentrated under reduced pressure. The residue was purified by silica gel chromatography (0-100% EtOAc/Hexane) to give I7B (17 g, 90%). LCMS m/z 457.3 (M+H)$^+$. $^1$H NMR (CDCl$_3$) δ 8.27 (s, 1H), 7.95 (br s, 1H), 7.62-7.58 (m, 4H), 7.44-7.31 (m, 6H), 3.84 (t, J=6.0 Hz, 2H), 3.74 (t, J=6.0 Hz, 2H), 1.08 (s, 9H).

N-4-(2-((tert-Butyldiphenylsilyl)oxy)ethyl)-6-chloropyrimidine-4,5-diamine (I7C)

A mixture of I7B (1.00 g, 17.5 mmol), Fe powder (5.00 g, 87.7 mmol), and NH$_4$Cl (4.70 g, 87.7 mmol) in a mixture of EtOH/H$_2$O (120 mL/40 mL) was stirred at RT for 2 hrs. The residue was partitioned between DCM and sat. aq. NaHCO$_3$. The organic layer was removed and washed with sat. aq. NH$_4$Cl, H$_2$O, and then brine. The organic layer was dried (Na$_2$SO$_4$) and then concentrated under reduced pressure. The residue was purified by silica gel chromatography (0-10% MeOH/DCM) to give I7C (775 mg, 83%). LCMS m/z 427.3 (M+H)$^+$. $^1$H NMR (CDCl$_3$) δ 7.99 (s, 1H), 7.64-7.61 (m, 4H), 7.44-7.26 (m, 6H), 3.89 (t, J=6.0 Hz, 2H), 3.62 (t, J=6.0 Hz, 2H), 1.07 (s, 9H).

2-((4-((2-((tert-Butyldiphenylsilyl)oxy)ethyl)amino)-6-chloropyrimidin-5-yl)amino)-2-oxoethyl acetate (I7D)

To a solution of I7C (775 mg, 1.82 mmol) in DCM (20 mL) was added dropwise DIEA (475 μL, 2.73 mmol) and 2-chloro-2-oxoethyl acetate (234 μL, 2.18 mmol) at RT. The resulting mixture was stirred at RT for 1 hr, then diluted with DCM and then washed with sat. aq. NaHCO$_3$, H$_2$O and brine. The organic layer was dried (Na$_2$SO$_4$), and then concentrated under reduced pressure to give I7D which was used directly for next step. LCMS m/z 527.3 (M+H)$^+$. $^1$H NMR (CDCl$_3$) δ 8.25 (s, 1H), 7.65-7.62 (m, 4H), 7.45-7.26 (m, 7H), 4.68 (s, 2H), 3.85 (t, J=6.5 Hz, 2H), 3.67 (t, J=6.5 Hz, 2H), 2.20 (s, 3H), 1.05 (s, 9H).

(9-(2-((tert-Butyldiphenylsilyl)oxy)ethyl)-6-chloro-9H-purin-8-yl)methyl acetate (I7E)

A mixture of I7D (957 mg, 1.82 mmol) and BSA (5 mL) was heated at 80° C. overnight. To the reaction mixture was added at RT sat. aq. NaHCO$_3$ and the resulting mixture was extracted with EtOAc (3×). The combined organic layers were washed with brine, dried (Na$_2$SO$_4$), and then concentrated under reduced pressure. The residue was purified by silica gel chromatography (0-100% EtOAc/Hexane) to give I7E (370 mg, 40%). LCMS m/z 509.3 (M+H)$^+$. $^1$H NMR (CDCl$_3$) δ 8.59 (s, 1H), 7.37-7.32 (m, 6H), 7.26-7.21 (m, 4H), 5.42 (s, 2H), 4.50 (t, J=6.0 Hz, 2H), 4.02 (t, J=6.0 Hz, 2H), 2.11 (s, 3H), 0.96 (s, 9H).

9-(2-((tert-Butyldiphenylsilyl)oxy)ethyl)-8-(hydroxymethyl)-1H-purin-6(9H)-one (I7F)

A mixture of I7E (0.30 g, 0.59 mmol) and ammonium acetate (6.00 g, 0.340 mmol) in AcOH (5 mL) was stirred at 120° C. for 1 hr and then concentrated under reduced pressure. The residue was neutralized with sat. aq. NaHCO$_3$ and extracted with EtOAc (3×). The combined organic layers were washed with brine, dried (Na$_2$SO$_4$) and then concentrated under reduced pressure. The residue was purified by silica gel chromatography (0-10% MeOH/DCM) to give I7F (100 mg, 38%). LCMS m/z 449.3 (M+H)$^+$. $^1$H NMR (CDCl$_3$) δ 8.00 (s, 1H), 7.42-7.36 (m, 6H), 7.31-7.26 (m, 4H), 4.88 (d, J=6.0 Hz, 1H), 4.37 (t, J=6.5 Hz, 2H), 3.98 (t, J=6.5 Hz, 2H), 2.03 (s, 3H), 0.96 (s, 9H).

8-((Bis(4-methoxyphenyl)(phenyl)methoxy)methyl)-9-(2-((tert-butyldiphenylsilyl)oxy) ethyl)-1H-purin-6(9H)-one (I7G)

A mixture of I7F (420 mg, 0.94 mmol) and DMTrCl (635 mg, 1.88 mmol) in pyridine (10 mL) was stirred at RT for 3 hrs. A solution of sat. aq. NaHCO$_3$ was added and the mixture was extracted with EtOAc (3×). The combined organic layers were washed with brine, dried (Na$_2$SO$_4$) and concentrated under reduced pressure. The residue was purified by silica gel chromatography (0-100% EtOAc/Hexane) to give I7G (540 mg, 77%). LCMS m/z 751.5 (M+H)$^+$. $^1$H NMR (CDCl$_3$) δ 7.91 (br d, 1H), 7.49 (m, 2H), 7.39-7.30 (m, 6H), 7.28-7.17 (m, 11H), 6.84-6.79 (m, 4H), 4.39 (s, 2H), 4.28 (t, J=4.8 Hz, 2H), 3.75 (s, 6H), 3.72 (t, J=4.8 Hz, 2H), 0.77 (s, 9H).

8-((Bis(4-methoxyphenyl)(phenyl)methoxy)methyl)-9-(2-hydroxyethyl)-1H-purin-6(9H)-one (I7H)

To a solution of I7G (630 mg, 0.840 mmol) in THF (20 mL) at RT was added dropwise a solution of TBAF in THF (1.0 M, 1.7 mL, 1.7 mmol) and the resulting solution was stirred at RT overnight. Then a solution of sat. aq. NaHCO$_3$ was added and the mixture was extracted with EtOAc (3×). The combined organic layers were washed with brine, dried (Na$_2$SO$_4$), and then concentrated under reduced pressure. The residue was purified by silica gel chromatography (0-10% MeOH/DCM) to give I7H (420 mg, 97%). LCMS m/z 513.4 (M+H)$^+$. $^1$H NMR (CDCl$_3$) δ 12.21 (br s, 1H), 8.05 (s, 1H), 7.500-7.15 (m, 10H), 6.86-6.82 (m, 3H), 4.39 (s, 2H), 4.16 (t, J=4.8 Hz, 2H), 3.86-3.73 (m, 7H), 3.49 (d, J=5.2 Hz, 2H), 3.03 (t, J=5.6 Hz, 1H).

2-(8-((Bis(4-methoxyphenyl)(phenyl)methoxy)methyl)-6-oxo-1H-purin-9(6H)-yl)ethyl (2-cyanoethyl) diisopropylphosphoramidite (Intermediate 7)

To a solution of I7H (420 mg, 0.820 mmol) in ACN (10 mL) was added DIEA (0.430 mL, 2.46 mmol) followed by dropwise addition of 3-((chloro(diisopropylamino)phosphino)oxy) propanenitrile (0.37 mL, 1.64 mmol). The reaction mixture was stirred at RT for 1 hr, and then partially concentrated under reduced pressure. The remaining solution was purified directly by RP-MPLC (0-100% ACN/H$_2$O) to give Intermediate 7 (446 mg, 51%) as a white foam. LCMS m/z 630.4 (M+H+OH-N,N-diisopropylamino)$^+$. $^1$H NMR (CDCl$_3$) δ 7.97 (s, 1H), 7.50-7.17 (m, 9H), 6.87-6.82 (m, 4H), 4.44-4.26 (m, 4H), 3.84-3.55 (m, 2H), 3.77 (s, 6H), 3.54-3.47 (m, 2H), 3.41-3.30 (m, 2H), 2.42 (t, J=6.4 Hz, 2H), 1.04 (d, J=6.8 Hz, 6H), 0.92 (d, J=6.8 Hz, 6H). $^{31}$P NMR (CDCl$_3$) δ 148.1 (s).

Example 3

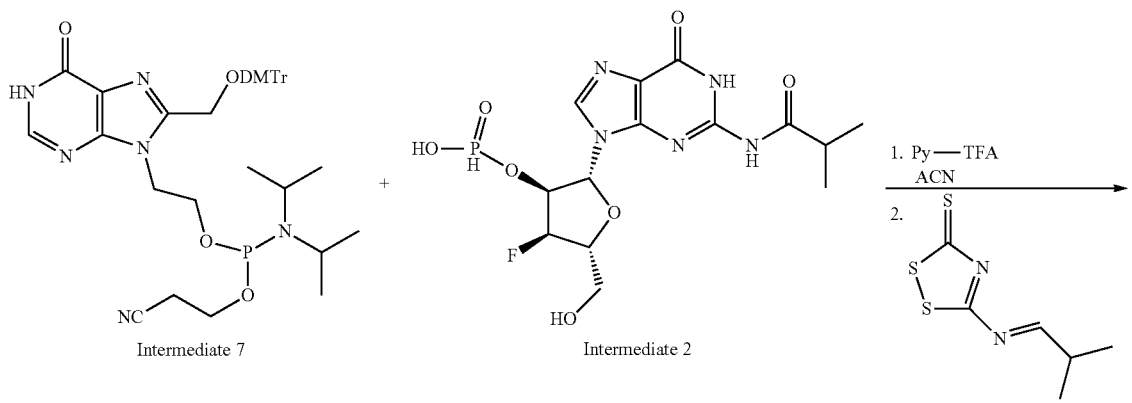

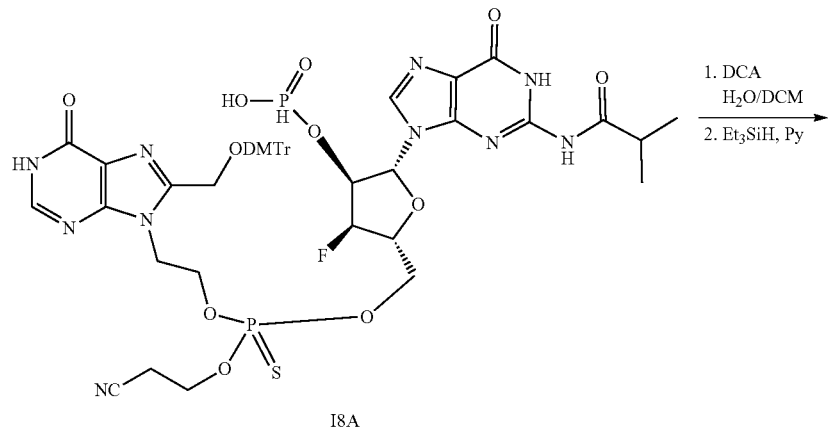

I8A

-continued

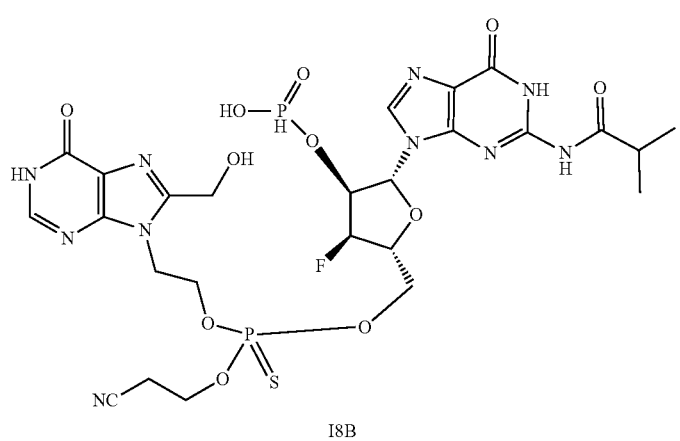 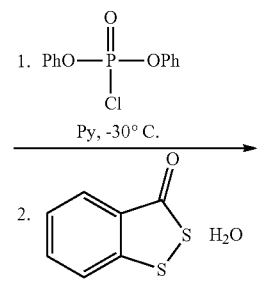

I8B

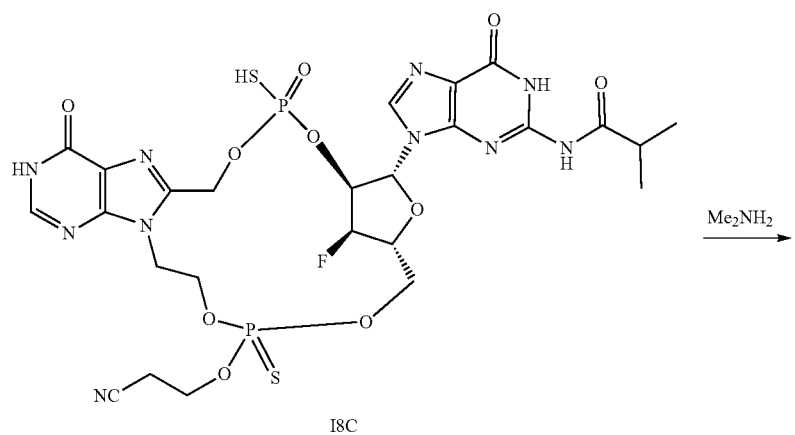

I8C

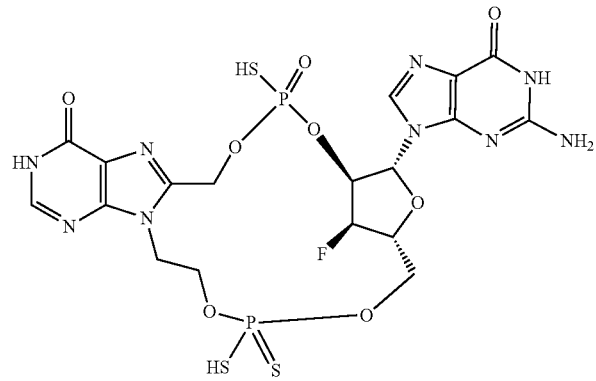

Example 3

Example 3 diastereomers (Diastereomers A-D) were prepared according to procedures analogous to those outlined in Example 1.

(2R,3S,4R,5R)-5-((((2-(8-((Bis(4-methoxyphenyl)(phenyl)methoxy)methyl)-6-oxo-1H-purin-9(6H)-yl)ethoxy)(2-cyanoethoxy)phosphorothioyl)oxy)methyl)-4-fluoro-2-(2-isobutyramido-6-oxo-1H-purin-9(6H)-yl)tetrahydrofuran-3-yl hydrogen phosphonate (I8A)

LCMS (Method A): $T_R$=1.21 min and 1.31 min, m/z 1061.2 (M–H)⁻. $^{31}$P NMR (CD$_3$OD) δ 67.8, 67.5, 2.64. $^{19}$F NMR (CD$_3$OD) δ –204.10, –204.15.

(2R,3S,4R,5R)-5-((((2-Cyanoethoxy)(2-(8-(hydroxymethyl)-6-oxo-1H-purin-9(6H)-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I8B)

LCMS (Method A): $T_R$=0.68 min, m/z 759.1 (M–H)⁻. $^{31}$P NMR (CD$_3$OD) δ 68.06, 67.81, 2.66. $^{19}$F NMR (CD$_3$OD) δ –202.56, –202.61.

N-{9-[(1S,21R,23R,24R)-18-(2-Cyanoethoxy)-24-fluoro-3,9-dioxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),11-trien-23-yl]-6-oxo-6,9-dihydro-1H-purin-2-yl}-2-methylpropanamide (I8C)

LCMS m/z 773.3 (M−H)⁻. $^{31}$P NMR (CD$_3$OD) δ 68.66, 68.12, 65.66, 65.15, 57.81, 56.55. $^{19}$F NMR (CD$_3$OD) δ −196.87, −197.70, −198.79, −199.75.

(1S,21R,23R,24R)-23-(2-Amino-6-oxo-6,9-dihydro-1H-purin-9-yl)-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),11-triene-3,9,18-trione (Example 3)

Example 3 diastereomers (Diastereomers A-D) were purified by prep. RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 3B (Diastereomer B): Prep. RP-HPLC: T$_R$=15.0 min. LCMS (Method D, T$_R$=1.11 min) m/z 652.2 (M+H)⁺. $^1$H NMR (D$_2$O) δ 8.21 (s, 1H), 7.96 (s, 1H), 6.08 (d, J=8.4 Hz, 1H), 5.50 and 5.37 (br dd, 1H), 5.26 (dd, J=12.8 Hz and 7.2 Hz, 2H), 5.16-4.98 (m, 2H), 4.54-4.32 (comp, 2H), 4.32-4.05 (m, 2H), 3.84-3.71 (m, 1H). $^{31}$P NMR (D$_2$O) δ 58.50, 57.46. $^{19}$F NMR (D$_2$O) δ −196.80. Example 3C (Diastereomer C): Prep. RP-HPLC: T$_R$=17.0 min. LCMS (Method D, T$_R$=1.19 min) m/z 652.1 (M+H)⁺. $^1$H NMR (D$_2$O) δ 8.21 (s, 1H), 7.75 (s, 1H), 6.04 (d, J=8.4 Hz, 1H), 5.48 (dd, J=52.8 Hz and 3.6 Hz, 2H), 5.28 (dd, J=12.48 Hz and 7.6 Hz, 2H), 5.20-5.05 (m, 2H) 4.71-4.38 (comp, 5H), 4.29-4.21 (m, 2H), 4.06-3.99 (m, 1H). Example 3D (Diastereomer D): Prep. RP-HPLC: T$_R$=17.6 min. LCMS (Method D, T$_R$=1.20 min) m/z 652.2 (M+H)⁺. $^1$H NMR (D$_2$O) δ 8.21 (s, 1H), 7.80 (s, 1H), 6.04 (d, J=8.4 Hz, 1H), 5.45 (d, J=52.8 Hz and 12.8 Hz, 1H), 5.28 (dd, J=12.4 Hz and 7.6 Hz, 1H), 5.19-5.05 (m, 1H), 4.71-4.38 (m, 5H), 4.29-4.21 (m, 1H), 4.06-3.99 (m, 1H). $^{31}$P NMR (D$_2$O) δ 55.80, 54.95. $^{19}$F NMR (D$_2$O) δ -198.90.

Intermediate 9

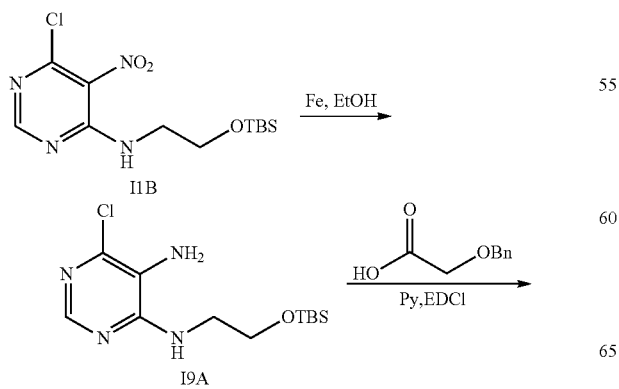

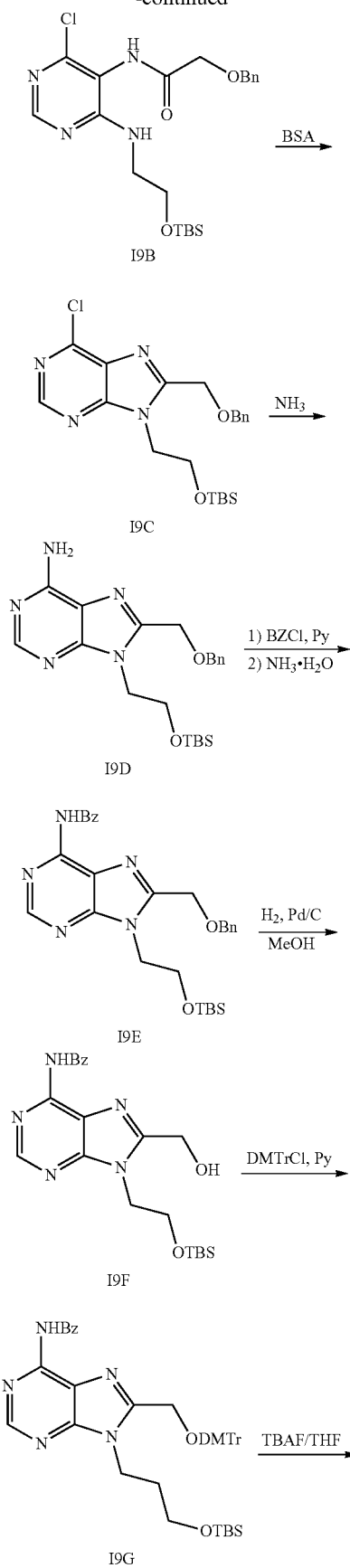

-continued

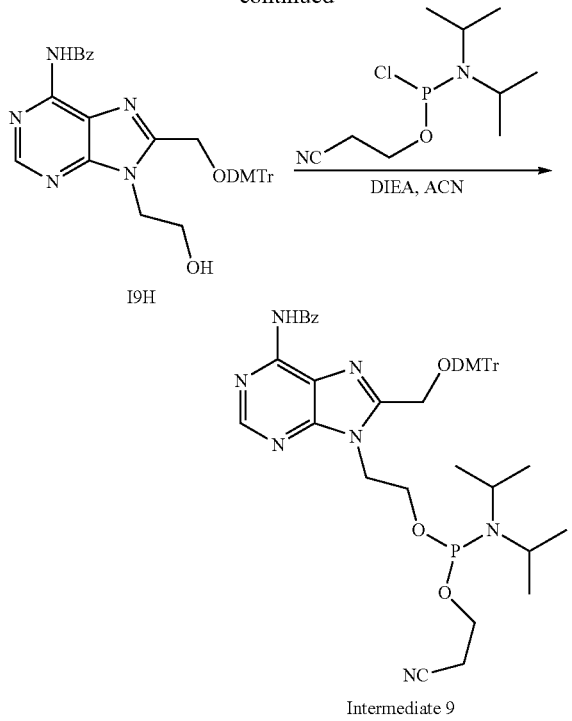

Intermediate 9

N4-(2-((tert-Butyldimethylsilyl)oxy)ethyl)-6-chloropyrimidine-4,5-diamine (I9A)

To a solution of I1B (81.0 g, 243 mmol) in EtOH (500 mL) and H$_2$O (250 mL) was added NH$_4$Cl (78.1 g, 1.46 mol, 51.1 mL), followed by iron powder (54.4 g, 973 mmol). The mixture was stirred at RT for 2 hrs. Solids were filtered off and washed with EtOH (3×100 mL). The combined solution mixture was partially concentrated under reduced pressure, and then diluted with water (200 mL). The mixture was extracted with EtOAc (800 mL), and the organic layer was washed with brine (200 mL), dried (Na$_2$SO$_4$), and concentrated under reduced pressure to give I9A (70.0 g, 95%) as a brown solid. LCMS m/z 303.2 (M+H)$^+$. $^1$H NMR (CDCl$_3$) δ 8.07 (s, 1H), 5.30 (s, 1H), 3.81-3.77 (m, 2H), 3.61 (br d, J=4.8 Hz, 2H), 3.39 (s, 2H), 0.91 (s, 9H), 0.07 (s, 6H).

2-(Benzyloxy)-N-(4-((2-((tert-butyldimethylsilyl) oxy)ethyl)amino)-6-chloropyrimidin-5-yl)acetamide (I9B)

To a solution of 2-(benzyloxy)acetic acid (28.4 mL, 198 mmol) in pyridine (300 mL) was added EDC (38.0 g, 198 mmol). The mixture was stirred at 25° C. for 0.5 hrs, then I9A (30.0 g, 99.1 mmol) was added. The mixture was stirred at 25° C. for 2.5 hrs, and then the reaction mixture was concentrated under reduced pressure and diluted with water (150 mL). The mixture was extracted with EtOAc (300 mL), and then the organic layer was washed with brine (100 mL), dried (Na$_2$SO$_4$), and concentrated under reduced pressure. The residue was purified by silica gel chromatography (1:100-1:1 EtOAc/petroleum ether) to give I9B (35.0 g, 78%) as yellow oil. LCMS m/z 451.2 (M+H)$^+$. $^1$H NMR (CDCl$_3$) δ 8.23 (s, 1H), 7.35-7.21 (m, 5H), 4.65 (s, 2H), 4.10 (s, 2H), 3.72-3.71 (m, 2H), 3.59-3.55 (m, 2H), 0.83 (s, 9H), 0.01 (s, 6H).

8-((Benzyloxy)methyl)-9-(2-((tert-butyldimethylsilyl)oxy)ethyl)-6-chloro-9H-purine (I9C)

To a solution of 19B (27.0 g, 59.9 mmol) was added BSA (118 mL, 479 mmol) at RT. The mixture was heated at 120° C. for 48 hrs. The reaction mixture was concentrated to dryness under reduced pressure. The residue was chased with MeOH (2×50 mL), and then concentrated under reduced pressure. The residue was treated with petroleum ether (100 mL), and then filtered to remove solids. The filtrate was concentrated under reduced pressure to give 19C (23.0 g, 89%) as a semi-pure yellow oil. LCMS m/z 433.2 (M+H)$^+$.

8-((Benzyloxy)methyl)-9-(2-((tert-butyldimethylsilyl)oxy)ethyl)-9H-purin-6-amine (I9D)

A solution of I9C (20.0 g, 46.2 mmol) in NH$_3$/THF (20.0 M, 200 mL) was stirred at 100° C. (2 MPa pressure) for 15 hrs in a sealed tube. The reaction mixture was concentrated to dryness to give 19D (15.0 g, crude) as a brown solid. LCMS m/z 414.3 (M+H)$^+$.

N-(8-((Benzyloxy)methyl)-9-(2-((tert-butyldimethylsilyl)oxy)ethyl)-9H-purin-6-yl)benzamide (I9E)

To a solution of 19D (20.0 g, 48.4 mmol) in pyridine (200 mL) was added benzoyl chloride (39.3 mL, 339 mmol) at 0° C. The resulting mixture was stirred at 20° C. for 2 hrs. H$_2$O (400 mL) and DCM (200 mL) were added, and the mixture was stirred at 0° C. for 30 min. Ammonium hydroxide (7 M, 200 mL) was added, and the mixture was stirred at 20° C. for 15 hrs. The reaction mixture was poured into water (200 mL) and DCM (200 mL), and then the organic layer was removed. The aqueous layer was extracted with DCM (2×100 mL). The combined organic layers were acidified to pH 4 with 1N HCl. The organic phase was separated and washed with sat. aq. NaHCO$_3$ (100 mL), dried (Na$_2$SO$_4$) and concentrated under reduced pressure to give 19E (15.6 g, 62% yield) as a yellow oil. LCMS m/z 518.3 (M+H)$^+$. $^1$H NMR (CDCl$_3$) δ 9.15 (s, 1H), 8.99 (m, 1H), 8.21 (br d, J=7.2 Hz, 2H), 7.79-7.69 (m, 3H), 7.53-7.48 (m, 5H), 5.09 (s, 2H), 4.80 (br s, 1H), 4.66 (t, J=5.2 Hz, 2H), 4.14 (t, J=5.2 Hz, 2H), 0.93 (s, 9H), −0.00 (s, 6H).

N-(9-(2-((tert-Butyldimethylsilyl)oxy)ethyl)-8-(hydroxymethyl)-9H-purin-6-yl)benzamide (I9F)

To a solution of 19E (12.0 g, 23.2 mmol) in MeOH (84.0 mL) was added 10% Pd/C (12.0 g). The suspension was degassed and purged with H$_2$ three times. The mixture was stirred under 50 psi H$_2$ at 60° C. for 15 hrs. The cooled reaction mixture was filtered through a pad of Celite® and the filter cake was washed with MeOH (3×100 mL). The filtrate was concentrated to dryness, and then the residue was purified by prep. RP-HPLC (YMC—Triart Prep C18-s 250 mm×50 mm; mobile phase: (22-58% ACN/10 mM aq. NH$_4$HCO$_3$ over 20 min) to give 19F (3.66 g, 37%) as a white solid. LCMS m/z 428.2 (M+H)$^+$. $^1$H NMR (CDCl$_3$) δ 9.31 (s, 1H), 8.80 (s, 1H), 8.07 (br d, J=7.4 Hz, 2H), 7.64-7.52 (m, 3H), 4.97 (s, 2H), 4.86 (br s, 1H), 4.43 (t, J=5.2 Hz, 2H), 4.01 (t, J=4.8 Hz, 2H), 0.76 (s, 9H), −0.13 (s, 6H).

N-(8-((Bis(4-methoxyphenyl)(phenyl)methoxy) methyl)-9-(2-((tert-butyldimethylsilyl)oxy)ethyl)-9H-purin-6-yl)benzamide (I9G)

A solution of 19F (1.00 g, 2.33 mmol) and DMTrCl (951 mg, 2.81 mmol) in pyridine (10 mL) was stirred at RT for 2 days. MeOH (1 mL) was added and the mixture was stirred at RT for 0.5 hrs, and then concentrated under reduced pressure. The residue was redissolved in MeOH, silica gel (5 g) was added, and then the mixture was concentrated to dryness under reduced pressure. The residue was purified by silica gel chromatography (0-1.75% MeOH/DCM) to give 19G (1.09 g, 64%) as a pale yellow foam. LCMS m/z 730.4 (M+H)+. 1H NMR (CDCl3) δ 9.46 (br s, 1H), 8.80 (s, 1H), 8.06 (d, J=7.3 Hz, 2H), 7.61-7.21 (comp, 12H), 6.83 (d, J=9.0 Hz, 4H), 4.49 (s, 2H), 4.34 (t, J=5.3 Hz, 2H), 3.79 (t, J=5.3 Hz, 2H), 3.75 (s, 6H), 0.59 (s, 9H), −0.35 (s, 6H).

N-(8-((Bis(4-methoxyphenyl)(phenyl)methoxy)methyl)-9-(2-hydroxyethyl)-9H-purin-6-yl)benzamide (I9H)

To a solution of 19G (1.09 g, 1.49 mmol) in THF (15 mL) cooled in an ice/acetone bath (ca. −5° C.) was added a solution of TBAF/THF (1M, 3.43 mL, 3.43 mmol) in a dropwise fashion. The reaction mixture was allowed to warm slowly to 10° C. over 2 hrs, then stored in the refrigerator (ca. 3° C.) overnight. The reaction mixture was removed from the refrigerator, then silica gel (5 g) was added while the mixture was rapidly stirred and cooled in an ice/acetone bath. The mixture was concentrated to dryness under reduced pressure, and the residue was purified by silica gel chromatography (0-10% MeOH/DCM) to give I9H (823 mg, 90%) as a yellow foam. LCMS m/z 616.3 (M+H)+. 1H NMR (CDCl3) δ 8.02 (br s, 1H), 8.75 (s, 1H), 8.01 (d, J=7.3 Hz, 2H), 7.62-7.22 (comp, 12H), 6.83 (d, J=8.8 Hz, 4H), 4.47 (s, 2H), 4.26-4.24 (m, 2H), 3.93-3.87 (m, 2H), 3.76 (s, 6H), 3.47 (br s, 1H).

2-(6-Benzamido-8-((bis(4-methoxyphenyl)(phenyl)methoxy)methyl)-9H-purin-9-yl)ethyl (2-cyanoethyl) diisopropylphosphoramidite (Intermediate 9)

To a solution of I9H (823 mg, 1.34 mmol) in DCM (10 mL) was added DIEA (699 μL, 4.01 mmol) followed by slow, dropwise addition of 3-((chloro(diisopropylamino)phosphino)oxy)propanenitrile (399 μL, 1.61 mmol). The mixture was stirred at RT for 2 hrs, then quenched by the addition of 5% aq. NaHCO3. The mixture was concentrated under reduced pressure, and the residue was purified by RP-MPLC (0-100% ACN/H2O containing 0.04% NH4HCO3) to give Intermediate 9 (926 mg, 85%) as a white solid. LCMS m/z (M+H+OH-N,N-diisopropylamino)+ 733.4. 1H NMR (CD3OD) δ 8.57 (s, 1H), 7.99 (d, J=7.3 Hz, 2H), 7.57-7.53 (m, 1H), 7.48-7.44 (m, 2H), 7.41-7.39 (m, 2H), 7.30-7.26 (comp, 4H), 7.22-7.19 (m, 2H), 7.13-7.09 (m, 1H), 6.78-6.74 (comp, 4H), 4.56-4.49 (comp, 2H), 4.37 (app t, J=5.4 Hz, 2H), 3.83-3.68 (comp, 2H), 3.64 (app s, 6H), 3.40-3.34 (comp, 2H), 3.28-3.21 (comp, 2H), 2.40 (app t, J=5.9 Hz, 2H), 0.94 (d, J=6.8 Hz, 6H), 0.78 (d, J=6.8 Hz, 6H). 31P NMR (CD3OD) δ 147.97.

Intermediate 10

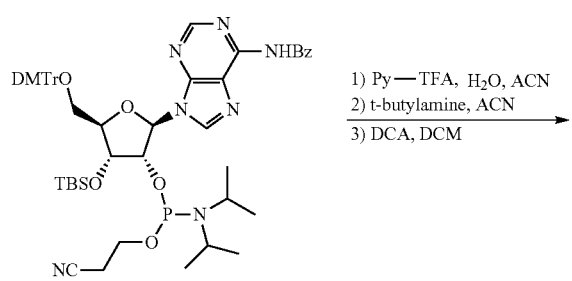

1) Py—TFA, H2O, ACN
2) t-butylamine, ACN
3) DCA, DCM

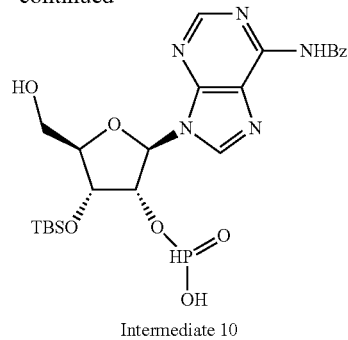

Intermediate 10

(2R,3R,4R,5R)-2-(6-Benzamido-9H-purin-9-yl)-4-((tert-butyldimethylsilyl)oxy)-5-(hydroxymethyl)tetrahydrofuran-3-yl hydrogen phosphonate (Intermediate 10)

To a solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (2.00 g, 2.02 mmol) in ACN (12 mL) was added H2O (73.0 mg, 4.06 mmol) followed by Py.TFA (470 mg, 2.43 mmol). The reaction mixture was stirred at RT for 15 min, and then t-butylamine (9.60 mL, 91.03 mmol) was rapidly introduced. The resulting mixture was stirred at RT for 15 min, and then concentrated under reduced pressure. The residue was redissolved in DCM (12 mL), then H2O (364 mg, 20.24 mmol) and 6% DCA in DCM (12 mL) were added. The resulting bright orange solution was stirred at RT for 2 hrs, and Et3SiH (10 mL) was added. The reaction mixture was stirred at RT for 1.5 hrs, and then a 1:1 mixture of pyridine:MeOH (10 mL) was added. The solvents were removed under reduced pressure and the residue was purified by silica gel chromatography (100% DCM-8:1:1 DCM:MeOH:EtOH) to give Intermediate 10 (1.04 g, 93%) as a white solid. LCMS m/z (M+H)+550.3. 31P NMR (CDCl3) δ 2.03.

Utilizing Intermediates 1 and 2 and the synthetic methods employed in Examples 1 and 2, the compounds set forth in Table 2 below were prepared.

Prep HPLC Conditions:

(A) XBridge Prep C18 OBD 5 μm, 19×150 mm column eluting with 0-10% ACN/H2O containing 5 mM NH4HCO3 over 20 min, flow rate-10.0 mL/min.

(B) XBridge BEH Prep OBD Amide 5 μm, 19×150 mm column eluting with 9:1 ACN:50 mM aq. NH4HCO2 to 3:2 ACN:50 mM aq. NH4HCO2 over 23 min, flow rate-10.0 mL/min.

(C) XBridge Prep C18 OBD 5 μm, 19×150 mm column eluting with 0-40% ACN/H2O containing 5 mM NH4HCO3 over 15 min, flow rate-10.0 mL/min.

TABLE 2

| Example | Structure | Coupling Method | Cyclization Method | LCMS Method/(m/z) | Prep HPLC Conditions/$T_R$ |
|---------|-----------|-----------------|--------------------|--------------------|-----------------------------|

(1S,21R,23R,24R)-23-(2-Amino-6-oxo-6,9-dihydro-1H-purin-9-yl)-24-fluoro-3,18-dihydroxy-2,4,17,19,22-pentaoxa-7,10,12,14-tetraaza-3lambda5,18lambda5-diphosphatetracyclo[19.2.1.06,14.08,13]tetracosa-6,8(13),9,11-tetraene-3,18-dione (Example 4)

| 4 | | B | B | C/602.1 (M − H)⁻ | A/10.8 min |

$^1$H NMR (D$_2$O) δ 8.84 (s, 1H), 8.82 (s, 1H), 7.48 (s, 1H), 5.86 (d, J = 8.0 Hz, 1H), 5.14 (dd, J = 14.3, 7.8 Hz, 1H), 4.96 (dd, J = 52.7, 3.8 Hz, 1H), 4.95 (dd, J = 14.1, 8.3 Hz, 1H), 4.75-4.55 (comp, 2H), 4.51-4.44 (m, 1H), 4.41-4.35 (m, 1H), 4.27-4.18 (comp, 2H), 3.89 (comp, 2H). $^{19}$F NMR (D$_2$O) δ −197.73. $^{31}$P NMR (D$_2$O) δ −0.44, −2.32.

(1S,21R,23R,24R)-23-(2-Amino-6-oxo-6,9-dihydro-1H-purin-9-yl)-24-fluoro-18-hydroxy-3-sulfanyl-2,4,17,19,22-pentaoxa-7,10,12,14-tetraaza-3lambda5,18lambda5-diphosphatetracyclo[19.2.1.06,14.08,13]tetracosa-6,8(13),9,11-tetraene-3,18-dione (Example 5)

| 5A (Diast A) | | B | A | C/618.2 (M − H)⁻ | B/17.9 min |

$^{19}$F NMR (D$_2$O) δ −198.07. $^{31}$P NMR (D$_2$O) δ 55.44, −0.57.

| 5B (Diast B) | | B | A | C/618.1 (M − H)⁻ | B/18.7 min |

$^{19}$F NMR (D$_2$O) δ −196.11. $^{31}$P NMR (D$_2$O) δ 57.40, -0.47.

(1S,21R,23R,24R)-23-(2-Amino-6-oxo-6,9-dihydro-1H-purin-9-yl)-24-fluoro-3-hydroxy-18-sulfanyl-2,4,17,19,22-pentaoxa-7,10,12,14-tetraaza-3lambda5,18lambda5-diphosphatetracyclo[19.2.1.06,14.08,13]tetracosa-6,8(13),9,11-tetraene-3,18-dione (Example 6)

TABLE 2-continued

| Example | Structure | Coupling Method | Cyclization Method | LCMS Method/(m/z) | Prep HPLC Conditions/$T_R$ |
|---|---|---|---|---|---|
| 6A (Diast A) | 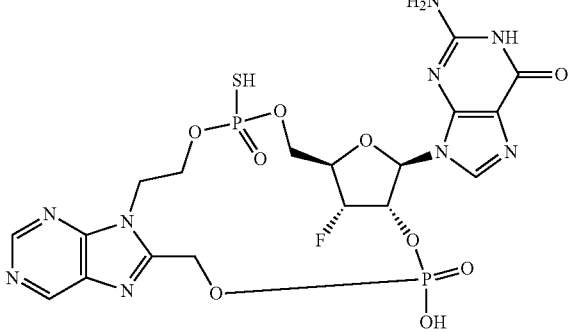 $^{19}$F NMR (D$_2$O) δ −197.87. $^{31}$P NMR (D$_2$O) δ 55.74, −2.27 | A | B | C/618.2 (M − H)$^-$ | C/7.5 min |
| 6B (Diast B) | 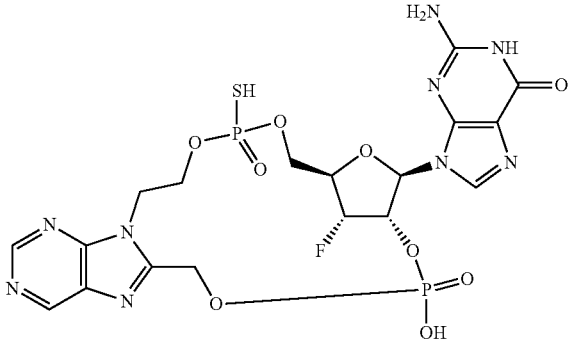 [SMILES: Nc1nc2c(ncn2[C@@H]2O[C@@H]3COP(=O)(S)OCCn4c(nc5cncnc54)COP(=O)(O)O[C@@H]2[C@@H]3F)c(=O)[nH]1] $^{19}$F NMR (D$_2$O) δ −197.97. $^{31}$P NMR (D$_2$O) δ 54.47, −2.48 | A | B | C/618.1 (M − H)$^-$ | C/8.2 min |

Utilizing Intermediates 2 and 9 and the synthetic methods employed in Examples 1 and 2, the compounds set forth in Table 3 below were prepared.

Prep HPLC Conditions: XBridge Prep C18 OBD 5 μm, 19×150 mm column eluting with 0-10% ACN/H$_2$O containing 5 mM NH$_4$HCO$_3$ over 19 min, then 10% ACN/H$_2$O containing 5 mM NH$_4$HCO$_3$ for 1.5 min, flow rate-10.0 mL/min.

TABLE 3

| Example | Structure | Coupling Method | Cyclization Method | LCMS Method/(m/z) | Prep HPLC $T_R$ |
|---|---|---|---|---|---|
| (1S,21R,23R,24R)-9-Amino-23-(2-ammo-6-oxo-6,9-dihydro-1H-purin-9-yl)-24-fluoro-3,18-disulfanyl-2,4,17,19,22-pentaoxa-7,10,12,14-tetraaza-3lambda5,18lambda5-diphosphatetracyclo[19.2.1.0$^{6,14}$.0$^{8,13}$]tetracosa-6,8(13),9,11-tetraene-3,18-dione (Example 7) | | | | | |
| 7A (Diast A) | 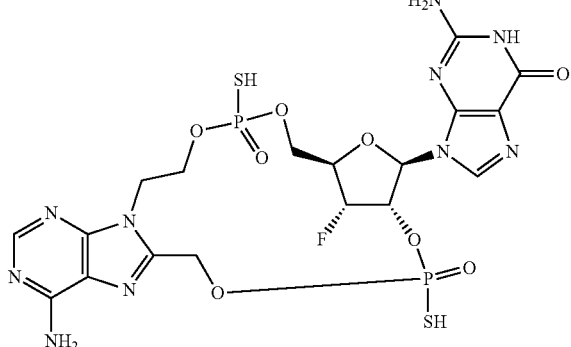 $^1$H NMR (D$_2$O) δ 8.17 (s, 1H), 7.66 (s, 1H), 5.90 (d, J = 8.0 Hz, 1H), 5.34 (dd, J = 53.2, 3.8 Hz, 1H), 5.18 (dd, J = 12.6, 8.0 Hz, 1H), 4.83 (dddd, J = 26.5, 12.3, 8.0, 3.8 Hz, 1H), 4.67-4.59 (comp, 2H), 4.46-4.24 (comp, 3H), 4.09 (app dq, 11.8, 2.3 Hz, 1H), 4.01-3.92 (comp, 2H). $^{19}$F NMR (D$_2$O) δ −198.44. $^{31}$P NMR (D$_2$O) δ 55.31, 55.13. | A | A | D/649.1 (M − H)$^-$ | 13.1 min early cut |

TABLE 3-continued

| Example | Structure | Coupling Method | Cyclization Method | LCMS Method/(m/z) | Prep HPLC $T_R$ |
|---|---|---|---|---|---|
| 7B (Diast B) | [structure] | A | A | D/649.0 (M − H)⁻ | 13.1 min late cut |

$^1$H NMR (D$_2$O) δ 8.12 (s, 1H), 7.68 (s, 1H), 5.89 (d, J = 8.3 Hz, 1H), 5.31 (dd, J = 53.0, 3.5 Hz, 1H, 5.18 (dd, J = 12.6, 8.0 Hz, 1H), 4.87 (dddd, J = 26.4, 12.0, 8.0, 3.5 Hz, 1H), 4.75-4.55 (comp, 2H), 4.40-4.26 (comp, 3H), 4.11-4.05 (m, 1H), 3.97-3.91 (comp, 2H). $^{19}$F NMR (D$_2$O) δ −198.45. $^{31}$P NMR (D$_2$O) δ 55.27, 54.96.

| 7C (Diast C) | [structure] | A | A | D/649.1 (M − H)⁻ | 17.2 min |

$^1$H NMR (D$_2$O) δ 8.11 (s, 1H), 7.52 (s, 1H), 5.85 (d, J = 8.3 Hz, 1H), 5.35, (dd, J = 53.2, 3.8 Hz, 1H), 5.18 (dd, J = 12.8, 8.5 Hz, 1H), 4.95-4.44 (comp, 4H), 4.34-4.17 (comp, 3H), 4.12-4.06 (m, 1H), 3.89-3.84 (m, 1H). $^{19}$F NMR (D$_2$O) δ −198.46. $^{31}$P NMR (D$_2$O) δ 54.56, 54.07.

| 7D (Diast D) | [structure] | A | A | D/649.0 (M − H)⁻ | 19.5 min |

$^{19}$F NMR (D$_2$O) δ −196.92; $^{31}$P NMR (D$_2$O) δ 56.40, 54.85.

Utilizing Intermediates 1 and 10 and the synthetic methods employed in Examples 1 and 2, the compounds set forth in Table 4 below were prepared.

Prep HPLC Conditions:
XBridge BEH Prep OBD Amide 5 μm, 19×150 mm column eluting with 9:1
ACN:50 mM aq. NH$_4$HCO$_2$ (isocratic), flow rate-10.0 mL/min.

TABLE 4

| Example | Structure | Coupling Method | Cyclization Method | LCMS Method/(m/z) | Prep HPLC $T_R$ |
|---|---|---|---|---|---|
| (1R,21R,23R,24R)-23-(6-Amino-9H-purin-9-yl)-24-hydroxy-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),9,11-tetraene-3,18-dione (Example 8) | | | | | |
| 8 (Diast B) | [structure] | A | A | B/616.1 (M − H)⁻ | 13.1 min |

¹H NMR (CD₃OD) δ 9.04 (s, 1H), 8.95 (s, 1H), 8.23 (s, 1H), 8.14 (s, 1H), 6.30 (d, J = 8.4 Hz, 1H), 5.48 (dxd, J = 3.2, 6.0 Hz, 1H), 5.20 (m, 1H), 5.07 (m, 1H), 4.84 (m, 2H, under water peak), 4.63-4.60 (m, 3H), 4.32 (m, 2H), 3.97 (m, 1H). ³¹P NMR (CD₃OD) δ 57.68, 54.81.

Utilizing Intermediates 1 or 4 and 2 or 5, and the synthetic methods employed in Examples 1 and 2, the compounds set forth in Table 5 below were prepared.

Separation/Purification Conditions:

(A) RP-MPLC (0-20% ACN/H₂O containing 0.04% NH₄HCO₃)

(B) RP-MPLC (0-10% ACN/H₂O containing 0.04% NH₄HCO₃), then NP-MPLC (0-100% MeOH/DCM)

(C) 1) RP-MPLC (0-30% ACN/H₂O containing 0.04% NH₄HCO₃); then 2) prep HPLC, XBridge BEH Prep OBD Amide 5 m, 19×150 mm column eluting with 9:1 ACN:50 mM aq. NH₄HCO₂ to 60% of a 3:2 mixture of ACN:50 mM aq. NH₄HCO₂ over 23 min, flow rate-10.0 mL/min; then 3) prep HPLC, XBridge Prep C18 OBD 5 μm, 19×150 mm column eluting with 50 mM aq. NH₄HCO₃ for 5 min, then 0-30% ACN/H₂O containing 5 mM NH₄HCO₃ over 15 min, flow rate-10.0 mL/min.

TABLE 5

| Example | Structure | Coupling Method | Cyclization Method | LCMS Method/ (m/z) | Separation/ Purification |
|---|---|---|---|---|---|
| (1R,22R,24R,25R)-24-(2-Amino-6-oxo-6,9-dihydro-1H-purin-9-yl)-25-hydroxy-3,19-disulfanyl-2,4,18,20,23-pentaoxa-7,10,12,14-tetraaza-3lambda5,19lambda5-diphosphatetracyclo[20.2.1.0⁶,¹⁴.0⁸,¹³]pentacosa-6,8,10,12-tetraene-3,19-dione (Example 9) | | | | | |
| 9 (Diast C/D) | [structure] | A | A | B/646.0 (M − H)⁻ | A |

¹H NMR (D₂O) δ 8.93 (s, 0.7H), 8.92 (s, 0.3H), 8.79 (s, 0.7H), 8.78 (s, 0.3H), 7.94 (s, 0.3H), 7.80 (s, 0.7H), 5.93 (d, J = 7.3 Hz, 0.7H), 5.90 (d, J = 7.5 Hz, 0.3H), 5.13 (dd, J = 12.3, 7.0 Hz, 1H), 5.03-4.96 (m, 1H), 4.91-4.87 (m, 1H), 4.60-3.81 (comp, 9H), 2.03-1.90 (m, 1H), 1.73-1.63 (m, 1H). ³¹P NMR (D₂O) δ 56.86 (s, 0.3P), 56.59 (overlapping s, 1.4P), 56.50 (s, 0.3P).

(1R,21R,23R,24R)-23-(2-Amino-6-oxo-6,9-dihydro-1H-purin-9-yl)-3,18,24-trihydroxy-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 10)

TABLE 5-continued

| Example | Structure | Coupling Method | Cyclization Method | LCMS Method/ (m/z) | Separation/ Purification |
|---|---|---|---|---|---|
| 10 | 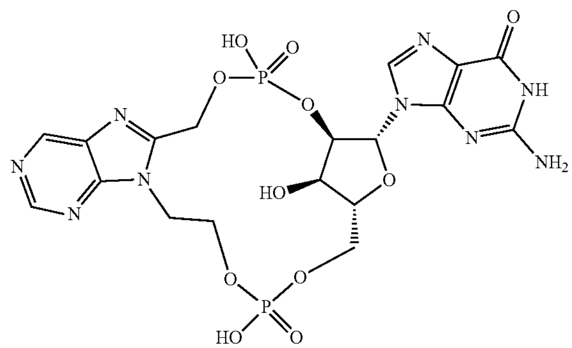 [SMILES: Nc1nc2c(ncn2[C@@H]2O[C@@H]3COP(=O)(O)OCCn4c(nc5cncnc54)COP(=O)(O)O[C@@H]2[C@@H]3O)c(=O)[nH]1] | B | B | D/600.0 (M − H)⁻ | B |

$^1$H NMR (D$_2$O) δ 8.88 (s, 1H), 8.34 (s, 1H), 7.52 (s, 1H), 5.83 (d, J = 8.0 Hz, 1H), 5.06 (ddd, J = 66.8, 14.0, 8.0 Hz, 2H), 4.67-4.54 (comp, 2H), 4.46-4.35 (comp, 1H), 4.28-4.13 (comp, 4H), 3.81-3.40 (comp, 2H). $^{31}$P NMR (D$_2$O) δ −0.29, −1.84.

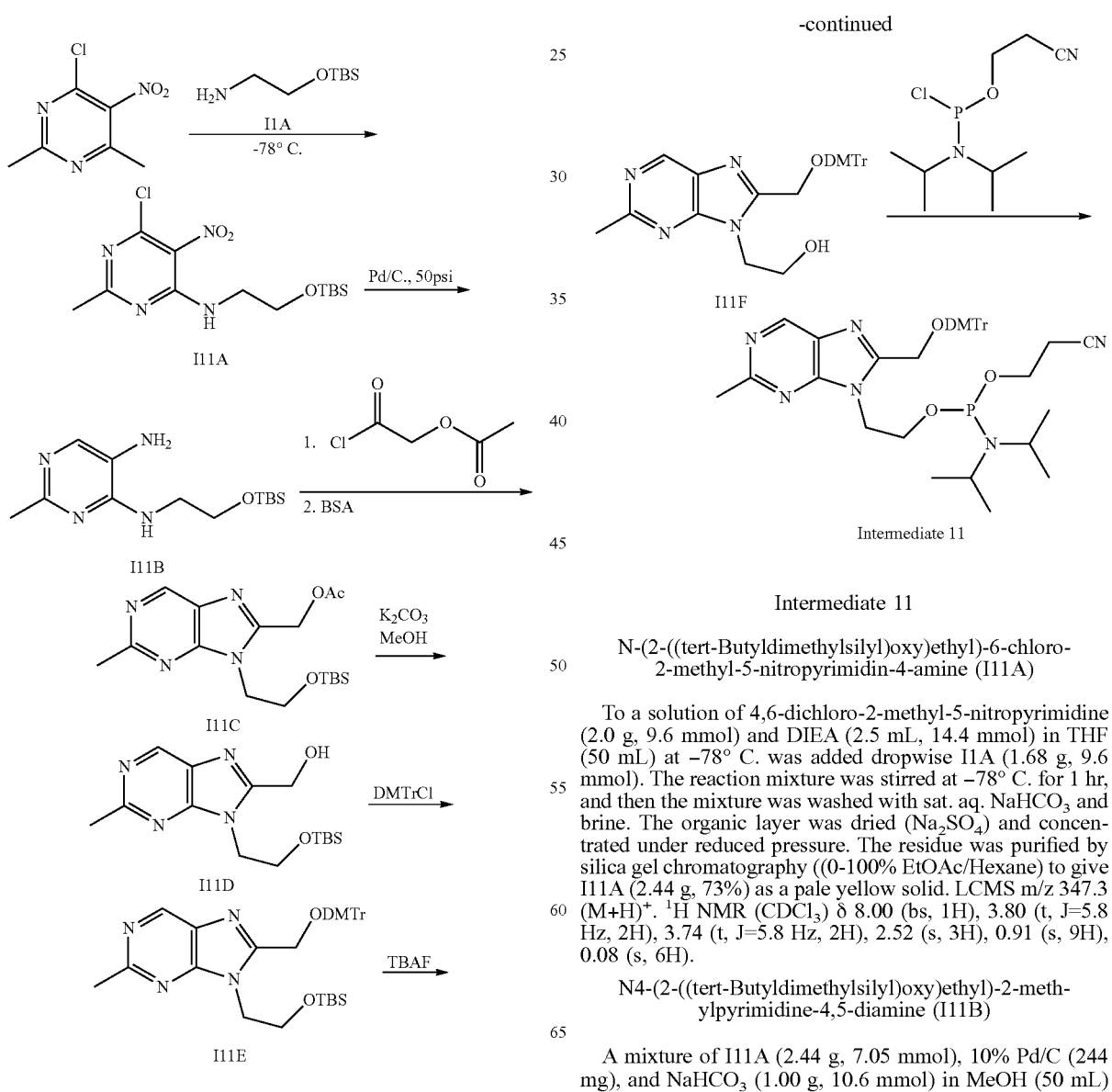

Intermediate 11

N-(2-((tert-Butyldimethylsilyl)oxy)ethyl)-6-chloro-2-methyl-5-nitropyrimidin-4-amine (I11A)

To a solution of 4,6-dichloro-2-methyl-5-nitropyrimidine (2.0 g, 9.6 mmol) and DIEA (2.5 mL, 14.4 mmol) in THF (50 mL) at −78° C. was added dropwise I1A (1.68 g, 9.6 mmol). The reaction mixture was stirred at −78° C. for 1 hr, and then the mixture was washed with sat. aq. NaHCO$_3$ and brine. The organic layer was dried (Na$_2$SO$_4$) and concentrated under reduced pressure. The residue was purified by silica gel chromatography ((0-100% EtOAc/Hexane) to give I11A (2.44 g, 73%) as a pale yellow solid. LCMS m/z 347.3 (M+H)$^+$. $^1$H NMR (CDCl$_3$) δ 8.00 (bs, 1H), 3.80 (t, J=5.8 Hz, 2H), 3.74 (t, J=5.8 Hz, 2H), 2.52 (s, 3H), 0.91 (s, 9H), 0.08 (s, 6H).

N4-(2-((tert-Butyldimethylsilyl)oxy)ethyl)-2-methylpyrimidine-4,5-diamine (I11B)

A mixture of I11A (2.44 g, 7.05 mmol), 10% Pd/C (244 mg), and NaHCO$_3$ (1.00 g, 10.6 mmol) in MeOH (50 mL)

was hydrogenated at 50 psi H$_2$ for 4 hrs using a Parr shaker. The reaction mixture was filtered through a pad of Celite® and the filtrate was concentrated under reduced pressure. The residue was partitioned between DCM and H$_2$O. The organic layer was washed with H$_2$O (3×) and brine, then dried (Na$_2$SO$_4$) and concentrated under reduced pressure. The residue was purified by silica gel chromatography (0-10% MeOH/DCM) to give I11B (1.96 g, 98%) as a light tan solid. LCMS m/z 284.3 (M+H)$^+$. $^1$H NMR (CD$_3$OD) δ 7.49 (s, 1H), 3.81 (t, J=6.3 Hz, 2H), 3.60 (t, J=6.3 Hz, 2H), 2.34 (s, 3H), 0.90 (s, 9H), 0.07 (s, 6H).

(9-(2-((tert-Butyldimethylsilyl)oxy)ethyl)-2-methyl-9H-purin-8-yl)$_m$ethyl acetate (I11C)

To a solution of I11B (1.96 g, 6.95 mmol) in DCM (50 mL) at RT was added DIEA (1.8 mL, 10.4 mmol) followed by a dropwise addition of 2-chloro-2-oxoethyl acetate (0.748 mL, 6.95 mmol). The resulting mixture was stirred at RT for 3 hrs. The reaction mixture was concentrated under reduced pressure. The residue was dissolved in BSA (30 mL) and heated at 130° C. overnight. Then the mixture was diluted with EtOAc, and washed with sat. aq. NaHCO$_3$ and brine. The organic layer was dried (Na$_2$SO$_4$), and concentrated under reduced pressure. The residue was purified by silica gel chromatography (0-100% EtOAc/Hexane) to give I11C (0.86 g, 34%). LCMS m/z 365.4 (M+H)$^+$. $^1$H NMR (CD$_3$OD) δ 8.92 (s, 1H), 5.49 (s, 2H), 4.52 (t, J=5.0 Hz, 2H), 4.02 (t, J=5.3 Hz, 2H), 2.77 (s, 3H), 2.16 (s, 3H), 0.73 (s, 9H), −0.15 (s, 6H).

(9-(2-((tert-Butyldimethylsilyl)oxy)ethyl)-2-methyl-9H-purin-8-yl)methanol (I11D)

A mixture of I11C (0.86 g, 2.4 mmol) and K$_2$CO$_3$ (20 mg, 0.24 mmol) in MeOH (30 mL) was stirred at RT for 1 hr, and then concentrated under reduced pressure. The residue was purified by silica gel chromatography (0-10% MeOH/DCM) to give I11D (0.73 g, 95%) as a pale yellow solid. LCMS m/z 323.3 (M+H)$^+$. $^1$H NMR (CD$_3$OD) δ 8.87 (s, 1H), 4.94 (s, 2H), 4.55 (t, J=5.3 Hz, 2H), 4.04 (t, J=5.3 Hz, 2H), 2.76 (s, 3H), 0.72 (s, 9H), −0.17 (s, 6H).

8-((Bis(4-methoxyphenyl)(phenyl)methoxy)methyl)-9-(2-((tert-butyldimethylsilyl)oxy)ethyl)-2-methyl-9H-purine (I11E)

A mixture of I11D (0.73 g, 2.27 mmol) and DMTrCl (1.15 g, 3.40 mmol) in pyridine (20 mL) was stirred at RT overnight. The reaction was quenched with sat. aq. NaHCO$_3$ (10 mL) and H$_2$O (40 mL) then extracted with EtOAc (2×). The organic layers were combined, washed with brine, dried (Na$_2$SO$_4$) and concentrated under reduced pressure. The residue was purified by silica gel chromatography (0-100% EtOAc/Hexane) to give I11E (1.13 g, 80%) as a light yellow foam. LCMS m/z 625.5 (M+H)$^+$. $^1$H NMR (CD$_3$OD) δ 8.89 (s, 1H), 7.51-7.20 (comp, 9H), 6.88 (d, J=9.0 Hz, 4H), 4.54 (s, 2H), 4.38 (t, J=5.3 Hz, 2H), 3.81 (t, J=5.3 Hz, 2H), 3.77 (s, 6H), 2.76 (s, 3H), 0.59 (s, 9H), −0.32 (s, 6H).

2-(8-((Bis(4-methoxyphenyl)(phenyl)methoxy)methyl)-2-methyl-9H-purin-9-yl)ethan-1-ol (I11F)

To a solution of I11E (1.13 g, 1.80 mmol) in THF (10 mL) at −5° C. was added a solution of TBAF in THF (1.0 M, 4.0 mL, 3.60 mmol) in a slow, dropwise fashion. The reaction mixture was stirred at RT for 2 hrs and then sat. aq. NH$_4$Cl solution (30 mL) was added followed by H$_2$O (30 mL) and the resulting mixture was extracted with EtOAc (2×). The organic layers were combined, washed with brine, dried (Na$_2$SO$_4$) and concentrated under reduced pressure. The residue was purified by silica gel chromatography (0-7% MeOH/DCM) to give I11F (824 mg, 90%) as a white solid. LCMS m/z 511.4 (M+H)$^+$. $^1$H NMR (CD$_3$OD) δ 8.84 (s, 1H), 7.51-7.23 (comp, 9H), 6.85 (d, J=9.0 Hz, 4H), 4.62 (s, 2H), 4.34 (t, J=5.3 Hz, 2H), 3.79-3.75 (comp, 8H), 2.76 (s, 3H).

2-(8-((Bis(4-methoxyphenyl)(phenyl)methoxy)methyl)-2-methyl-9H-purin-9-yl)ethyl (2-cyanoethyl) diisopropylphosphoramidite (Intermediate 11)

To a solution of I11F (0.5 g, 0.98 mmol) and DIEA (511 μL, 2.94 mmol) in ACN (8 mL) was added dropwise 3-((chloro(diisopropylamino)phosphino)oxy) propanenitrile (436 μL, 1.96 mmol). The reaction mixture was stirred at RT for 2 hrs, and then quenched by the addition of sat. aq. NaHCO$_3$ (1 mL) and H2O (1 mL). The resulting mixture was purified by RP-MPLC (0-100% ACN/H$_2$O) to give Intermediate 11 (0.39 g, 56%) as a white foam. LCMS m/z 628.4 (M+H+OH-N,N-diisopropylamino)+. 1H NMR (CD$_3$CN) δ 8.86 (s, 1H), 7.54-7.21 (comp, 9H), 6.88 (d, J=8.8 Hz, 4H), 4.43 (d, J=2.0 Hz, 2H), 4.34 (td, J=5.4 and 2.0 Hz, 2H), 3.85-3.75 (comp, 8H), 3.48-3.43 (m, 2H), 3.34-3.30 (m, 2H), 2.69 (s, 3H), 2.42 (t, J=6.2 Hz, 2H), 1.01 (d, J=6.8 Hz, 6H), 0.83 (d, J=6.8 Hz, 6H). 31P NMR (CD$_3$CN) δ 147.37.

Example 11

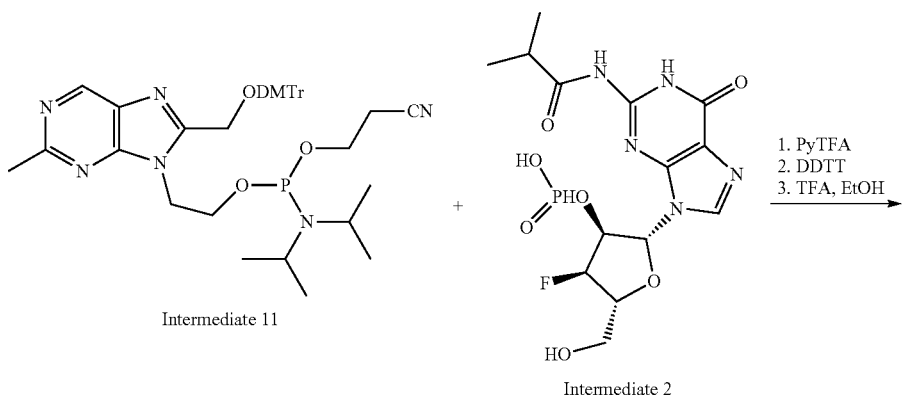

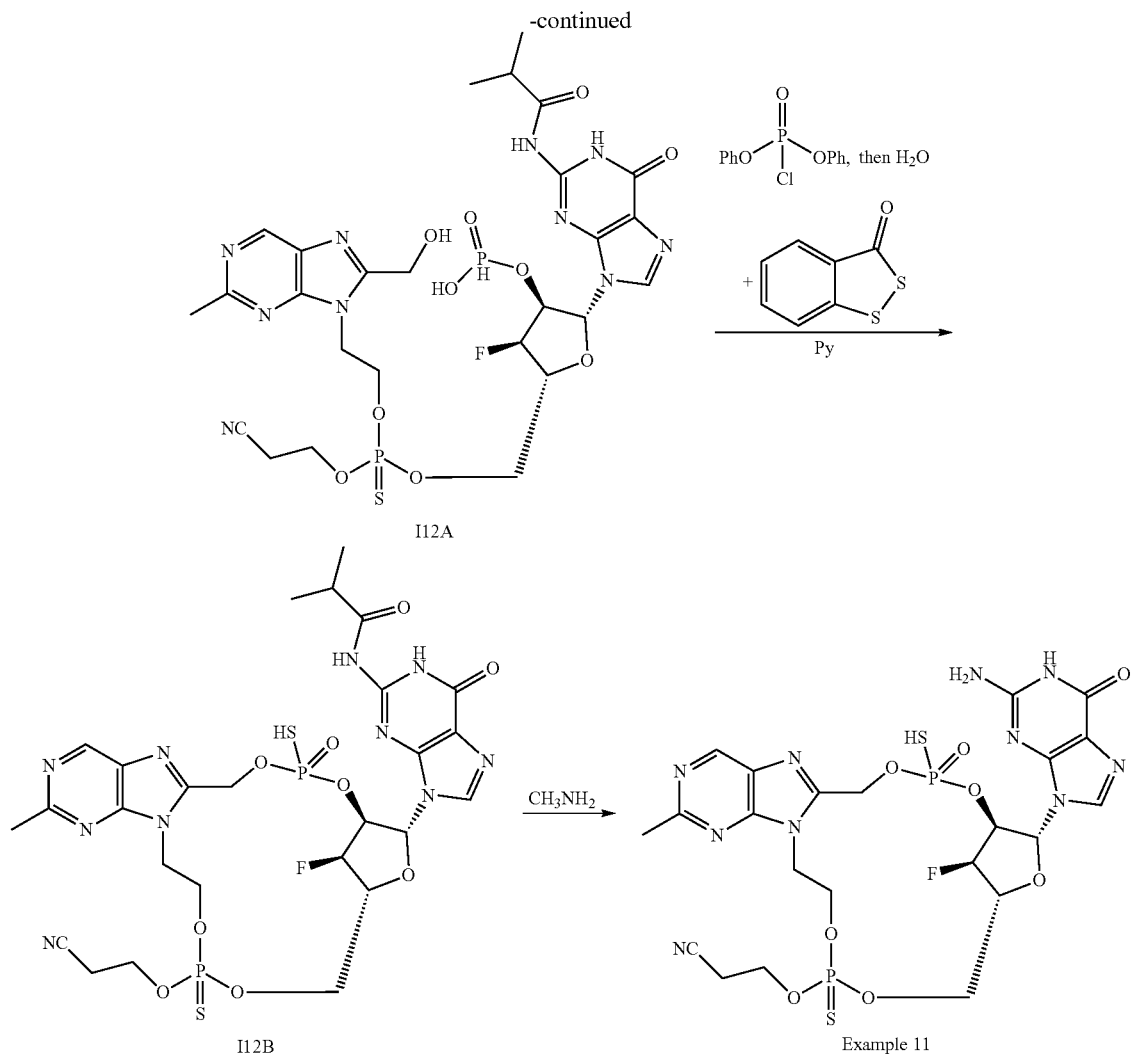

Example 11 diastereomers (Diastereomers A-D) were prepared according to procedures analogous to those outlined in Example 1.

(2R,3S,4R,5R)-5-((((2-Cyanoethoxy)(2-(8-(hydroxymethyl)-2-methyl-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I12A)

LCMS (Method D, TR=1.08 min) m/z 757.1 (M−H)−. $^{31}$P NMR (CD$_3$OD) δ 68.03, 67.71, 2.52. $^{19}$F NMR (CD$_3$OD) δ −201.10, −201.29.

N-{9-[(1S,21R,23R,24R)-18-(2-Cyanoethoxy)-24-fluoro-11-methyl-3-oxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracsa-6,8,10,12-tetraecotetraen-23-yl]-6-oxo-6,9-dihydro-1H-purin-2-yl}-2-methylpropanamide (I12B)

LCMS (Method D, T$_R$=1.22 min) m/z 771.3 (M−H)+. $^{31}$P NMR (CD$_3$OD) δ 68.91, 67.83, 65.48, 65.23, 60.80, 60.26, 57.77, 56.69, $^{19}$F NMR (CD$_3$OD) δ −196.90, −197.60, −198.92, −199.69.

(1S,21R,23R,24R)-23-(2-Amino-6-oxo-6,9-dihydro-H-purin-9-yl)-24-fluoro-11-methyl-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 11)

Example 11 diastereomers (Diastereomers A-D) were purified by prep. RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 11A (mixture of 40% Diastereomer A and 60% Diastereomer B): Prep. RP-HPLC: T$_R$=12.7 min. LCMS (Method D, T$_R$=1.12 and 1.18 min), m/z 650.0 (M+H)+. $^1$H NMR (D$_2$O) δ 9.03 (s, 1H), 9.00 (s, 0.4H), 8.03 (s, 0.4H), 7.81 (s, 1H), 6.07 (d, J=8.0 Hz, 1H), 6.05 (d, J=7.8 Hz, 0.4H), 5.50 (dd, J=52.8 Hz and 3.6 Hz, 0.8H), 5.41 (dd, J=13.2 Hz and 7.6 Hz, 1.6H), 5.24-5.18 (m, 1.6H), 4.79-3.97 (comp, 15.4H), 2.86 (s, 3H), 2.85 (s, 1.2H). $^{31}$P NMR (D$_2$O) 57.10 (minor diastereomer), 55.64 (minor diastereomer), 55.53 (major diastereomer), 55.48 (major diastereomer), $^{19}$F NMR (D$_2$O) δ −196.99 (minor diastereomer), −198.62 (major diastereomer). Example 11C (Diastereomer C): Prep. RP-HPLC: $T_R$=16.8 min. LCMS (Method D, $T_R$=1.17 min) m/z 650.0 (M+H)+. $^1$H NMR (D$_2$O) 9.09 (s, 1H), 7.65 (s, 1H), 6.06 (d, J=7.8 Hz, 1H), 5.55 (dd, J=53.0 and 3.8 Hz, 1H), 5.40 (dd, J=12.8 and 8.0 Hz, 1H), 4.97-4.39 (comp, 7H), 4.24 (dd, J=11.3 and 4.5 Hz, 1H), 4.04 (m, 1H), 2.89 (s, 3H). $^{31}$P NMR (D$_2$O) δ 55.11, 54.71, $^{19}$F NMR (D$_2$O) δ −198.55. Example 11D (Diastereomer D): Prep. RP-HPLC: $T_R$=18.7 min. LCMS (Method D, $T_R$=1.20 min) m/z 650.0 (M+H)+. $^1$H NMR (D$_2$O) δ 9.04 (s, 1H), 7.80 (s, 1H), 6.04 (d, J=7.8 Hz, 1H), 5.25-5.00 (comp, 4H), 4.76-4.52 (comp, 3H), 4.43 (dd, J=10.0 and 5.2 Hz, 2H), 4.24 (dd, J=11.0 and 6.5 Hz, 1H), 4.04 (d, J=12 Hz, 1H), 2.88 (s, 3H), $^{31}$P NMR (D$_2$O) δ 56.82, 55.63. $^{19}$F NMR (D$_2$O) δ −197.21.

Intermediate 13

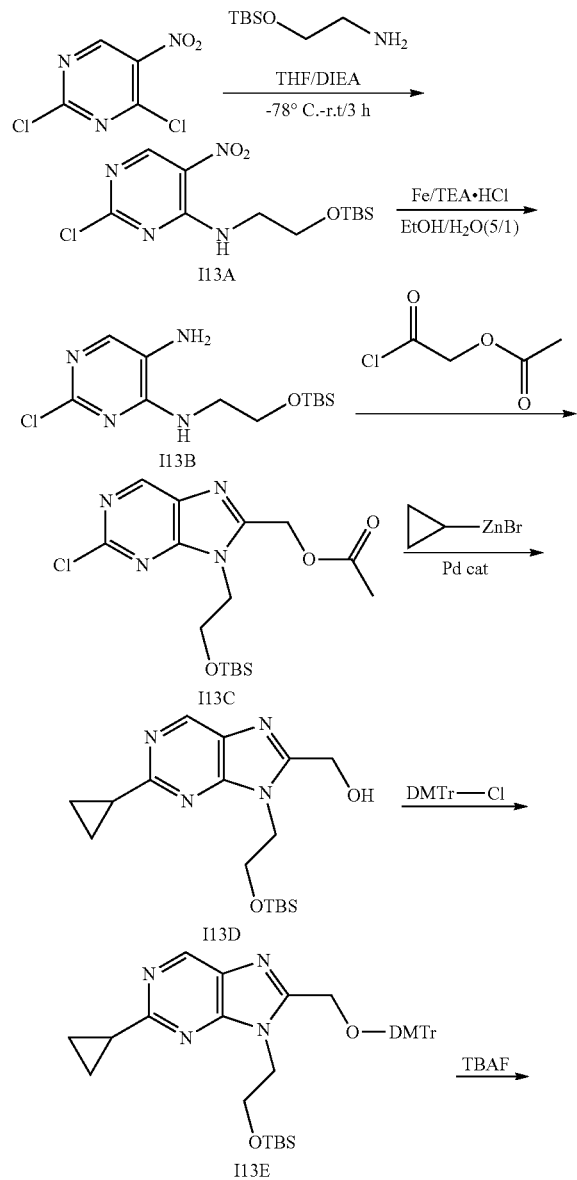

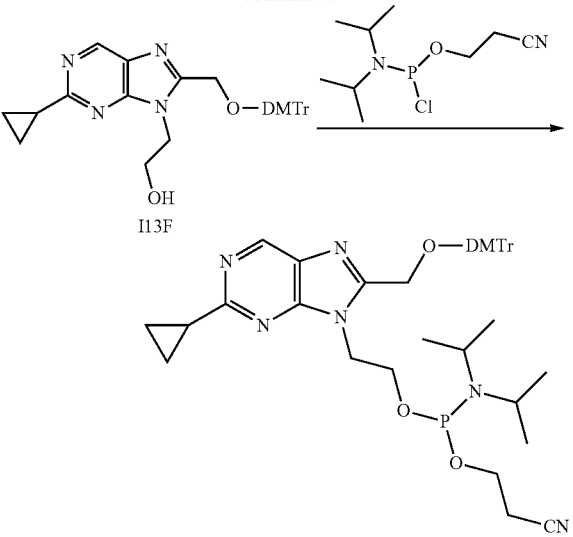

Intermediate 13

N-(2-((tert-Butyldimethylsilyl)oxy)ethyl)-2-chloropyrimidine-4,5-diamine (I13A)

To a solution of 2,4-dichloro-5-nitropyrimidine (2.00 g, 10.4 mmol) in THF (100 mL) cooled to −78° C. was slowly added DIEA (2.70 mL, 15.5 mmol) followed by 2-((tert-butyldimethylsilyl)oxy)ethanamine (1.80 g, 10.4 mmol) as a solution in THF (10 mL). The reaction mixture was stirred at −78° C. for 5 hrs, then at RT overnight. The resulting solution was concentrated under reduced pressure. The residue was purified by silica gel chromatography (0-10% EtOAc/Hexane) to give I13A (3.04 g, 90%) as a yellow solid. LCMS m/z 333.1 (M+H)+. $^1$H NMR (CDCl$_3$) δ 9.02 (d, J=22.8 Hz, 1H), 6.31 (br s, 1H), 3.77 (t, J=4.8 Hz, 2H), 3.62 (q, J=4.8 Hz, 2H), 0.87 (s, 9H); 0.04 (s, 6H).

N4-(2-((tert-Butyldimethylsilyl)oxy)ethyl)-2-chloropyrimidine-4,5-diamine (I13B)

To a solution of I13A (2.70 g, 8.13 mmol) in a mixture of EtOH (135 mL) and water (27 mL) was added iron powder (2.30 g, 40.7 mmol) and TEA-HCl (5.6 g, 40.65 mmol). After degassing the mixture was stirred overnight. The mixture was filtered through Celite and concentrated. The residue was dissolved in 150 ml EtOAc (150 mL) and washed with sat. aq. NaHCO$_3$, and brine. The organic layer was dried over Na$_2$SO$_4$ and concentrated. The residue was purified by silica gel chromatography (0-100% EtOAc/Hexane) to give I13B (1.37 g, 56%) as a brown solid. LCMS m/z 303.1 (M+H)+. $^1$H NMR (CDCl$_3$): δ 7.55 (s, 1H), 5.55 (br s, 1H), 3.76 (t, J=5.6 Hz, 2H), 3.56 (q, J=5.6 Hz, 2H), 2.99 (br s, 2H), 0.86 (s, 9H), 0.03 (s, 6H).

(9-(2-((tert-Butyldimethylsilyl)oxy)ethyl)-2-chloro-9H-purin-8-yl)methyl acetate (I13C)

To a solution of I13B (1.40 g, 4.53 mmol) in DCM (100 mL) at 0° C. was added DIEA (1.60 mL, 9.07 mmol) followed by a dropwise addition of 2-chloro-2-oxoethyl acetate (0.486 mL, 4.53 mmol). After stirring overnight, the mixture was concentrated and dissolved in BSA (8.8 mL). The mixture was heated at 100° C. for 2 hrs, than cooled to 0° C. After slow addition of water (100 mL), the mixture was extracted with EtOAc (3×). The combined organic layers were washed with sat. aq. NaHCO$_3$ and brine. The organic layer was dried (Na$_2$SO$_4$) and concentrated. The residue was purified by silica gel chromatography (0-100% EtOAc/Hexane) to give I13C as an orange solid (951 mg, 55%). LCMS m/z 384.1 (M+H)$^+$. $^1$H NMR (CDCl$_3$): δ 8.91 (s, 1H), 5.41 (s, 2H), 4.44 (t, J=5.6 Hz, 2H), 3.93 (t, J=5.6 Hz, 2H), 2.14 (s, 3H), 0.74 (s, 9H), −0.155 (s, 6H).

(9-(2-((tert-Butyldimethylsilyl)oxy)ethyl)-2-cyclopropyl-9H-purin-8-yl)methanol (I13D)

To a solution of I13C (951 mg, 2.48 mmol) in THF (20 mL) under nitrogen was added at RT a portion of (dppf) PdCl$_2$ (204 mg, 0.250 mmol), followed by cyclopropylzinc (II) bromide (12.4 mL, 6.20 mmol, 0.5 M in THF). The mixture was heated at 60° C. for 1 hr, then concentrated to half the volume and partitioned between EtOAc (100 mL) and water (100 mL). The organic layer was washed with 1% HOAc (3×50 mL), sat. aq. NaHCO$_3$ and brine. The organic layer was dried (Na$_2$SO$_4$) and concentrated under reduced pressure. The residue was purified by silica gel chromatography (0-100% EtOAc/Hexane) to give I13D (593 mg, 69%) as a brown oil. LCMS m/z 348.1 (M+H)$^+$. $^1$H-NMR (CDCl$_3$) δ 8.82 (s, 1H), 4.92 (d, J=4.8 Hz, 2H); 4.38 (t, J=4.8 Hz, 2H), 4.33 (br s, 1H), 3.95 (t, J=4.8 Hz, 2H), 2.28 (m, 1H), 1.11 (m, 2H), 1.03 (m, 2H), 0.74 (s, 9H), −0.17 (s, 6H).

8-((Bis(4-methoxyphenyl)(phenyl)methoxy)methyl)-9-(2-((tert-butyldimethylsilyl)oxy)ethyl)-2-cyclopropyl-9H-purine (I13E)

To an ice cold solution of I13D (593 mg, 1.71 mmol) in pyridine (20 mL) was added DMTrCl (635 mg, 1.88 mmol). The mixture was stirred overnight and concentrated under reduced pressure. The residue was purified by silica gel chromatography (0-100% EtOAc/Hexane) to give I13E as a colorless oil (395 mg, 59%). LCMS m/z 651.1 (M+H)$^+$. $^1$H NMR (CDCl$_3$) δ 9.16 (s, 1H), 7.75 (d, J=6.8 Hz, 2H); 7.66 (d, J=6.8 Hz, 4H), 7.54 (t, J=7.2 Hz, 2H), 7.49 (t, J=7.2 Hz, 1H), 7.11 (d, J=9.2 Hz, 4H), 4.70 (s, 2H), 4.53 (t, J=5.6 Hz, 2H), 4.03 (s, 6H), 3.99 (t, J=5.6 Hz, 2H), 2.58 (m, 1H), 1.40 (m, 2H), 1.32 (m, 2H), 0.87 (s, 9H), −0.07 (s, 6H).

2-(8-((Bis(4-methoxyphenyl)(phenyl)methoxy) methyl)-2-cyclopropyl-9H-purin-9-yl)ethanol (I13F)

To a solution of I13E (395 mg, 0.61 mmol) in THF (20 mL) at RT was added TBAF (0.67 mL, 1 M in THF). The mixture was stirred for 1 hr and concentrated under reduced pressure. The residue was dissolved in EtOAc (100 mL) and washed with water (3×50 mL), brine, dried (Na$_2$SO$_4$) and concentrated. The residue was purified by silica gel chromatography (0-100% EtOAc/Hexane) to give product I13F (269 mg, 82%) as white solid. LCMS m/z 537.1 (M+H)$^+$. $^1$H NMR (CDCl$_3$): δ 8.86 (s, 1H), 7.48 (d, J=7.6 Hz, 2H), 7.39 (d, J=6.8 Hz, 4H), 7.31 (t, J=7.2 Hz, 2H), 7.25 (t, J=7.2 Hz, 1H), 6.86 (d, J=8.8 Hz, 4H), 4.44 (s, 2H), 4.42 (t, J=6.0 Hz, 1H); 4.19 (t, J=4.8 Hz, 2H), 3.89 (q, J=5.2 Hz, 2H), 3.78 (s, 6H), 2.29 (m, 1H), 1.14 (m, 2H), 1.08 (m, 2H).

2-(8-((Bis(4-methoxyphenyl)(phenyl)methoxy) methyl)-2-cyclopropyl-9H-purin-9-yl)ethyl (2-cyanoethyl) diisopropylphosphoramidite (Intermediate 13)

To a solution of I13F (269 mg, 0.50 mmol) in ACN (20 mL) at 0° C. was added DIEA (262 µL, 1.50 mmol) followed by a dropwise addition of 3-((chloro(diisopropylamino) phosphino)oxy) propanenitrile (142 µL, 0.60 mmol). The mixture was stirred at 0° C. for 1 hr, then concentrated under reduced pressure and directly purified by RP-MPLC (0-100% ACN/H$_2$O) to give Intermediate 13 (197 mg, 53%) as a white solid. LCMS m/z 654.1 (M+H+OH-N,N-diisopropylamino)$^+$. $^1$H NMR (CDCl$_3$) δ 8.77 (s, 1H), 7.37 (d, J=7.2 Hz, 2H), 7.28 (dd, J=6.8, 2.0 Hz, 4H), 7.17 (t, J=7.2 Hz, 2H), 7.12 (t, J=7.2 Hz, 1H), 6.72 (dd, J=7.2, 2.0 Hz, 4H), 4.35 (dd, J=11.2, 7.2 Hz, 2H), 4.27 (dd, J=6.8, 6.0 Hz, 2H), 3.68 (m, 2H), 3.66 (s, 6H), 3.36 (q, J=6.8 Hz, 2H), 3.23 (m, 2H), 2.27 (t, J=6.4 Hz, 2H), 2.20 (septet, J=4.4 Hz, 1H), 1.13 (s, 1H), 1.03 (m, 2H), 0.94 (d, J=6.8 Hz, 6H), 0.77 (d, J=6.8 Hz, 6H). $^{31}$P-NMR (CDCl$_3$) δ 148.03.

Example 12

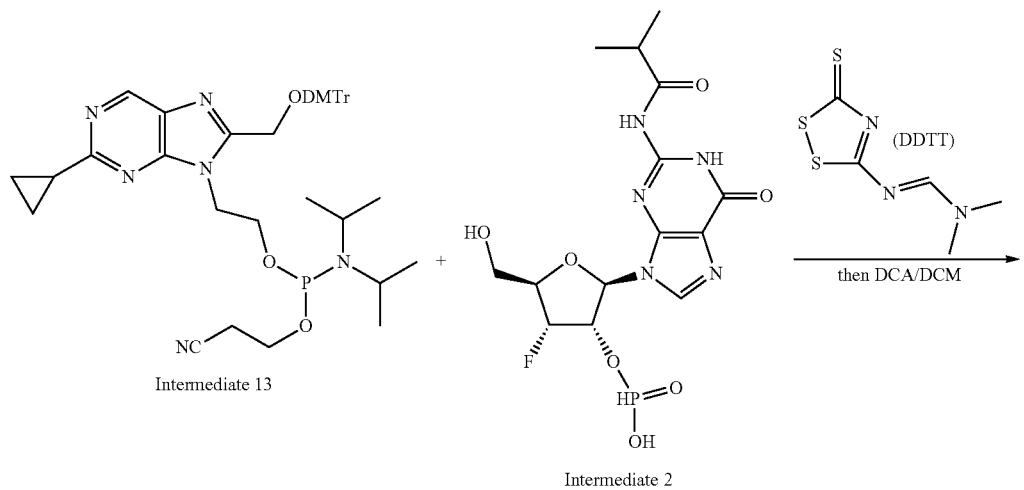

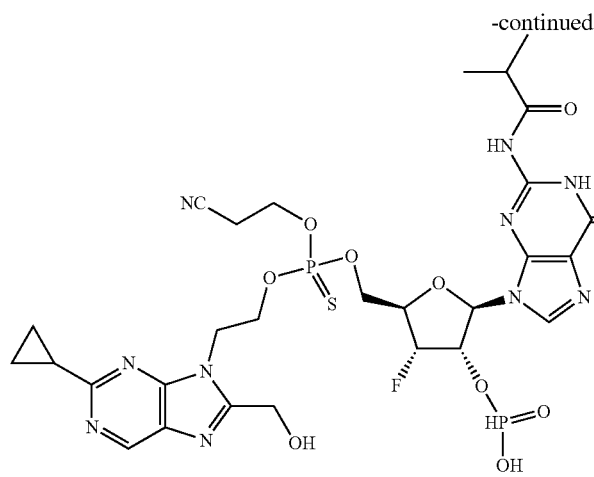

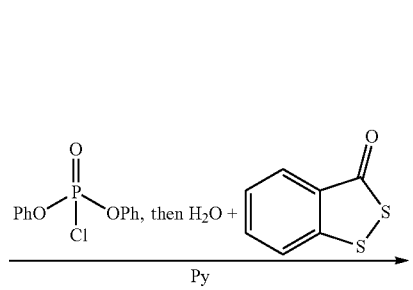

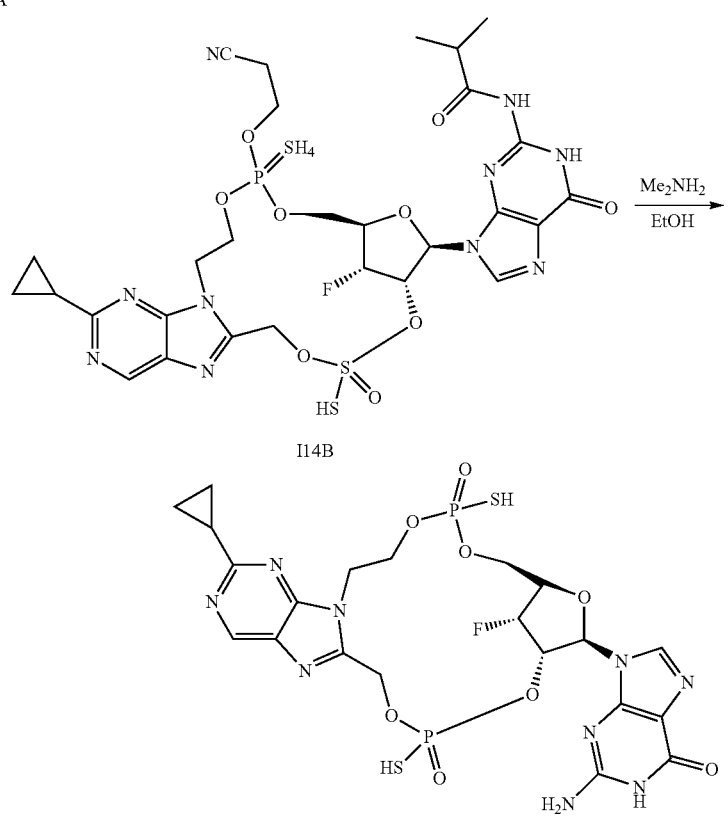

Example 12

Example 12 diastereomers (Diastereomers A-D) were prepared according to procedures analogous to those outlined in Example 1.

(2R,3S,4R,5R)-5-((((2-Cyanoethoxy)(2-(2-cyclopropyl-8-(hydroxymethyl)-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I14A)

LCMS (m/z): 783 (M–H)⁻. $^{31}$P NMR (CD$_3$OD) δ 68.21, 67.91, 2.43, 2.57. $^{19}$F NMR (CD$_3$OD) δ –201.63, –201.85.

N-{9-[(1S,21R,23R,24R)-18-(2-Cyanoethoxy)-11-cyclopropyl-24-fluoro-3-oxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraen-23-yl]-6-oxo-6,9-dihydro-1H-purin-2-yl}-2-methylpropanamide (I14B)

LCMS (m/z) 797 (M–H)⁻. $^{19}$F NMR (CD$_3$OD): δ –196.79, –197.68, –198.75, –199.59 ratio 1/1.26/2.95/3.06. $^{31}$P NMR (CD$_3$OD) δ 68.95, 68.05, 65.48, 65.22, 60.93, 60.32, 57.68, 56.76 (ratio 1.06:3.14:1.29:2.04:1.00:1.28:3.10:2.95).

(1S,21R,23R,24R)-23-(2-Amino-6-oxo-6,9-dihydro-1H-purin-9-yl)-11-cyclopropyl-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 12)

Example 12 diastereomers (Diastereomers A-D) were purified by prep. RP-HPLC (XBridge Prep C18 OBD 5 μm, 19×150 mm column) using aq. NH₄HCO₃ (50 mM) (A) and ACN (B) as eluents. Gradient: 0-2.0 min—Isocratic—100% A; 2.1-20.0 min—Linear gradient 0%-13% B. Flow rate: 10 mL/min. Example 12A (Diastereomer A): Prep. RP-HPLC: $T_R$=11.04 min. LCMS (Method D): $T_R$=1.34 min, m/z 674.1 (M−H)⁻. ¹H NMR (CD₃OD)) δ 8.93 (s, 1H), 8.25 (s, 1H), 6.10 (d, J=8.4 Hz, 1H), 5.62 (dd, J=53.2 Hz and 3.2 Hz, 1H), 5.42 (dd, J=12.8 Hz and 7.2 Hz, 1H), 5.34-5.19 (m, 1H), 4.49 (m, 4H), 4.28 (m, 1H), 4.19 (m, 1H), 3.95 (m, 1H), 3.68 (s, 1H), 2.26 (m, 1H), 1.19 (m, 2H), 1.10 (m, 2H). ¹⁹F NMR (CD₃OD) δ −199.79. ³¹P NMR (CD₃OD) δ 57.29, 57.20 Example 12B (Diastereomer B with 22% A): Prep. RP-HPLC: $T_R$=11.45 min. LCMS (Method D): $T_R$=1.34 min, 674.1 (M−H)⁻. ¹H NMR (CD₃OD) δ 8.85 (s, 1H), 8.54 (s, 1H), 6.09 (d, J=8.0 Hz, 1H), 5.73-5.55 (m, 1H), 5.39 (m, 1H), 5.22 (d, J=3.6 Hz, 1H), 5.11-5.04 (m, 2H), 4.74-4.31 (comp, 5H), 3.97 (m, 1H), 2.32 (m, 1H), 1.19 (m, 2H), 1.11 (m, 2H). ¹⁹F NMR (CD₃OD) δ −198.46. ³¹P NMR (CD₃OD) δ 60.41, 57.26. Example 12C (Diastereomer C): Prep. RP-HPLC: $T_R$=11.48 min. LCMS (Method D): $T_R$=1.34 min, 674.1 (M−H)⁻. ¹H NMR (CD₃OD) δ 9.14 (s, 1H), 8.11 (s, 1H), 6.09 (d, J=8.0 Hz, 1H), 5.58 (dd, J=53.6 Hz, 3.2 Hz, 1H), 5.48 (dd, J=13.2 Hz, 6.4 Hz, 1H), 5.31 (m, 1H), 5.05 (m, 1H), 4.80-4.46 (m, 2H), 4.36-3.99 (m, 1H), 2.24 (s, 1H), 1.39-1.15 (comp, 4H). ¹⁹F NMR (CD₃OD) δ −198.46. ³¹P NMR (CD₃OD) δ 60.41, 57.26. Example 12D (Diastereomer D with 18% C): Prep. RP-HPLC: $T_R$=1.51 min. LCMS (Method D): $T_R$=1.51 min, 674.1 (M−H)⁻. ¹H-NMR (CD₃OD) δ 8.82 (s, 1H), 8.20 (s, 1H), 6.09 (d, J=8.4 Hz, 1H), 5.72-5.57 (m, 1H), 5.39 (dd, J=12.4 Hz, 7.6 Hz, 1H), 5.25 (m, 1H), 5.09 (m, 2H), 4.60-4.38 (comp, 4H), 4.30 (m, 1H), 4.13 (m, 1H), 2.33 (m, 1H), 1.26-1.06 (m, 4H). ¹⁹F NMR (CD₃OD) δ −197.57. ³¹P NMR (CD₃OD) δ 60.40, 57.98.

Intermediate 15

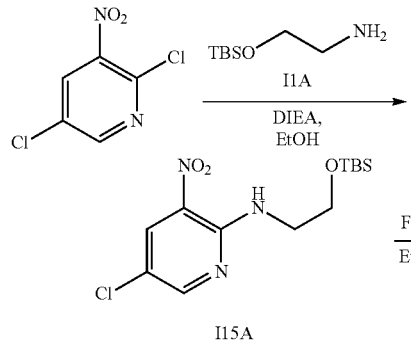

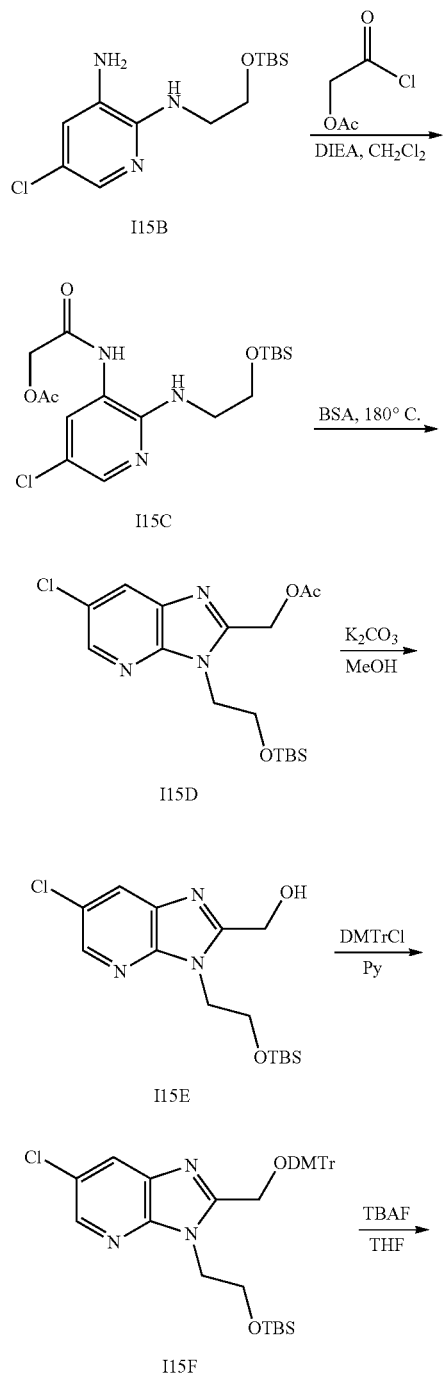

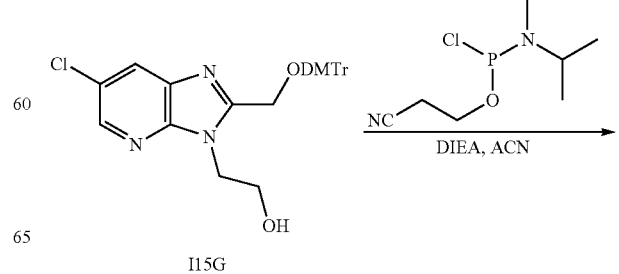

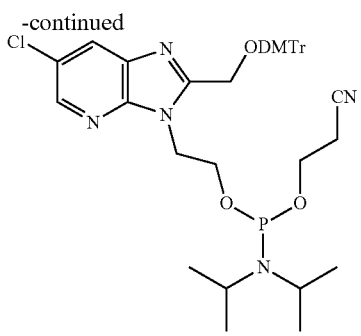

Intermediate 15

N-(2-((tert-Butyldimethylsilyl)oxy)ethyl)-5-chloro-3-nitropyridin-2-amine (I15A)

To a solution of 2,5-dichloro-3-nitropyridine (2.50 g, 13.0 mmol) in EtOH (50 mL) was added TEA (2.35 mL, 16.84 mmol) followed by I1A (2.84 g, 16.2 mmol). The reaction mixture was heated to reflux for 2 hrs. After cooling the solvent was removed in vacuo. The residue was separated between EtOAc and water. The organic layers were combined, washed with water (2×), and dried over $Na_2SO_4$. After evaporation the residue was purified by silica gel chromatography (0-10% MeOH/DCM) to give I15A (3.93 g, 91%) as a pale yellow solid. LCMS (Method E): $T_R$=1.68 min, m/z 332.3 (M+H)⁺. ¹H NMR (CDCl₃) δ 8.46 (br s, 1H), 8.41 (d, J=2.5 Hz, 1H), 8.34 (d, J=2.5 Hz, 1H), 3.84 (t, J=5.3 Hz, 2H), 3.75 (q, J=5.3 Hz, 2H), 0.91 (s, 9H), 0.08 (s, 6H).

N2-(2-((tert-Butyldimethylsilyl)oxy)ethyl)-5-chloropyridine-2,3-diamine (I15B)

A mixture of I15A (0.30 g, 0.90 mmol), iron powder (252 mg, 4.52 mmol), and $NH_4Cl$ (457 mg, 4.52 mmol) in 1:1 EtOH:$H_2O$ (20 mL) was heated to 80° C. for 3 hrs. The reaction was filtered and concentrated under reduced pressure. The residue was diluted with EtOAc and washed with sat. aq. $NH_4Cl$, $H_2O$, and brine. The organic layer was dried ($MgSO_4$) and then concentrated under reduced pressure. The residue was purified by silica gel chromatography (0-10% MeOH/DCM) to give I15B (247 mg, 91%) as a light tan solid. LCMS (Method E): $T_R$=1.00 min, m/z 302.3 (M+H)⁺. ¹H NMR (CDCl₃) δ 7.65 (d, J=7.0 Hz, 1H), 7.67 (s, 1H), 6.83 (d, J=8.5 Hz, 1H), 4.53 (br s, 1H), 3.84 (m, 2H), 3.50 (m, 2H), 3.28 (br s, 2H), 0.90 (s, 9H), 0.06 (s, 6H).

2-((2-((2-((tert-Butyldimethylsilyl)oxy)ethyl)amino)-5-chloropyridin-3-yl)amino)-2-oxoethyl acetate (I15C)

To a solution of I15B (964 mg, 3.19 mmol) in THF (21.3 mL) was added DIEA (1.70 mL, 9.58 mmol, 3.0 eq), and the resulting mixture was cooled to 0° C. To this mixture was added 2-chloro-2-oxoethyl acetate (0.43 mL, 3.99 mmol, 1.2 eq) in a dropwise fashion. The resulting mixture was stirred at 0° C. for 0.5 hrs, then allowed to warm to RT and stirred for 4 hrs. The reaction mixture was diluted with EtOAc, and washed with sat. aq. $NaHCO_3$, $H_2O$, and brine. The organic layer was dried ($MgSO_4$), and then concentrated under reduced pressure to give I15C (978 mg, 76%) as a pale yellow oil. This material was used directly in the next step without further purification. LCMS (Method A): $T_R$=1.45 min, m/z 402.4 (M+H)⁺.

(3-(2-((tert-Butyldimethylsilyl)oxy)ethyl)-6-chloro-3H-imidazo[4,5-b]pyridin-2-yl)methyl acetate (I15D)

A mixture of I15C (978 mg, 2.43 mmol) and BSA (5 mL) was heated at 180° C. overnight, and then cooled to RT. The reaction mixture was diluted with DCM, and washed with sat. aq. $NaHCO_3$, $H_2O$, and brine. The organic layer was dried over $MgSO_4$, and then filtered. To the filtrate was added silica gel (10 g), and then the mixture was concentrated under reduced pressure. The pre-adsorbed material was purified by silica gel chromatography (0-60% EtOAc/Hexane) to give I15D (536 mg, 57%) as an off-white solid. LCMS (Method A): $T_R$=1.54 min, m/z 384.3 (M+H)⁺. ¹H NMR (CDCl₃) δ 8.32 (d, J=2.2 Hz, 1H), 8.02 (d, J=2.2 Hz, 1H), 5.43 (s, 2H), 4.84 (t, 2H), 3.96 (t, 2H), 2.15 (s, 3H), 0.75 (s, 9H), −0.18 (s, 6H).

(3-(2-((tert-Butyldimethylsilyl)oxy)ethyl)-6-chloro-3H-imidazo[4,5-b]pyridin-2-yl)methanol (I15E)

A mixture of I15D (514 mg, 1.34 mmol) and $K_2CO_3$ (19 mg, 0.13 mmol, 0.1 eq) in MeOH (20 mL) was stirred at RT for 40 min, and then concentrated under reduced pressure and absorbed onto Celite. The absorbed material was purified via silica gel chromatography (0-100% EtOAc/Hexane) to give I15E (428 mg, 94%). LCMS (Method A): $T_R$=1.37 min, m/z 342.3 (M+H)⁺. ¹H NMR (CDCl₃) δ 8.30 (d, 1H), 7.98 (d, 1H), 4.96 (s, 2H), 4.47 (t, 2H), 4.01 (t, 2H), 0.75 (s, 9H), −0.16 (s, 6H).

2-((Bis(4-methoyphenyl)(phenyl)methoxy)methyl)-3-(2-((tert-butyldimethylsilyl)oxy)ethyl)-6-chloro-3H-imidazo[4,5-b]pyridine (I15F)

A mixture of I15E (423 mg, 1.38 mmol) and DMTrCl (701 mg, 2.07 mmol, 1.5 eq) in pyridine (5.5 mL) was stirred at RT overnight. The resulting mixture was concentrated under reduced pressure, and dissolved in DCM (20 mL). Silica gel (5 g) was added, and the mixture was concentrated to dryness under reduced pressure. The residue was purified by silica gel chromatography (0-100% EtOAc/Hexane) to give I15F (701 mg, 83%) as a white solid. LCMS m/z 644.4 (M+H)⁺. ¹H NMR (CDCl₃) δ 8.31 (d, J=2.3 Hz, 1H), 8.00 (d, J=2.3 Hz, 1H), 7.5-7.16 (comp, 9H), 6.83 (dd, J=9.0 and 5.3 Hz, 4H), 4.47 (s, 2H), 4.35 (t, J=5.5 Hz, 2H), 3.80-3.78 (comp, 8H), 0.60 (s, 9H), −0.38 (s, 6H).

2-(2-((Bis(4-methoxyphenyl)(phenyl)methoxy)methyl)-6-chloro-3H-imidazo[4,5-b]pyridin-3-yl)ethanol (I15G)

To a solution of I15F (500 mg, 0.78 mmol) in THF (20 mL) cooled to −5° C. was added TBAF in THF (1.0 M, 0.93 mL, 0.93 mmol, 1.2 eq) in a slow, dropwise fashion. The reaction mixture was stirred at 0° C. for 1.5 hrs, whereupon silica gel (5 g) was added. The resulting mixture was concentrated under reduced pressure, and then purified by silica gel chromatography (0-10% MeOH/DCM) to give I15G (0.31 g, 75%) as a white solid. LCMS (Method A): $T_R$=1.43 min, m/z 530.3 (M+H)⁺. ¹H NMR (CDCl₃) δ 8.29 (d, J=2.0 Hz, 1H), 7.97 (d, J=2.3 Hz, 1H), 7.48-7.23 (comp, 9H), 6.86 (d, J=8.8 Hz, 4H), 4.45 (s, 2H), 4.24 (dd, J=6.1 and 3.8 Hz, 2H), 3.88 (m, 2H), 3.79 (s, 6H).

2-(2-((Bis(4-methoxyphenyl)(phenyl)methoxy)methyl)-6-chloro-3H-imidazo[4,5-b]pyridin-3-yl)ethyl-(2-cyanoethyl)-diisopropylphosphoramidite (Intermediate 15)

To a solution of I15G (0.310 g, 0.58 mmol) in DCM (4 mL) was added DIEA (0.31 mL, 1.75 mmol, 3.0 eq) followed by dropwise addition of 2-cyanoethyl-N,N-diisopropylchlorophosphoramidite (0.29 mL, 1.17 mmol, 2.0 eq) in DCM. The reaction mixture was stirred at RT for 1 hr, diluted with DCM and washed with a solution of 5% aq. NaHCO$_3$. The organic layer was dried (MgSO$_4$) and concentrated under reduced pressure. The crude material was purified by RP-MPLC (0-100% ACN/H$_2$O). The appropriate fractions were combined and solvent partially concentrated and lyophilized to give Intermediate 15 (0.321 g, 75%) as a solid. LCMS (Method A): T$_R$=1.39 min, m/z 647.3 (M+H+OH-N,N-diisopropylamino)$^+$. $^1$H NMR (CDCl$_3$) δ 8.31 (d, J=2.3 Hz, 1H), 7.99 (d, J=2.3 Hz, 1H), 7.50-7.23 (comp, 9H), 6.85 (d, J=8.8 Hz, 4H), 4.54-4.44 (comp, 4H), 3.82-3.79 (comp, 8H), 3.48-3.45 (comp, 2H), 3.33-3.24 (comp, 2H), 2.40 (t, J=6.3 Hz, 2H), 1.04 (d, J=6.8 Hz, 6H), 0.87 (d, J=6.8 Hz, 6H). $^{31}$P NMR (CDCl$_3$) δ 147.98.

Intermediate 16

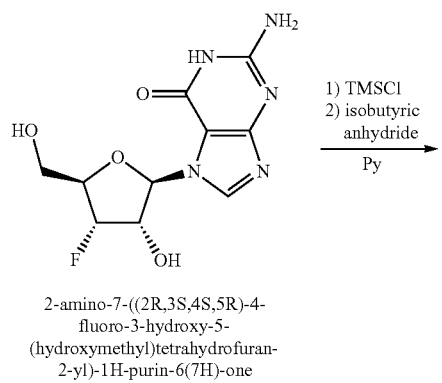

2-amino-7-((2R,3S,4S,5R)-4-fluoro-3-hydroxy-5-(hydroxymethyl)tetrahydrofuran-2-yl)-1H-purin-6(7H)-one

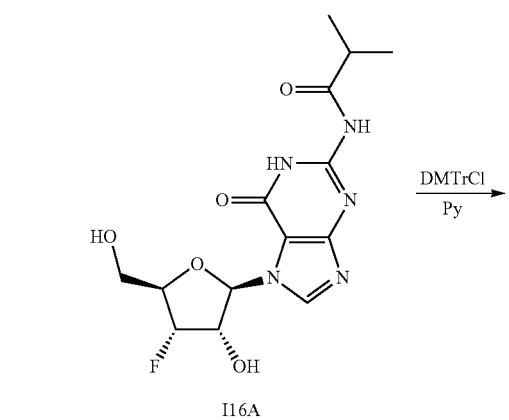

I16A

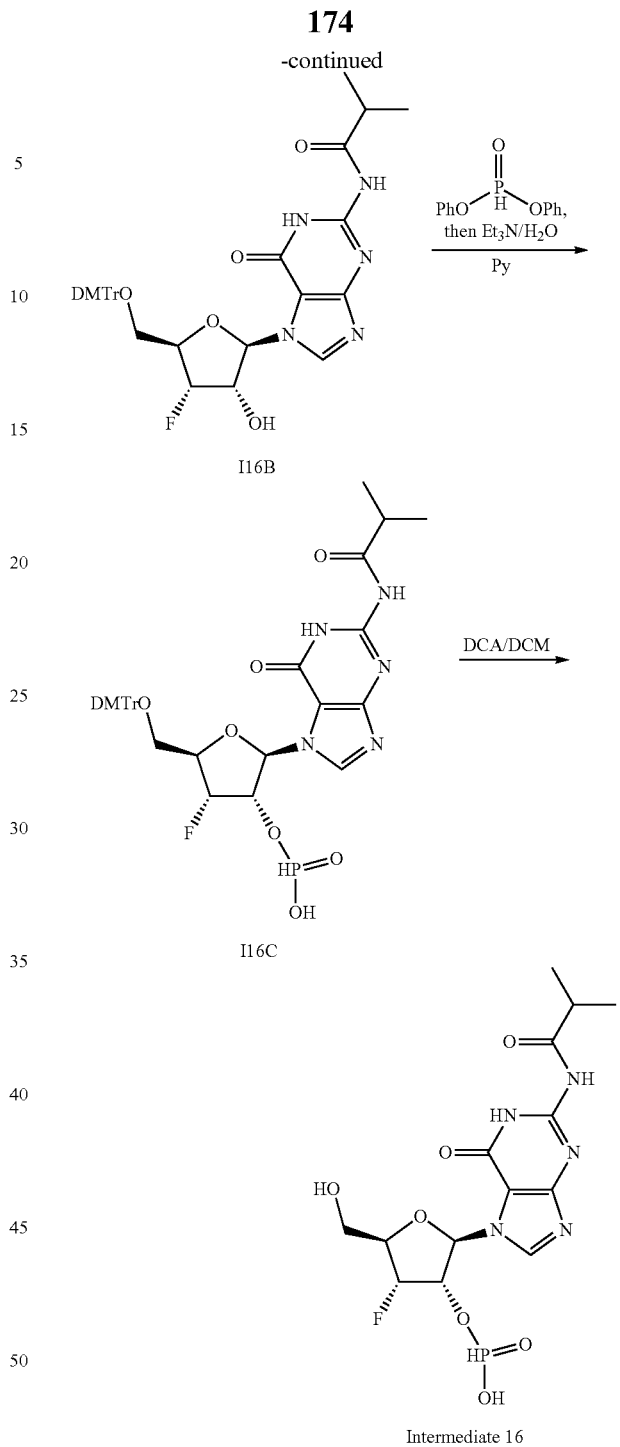

Intermediate 16 was prepared using the identical procedure used for the preparation of Intermediate 2 but starting from 2-amino-7-((2R,3S,4S,5R)-4-fluoro-3-hydroxy-5-(hydroxymethyl)tetrahydrofuran-2-yl)-1H-purin-6(7H)-one (ChemGenes Corporation). Intermediate 16 (0.321 g, 75%) LCMS (Method A): T$_R$=0.92 min, m/z 418.1 (M–H)$^-$. $^1$H NMR (CD$_3$OD) δ 8.59 (s, 1H), 6.67 (dd, J=638.2 Hz, 1.2 Hz, 1H), 6.33 (d, J=7.6 Hz, 1H), 5.40-5.26 (m, 1H), 5.25 (ddd, J=54.2 Hz, 4.5 Hz, 0.9 Hz, 1H), 4.40 (dt, J=27.0, 3.3 Hz, 1H), 3.82 (qd, J=12.3 Hz, 3.3 Hz, 2H), 2.77 (hept, J=6.8 Hz, 1H), 1.21 (d, J=6.8 Hz, 6H) [pyridine, 2CH 8.81 (d, J=4.8 Hz, 0.51H), CH 8.53 (t, J=7.7 Hz, 0.26H), 2CH 8.00 (m, 0.51H)], [triethyl amine, 3CH2, 3.18 (q, J=7.3 Hz, 3.01H), 3CH3 1.29 (t, J=7.3 Hz, 4.51H)]. $^{19}$F NMR (CD$_3$OD) δ −198.14. $^{31}$P NMR (CD$_3$OD) δ 2.37.

Example 13
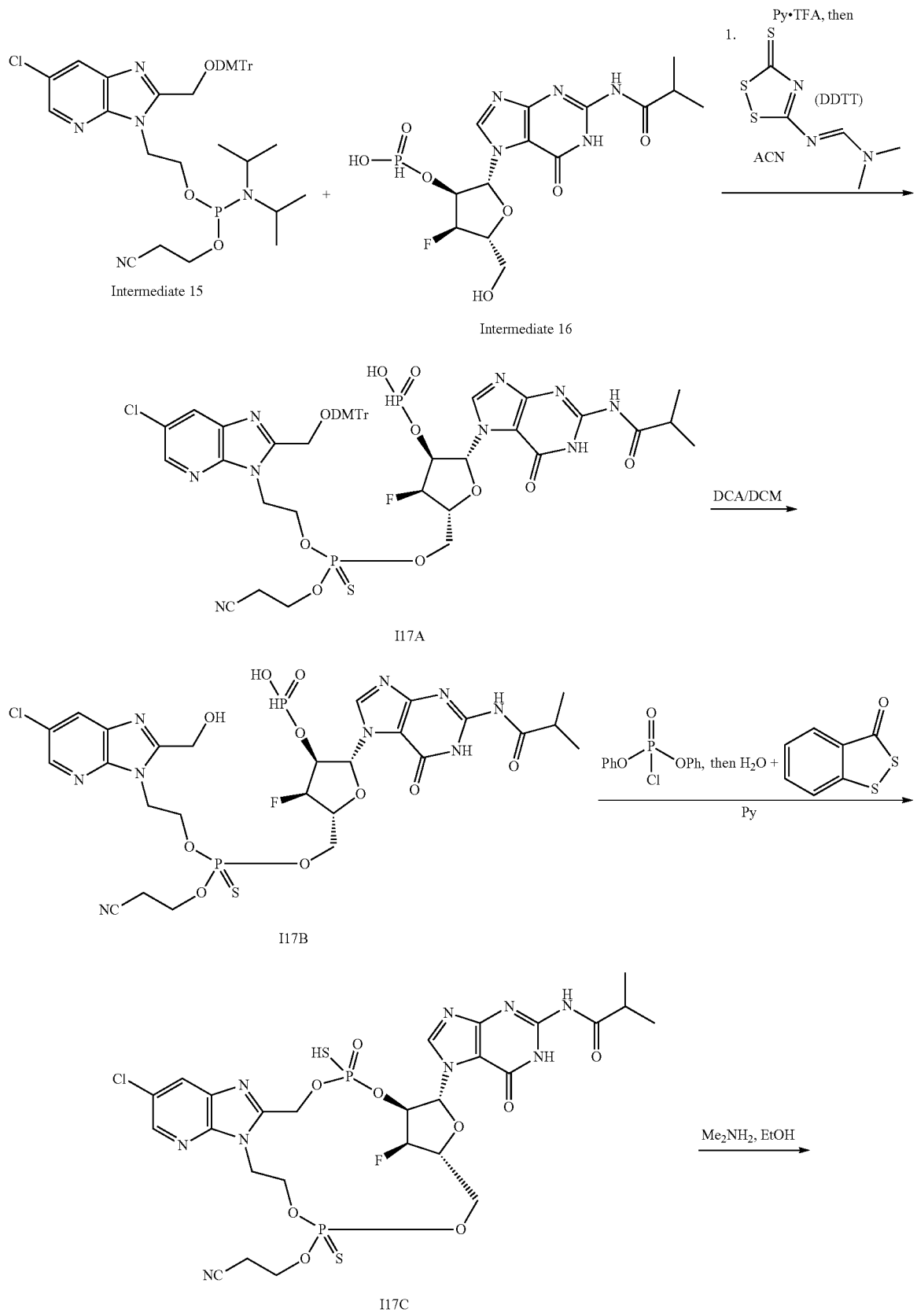

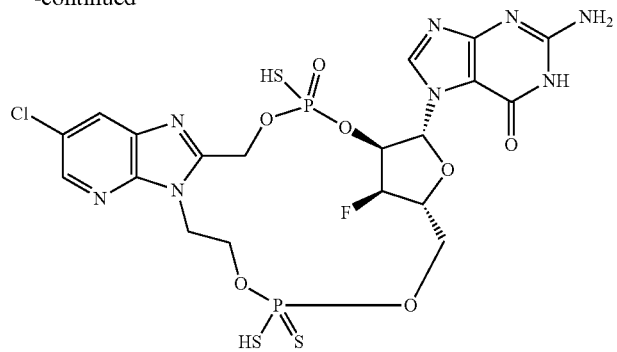

Example 13

(1S,21R,23R,24R)-23-(2-Amino-6-oxo-6,7-dihydro-1H-purin-7-yl)-10-chloro-24-fluoro-3,18-disulfanyl-2,4,17,19,22-pentaoxa-7,12,14-triaza-3lambda5,18lambda5-diphosphatetracyclo[19.2.1.06,14.08,13]tetracosa-6,8,10,12-tetraene-3,18-dione (Example 13)

Example 13 diastereomers (Diastereomers A- and B) were prepared according to procedures analogous to those outlined in Example 1. Example 13 diastereomers (Diastereomers A and B) were purified by prep. RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 13A (Diastereomer A): Prep. RP-HPLC: T$_R$=16.75 min. LCMS (Method D, T$_R$=0.95 min) m/z 667.1 (M–H)$^-$. $^1$H NMR (D$_2$O) δ 8.41 (s, 1H), 8.18 (s, 1H), 8.06 (s, 1H), 6.47 (d, J=8.2 Hz, 1H), 5.52-5.30 (comp, 2H), 4.4 (comp, 1H), 4.76-4.61 (m, 2H) 4.52-4.37 (comp, 2H), 4.28-4.16 (comp, 2H) 4.09 (m, 1H). $^{19}$F NMR (D$_2$O) 8-198.33. $^{31}$P NMR (D$_2$O) δ 55.65, 55.20. Example 13B (Diastereomer B): Prep. RP-HPLC: T$_R$=21.34 min. LCMS (Method D, T$_R$=0.99 min) m/z 667.1 (M–H)$^-$. $^1$H NMR (D$_2$O) δ 8.42 (s, 1H), 8.33 (s, 1H), 8.15 (s, 1H), 6.48 (d, J=8.3 Hz, 1H), 5.26-5.12 (comp, 2H), 5.05-4.90 (comp, 2H), 4.84 (m, 1H), 4.69-4.53 (comp, 3H) 4.44 (m, 1H) 4.35 (m, 1H), 4.13 (m, 1H) 4.01 (m, 1H). $^{19}$F NMR (D$_2$O) 8-196.30. $^{31}$P NMR (D$_2$O) δ 57.57, 56.54.

Example 14

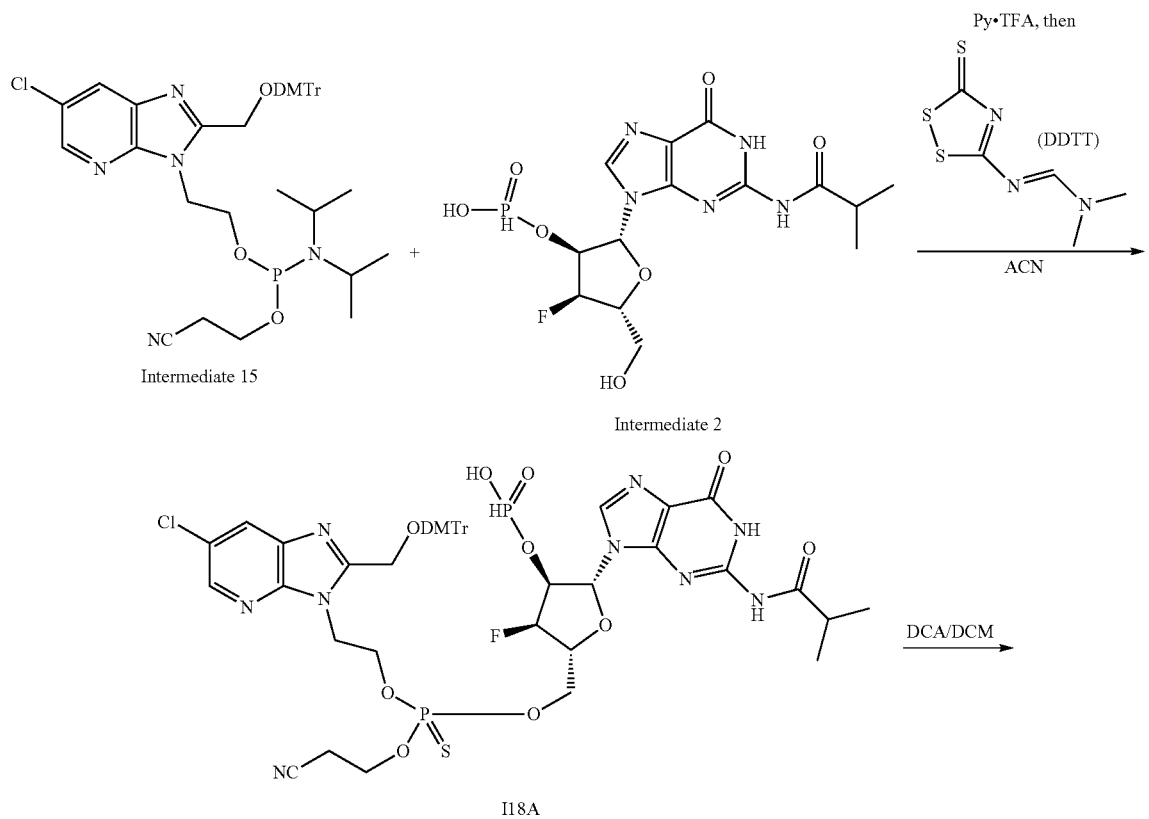

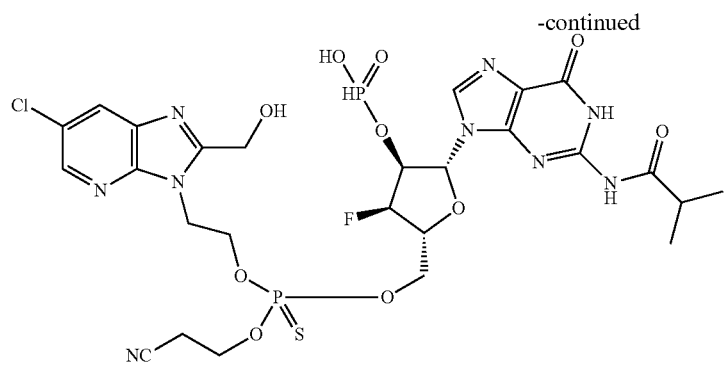

I18B

-continued

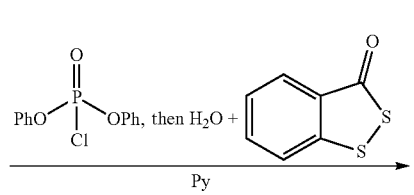

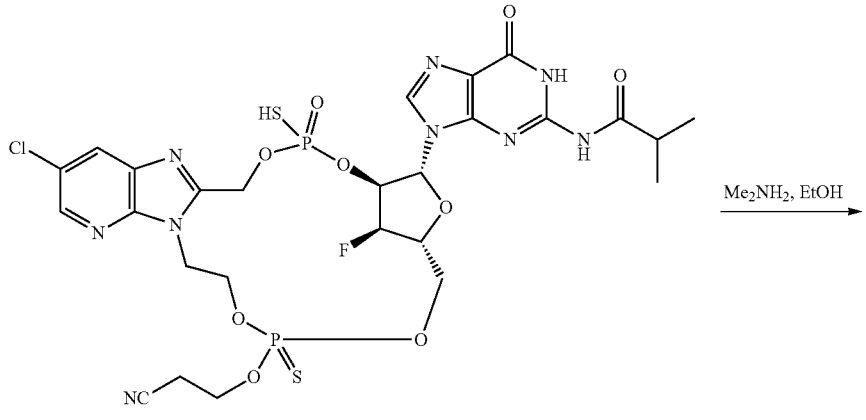

I18C

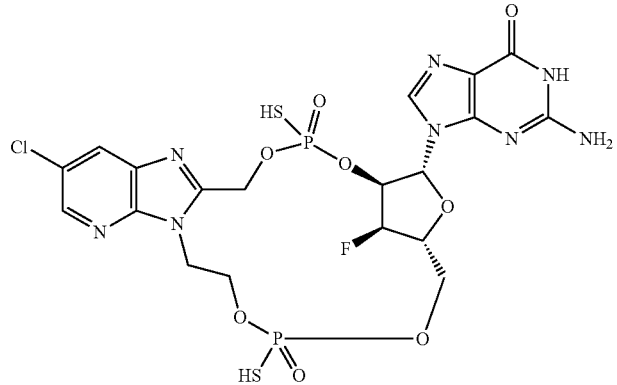

Example 14

(1S,21R,23R,24R)-23-(2-Amino-6-oxo-6,9-dihydro-1H-purin-9-yl)-10-chloro-24-fluoro-3,18-disulfanyl-2,4,17,19,22-pentaoxa-7,12,14-triaza-3lambda5,18lambda5-diphosphatetracyclo[19.2.1.06,14.08,13]tetracosa-6,8,10,12-tetraene-3,18-dione (Example 14)

Example 14 diastereomers (Diastereomers A-D) were prepared according to procedures analogous to those outlined in Example 1. Example 14 diastereomers (Diastereomers A-D) were purified by prep. RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 14A (Diastereomer A): Prep. RP-HPLC: T$_R$=16.84 min. LCMS (Method D): T$_R$=0.80 min, m/z 667.0 (M−H)$^−$. $^1$H NMR (D$_2$O) δ 8.41 (s, 1H), 8.08 (s, 1H), 7.94 (s, 1H), 6.01 (d, J=7.8 Hz, 1H), 5.60-5.37 (comp, 2H), 5.04-4.83 (comp, 3H), 5.05-4.90 (comp, 2H), 4.78-4.68 (comp, 2H), 4.63 (m, 1H), 4.52 (m, 1H) 4.39 (m, 1H) 4.25 (m, 1H), 4.10 (m, 2H). $^{19}$F NMR (D$_2$O) 8-198.57. $^{31}$P NMR (D$_2$O) δ 55.50, 55.36 Example 14C (Diastereomer C): Prep. RP-HPLC: T$_R$=24.36 min. LCMS (Method D): T$_R$=0.92 min, m/z 667.1 (M−H)$^−$. $^1$H NMR (D$_2$O) δ 8.42 (d, J=2.1 Hz, 1H), 8.13 (d, J=2.1 Hz, 1H), 7.80 (s, 1H), 6.02 (d, J=8.3 Hz, 1H), 5.56-5.36 (comp, 2H), 4.98-4.83 (comp, 2H), 5.05-4.90 (comp, 2H), 4.55-4.41 (comp, 2H), 4.35 (m, 1H), 4.23 (m, 1H) 4.02 (m, 1H). $^{19}$F NMR (D$_2$O) δ −198.51. $^{31}$P NMR (D$_2$O) δ 54.92, 54.59. Example 14D (Diastereomer D): Prep. RP-HPLC: T$_R$=25.94 min. LCMS (Method D): T$_R$=0.95 min, m/z 667.0 (M−H)$^−$. $^1$H NMR (D$_2$O) δ 8.42 (d, J=3.1 Hz, 1H), 8.10 (d, J=2.4 Hz, 1H), 7.95 (s, 1H), 6.03 (d, J=8.2 Hz, 1H), 5.26-5.06 (comp, 4H), 4.72-4.52 (comp, 3H), 4.41 (m, 2H), 4.18 (m, 1H), 3.99 (m, 1H). $^{19}$F NMR (D$_2$O) δ −196.99. $^{31}$P NMR (D$_2$O) δ 56.78, 55.45.

Example 15
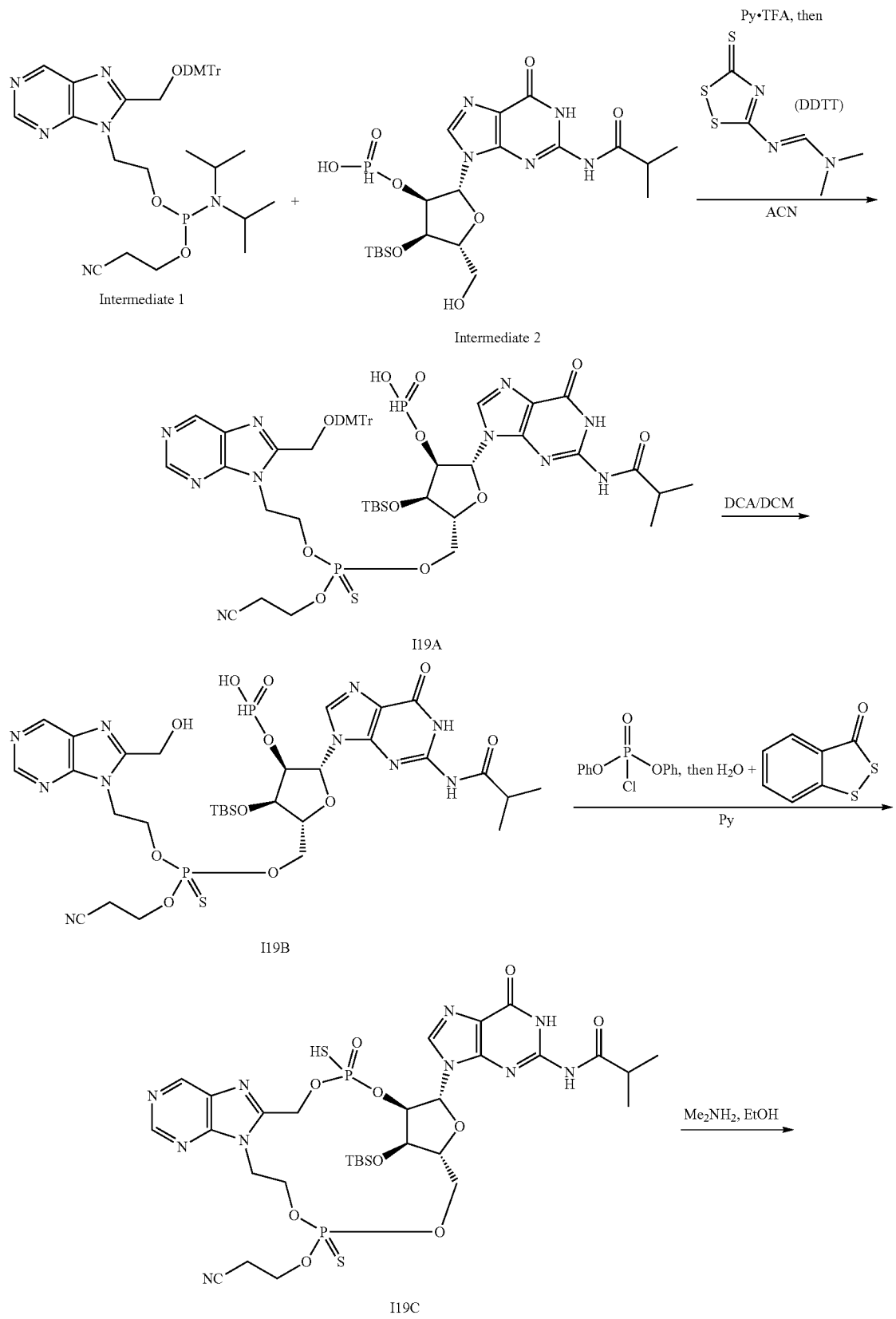

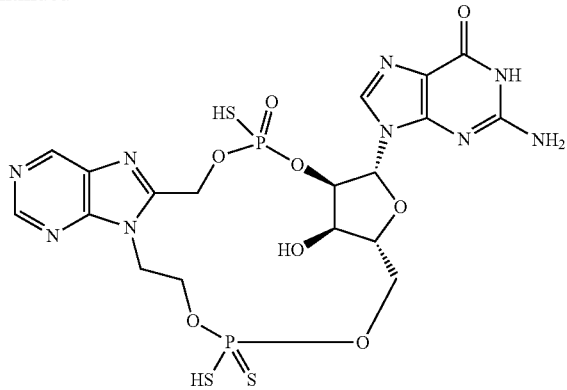

Example 15

(1R,21R,23R,24R)-23-(2-Amino-6-oxo-6,9-dihydro-1H-purin-9-yl)-24-hydroxy-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 15)

Example 15 diastereomers (Diastereomers A-D) were prepared according to procedures analogous to those outlined in Example 1 and Example 2. Example 15 diastereomers (Diastereomers A and D) were purified by RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 15A (Mixture of Diastereomer A and B): RP-HPLC: T$_R$=11.06 min. (60:40 mixture of minor isomers) LCMS (Method D): T$_R$=1.06 min, 1.09 min, m/z 632.2 (M–H)⁻. ¹H NMR (D$_2$O) δ 9.13 (s, 0.4H), 9.05 (s, 0.6H), 8.96 (m, 1H), 7.83 (s, 0.6H), 7.56 (s, 0.4H), 6.01 (d, J=8.1 Hz, 1H), 5.38-5.27 (comp, 1H), 5.24-5.16 (comp, 0.6H), 5.05-4.98 (comp, 0.8H), 4.95-4.85 (comp, 1H), 4.71-4.59 (comp, 3H), 4.56-4.38 (comp, 3H), 4.34 (m, 1H), 4.21-4.16 (m, 1H) 4.12-4.05 (m, 1H) 4.01-3.95 (m, 1H). ³¹P NMR (D$_2$O) δ 57.01 (s, 0.6P), 55.70 (s, 0.6P), 54.98 (s 0.4P), 54.56 (s,0.4P). Example 15C (Diastereomer C): RP-HPLC: T$_R$=12.09 min. LCMS (Method D): T$_R$=1.02 min, m/z 632.2 (M–H)⁻. ¹H NMR (D$_2$O) δ 9.03 (s, 1H), 8.90 (s, 1H), 7.73 (s, 1H), 5.95 (d, J=8.1 Hz, 1H), 5.34 (m, 1H), 4.9-4.77 (comp, 2H), 4.50-4.35 (comp, 3H), 4.21-4.16 (m, 1H) 4.12-4.05 (m, 1H) 4.01-3.95 (m, 1H). ³¹P NMR (D$_2$O) δ 55.39, 55.17. Example 15D (Diastereomer D): RP-HPLC: T$_R$=12.82 min. LCMS (Method D): T$_R$=1.06 min, m/z 632.1 (M–H)⁻. ¹H NMR (D$_2$O) δ 9.10 (s, 1H), 8.96 (s, 1H), 7.61 (s, 1H), 5.97 (d, J=8.0 Hz, 1H), 5.38 (m, 1H), 4.92-4.83 (comp, 2H), 4.70 (m, 1H) 4.56-4.35 (comp, 4H), 4.23-4.15 (m, 1H) 4.01 (m, 1H). ³¹P NMR (D$_2$O) δ 54.89, 54.46.

Intermediate 20

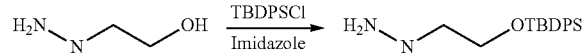

Intermediate 20

(2-((tert-Butyldiphenylsilyl)oxy)ethyl)hydrazine (Intermediate 20)

To a solution of 2-hydrazinylethan-1-ol (3.0 g, 39.4 mmol) and imidazole (5.4 g, 78.8 mmol) in DCM (100 mL) was added dropwise a solution of TBDPSCl (14 mL, 51.3 mmol) in DCM (100 mL) at RT over 10 min. The reaction mixture was stirred at RT for 1 hr, whereupon it was washed with sat. aq. NaHCO$_3$, then brine. The organic layer was dried (Na$_2$SO$_4$) and then concentrated under reduced pressure. The residue was purified by silica gel chromatography (0-10% MeOH/DCM) to give Intermediate 20 (5.0 g, 40%) as a colorless oil. LCMS m/z 315.4 (M+H)⁺. ¹H NMR (CDCl$_3$) δ 7.67-7.63 (m, 4H), 7.43-7.35 (m, 6H), 3.77 (t, J=4.8 Hz, 1H), 2.88 (t, J=4.8 Hz, 2H), 1.04 (s, 9H).

Intermediate 21

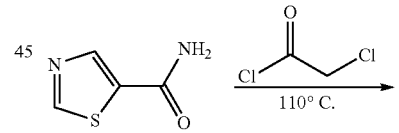

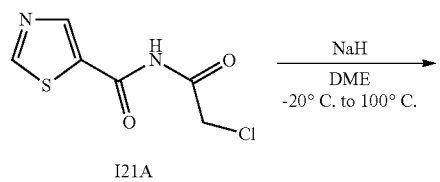

I21A

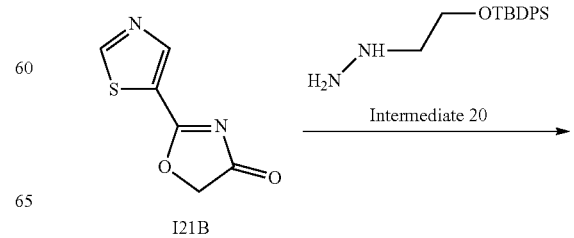

I21B

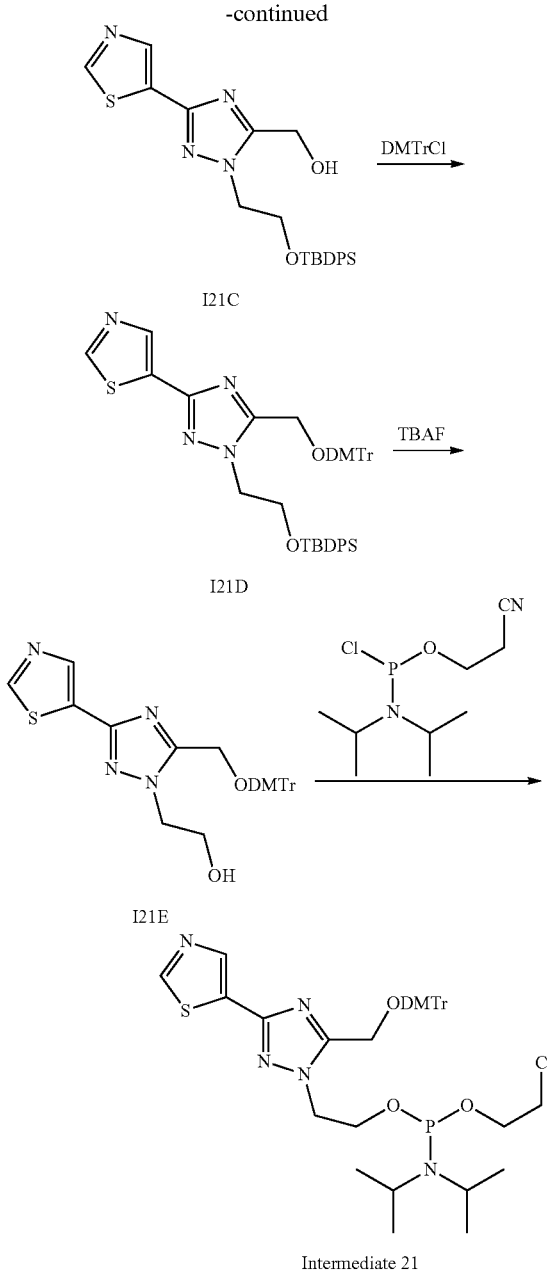

I21C

I21D

I21E

Intermediate 21

N-(2-Chloroacetyl)thiazole-5-carboxamide (I21A)

Thiazole-5-carboxamide (1.38 g, 10.8 mmol) was stirred in 2-chloroacetyl chloride (6 mL) at 110° C. for 2 hrs then the reaction mixture was allowed to cool to RT. Solids were filtered off and washed with Et$_2$O (4×15 mL). The crude product was purified by silica gel chromatography (0-10% MeOH/DCM) to give I21A (0.73 g, 34%). LCMS m/z 205.1 (M+H)$^+$. $^1$H NMR (CD$_3$CN) δ 9.15 (s, 1H), 8.53 (s, 1H), 4.71 (s, 2H).

2-(Thiazol-5-yl)oxazol-4(5H)-one (I21B)

A portion of I21A (180 mg, 0.88 mmol) was added to a mixture of NaH (60% in mineral oil; 0.035 g, 0.88 mmol) in DME (1.0 mL) at −20° C. The resulting mixture was stirred at RT under N$_2$ until gas evolution ceased, then heated at 100° C. for 1 hr. The reaction mixture was filtered through a pad of Celite® and the filter cake was washed with ACN (3×20 mL). The filtrate was concentrated under reduced pressure to give I21B (0.125 g, 65% yield). LCMS m/z 169.1 (M+H)$^+$. $^1$H NMR (CD$_3$CN) δ 9.29 (s, 1H), 8.76 (s, 1H), 4.77 (s, 2H).

(1-(2-((tert-Butyldiphenylsilyl)oxy)ethyl)-3-(thiazol-5-yl)-1H-1,2,4-triazol-5-yl)methanol (I21C)

To a solution of I21B (254 mg, 1.51 mmol) in EtOH (5 mL) was added at RT Intermediate 20 (0.70 mg, 2.23 mmol). The resulting solution was stirred at RT for 1 hr. The reaction mixture was concentrated and the residue purified by silica gel chromatography (EtOAc/hexanes) to give I21C (0.67 g, 76%). LCMS m/z 465.2 (M+H)$^+$. $^1$H NMR (CDCl$_3$) δ 8.80 (s, 1H), 8.43 (s, 1H), 7.45-7.7.42 (m, 4H), 7.38-7.7.26 (m, 6H), 4.85 (d, J=6.0 Hz 2H), 4.370 (t, J=4.8 Hz 2H), 3.98 (t, J=4.8 Hz, 2H), 0.88 (s, 9H).

5-(5-((Bis(4-methoxyphenyl)(phenyl)methoxy)methyl)-1-(2-((tert-butyldiphenylsilyl) oxy)ethyl)-1H-1,2,4-triazol-3-yl)thiazole (I21D)

To a mixture of I21C (843 mg, 1.82 mmol) in pyridine (20 mL) at RT was added DMTrCl (922 mg, 2.73 mmol). The resulting solution was stirred for 3 hrs, then concentrated and the residue purified by silica gel chromatography (0-100% EtOAc/Hexane) to give I21D (1.3 g, 93%). LCMS m/z 767.2 (M+H)$^+$. $^1$H NMR (CDCl$_3$) δ 8.79 (s, 1H), 8.40 (s, 1H), 7.45-7.43 (m, 2H), 7.36-7.31 (m, 8H), 7.27-7.21 (m, 12H), 6.81-6.79 (m, 4H), 4.41 (s, 2H), 4.25 (t, J=4.8 Hz, 2H), 3.85 (t, J=4.8 Hz, 2H), 1.53 (s, 6H), 0.02 (s, 9H).

2-(5-((Bis(4-methoxyphenyl)(phenyl)methoxy)methyl)-3-(thiazol-5-yl)-1H-1,2,4-triazol-1-yl)ethan-1-ol (I21E)

To a solution of 121D (1.3 g, 1.69 mmol) in THF (10 mL) at RT was added at TBAF in THF (1.0 M, 4 mL, 3.39 mmol) and the resulting solution was stirred overnight. The reaction mixture was concentrated under reduced pressure, diluted with EtOAc and washed with sat. aq. NaHCO$_3$ and brine. The organic layer was dried (Na$_2$SO$_4$), concentrated under reduced pressure and the residue was purified by silica gel chromatography (0-10% MeOH/DCM) to give I21E (0.97 g, quant). LCMS m/z 529.2 (M+H)$^+$. $^1$H NMR (CDCl$_3$) δ 8.65 (s, 1H), 8.29 (s, 1H), 7.47-7.17 (comp, 9H), 6.85-6.78 (m, 4H), 4.39 (s, 2H), 4.14 (t, J=4.8 Hz, 2H), 3.89 (bt, J=4.4 Hz, 2H), 3.73 (s, 6H).

2-(5-((Bis(4-methoxyphenyl)(phenyl)methoxy)methyl)-3-(thiazol-5-yl)-1H-1,2,4-triazol-1-yl)ethyl (2-cyanoethyl) diisopropylphosphoramidite (Intermediate 21)

To a solution of I21E (0.45 g, 0.85 mmol) in ACN (8 mL) at RT was added DIEA (0.44 mL, 2.55 mmol) followed by a dropwise addition of 3-((chloro(diisopropylamino)phosphino)oxy)propanenitrile (380 µL, 1.71 mmol). The mixture was stirred at RT for 1 hr, and then quenched by the addition of 5% aq. NaHCO$_3$. The mixture was concentrated under reduced pressure, and the residue was purified by RP-MPLC (0-100% ACN/H$_2$O) to give Intermediate 21 (170 mg, 28%) as a white solid. LCMS m/z 646.3 (M+H+OH-N,N-diisopropylamino)$^+$. $^1$H NMR (CD$_3$CN) δ 8.86 (s, 1H), 8.28 (s, 1H), 7.49-7.47 (m, 2H), 7.38-7.23 (m, 6H), 6.90-6.86 (m, 4H), 4.32 (d, J=2.8 Hz, 2H), 4.28-4.23 (m, 2H), 3.85-3.82 (m, 2H), 3.57-3.52 (m, 2H), 3.42-3.36 (m, 2H), 2.47 (t, J=6 Hz, 2H), 2.14 (s, 2H), 1.05 (d, J=6.8 Hz, 6H), 0.94 (d, J=6.8 Hz, 6H). $^{31}$P NMR (CD$_3$CN) δ 147.82.

Example 16

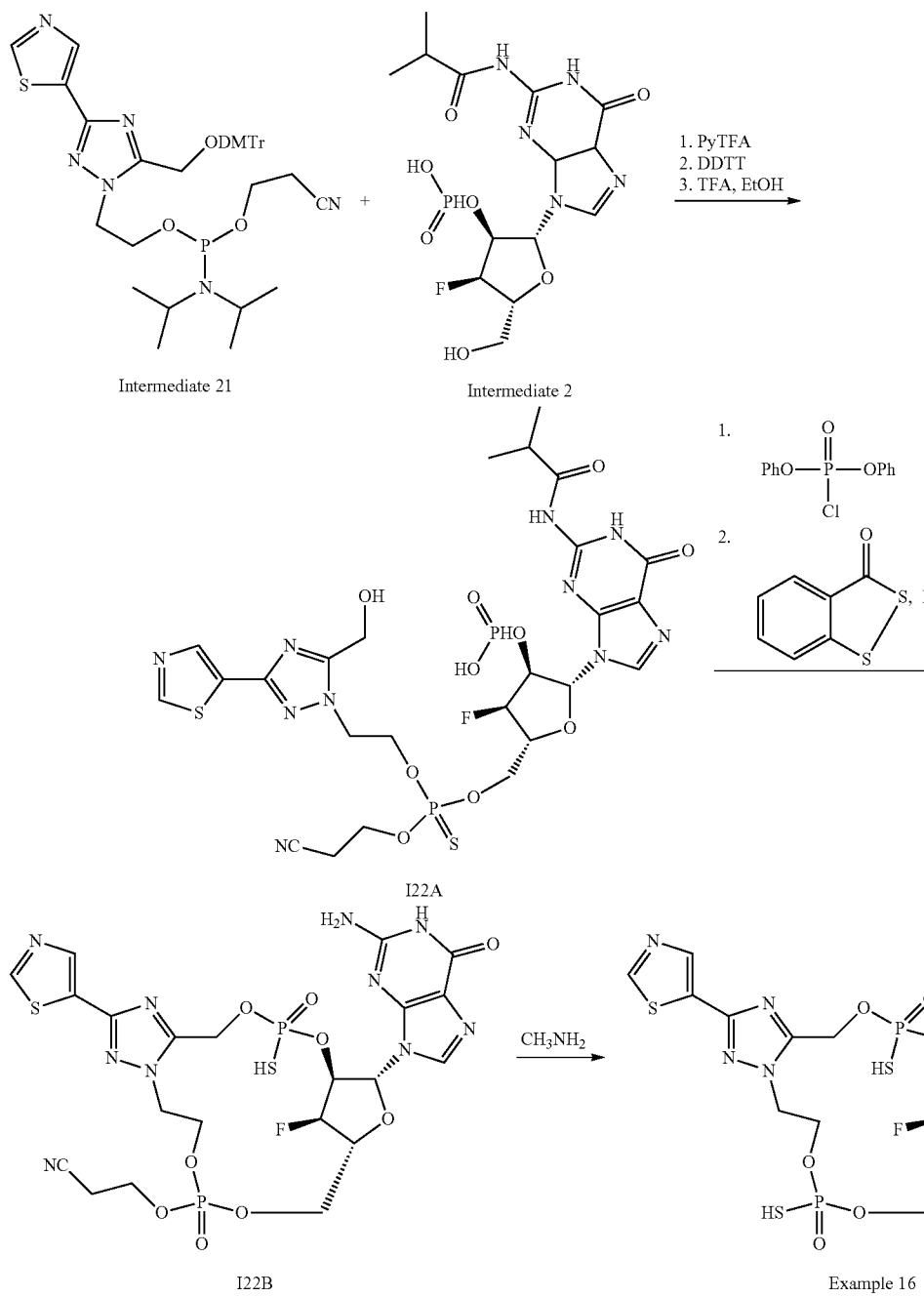

(2R,3S,4R,5R)-5-((((2-Cyanoethoxy)(2-(5-(hydroxymethyl)-3-(thiazol-5-yl)-1H-1,2,4-triazol-1-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I22A)

A suspension of Intermediate 21 (201 mg, 0.48 mmol) and crushed, freshly activated 3 Å MS (200 mg) in ACN (6 mL) was stirred with occasional sonication for 45 min. In the meantime, a suspension of Intermediate 2 (310 mg, 0.48 mmol), Py.TFA (185 mg, 0.96 mmol), and crushed, freshly activated 3 Å MS (200 mg) in ACN (4 mL) was stirred with occasional sonication for 45 min. The supernatant containing Intermediate 21 was added to the suspension of Intermediate 2 in a dropwise fashion, via syringe. The flask and residual sieves that contained Intermediate 21 was washed with ACN (2 mL) and the supernatant was again added to the mixture containing Intermediate 2. The resulting mixture was stirred at RT for 45 min, whereupon DDTT (219 mg, 1.07 mmol) was added in one portion. The reaction mixture was stirred at RT for 1 hr, and then EtOH (0.20 mL) and TFA (0.20 mL) were added and the mixture stirred at RT for 1 hr. The reaction mixture was filtered to remove the sieves. The filtrate was concentrated under reduced pressure, and the residue was purified by RP-MPLC (C18, 10-100% ACN/H₂O) to give I22A (155 mg, 47%) as a white solid. LCMS (Method D, $T_R$=1.10 min) m/z 775.0 (M–H)⁺. ³¹P NMR (CD₃OD) δ 67.81, 67.72, 2.58. ¹⁹F NMR (CD₃OD) δ –201.73, –201.79.

Remaining steps of Example 16 (Diastereomers A-D) were prepared according to procedures analogous to those outlined in Example 1.

3-{[(1S,17R,19R,20R)-19-(2-Amino-6-oxo-6,9-dihydro-1H-purin-9-yl)-20-fluoro-3-oxo-3-sulfanyl-14-sulfanylidene-8-(1,3-thiazol-5-yl)-2,4,13,15,18-pentaoxa-7,9,10-triaza-3lambda5,14lambda5-diphosphatricyclo[15.2.1.06,10]icosa-6,8-dien-14-yl]oxy}propanenitrile (I22B)

LCMS (Method D, $T_R$=1.34 min) m/z 788.8 (M–H)⁺. ³¹P NMR (CD₃OD) δ 69.06, 68.99, 65.73, 65.57, 61.19, 60.84, 57.77, 57.52, ¹⁹F NMR (CD₃OD) δ –196.40, –197.30, –198.22, –199.27.

(1S,17R,19R,20R)-19-(2-Amino-6-oxo-6,9-dihydro-1H-purin-9-yl)-20-fluoro-3,14-disulfanyl-8-(1,3-thiazol-5-yl)-2,4,13,15,18-pentaoxa-7,9,10-triaza-3lambda5,14lambda5-diphosphatricyclo[15.2.1.06,10]icosa-6,8-diene-3,14-dione (Example 16)

Example 16 (Diastereomers A-D) were purified by prep. RP-HPLC (XBridge Prep C18 OBD 5 μm, 19×150 mm column) using aq. NH₄HCO₃ (50 mM) (A) and ACN (B) as eluents. Gradient: 0-2.0 min—Isocratic—100% A; 2.1-20.0 min—Linear gradient 0%-13% B. Flow rate: 10 mL/min. Example 16A (Diastereomer A): Prep. RP-HPLC: $T_R$=16.9 min. LCMS (Method D, $T_R$=0.73 min) m/z 668.0 (M+H)⁺. ¹H NMR (D₂O) δ 9.07 (s, 1H), 8.37 (s, 1H), 7.94 (s, 1H), 6.06 (d, J=8 Hz, 1H), 5.38 (dd, J=49 Hz and 8 Hz, 1H), 5.31 (dd, J=9.2 Hz and 3.4 Hz, 1H), 5.09-4.93 (m, 1H), 4.77-4.60 (m, 2H), 4.50-4.10 (comp, 4H). ³¹P NMR (D₂O) δ 55.91, 55.50. ¹⁹F NMR (D₂O) 8-198.04. Example 16B (Diastereomer B): Prep. RP-HPLC: $T_R$=17.5 min. LCMS (Method D, $T_R$=0.73 min) m/z 668.0 (M+H)⁺. ¹H NMR (D₂O) δ 9.06 (s, 1H), 8.37 (s, 1H), 8.16 (s, 1H), 6.05 (d, J=8.4 Hz, 1H), 5.31-5.17 (comp, 1H), 5.29 (dd, J=39.6 Hz and 8 Hz, 1H), 5.15 (dd, J=12.8 Hz and 8 Hz), 4.93-4.88 (m, 1H), 4.67-4.50 (comp, 4H), 4.47-4.37 comp, 2H), 4.21-4.05 (comp, 3H). ³¹P NMR (D₂O) δ 57.42, 55.99. ¹⁹F NMR (D₂O) 8-196.29. Example 16C (Diastereomer C): Prep. RP-HPLC: $T_R$=24.9 min. LCMS (Method D, $T_R$=0.84 min) m/z 668.0 (M+H)⁺. ¹H NMR (D₂O) δ 9.08 (s, 1H), 8.38 (s, 1H), 7.85 (s, 1H), 6.05 (d, J=8 Hz, 1H), 5.34 (dd, J=33.6 Hz and 3.6 Hz, 1H), 5.32 (dd, J=12.8 Hz and 9.2 Hz) 5.11-4.95 (comp, 1H), 4.74-4.26 (comp, 6H), 4.08-3.99 (comp, 1H). ³¹P NMR (D₂O) δ 55.63, 55.59. ¹⁹F NMR (D₂O) 8-197.83. Example 16D (Diastereomer D): Prep. RP-HPLC: $T_R$=25.9 min. LCMS (Method D, $T_R$=0.84 min) m/z 668.0 (M+H)⁺. ¹H NMR (D₂O) δ 9.07 (s, 1H), 8.37 (s, 1H), 7.98 (s, 1H), 6.04 (d, 1H), 5.31-5.16 (comp, 1H), 5.10 (dd, J=33.2 Hz and 8.8 Hz, 1H), 5.09 (dd, J=8.8 Hz and 6 Hz, 1H), 4.95-4.88 (m, 1H), 4.71-4.24 (comp, 8H), 4.08-4.00 (comp, 1H). ³¹P NMR (D₂O) δ 57.12, 55.36. ¹⁹F NMR (D₂O) 8-196.13.

Intermediate 23

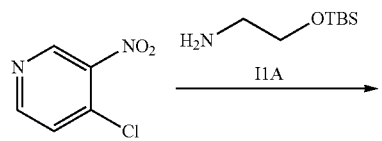

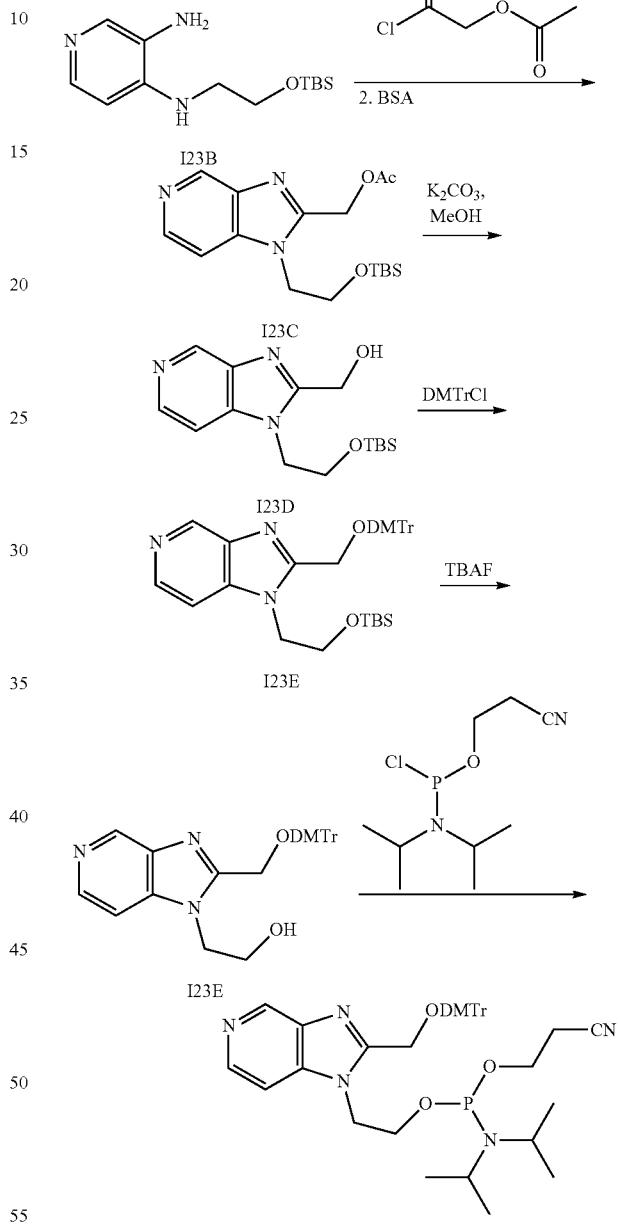

Intermediate 23

N-(2-((tert-Butyldimethylsilyl)oxy)ethyl)-3-nitropyridin-4-amine (I23A)

To a solution of 4-chloro-3-nitropyridine (5.0 g, 31.6 mmol) and TEA (1.2 mL, 47.5 mmol) in THF (100 mL) at RT was added dropwise I1A (5.54 g, 31.6 mmol). The reaction mixture was stirred at RT overnight. The mixture was washed with sat. aq. NaHCO₃, and then brine. The organic layer was dried (Na₂SO₄), then concentrated under reduced pressure. The residue was purified by silica gel chromatography (0-100% EtOAc/Hexane) to give I23A (8.7 g, 93%) as a pale yellow solid. LCMS m/z 298.3 (M+H)⁺. ¹H NMR (CD₃OD) δ 9.06 (s, 1H), 8.18 (d, J=6.3 Hz, 1H), 7.05 (d, J=6.5 Hz, 1H), 3.90 (t, J=5.0 Hz, 2H), 3.55 (t, J=5.3 Hz, 2H), 0.89 (s, 9H), 0.07 (s, 6H). N4-(2-((tert-Butyldimethylsilyl)oxy)ethyl)pyridine-3,4-diamine (I23B)

A mixture of I23A (8.4 g, 28.3 mmol), 10% Pd/C (1.0 g) in MeOH (150 mL) was hydrogenated at 50 psi H₂ for 5.5 hrs using a Parr shaker. The reaction mixture was filtered through a pad of Celite® and the filtrate was concentrated under reduced pressure to give I23B (7.11 g, 94%) which was used without further purification. LCMS m/z 268.3 (M+H)⁺. ¹H NMR (CDCl₃) δ 7.94 (d, J=5.3 Hz, 1H), 7.87 (s, 1H), 6.46 (d, J=5.3 Hz, 1H), 3.85 (t, J=5.3 Hz, 2H), 3.19 (q, J=5.4 Hz, 2H), 0.90 (s, 9H), 0.07 (s, 6H).

(1-(2-((tert-Butyldimethylsilyl)oxy)ethyl)-1H-imidazo[4,5-c]pyridin-2-yl)methyl acetate (I23C)

To a solution of I23B (7.11 g, 26.6 mmol) and DIPEA (7.0 mL, 39.9 mmol) in DCM (150 mL) at RT was added dropwise 2-chloro-2-oxoethyl acetate (2.25 mL, 26.6 mmol). The resulting mixture was stirred at RT for 2 hrs. The reaction mixture was concentrated under reduced pressure. The residue was dissolved in BSA (50 mL) and heated at 130° C. for 3 hrs. The mixture was diluted with EtOAc, and washed with sat. aq. NaHCO₃ and brine. The organic layer was dried (Na₂SO₄), and concentrated under reduced pressure. The residue was purified by silica gel chromatography (EtOAc/Hexane then 0-10% MeOH/DCM) to give I23C (5.4 g, 58%). LCMS m/z 350.4 (M+H)⁺. ¹H NMR (CDCl₃) δ 9.07 (d, J=1 Hz, 1H), 8.43 (d, J=5.5 Hz, 1H), 7.33 (dd, J=5.5 and 1 Hz, 1H), 5.42 (s, 2H), 4.37 (t, J=5.0 Hz, 2H), 3.92 (t, J=5.3 Hz, 2H), 2.14 (s, 3H), 0.74 (s, 9H), −0.2 (s, 6H).

(1-(2-((tert-Butyldimethylsilyl)oxy)ethyl)-1H-imidazo[4,5-c]pyridin-2-yl)methanol (I23D)

A mixture of I23C (5.4 g, 15.5 mmol) and K₂CO₃ (540 mg, 3.9 mmol) in MeOH (100 mL) was stirred at RT for 1 hr, and then concentrated under reduced pressure. The residue was purified by silica gel chromatography (0-10% MeOH/DCM) to give I23D (3.5 g, 74%) as a pale yellow solid. LCMS m/z 308.3 (M+H)⁺. ¹H NMR (CDCl₃) δ 8.99 (d, J=1.0 Hz, 1H), 8.39 (d, J=5.5 Hz, 1H), 7.28 (dd, J=5.8 and 1.0 Hz, 1H), 4.96 (s, 2H), 4.38 (t, J=5.0 Hz, 2H), 3.96 (t, J=5.3 Hz, 2H), 2.02 (s, 3H), 0.73 (s, 9H), −0.19 (s, 6H).

2-((Bis(4-methoxyphenyl)(phenyl)methoxy)methyl)-1-(2-((tert-butyldimethylsilyl)oxy)ethyl)-1H-imidazo[4,5-c]pyridine (I23E)

A mixture of I23D (3.5 g, 11.4 mmol) and DMTrCl (5.8 g, 17.1 mmol) in pyridine (60 mL) was stirred at RT overnight. The reaction was quenched with sat.aq. NaHCO₃, water was added and the mixture extracted with EtOAc (2×). The combined organic layers were washed with brine, dried (Na₂SO₄) and concentrated under reduced pressure. The residue was purified by silica gel chromatography (0-100% EtOAc/Hexane) to give I23E (5.5 g, 79%) as a light yellow form. LCMS m/z 610.6 (M+H)⁺. ¹H NMR (CDCl₃) δ 9.08 (s, 1H), 8.40 (d, J=5.5 Hz, 1H), 7.50-7.22 (comp, 10H), 6.85 (d, J=8.8 Hz, 4H), 4.48 (s, 2H), 4.15 (t, J=5.0 Hz, 2H), 3.79 (s, 6H), 3.71 (m, 2H), 0.66 (s, 9H), −0.31 (s, 6H).

2-(2-((Bis(4-methoxyphenyl)(phenyl)methoxy)methyl)-1H-imidazo[4,5-c]pyridin-1-yl)ethan-1-ol (I23F)

To a solution of I23E (5.5 g, 9.0 mmol) in THF (45 mL) at RT was added dropwise TBAF in THF (1.0 M, 18 mL, 18.0 mmol). The reaction mixture was stirred at RT for 1 hr and then quenched with sat. aq. NH₄Cl. Water was added and the mixture extracted with EtOAc (2×). The combined organic layers were washed with brine, dried (Na₂SO₄) and concentrated under reduced pressure. The residue was purified by silica gel chromatography (0-7% MeOH/DCM) to give I23F (4.2 g, 94%) as a white form. LCMS m/z 496.4 (M+H)⁺. 1H NMR (CDCl₃) δ 8.96 (s, 1H), 8.30 (d, J=5.5 Hz, 1H), 7.50-7.20 (comp, 13H), 6.86 (d, J=9.1 Hz, 4H), 4.48 (s, 2H), 4.13 (t, J=5.3 Hz, 2H), 3.81-3.78 (comp, 8H).

2-(2-((Bis(4-methoxyphenyl)(phenyl)methoxy)methyl)-1H-imidazo[4,5-c]pyridin-1-yl)ethyl (2-cyanoethyl) diisopropylphosphoramidite (Intermediate 23)

To a solution of I23F (1.0 g, 2.0 mmol) and DIEA (1.0 mL, 6.0 mmol) in ACN (12 mL) was added dropwise 3-((chloro(diisopropylamino)phosphino)oxy)propanenitrile (0.89 mL, 4.0 mmol). The reaction mixture was stirred at RT for 1 hr, and then quenched by addition of sat. aq. NaHCO₃ (1 mL) and H₂O (1 mL). The resulting mixture was purified directly by RP-MPLC (0-100% ACN/H₂O) to give Intermediate 23 (1.03 g, 74%) as a white foam. LCMS m/z 613.5 (M+H+OH-N,N-diisopropylamino)⁺. ¹H NMR (CDCl₃) δ 9.05 (d, J=1 Hz, 1H), 8.41 (d, J=5.5 Hz, 1H), 7.50-7.24 (comp, 10H), 6.85 (d, J=8.8 Hz, 4H), 4.49 (dd, J=19.5 and 11.5 Hz, 2H), 4.26 (q, J=5.3 Hz, 2H), 3.80-3.60 (comp, 8H), 3.49 (qd, J=6.5 and 1.0 Hz, 2H), 3.38-3.35 (m, 2H), 2.39 (t, J=6.3 Hz, 2H), 1.05 (d, J=6.8 Hz, 6H), 0.89 (d, J=6.8 Hz, 6H). ³¹P NMR (CD₃CN) δ 148.30.

Example 17

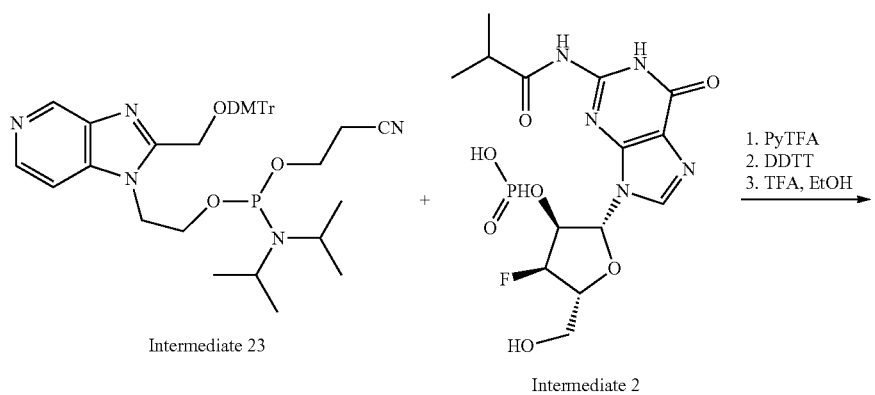

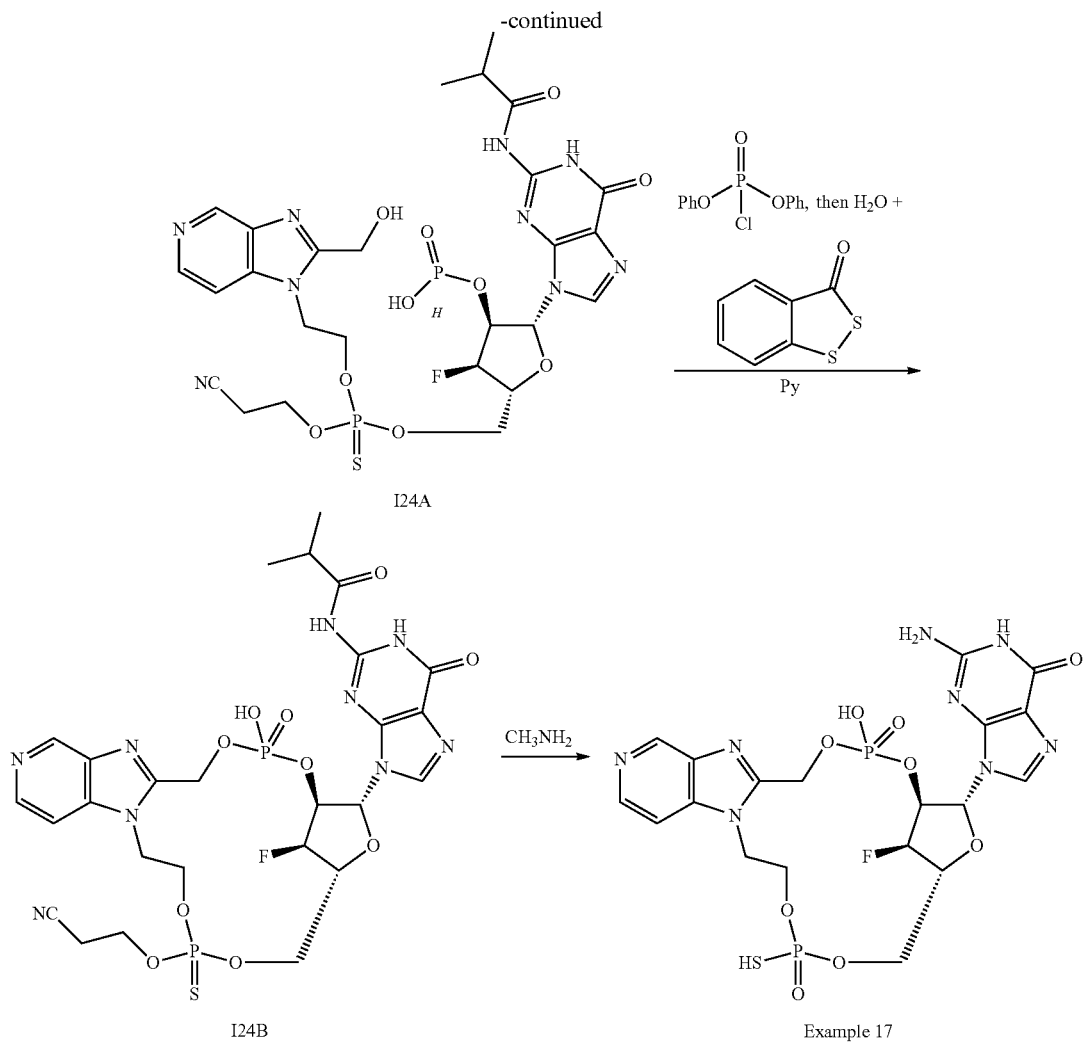

(1S,21R,23R,24R)-23-(2-Amino-6-oxo-6,9-dihydro-1H-purin-9-yl)-24-fluoro-3,18-disulfanyl-2,4,17,19,22-pentaoxa-7,10,14-triaza-3lambda5,18lambda5-diphosphatetracyclo[19.2.1.06,14.08,13]tetracosa-6,8,10,12-tetraene-3,18-dione (Example 17)

Example 17 diastereomers (Diastereomers A-D) were prepared according to procedures analogous to those outlined in Example 1.

(2R,3S,4R,5R)-5-(((2-Cyanoethoxy)(2-(2-(hydroxymethyl)-1H-imidazo[4,5-c]pyridin-1-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I24A)

LCMS (Method D, $T_R$=1.01 min) m/z 742.5 (M−H)+. $^{31}$P NMR (CD$_3$OD) δ 68.03, 67.89, 2.68. $^{19}$F NMR (CD$_3$OD) δ −201.30, −201.47.

N-{9-[(1S,21R,23R,24R)-18-(2-Cyanoethoxy)-24-fluoro-3-oxo-3-sulfanyl-18-sulfanylidene-2,4,17,19,22-pentaoxa-7,10,14-triaza-3lambda5,18lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (I24B)

LCMS (Method D, $T_R$=1.16 min) m/z 756.5 (M−H)+. $^{31}$P NMR (CD$_3$OD) δ 67.61, 67.48, 65.42, 64.80, 60.64, 60.41, 57.28, 56.54. $^{19}$F NMR (CD$_3$OD) δ −196.93, −197.53, −198.74, −199.26.

Example 17 diastereomers (Diastereomers A-D) were purified by prep. RP-HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 17C (Diastereomer C): Prep. RP-HPLC: $T_R$=20.0 min. LCMS (Method D, $T_R$=1.11 min) m/z 635.2 (M+H)+. $^1$H NMR (D$_2$O) δ 9.15 (s, 1H), 8.55 (d, J=6.4 Hz, 1H), 8.15 (d, J=6.4 Hz, 1H), 7.40 (s, 1H), 5.99 (d, J=8.0 Hz, 1H), 5.52 (dd, J=52.8 Hz and 4.0 Hz, 2H), 5.44 (dd, J=12.4 Hz and 8.8 Hz), 4.91-4.64 (comp), 4.46 (m, 2H), 4.28-3.99 (comp, 3H). $^{31}$P NMR (D$_2$O) δ 55.10, 54.31. $^{19}$F NMR (D$_2$O) δ −198.26.

Example 18
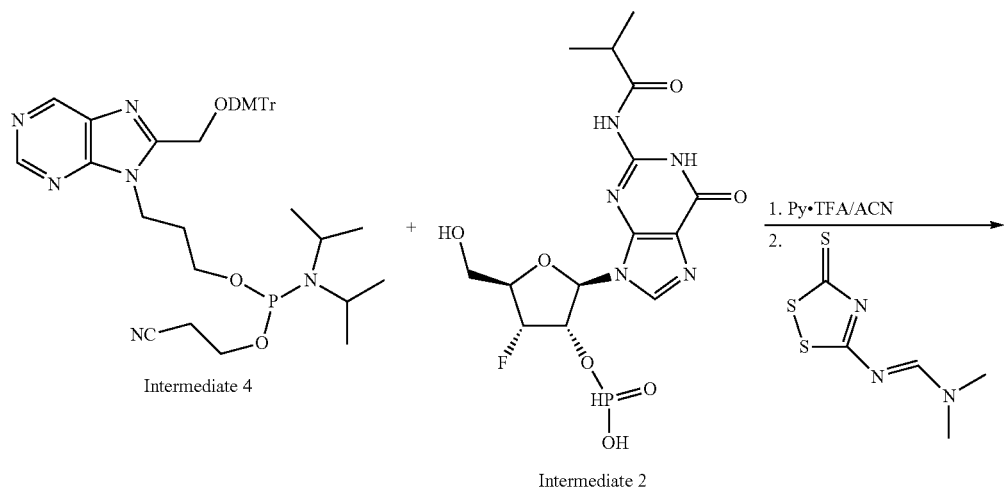

-continued

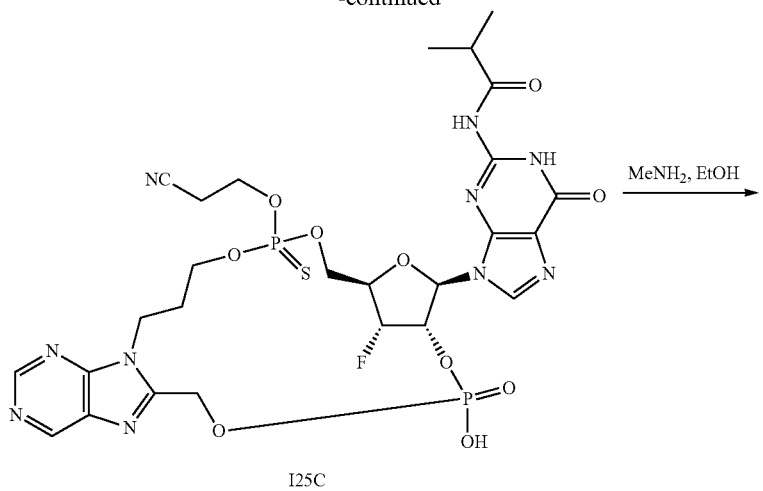

I25C

MeNH₂, EtOH →

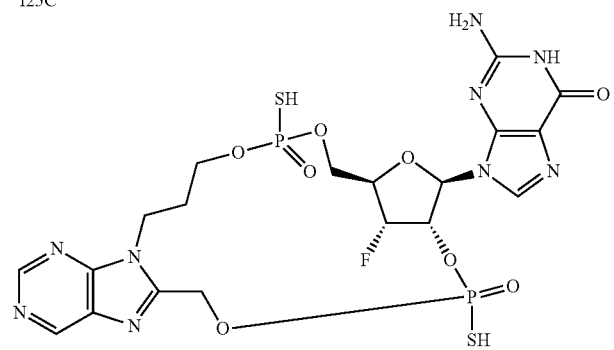

Example 18

(1S,22R,24R,25R)-24-(2-Amino-6-oxo-6,9-dihydro-1H-purin-9-yl)-25-fluoro-3,19-disulfanyl-2,4,18,20,23-pentaoxa-7,10,212,14-tetraaza-3lambda5,19lambda5-diphosphatetracyclo[20.2.1.06,14.08,13]pentacosa-6,8,10,12-tetraene-3,19-dione (Example 18)

Example 18 diastereomers (Diastereomers A-D) were prepared according to procedures analogous to those outlined in Example 1.

Example 18 The residue was first purified by RP-MPLC (C18, 0-30% ACN/H₂O containing 0.04% NH₄HCO₃) to give two sets of diastereomers. These were purified further by preparative HPLC(XBridge Prep BEH OBD Amide 5 m 19×150 mm column eluting with 10-24% H₂O containing 0.04% HCOOH (50 mM)/ACN, Flow rate=10 mL/min) followed by RP-HPLC(XBridge Prep C18 OBD 5 μm, 19×150 mm column eluting with 0-30% ACN/H₂O containing 0.04% NH₄HCO₃, Flow rate=10 mL/min) to give pure diastereomers. Example 18C (Diastereomer C): Preparative. HPLC:T$_R$=18.2 min. LCMS (Method D, T$_R$=1.29 min) m/z 648.1 (M−H)⁻. ¹H NMR (D₂O) δ 9.14 (s, 1H), 9.01 (s, 1H), 8.03 (s, 1H), 6.16 (d, J=7.2 Hz, 1H), 5.54 (dd, J=4.0, 52.8 Hz, 1H), 5.30 (dd, J=6.8, 12.4 Hz, 1H), 4.93 (m, 3H, under water peak), 4.20 (m, 6H), 2.15 (m, 1H), 1.85 (m, 1H). ³¹P NMR (D₂O) δ 56.66. ¹⁹F NMR (D₂O) 8-198.19. Example 18D (Diastereomer D): Preparative HPLC:T$_R$=19.4 min. LCMS (Method D, T$_R$=1.31 min) m/z 648.1 (M−H)⁻. ¹H NMR (D₂O) δ 9.16 (s, 1H), 9.03 (s, 1H), 8.21 (s, 1H), 6.14 (d, J=7.6 Hz, 1H), 5.33 (dd, J=4.0, 53.6 Hz, 1H), 5.24 (m, 1H), 5.19 (m, 1H), 5.10 (m, 1H), 4.73 (m, 1H, under water peak), 4.64 (m, 3H), 4.13 (m, 3H), 2.27 (m, 2H). ³¹P NMR (D₂O) δ 56.88, 56.51. ¹⁹F NMR (D₂O) δ −196.40.

Intermediate 26

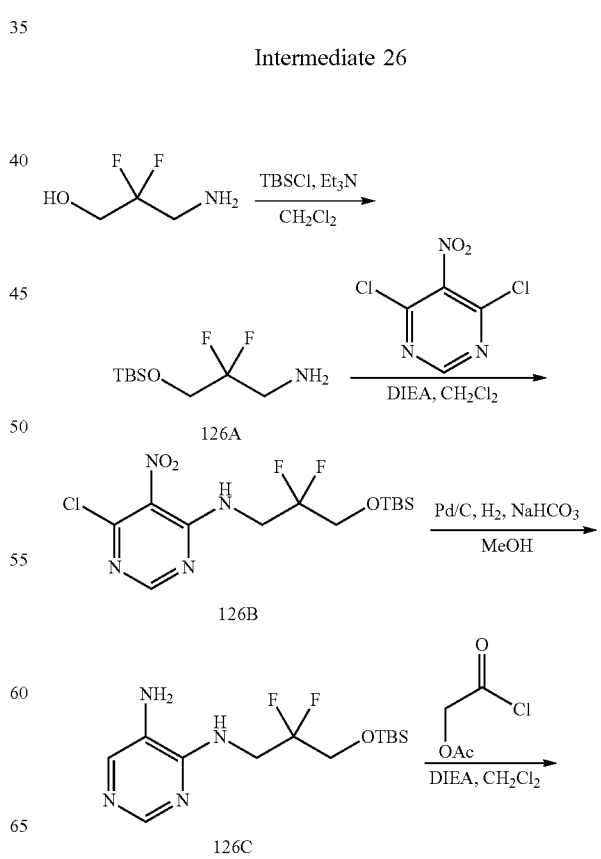

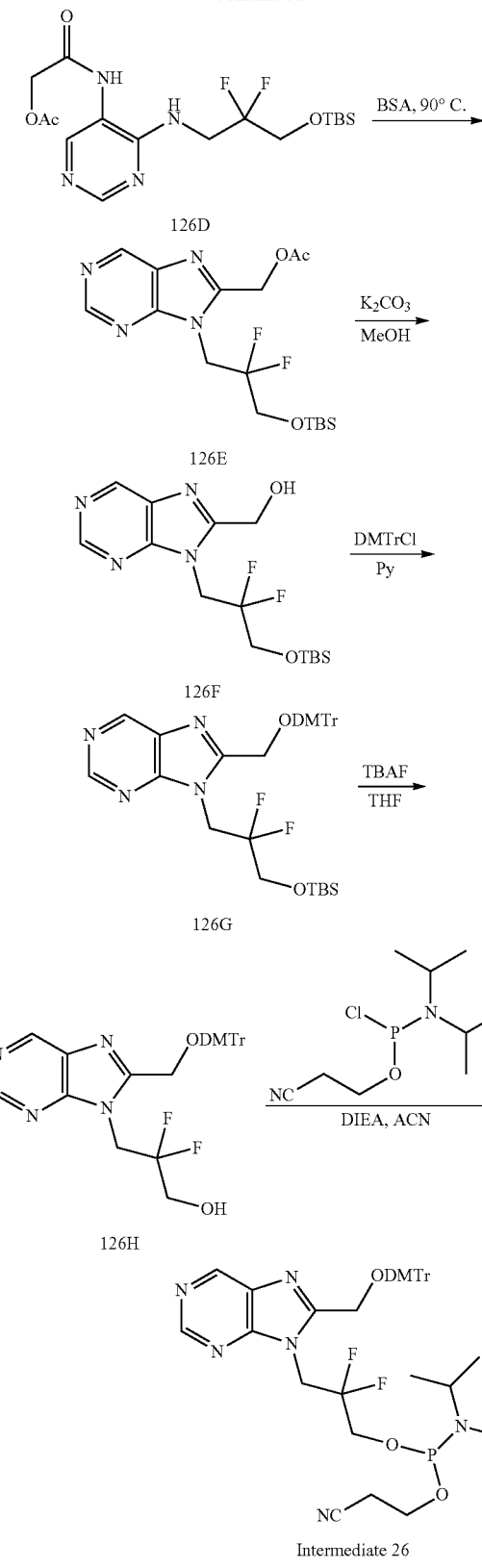

Intermediate 26 was prepared according to procedures analogous to those outlined in Intermediate 4 using 2,2-difluoropropan-1-ol as starting material.

3-((tert-Butyldimethylsilyl)oxy)-2,2-difluoropropan-1-amine (I26A)

LCMS m/z (M+H)⁺226.0. ¹H NMR (CDCl₃) δ 3.72 (t, J=12.0 Hz, 2H), 2.99 (t, J=14.8 Hz, 2H), 0.88 (s, 9H), 0.07 (s, 6H). ¹⁹F NMR (CDCl₃) δ −115.43.

N-(3-((tert-Butyldimethylsilyl)oxy)-2,2-difluoropropyl)-6-chloro-5-nitropyrimidin-4-amine (I26B)

LCMS m/z (M+H)⁺383.3. ¹H NMR (CDCl₃) δ 8.43 (s, 1H), 7.75 (br s, 1H), 4.23 (td, J=6.0, 14.0 Hz, 2H), 3.86 (t, J=11.6 Hz, 2H), 0.91 (s, 9H), 0.11 (s, 6H). ¹⁹F NMR (CDCl₃) δ − 111.99.

N4-(3-((tert-Butyldimethylsilyl)oxy)-2,2-difluoropropyl)pyrimidine-4,5-diamine (I26C)

LCMS m/z (M+H)⁺319.0. ¹H NMR (CDCl₃) δ 8.31 (s, 1H), 7.82 (s, 1H), 5.15 (m, 1H), 4.09 (td, J=6.4, 14.4 Hz, 2H), 3.86 (t, J=12.4 Hz, 2H), 0.91 (s, 9H), 0.09 (s, 6H). ¹⁹F NMR (CDCl₃) δ −112.70.

2-((4-((3-((tert-Butyldimethylsilyl)oxy)-2,2-difluoropropyl)amino)pyrimidin-5-yl)amino)-2-oxoethyl acetate (I26D)

LCMS m/z (M+H)⁺419.4. ¹H NMR (CDCl₃) δ 8.54 (s, 1H), 8.12 (s, 1H), 7.62 (s, 1H), 5.58 (t, J=5.6 Hz, 1H), 4.72 (s, 2H), 4.12 (td, J=6.4, 14.4 Hz, 2H), 3.83 (t, J=12.4 Hz, 2H), 2.23 (s, 3H), 0.90 (s, 9H), 0.07 (s, 6H). ¹⁹F NMR (CDCl₃) δ −112.87.

(9-(3-((tert-Butyldimethylsilyl)oxy)-2,2-difluoropropyl)-9H-purin-8-yl)methyl acetate (I26E)

LCMS m/z (M+H)⁺401.4. ¹H NMR (CDCl₃) δ 9.13 (s, 1H), 9.01 (s, 1H), 5.41 (s, 2H), 4.93 (t, J=14.4 Hz, 2H), 3.93 (t, J=12.0 Hz, 2H), 2.16 (s, 3H), 0.92 (s, 9H), 0.11 (s, 6H). ¹⁹F NMR (CDCl₃) δ −110.79.

(9-(3-((tert-Butyldimethylsilyl)oxy)-2,2-difluoropropyl)-9H-purin-8-yl)methanol (I26F)

LCMS m/z (M+H)⁺359.4. ¹H NMR (CDCl₃) δ 9.06 (s, 1H), 8.97 (s, 1H), 5.02 (s, 2H), 4.88 (t, J=14.4 Hz, 2H), 3.92 (t, J=12.0 Hz, 2H), 0.91 (s, 9H), 0.11 (s, 6H). ¹⁹F NMR (CDCl₃) δ −110.57.

8-((Bis(4-methoxyphenyl)(phenyl)methoxy)methyl)-9-(3-((tert-butyldimethylsilyl)oxy)-2,2-difluoropropyl)-9H-purine (I26G)

LCMS (Method E) m/z (M+H)⁺661.5. ¹H NMR (CDCl₃) δ 9.05 (s, 1H), 8.96 (s, 1H), 7.46 (m, 2H), 7.36 (m, 4H), 7.31-7.27 (m, 2H), 7.22 (m, 1H), 6.82 (m, 4H), 4.86 (t, J=14.4 Hz, 2H), 4.62 (s, 2H), 3.76 (s, 6H), 3.74 (t, J=12.0 Hz, 2H), 0.85 (s, 9H), 0.02 (s, 6H). ¹⁹F NMR (CDCl₃) δ −110.19.

3-(8-((Bis(4-methoxyphenyl)(phenyl)methoxy)methyl)-9H-purin-9-yl)-2,2-difluoropropan-1-ol (I26H)

LCMS m/z (M+H)⁺547.4. ¹H NMR (CDCl₃) δ 9.15 (s, 1H), 8.97 (s, 1H), 7.49-7.47 (m, 2H), 7.41-37 (m, 4H), 7.34-7.30 (m, 2H), 7.24-7.22 (m, 1H), 6.87-6.83 (m, 4H), 4.78 (t, J=11.6 Hz, 2H), 4.57 (s, 2H), 3.78 (s, 6H), 3.45 (m, 2H). $^{19}$F NMR (CDCl$_3$) δ −110.06.
2-Difluoro-3-(8-((bis(4-methoxyphenyl)(phenyl)methoxy)methyl)-9H-purin-9-yl)propyl (2-cyanoethyl) diisopropylphosphoramidite (Intermediate 26)
LCMS m/z (M+H+OH-N,N-diisopropylamino)$^+$664.5. $^1$H NMR (CD$_3$OD) δ 9.01 (s, 1H), 8.93 (s, 1H), 7.50 (m, 2H), 7.38 (m, 4H), 7.32 (m, 2H), 7.23 (m, 1H), 6.90-6.83 (m, 4H), 4.97 (m, 2H), 4.72 (s, 2H), 3.80 (m, 2H), 3.75 (s, 6H), 3.62 (m, 2H), 3.32 (m, 2H), 3.32 (m, 2H), 2.69 (m, 2H), 1.22 (s, 3H), 1.20 (s, 3H), 1.17 (s, 3H), 1.15 (s, 3H). $^{31}$P NMR (CD$_3$OD) δ 151.09. $^{19}$F NMR (CD$_3$OD) δ−110.30, −110.31, −110.35, −110.36.
Example 19
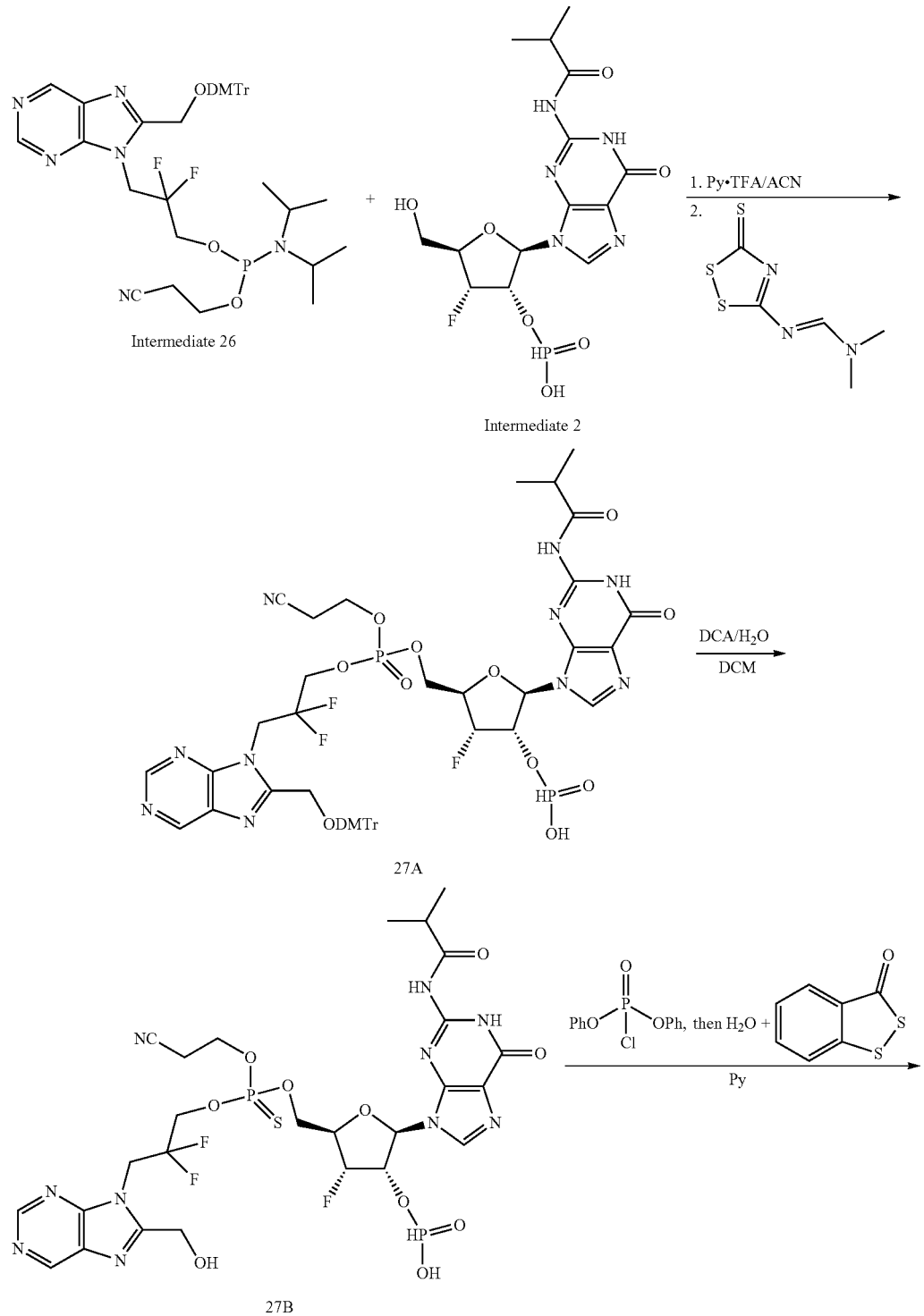

-continued

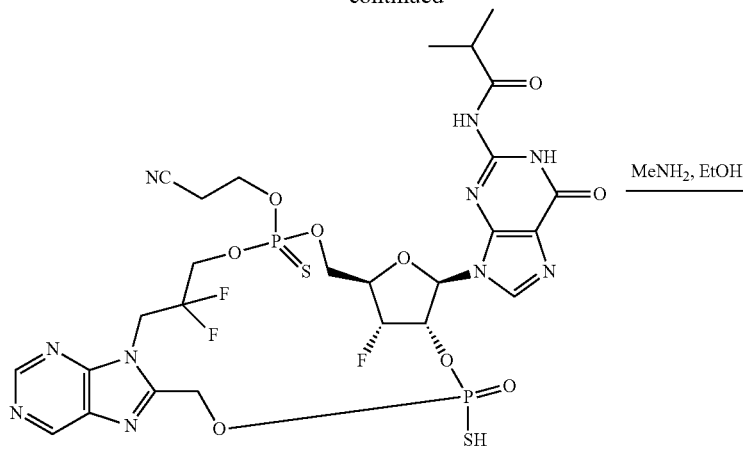

27C

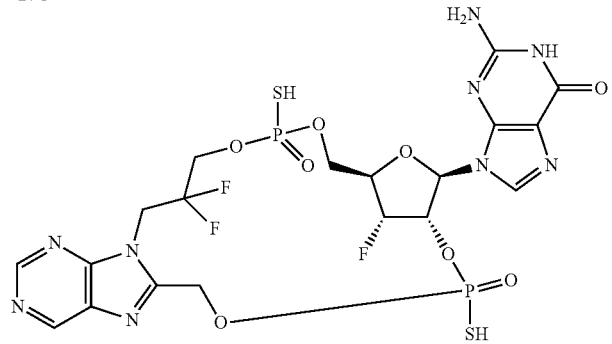

Example 19

(1S,22R,24R,25R)-24-(2-Amino-6-oxo-6,9-dihydro-1H-purin-9-yl)-16,16,25-trifluoro-3,19-disulfanyl-2,4,18,20,23-pentaoxa-7,10,12,14-tetraaza-3lambda5,19lambda5-diphosphatetracyclo[20.2.1.06,14.08,13]pentacosa-6,8,10,12-tetraene-3,19-dione (Example 19)

Example 19 diastereomers (Diastereomers A-D) were prepared according to procedures analogous to those outlined in Example 1. The mixture of diastereomers was first purified by RP-MPLC (C18, 0-30% ACN/H₂O containing 0.04% NH₄HCO₃) to give 2 pairs of diastereomers. Each pair of diastereomers was then purified further by RP-HPLC (Sunfire Prep C18, 5 μm, 19×100 mm column eluting with 0-25% ACN/H₂O containing 0.04% NH₄HCO₃, Flow rate=10 mL/min). Example 19A (Diastereomer A): Prep. RP-HPLC $T_R$=13.8 min. LCMS (Method D, $T_R$=1.30 min) m/z 684.2 (M-H)⁻. $^1$H NMR (D₂O) δ 9.10 (s, 1H), 8.95 (s, 1H), 8.34 (s, 1H), 6.14 (d, J=7.6 Hz, 1H), 5.40 (dd, J=4.0, 52.8 Hz, 1H), 5.31-5.22 (m, 1H), 5.22-5.04 (m, 2H), 4.84 (m, 1H), 4.61-4.353 (m, 1H), 4.61-4.53 (m, 1H), 4.41-4.34 (m, 2H), 4.28-4.24 (m, 1H). $^{31}$P NMR (D₂O) δ 57.37, 57.32. $^{19}$F NMR (D₂O) δ −109.56, −110.23, −110.30, −110.96, −196.16. Example 19B (Diastereomer B): Prep. RP-HPLC $T_R$=15.3 min. LCMS (Method D, $T_R$=1.37 min) m/z 684.2 (M-H)⁻. $^1$H NMR (D₂O) δ 9.14 (s, 1H), 9.00 (s, 1H), 8.29 (s, 1H), 6.18 (d, J=7.6 Hz, 1H), 5.61 (dd, J=4.0, 52.8 Hz, 1H), 5.30 (dd, J=6.0, 12.8 Hz, 1H), 4.95-4.74 (m, 3H), 4.74-4.42 (m, 5H), 4.24-4.20 (m, 1H). $^{31}$P NMR (D₂O) δ 57.51, 56.33. $^{19}$F NMR (D₂O) δ −109.04, −109.70, −110.52, −111.19, −198.26. Example 19C (Diastereomer C): Prep. RP-HPLC $T_R$=20.7 min. LCMS (Method D, $T_R$=1.65 min) m/z 684.2 (M-H)⁻. $^1$H NMR (D₂O) δ 9.10 (s, 1H), 8.95 (s, 1H), 8.12 (s, 1H), 6.13 (d, J=7.6 Hz, 1H), 5.39 (dd, J=4.0, 53.6 Hz, 1H), 5.30-5.17 (m, 2H), 5.10-5.05 (m, 1H), 4.99-4.89 (m, 4H), 4.49-4.36 (m, 2H), 4.21-4.18 (m, 1H). $^{31}$P NMR (D₂O) δ 56.94, 56.82. $^{19}$F NMR (D₂O) δ −109.01, −109.68, −110.13, −110.80, −196.21. Example 19D (Diastereomer D): Prep. RP-HPLC $T_R$=21.9 min. LCMS (Method D, $T_R$=1.71 min) m/z 684.2 (M-H)⁻. $^1$H NMR (D₂O) δ 9.15 (s, 1H), 9.00 (s, 1H), 8.15 (s, 1H), 6.19 (d, J=7.6 Hz, 1H), 5.57 (dd, J=4.0, 53.2 Hz, 1H), 5.35 (dd, J=6.8, 12.4 Hz, 1H), 4.95-4.80 (m, under D₂O), 4.747-4.42 (m, 5H), 4.25-4.21 (m, 1H). $^{31}$P NMR (D₂O) δ 57.12, 56.65. $^{19}$F NMR (D₂O) δ −−108.58, −109.24, −111.01, −111.67, −198.57.

Intermediate 28

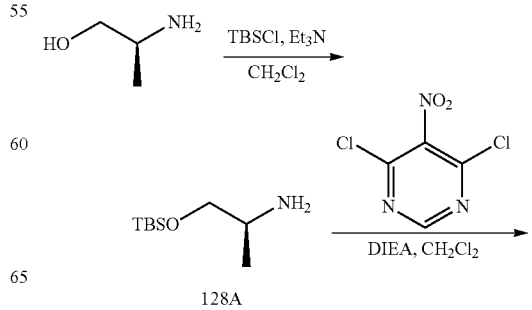

128A

Intermediate 28 was prepared according to procedures analogous to those outlined in Intermediate 1 using (S)-2-aminopropan-1-ol as starting material.

(S)-1-((tert-Butyldimethylsilyl)oxy)propan-2-amine (128A)

¹H NMR (CDCl₃) δ 3.50 (dd, J=4.4, 10.0 Hz, 1H), 2.25 (dd, J=7.2, 10.0 Hz, 1H), 2.95 (m, 1H), 1.00 (d, J=6.4 Hz, 3H), 0.89 (s, 9H), 0.05 (s, 6H)

(S)—N-(1-((tert-Butyldimethylsilyl)oxy)propan-2-yl)-6-chloro-5-nitropyrimidin-4-amine (128B)

LCMS m/z 347.3 (M+H)⁺. ¹H NMR (CDCl₃) δ 8.35 (s, 1H), 7.84 (d, J=6.8 Hz, 1H exchangeable proton), 4.45 (m, 1H), 3.74 (dd, J=3.6, 10.0 Hz, 1H), 3.63 (dd, J=3.6, 10.0 Hz, 1H), 1.28 (d, J=6.4 Hz, 3H), 0.91 (s, 9H), 0.07 (s, 3H), 0.06 (s, 3H).

(S)—N4-(1-((tert-Butyldimethylsilyl)oxy)propan-2-yl)pyrimidine-4,5-diamine (128C)

LCMS m/z 283.3 (M+H)⁺. Intermediate used without purification.

(S)-2-((4-((1-((tert-Butyldimethylsilyl)oxy)propan-2-yl)amino)pyrimidin-5-yl)amino)-2-oxoethyl acetate (128D)

LCMS m/z 383.6 (M+H)⁺. ¹H NMR (CDCl₃) δ 8.50 (s, 1H), 7.47 (br s, 1H), 8.07 (s, 1H), 5.43 (br d, J=7.6 Hz, 1H), 4.71 (s, 2H), 4.33 (m, 1H), 3.66 (m, 2H), 2.23 (s, 3H), 1.25 (d, J=6.8 Hz, 3H), 0.89 (s, 9H), 0.07 (s, 3H), 0.05 (s, 3H)

(S)-(9-(1-((tert-Butyldimethylsilyl)oxy)propan-2-yl)-9H-purin-8-yl)methyl-acetate (128E)

LCMS m/z 365.4 (M+H)⁺. ¹H NMR (CDCl₃) δ 9.08 (s, 1H), 8.91 (s, 1H), 5.44 (d, J=13.6 Hz, 1H), 5.35 (d, J=5.1 Hz, 1H), 4.65 (m, 1H), 4.31 (t, J=10.4 Hz, 1H), 3.89 (dd, J=10.4, 4.4 Hz, 1H), 2.17 (s, 3H), 1.76 (d, J=7.2 Hz, 3H), 0.65 (s, 9H), −0.19 (s, 3H), −0.37 (s, 3H).

(S)-(9-(1-((tert-Butyldimethylsilyl)oxy)propan-2-yl)-9H-purin-8-yl)methanol (128F)

LCMS m/z 323.4 (M+H)⁺. Intermediate used without purification.

(S)-8-((Bis(4-methoxyphenyl)(phenyl)methoxy)methyl)-9-(1-((tert-butyldimethylsilyl)oxy)propan-2-yl)-9H-purine (128G)

LCMS (Method E) m/z 625.6 (M+H)⁺. ¹H NMR (CDCl₃) δ 9.09 (s, 1H), 8.92 (s, 1H), 7.47-7.23 (comp, 9H), 6.86 (comp, 4H), 4.55 (d, J=11.6 Hz, 1H), 4.45 (m, 1H), 4.33 (d, J=11.6 Hz, 1H), 4.18 (t, J=10.4 Hz, 1H), 3.79 (s, 3H), 3.78 (s, 3H), 3.65 (m, 1H), 1.69 (d, J=7.2 Hz, 3H), 0.52 (s, 9H), −0.28 (s, 3H), −0.54 (s, 3H).

(S)-2-(8-((Bis(4-methoxyphenyl)(phenyl)methoxy)methyl)-9H-purin-9-yl)propan-1-ol (128H)

LCMS m/z 511.5 (M+H)+. $^1$H NMR (CDCl$_3$) δ 9.10 (s, 1H), 8.90 (s, 1H), 7.50-7.23 (comp, 9H), 6.89-6.86 (comp, 4H), 4.47 (d, J=3.6 Hz, 2H), 4.41 (m, 1H), 3.97 (m, 2H), 3.80 (s, 6H), 1.47 (d, J=6.8 Hz, 3H).

(S)-2-(8-((Bis(4-methoxyphenyl)(phenyl)methoxy)methyl)-9H-purin-9-yl)propyl (2-cyanoethyl) diisopropylphosphoramidite (Intermediate 28)

LCMS m/z (M+H+OH-N,N-diisopropylamino)+628.4. $^1$H NMR (CDCl$_3$) δ 9.07 (s, 0.5H), 9.06 (s, 0.5H), 8.91 (s, 0.5H), 8.90 (s, 0.5H), 4.57 (m, 2H), 4.37 (m, 2H), 3.79-3.70 (m, 1H), 3.51 (m, 1H), 3.31-3.18 (comp, 3H), 2.44 (t, J=6.4 Hz, 1H), 2.26 (t, J=6.4 Hz, 1H), 1.71 (m, 3H), 1.02 (s, 1.5H), 1.00 (s, 1.5H), 0.98 (s, 1.5H), 0.96 (s, 1.5H), 0.93 (s, 1.5H), 0.92 (s, 1.5H), 0.68 (s, 1.5H), 0.67 (s, 1.5H). $^{31}$P NMR (CDCl$_3$) δ 148.02, 147.45.

Example 20

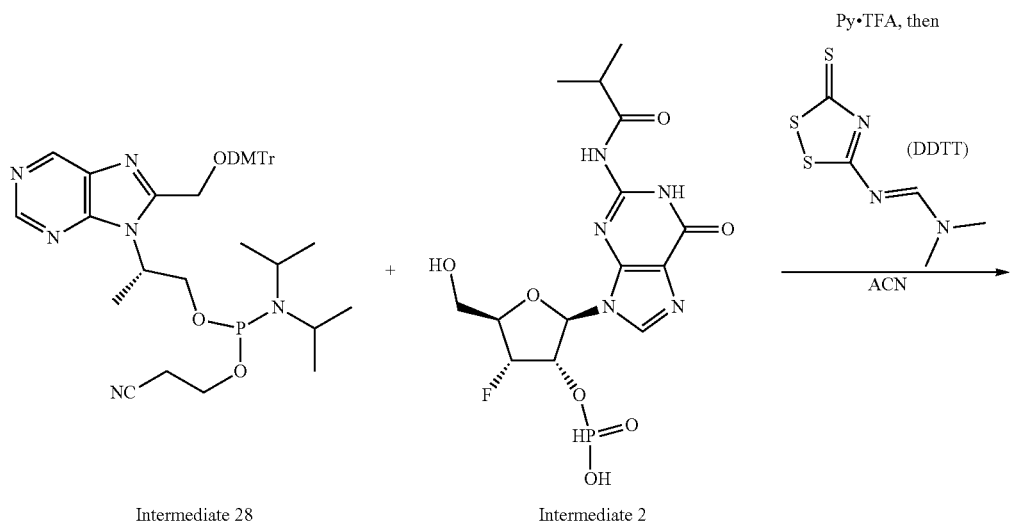

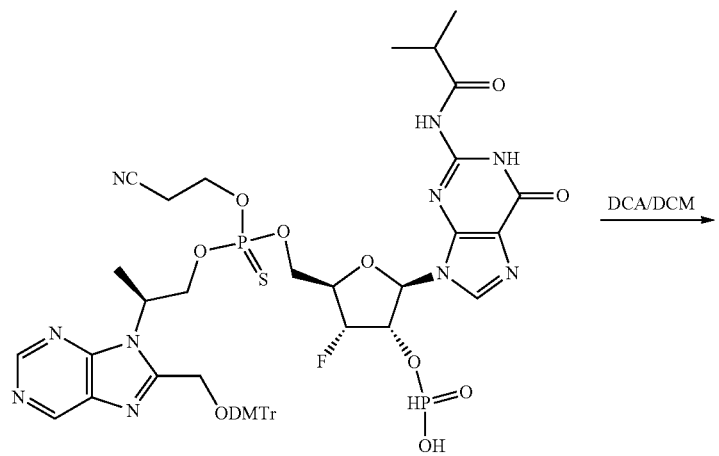

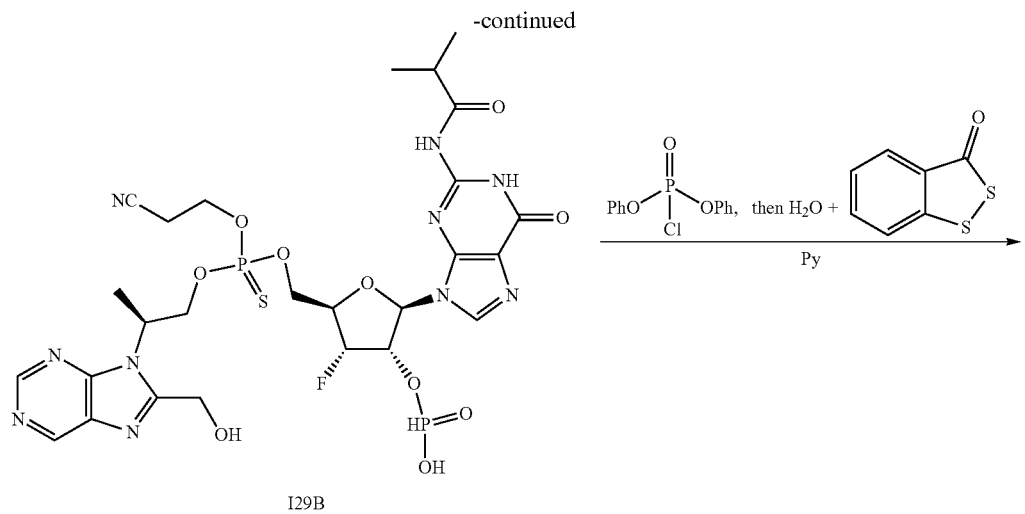

I29B

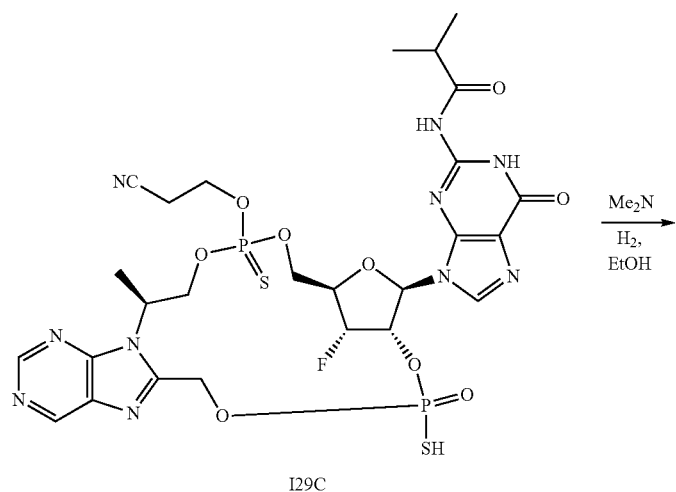

I29C

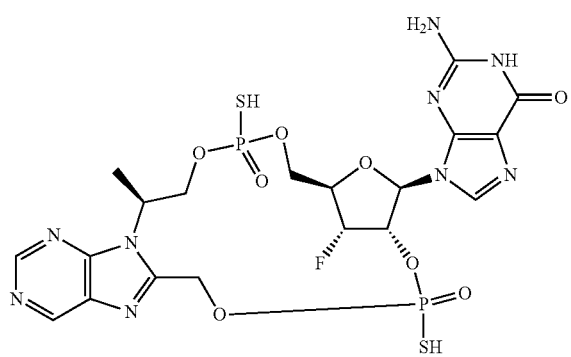

Example 20

(1S,15S,21R,23R,24R)-23-(2-Amino-6-oxo-6,9-dihydro-1H-purin-9-yl)-24-fluoro-15-methyl-3,18-disulfanyl-2,4,17,19,22-pentaoxa-7,10,12,14-tetraaza-3lambda5,18lambda5-diphosphatetracyclo[19.2.1.06,14.08,13]tetracosa-6,8,10,12-tetraene-3,18-dione (Example 20)

Example 20 diastereomers were prepared according to procedures analogous to those outlined in Example 1. Example 20 diastereomers (Diastereomers A-D) were purified by prep. RP-HPLC (Sunfire Prep C18, 5 μm, 19×100 mm column eluting with 0-10% ACN/H$_2$O containing 0.04% NH$_4$HCO$_3$, Flow rate=10 mL/min). Example 20D (Diastereomer D): Prep. RP-HPLC T$_R$=28.0 min. LCMS (Method D, T$_R$=1.30 min) m/z 648.1 (M−2H)$^-$. $^1$H NMR (D$_2$O) δ 9.03 (s, 1H), 8.89 (s, 1H), 7.66 (s, 1H), 6.01 (d, J=8.0 Hz, 1H), 5.44 (dd, J=4.0 and 52.8 Hz, 1H), 5.31 (dd, J=8.4 and 12.4 Hz, 1H), 5.01-4.85 (comp, 2H), 4.70 (comp, 2H, under water peak), 4.58-4.38 (comp, 3H), 4.04 (m, 1H), 1.60 (d, J=6.8 Hz, 3H). $^{31}$P NMR (D$_2$O) δ 56.13, 55.54. $^{19}$F NMR (D$_2$O) 8-198.61.

Intermediate 30

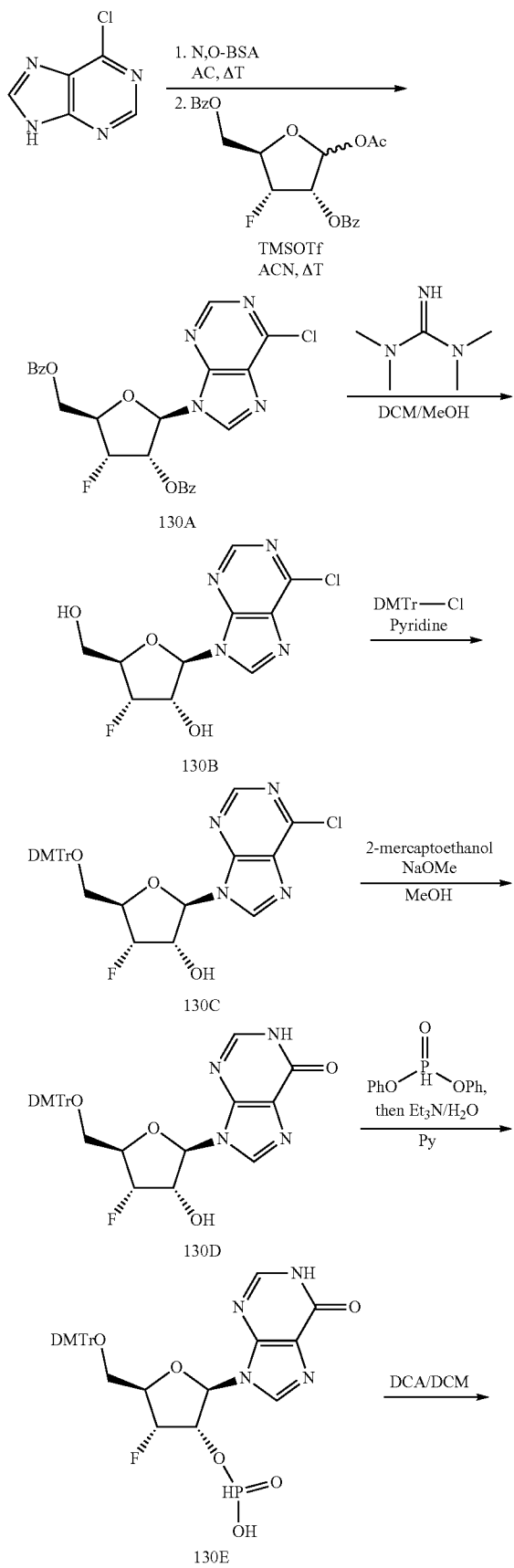

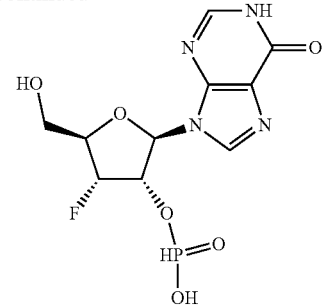

Intermediate 30

(((2R,3R,4S,5R)-4-(Benzoyloxy)-5-(6-chloro-9H-purin-9-yl)-3-fluorotetrahydrofuran-2-yl)methyl benzoate (I30A)

The 6-chloropurine (768 mg, 5.0 mmol) was dissolved in ACN (27 mL) and BSA (2.43 mL, 20.0 mmol) was added. The mixture was refluxed for 3 hrs and allowed to cool to RT whereupon a solution of ((2R,3R,4S)-5-acetoxy-4-(benzoyloxy)-3-fluorotetrahydrofuran-2-yl)methyl benzoate (1.0 g, 2.48 mmol) in ACN (17 mL) was added followed by TMSOTf (1.80 mL, 20.0 mmol). The mixture was refluxed for 3 hrs, cooled to RT and then stirred. The mixture was diluted with DCM, washed with sat. aq. NaHCO$_3$, dried over Na$_2$SO$_4$ and concentrated under reduced pressure. The residue was purified by silica gel chromatography (0-100% EtOAc/DCM) to give I30A (760 mg, 62%) as white foam. LCMS m/z 497.2 (M+H)$^+$. $^1$H NMR (CDCl$_3$) δ 8.49 (s, 1H), 8.24 (s, 1H), 8.10 (m, 2H), 8.03 (m, 2H), 7.62 (m, 2H), 7.48 (m, 4H), 6.46 (d, J=6.0 Hz, 1H), 6.39-6.32 (comp, 1H), 5.78 (ddd, J=53.2, 4.4, 2.0 Hz, 1H), 4.898-4.799 (comp, 2H), 4.62 (m, 1H). $^{19}$F NMR (CDCl$_3$) δ −199.25.

(2R,3S,4S,5R)-2-(6-Chloro-9H-purin-9-yl)-4-fluoro-5-(hydroxymethyl)tetrahydrofuran-3-ol (I30B)

To a solution of I30A (720 mg, 1.45 mmol) in DCM/MeOH (1:1, 15 mL) was added 1,1,3,3-tetramethylguanidine (182 µL, 1.45 mmol). The reaction mixture was stirred at RT for 2 hrs, and then quenched with Amberlyst resin H$^+$. The resin was filtered off and the filtrate was concentrated under reduce pressure. The crude product was purified by RP-MPLC (0-100% ACN/H$_2$O) followed by co-evaporation with acetonitrile to afford a white solid I30B (330 mg, 79%). LCMS m/z 289.1 (M+H)$^+$. $^1$H NMR (CD$_3$OD) δ 8.84 (s, 1H), 8.78 (s, 1H), 6.22 (d, J=6.8 Hz, 1H), 5.16 (dd, J=4.0, 53.6 Hz, 1H), 5.00 (ddd, J=23.6, 7.2, 4.0 Hz, 1H), 4.50-4.413 (comp, 2H), 3.85 (m, 2H). $^{19}$F NMR (CD$_3$OD) δ −200.61.

(2R,3S,4S,5R)-5-((Bis(4-methoxyphenyl)(phenyl)methoxy)methyl)-2-(6-chloro-9H-purin-9-yl)-4-fluorotetrahydrofuran-3-ol (I30C)

I30B (330 mg, 1.14 mmol) is co-evaporated 2 times with pyridine prior to the reaction. A mixture of I30B and DMTrCl (407 mg, 1.20 mmol) in pyridine (15 mL) was stirred at RT overnight. The resulting mixture was concentrated under reduced pressure. The residue was filtered by silica gel chromatography (0-10% MeOH/DCM) to give I30C (650 mg, quant) as a yellow foam. This material was used in subsequent reactions without additional purification. LCMS m/z 592.2 (M+H)⁺.

9-((2R,3S,4S,5R)-5-((Bis(4-methoxyphenyl)(phenyl) methoxy)methyl)-4-fluoro-3-hydroxytetrahydro-furan-2-yl)-1H-purin-6(9H)-one (I30D)

To a solution of I30C (690 mg, 1.17 mmol) in methanol (45 mL) was added 2-mercaptoethanol (164 µL, 2.34 mmol), and then MeONa (189 mg, 3.51 mmol). The reaction mixture was refluxed overnight, allowed to cool to RT and concentrated under reduced pressure. The residue was purified by silica gel chromatography (0-10% MeOH/DCM) to give I30D (350 mg, 52%) as a white solid. LCMS m/z 573.3 (M+H)⁺. ¹H NMR (CD₃OD) δ 8.16 (s, 1H), 7.87 (s, 1H), 7.42 (d, J=7.2 Hz, 2H), 7.32-7.21 (comp, 7H), 6.83 (d, J=8.8 Hz, 4H), 6.05 (d, J=7.2 Hz, 1H), 5.22-5.06 (comp, 2H), 4.45 (td, J=4.0, 26.4 Hz, 1H), 3.78 (s, 6H), 3.43 (m, 2H). ¹⁹F NMR (CD₃OD) δ −200.03.

(2R,3S,4R,5R)-5-((Bis(4-methoxyphenyl)(phenyl) methoxy)methyl)-4-fluoro-2-(6-oxo-1H-purin-9 (6H)-yl)tetrahydrofuran-3-yl hydrogen phosphonate (I30E)

To a solution of I30D (385 mg, 0.67 mmol) in pyridine (4 mL) was added diphenyl phosphite (386 µL, 2.01 mmol). The reaction mixture was stirred at RT for 20 min, and then cooled in an ice/acetone bath, whereupon Et₃N (672 µL) and H₂O (672 µL) were added. The bath was removed and the reaction mixture was stirred at RT for 40 min, and concentrated under reduced pressure and the residue was purified by RP-MPLC (C18, 0-100% ACN/H₂O) to give I30E (255 mg, 60%) containing trace triethylammonium salt. This material was used "as is" in subsequent transformations. LCMS m/z 637.3 (M+H)⁺. ¹H NMR (CD₃OD) δ 8.20 (s, 1H), 7.82 (s, 1H), 7.43 (m, 2H), 7.34-7.14 (comp, 7H), 6.86-6.76 (comp, 4H), 6.74 (dd, J=630.0 Hz, 1.2 Hz, 1H), 6.21 (d, J=7.2 Hz, 1H), 5.79-5.69 (m, 1H), 5.43 (ddd, J=53.6, 4.4, 1.6 Hz, 1H), 4.49 (app dt, J=25.6, 2.4 Hz, 1H), 3.79 (s, 3H), 3.78 (s, 3H), 3.52-3.49 (m, 1H), 3.42-3.38 (m, 1H), 3.19 (q, J=7.6 Hz, 1H), 1.30 (t, J=7.6 Hz, 3H). ³¹P NMR (CD₃OD) δ 2.69.

(2R,3S,4R,5R)-4-Fluoro-5-(hydroxymethyl)-2-(6-oxo-1H-purin-9(6H)-yl)tetrahydrofuran-3-yl hydrogen phosphonate (Intermediate 30)

To a suspension of I30E (255 mg, 0.4 mmol) in DCM (5 mL) was added H₂O (72 µl, 4.0 mmol) followed by a solution of DCA 6% in DCM (5 mL). The reaction mixture was stirred and sonicated occasionally for 20 min at RT, and then TES (10 mL) was added. After stirring and sonicating for an additional 1.5 hrs, pyridine (2 mL) was added. The mixture was concentrated under reduced pressure, and the residue was purified by silica gel chromatography (0-100% MeOH/DCM) to give Intermediate 30 (85 mg, 74%) as a white solid. LCMS m/z 333.1 (M–H)⁻. ¹H NMR (CD₃OD) δ 8.39 (s, 1H), 8.08 (s, 1H), 6.63 (dd, J=629.6 Hz, 1.2 Hz, 1H), 6.21 (d, J=8.0 Hz, 1H), 5.48-5.39 (comp, 2H), 5.31 (dd, J=4.0, 52.0 Hz, 1H), 4.45 (td, J=2.4, 26.4 Hz, 1H), 3.83 (m, 2H), 3.32 (m, 1H). ³¹P NMR (CD₃OD) δ 2.25.

Example 21

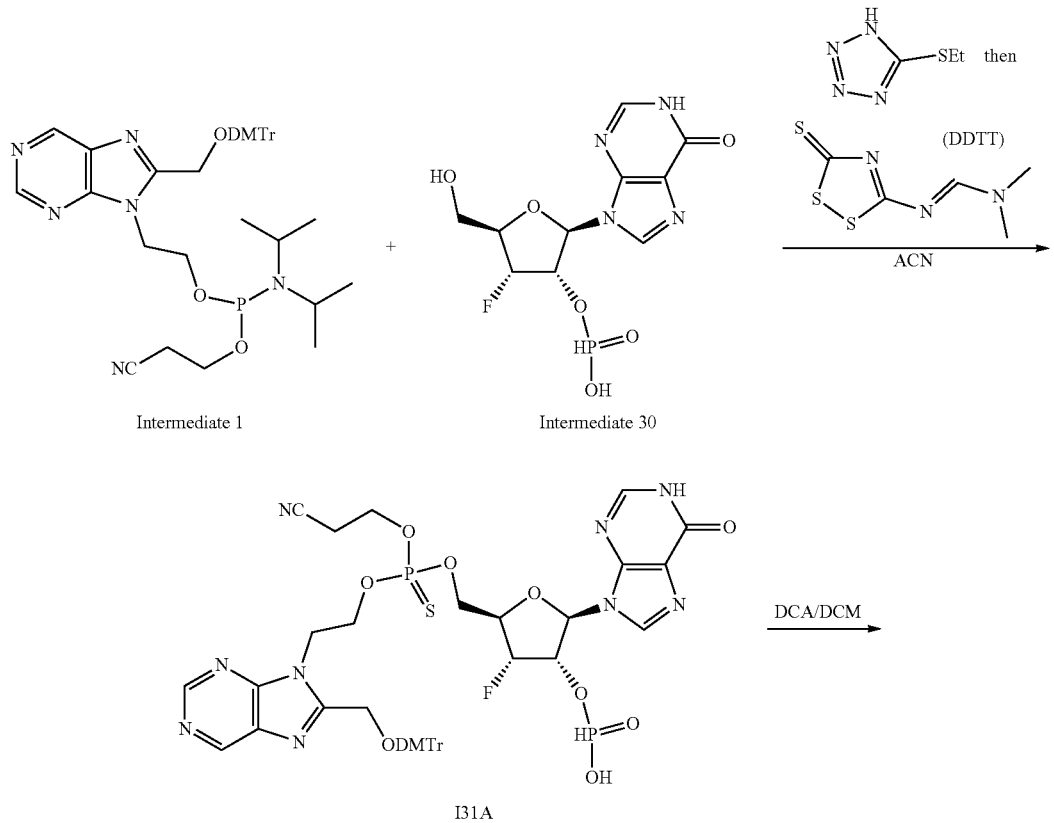

I31A

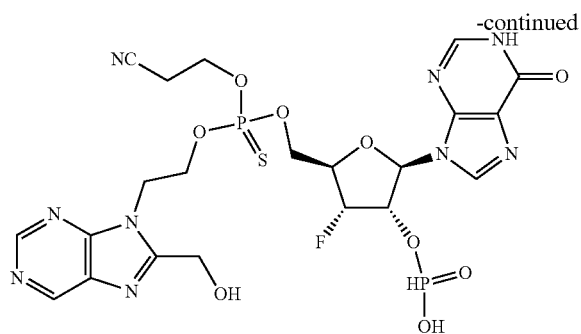

I31B

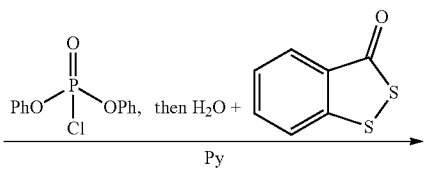

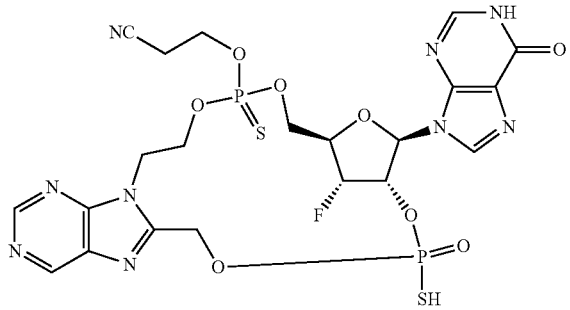

I31C

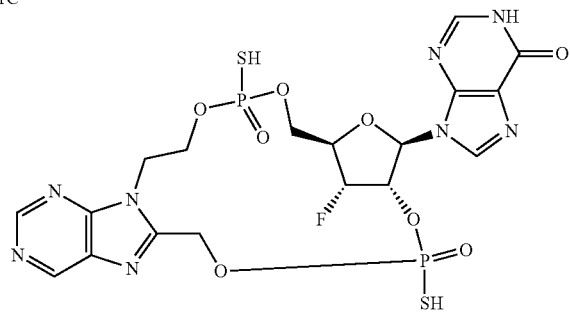

Example 21

(1S,21R,23R,24R)-24-Fluoro-23-(6-oxo-6,9-dihydro-1H-purin-9-yl)-3,18-disulfanyl-2,4,17,19,22-pentaoxa-7,10,12,14-tetraaza-3lambda5,8lambda5-diphosphatetracyclo[19.2.1.0⁶,¹⁴.0⁸,¹³]tetracosa-6,8,10,12-tetraene-3,18-dione (Example 21)

Example 21 diastereomers (Diastereomers A-D) were prepared according to procedures analogous to those outlined in Example 1. Example 21 diastereomers (Diasterepmers A-D) were purified by prep. RP-HPLC (Waters, X Bridge C18, 5 μm, 19×150 mm column eluting with 1-5% ACN/H$_2$O containing 0.04% NH$_4$HCO$_3$, Flow rate=10 mL/min). Example 21 B (Diastereomer B): Prep. RP-HPLC: T$_R$=21.9 min. LCMS (Method D, T$_R$=1.18 min) m/z 619.0 (M−H)⁻. $^1$H NMR (D$_2$O) δ 9.21 (s, 1H), 9.09 (s, 1H), 8.28 (s, 1H), 8.24 (s, 1H), 6.36 (d, J=7.6 Hz, 1H), 5.60 (dd, J=52.8, 3.6 Hz, 1H), 5.44 (dd, J=12.8, 7.6 Hz, 1H), 5.09-4.96 (m, 1H), 4.89-4.84 (comp, 2H), 4.75-4.72 (comp, 1H), 4.57 (m, 1H), 4.40 (m, 1H), 4.22 (m, 2H). $^{31}$P NMR (D$_2$O) δ 55.66, 55.59. $^{19}$F NMR (D$_2$O) δ −198.20. Example 21C (Diastereomer C): Prep. RP-HPLC T$_R$=34.9 min. LCMS (Method D, T$_R$=1.20 min) m/z 619.0 (M−H)⁻. $^1$H NMR (D$_2$O) δ 9.13 (d, J=2.0 Hz, 1H), 8.96 (d, J=2.0 Hz, 1H), 8.12 (d, J=2.0 Hz, 1H), 7.87 (d, J=2.4 Hz, 1H), 6.24 (d, J=7.6 Hz, 1H), 5.50 (m, 1H), 5.32 (m, 2H), 4.74 (comp, 2H), 4.70 (comp, 2H), 4.49-4.41 (comp, 2H), 4.25 (m, 1H), 4.08 (m, 1H). $^{31}$P NMR (D$_2$O) δ 55.44, 54.91. $^{19}$F NMR (D$_2$O) δ −198.47. Example 21D (Diastereomer D): Prep. RP-HPLC T$_R$=37.8 min. LCMS (Method D, T$_R$=1.24 min) m/z 619.0 (M−H)⁻. $^1$H NMR (D$_2$O) δ 9.06 (s, 1H), 8.95 (s, 1H), 8.16 (s, 1H), 8.12 (s, 1H), 6.26 (d, J=7.2 Hz, 1H), 5.15 (comp, 2H), 5.02 (m, 1H), 4.69-4.66 (comp, 2H), 4.58-4.54 (m, 1H), 4.43 (comp, 2H), 4.21 (m, 1H), 4.01 (m, 2H). $^{31}$P NMR (D$_2$O) δ 57.15, 56.11. $^{19}$F NMR (D$_2$O) δ −196.96.

Intermediate 32

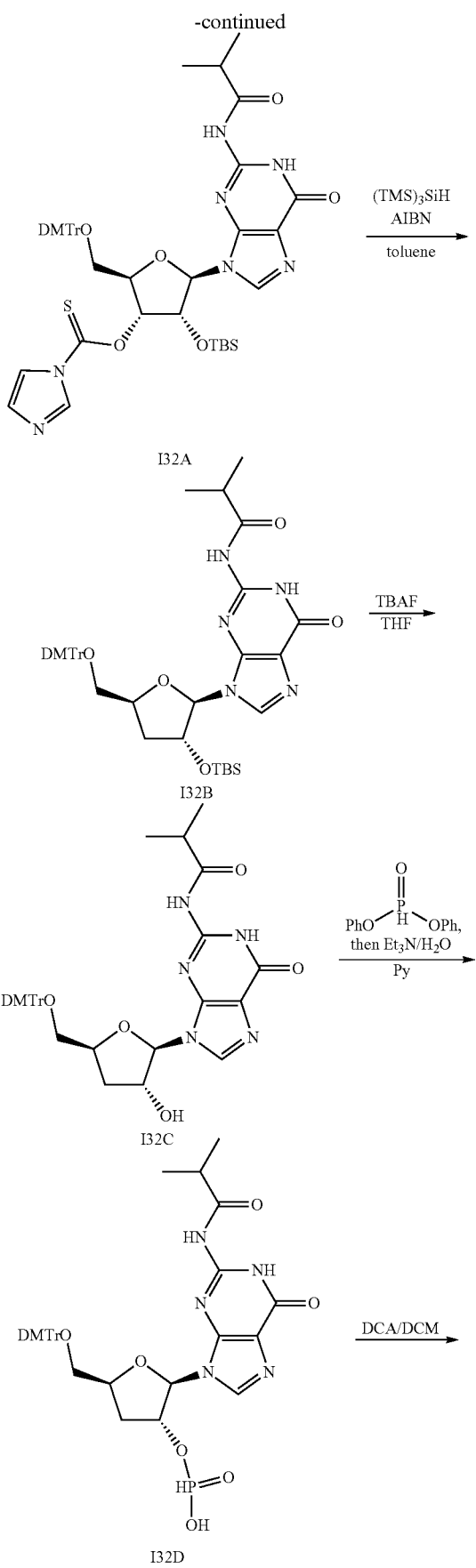

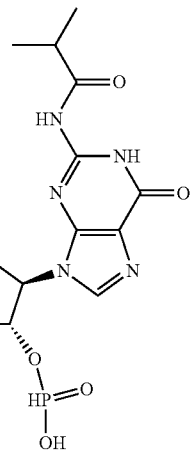

Intermediate 32

O-((2R,3R,4R,5R)-2-((Bis(4-methoxyphenyl)(phenyl)methoxy)methyl)-4-((tert-butyldimethylsilyl)oxy)-5-(2-isobutyramido-6-oxo-1H-purin-9(6H)-yl)tetrahydrofuran-3-yl) 1H-imidazole-1-carbothioate (I32A)

To a stirred solution of N-(9-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-6-oxo-6,9-dihydro-1H-purin-2-yl)isobutyramide (4.62 g, 6.00 mmol) in MeCN (100 mL) was added 1,1'-thiocarbonyldiimidazole (4.30 g, 24.1 mmol) as a solid, portion-wise. To this mixture was added pyridine (0.56 mL, 6.90 mmol) dissolved in ACN (12 mL) via syringe pump over 6 hrs at RT. After 24 hrs, an additional portion of 1,1'-thiocarbonyldiimidazole (0.24 g, 1.35 mmol) was added and the mixture stirred for another 2 hrs then concentrated under reduced pressure. The residue was purified by silica gel chromatography (0.5-5% MeOH/DCM) to give ~9:1 ($^1$H NMR estimate) mixture of I32A and an isomer [O-((2R,3R,4R,5R)-5-((bis(4-methoxyphenyl)(phenyl)methoxy)methyl)-4-((tert-butyldimethylsilyl)oxy)-2-(2-isobutyramido-6-oxo-1H-purin-9(6H)-yl)tetrahydrofuran-3-yl) 1H-imidazole-1-carbothioate] (4.87 g, 92%) as a white solid. This material was used "as is" in subsequent transformations. For I32A: LCMS m/z 880.3 (M+H)$^+$. $^1$H NMR (CD$_3$OD) δ 8.52-8.51 (m, 1H), 8.15 (s, 1H), 7.85-7.83 (m, 1H), 7.51-7.45 (m, 2H), 7.40-7.33 (m, 4H), 7.28 (t, J=7.4 Hz, 2H), 7.22 (t, J=7.2 Hz, 1H), 7.11 (dd, J=1.7, 0.9 Hz, 1H), 6.85 (dd, J=8.9, 0.9 Hz, 4H), 6.19 (dd, J=5.4, 1.5 Hz, 1H), 6.13 (d, J=7.4 Hz, 1H), 5.16 (dd, J=7.3, 5.4 Hz, 1H), 4.50 (d, J=1.5 Hz, 1H), 3.75 (s, 3H), 3.75 (s, 3H), 3.58 (qd, J=10.9, 3.1 Hz, 2H), 2.71 (hept, J=6.9 Hz, 1H), 1.13 (d, J=6.8 Hz, 3H), 1.09 (d, J=6.9 Hz, 3H), 0.67 (s, 9H), 0.06 (s, 3H), −0.31 (s, 3H).

N-(9-((2R,3R,5S)-5-((Bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)isobutyramide (I32B)

To a solution of I32A (5.03 g, 5.72 mmol) in toluene (30 mL) at RT was added AIBN (0.22 g, 1.3 mmol) and then tris(trimethylsilyl)silane (3.0 mL, 9.8 mmol). The resulting mixture was heated at 85° C. for 3 hrs and then additional AIBN (0.12 g, 0.74 mmol) and tris(trimethylsilyl)silane (1.4 mL, 4.6 mmol) were added. After heating for an additional 2 hrs the mixture was concentrated to a residue and then absorbed on silica (10 g) and purified by silica gel chromatography (0-100% EA/hexanes) to give I32B (1.91 g, 39%) as a white solid. LCMS m/z 754.5 (M+H)+. $^1$H NMR (CDCl$_3$) δ 11.88 (s, 1H), 7.79 (s, 1H), 7.61 (s, 1H), 7.55-7.49 (m, 2H), 7.38 (dd, J=8.9, 2.1 Hz, 4H), 7.25 (dd, J=10.3, 4.3 Hz, 2H), 7.22-7.17 (m, 1H), 6.89-6.73 (m, 4H), 5.67 (d, J=3.6 Hz, 1H), 4.83 (dd, J=8.9, 5.1 Hz, 1H), 4.57-4.48 (m, 1H), 4.10 (dd, J=14.3, 7.1 Hz, 1H), 3.76 (s, 3H), 3.75 (s, 3H), 3.44 (dd, J=10.6, 2.4 Hz, 1H), 3.10 (dd, J=10.6, 4.3 Hz, 1H), 2.31-2.20 (m, 1H), 2.01-1.89 (m, 2H), 1.24 (t, J=7.1 Hz, 2H), 1.04 (d, J=6.9 Hz, 3H), 0.84 (s, 9H), 0.02 (s, 3H), −0.01 (s, 3H).

N-(9-((2R,3R,5S)-5-((Bis(4-methoxyphenyl)(phenyl)methoxy)methyl)-3-hydroxytetrahydrofuran-2-yl)-6-oxo-6,9-dihydro-1H-purin-2-yl)isobutyramide (I32C)

To a solution of I32B (1.91 g, 2.53 mmol) in THF (30 mL) at RT was added TBAF (1.0 M in THF, 3.04 mL, 3.0 mmol) slowly. The resulting mixture was stirred at RT overnight and then concentrated under reduced pressure. The residue was purified using RP-MPLC (C18, 45-55% ACN/H$_2$O containing 0.04% NH$_4$HCO$_3$) to give I32C (1.20 g, 74%) as a white solid. LCMS m/z 640.2 (M+H)+. $^1$H NMR (CDCl$_3$) δ 12.09 (br s, 1H), 9.54 (very br s, 1H), 7.73 (s, 1H), 7.42 (d, J=7.6 Hz, 2H), 7.31 (dd, J=8.4, 5.5 Hz, 4H), 7.21 (t, J=7.5 Hz, 2H), 7.13 (t, J=7.2 Hz, 1H), 6.77 (dd, J=8.6, 6.3 Hz, 4H), 5.74 (d, J=3.2 Hz, 1H), 5.00 (s, 1H), 4.50 (s, 1H), 3.72 (s, 3H), 3.72 (s, 3H), 3.33 (dd, J=10.3, 2.3 Hz, 1H), 3.12 (dd, J=10.2, 4.1 Hz, 1H), 2.37-2.21 (m, 2H), 2.14-2.01 (m, 2H), 1.05 (d, J=6.7 Hz, 3H), 0.94 (d, J=6.5 Hz, 3H).

(2R,3R,5S)-5-((Bis(4-methoxyphenyl)(phenyl)methoxy)methyl)-2-(2-isobutyramido-6-oxo-1H-purin-9(6H)-yl)tetrahydrofuran-3-yl hydrogen phosphonate (I32D)

Starting material, I32C (1.65 g, 2.58 mmol), was dissolved in pyridine (20 mL) and to this solution was added diphenyl phosphite (3.00 mL, 15.6 mmol) dropwise. The reaction mixture was stirred at RT for 4 hrs and then cooled in an ice/acetone bath, whereupon TEA (4.7 mL) and then H$_2$O (4.7 mL) were added dropwise. The bath was removed and the reaction mixture was stirred at RT for 1 hr and then concentrated under reduced pressure. The residue was purified using RP-MPLC (C18, 5-80% ACN/H$_2$O) to give I32D (1.59 g, as an admixture; 12% triethylamine by weight, 88% product by weight assigned by $^1$H NMR, 77%) as a white solid. This material was used "as is" in subsequent transformations. LCMS m/z 704.2 (M+H)+.

(2R,3R,5S)-5-(Hydroxymethyl)-2-(2-isobutyramido-6-oxo-1H-purin-9(6H)-yl)tetrahydrofuran-3-yl hydrogen phosphonate (Intermediate 32)

To a suspension of I32D (1.40 g, 88% by weight, 1.75 mmol) in DCM (60 mL) was added H$_2$O (0.36 mL, 20 mmol) followed by a solution of DCA (1.47 mL, 17.9 mmol) in DCM (30 mL). The reaction mixture was stirred overnight at RT and then TES (23 mL) was added. After stirring for an additional 1 hrs, pyridine (3.4 mL) was added and stirred 1 hr further. The mixture was concentrated under reduced pressure and the residue was purified by silica gel chromatography (0-80% MeOH/DCM) to give Intermediate 32 (0.75 g, as a salt; 4% triethyl amine by weight, 8% pyridine by weight, 89% product by weight assigned by $^1$H NMR, 95%) as a white solid. LCMS m/z 402.1 (M+H). $^1$H NMR (CD$_3$OD) δ 8.60 (s, 1H), 6.88 (d, J=632.5 Hz, 1H), 6.14 (s, 1H), 5.17 (dd, J=9.2, 4.4 Hz, 1H), 4.56 (dtd, J=8.2, 5.4, 2.9 Hz, 1H), 3.96 (dd, J=12.4, 2.6 Hz, 1H), 3.71 (dd, J=12.4, 3.4 Hz, 1H), 2.73 (hept, J=6.9 Hz, 1H), 2.33 (ddd, J=15.1, 10.6, 4.8 Hz, 1H), 2.15 (dd, J=13.6, 5.2 Hz, 1H), 1.23 (d, J=6.9 Hz, 3H), 1.23 (d, J=6.8 Hz, 3H) [pyridine, 2CH 8.86 (d, J=5.2 Hz, 0.89H), CH 8.65-8.56 (m, 0.4H), 2CH 8.05 (dd, J=7.7, 6.6 Hz, 0.86H)][triethyl amine, 3CH$_2$ 3.20 (q, J=7.3 Hz, 1.04H), 3CH$_3$ 1.30 (t, J=7.3 Hz, 1.56)]. $^{31}$P NMR (CD$_3$OD) δ 2.75.

Example 22

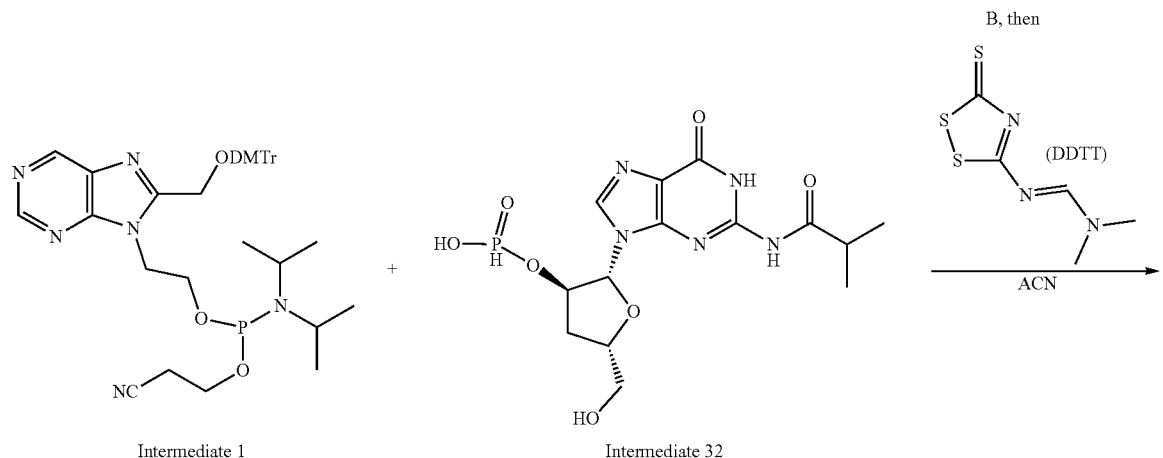

Intermediate 1     Intermediate 32

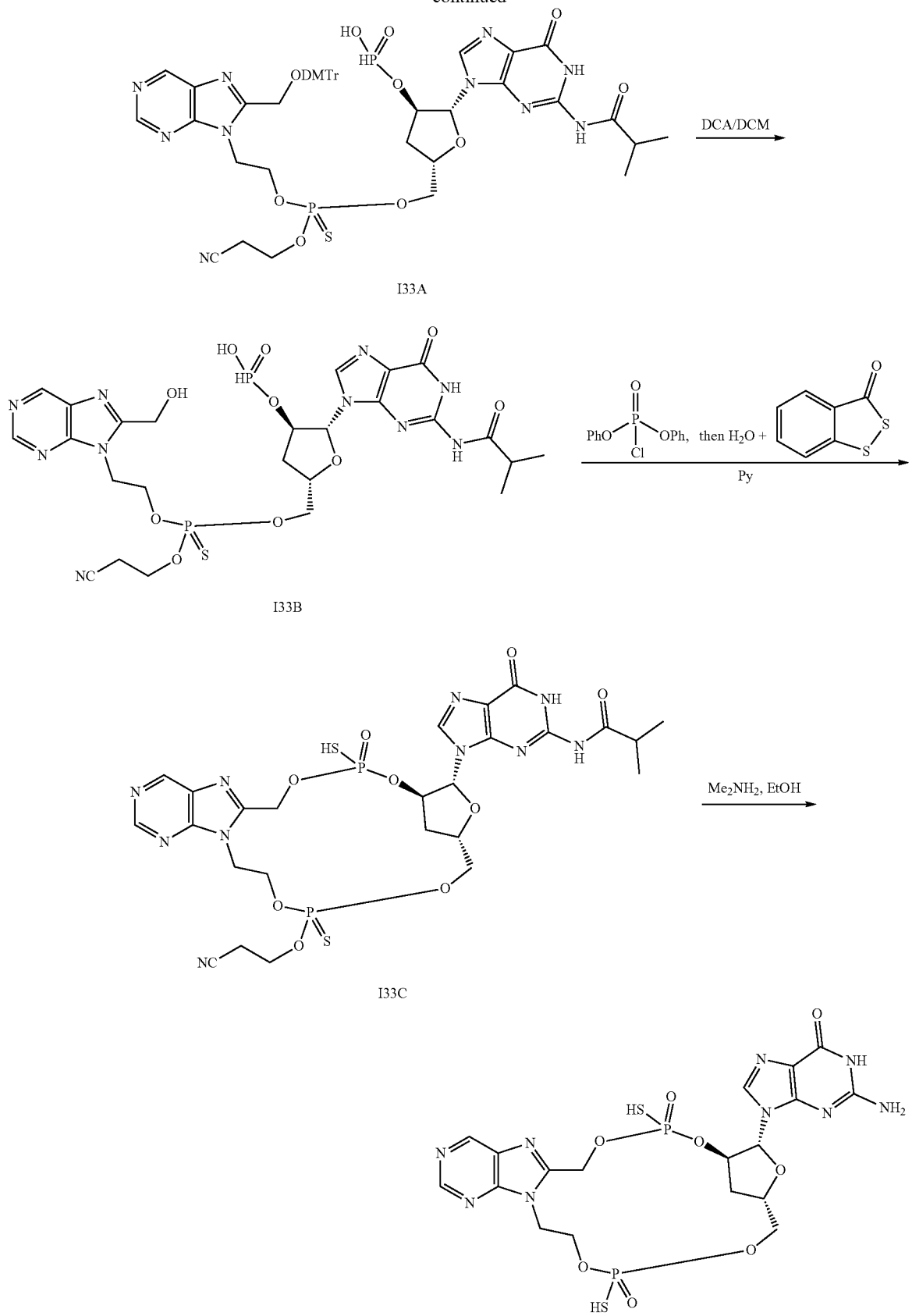

(1R,21S,23R)-23-(2-Amino-6-oxo-6,9-dihydro-1H-purin-9-yl)-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 22)

Example 22 diastereomers (Diastereomers A-D) were prepared according to procedures analogous to those outlined in Example 1.

(2R,3R,5S)-5-((((2-(8-((Bis(4-methoxyphenyl)(phenyl)methoxy)methyl)-9H-purin-9-yl)ethoxy)(2-cyanoethoxy)phosphorothioyl)oxy)methyl)-2-(2-isobutyramido-6-oxo-1H-purin-9(6H)-yl)tetrahydrofuran-3-yl hydrogen phosphonate (I33A)

LCMS ($T_R$=1.22 min) m/z 1027.2 (M−H)⁻. ³¹P NMR ($D_2O$) δ 68.27, 68.13, 2.57, 2.54.

(2R,3R,5S)-5-((((2-Cyanoethoxy)(2-(8-(hydroxymethyl)-9H-purin-9-yl)ethoxy)phosphorothioyl)oxy)methyl)-2-(2-isobutyramido-6-oxo-1H-purin-9(6H)-yl)tetrahydrofuran-3-yl hydrogen phosphonate (I33B)

LCMS ($T_R$=0.69 min) m/z 727.2 (M+H ³¹P NMR ($D_2O$) δ 68.38, 68.35, 2.60.

N-{9-[(1R,21S,23R)-18-(2-Cyanoethoxy)-3-oxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraen-23-yl]-6-oxo-6,9-dihydro-1H-purin-2-yl}-2-methylpropan amide (I33C)

LCMS ($T_R$=0.81 and 0.83 min) m/z 741.2 (M+H). ³¹P NMR ($D_2O$) δ 69.49, 68.81, 66.06, 65.74, 59.50, 58.62, 57.35, 56.52.

Example 22 diastereomers (Diasterepmers A-D) were purified by reverse phase prep. RP-HPLC (Waters, X Bridge C18, 5 μm, 19×150 mm column eluting with 2-7% ACN/$H_2O$ containing 0.04% $NH_4HCO_3$, Flow rate=10 mL/min). Example 22 Disatereomer D was purified again by reverse phase prep. RP-HPLC Waters, X Bridge C18, 5 μm, 19×150 mm column eluting with 3-10% ACN/$H_2O$ containing 0.04% $NH_4HCO_3$, Flow rate=7 mL/min). Example 22A (Diastereomer A): Prep. RP-HPLC $T_R$=13.8 min. LCMS (Method D, $T_R$=1.08 min) m/z 616.1 (M−H)⁻. ¹H NMR ($D_2O$) δ 9.06 (s, 1H), 8.95 (s, 1H), 7.80 (s, 1H), 5.84 (d, J=6.8 Hz, 1H), 5.40 (dd, J=7.6, 12.8 Hz, 1H), 5.04-4.95 (m, 1H), 4.91 (dd, J=4.0, 12.8 Hz, 1H), 4.69-4.51 (comp, 3H), 4.46 (m, 1H), 4.16 (m, 2H), 3.87 (m, 1H), 2.49 (m, 2H). ³¹P NMR ($D_2O$) δ 55.28, 55.22. Example 22B (Diastereomer B with 34% A): Prep. RP-HPLC $T_R$=14.9 min. LCMS (Method D, $T_R$=1.06 and 1.08 min) m/z 616.0 (M−H)⁻. ¹H NMR ($D_2O$) δ 9.09 and 9.06 (2s, 1H), 8.98 and 8.97 (2s, 1H), 8.11 and 7.89 (2s, 1H), 5.86 and 5.85 (2d, J=6.4 Hz and 6.4 Hz, 1H), 5.44-5.19 (comp, 2H), 5.17-4.84 (comp, 2H), 4.71-4.37 (comp, 4H), 4.20-3.74 (comp, 2H), 2.58-2.04 (comp, 2H). ³¹P NMR ($D_2O$) δ 56.82 (B), 55.57 (B), 55.31 (A), 55.28 (A). Example 22C (Diastereomer C): Prep. RP-HPLC $T_R$=24.2 min. LCMS (Method D, $T_R$=1.18 min) m/z 616.0 (M−H)⁻. ¹H NMR ($D_2O$) δ 9.01 (s, 1H), 8.95 (s, 1H), 7.78 (s, 1H), 5.82 (d, J=7.2 Hz, 1H), 5.30-5.16 (comp, 2H), 5.06 (m, 1H), 4.74-4.68 (m, 1H), 4.62-4.53 (comp, 2H), 4.45 (m, 2H), 3.96 (m, 2H), 2.48-2.23 (m, 2H). ³¹P NMR ($D_2O$) δ 56.63, 55.65. Example 22D (Diastereomer D): Prep.

RP-HPLC $T_R$=25.8 min. LCMS (Method D, $T_R$=1.20 min) m/z 616.0 (M−H)⁻. ¹H NMR ($D_2O$) δ 9.07 (s, 1H), 8.95 (s, 1H), 7.67 (s, 1H), 5.81 (d, J=6.8 Hz, 1H), 5.39 (dd, J=8.4, 12.8 Hz, 1H), 4.99-4.92 (comp, 2H), 4.89-4.86 (m, 1H), 4.76-4.70 (m, 1H), 4.60 (m, 1H), 4.56-4.45 (comp, 2H), 4.40 (m, 1H), 3.99 (m, 2H), 2.62-2.42 (m, 2H). ³¹P NMR ($D_2O$) δ 54.96, 54.88.

Intermediate 34

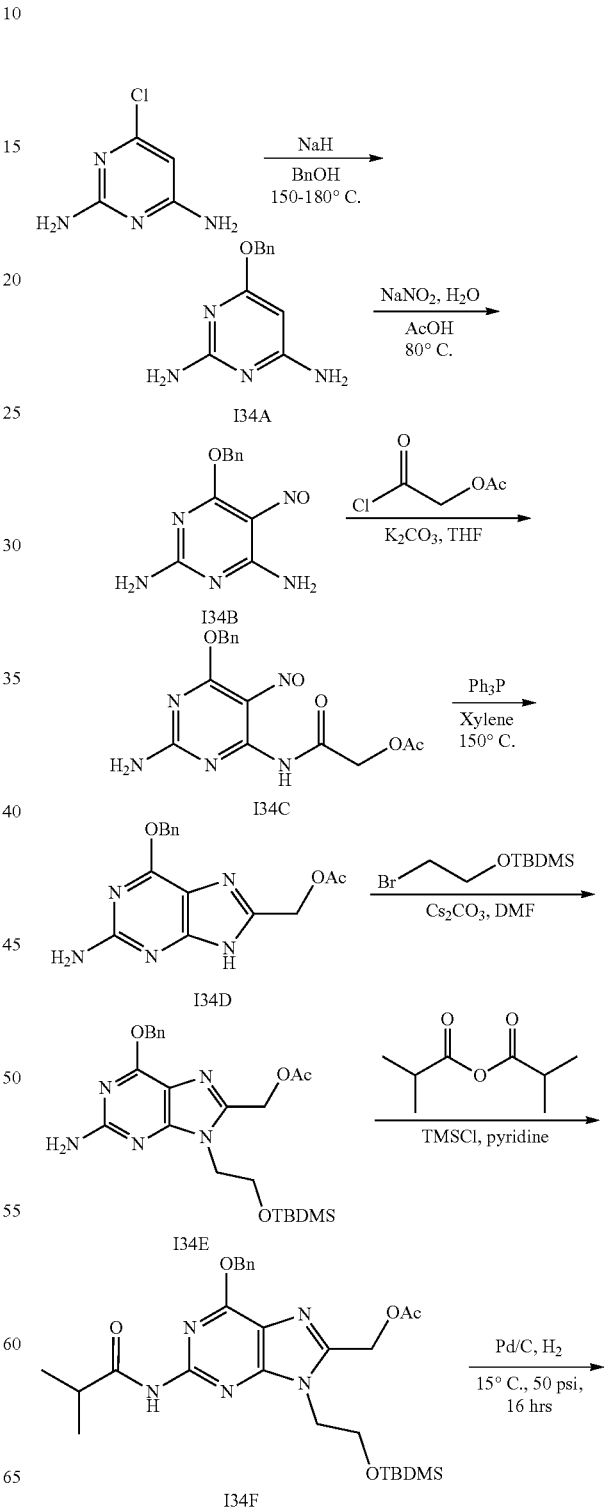

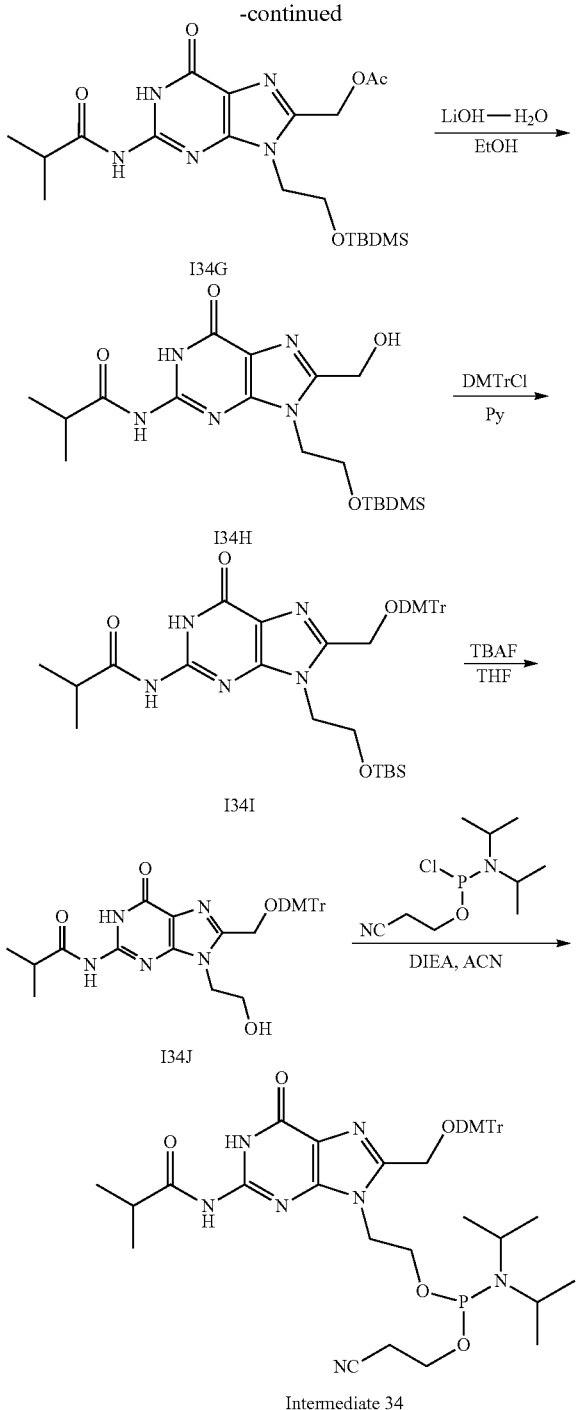

Intermediate 34

6-(Benzyloxy)pyrimidine-2,4-diamine (I34A)

NaH (166 g, 4.15 mol, 60% purity) was added to benzyl alcohol (2.78 kg, 25.7 mols) and the mixture was heated at 150° C. for 1.5 hrs. To the reaction mixture was slowly added 6-chloropyrimidine-2,4-diamine (500 g, 3.46 mol) and the reaction mixture was stirred at 180° C. for a further 2 hrs. The reaction mixture was concentrated under reduced pressure and the crude product was purified by silica gel chromatography (0-10% EtOAc/petroleum ether) to give compound I34A (420 g, ~90% pure by $^1$H NMR) as a white solid. $^1$H NMR (DMSO-$d_6$) δ 7.43-7.23 (m, 5H), 6.05 (s, 2H), 5.93 (s, 2H), 5.21 (s, 2H), 5.10 (s, 1H).

6-(Benzyloxy)-5-nitrosopyrimidine-2,4-diamine (I34B)

Compound I34A (420 g, 1.94 mol) was dissolved in warm AcOH (2.33 kg, 11.7 mol, 30.0%) and the reaction mixture was heated to 80° C. A solution of NaNO$_2$ (186 g, 2.70 mol) in H$_2$O (2.10 kg, 117 mol) was added dropwise over 1 hr and then the solution was stirred at 80° C. for 17 hrs. When an excess of oxidant was evident by starch—iodide paper, the reaction mixture was allowed to cool to 19° C., filtered and the filter cake was dried to give the crude compound I34B (409 g, 86%) as a purple solid, which was used in the next step without further purification. $^1$H NMR (DMSO-$d_6$) δ 10.1 (br d, J=4.0 Hz, 1H), 10.1-9.98 (m, 1H), 8.05 (br d, J=4.0 Hz, 1H), 7.95-7.76 (m, 2H), 7.58-7.29 (m, 6H), 5.67-5.51 (m, 2H).

2-((2-Amino-6-(benzyloxy)-5-nitrosopyrimidin-4-yl)amino)-2-oxoethyl acetate (I34C)

A suspension of compound I34B (205 g, 834 mmol) in THF (4.09 L) was cooled to 0° C. and to this mixture was added K$_2$CO$_3$ (231 g, 1.67 mol) and then 2-chloro-2-oxoethyl acetate (98.6 mL, 917 mmol) over 30 min. The reaction mixture was stirred for 3 hrs at 15° C. The mixture was quenched with H$_2$O (250 mL) and concentrated and the residue was treated with H$_2$O (250 mL). The solid was filtered off, washed with H$_2$O (250 mL), and dried to give I34C (216 g, 75%) as a green solid. $^1$H NMR (DMSO-$d_6$) δ 12.3 (br s, 1H), 8.80 (br s, 2H), 7.63-7.22 (m, 10H), 5.65 (s, 2H), 5.09 (s, 2H), 2.20-2.16 (m, 3H).

(2-Amino-6-(benzyloxy)-9H-purin-8-yl)methyl acetate (I34D)

A suspension of compound I34C (140 g, 405 mmol) and triphenylphosphine (255 g, 973 mmol) in o-xylene (2.66 L) was heated to 150° C. for 4 hrs. After cooling the solution to 4° C., the resulting suspension was kept at 4° C. for 16 hrs and filtered. The solid was ground and washed with toluene (1.00 L) to give I34D (88 g, 69%) as a red solid. $^1$H NMR (DMSO-$d_6$) δ 13.0-12.1 (m, 1H), 7.53-7.30 (m, 6H), 6.35 (br s, 2H), 5.47 (s, 2H), 5.07 (s, 2H), 2.08 (s, 3H).

(2-Amino-6-(benzyloxy)-9-(2-((tert-butyldimethylsilyl)oxy)ethyl)-9H-purin-8-yl)methyl acetate (I34E)

A solution of compound (2-bromoethoxy)(tert-butyl)dimethylsilane (92.4 g, 386 mmol) in DMF (770 mL) was heated to 50° C., and Cs$_2$CO$_3$ (229 g, 702 mmol) and then compound I34D (110 g, 351 mmol) were added in portions. The mixture was stirred for 12 hrs at 50° C. and then cooled to 15° C. Insoluble material was removed by filtration and the filtrate was concentrated under reduced pressure. The residue was purified by silica gel chromatography (10-50% EtOAc/petroleum ether) to give compound I34E (66.0 g, 40%) as a white solid. $^1$H NMR (DMSO-$d_6$) δ 7.51-7.29 (m, 5H), 7.21 (s, 2H), 5.49 (s, 2H), 5.19 (s, 2H), 4.17 (t, J=8.0 Hz, 2H), 3.85 (t, J=8.0 Hz, 2H), 2.07 (s, 3H), 0.80-0.70 (m, 9H), −0.12--0.20 (m, 6H).

(6-(Benzyloxy)-9-(2-((tert-butyldimethylsilyl)oxy)ethyl)-2-isobutyramido-9H-purin-8-yl)methyl acetate (I34F)

Compound I34E (30.0 g, 63.6 mmol) was dissolved in pyridine (300 mL) and treated with TMSCl (16.2 mL, 127 mmol). The reaction mixture was stirred for 15 min then isobutyric anhydride (12.7 mL, 76.3 mmol) was added in a dropwise fashion and the solution was left to stand at 15° C. for 3 hrs. After the reaction mixture has been cooled in an ice bath, 0.25 mL of water was added. After 5 min, 25% aq. NH$_4$OH (0.25 mL) was added and the mixture stirred for 15 min. The mixture was concentrated under reduced pressure and the residue purified by silica gel chromatography (1-50% EtOAc/petroleum ether) to give I34F (34.0 g, 83%) as a white solid. $^1$H NMR (DMSO-d$_6$) δ 10.4 (s, 1H), 7.61-7.28 (m, 5H), 5.62 (s, 2H), 5.30 (s, 2H), 4.31 (br t, J=8.0 Hz, 2H), 3.91 (t, J=8.0 Hz, 2H), 2.96 (td, J=8.0, 12.0 Hz, 1H), 3.02-2.89 (m, 1H), 2.09 (s, 3H), 1.10 (d, J=4.0 Hz, 6H), 0.71 (s, 9H), −0.18 (s, 6H).

(9-(2-((tert-Butyldimethylsilyl)oxy)ethyl)-2-isobutyramido-6-oxo-6,9-dihydro-1H-purin-8-yl)methyl acetate (I34G)

To a solution of compound I34F (31.0 g, 57.2 mmol) in THF (300 mL) was added 10% Pd/C (6.00 g). The suspension was degassed under reduced pressure and purged with H$_2$ several times. The mixture was stirred under H$_2$ (50.0 psi) at 25° C. for 16 hrs. The reaction mixture was filtered and concentrated to give compound I34G (24.0 g, 93%) as a yellow oil. $^1$H NMR (DMSO-d$_6$) δ 11.9 (br s, 2H), 5.22 (s, 2H), 4.24 (br s, 1H), 4.32-4.18 (m, 1H), 3.87 (br d, J=4.0 Hz, 2H), 2.78 (td, J=6.0, 12.0 Hz, 1H), 2.08 (s, 3H), 1.11 (br d, J=6.0 Hz, 6H), 0.73 (s, 9H), −0.17 (s, 6H).

N-(9-(2-((tert-Butyldimethylsilyl)oxy)ethyl)-8-(hydroxymethyl)-6-oxo-6,9-dihydro-1H-purin-2-yl) isobutyramide (I34H)

To EtOH (100 mL) and H$_2$O (50.0 mL) was added I34G (10.0 g, 22.1 mmol) and LiOH.H$_2$O (1.86 g, 44.3 mmol) and the mixture was stirred for 5 hrs at 15° C. The reaction mixture was filtered and concentrated under reduced pressure to give a residue which was triturated with EtOAc (30.0 mL) to give I34H (7.00 g, 74%, 96% purity) as a white solid. $^1$H NMR (DMSO-d$_6$) δ 12.04 (br s, 1H), 11.65 (br s, 1H), 5.57 (t, J=6.0 Hz, 1H), 4.61 (d, J=6.0 Hz, 2H), 4.26 (t, J=6.0 Hz, 2H), 3.89 (t, J=4.0 Hz, 2H), 2.78 (q, J=8.0 Hz, 1H), 1.11 (d, J=8.0 Hz, 6H), 0.74 (s, 9H), −0.16 (s, 6H).

N-(8-((Bis(4-methoxyphenyl)(phenyl)methoxy) methyl)-9-(2-((tert-butyldimethylsilyl)oxy)ethyl)-6-oxo-6,9-dihydro-1H-purin-2-yl)isobutyramide (I34I)

To a mixture of I34H (0.85 g, 2.08 mmol) in pyridine (15 mL) cooled to −5° C. was added DMTrCl (0.84 g, 2.49 mmol). The mixture was allowed to warm to RT and stirred overnight. The reaction was concentrated under reduced pressure and the residue purified by silica gel chromatography (0-5% MeOH/DCM) to give 1341 (1.40 g, 95%) as a white solid. LCMS m/z (M+H)$^+$ 712.3. $^1$H NMR (CDCl$_3$) δ 11.88 (s, 1H), 8.13 (s, 1H), 7.48-7.41 (m, 2H), 7.38-7.33 (m, 4H), 7.30-7.24 (m, 3H), 7.19 (dt, J=9.2, 6.4 Hz, 1H), 6.86-6.78 (m, 4H), 4.30 (s, 2H), 4.03 (t, J=5.5 Hz, 2H), 3.76 (s, 6H), 3.62 (t, J=5.5 Hz, 2H), 2.58 (hept, J=6.9 Hz, 1H), 1.26 (d, J=6.9 Hz, 6H), 0.65 (s, 9H), −0.32 (s, 6H).

N-(8-((Bis(4-methoxyphenyl)(phenyl)methoxy) methyl)-9-(2-hydroxyethyl)-6-oxo-6,9-dihydro-1H-purin-2-yl)isobutyramide (I34J)

To a solution of 1341 (1.40 g, 1.97 mmol) in THF (15 mL) cooled to 0° C. was added TBAF (1.0 M in THF, 2.36 mL, 2.36 mmol) in a dropwise fashion. The reaction mixture was stirred at −5° C. for 10 min then warmed to RT and stirred overnight. The reaction was recooled to 0° C. and TBAF (1.0 M in THF, 0.60 mL, 0.60 mmol) was added in a dropwise fashion and mixture stirred at RT for several hrs. The procedure was repeated one final time: cooling; TBAF (1.0 M in THF, 0.50 mL, 0.50 mmol); and stirring overnight. The reaction was concentrated under reduced pressure, taken up in EtOAc (50 mL) and washed with water (25 mL), dried (Na$_2$SO$_4$) and concentrated under reduced pressure. The residue was purified by silica gel chromatography (0-4% MeOH/DCM) to give I34J (0.76 g, 64%) as a white solid. LCMS m/z (M+H)$^+$598.2. $^1$H NMR (CD$_3$OD) δ 7.49-7.44 (m, 2H), 7.39-7.33 (m, 4H), 7.32-7.27 (m, 2H), 7.21 (tt, J=7.3, 2.0, 1H), 6.89-6.84 (m, 4H), 4.39 (s, 2H), 4.14 (t, J=5.7 Hz, 2H), 3.77 (s, 6H), 3.71 (t, J=5.6 Hz, 2H), 3.37 (hept, J=6.9 Hz, 1H), 1.21 (d, J=6.9 Hz, 6H).

3-(8-((Bis(4-methoxyphenyl)(phenyl)methoxy) methyl)-9H-purin-9-yl)propyl (2-cyanoethyl) diisopropylphosphoramidite (Intermediate 34)

To a solution of I34J (0.78 g, 1.30 mmol) in ACN (25 mL) was added DIEA (0.68 mL, 3.92 mmol) followed by addition of neat 3-((chloro(diisopropylamino)phosphino)oxy) propanenitrile (0.44 mL, 1.96 mmol) dropwise. The reaction mixture was stirred at RT for 2 hrs and then concentrated under reduced pressure. The residue was purified directly by RP-MPLC (5-100% ACN/H$_2$O containing 0.04% NH$_4$HCO$_3$) to give Intermediate 34 (0.71 g, 68%) as a white foam. LCMS m/z (M+H+OH-N,N-diisopropylamino)$^+$ 715.2. $^1$H NMR (CDCl$_3$) δ 11.80 (br s, 1H), 8.78 (s, 1H), 7.48-7.42 (m, 2H), 7.35 (dd, J=12.0, 5.1 Hz, 4H), 7.27 (t, J=7.6 Hz, 2H), 7.19 (t, J=7.3 Hz, 1H), 6.86-6.79 (m, 4H), 4.28 (dd, J=26.7, 11.3 Hz, 2H), 4.21-4.05 (m, 2H), 3.85-3.78 (m, 2H), 3.77 (s, 6H), 3.71 (ddd, J=16.3, 9.3, 4.8 Hz, 1H), 3.58 (ddd, J=12.8, 10.8, 5.7 Hz, 1H), 2.63-2.50 (m, 2H), 1.22 (d, J=6.9 Hz, 6H), 1.06 (d, J=6.8 Hz, 6H), 0.95 (d, J=6.8 Hz, 6H). $^{31}$P NMR (CDCl$_3$) δ 147.75.

Intermediate 35

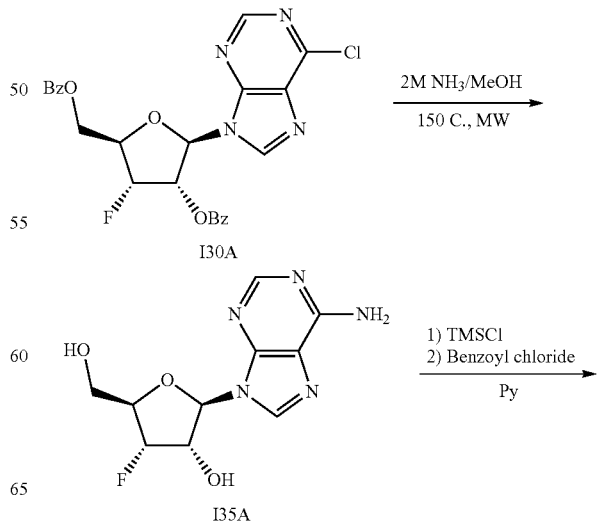

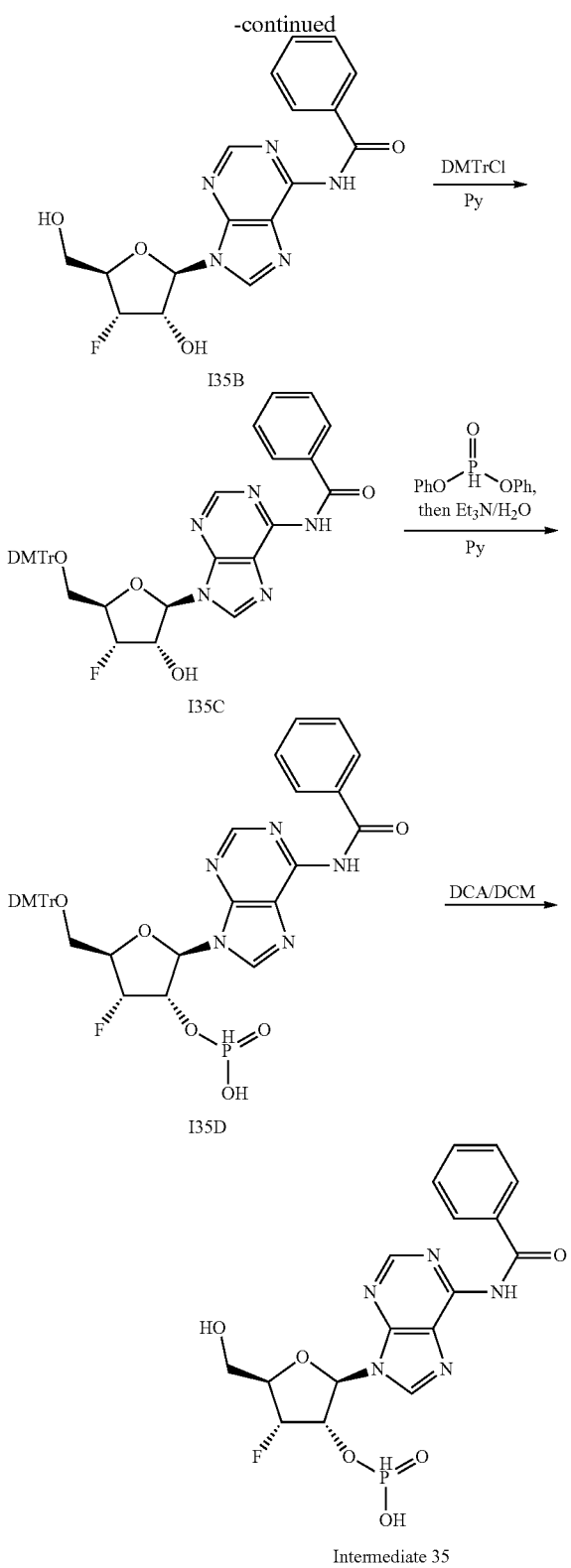

((2R,3R,4S,5R)-5-(6-Amino-9H-purin-9-yl)-4-(benzoyloxy)-3-fluorotetrahydrofuran-2-yl)methyl benzoate (I35A)

A portion of Intermediate I30A (0.5 g, 1.01 mmol) is dissolved in methanolic ammonia (12 mL, 2.0 M) and heated at 150° C. for 90 min under microwave conditions. The reaction mixture was concentrated under reduced pressure and the residue purified on RP-MPLC (5-30% ACN/H$_2$O) to give I35A (0.25 g, 91%) as a white solid. LCMS (Method C) m/z 270.1 (M+H)$^+$. $^1$H NMR (CD$_3$OD) δ 8.29 (s, 1H), 8.18 (s, 1H), 6.00 (d, J=8.4 Hz, 1H), 5.13 (dd, J=4.4, 54.8 Hz, 1H), 4.98 (ddd, J=4.4, 8.0, 25.2 Hz, 1H), 4.44 (td, J=2.4, 27.6 Hz, 1H), 3.83 (m, 2H).

N-(9-((2R,3S,4S,5R)-4-Fluoro-3-hydroxy-5-(hydroxymethyl)tetrahydrofuran-2-yl)-9H-purin-6-yl)benzamide (I35B)

To a rapidly stirred suspension of I35A (200 mg, 0.74 mmol) in pyridine (7.4 mL) at 0° C. was added TMSCl (0.47 mL, 3.72 mmol) in a dropwise fashion. The bath was removed and the reaction mixture was allowed to stir at RT overnight. The reaction was cooled again at 0° C. to add benzoyl chloride (0.43 mL, 3.72 mmol) in a dropwise fashion. The reaction was stirred at 0° C. for 2 hrs and then quenched by the addition of con. aq, ammonium hydroxide (1.5 mL) in a dropwise fashion at 0° C. After stirring at 0° C. for 30 min the reaction mixture was concentrated under reduced pressure. To the residue was added DCM (2.5 mL) and MeOH (2.5 mL) and the resulting mixture was sonicated briefly, and then filtered. The filtrate was concentrated under reduced pressure and purified by silica gel chromatography (0-50% MeOH/DCM) to give I35B (210 mg, 76%) as a white solid. LCMS ((Method B) m/z 374.2 (M+H)$^+$. $^1$H NMR (DMSO-d$_6$) δ 8.78 (s, 1H), 8.74 (s, 1H), 8.05 (m, 2H), 7.66 (m, 1H), 7.56 (m, 2H), 6.10 (d, J=8.0 Hz, 1H), 6.04 (d, J=6.4 Hz, 1H), 5.37 (t, J=5.6 Hz, 1H), 5.14 (dd, J=4.4, 54.8 Hz, 1H), 5.05-4.98 (m, 1H), 4.32 (td, J=4.4, 27.2 Hz, 1H), 3.68 (m, 2H).

N-(9-((2R,3S,4S,5R)-5-((Bis(4-methoxyphenyl)(phenyl)methoxy)methyl)-4-fluoro-3-hydroxytetrahydrofuran-2-yl)-9H-purin-6-yl)benzamide (I35C)

To a solution of I35B (442 mg, 1.18 mmol) in pyridine (10 mL) at −5° C. was added DMTrCl (420 mg, 1.24 mmol) in one portion. The resulting mixture was stirred at RT for 3 hrs, and then concentrated under reduced pressure. The residue was purified by silica gel chromatography (0-10% MeOH/DCM) to give I35C (490 mg, 61%) as a white solid. LCMS m/z 676.4 (M+H)$^+$. $^1$H NMR (CD$_3$OD) δ 8.57 (s, 1H), 8.49 (s, 1H), 8.09 (m, 2H), 7.65 (m, 1H), 7.57 (m, 2H), 7.43 (m, 2H), 7.33-7.20 (comp, 7H), 6.82 (comp, 4H), 6.18 (d, J=7.2 Hz, 1H), 5.39 (ddd, J=4.4, 7.2, 22.8 Hz, 1H), 5.20 (ddd, J=0.8, 4.0, 54.4 Hz, 1H), 4.49 (m, 1H), 3.77 (s, 6H), 3.47 (d, J=4.4 Hz, 2H).

(2R,3S,4R,5R)-2-(6-Benzamido-9H-purin-9-yl)-5-((bis(4-methoxyphenyl) (phenyl)methoxy)methyl)-4-fluorotetrahydrofuran-3-yl hydrogen phosphonate (I35D)

To a solution of I35C (490 mg, 0.73 mmol) in pyridine (5.5 mL) was added diphenyl phosphite (0.42 mL, 2.18 mmol). The reaction mixture was stirred at RT for 30 min, and then cooled in an ice/acetone bath, whereupon TEA (0.75 mL) and H$_2$O (0.75 mL) were added. The bath was removed and the reaction mixture was stirred at RT for 1 hr. The mixture was concentrated under reduced pressure and the residue was purified by RP-MPLC (C18 column, 5-80% ACN/H$_2$O) to provide I35D (410 mg as a triethyl amine salt, 87% product by weight assigned by $^1$H NMR, (69% yield) as a white solid. This material was used "as is" in subsequent transformations. LCMS m/z 740.1 (M+H)$^+$.

(2R,3S,4R,5R)-2-(6-Benzamido-9H-purin-9-yl)-4-fluoro-5-(hydroxymethyl)tetrahydrofuran-3-yl hydrogen phosphonate (Intermediate 35)

To a suspension of I35D (0.57 g, 87% by weight, 0.67 mmol) in DCM (10 mL) was added H$_2$O (0.25 mL) followed by a solution of DCA (0.57 mL, 6.9 mmol) in DCM (6 mL). The reaction mixture was stirred for 30 min at RT and then TES (6 mL) was added. After stirring for an additional 2 hrs, pyridine (1.3 mL) was added. The mixture was concentrated under reduced pressure and the residue purified by silica gel chromatography (0-80% MeOH/DCM) to give Intermediate 35 (0.26 g as a salt; 9% triethyl amine by weight, 6% pyridine by weight, 86% by weight assigned by $^1$H NMR, 77% yield) as a white solid. LCMS (Method A, T$_R$=0.63 min) m/z 438.11 (M+H)$^+$. $^1$H NMR (DMSO-d$_6$) δ 8.77 (s, 1H), 8.75 (s, 1H), 8.05 (m, 2H), 7.65 (m, 1H), 7.56 (m, 2H), 6.54 (d, J=618.8 Hz, 1H), 6.22 (d, J=8.0 Hz, 1H), 5.56-5.44 (comp, 2H), 5.30 (dd, J=4.4, 54.0 Hz, 1H), 5.37 (td, J=4.0, 27.2 Hz, 1H), 3.68 (m, 2H). [pyridine, 2CH 8.58 (m, 0.76H), CH 7.83 (m, 0.41H), 2CH 742 (m, 0.78H)] [triethylamine, 3CH$_2$ 2.99 (q, J=7.3 Hz, 2.55H), 3CH$_3$ 1.11 (t, J=7.2 Hz, 4.40H)]. $^{19}$F NMR (DMSO-d$_6$) δ −195.96. $^{31}$P NMR (DMSO-d$_6$) δ 0.76.

Example 23

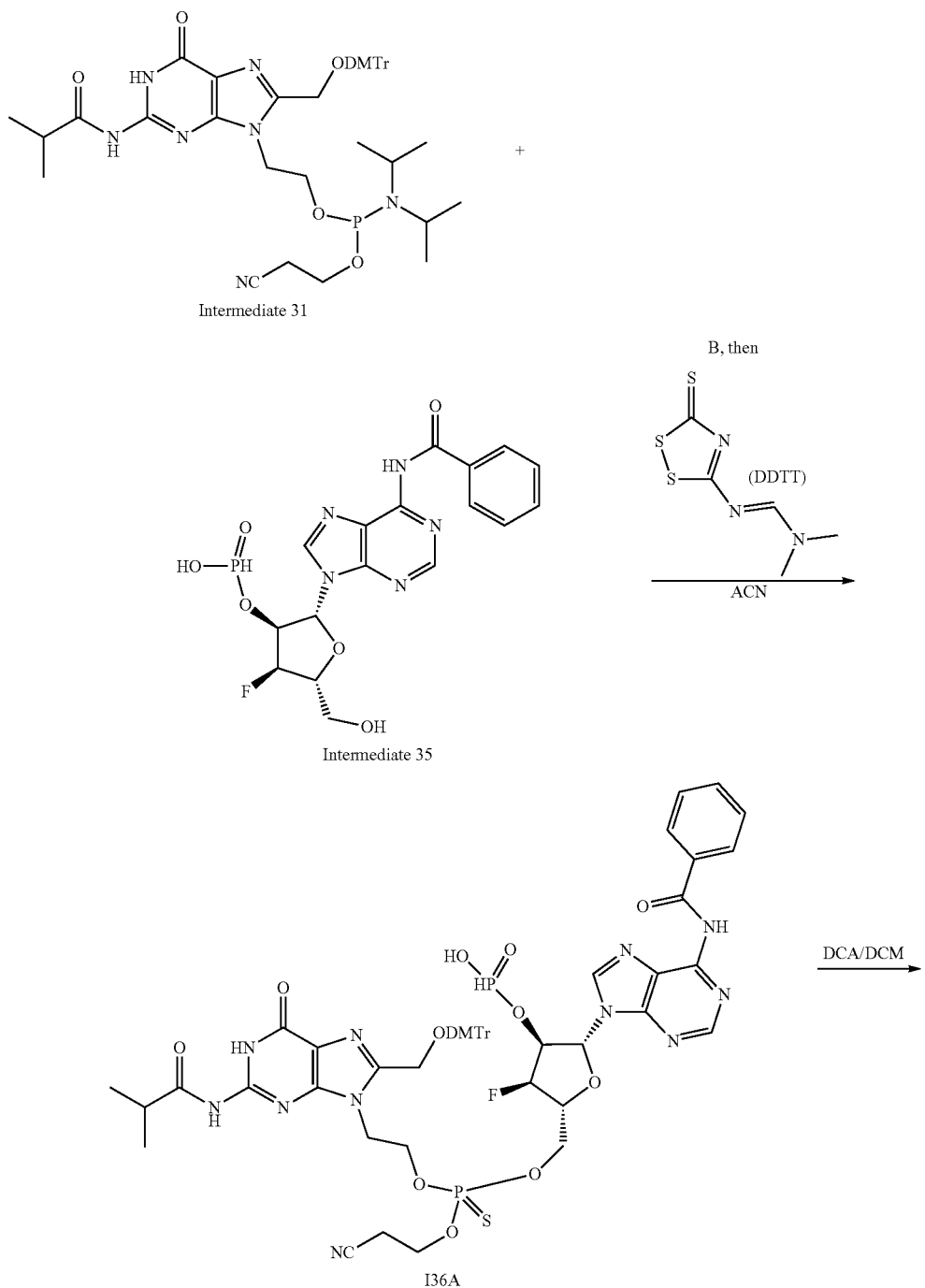

233

-continued

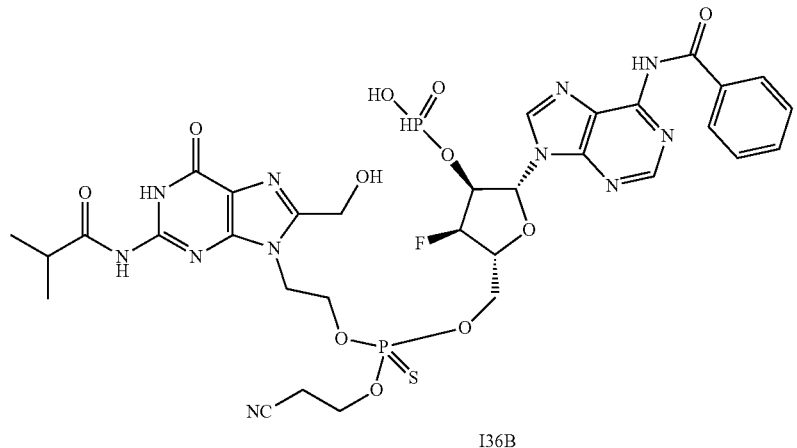

I36B

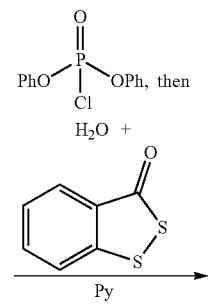

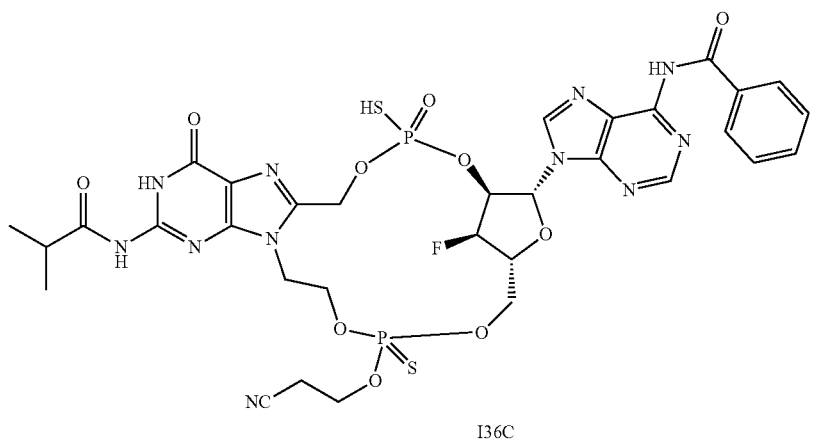

I36C

234

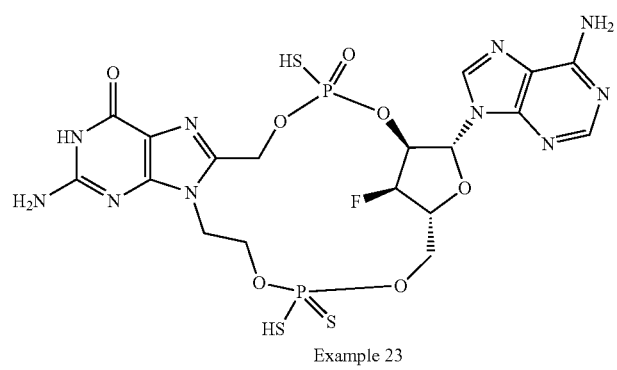

Example 23

{[(2R,3S,4R,5R)-2-(6-Benzamido-9H-purin-9-yl)-5-[({[2-(8-{[bis(4-methoxyphenyl)(phen yl)methoxy]methyl}-2-(2-methylpropanamido)-6-oxo-6,9-dihydro-1H-purin-9-yl)ethoxy](2-cyanoethoxy)sulfanylidene-lambda5-phosphanyl}oxy)methyl]-4-fluorooxolan-3-yl]oxy}phosphinic acid (I36A)

LCMS ($T_R$=1.29 min) m/z 1165.9 (M+H)⁺. ¹⁹F NMR ($D_2O$) δ −199.94,−200.51. ³¹P NMR ($D_2O$) δ 67.68, 67.54, 2.63, 2.55.

(2R,3S,4R,5R)-2-(6-Benzamido-9H-purin-9-yl)-5-(((((2-cyanoethoxy)(2-(8-(hydroxymethyl)-2-isobutyramido-6-oxo-1H-purin-9(6H)-yl)ethoxy)phosphorothioyl)oxy)methyl)-4-fluorotetrahydrofuran-3-yl hydrogen phosphonate (I36B)

LCMS ($T_R$=0.83 min) m/z 863.9 (M+H)⁺. ¹⁹F NMR ($D_2O$) δ −198.19, −199.45. ³¹P NMR ($D_2O$) δ 67.89, 67.80, 2.92, 2.86.

235

N-{9-[(1S,21R,23R,24R)-18-(2-Cyanoethoxy)-24-fluoro-11-(2-methylpropanamido)-3,9-dioxo-3-sulfanyl-18-sulfanylidene-2,4,17,19,22-pentaoxa-7,10,12,14-tetraaza-3lambda5,18 lambda5-diphosphatetracyclo[19.2.1.0⁶,¹⁴.0⁸,¹³]tetracosa-6,8(13), 1-trien-23-yl]-9H-purin-6-yl}benzamide (I36C)

LCMS ($T_R$=0.97 and 1.00 min) m/z 878.1 (M+H)⁺.

(1S,21R,23R,24R)-11-Amino-23-(6-amino-9H-purin-9-yl)-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),11-triene-3,9,18-trione (Example 23)

A solution of I33C (225 mg, 0.256 mmol) in MeNH₂/EtOH (33%, 10 mL) was stirred at RT for 5 hrs, and then concentrated under reduced pressure. The residue was purified by prep. RP-HPLC (Waters, X Bridge C18, 5 µm, 19×150 mm column eluting with 0-30% ACN/H₂O containing 0.04% NH₄HCO₃, Flow rate=10 mL/min) to give 2 pure diastereomers and a mixture of 2 diastereomers (Diastereomer A: $T_R$=15.7 min, 7.9 mg; Diastereomer B and C: $T_R$=17.5 min, 50 mg; Diastereomer D: $T_R$=24.7 min, 11.7 mg, Total: 69.6 mg, 42%) of Example 23. Example 23B (1:1 mixture of diastereomer B and C): Prep. RP-HPLC $T_R$=17.5 min. LCMS (Method D, $T_R$=1.18 min and 1.20 min) m/z 651.1 (M+H)⁺. ¹H NMR (D₂O) δ 8.30 (s, 1H), 8.22 (s, 1H), 8.21 (s, 1H), 8.00 (s, 1H), 6.28 (d, J=8.0 Hz, 2H), 5.45 (dd, J=53.6, 3.2 Hz, 2H), 5.08-5.01 (comp, 2H), 4.96-4.86 (comp, 4H), 4.44-4.07 (comp, 14H). ¹⁹F NMR (D₂O) δ -198.47, -198.70. ³¹P NMR (D₂O) δ 55.97, 55.25, 55.05, 55.00. Example 23D (Diastereomer D): Prep. RP-HPLC $T_R$=24.7 min. LCMS (Method D, $T_R$=1.23 min) m/z 651.1 (M+H)⁺. ¹H NMR (D₂O) δ 8.31 (s, 1H), 8.27 (s, 1H), 6.30 (d, J=7.6 Hz, 1H), 5.17-5.03 (comp, 2H), 4.88 (m, 2H), 4.71 (m, 1H), 4.46-4.40 (m, 1H), 4.33-4.24 (comp, 4H), 4.07 (m, 1H). ¹⁹F NMR (D₂O) δ -196.76. ³¹P NMR (D₂O) δ 56.59, 55.60.

Intermediate 37

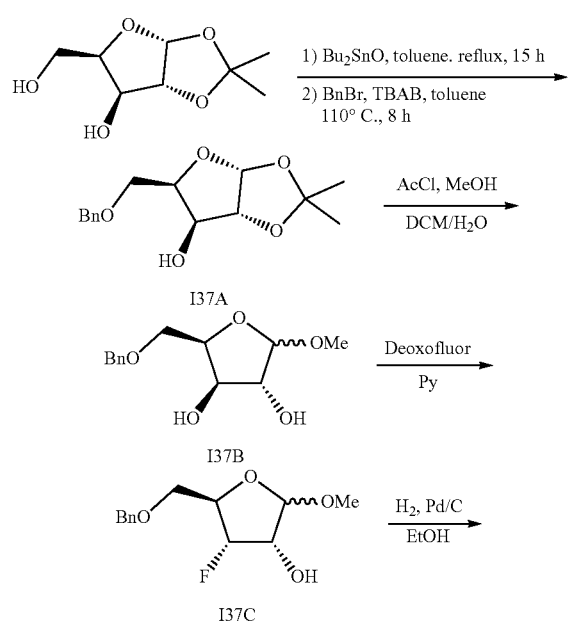

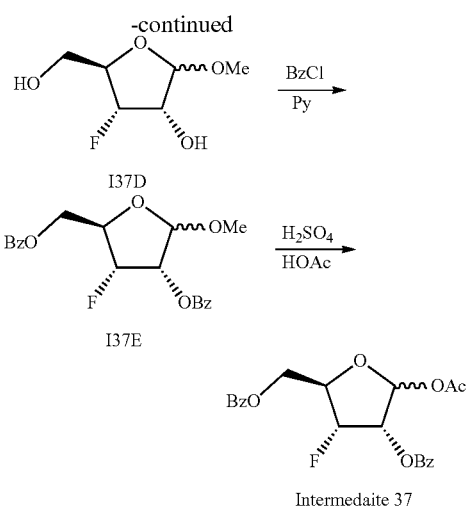

Intermedaite 37

(3aR,5R,6S,6aR)-5-((Benzyloxy)methyl)-2,2-dimethyltetrahydrofuro[2,3-d][1,3]dioxol-6-ol (I37A)

A solution of (3aR,5R,6S,6aR)-5-(hydroxymethyl)-2,2-dimethyltetrahydrofuro[2,3-d][1,3]dioxol-6-ol (200 g, 10.5 mol) in toluene (2 L) was treated with Bu₂SnO (290 g, 11.6 mol). The mixture was refluxed at 130° C. with a Dean-Stark apparatus overnight. After the reaction mixture was cooled to RT, benzyl bromide (190 mL, 15.8 mol) and tetra-n-butylammonium bromide (170 g, 5.3 mol) were added and the mixture was stirred at 110° C. for 8 hrs. The resulting mixture was extracted with EtOAc (3×1 L), the organic phase was washed with brine, dried over Na₂SO₄, filtered and concentrated. The residue was purified by silica column chromatography (20%-25% EtOAc/PE) to give I37A as a yellow oil (240 g, 81%). ¹H NMR (400 MHz, CDCl₃): δ 7.30-7.21 (m, 1H), 5.91 (d, J=4.0 Hz, 1H), 4.59-4.49 (m, 2H), 4.44 (d, J=4.0 Hz, 1H), 4.22-4.16 (m, 2H), 3.90-3.82 (m, 2H), 1.41 (s, 3H), 1.25 (s, 3H).

(2R,3R,4R)-2-((Benzyloxy)methyl)-5-methoxytetrahydrofuran-3,4-diol (I37B)

To a solution of MeOH (1 L) cooled to -30° C. was added AcCl (55 mL, 0.77 mol). The mixture was stirred at -30° C. for 30 min and warmed to RT. A mixture of I37A (120 g, 428 mmol) in DCM/MeOH/H₂O (2:2:1, 1 L) was added dropwise to the cooled solution and the reaction was stirred at RT for 16 h. The resulting mixture was neutralized with sat. aq. NaHCO₃ and extracted with DCM. The organic phase was washed with brine, dried over Na₂SO₄, filtered and concentrated. The crude product was purified by silica column chromatography (20%-33% EtOAc/PE) to afford I37B as a yellow oil (61 g, 56%). ¹H NMR (400 MHz, CDCl₃): δ 7.37-7.28 (m), 4.97 (d), 4.83 (s), 4.61-4.51 (m), 4.45-4.05 (m), 3.77-3.66 (m), 3.47 (s), 3.35 (s), 3.25 (d), 3.07 (d), 2.82 (t).

(3S,4S,5R)-5-((Benzyloxy)methyl)-4-fluoro-2-methoxytetrahydrofuran-3-ol (I37C)

To a solution of I37B (10 g, 39.3 mmol) in DCM (200 mL) was added Deoxofluor (28 mL, 59 mmol) and pyridine (20 mL, 236 mmol) The mixture was stirred at RT for 16 h and then quenched with sat. aq. NaHCO₃, extracted with DCM and combined organics were washed with brine, dried over Na$_2$SO$_4$, filtered and concentrated. The residue was purified by silica column chromatography (10%-20% EtOAc/PE) to afford I37C as a yellow oil (2.4 g, 24%). $^1$H NMR (400 MHz, CDCl$_3$): δ 7.40-7.30 (m, 5H), 5.12 (t, J=4.0 Hz, 0.5H), 4.98 (t, J=4.0 Hz, 0.5H), 4.91 (t, J=4.0 Hz, 1H), 4.65-4.58 (m, 2H), 4.46-4.37 (m, 1H), 4.23-4.18 (m, 1H), 3.66-3.58 (m, 2H), 3.42 (s, 3H).

(3S,4S,5R)-4-Fluoro-5-(hydroxymethyl)-2-methoxytetrahydrofuran-3-ol (I37D)

To a solution of I37C (2.5 g, 10.0 mmol) in EtOH (200 mL) was added 10% Pd/C (1.8 g). The mixture was stirred at RT under H$_2$ for 3 days. The resulting mixture was filtered and concentrated to afford I37D (1.5 g, 92%) as a yellow oil which was used in next step without further purification.

((2R,3R,4S)-4-(Benzoyloxy)-3-fluoro-5-methoxytetrahydrofuran-2-yl)methyl benzoate (I37E)

To a solution of I37D (6.2 g, 37.4 mmol) in DCM (100 mL) at 0° C. was added pyridine (11.8 g, 149 mmol) and benzoyl chloride (13.2 g, 93.2 mmol) and the mixture was stirred at RT for 3 hrs. Water was added and the resulting mixture extracted with DCM, the organic phase was washed with brine, dried over Na$_2$SO$_4$, filtered and concentrated. The crude product was purified by silica gel chromatography (5%-10% EtOAc/PE) to afford I37E as a yellow oil (13.1 g, 93%). $^1$H NMR (400 MHz, CDCl$_3$): δ 8.11-8.05 (m), 7.64-7.45 (m), 5.53-5.10 (m), 4.75-4.28 (m), 3.50 (s), 3.38 (s).

((2R,3R,4S)-5-Acetoxy-4-(benzoyloxy)-3-fluorotetrahydrofuran-2-yl)methyl benzoate (Intermediate 37)

To a solution of I37E (2.1 g, 5.3 mmol) in HOAc (10 mL) was added Ac$_2$O (2 mL) and conc. sulfuric acid (1.2 mL), the mixture was stirred at RT for 16 hrs. The resulting mixture was poured into ice-water and the pH was adjusted by adding sat. aq. NaHCO$_3$, followed by extraction with DCM. Combined organics were washed with brine, dried over Na$_2$SO$_4$, filtered and concentrated. The residue was purified by silica gel chromatography (10%-20% EtOAc/PE) to afford Intermediate 37 as a colorless oil (1.9 g, 90%). $^1$H NMR (400 MHz, CDCl$_3$): δ 8.12-8.04 (m), 7.62-7.46 (m), 6.66 (d), 6.41 (t), 5.58 (ddd), 5.46 (dt), 5.37 (ddd), 5.35 (dt), 4.85 (ddt), 4.74 (ddd), 4.68 (dd), 4.58 (dd), 4.51 (dd), 4.48 (dd), 2.17 (s), 1.98 (s).

Intermediate 38

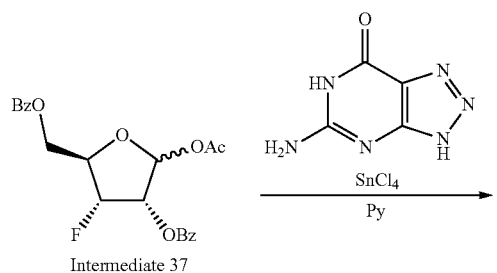

Intermediate 37

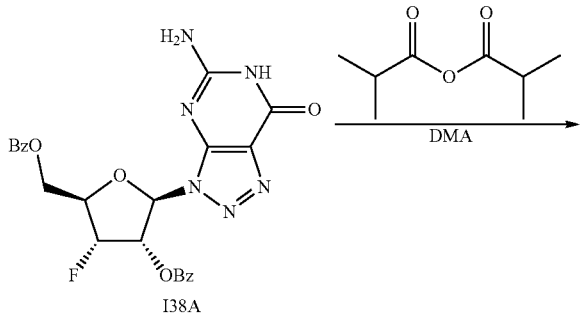

I38A

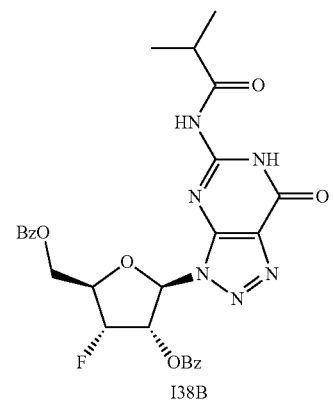

I38B

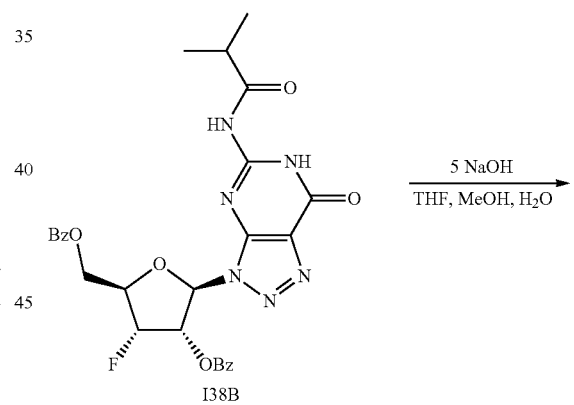

I38B

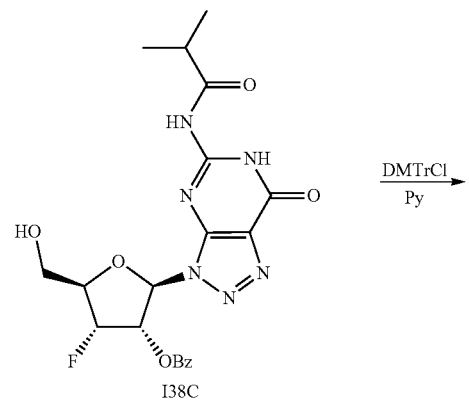

I38C

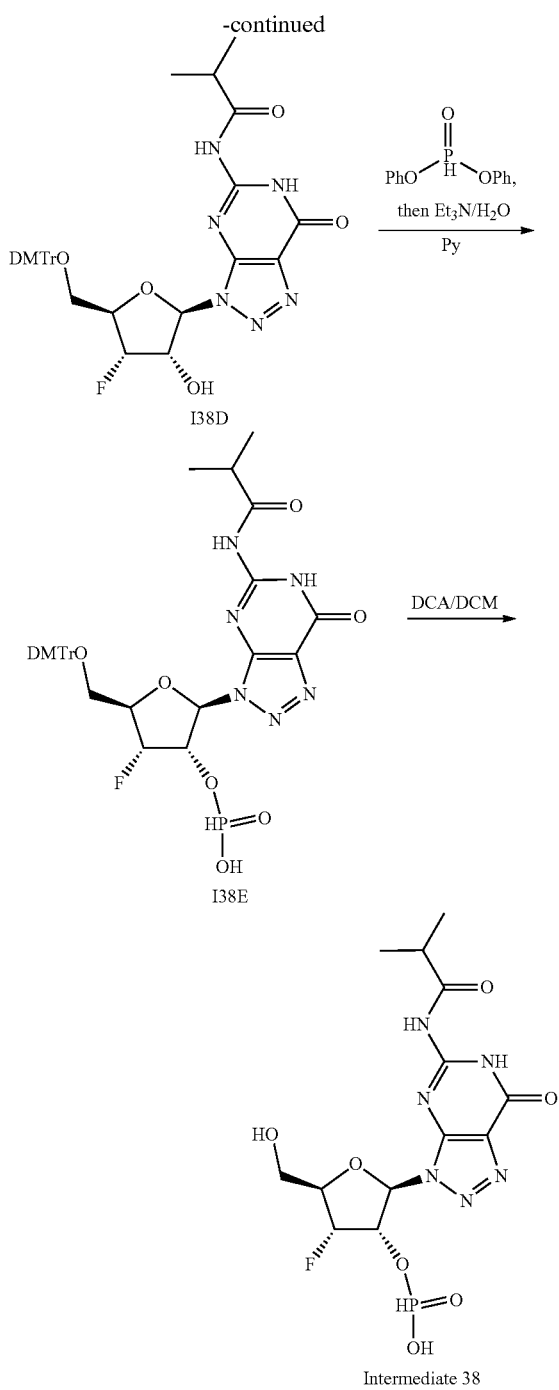

((2R,3R,4S,5R)-5-(5-Amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate (I38A)

To 8-azaguanine (0.15 g, 0.99 mmol) in ACN (3 mL) was added BSA (0.50 mL) and the mixture heated at 70° C. for 2 hrs. After cooling to RT, Intermediate 37 (0.21 g, 0.52 mmol) in ACN (2 mL) was added to the mixture followed by the dropwise addition of SnCl$_4$ (0.24 mL, 2.09 mmol). This mixture was heated at 70° C. for 2 hrs and then concentrated under reduced pressure. The residue was taken up in EtOAc (10 mL) and washed with sat. aq. NaHCO$_3$ (3 mL). The aq. layer was extracted with EtOAc (3×5 mL). Combined organics were washed with water (2×5 mL), brine (5 mL), dried over Na$_2$SO$_4$, filtered and concentrated to provide 0.21 g of I38A as a tan solid that was used without further purification. LCMS m/z 495.2 (M+H)$^+$. $^1$H NMR (CD$_3$CN) δ 9.30 (br s, 1H), 8.04 (ddd, J=17.3, 8.4, 1.3 Hz, 4H), 7.68-7.61 (m, 2H), 7.53-7.47 (m, 4H), 6.50 (dd, J=4.7, 1.1 Hz, 1H), 6.39 (dt, J=11.8, 4.8 Hz, 1H), 5.91 (dt, J=52.6, 4.6 Hz, 1H), 5.79 (br s, 2H), 4.80 (ddd, J=20.7, 8.3, 4.2 Hz, 1H), 4.68 (dd, J=12.3, 3.8 Hz, 1H), 4.68 (dd, J=12.3, 4.4 Hz, 1H). $^{19}$F NMR (CD$_3$CN) δ -205.59.

((2R,3R,4S,5R)-4-(Benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate (I38B)

To a solution of I38A (0.22 g, 0.44 mmol) in DMA (2 mL) at RT was added isobutyric anhydride (0.11 mL, 0.67 mmol) slowly, and the mixture was heated to 140° C. for 4 hrs. After cooling the mixture was diluted in EtOAc (10 mL), washed with sat. aq. NH$_4$Cl (4×2 mL), brine (5 mL), dried over Na$_2$SO$_4$, filtered and concentrated. The residue was purified by silica gel chromatography (5-100% EtOAc/Hexane) to give I38B (0.22 g, 88%) as a white solid. LCMS m/z 565.1 (M+H)$^+$. $^1$H NMR (CDCl$_3$) δ 7.70 (ddd, J=17.3, 8.3, 1.2 Hz, 4H), 7.33-7.25 (m, 2H), 7.14 (dt, J=11.1, 7.8 Hz, 4H), 6.30 (d, J=4.4 Hz, 1H), 6.06 (dt, J=11.2, 4.6 Hz, 1H), 5.57 (dt, J=52.3, 4.6 Hz, 1H), 4.52 (ddd, J=20.2, 8.6, 4.3 Hz, 1H), 4.36-4.34 (m, 2H), 4.32 (br s, 2H), 2.37 (hept, J=6.9 Hz, 1H), 0.90 (d, J=6.9 Hz, 6H).

N-(3-((2R,3S,4S,5R)-4-Fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide (I38C)

To a solution of I38B (0.59 g, 1.04 mmol) in THF (3 mL), MeOH (1.6 mL), and water (0.4 mL) at -5° C. was added 5 M aq. NaOH (0.48 mL, 2.40 mmol) dropwise. The resulting mixture was stirred at -5° C. for 1 hr and then quenched with formic acid (0.13 mL 3.14 mmol). The mixture was concentrated under reduced pressure and the residue was absorbed on Celite. The compound was purified by silica gel chromatography (3-10% MeOH/DCM) to give I38C (0.34 g, 92%) as a white solid. LCMS m/z 357.2 (M+H)$^+$. $^1$H NMR (CD$_3$OD) δ 6.19 (d, J=6.7 Hz, 1H), 5.31-5.28 (m, 1H), 5.20 (ddd, J=6.3, 5.4, 3.2 Hz, 1H), 4.37 (dtd, J=24.8, 4.8, 1.6 Hz, 1H), 3.73 (d, J=4.9 Hz, 2H), 2.73 (hept, J=6.9 Hz, 1H), 1.22 (d, J=6.9 Hz, 6H). $^{19}$F NMR (CD$_3$OD) δ -203.48.

N-(3-((2R,3S,4S,5R)-5-((Bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide (I38D)

To a solution of I38C (1.72 g, 4.83 mmol) in pyridine (33 mL) at -5° C. was added DMTrCl (2.01 g, 5.94 mmol) in one portion. The resulting mixture was stirred at RT for 3 hrs, and then concentrated under reduced pressure. The residue was purified by silica gel chromatography (0.5-10% MeOH/DCM) to give I38D (2.37 g, 74%) as a white solid. LCMS m/z 659.3 (M+H)+. 1H NMR (CDCl3) δ 12.06 (br s, 1H), 8.03 (s, 1H), 7.48 (d, J=7.1 Hz, 2H), 7.34 (dd, J=8.9, 3.6 Hz, 4H), 7.25-7.16 (comp, 4H), 6.78 (dd, J=10.2, 9.0 Hz, 4H), 6.23 (d, J=7.6 Hz, 1H), 5.52 (ddd, J=21.5, 7.2, 4.6 Hz, 1H), 5.22 (dd, J=54.9, 4.2 Hz, 1H), 4.42 (d, J=27.9 Hz, 1H), 3.75 (s, 3H), 3.74 (s, 3H), 3.50 (dd, J=10.8, 2.8 Hz, 1H), 3.07 (dd, J=10.8, 3.4 Hz, 1H), 1.71 (hept, J=6.9 Hz, 1H), 0.91 (d, J=6.8 Hz, 3H), 0.69 (d, J=6.9 Hz, 3H). 19F NMR (CDCl3) δ −198.70.

(2R,3S,4R,5R)-5-((Bis(4-methoxyphenyl)(phenyl)methoxy)methyl)-4-fluoro-2-(5-isobutyramido-7-oxo-6,7-dihydro-3H-[1,2,3]triazolo[4,5-d]pyrimidin-3-yl)tetrahydrofuran-3-yl hydrogen phosphonate (I38E)

To a solution of I38D (1.03 g, 1.56 mmol) in pyridine (10 mL) was added diphenyl phosphite (0.90 mL, 4.69 mmol). The reaction mixture was stirred at RT for 30 min, and then cooled in an ice/acetone bath, whereupon Et3N (1.7 mL) and H2O (1.7 mL) were added. The bath was removed and the reaction mixture was stirred at RT for 1 hr. The mixture was concentrated under reduced pressure and the residue was purified by RP-MPLC (C18 column, 15-35% ACN/H2O) to provide I38E (1.06 g as a triethyl ammonium salt, 90% product by weight assigned by 1H NMR, 84%) as a white solid. This material was used "as is" in subsequent transformations. LCMS m/z 721.3 (M−H)−.

(2R,3S,4R,5R)-4-Fluoro-5-(hydroxymethyl)-2-(5-isobutyramido-7-oxo-6,7-dihydro-3H-[1,2,3]triazolo[4,5-d]pyrimidin-3-yl)tetrahydrofuran-3-yl hydrogen phosphonate (Intermediate 38)

To a suspension of I38E (1.06 g, 1.32 mmol) in DCM (10 mL) was added H2O (0.25 mL, 1.32 mmol) followed by a solution of DCA (1.0 mL, 12.2 mmol) in DCM (10 mL). The reaction mixture was stirred for 30 min at RT and then TES (12 mL) was added. After stirring for an additional 2 hrs, pyridine (2.3 mL) was added. The mixture was concentrated under reduced pressure, and the residue was purified by silica gel chromatography (5-65% MeOH/DCM) to give Intermediate 38 (0.60 g as a salt; 9% triethyl amine by weight, 6% pyridine by weight, 86% product by weight assigned by 1H NMR, 93%) as a white solid. LCMS (Method A, TR=0.65 min) m/z 421.1 (M+H)+. 1H NMR (CD3OD) δ 6.76 (d, J=636.5 Hz, 1H), 6.37 (d, J=5.9 Hz, 1H), 5.73 (ddd, J=16.8, 9.9, 5.1 Hz, 1H), 5.51-5.33 (m, 1H), 4.41 (ddd, J=22.7, 7.2, 4.6 Hz, 1H), 3.80-3.71 (m, 2H), 2.77 (hept, J=6.8 Hz, 1H), 1.23 (d, J=7.3 Hz, 6H) [pyridine, 2CH 8.83 (br s, 0.71H), CH 8.55 (t, 0.34H), 2CH 8.02 (m, 0.71H)][triethyl amine, 3CH2 3.19 (q, J=7.3 Hz, 2.55H), 3CH3 1.30 (t, J=7.3 Hz, 4.14H)]. 19F NMR (CD3OD) δ −203.02. 31P NMR (CD3OD) δ 2.88.

Example 24

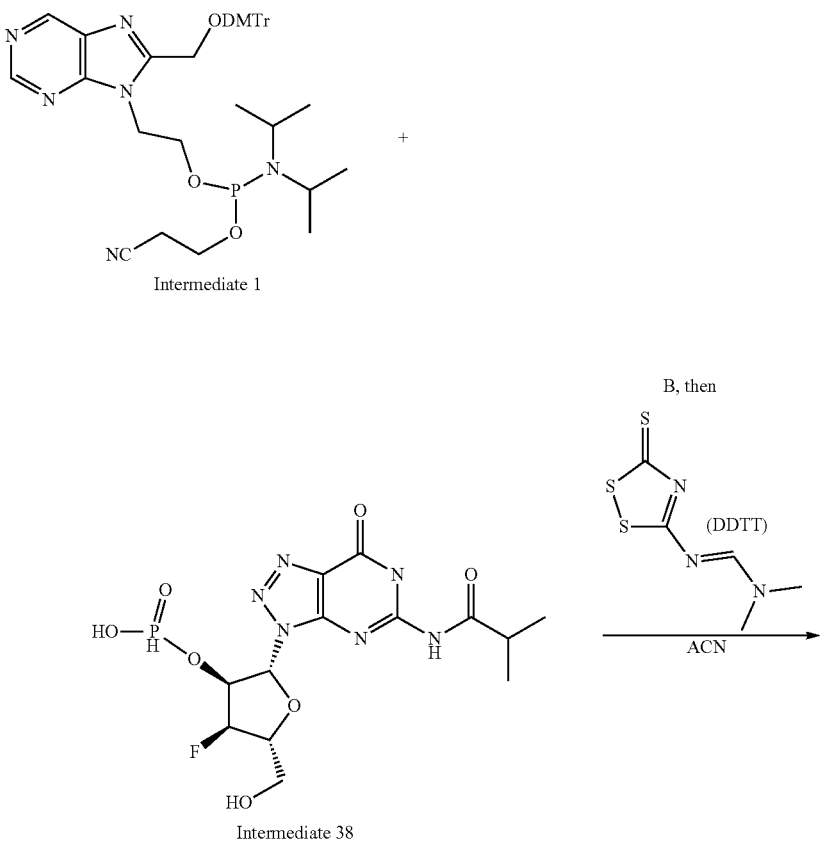

-continued
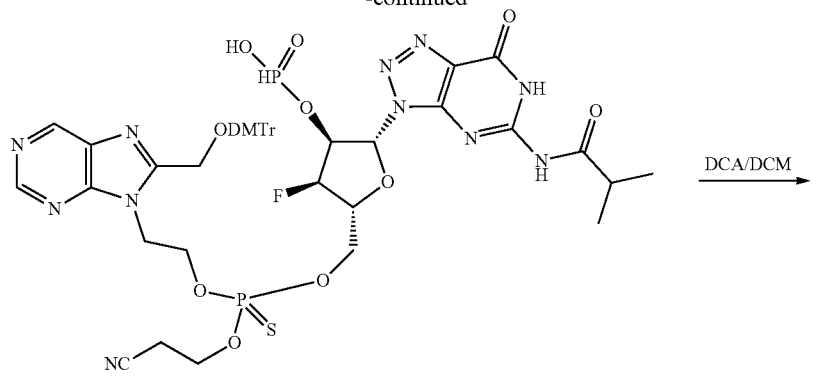
I39A
DCA/DCM →
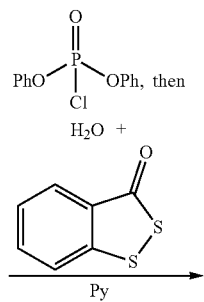
PhO-P(=O)(Cl)-OPh, then
H₂O +
I39B
Py →
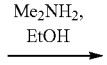
Me₂NH₂,
EtOH →
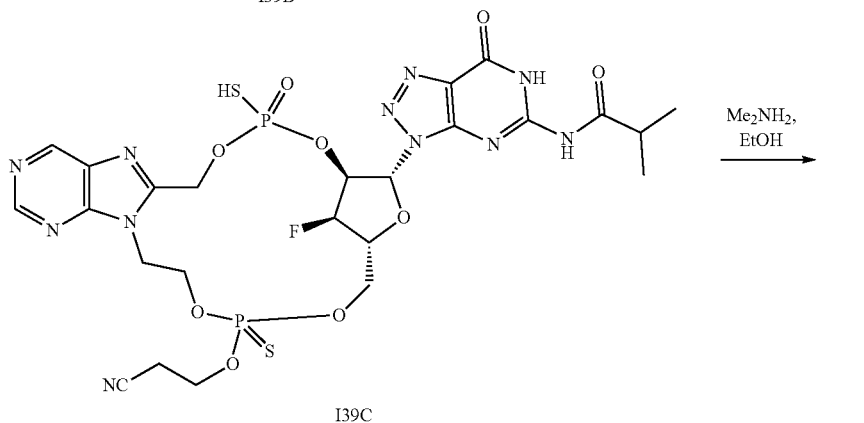
I39C
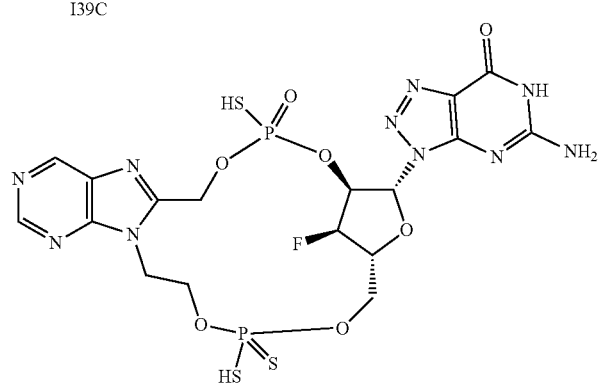
Example 24

(1S,21R,23R,24R)-23-{5-Amino-7-oxo-3H,6H,7H-[1,2,3]triazolo[4,5-d]pyrimidin-3-yl}-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 24)

Example 24 diastereomers (Diastereomers A-D) were prepared according to procedures analogous to those outlined in Example 1.

(2R,3S,4R,5R)-5-((((2-(8-((Bis(4-methoxyphenyl)(phenyl)methoxy)methyl)-9H-purin-9-yl)ethoxy)(2-cyanoethoxy)phosphorothioyl)oxy)methyl)-4-fluoro-2-(5-isobutyramido-7-oxo-6,7-dihydro-3H-[1,2,3]triazolo[4,5-d]pyrimidin-3-yl)tetrahydrofuran-3-yl hydrogen phosphonate (139A)

LCMS ($T_R$=1.24 min) m/z 1045.9 (M–H)⁻. $^{31}$P NMR (CD$_3$OD)) δ 67.85, 67.49, 3.07. $^{19}$F NMR (CD$_3$OD) δ –205.26, –205.88.

(2R,3S,4R,5R)-5-((((2-Cyanoethoxy)(2-(8-(hydroxymethyl)-9H-purin-9-yl)ethoxy)phosphorothioyl)oxy)methyl)-4-fluoro-2-(5-isobutyramido-7-oxo-6,7-dihydro-3H-[1,2,3]triazolo[4,5-d]pyrimidin-3-yl)tetrahydrofuran-3-yl hydrogen phosphonate (139B)

LCMS ($T_R$=0.75 min) m/z 744.0 (M–H)⁻. $^{31}$P NMR (CD$_3$OD) δ 67.88, 67.75, 3.02. $^{19}$F NMR (CD$_3$OD) δ–204.79, –204.80, –204.82, –204.83.

N-{3-[(1S,21R,23R,24R)-18-(2-Cyanoethoxy)-24-fluoro-3-oxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraen-23-yl]-7-oxo-3H,6H,7H-[1,2,3]triazolo[4,5-d]pyrimidin-5-yl}-2-methylpropanamide (I39C)

LCMS (Method C, $T_R$=1.32 and 1.37 min) m/z 757.9 (M–H)⁻. $^{31}$P NMR (CD$_3$OD) δ 66.45, 65.83, 65.03, 64.77, 59.04, 58.30, 58.07, 56.75. $^{19}$F NMR (CD$_3$OD) δ –197.60, –199.31, –199.55, –200.41.

A solution of I39C (0.22 g, 0.29 mmol, a mixture of diastereomers) in MeNH$_2$/EtOH (33%, 10 mL) was stirred at RT for 2.5 hrs, and then concentrated under reduced pressure. The residue was purified by prep. RP-HPLC (Waters, X Bridge C18, 5 μm, 19×150 mm column eluting with 2-10% [33 min] ACN/H$_2$O containing 0.04% NH$_4$HCO$_3$, Flow rate=7 mL/min) to give 4 pure diastereomers (Diastereomer A: 8.2 mg; Diastereomer B: 43.6 mg; Diastereomer C: 37.3 mg; Diastereomer D: 24.8 mg; Total: 0.1239 g, 67%) of Example 24. Example 24A (Diastereomer A): Prep. RP-HPLC: $T_R$=11.07 min. LCMS (Method D, $T_R$=1.07 min) m/z 635.0 (M–H)⁻. $^1$H NMR (D$_2$O) δ 8.98 (s, 1H), 8.86 (s, 1H), 8.15 (s, 1H), 6.19 (d, J=8.3 Hz, 1H), 5.56 (d, J=3.4 Hz, 1H), 5.43 (d, J=3.5 Hz, 1H), 5.31 (dd, J=12.6, 7.7 Hz, 1H), 5.31-5.11 (m, 3H), 4.59-4.42 (m, 2H), 4.31-4.23 (m, 2H), 4.02 (app dd, J=23.9, 12.6 Hz, 2H). $^{19}$F NMR (D$_2$O) δ-198.9. $^{31}$P NMR (D$_2$O) δ 55.4, 54.6. Example 24B (Diastereomer B): Prep. RP-HPLC: $T_R$=12.03 min. LCMS (Method D, $T_R$=1.10 min) m/z 635.0 (M–H)⁻. $^1$H NMR (D$_2$O) δ 8.96 (s, 1H), 8.84 (s, 1H), 6.20 (d, J=8.3 Hz, 1H), 5.54-5.40 (m, 2H), 5.20 (d, J=3.8 Hz, 1H), 5.15-5.00 (m, 2H), 4.58-4.47 (m, 2H), 4.43-4.27 (m, 2H), 4.06-3.92 (m, 2H) $^{19}$F NMR (D$_2$O) δ-197.7. $^{31}$P NMR (D$_2$O) δ 56.0, 55.2. Example 24C (Diastereomer C): Prep. RP-HPLC: $T_R$=12.40 min. LCMS (Method D, $T_R$=1.15 min) m/z 635.0 (M–H)⁻. $^1$H NMR (D$_2$O) δ 8.98 (s, 1H), 8.86 (s, 1H), 6.20 (d, J=8.3 Hz, 1H), 5.59 (d, J=3.6 Hz, 1H), 5.46 (d, J=3.8 Hz, 1H), 5.32 (dd, J=12.6, 8.0 Hz, 1H), 5.27-5.13 (m, 2H), 4.65-4.59 (m, 1H), 4.50-4.30 (m, 3H), 4.15-4.09 (m, 1H), 3.85 (app d, J=11.5 Hz, 1H). $^{19}$F NMR (D$_2$O) δ –199.0. $^{31}$P NMR (D$_2$O) δ 54.6, 53.7. Example 24D (Diastereomer D): Prep. RP-HPLC: $T_R$=20.08 min. LCMS (Method D, $T_R$=1.14 min) m/z 635.0 (M–H)⁻. $^1$H NMR (D$_2$O) δ 8.94 (s, 1H), 8.84 (s, 1H), 6.20 (d, J=8.3 Hz, 1H), 5.46-5.31 (m, 2H), 5.22 (d, J=3.4 Hz, 1H), 5.08 (app dt, J=15.3, 6.3 Hz, 2H), 4.58-4.45 (m, 2H), 4.39-4.28 (m, 2H), 4.16-4.07 (m, 1H), 3.90-3.81 (m, 1H). $^{19}$F NMR (D$_2$O) δ-197.8. $^{31}$P NMR (D$_2$O) δ 56.0, 54.6.

Intermediate 40

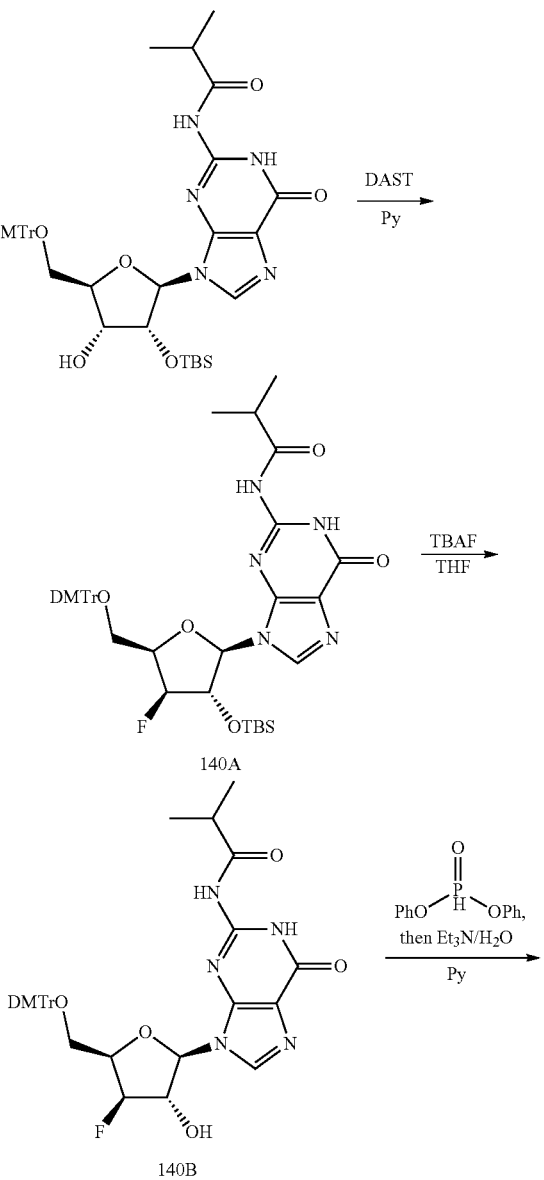

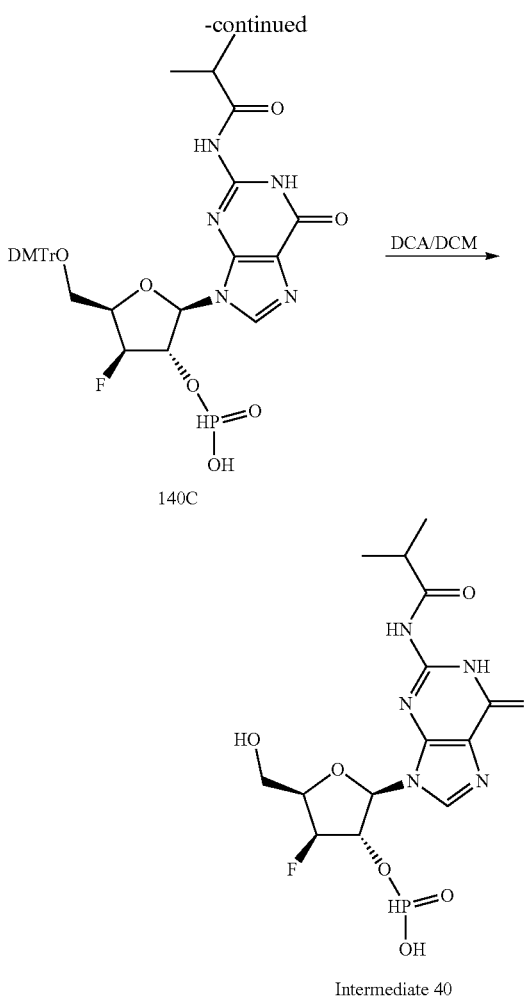

140C

Intermediate 40

N-(9-((2R,3S,4S,5R)-5-((Bis(4-methoxyphenyl)(phenyl)methoxy)methyl)-3-((tert-butyldimethylsilyl)oxy)-4-fluorotetrahydrofuran-2-yl)-6-oxo-6,9-dihydro-1H-purin-2-yl)isobutyramide (I40A)

To a stirred solution of N-(9-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-6-oxo-6,9-dihydro-1H-purin-2-yl)isobutyramide (4.56 g, 5.92 mmol) in DCM (50 mL) was added pyridine (3.82 mL, 47.4 mmol) and then cooled to −5° C. whereupon DAST (3.13 mL, 23.7 mmol) was added in a dropwise fashion. The reaction was stirred at −5° C. for 2 hrs and then at RT for 4 hrs, whereupon the mixture was cooled to 0° C. To the cooled mixture was slowly added sat. aq. NaHCO$_3$ (100 mL) and the mixture was continued stirring at RT for 20 min. The mixture was extracted with DCM (6×20 mL) then combined organics washed with sat. aq. NaHCO$_3$ (100 mL), brine (100 mL), dried over Na$_2$SO$_4$, filtered and concentrated. The residue was purified by silica gel chromatography (1-10% MeOH/DCM containing 0.1% TEA) then purified using RP-MPLC (C18, 60-100% ACN/H$_2$O containing 0.04% NH$_4$HCO$_3$) to give I40A (1.57 mg, 34%) as a white solid. LCMS m/z 772.5 (M+H)$^+$. $^1$H NMR (CD$_3$OD) δ 7.87 (s, 1H), 7.47-7.42 (m, 2H), 7.36-7.29 (m, 1H), 7.27-7.15 (m, 3H), 5.98 (d, J=2.6 Hz, 1H), 5.03 (ddd, J=52.3, 3.5, 2.0 Hz, 1H), 4.83-4.76 (m, 1H), 4.48-4.35 (m, 1H), 3.75 (s, 3H), 3.75 (s, 3H), 3.56 (dd, J=10.2, 6.7 Hz, 1H), 3.42 (dd, J=10.3, 4.6 Hz, 1H), 4.81-4.70 (m, 1H), 4.21 (dt, J=27.6, 4.5 Hz, 1H), 3.59 (t, J=4.9 Hz, 2H), 2.71 (hept, J=6.9 Hz, 1H), 1.21 (d, J=6.9 Hz, 3H), 1.20 (d, J=6.8 Hz, 3H), 0.89 (s, 9H), 0.10 (s, 3H), 0.05 (s, 3H), 3.75 (s, 3H). $^{19}$F NMR (CD$_3$OD) δ −201.20.

N-(9-((2R,3S,4R,5R)-5-((Bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (I40B)

To a solution of I40A (3.15, 4.08 mmol) in THF (30 mL) at RT was added TBAF (1.0 M in THF, 4.90 mL, 4.9 mmol) slowly. The resulting mixture was stirred at RT for 3 hrs and then concentrated under reduced pressure. The residue was purified using RP-MPLC (C18, 60-100% ACN/H$_2$O containing 0.04% NH$_4$HCO$_3$) to give I40B (2.24 g, as an admixture; 8% tetrabutylammonia by weight, 92% product by weight assigned by $^1$H NMR, 77% yield) as a white solid. This material was used "as is" in subsequent transformations. LCMS m/z 658.1 (M+H)$^+$. $^1$H NMR (CD$_3$OD) δ 7.72 (s, 1H), 7.47-7.43 (m, 2H), 7.36-7.30 (m, 4H), 7.29-7.16 (m, 3H), 6.85-6.80 (m, 4H), 6.04 (d, J=1.2 Hz, 1H), 5.03 (ddd, J=51.3, 2.7, 1.1 Hz, 1H), 4.60 (d, J=13.1 Hz, 1H), 6.80 (d, J=8.5 Hz, 2H), 6.06 (d, J=6.0 Hz, 1H), 5.85 (d, J=7.3 Hz, 1H), 5.13 (dd, J=54.0, 3.0 Hz, 1H), 4.61-4.48 (m, 1H), 3.76 (s, 3H), 3.76 (s, 3H), 3.59-3.50 (m, 1H), 3.41 (dd, J=9.9, 5.0 Hz, 1H), 2.70 (hept, J=6.8 Hz, 1H), 1.21 (d, J=6.9 Hz, 3H), 1.20 (d, J=6.9 Hz, 3H)[tetrabutylammonium, 4CH$_2$ 3.26-3.19 (m, 2.65H), 4CH$_2$ 1.70-1.59 (m, 2.78H), 4CH$_2$ 1.40 (dq, J=14.7, 7.4 Hz, 2.79H), 4CH$_3$ 1.01 (t, J=7.4 Hz, 4.27)]. $^{19}$F NMR (CD$_3$OD) δ −201.60.

(2R,3S,4S,5R)-5-((Bis(4-methoxyphenyl)(phenyl)methoxy)methyl)-4-fluoro-2-(2-isobutyramido-6-oxo-1H-purin-9(6H)-yl)tetrahydrofuran-3-yl hydrogen phosphonate (I40C)

Starting material, I40B (3.04 g, 92% by weight, 4.25 mmol), was co-evaporated with pyridine (3×15 mL) then dissolved in pyridine (30 mL) and to this solution was added diphenyl phosphite (3.00 mL, 15.6 mmol). The reaction mixture was stirred at RT for 1 hr and then cooled in an ice/acetone bath, whereupon TEA (4.7 mL, slowly) and then H$_2$O (4.7 mL, dropwise) were added. The bath was removed and the reaction mixture was stirred at RT for 2 hrs and then concentrated under reduced pressure. The residue was purified using RP-MPLC (C18, 15-35% ACN/H$_2$O) to give I40C (1.73 g, as an admixture; 19% triethylamine by weight, 81% product by weight assigned by $^1$H NMR, 46% yield) as a white solid. This material was used "as is" in subsequent transformations. LCMS m/z 722.3 (M+H)$^+$.

(2R,3S,4S,5R)-4-Fluoro-5-(hydroxymethyl)-2-(2-isobutyramido-6-oxo-1H-purin-9(6H)-yl)tetrahydrofuran-3-yl hydrogen phosphonate (Intermediate 40)

To a suspension of I40C (1.73 g, 81% by weight, 1.94 mmol) in DCM (10 mL) was added H$_2$O (0.35, 19.4 mmol)

followed by a solution of DCA (1.44 mL, 17.5 mmol) in DCM (21 mL). The reaction mixture was stirred for 1 hr at RT and then TES (20 mL) was added. After stirring for an additional 2 hrs, pyridine: MeOH (1:1, 10 mL) was added. The mixture was concentrated under reduced pressure and the residue was purified by silica gel chromatography (10-80% MeOH/DCM) to give Intermediate 40 (0.93 g as a salt; 6% triethyl amine by weight, 6% pyridine by weight, 88% product by weight assigned by $^1$H NMR, quantitative yield) as a white solid. LCMS (Method C, $T_R$=0.93 min) m/z 418.2 (M-H)$^-$.

$^1$H NMR (CD$_3$OD) δ 8.11 (s, 1H), 6.92 (d, J=638.2 Hz, 1H), 6.20 (s, 1H), 5.31 (d, J=30.7 Hz, 1H), 5.24 (d, J=30.7 Hz, 1H), 4.41 (dtd, J=12.1, 5.9, 2.4 Hz, 1H), 4.03-3.90 (m, 2H), 2.77 (hept, J=6.8 Hz, 1H), 1.23 (d, J=6.9 Hz, 6H) [pyridine, 2CH 8.85 (d, J=5.2 Hz, 0.72H), CH 8.59 (t, J=7.9 Hz, 0.36H), 2CH 8.05 (m, 0.69H)][triethyl amine, 3CH$_2$ 3.20 (q, J=7.3 Hz, 1.53H), 3CH$_3$ 1.30 (t, J=7.3 Hz, 2.41H)] 0.19F NMR (CD$_3$OD) δ -203.13. $^{31}$P NMR (CD$_3$OD) δ 2.64.

Example 25

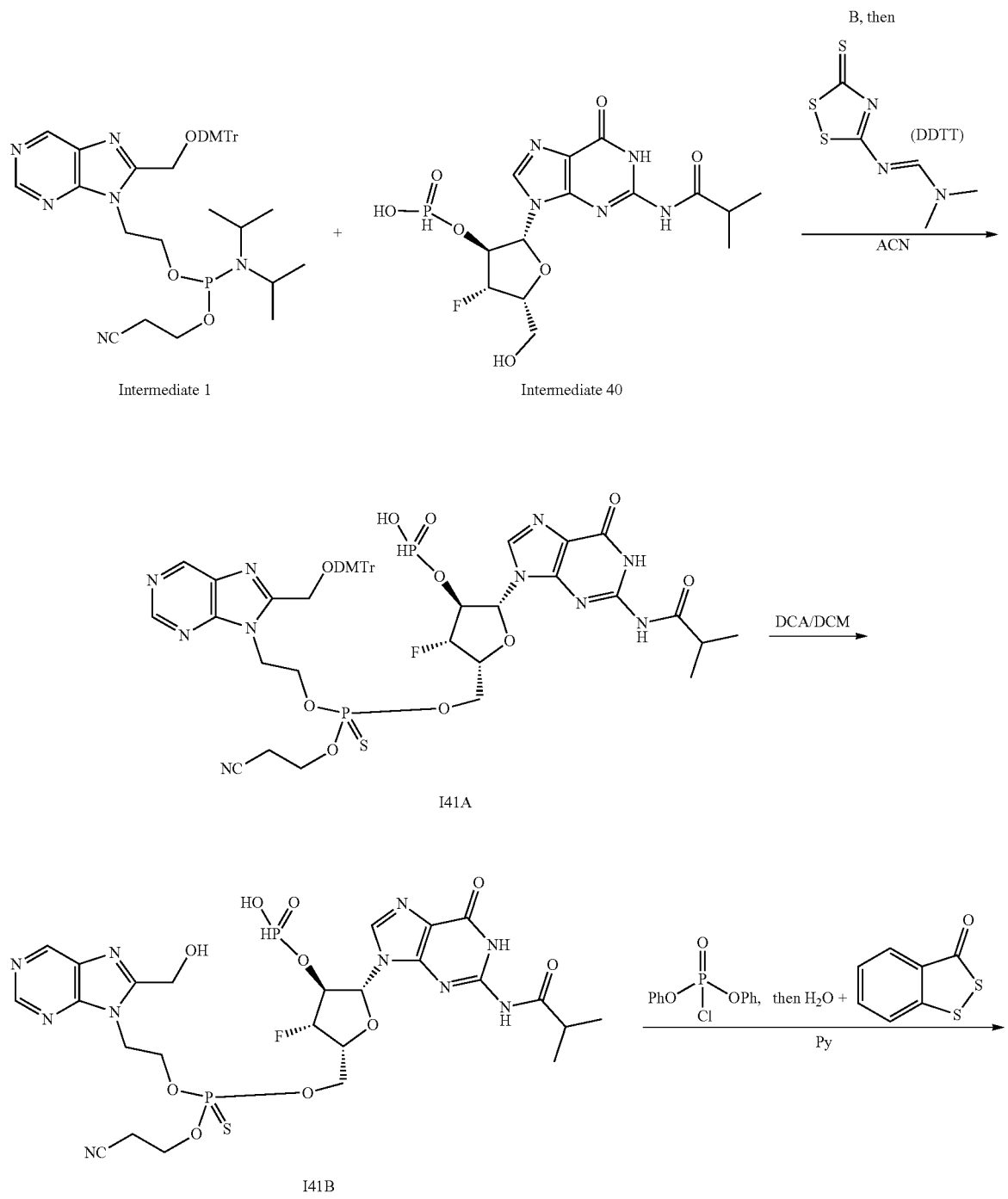

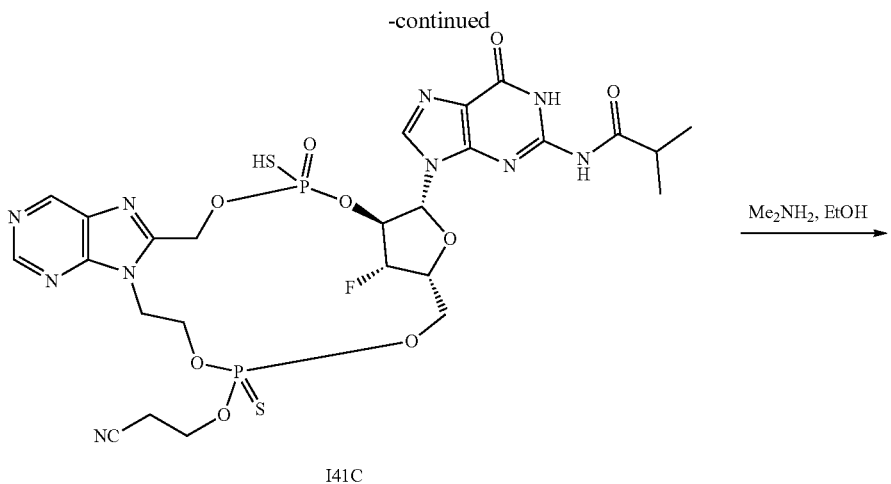

I41C (1S,21R,23R,24S)-23-(2-Amino-6-oxo-6,9-dihydro-1H-purin-9-yl)-24-fluoro-3,18-disulfanyl-2,4,17,19,22-pentaoxa-7,10,12,14-tetraaza-3lambda5,18lambda5-diphosphatetracyclo[19.2.1.06,14.08,13]tetracosa-6,8,10,12-tetraene-3,18-dione (Example 25)

Example 25 diastereomers (Diastereomers A-D) were prepared according to procedures analogous to those outlined in Example 1.

(2R,3S,4S,5R)-5-((((2-(8-((Bis(4-methoxyphenyl)(phenyl)methoxy)methyl)-9H-purin-9-yl)ethoxy)(2-cyanoethoxy)phosphorothioyl)oxy)methyl)-4-fluoro-2-(2-isobutyramido-6-oxo-1H-purin-9(6H)-yl)tetrahydrofuran-3-yl hydrogen phosphonate (I41A)

LCMS (T$_R$=1.27 min) m/z 1045.3 (M–H)$^-$. $^{31}$P NMR (CD$_3$OD) δ 68.54, 68.22, 2.51, 2.47. $^{19}$F NMR (CD$_3$OD) δ –202.52, –202.59.

(2R,3S,4S,5R)-5-((((2-Cyanoethoxy) (2-(8-(hydroxymethyl)-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I41B)

LCMS (T$_R$=0.71 min) m/z 743.3 (M–H)$^-$. $^{31}$P NMR (CD$_3$OD) δ 68.64, 68.40, 2.62, 2.59. $^{19}$F NMR (CD$_3$OD) δ –202.71, –202.74.

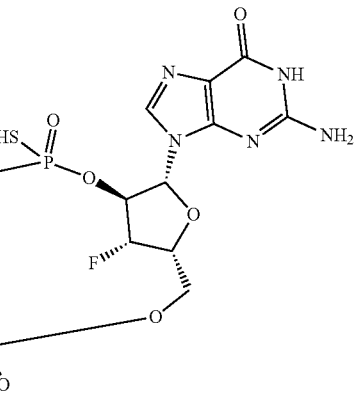

Example 25

N-{9-[(1S,21R,23R,24S)-18-(2-Cyanoethoxy)-24-fluoro-3-oxo-3-sulfanyl-18-sulfanylidene-2,4,17,19,22-pentaoxa-7,10,12,14-tetraaza-3lambda5,8lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (I41C)

LCMS (Method C, T$_R$=1.24 and 1.27 min) m/z 757.2 (M–H)$^-$. $^{19}$F NMR (CD$_3$OD) δ –204.25, –204.78,–205.43, –206.32.

Example 25 diastereomers (Diastereomers A-D) were purified by prep. RP-HPLC (Waters, X Bridge C18, 5 μm, 19×150 mm column eluting with 0-10% [32 min], 10-100% [35 min] ACN/H$_2$O containing 0.04% NH$_4$HCO$_3$, Flow rate=7 mL/min) to give 4 pure diastereomers (Diastereomer A: 13.9 mg; Diastereomer B: 9.0 mg; Diastereomer C: 7.0 mg; Diastereomer D: 29.3 mg; Total: 59.2 mg, 50%) of Example 25. Example 25B (Diastereomer B): Prep. RP-HPLC: T$_R$=24.0 min. LCMS (Method D, T$_R$=1.18 min) m/z 634.0 (M–H)$^-$. $^1$H NMR (D$_2$O) δ 8.89 (s, 1H), 8.76 (s, 1H), 7.95 (s, 1H), 5.84 (d, J=5.0 Hz, 1H), 5.41 (dd, J=11.7, 5.7 Hz, 1H), 5.33-5.22 (m, 2H), 5.15 (dd, J=13.5, 7.6 Hz, 1H), 5.05 (dd, J=13.7, 5.8 Hz, 1H), 4.46 (app dt, J=13.8, 8.3 Hz, 2H), 4.25 (app dd, J=10.7, 5.5 Hz, 1H), 4.20-4.13 (m, 1H), 4.03-3.89 (m, 2H). $^{19}$F NMR (D$_2$O) 8-206.9. $^{31}$P NMR (D$_2$O) δ 56.5, 56.2. Example 25C (Diastereomer C): Prep. RP-HPLC: T$_R$=25.5 min. LCMS (Method D, T$_R$=1.21 min) m/z 634.0 (M–H)$^-$. $^1$H NMR (D$_2$O) δ 8.89 (s, 1H), 8.76 (s, 1H), 7.74 (s, 1H), 5.84 (d, J=5.0 Hz, 1H), 5.40 (app t, J=5.9 Hz, 1H), 5.25 (app ddd, J=19.9, 10.3, 5.4 Hz, 2H), 5.14 (dd, J=13.6, 7.7 Hz, 1H), 5.02 (dd, J=13.6, 5.9 Hz, 1H), 4.56-4.38 (m, 2H), 4.29-4.16 (m, 2H), 4.15-4.07 (m, 1H), 3.97-3.85 (m, 1H). $^{19}$F NMR (D$_2$O) δ -206.6. $^{31}$P NMR (D$_2$O) δ 56.4, 55.9. Example 25D (Diastereomer D): Prep. RP-HPLC: T$_R$=32.5 min. LCMS (Method D, T$_R$=1.33 min) m/z 634.0 (M−H)$^-$. $^1$H NMR (D$_2$O) δ 8.96 (s, 1H), 8.81 (s, 1H),
7.63 (s, 1H), 5.84 (d, J=5.4 Hz, 1H), 5.38 (dt, J=52.4, 6.1 Hz, 1H), 5.18 (app qd, J=10.8, 5.9 Hz, 2H), 4.87 (dd, J=13.2, 5.1 Hz, 2H), 4.53-4.44 (m, 1H), 4.44-4.35 (m, 1H), 4.25 (app td, J=9.4, 4.6 Hz, 2H), 4.13 (dd, J=11.1, 8.5 Hz, 1H), 3.98-3.89 (m, 1H). $^{19}$F NMR (D$_2$O) δ -205.4. $^{31}$P NMR (D$_2$O) δ 55.6, 55.5.
Example 26
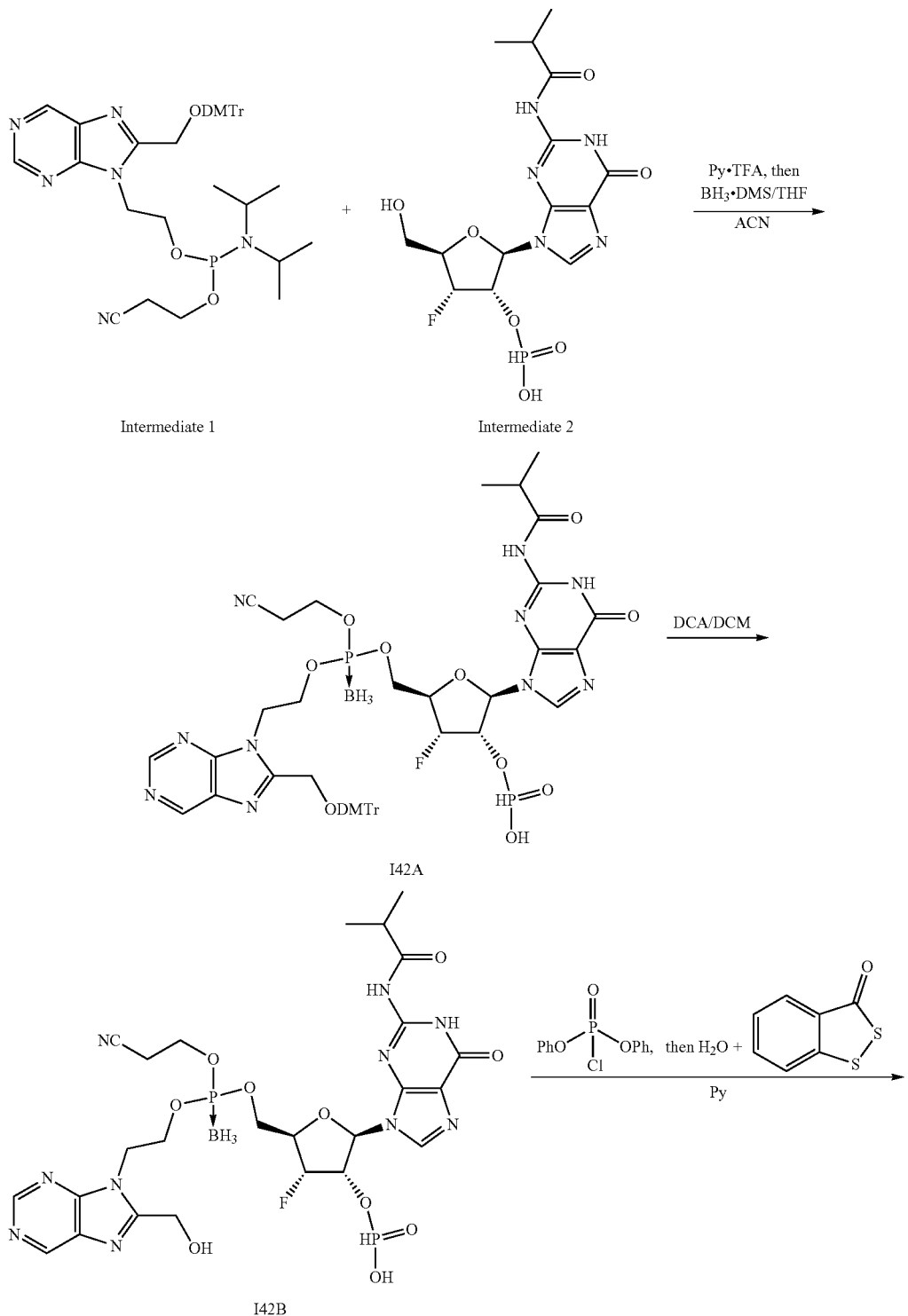

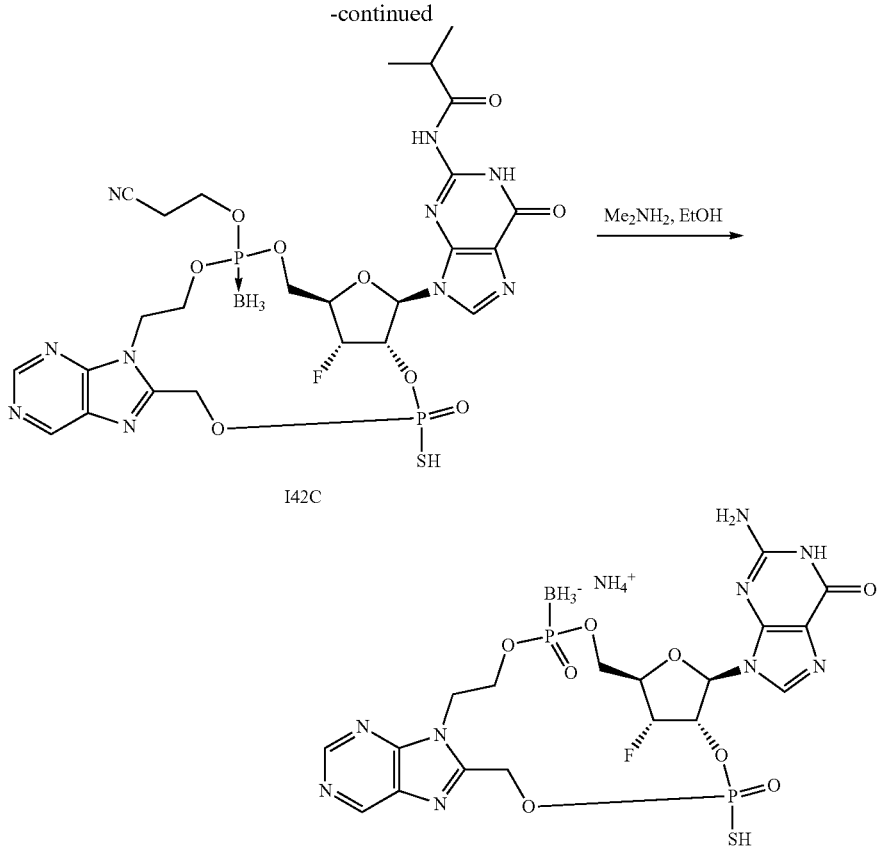

I42C

Example 26

Intermediate 42A (I42A)

A suspension of Intermediate 1 (199 mg, 0.29 mmol) and crushed, freshly activated 3 Å MS (200 mg) in ACN (3 mL) was stirred for 45 min. In the meantime, a suspension of Intermediate 2 (100 mg, 0.24 mmol), Py.TFA (69 mg, 0.36 mmol), and crushed, freshly activated 3 Å MS (200 mg) in ACN (5 mL) was stirred with for 45 min. The supernatant containing Intermediate 1 was added to the suspension of Intermediate 2 in a dropwise fashion, via syringe. The flask and residual MS that contained Intermediate 1 were washed with ACN (1 mL) and the supernatant was again added to the mixture containing Intermediate 2. The resulting mixture was stirred at RT for 1 hr, and then concentrated under reduced pressure. The residue was suspended in DCM (10 mL) and the suspension was cooled to 0° C., whereupon a solution of borane-dimethylsulfide complex in THF (2.0 M, 393 µL, 0.79 mmol) was added in a dropwise fashion. The reaction mixture was stirred at RT for 1 hr and then filtered, followed by washing with ACN. The filtrate was concentrated under reduced pressure, then redissolved in MeOH (50 mL) and silica gel (3 g) was added. The mixture was concentrated under reduced pressure and the residue was purified by silica gel chromatography (0-100% MeOH/DCM) to give I42A (62 mg, 25%) as a mixture of 2 diastereomers: LCMS (Method A) m/z 1027.2 (M−H)⁻. $^{19}$F NMR (CD$_3$OD) δ −198.35 (br s), −198.38 (br s). $^{31}$P NMR (CD$_3$OD) δ P–BH$_3$ 116.96 (br s), P=O 2.36.

Intermediate 42B (I42B)

To a rapidly stirred mixture of I42A (62 mg, 0.060 mmol) and H$_2$O (30 mg, 1.67 mmol) in DCM (5 mL) was added a solution of 6% dichloroacetic acid in DCM (5 mL). After 15 min at RT TES (5 mL) was introduced and the reaction mixture was stirred for 15 min. A 1:1 mixture of pyridine and MeOH (2 mL) was added, and then the reaction mixture was concentrated under reduced pressure. The residue was dissolved in MeOH (50 mL), and silica gel (4 g) was added. The mixture was concentrated to dryness, and purified by silica gel chromatography (0-100% MeOH/DCM) to give semi-pure I42B (42 mg, 95%) as a mixture of 2 diastereomers: LCMS (Method A) m/z 725.5 (M−H)⁻. $^{19}$F NMR (CD$_3$OD) δ −198.29 (br s), −198.45 (br s). $^{31}$P NMR (CD$_3$OD) δ P–BH$_3$ 117.36 (br s), P=O 2.50.

Intermediate 42C (I42C)

To dry pyridine (4 mL) cooled to −30° C. was added diphenyl phosphoryl chloride (240 µL, 0.12 mmol). After 5 min, a solution of I42B (42 mg, 0.058 mmol) in pyridine (2 mL) was added in a dropwise fashion over 20 min while maintaining the bath temperature between −35 and −30° C. After stirring at −30° C. for 30 min, H$_2$O (52 mg, 0.29 mmol) and 3H-benzo[c][1,2]dithiol-3-one (15 mg, 0.087 mmol) were added in rapid succession. The reaction mixture was allowed to warm slowly to RT as the bath warmed, and then stirred for 0.5 hrs. The reaction mixture was added in a dropwise fashion to a solution of 0.04% NH$_4$HCO$_3$ in H$_2$O (8 mL) at 0° C. The mixture was partially concentrated (to ca. 3 mL) under reduced pressure, then purified using RP-MPLC (C18, 0-60% ACN/H$_2$O containing 0.04% NH$_4$HCO$_3$) to give I42C (25 mg, 58% of a 1.0:1.3:1.7:2.8 mixture of diastereomers by $^{19}$F NMR) as a white solid.

LCMS (Method C) m/z 739.2 (M−H)⁻. ¹⁹F NMR (D₂O) δ −195.72, −196.14, −197.81 (major), −198.33 (major). ³¹P NMR (D₂O) δ P—BH₃ 117.33 (br s), P—BH₃ 114.21 (br s), P=S 58.86, P=S 58.08, P=S 55.63 (2 overlapping singlets).

[(1S,21R,23R,24R)-23-(2-Amino-6-oxo-6,9-dihydro-1H-purin-9-yl)-24-fluoro-3,18-dioxo-3-sulfanyl-2,4,17,19,22-pentaoxa-7,10,12,14-tetraaza-3lambda5,18lambda5-diphosphatetracyclo [19.2.1.06,14.08,13]tetracosa-6,8,10,12-tetraen-18-yl]boranuide (Example 26)

A solution of I42C (25 mg, 0.034 mmol, 1.0:1.3:1.7:2.8 mixture of diastereomers) in MeNH₂/EtOH (33%, 3 mL) was stirred at RT for 48 hrs, and then concentrated under reduced pressure. The residue was purified by prep. RP-HPLC(XBridge Prep C18 OBD, 5 μm, 19×150 mm column eluting with 0-10% ACN/50 mM aq. NH₄HCO₃ over 15 min, then 10-20% ACN/50 mM aq. NH₄HCO₃ over 10 min, Flow rate=10 mL/min) to give 4 pure diastereomers of Example 26 (Diastereomer A: T$_R$=12.5 min; Diastereomer B: T$_R$=13.1 min, 1.7 mg; Diastereomer C: T$_R$=17.7 min, 2.1 mg; Diastereomer D: T$_R$=19.4 min). Example 26C (Diastereomer C): LCMS (Method D, T$_R$=1.38 min) m/z 616.0 (M−H)⁻. ¹H NMR (D₂O) δ 9.06 (s, 1H), 8.89 (s, 1H), 8.20 (s, 1H), 6.34 (d, J=7.5 Hz, 1H), 5.26 (dd, J=13.1, 8.0 Hz, 1H), 5.15 (dd, J=53.0, 3.8 Hz, 1H), 4.80-4.21 (comp, 7H), 4.02-3.87 (comp, 2H). ³¹P NMR (D₂O) δ 97.24 (br s, 1P), 56.14 (s, 1P). ¹⁹F NMR (D₂O) δ −198.42.

Intermediate 43

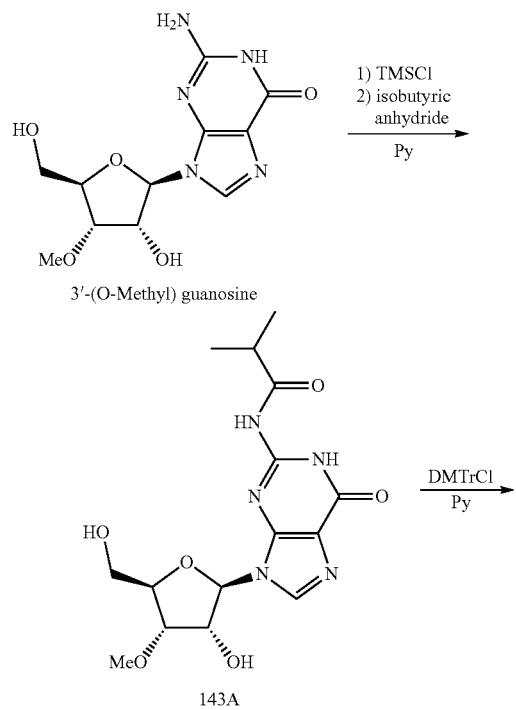

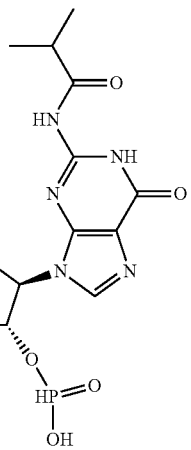

Intermediate 43

Intermediate 43 was prepared according to procedures analogous to those outlined in WO 2018/138684.

N-(9-((2R,3R,4S,5R)-3-Hydroxy-5-(hydroxymethyl)-4-methoxytetrahydrofuran-2-yl)-6-oxo-6,9-dihydro-1H-purin-2-yl)isobutyramide (I43A)

To a suspension of 3'-(O-Methyl) guanosine (1.11 g, 3.73 mmol, ChemGenes Corporation) in pyridine (20 mL) at RT was added TMSCl (2.37 mL, 18.67 mmol) in a dropwise fashion. After 2 hrs at RT, isobutyric anhydride (1.86 mL, 11.20 mmol) was added in a slow, dropwise fashion. The reaction mixture was stirred at RT for 2 hrs, whereupon MeOH (3.8 mL) was added followed by conc. aq. ammonium hydroxide (7.6 mL) in a dropwise fashion with occasional cooling in a water bath. The mixture was concentrated under reduced pressure, and then purified by silica gel chromatography (0-10% MeOH/DCM) to give I43A (532 mg, 39%) as a white solid. LCMS m/z 368.2 (M+H)$^+$. $^1$H NMR (CD$_3$OD) δ 8.34 (s, 1H), 6.00 (d, J=5.0 Hz, 1H), 4.70 (app t, J=5.0 Hz, 1H), 4.20-4.17 (m, 1H), 4.03 (app t, J=4.8 Hz, 1H), 3.89 (dd, J=12.1, 3.3 Hz, 1H), 3.77 (dd, J=12.3, 3.5 Hz, 1H), 3.54 (s, 3H), 2.76 (sept, J=7.0 Hz, 1H), 1.27 (d, J=7.0 Hz, 6H).

N-(9-((2R,3R,4S,5R)-5-((Bis(4-methoxyphenyl) (phenyl)methoxy)methyl)-3-hydroxy-4-methoxytetrahydrofuran-2-yl)-6-oxo-6,9-dihydro-1H-purin-2-yl)isobutyramide (I43B)

To a solution of I43A (232 mg, 0.63 mmol) in pyridine (10 mL) cooled to 0° C. was added DMTrCl (321 mg, 0.95 mmol). The bath was removed and the reaction mixture was allowed to stir at RT overnight. The mixture was concentrated to dryness under reduced pressure, and then the residue was purified by silica gel chromatography (0-10% MeOH/DCM containing 1% TEA) to give I43B (423 mg, 100%) as a white solid. LCMS m/z 670.3 (M+H)$^+$. $^1$H NMR (CDCl$_3$ one drop of CD$_3$OD) δ 7.81 (s, 1H), 7.45-7.18 (comp, 9H), 6.83-6.76 (comp, 4H), 5.83 (d, J=5.8 Hz, 1H), 4.84 (app t, J=5.5 Hz, 1H), 4.26-4.23 (m, 1H), 3.97 (dd, J=5.3, 3.8 Hz, 1H), 3.47-3.43 (m, 1H), 3.45 (s, 3H), 3.30-3.27 (m, 1H), 2.32 (sept, J=6.9 Hz, 1H), 1.13 (d, J=6.9 Hz, 3H), 1.05 (d, J=6.9 Hz, 3H).

(2R,3R,4R,5R)-5-((Bis(4-methoxyphenyl)(phenyl) methoxy)methyl)-2-(2-isobutyramido-6-oxo-1H-purin-9(6H)-yl)-4-methoxytetrahydrofuran-3-yl hydrogen phosphonate (I43C)

To a solution of I43B (423 mg, 0.63 mmol) in pyridine (10 mL) was added diphenyl phosphite (484 µL, 2.53 mmol). The resulting solution was stirred at RT for 1 hr, then cooled to 0° C., whereupon TEA (2 mL) was added followed by H$_2$O (2 mL). The mixture was stirred at RT for 1 hr, then concentrated under reduced pressure to give crude I43C which was used without further purification. LCMS m/z 734.4 (M+H)$^+$.

(2R,3R,4R,5R)-5-(Hydroxymethyl)-2-(2-isobutyramido-6-oxo-1H-purin-9(6H)-yl)-4-methoxytetrahydrofuran-3-yl hydrogen phosphonate (Intermediate 43)

To a solution of crude I43C (463 mg, 0.63 mmol) in DCM (7 mL) was added H$_2$O (114 µL, 6.31 mmol) followed by a solution of DCA (468 µL, 5.68 mmol) in DCM (7 mL). The resulting bright orange solution was stirred at RT for 15 min, whereupon TES (1 mL) was added. After 1 hr at RT, pyridine (2 mL) was added, and then the mixture was concentrated under reduced pressure. The residue was redissolved in MeOH (10 mL) and silica gel (4 g) was added. The mixture was concentrated to dryness, and then the residue was purified by silica gel chromatography (0-100% MeOH/DCM) to give Intermediate 43, which was still contaminated with phosphorus reagents from I43C. LCMS m/z 430.1 (M−H)$^−$.

Example 27

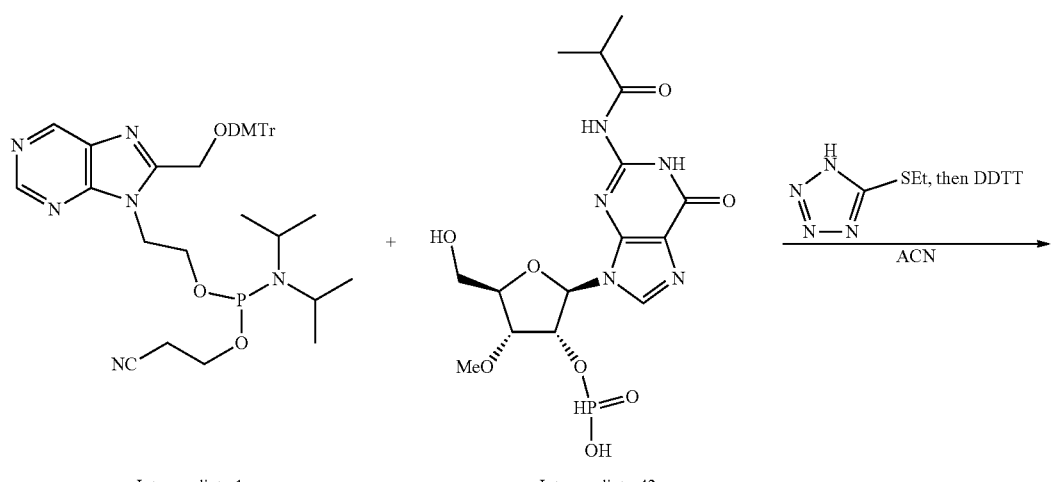

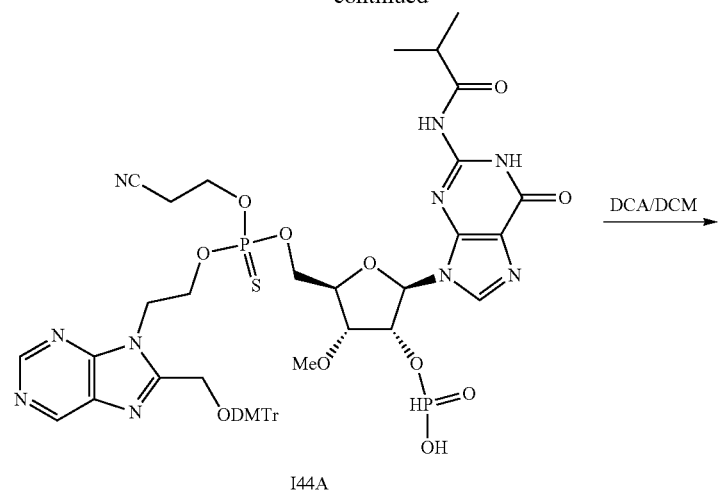
I44A
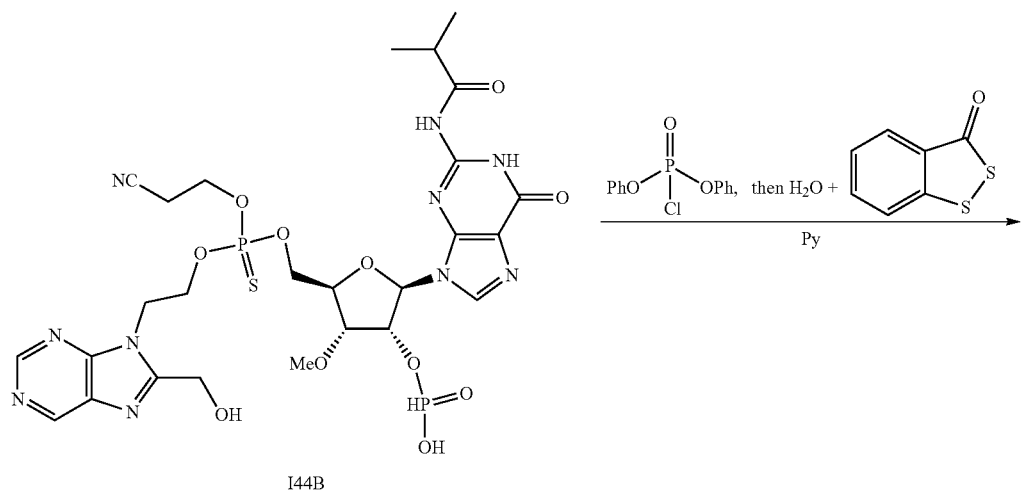
I44B
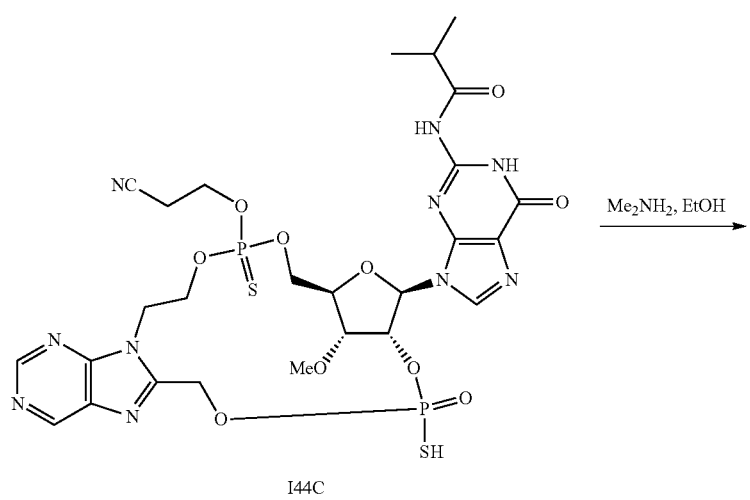
I44C

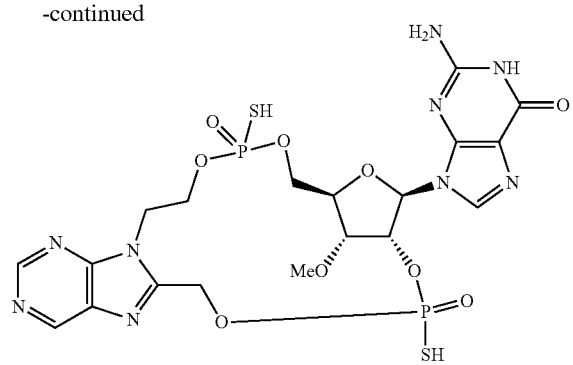

Example 27

(2R,3R,4R,5R)-5-((((2-(8-((Bis(4-methoxyphenyl) (phenyl)methoxy)methyl)-9H-purin-9-yl)ethoxy)(2-cyanoethoxy)phosphorothioyl)oxy)methyl)-2-(2-isobutyramido-6-oxo-1H-purin-9(6H)-yl)-4-methoxytetrahydrofuran-3-yl hydrogen phosphonate (I44A)

A suspension of Intermediate 1 (690 mg, 0.99 mmol) and crushed, freshly activated 3 Å MS (1 g) in ACN (10 mL) was stirred at RT for 1 hr. In the meantime, a suspension of crude Intermediate 43 (427 mg, 0.99 mmol), (ethylthio)tetrazole (258 mg, 1.98 mmol), and crushed, freshly activated 3 Å MS (1 g) in ACN (10 mL) was stirred at RT for 1 hr under $N_2$. The supernatant containing Intermediate 1 was added to the suspension of Intermediate 43 in a dropwise fashion, via syringe. The flask and residual molecular sieves that contained Intermediate 1 was washed with ACN (2×1 mL) and the supernatant was again added to the mixture containing Intermediate 43. The resulting mixture was stirred at RT for 1 hr, whereupon DDTT (264 mg, 1.29 mmol) was added in one portion. The reaction mixture was stirred at RT for 2 hrs, and then filtered to remove the sieves. The filtrate was concentrated under reduced pressure, and the residue was purified by RP-MPLC (C18, 0-50% ACN/$H_2O$ containing 0.04% $NH_4HCO_3$) to give I44A (126 mg, 19% of a 1:1 mixture of diastereomers by $^{31}P$ NMR) as a pale yellow solid. LCMS m/z (M–H)$^-$ 1057.3. $^{31}P$ NMR ($D_2O$) δ 67.75 (P=S), 67.26 (P=S), 4.52 (P=O).

(2R,3R,4R,5R)-5-((((2-Cyanoethoxy) (2-(8-(hydroxymethyl)-9H-purin-9-yl)ethoxy)phosphorothioyl)oxy)methyl)-2-(2-isobutyramido-6-oxo-1H-purin-9(6H)-yl)-4-methoxytetrahydrofuran-3-yl hydrogen phosphonate (I44B)

To a rapidly stirred mixture of I44A (126 mg, 0.12 mmol, 1.0:1.2 mixture of diastereomers) and $H_2O$ (43 mg, 2.38 mmol) in DCM (5 mL) was added DCA (98 µL, 1.19 mmol) in DCM (5 mL). After 15 min at RT, $Et_3SiH$ (0.5 mL) was introduced and the reaction mixture was stirred for 30 min. Pyridine (0.5 mL) was added, and then the reaction mixture was concentrated under reduced pressure. The residue was dissolved in MeOH (5 mL), and silica gel (2 g) was added. The mixture was concentrated to dryness, and purified by silica gel chromatography (0-100% MeOH/DCM) to give I44B (42 mg, 47% of a 1.0:1.1 mixture of diastereomers by $^{31}P$ NMR) as a white solid: LCMS m/z 755.1 (M–H)$^-$. $^{31}P$ NMR ($CD_3OD$) δ 68.49 (P=S), 68.35 (P=S), 2.83 (P=O).

N-{9-[(1R,21R,23R,24R)-18-(2-Cyanoethoxy)-24-methoxy-3-oxo-3-sulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraen-23-yl]-6-oxo-6,9-dihydro-1H-purin-2-yl}-2-methylpropanamide (I44C)

To dry pyridine (5 mL) cooled to –30° C. was added diphenyl phosphoryl chloride (231 µL, 1.11 mmol). After 5 min, a solution of I44B (42 mg, 0.056 mmol) in pyridine (1.5 mL) was added in a dropwise fashion over 20 min while maintaining the bath between –35 and –30° C. After stirring at –30° C. for 45 min, $H_2O$ (50 mg, 2.78 mmol) and 3H-benzo[c][1,2]dithiol-3-one (14 mg, 0.083 mmol) were added in rapid succession. The reaction mixture was allowed to warm to –5° C. as the bath warmed over 1 hr, then the bath was removed and the reaction mixture was stirred at RT for 30 min. The reaction mixture then quenched by adding in a dropwise fashion to a –5° C. solution of sodium thiosulfate (50 mg) in $H_2O$ (7 mL). The mixture was concentrated under reduced pressure, and then the residue was purified using RP-MPLC (C18, 0-50% ACN/$H_2O$ containing 0.04% $NH_4HCO_3$) to give I44C (21 mg, 49% of a 1.0:1.3:2.5:5.5 mixture of diastereomers by $^{31}P$ NMR) as a white solid: LCMS m/z 769.1 (M–H)$^-$. $^{31}P$ NMR ($CD_3OD$) δ 69.00, 67.83, 65.76, 65.27, 57.80, 57.69, 56.68, 56.42.

(1R,21R,23R,24R)-23-(2-Amino-6-oxo-6,9-dihydro-1H-purin-9-yl)-24-methoxy-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 27)

A solution of I44C (21 mg, 0.027 mmol, 1.0:1.4:2.3:3.0 mixture of diastereomers) in $MeNH_2$/EtOH (33%, 4 mL) was stirred at RT for 4 hrs, and then concentrated under reduced pressure. The residue was purified by prep. RP-HPLC (XBridge C18, 5 µm, 18×150 mm column) eluting with 0-10% ACN/50 mM aq. $NH_4HCO_3$ over 15 min, then 10-20% ACN/50 mM aq. $NH_4HCO_3$ over 3 min with a flow rate=10 mL/min to give 4 pure diastereomers (Diastereomer A: $T_R$=11.7 min, 2.0 mg; Diastereomer B: $T_R$=12.1 min, 4.6 mg; Diastereomer C: $T_R$=14.4 min, 5.2 mg; Diastereomer D: $T_R$=16.5 min, 2.6 mg; Total: 14.4 mg, 80%) of Example 27. Example 27B (Diastereomer B): LCMS (Method D, $T_R$=1.17 min) m/z 646.1 (M–H)$^-$. $^1H$ NMR ($D_2O$) δ 8.96 (s, 1H), 8.84 (s, 1H), 7.67 (s, 1H), 5.81 (d, J=8.0 Hz, 1H), 5.25 (dd, J=12.8, 7.5 Hz, 1H), 4.81-4.75 (m, 1H), 4.70-4.50 (comp, 2H), 4.44-4.43 (m, 1H), 4.41-4.27 (comp, 2H), 4.25 (d, J=4.8 Hz, 1H), 4.12 (ddd, J=11.5, 4.8, 1.8 Hz, 1H), 4.02-3.96 (m, 1H), 3.88 (app dt, J=12.3, 2.5 Hz, 1H), 3.46 (s, 3H). $^{31}$P NMR (D$_2$O) δ 55.51, 55.22. Example 27C (Diastereomer C): LCMS (Method D, T$_R$=1.21 min) m/z 646.1 (M−H)$^-$. $^1$H NMR (D$_2$O) δ 8.99 (s, 1H), 8.86 (s, 1H), 7.50 (s, 1H), 5.69 (d, J=8.0 Hz, 1H), 5.24 (dd, J=12.8, 8.0 Hz, 1H), 4.79-4.70 (m, 1H), 4.68-4.59 (comp, 2H), 4.44-4.43 (m, 1H), 4.39-4.32 (comp, 2H), 4.29-4.27 (m, 1H), 4.25 (d, J=4.8 Hz, 1H), 4.04 (ddd, J=11.5, 4.5, 1.3 Hz, 1H), 3.89 (ddd, J=11.5, 2.8, 1.8 Hz, 1H), 3.45 (s, 3H). $^{31}$P NMR (D$_2$O) δ 55.01, 54.56. Example 27D (Diastereomer D): LCMS (Method D, T$_R$=1.26 min) m/z 646.1 (M−H)$^-$. $^1$H NMR (D$_2$O) δ 8.92 (s, 1H), 8.80 (s, 1H), 7.69 (s, 1H), 5.78 (d, J=8.0 Hz, 1H), 5.09-4.98 (comp, 3H), 4.71-4.54 (comp, 2H), 4.48-4.41 (m, 1H), 4.35-4.24 (comp, 2H), 3.99 (ddd, J=11.5, 6.8, 1.5 Hz, 1H), 3.88-3.84 (comp, 2H), 3.36 (s, 3H). $^{31}$P NMR (D$_2$O) δ 56.51, 55.76.

Intermediate 45

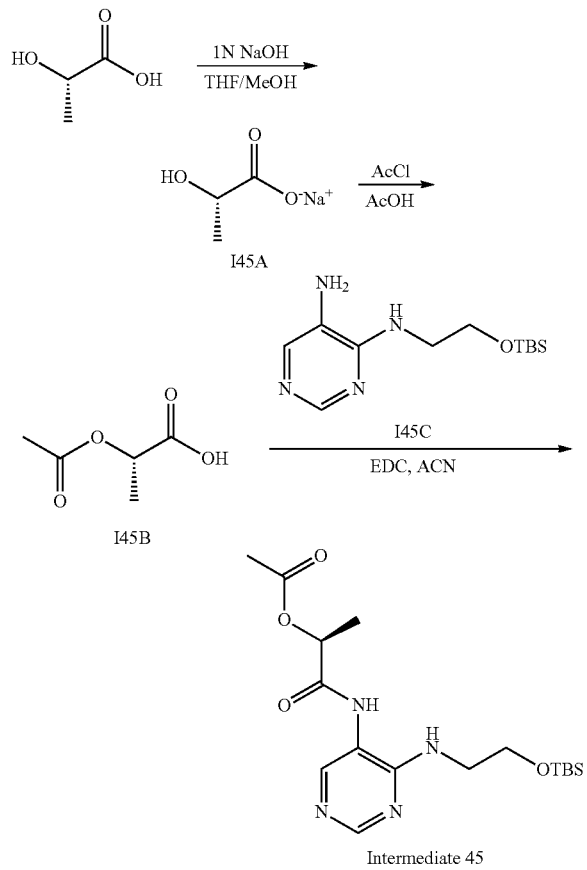

Sodium (S)-2-hydroxypropanoate (I45A)

To a solution of L-(+)-lactic acid (5.0 g, 55.5 mmol) in THF (100 mL) and MeOH (100 mL) was added 1N NaOH (83 mL, 83.3 mmol). The reaction mixture was stirred at RT for 3 hrs, and then concentrated under reduced pressure. The residue was co-evaporated with toluene 5 times to provide crude I45A which was used in the next step without further purification.

(S)-2-Acetoxypropanoic acid (I45B)

To a solution of I45A in acetic acid (25 mL) was added acetyl chloride (13.1 g, 167 mmol). The reaction mixture was stirred at RT for 3 hrs, and then concentrated under reduced pressure. The residue was partioned between diethyl ether and H$_2$O. The organic phase was washed with brine, dried over MgSO$_4$ and concentrated to give crude I45B (3.12 g, 43%), which was used "as is" in the next transformation.

(S)-1-((4-((2-((tert-Butyldimethylsilyl)oxy)ethyl)amino)pyrimidin-5-yl)amino)-1-oxopropan-2-yl acetate (I45C)

To a solution of I45B (2.19 g, 8.16 mmol) and I1C (1.40 g, 10.6 mmol) in ACN (40 mL) was added EDC (2.03 g, 10.6 mmol). The reaction mixture was stirred at RT for 5 hrs, and then concentrated under reduced pressure. The residue was purified by silica gel chromatography (0-10% MeOH/DCM) to give Intermediate 45 (2.34 g, 75%). LCMS m/z 383.4 (M+H)$^+$. $^1$H NMR (CDCl$_3$) δ 8.51 (s, 1H), 8.09 (s, 1H), 7.43 (br s, 1H), 5.61 (br t, J=5.3 Hz, 1H), 5.27 (q, J=6.8 Hz, 1H), 3.79 (app t, J=5.5 Hz, 2H), 3.64-3.60 (comp, 2H), 2.20 (s, 3H), 1.58 (d, J=7.0 Hz, 3H), 0.89 (s, 9H), 0.06 (s, 6H).$^+$ Example 28

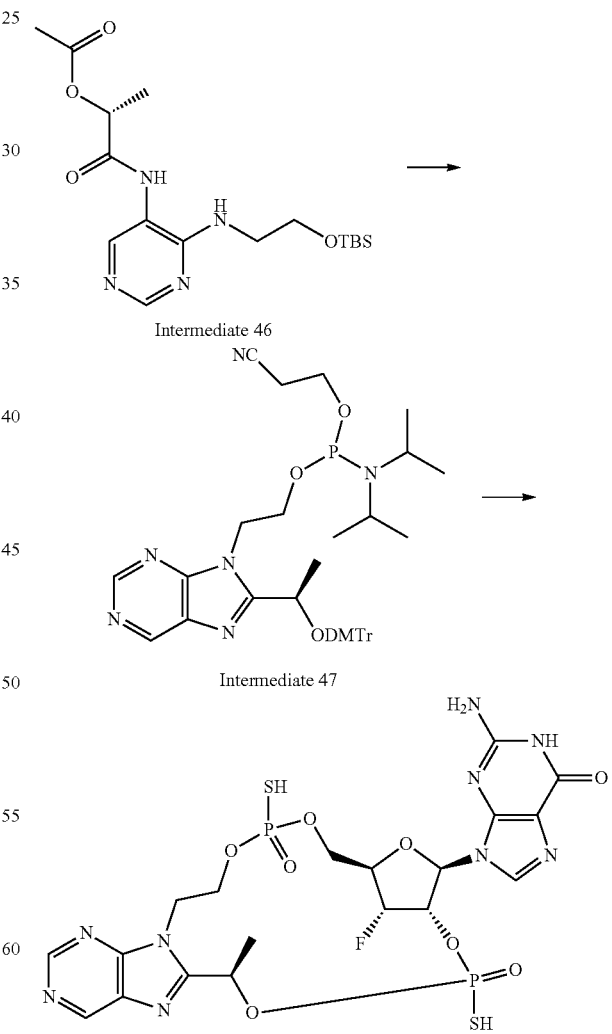

Example 28

Intermediate 46 was prepared using the identical procedure used for the preparation of Intermediate 45 but starting with D-(−)-lactic acid. Utilizing Intermediate 46 and the identical chemistry for the transformation of I1D to Intermediate 1, Intermediate 47 was prepared.

(1S,5R,21R,23R,24R)-23-(2-Amino-6-oxo-6,9-dihydro-1H-purin-9-yl)-24-fluoro-5-methyl-3,18-disulfanyl-2,4,17,19,22-pentaoxa-7,10,12,14-tetraaza-3lambda5,18lambda5-diphosphatetracyclo[19.2.1.06,14.08,13]tetracosa-6,8,10,12-tetraene-3,18-dione (Example 28)

Utilizing Intermediate 47 and Intermediate 2 along with identical chemistry for the preparation of Example 1, Example 28 was prepared. Example 28D (Diastereomer D): LCMS (Method D, T$_R$=1.24 min) m/z 648.0 (M−H)$^-$. $^1$H NMR (D$_2$O) δ 8.90 (s, 1H), 8.86 (s, 1H), 7.49 (s, 1H), 5.90 (d, J=7.8 Hz, 1H), 5.70 (dd, J=51.5, 3.5 Hz, 1H), 5.24-5.16 (m, 1H), 4.70-4.52 (comp, 4H), 4.43-4.36 (m, 1H), 4.29-4.27 (m, 1H), 4.10 (dd, J=11.0, 6.3 Hz, 1H), 3.82 (app br d, J=10.8 Hz, 1H), 1.45 (d, J=7.0 Hz, 3H). $^{19}$F NMR (D$_2$O) δ −197.92. $^{31}$P NMR (D$_2$O) δ 54.49, 51.82.

Example 29

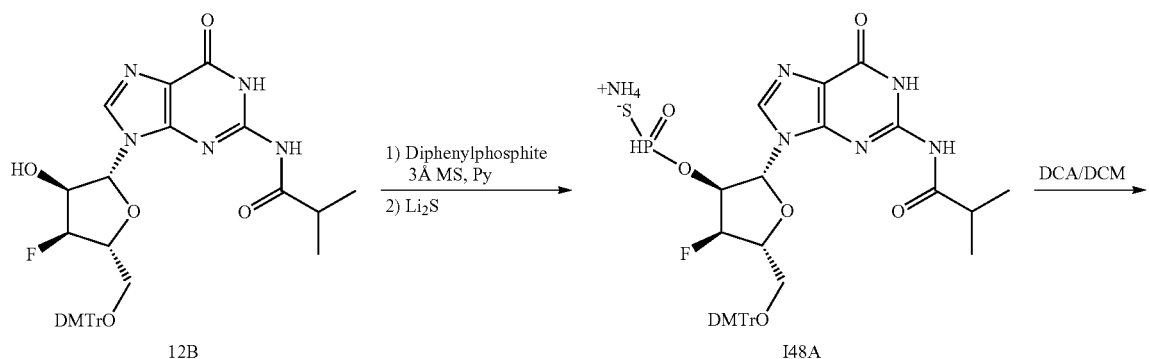

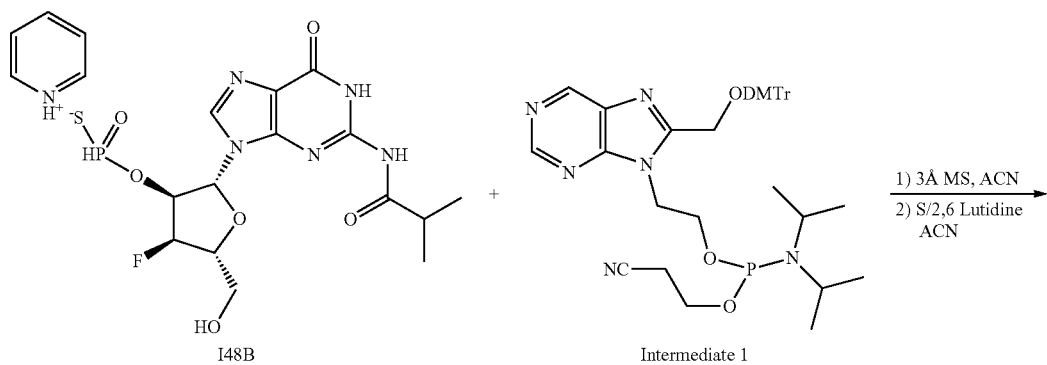

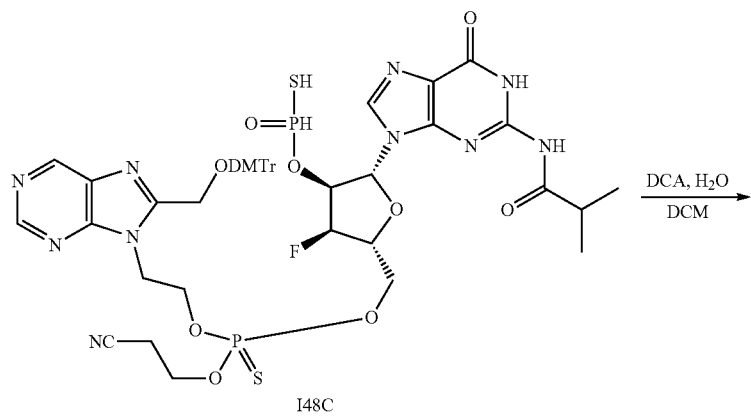

-continued

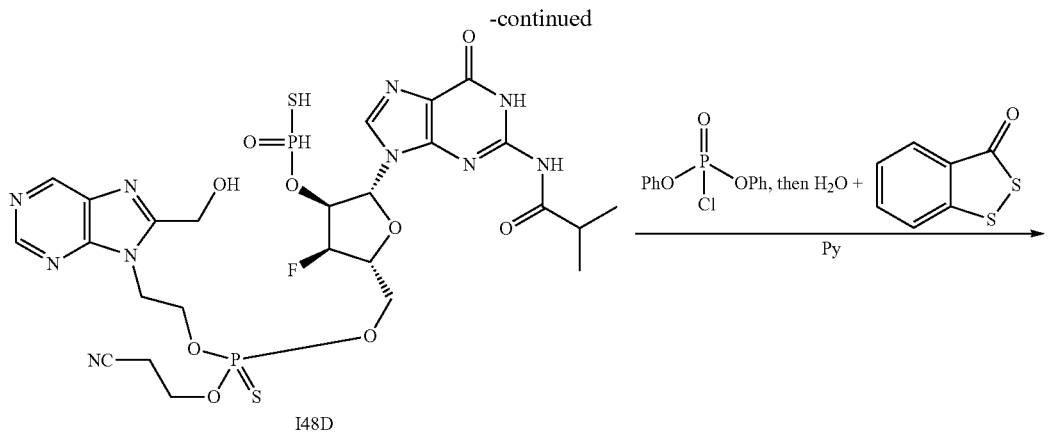

I48D

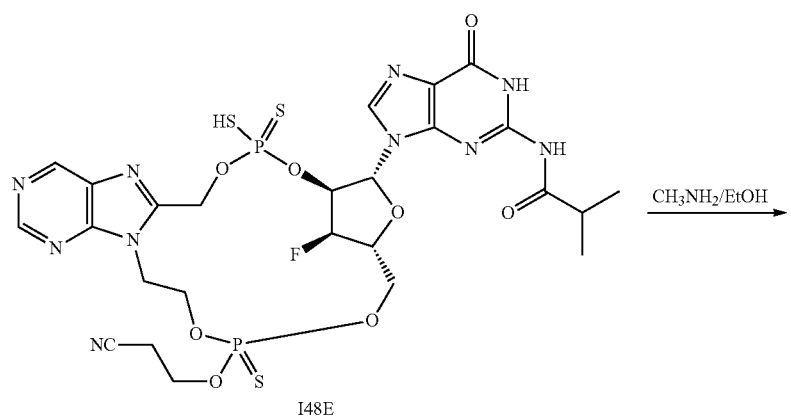

I48E

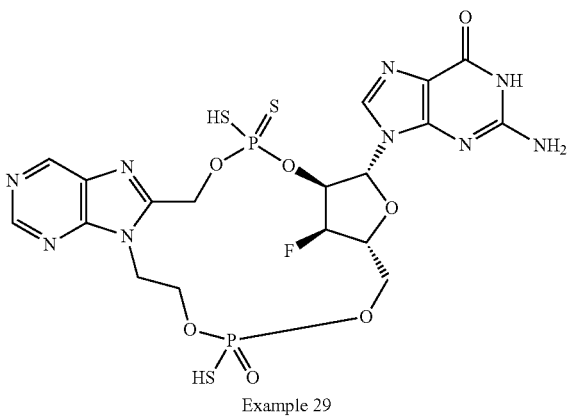

Example 29

O-((2R,3S,4R,5R)-5-((Bis(4-methoxyphenyl)(phenyl)methoxy)methyl)-4-fluoro-2-(2-isobutyramido-6-oxo-1H-purin-9(6H)-yl)tetrahydrofuran-3-yl) S-hydrogen phosphonothioate (I48A)

I2B (1.80 g, 2.74 mmol) was co-evaporated with pyridine three times then dissolved in pyridine (15 mL) and stirred with powdered, freshly activated 3 Å MS for 30 min. To this mixture was added diphenyl phosphite (2.50 mL, 13.0 mmol) in a dropwise fashion over 10 min. The reaction mixture was stirred at RT for 30 min, then cooled to 0° C., whereupon Li$_2$S (0.63 g, 13.7 mmol) was added in one portion. The mixture was stirred at 0° C. for 1 hr, and then warmed to RT and stirred overnight. The mixture was filtered and the filtrate was concentrated under reduced pressure, then purified by RP-MPLC (C18, 0-100% ACN/H$_2$O containing 0.4% NH$_4$HCO$_3$) to give 148A (0.95 g, 47%). LCMS m/z 736.4 (M−H)⁻.

O-((2R,3S,4R,5R)-4-Fluoro-5-(hydroxymethyl)-2-(2-isobutyramido-6-oxo-1H-purin-9(6H)-yl)tetrahydrofuran-3-yl) S-hydrogen phosphonothioate (I48B)

To a suspension of I48A (0.95 g, 1.26 mmol) in DCM (12 mL) was added H$_2$O (200 mg, 11.1 mmol) followed by a 6% solution of DCA in DCM (12 mL). The reaction mixture was stirred for 1 hr at RT, and then TES (6 mL) was added. After stirring for an additional 1 hr, pyridine (4 mL) was added. The mixture was concentrated under reduced pressure to give crude I48B (2.29 g) which was used as is in the next step. LCMS m/z 434.2 (M−H)⁻.

O-((2R,3S,4R,5R)-5-((((2-(8-((Bis(4-methoxyphenyl)(phenyl)methoxy)-9H-purin-9-yl)ethoxy)(2-cyanoethoxy)phosphorothioyl)oxy)methyl)-4-fluoro-2-(2-isobutyramido-6-oxo-1H-purin-9(6H)-yl)tetrahydrofuran-3-yl) S-hydrogen phosphonothioate (I48C)

A suspension of Intermediate 1 (0.48 g, 0.68 mmol) and crushed, freshly activated 3 Å MS (1.0 g) in ACN (15 mL) was stirred for 45 min under $N_2$. In the meantime, a suspension of I48B (1.03 g, 0.567 mmol) and crushed, freshly activated 3 Å MS (1.0 g) in ACN (15 mL) was stirred 45 min. The supernatant containing Intermediate 1 was added to the suspension of I48B in a dropwise fashion, via syringe over 15 min. The resulting mixture was stirred at RT for 1 hr, whereupon sulfur (1.80 g, 56.7 mmol) and 2,6-lutidine (0.66 mL, 5.66 mmol) were added. The reaction mixture was stirred at RT for 2 hrs, and then filtered to remove the sieves. The filtrate was concentrated under reduced pressure to give crude I48C which was used as is in the next step. LCMS m/z 1061.0 (M–H)$^-$.

O-((2R,3S,4R,5R)-5-((((2-Cyanoethoxy)(2-(8-(hydroxymethyl)-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl) S-hydrogen phosphonothioate (I48D)

To a solution of I48C (assumed 0.567 mmol) in DCM (10 mL) was added $H_2O$ (250 mg, 13.9 mmol) followed by a 6% solution of DCA in DCM (10 mL). The reaction mixture was stirred at RT for 1 hr, and then TES (6 mL) was added. After stirring for an additional 1 hr, TES (2 mL) was added and the mixture was stirred 15 min. Pyridine (4 mL) was added and the mixture was stirred 5 min, and then concentrated under reduced pressure. The residue purified using RP-MPLC (C18, 0-100% ACN/$H_2O$ containing 0.04% $NH_4HCO_3$) to give semi-pure I48D. The material was again purified using RP-MPLC (C18, 0-40% ACN/$H_2O$ containing 0.04% $NH_4HCO_3$) to give pure 148D (0.025 g, 6% over 3 steps). LCMS m/z 759.3 (M–H)$^-$.

N-{9-[(1S,21R,23R,24R)-18-(2-Cyanoethoxy)-24-fluoro-3-sulfanyl-3,18-disulfanylidene-2,4,17,19,22-pentaoxa-7,10,12,14-tetraaza-3lambda5,18lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (I48E)

To dry pyridine (8 mL) cooled to –40° C. was added diphenyl phosphoryl chloride (245 μL, 1.18 mmol). After 5 min, a solution of I48D (45 mg, 0.059 mmol) in pyridine (3 mL) was added in a dropwise fashion over 20 min while maintaining the bath between –40 and –35° C. After stirring at –40° C. for 30 min, $H_2O$ (53 mg, 2.96 mmol) and 3H-benzo[c][1,2]dithiol-3-one (15 mg, 0.089 mmol) were added in rapid succession. The –40° C. bath was replaced with a RT bath and the reaction mixture was stirred for 1 hr. The mixture was concentrated under reduced pressure, and then the residue was purified using RP-MPLC (C18, 0-100% ACN/$H_2O$ containing 0.04% $NH_4HCO_3$) to give I48E (3 mg, 7%). LCMS m/z 773.3 (M–H)$^-$.

(1S,21R,23R,24R)-23-(2-Amino-6-oxo-6,9-dihydro-1H-purin-9-yl)-24-fluoro-3,18-disulfanyl-3-sulfanylidene-2,4,17,19,22-pentaoxa-7,2-pentaoxa-7,10,12,14-tetraaza-3lambda5,18lambda5-diphosphatetracyclo[19.2.1.06,14.08,13]tetracosa-6,8,10,12-tetraen-18-one (Example 29)

A solution of I48E (3 mg, 0.0039 mmol) in $MeNH_2$/EtOH (33%, 1.0 mL) was stirred at RT for 3 hrs, and then concentrated under reduced pressure. The residue was purified by prep. RP-HPLC (XBridge Prep C18, OBD 5 μm, 19×150 mm column eluting with 0-30% ACN/$H_2O$ over 20 min. containing 0.4% $NH_4HCO_3$, Flow rate=10 mL/min) to give two pure diastereomers of Example 29 (Diastereomer A: $T_R$=9.4 min, 0.64 mg; Diastereomer B: $T_R$=11.4 min, 1.13 mg; Total: 1.77 mg, 71%). Example 29A (Diastereomer A): LCMS (Method D, $T_R$=1.20 min) m/z 650.0 (M–H)$^-$. $^1$H NMR ($D_2O$) δ 8.96 (s, 1H), 8.82 (s, 1H), 7.83 (s, 1H), 5.93 (d, J=8.0 Hz, 1H), 5.21-5.07 (comp, 3H), 4.87 (dd, J=12.6, 5.8 Hz, 1H), 4.72-4.58 (m, 1H), 4.55-4.48 (comp, 2H), 4.40-4.33 (m, 1H), 4.11-4.03 (comp, 2H), 3.91-3.86 (m, 1H). $^{19}$F NMR ($D_2O$) δ -197.54. $^{31}$P NMR ($D_2O$) δ 115.54, 55.17. Example 29B (Diaststereomer B): LCMS (Method D, $T_R$=1.34 min) m/z 650.0 (M–H)$^-$. $^1$H NMR ($D_2O$) δ 9.02 (s, 1H), 8.87 (s, 1H), 7.67 (s, 1H), 5.93 (d, J=8.0 Hz, 1H), 5.32-5.01 (comp, 3H), 4.84 (dd, J=12.5, 5.5 Hz, 1H), 4.75-4.37 (comp, 4H), 4.30-4.24 (m, 1H), 4.07 (dd, J=11.3, 5.8 Hz, 1H), 3.91-3.86 (m, 1H). $^{19}$F NMR ($D_2O$) δ -197.74. $^{31}$P NMR ($D_2O$) δ 114.86, 55.04.

Example 30

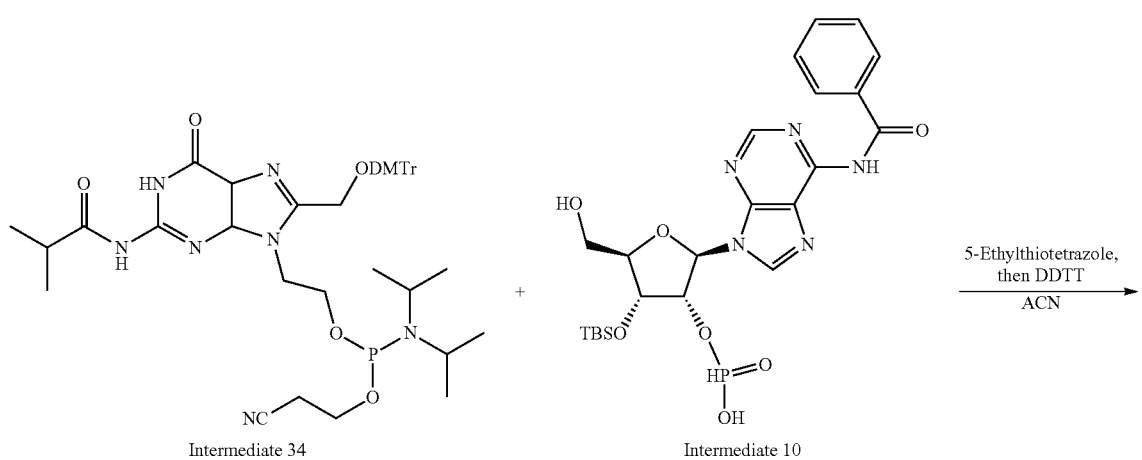

-continued
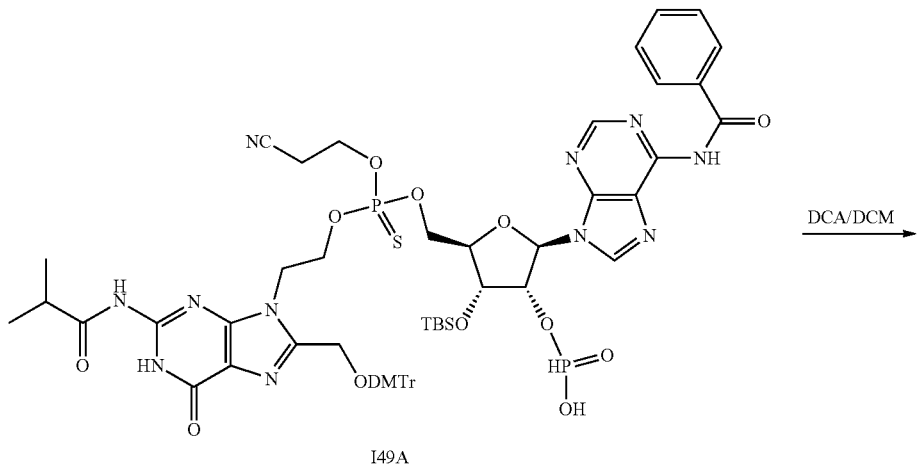
I49A
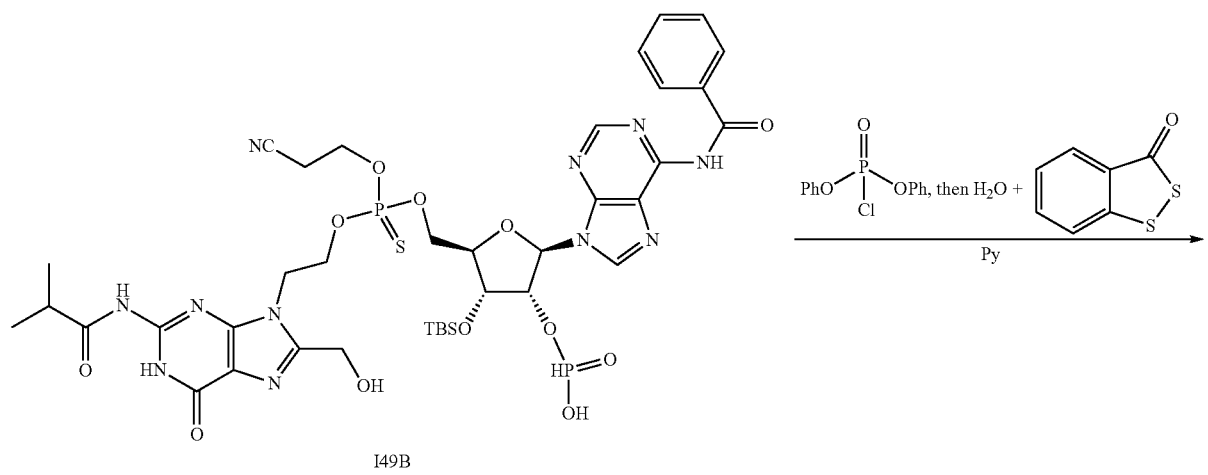
I49B
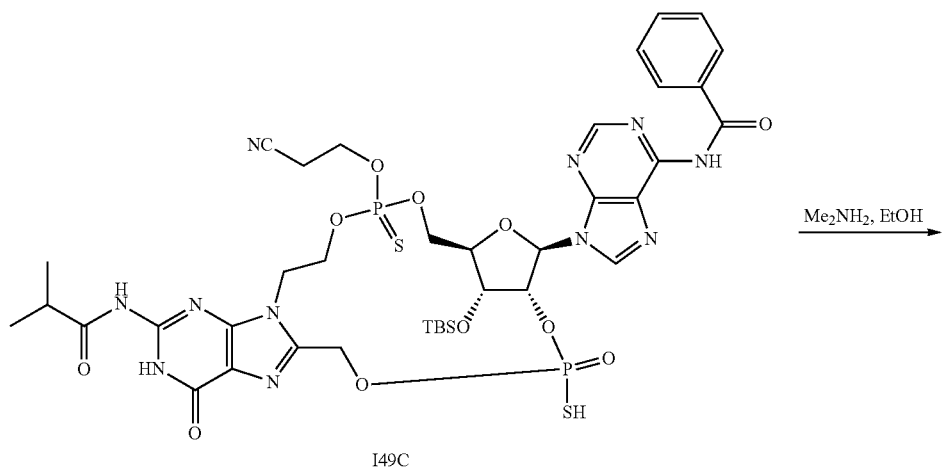
I49C

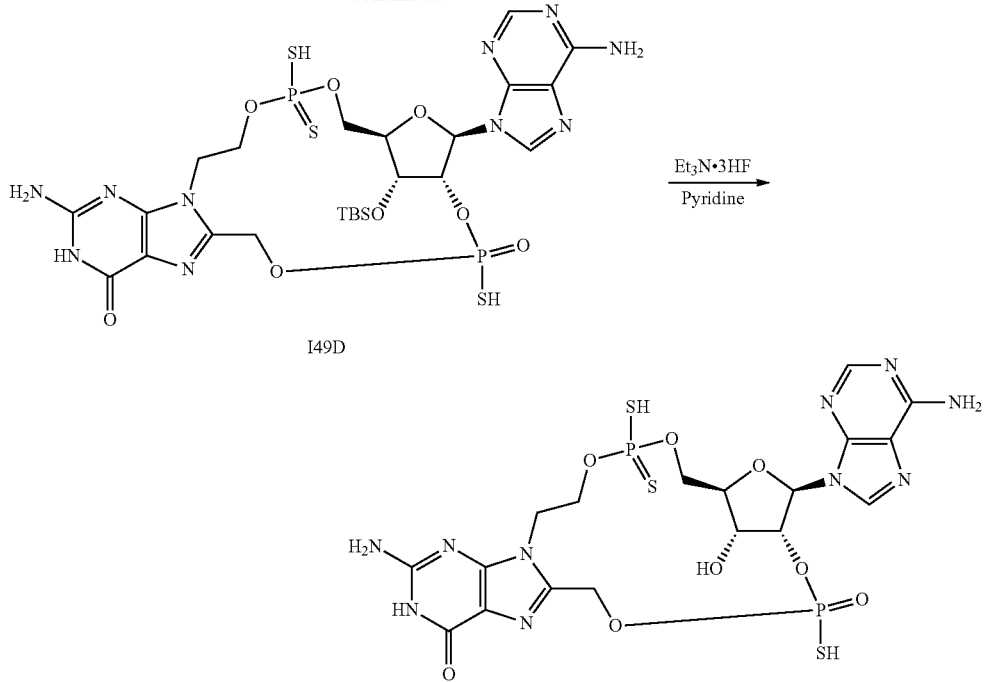

Example 30

(2R,3R,4R,5R)-2-(6-Benzamido-9H-purin-9-yl)-5-
(((((2-(8-((bis(4-methoxyphenyl)(phenyl)methoxy)
methyl)-2-isobutyramido-6-oxo-1H-purin-9(6H)-yl)
ethoxy)(2-cyanoethoxy)phosphorothioyl)oxy)
methyl)-4-((tert-butyldimethylsilyl)oxy)
tetrahydrofuran-3-yl hydrogen phosphonate (I49A)

A suspension of Intermediate 34 (615 mg, 0.771 mmol) and crushed, freshly activated 3 Å MS (200 mg) in ACN (5 mL) was stirred at RT for 1 hr. In the meantime, a suspension of Intermediate 10 (353 mg, 0.642 mmol), 5-ethylthiotetrazole (117 mg, 0.899 mmol), and crushed, freshly activated 3 Å MS (200 mg) in ACN (3.5 mL) was stirred for 1 hr. The supernatant containing Intermediate 34 was added to the suspension of Intermediate 10 in a dropwise fashion, via syringe. The resulting mixture was stirred at RT for 1.5 hrs, whereupon DDTT (145 mg, 0.707 mmol) was added in one portion. The reaction mixture was stirred at RT for 1 hr, and then filtered to remove the sieves. The filtrate was concentrated under reduced pressure, and the residue was purified by RP-MPLC (C18, 0-100% ACN/H$_2$O containing 0.04% NH$_4$HCO$_3$) to give I49A (590 mg, 60%). LCMS m/z 1276.2 (M−H)$^-$.

(2R,3R,4R,5R)-2-(6-Benzamido-9H-purin-9-yl)-4-
((tert-butyldimethylsilyl)oxy)-5-((((2-cyanoethoxy)
(2-(8-(hydroxymethyl)-2-isobutyramido-6-oxo-1H-
purin-9(6H)-yl)ethoxy)phosphorothioyl)oxy)methyl)
tetrahydrofuran-3-yl hydrogen phosphonate (I49B)

To a rapidly stirred mixture of I49A (590 mg, 0.462 mmol) and H$_2$O (83.0 mg, 4.62 mmol) in DCM (10 mL) was added a 6% solution of DCA in DCM (10 mL). After 2 hrs at RT, Et$_3$SiH (7.0 mL) was introduced and the reaction mixture was stirred for 1 hr. Pyridine (2.5 mL) and MeOH (2.5 mL) were added, and the mixture was stirred for 5 min, then concentrated under reduced pressure. The residue was purified by silica gel chromatography (0-50% MeOH/DCM) to give I49B (270 mg, 60%) as a ca. 1:1 mixture of diastereomers as indicated by $^{31}$P-NMR. LCMS m/z 974.4 (M−H)$^-$. $^{31}$P NMR (CD$_3$OD) δ 67.91 (P=S), 67.86 (P=S), 3.44 (O=P—H), 3.26 (O=P—H).

N-{9-[(1R,21R,23R,24R)-24-[(tert-Butyldimethylsi-
lyl)oxy]-18-(2-cyanoethoxy)-11-(2-methylpropana-
mido)-3,9-dioxo-3-sulfanyl-18-sulfanylidene-2,4,17,
19,22-pentaoxa-7,10,12,14-tetraaza-3lambda5,
18lambda5-diphosphatetracyclo[19.2.1.0$^{6,14}$.0$^{8,13}$]
tetracosa-6,8(13),11-trien-23-yl]-9H-purin-6-
yl}benzamide (I49C)

To dry pyridine (48 mL) cooled to −30° C. was added diphenyl phosphoryl chloride (1.15 mL, 5.53 mmol). After 5 min, a solution of I49B (270 mg, 0.277 mmol) in pyridine (14 mL) was added in a dropwise fashion over 25 min while maintaining the bath between −35 and −30° C. After stirring at −30° C. for 45 min, H$_2$O (250 mg, 1.38 mmol) and 3H-benzo[c][1,2]dithiol-3-one (70 mg, 0.42 mmol) were added in rapid succession. The −30° C. bath was replaced with a RT bath and the reaction mixture was stirred for 1.5 hrs. The reaction mixture was cooled to 0° C., then quenched by adding a solution of sodium thiosulfate (174 mg) in H$_2$O (60 mL) in a dropwise fashion. The bath was removed and the mixture was stirred at RT for 5 min, partially concentrated under reduced pressure, then purified using RP-MPLC (C18, 0-60% ACN/H$_2$O containing 0.04% NH$_4$HCO$_3$) to give I49C (137 mg, 50%). LCMS m/z 990.4 (M+H)$^+$.

(1R,21R,23R,24R)-1-Amino-23-(6-amino-9H-purin-9-yl)-24-[(tert-butyldimethylsilyl)oxy]-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13), 1-triene-3,9,18-trione (149D)

A solution of 149C (135 mg, 0.136 mmol) in MeNH$_2$/EtOH (33%, 8 mL) was stirred at RT for 5 hrs, and then concentrated under reduced pressure to give crude 149D which was used "as is" in the next step without further purification. LCMS m/z 763.2 (M+H)$^+$.

(1R,21R,23R,24R)-11-Amino-23-(6-amino-9H-purin-9-yl)-24-hydroxy-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),11-triene-3,9,18-trione (Example 30)

In a plastic vial, Et$_3$N.HF (0.495 mL, 2.73 mmol) was added to a solution of crude 118D in pyridine (4 mL). The mixture was heated at 50° C. for 18 hrs, and then concentrated under reduced pressure. The residue was dissolved in H$_2$O (1 mL), and then sat. aq. NaHCO$_3$ (4 mL) was added slowly. The resulting mixture was purified by prep. RP—HPLC (HILIC, 0-30% ACN/H$_2$O containing 50 mM ammonium formate) to give Example 30 (28 mg, 32%). Example 30A (Diastereomer A): LCMS (Method D, T$_R$=1.03 min) m/z 647.0 (M−H)$^−$. $^1$H NMR (D$_2$O) δ 8.20 (s, 1H), 7.97 (s, 1H), 6.13 (d, J=7.8 Hz, 1H), 4.90 (dd, J=12.0, 7.8 Hz, 1H), 4.71-4.68 (m, 1H), 4.49 (app d, J=4.3 Hz, 1H), 4.40-4.39 (m, 1H), 4.27-4.05 (comp, 6H), 3.96-3.93 (m, 1H). $^{31}$P NMR (D$_2$O) δ 55.33, 55.08

Example 31

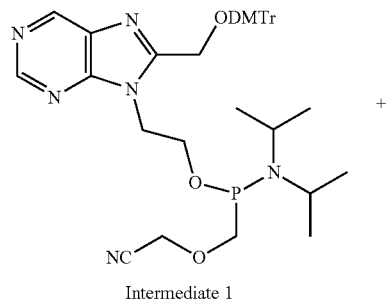

Intermediate 1

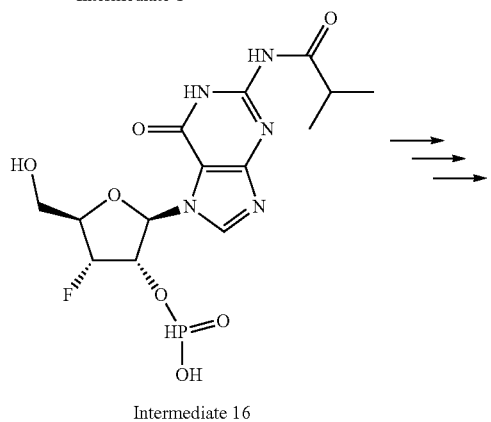

Intermediate 16

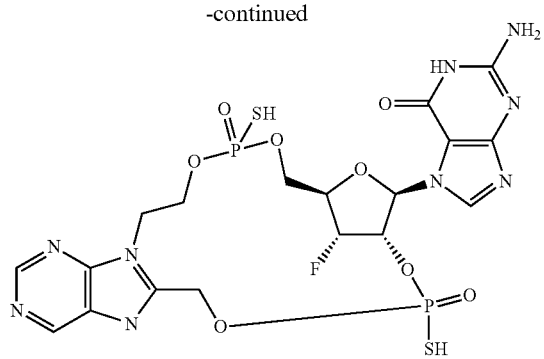

Example 31

Utilizing Intermediate 1, Intermediate 16 (prepared from the unprotected N$^7$-guanosine (ChemGenes Corporation) using the chemistry methods for Intermediate 2), and the identical procedures used for the preparation of Example 1, Example 31 was prepared.

(1S,21R,23R,24R)-23-(2-Amino-6-oxo-6,7-dihydro-1H-purin-7-yl)-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8,10,12-tetraene-3,18-dione (Example 31)

Purified by prep. RP—HPLC (XBridge C18, 5 μm, 18×150 mm column) eluting with 0-10% ACN/50 mM aq. NH$_4$HCO$_3$ over 15 min, then 10-20% ACN/50 mM aq. NH$_4$HCO$_3$ over 3 min with a flow rate=10 mL/min to give two mixed and two pure diastereomers (Diastereomer A/B: T$_R$=11.4 min; Diastereomer C: T$_R$=13.9 min, 6.0 mg, 29%; Diastereomer D: T$_R$=17.1 min) of Example 31. Example 31C (Diastereomer C): LCMS (Method D, T$_R$=1.21 min) m/z 633.8 (M−H)$^−$. $^1$H NMR (D$_2$O) δ 9.06 (s, 1H), 8.86 (s, 1H), 7.86 (s, 1H), 6.34 (d, J=7.5 Hz, 1H), 5.34 (dd, J=52.7, 3.8 Hz, 1H), 5.25 (dd, J=12.6, 8.0 Hz, 1H), 4.75-4.55 (comp, 4H), 4.40-4.27 (comp, 2H), 4.20-4.08 (comp, 2H), 3.96-3.91 (m, 1H). $^{19}$F NMR (D$_2$O) δ -198.34. $^{31}$P NMR (D$_2$O) δ 55.51, 55.07.

Example 32

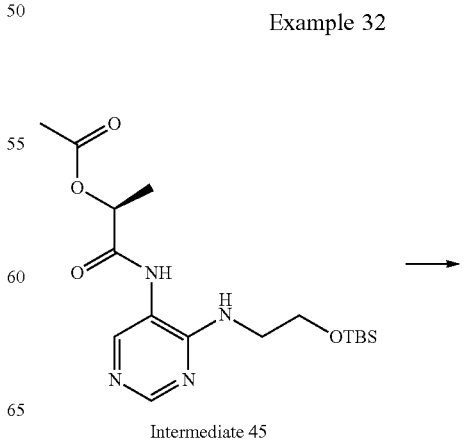

Intermediate 45

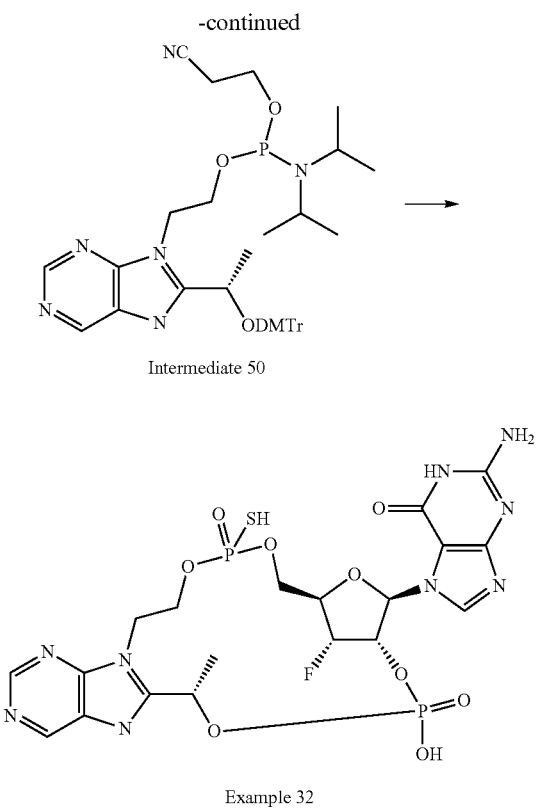

Intermediate 50

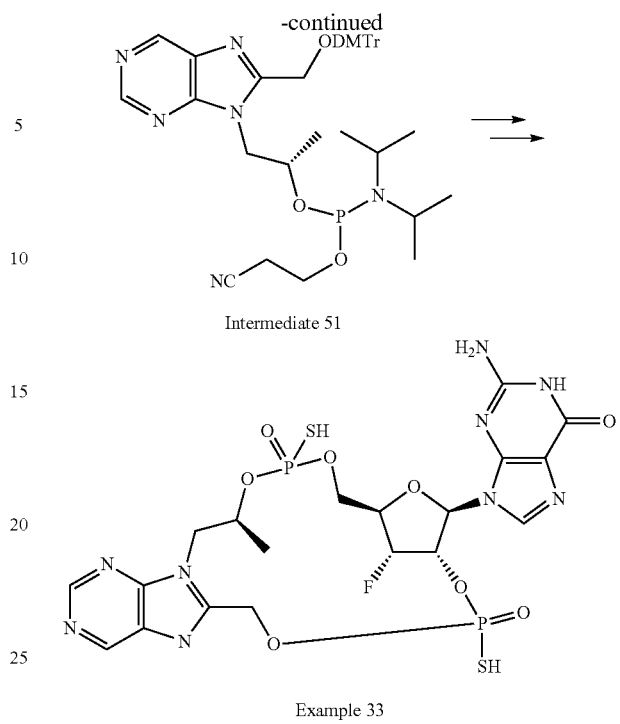

Intermediate 51

Example 32

(1S,5S,21R,23R,24R)-23-(2-Amino-6-oxo-6,7-dihydro-1H-purin-7-yl)-24-fluoro-5-methyl-3,18-disulfanyl-2,4,17,19,22-pentaoxa-7,10,12,14-tetraaza-3lambda5,18lambda5-diphosphatetracyclo[19.2.1.06,14.08,13]tetracosa-6,8,10,12-tetraene-3,18-dione (Example 32)

Utilizing Intermediate 45 and the identical chemistry for the transformation of I1D to Intermediate 1, Intermediate 50 was prepared. Then utilizing Intermediate 45 and Intermediate 50 along with identical chemistry for the preparation of Example 1, Example 32 was prepared. Example 33C (Diastereomer C): LCMS (Method D, $T_R$=1.17 min) m/z 648.0 (M−H)−. $^1$H NMR (D$_2$O) δ 8.95 (s, 1H), 8.88 (s, 1H), 7.66 (s, 1H), 5.89 (d, J=7.8 Hz, 1H), 5.70-5.63 (m, 1H), 4.93-4.72 (comp, 3H), 4.55-4.41 (comp, 2H), 4.30 (app q, J=4.8 Hz, 2H), 4.03 (dd, J=11.3, 6.5 Hz, 1H), 3.85 (app br d, J=11.3 Hz, 1H), 1.49 (d, J=6.5 Hz, 3H) $^{19}$F NMR (D$_2$O) δ −197.08. $^{31}$P NMR (D$_2$O) δ 55.19, 54.47.

Example 33

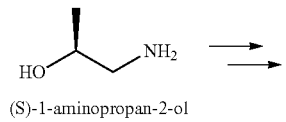

(S)-1-aminopropan-2-ol

Example 33

(1S,16S,21R,23R,24R)-23-(2-Amino-6-oxo-6,9-dihydro-1H-purin-9-yl)-24-fluoro-16-methyl-3,18-disulfanyl-2,4,17,19,22-pentaoxa-7,10,12,14-tetraaza-3lambda5,8lambda5-diphosphatetracyclo[19.2.1.06,14.08,13]tetracosa-6,8,10,12-tetraene-3,18-dione (Example 33)

Starting from (S)-1-aminopropan-2-ol and using the identical chemistry for the preparation of Intermediate 1, Intermediate 51 was prepared. Then utilizing Intermediate 51 and Intermediate 2 along with identical chemistry for the preparation of Example 1, Example 33 was prepared. Example 33B (Diastereomer B): LCMS (Method D, $T_R$=1.10 min) m/z 648.1 (M−H)−. $^1$H NMR (D$_2$O) δ 8.87 (s, 1H), 8.83 (s, 1H), 7.82 (s, 1H), 5.90 (d, J=8.3 Hz, 1H), 5.57 (dd, J=52.7, 3.5 Hz, 1H), 5.46 (dd, J=15.6, 8.8 Hz, 1H), 5.05 (dd, J=15.3, 3.0 Hz, 1H), 4.95-4.88 (m, 1H), 4.82-4.70 (m, 1H), 4.60-4.51 (m, 1H), 4.30 (app dt, J=15.3, 2.8 Hz, 1H), 4.15 (dd, J=15.1, 10.0 Hz, 1H), 3.99-3.89 (comp, 2H), 1.38 (d, J=6.5 Hz, 3H). $^{31}$P NMR (D$_2$O) δ 56.20, 34.36. Example 33C (Diastereomer C): LCMS (Method D, $T_R$=1.35 min) m/z 648.0 (M−H)−. $^1$H NMR (D$_2$O) δ 8.93 (s, 1H), 8.82 (s, 1H), 8.00 (s, 1H), 5.93 (d, J=8.3 Hz, 1H), 5.28 (dd, J=13.3, 7.8 Hz, 1H), 5.16-5.02 (comp, 2H), 4.99-4.86 (m, 1H), 4.76-4.70 (m, 1H), 4.49-4.40 (comp, 2H), 4.27 (app dt, J=15.1, 2.7 Hz, 1H), 3.95 (app t, J=11.0 Hz, 1H, 3.83-3.80 (m, 1H), 1.38 (d, J=6.3 Hz, 3H). $^{31}$P NMR (D$_2$O) δ 58.63, 55.33. Example 33D (Diastereomer D): LCMS (Method D, $T_R$=1.47 min) m/z 648.1 (M−H)−. $^1$H NMR (D$_2$O) δ 8.92 (s, 1H), 8.86 (s, 1H), 7.82 (s, 1H), 5.92 (d, J=8.3 Hz, 1H), 5.41 (dd, J=14.8, 8.5 Hz, 1H), 5.36 (dd, J=52.7, 3.8 Hz, 1H), 5.09 (dd, J=14.8, 4.8 Hz, 1H), 5.04-4.92 (m, 1H), 4.86-4.80 (m, 1H), 4.55-4.48 (m, 1H), 4.34-4.24 (comp, 2H), 4.11-4.06 (m, 1H), 3.81-3.78 (m, 1H), 1.43 (d, J=6.3 Hz, 3H). $^{31}$P NMR (D$_2$O) δ 54.71, 54.16.

Intermediate 52

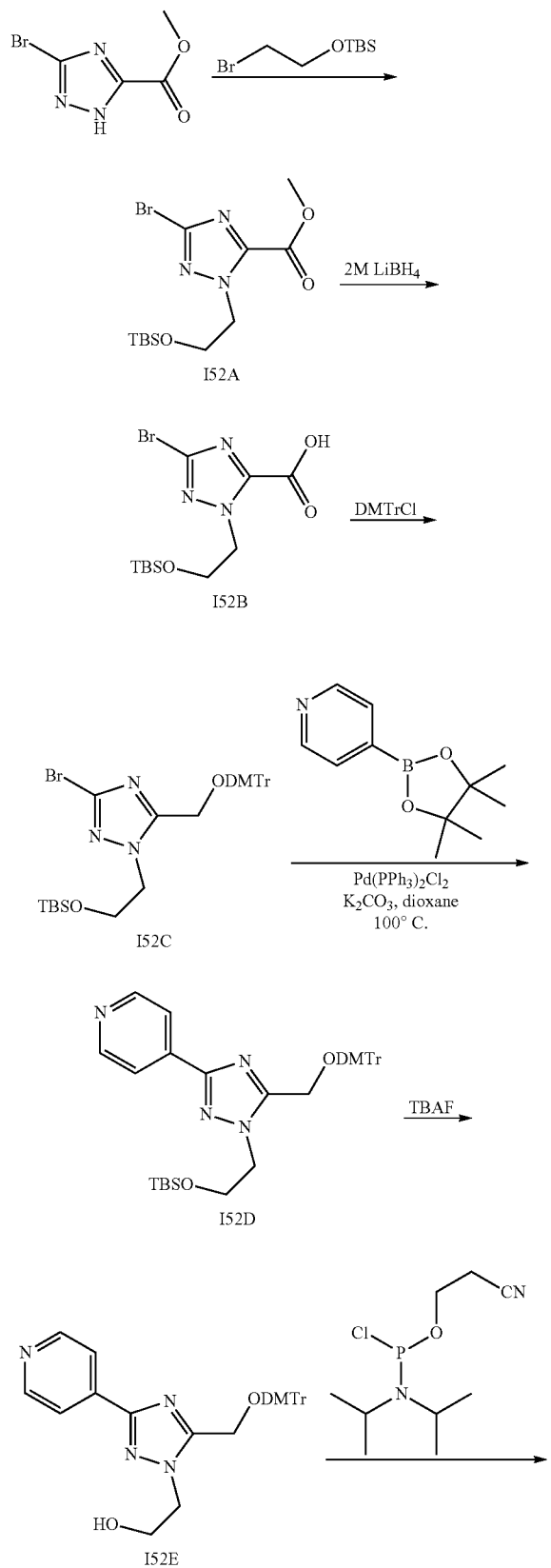

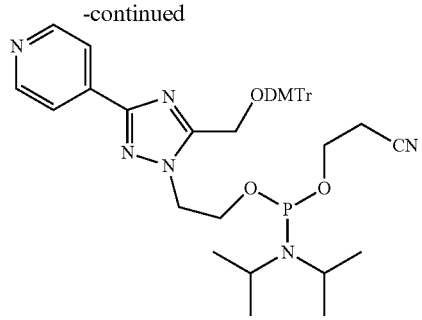

Intermediate 52

Methyl 3-bromo-1-(2-((tert-butyldimethylsilyl)oxy)ethyl)-1H-1,2,4-triazole-5-carboxylate (I52A)

A mixture of methyl 3-bromo-1H-1,2,4-triazole-5-carboxylate (100 mg, 0.49 mmol), (2-bromoethoxy)(tert-butyl)dimethylsilane (176 mg, 0.74 mmol) and $Cs_2CO_3$ (318 mg, 0.98 mmol) in DMF (2 mL) was stirred at RT for 3 days. The crude reaction mixture was then purified by RP-MPLC (0-100% ACN/$H_2O$) to give I52A (91m g, 51%) as a light yellow oil. LCMS m/z (M+H)$^+$364.0/366.2. $^1$H NMR (CD$_3$OD) δ 4.76 (t, J=5.0 Hz, 2H), 3.97 (t, J=5.3 Hz, 2H), 3.96 (s, 3H), 0.792 (s, 9H), −0.07 (s, 6H).

(3-Bromo-1-(2-((tert-butyldimethylsilyl)oxy)ethyl)-1H-1,2,4-triazol-5-yl)methanol (I52B)

To a solution of I52A (90 mg, 0.25 mmol) in THF at RT was added LiBH$_4$ (0.5 mL, 2 M). The mixture was continued stirred at RT for 1 hr. To the reaction mixture was added a portion of Na$_2$SO$_4$ (20 mg) and a drop of H$_2$O and stirring at RT was continued for 10 min. The reaction mixture was diluted with EtOAc and the organic layer was washed with H$_2$O, brine, and then dried (Na$_2$SO$_4$). Volatiles were removed under reduced pressure and the residue was purified by RP-MPLC (0-100% ACN/H$_2$O) give I52B (71 mg, 85%). LCMS m/z (M+H)$^+$336.0/338.2. $^1$H NMR (CDCl$_3$) δ 4.60 (s, 2H), 4.33 (t, J=5.0 Hz, 2H), 3.91 (t, J=5.3 Hz, 2H), 0.81 (s, 9H), −0.06 (s, 6H).

5-((Bis(4-methoxyphenyl)(phenyl)methoxy)methyl)-3-bromo-1-(2-((tert-butyldimethylsilyl) oxy)ethyl)-1H-1,2,4-triazole (I52C)

To a mixture of I52B (30 mg, 0.09 mmol) in pyridine (1 mL) was added at RT a portion of DMTrCl (45 mg, 0.13 mmol). After stirring at RT overnight the reaction mixture was concentrated and purified by silica gel chromatography (0%-100% EtOAc/Hexane) to give I52C (57 mg, 99%). LCMS m/z (M+H)$^+$638.0/640.2. $^1$H NMR (CD$_3$OD) δ 7.45 (d, J=7.3 Hz, 2H), 7.34 (d, J=9.0 Hz, 4H) 7.31-7.19 (comp, 3H), 6.87 (d, J=8.8 Hz, 4H), 4.30 (s, 2H), 4.15 (t, J=4.8 Hz, 2H), 3.81 (t, J=5.3 Hz, 2H), 3.78 (s, 6H), 0.69 (s, 9H), −0.17 (s, 6H).

4-(5-((Bis(4-methoxyphenyl)(phenyl)methoxy)methyl)-1-(2-((tert-butyldimethylsilyl)oxy) ethyl)-1H-1,2,4-triazol-3-yl)pyridine (I52D)

A mixture of I52C (57 mg, 0.09 mmol), 4-(4,4,5,5-tetramethyl-1,3,2-dioxaborolan-2-yl)pyridine (23 mg, 0.11 mmol) and K$_2$CO$_3$ (37 mg, 0.27 mmol) in 1,4-dioxane (2 mL) at RT was degassed for 5 min. Then a portion of Pd(PPh$_3$)$_2$Cl$_2$ (32 mg, 0.05 mmol) was added at RT and the resulting mixture was heated to 100° C. for 6 hrs. The reaction mixture was filtered, concentrated and purified by silica gel chromatography (0%-100% EtOAc/Hexane) to give I52D (10 mg, 18%). LCMS m/z (M+H)$^+$637.6. $^1$H NMR (CD$_3$OD) δ 8.63 (d, J=6.3 Hz, 2H), 8.00 (d, J=6.3 Hz, 2H), 7.49 (d, J=7.3 Hz, 2H), 7.38 (d, J=9.0 Hz, 4H). 7.32 (t, J=7.5 Hz, 2H), 7.23 (t, J=7.3 Hz, 1H), 6.88 (d, J=9.0 Hz, 4H), 4.45 (s, 2H), 4.28 (t, J=5.0 Hz, 2H), 3.91 (t, J=5.0 Hz, 2H), 3.76 (s, 6H), 0.68 (s, 9H), −0.19 (s, 6H).

2-(5-((Bis(4-methoxyphenyl)(phenyl)methoxy) methyl)-3-(pyridin-4-yl)-1H-1,2,4-triazol-1-yl)ethan-1-ol (I52E)

To a solution of I52D (170 mg, 0.27 mmol) in THF (2 mL) at RT was added slowly TBAF in THF (1 M, 1 mL, 1.0 mmol). After stirring at RT for 4 hrs the reaction mixture was concentrated, diluted with EtOAc and washed with sat., aq. NaHCO$_3$ and brine. The organic layer was dried (Na$_2$SO$_4$), concentrated under reduced pressure purified by silica gel chromatography (0-10% MeOH/DCM) to give I52E (140 mg, 100%). LCMS m/z (M+H)$^+$523.5. $^1$H NMR (CD$_3$OD) δ 8.62 (d, J=6.3 Hz, 2H), 7.99 (d, J=6.3 Hz, 2H), 7.50 (d, J=7.3 Hz, 2H), 7.38 (d, J=9.0 Hz, 4H), 7.32 (t, J=7.3 Hz, 2H), 7.23 (t, J=7.3 Hz, 1H), 6.88 (d, J=9.0 Hz, 4H), 4.54 (s, 2H), 4.27 (t, J=5.3 Hz, 2H), 3.88 (t, J=5.5 Hz, 2H), 3.75 (s, 6H).

2-(5-((Bis(4-methoxyphenyl)(phenyl)methoxy) methyl)-3-(pyridin-4-yl)-1H-1,2,4-triazol-1-yl)ethyl (2-cyanoethyl) diisopropylphosphoramidite (Intermediate 52)

To a solution of I52E (140 mg, 0.26 mmol) in DCM (2 mL) at RT was added DIEA (0.14 mL, 0.81 mmol) followed by a dropwise addition of 3-((chloro(diisopropylamino) phosphino)oxy)propanenitrile (120 μL, 0.52 mmol). The mixture was stirred at RT for 1 hr, then quenched by the addition of 5% aq. NaHCO$_3$. The mixture was concentrated under reduced pressure, and the residue was purified by RP-MPLC (0-100% ACN/H$_2$O) to give Intermediate 52 (122 mg, 65%) as a white solid. LCMS m/z (M+H+OH-N, N-diisopropylamino)+640.5. $^1$H NMR (CD$_3$CN) δ 8.65 (d, J=6.0 Hz, 2H), 7.89 (d, J=6.0 Hz, 2H), 7.50 (d, J=7.3 Hz, 2H), 7.39 (d, J=8.8 Hz, 4H), 7.35 (t, J=7.8 Hz, 2H), 7.26 (t, J=7.3 Hz, 1 Hz, 1H) 6.90 (d, J=9.0 Hz, 4H), 4.40-4.28 (comp, 4H), 3.94-3.91 (m, 2H), 3.76 (s, 6H), 3.59-3.41 (m, 4H), 2.48 (t, J=6.3 Hz, 2H), 1.06 (t, J=6.8 Hz, 6H), 0.94 (d, J=6.8 Hz, 6H). $^{31}$P NMR (CD$_3$CN) δ 147.82.

Example 34

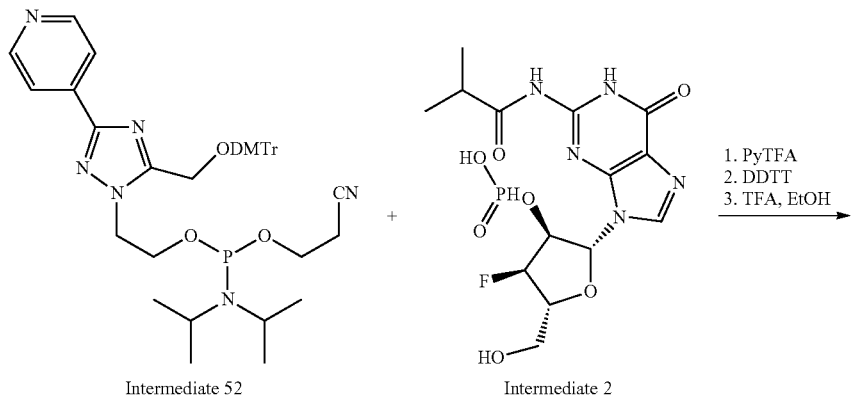

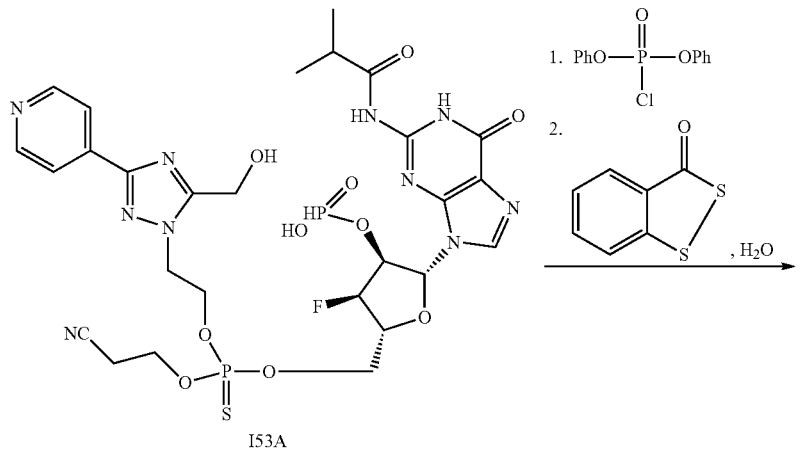

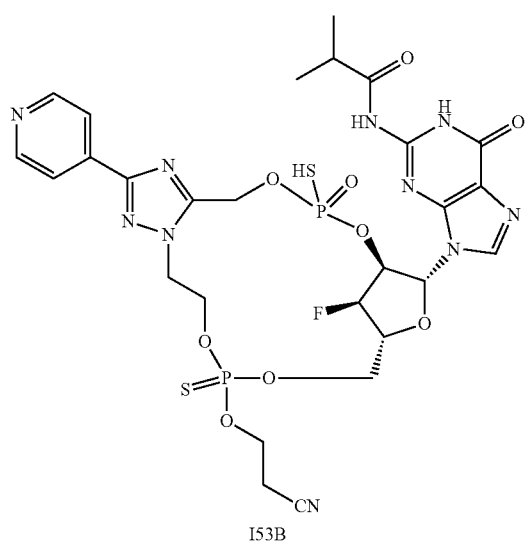

I53B

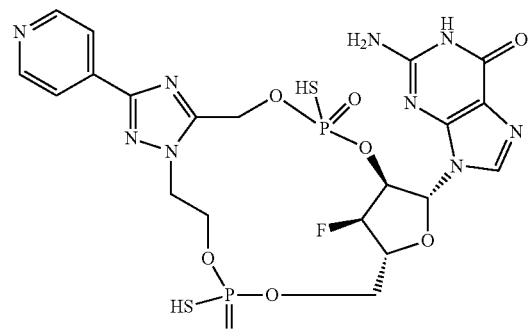

Example 34

(2R,3S,4R,5R)-5-((((2-Cyanoethoxy)(2-(5-(hydroxymethyl)-3-(pyridin-4-yl)-1H-1,2,4-triazol-1-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I53A)

LCMS (Method D, $T_R$=2.03 min/2.07 min) m/z 769.3 (M−H)$^+$. $^{31}$P NMR (CD$_3$OD) δ 67.88, 67.77, 2.57. $^{19}$F NMR (CD$_3$OD) δ −202.19, −202.22.

N-{9-[(1S,17R,19R,20R)-14-(2-Cyanoethoxy)-20-fluoro-3-oxo-8-(pyridin-4-yl)-3-sulfanyl-14-sulfanylidene-2,4,13,15,18-pentaoxa-7,9,10-triaza-3lambda5,14lambda5-diphosphatricyclo[15.2.1.06,10]icosa-6,8-dien-19-yl]-6-oxo-6,9-dihydro-1H-purin-2-yl}-2-methylpropanamide (I53B)

LCMS (Method D, $T_R$=2.37 min) m/z 783.3 (M−H)$^+$. $^{31}$P NMR (CD$_3$OD) δ 69.03, 68.89, 65.80, 65.45, 61.04, 60.67, 57.83, 57.59. $^{19}$F NMR (CD$_3$OD) δ −196.42, 197.35, 198.38, 199.39.

(1S,17R,19R,20R)-19-(2-Amino-6-oxo-6,9-dihydro-1H-purin-9-yl)-20-fluoro-8-(pyridin-4-yl)-3,14-disulfanyl-2,4,13,15,18-pentaoxa-7,9,10-triaza-3lambda5,14lambda5-diphosphatricyclo[15.2.1.06,10]icosa-6,8-diene-3,14-dione (Example 34)

Example 34 diastereomers (Diastereomers A-D) were prepared according to procedures analogous to those outlined in Example 1. Diastereomers A-D were purified by prep. RP—HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 34B (Diastereomer B): Prep. RP—HPLC: $T_R$=22.21 min. LCMS (Method D, $T_R$=1.10 min) m/z 662.3 (M+H)$^+$. $^1$H NMR (D$_2$O) δ 8.64 (d, J=6.0 Hz, 2H), 8.14 (s, 1H), 7.94 (d, J=6.3 Hz, 2H), 6.01 (d, J=8.0 Hz, 1H), 5.29-5.08 (comp, 3H), 4.71-4.41 (comp, 6H), 4.18-4.04 (comp, 2H). $^{31}$P NMR (D$_2$O) δ 57.43, 55.97. $^{19}$F NMR (D$_2$O) δ −196.24. Example 34C (Diastereomer C): Prep. RP—HPLC: $T_R$=36.15 min. LCMS (Method D, $T_R$=1.20 min) m/z 662.2 (M+H)$^+$. $^1$H NMR (D$_2$O) δ 8.66 (d, J=6.0 Hz, 2H), 7.93 (d, J=6.3 Hz, 2H), 7.74 (s, 1H), 6.02 (d, J=8.3 Hz, 2H), 5.36 (dd, J=13.0 and 9.5 Hz, 1H), 5.32 (dd, J=53.2 and 4.0 Hz, 1H), 5.08-4.94 (comp, 1H), 4.75-4.50 (comp, 4H), 4.48-4.38 (comp, 1H), 4.28 (dd, J=7.0 Hz, 1H), 4.02 (d, J=10.8 Hz, 1H). $^{31}$P NMR (D$_2$O) δ 55.59, 55.56. $^{19}$F NMR (D$_2$O) 8-197.83. Example 34D (Diastereomer D): Prep. RP—HPLC: $T_R$=37.37 min. LCMS (Method D, $T_R$=0.84 min) m/z 668.0 (M+H)$^+$. $^1$H NMR (D$_2$O) δ 8.64 (d, J=6.3 Hz, 2H), 7.95 (s, 1H), 7.93 (d, J=6.3 Hz, 2H), 6.02 (d, J=8.0 Hz, 1H), 5.28-5.06 (comp, 3H),4.75-4.65 (comp, 2H), 4.60-4.49 (comp, 3H), 4.44-4.36 (comp, 1H), 4.26 (t, J=10.8 Hz, 1H), 4.01 (d, J=11.8 Hz, 1H). $^{31}$P NMR (D$_2$O) δ 57.12, 56.33. $^{19}$F NMR (D$_2$O) δ −196.07.

Intermediate 54

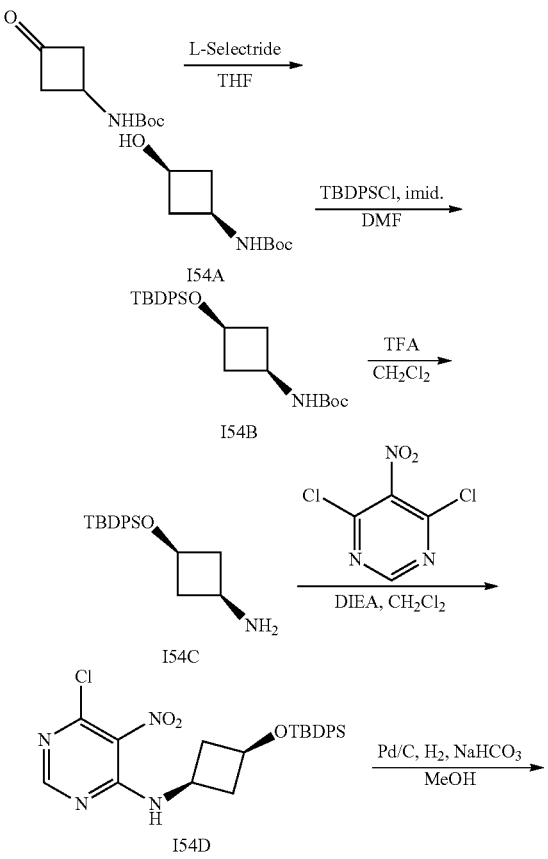

-continued

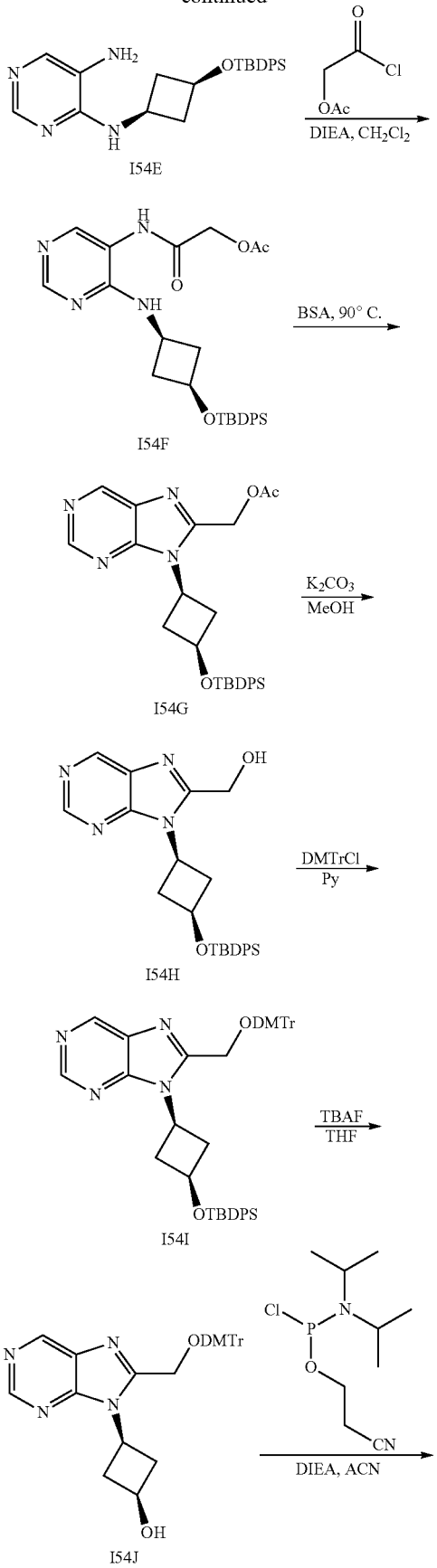

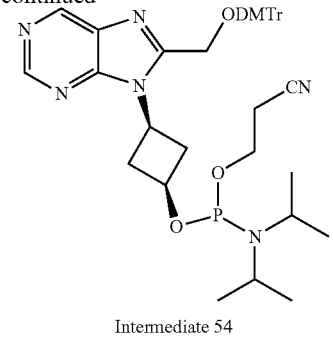

Intermediate 54 tert-Butyl ((cis-1,3)-3-hydroxycyclobutyl)carbamate (I54A)

To a solution of tert-butyl (3-oxocyclobutyl)carbamate (1.00 g, 5.40 mmol) in THF (20 mL) at −78° C. was added L-Selectride (1.0M in THF, 6.5 mL) dropwise over 15 min. After stirring for 5 hrs at −78° C. the mixture was allowed to warm to RT and stirred overnight. The reaction mixture was poured over ice water (100 g) and then extracted with EtOAc (4×15 mL). Combined organics were washed with brine, dried ($Na_2SO_4$), filtered, and concentrated under reduced pressure. The residue was purified by silica gel chromatography (20% EtOAc/Hexane to 2% MeOH/EtOAc) to give I54A (0.82 g, 81%) as a white solid. LCMS m/z 188.2 (M+H)$^+$. $^1$H NMR (CD$_3$OD) δ 3.89 (m, 1H), 2.77 (td, J=16.3, 8.0 Hz, 1H), 2.60 (m, 2H), 1.76 (m, 2H), 1.42 (s, 9H).

tert-Butyl ((cis-1,3)-3-((tert-butyldiphenylsilyl)oxy) cyclobutyl)carbamate (I54B)

To a solution of I54A (0.82 g, 4.38 mmol) in DMF (15 mL) at RT was added imidazole (0.74 g, 10.9 mmol) followed by a solution of TBDPSCl (1.70 mL, 6.44 mmol) dropwise. The reaction mixture was stirred at RT for 4 hrs, whereupon it was diluted with ethyl acetate (150 mL), washed with sat. aq. NH$_4$Cl (3×15 mL), and brine (5×25 mL). The organic layer was dried (Na$_2$SO$_4$), filtered, and concentrated under reduced pressure. The residue was purified by silica gel chromatography (0-2% MeOH/DCM) to give a mixture of I54B (75% by weight, determined by $^1$HNMR) and tert-butyldiphenylsilanol (2.02 g, 81%) as a clear, colorless oil; used without further purification in the next step. LCMS m/z 448.3 (M+Na)$^+$.

((cis-1,3)-3-((tert-Butyldiphenylsilyl)oxy)cyclobutanamine (I54C)

To a solution of I54B (2.02 g, 75% by weight, 3.56 mmol) in DCM (15 mL) at RT was added TFA (1.8 mL) and the mixture was stirred at RT overnight, whereupon it was concentrated under reduced pressure. The residue was purified by silica gel chromatography (1-10% MeOH/DCM) to give I54C (1.04 g, 90%) as a clear, colorless oil. LCMS m/z 326.3 (M+H)$^+$. $^1$H NMR (CDCl$_3$) 7.64 (m, 4H), 7.42 (m, 6H), 4.10 (m, 1H), 3.17 (tt, J=8.9, 7.3 Hz, 1H), 2.58 (m, 2H), 2.17 (qdd, J=10.1, 5.4, 2.5 Hz, 2H), 1.03 (s, 9H).

N-((cis-1,3)-3-((tert-Butyldiphenylsilyl)oxy)cyclobutyl)-6-chloro-5-nitropyrimidin-4-amine (I54D)

To a solution of 4,6-dichloro-5-nitropyrimidine (0.61 g, 3.05 mmol) in DCM (15 mL) at RT was added a solution of I54C (1.04 g, 3.20 mmol) in DCM (20 mL) followed by dropwise addition of DIEA (0.78 mL, 4.48 mmol). The reaction mixture was allowed to stir at RT overnight. More DCM (55 mL) was added and the mixture was washed with sat. aq. NH$_4$Cl (20 mL), sat. aq. NaHCO$_3$ (20 mL), and then brine (20 mL). The organic layer was dried (Na$_2$SO$_4$), concentrated under reduced pressure and purified by silica gel chromatography (5-25% EtOAc/Hexane) to give I54D (0.95 g, 63%) as a pale yellow solid. LCMS m/z 483.2 (M+H)$^+$. $^1$H NMR (CDCl$_3$) δ 8.31 (s, 1H), 7.63 (dd, J=7.9, 1.5 Hz, 4H), 7.39 (m, 6H), 4.05 (m, 2H), 2.71 (tdd, J=9.5, 6.9, 2.9 Hz, 2H), 2.04 (m, 2H), 1.03 (s, 9H).

N$^4$-((cis-1,3)-3-((tert-Butyldiphenylsilyl)oxy)cyclobutyl)pyrimidine-4,5-diamine (I54E)

A mixture of I54D (0.95 g, 1.97 mmol), 10% Pd/C (0.21 g), and NaHCO$_3$ (0.26 g, 2.2 mmol) in MeOH (60 mL) was hydrogenated at 50 psi H$_2$ for 6 hrs using a Parr shaker. The reaction mixture was filtered through a pad of Celite® and the filtrate was concentrated under reduced pressure and the residue (I54E, 0.97 g) used without further purification in the next step. LCMS m/z 419.6 (M+H)$^+$.

2-((4-(((cis-1,3)-3-((tert-Butyldiphenylsilyl)oxy)cyclobutyl)amino) pyrimidin-5-yl)amino)-2-oxoethyl acetate (I54F)

To a solution of 154E (0.97 g, ~1.97 mmol) in DCM (10 mL) at RT was added DIEA (1.03 mL, 5.91 mmol) then 2-chloro-2-oxoethyl acetate (0.23 mL, 2.07 mmol) was added in a dropwise fashion. The resulting mixture was stirred at RT for 2 hrs and then concentrated under reduced pressure. The residue was taken up in EtOAc (50 mL) and washed with sat. aq. NH$_4$Cl (2×10 mL), sat. aq. NaHCO$_3$ (2×10 mL), and then brine (10 mL). The organic layer was dried (Na$_2$SO$_4$), concentrated under reduced pressure and the crude I54F was used without further purification. LCMS m/z 519.3 (M+H)$^+$.

(9-((cis-1,3)-3-((tert-Butyldiphenylsilyl)oxy)cyclobutyl)-9H-purin-8-yl)methyl acetate (I54G)

A mixture of I54F (1.97 mmol) and BSA (4 mL) was heated at 90° C. for 2 hrs, and then cooled to RT. The reaction mixture was concentrated, diluted with EtOAc (50 mL) and washed with brine (2×20 mL). The organic layer was dried (Na$_2$SO$_4$), concentrated under reduced pressure and purified by silica gel chromatography (1-5% MeOH/DCM) to give I54G (0.40 g, 41% over three steps) as an orange oil. LCMS m/z (M+H)$^+$501.3. $^1$H NMR (CDCl$_3$) δ 9.08 (s, 1H), 8.99 (s, 1H), 7.68 (m, 4H), 7.41 (m, 6H), 5.28 (s, 2H), 4.28 (ddd, J=19.1, 9.6, 7.4 Hz, 1H), 4.15 (td, J=14.2, 7.1 Hz, 1H), 3.28 (m, 2H), 2.74 (m, 2H), 2.10 (s, 6H), 1.06 (s, 9H).

(9-((cis-1,3)-3-((tert-Butyldiphenylsilyl)oxy)cyclobutyl)-9H-purin-8-yl)methanol (I54H)

A mixture of I54G (0.40 g, 0.80 mmol) and K$_2$CO$_3$ (11.4 mg, 0.082 mmol) in MeOH (10 mL) was stirred at RT for 1 hr and then concentrated under reduced pressure. The residue was purified by silica gel chromatography (1-10% MeOH/DCM) to give I54H (0.31 g, 85%) as a tan solid. LCMS m/z (M+H)$^+$459.4. $^1$H NMR (CDCl$_3$) δ 9.00 (s, 1H), 8.96 (s, 1H), 7.68 (m, 4H), 7.41 (m, 6H), 5.85 (s, 2H), 4.32 (ddd, J=9.6, 7.5, 2.2 Hz, 1H), 4.15 (m, 1H), 3.78 (s, 1H), 3.21 (m, 2H), 2.77 (dddd, J=11.7, 9.3, 6.5, 2.8 Hz, 2H), 1.06 (s, 9H).

8-((Bis(4-methoxyphenyl)(phenyl)methoxy)methyl)-9-((cis-1,3)-3-((tert-butyldiphenylsilyl)oxy)cyclobutyl)-9H-purine (I54I)

A portion of I54H (0.31 g, 0.68 mmol) was co-evaporated with pyridine (3×6 mL) and then taken up in pyridine (6 mL), cooled to −5° C. and DMTrCl (0.28 g, 0.83 mmol) was added in one portion. This mixture was stirred at −5° C. for 10 min and at RT for 5 hrs and then concentrated under reduced pressure. To the residue was added MeOH (5 mL), TEA (0.05 mL) and absorbed on silica gel (1.5 g) and purified by silica gel chromatography (0.5-10% MeOH/DCM) to give I54I (0.42 g, 81%) as a light yellow solid. LCMS m/z (M+H)$^+$761.4. $^1$H NMR (CDCl$_3$) δ 9.04 (s, 1H), 8.98 (s, 1H), 7.67 (dd, J=8.0, 1.5 Hz, 2H), 7.39 (m, 8H), 7.28 (m, 5H), 7.19 (m, 2H), 6.75 (m, 4H), 4.35 (s, 2H), 3.92 (m, 2H), 3.26 (ddd, J=19.1, 8.3, 2.8 Hz, 2H), 2.44 (ddd, J=16.4, 8.1, 3.0 Hz, 2H), 1.04 (s, 9H).

((cis-1,3)-3-(8-((Bis(4-methoxyphenyl)(phenyl)methoxy)methyl)-9H-purin-9-yl)cyclobutanol (I52J)

To a solution of I54I (0.42 g, 0.55 mmol) in THF (5 mL) at RT was added TBAF/THF (1 M, 0.66 mL, 0.66 mmol) in a slow, dropwise fashion. The reaction mixture was stirred at RT overnight and concentrated under reduced pressure. The residue was purified by silica gel chromatography (1-5% MeOH/DCM) to give I54J (0.26 g, 90%) as a white solid. LCMS m/z (M+H)$^+$523.3. $^1$H NMR (CDCl$_3$) δ 9.09 (s, 1H), 8.96 (s, 1H), 7.44 (m, 2H), 7.35 (m, 4H), 7.30 (m, 2H), 7.23 (m, 1H), 6.84 (app. d, J=8.9 Hz, 4H), 4.60 (t, J=10.7 Hz, 1H), 4.50 (dt, J=15.6, 7.8 Hz, 1H), 4.42 (s, 2H), 3.77 (s, 6H), 2.95 (t, J=6.6 Hz, 1H).

((cis-1,3)-3-(8-((Bis(4-methoxyphenyl)(phenyl)methoxy)methyl)-9-purin-9-yl)cyclobutyl (2-cyanoethyl) diisopropylphosphoramidite (Intermediate 54)

To a solution of I54J (0.26 g, 0.50 mmol) in ACN (5 mL) was added DIEA (0.56 mL, 3.23 mmol) followed by dropwise addition of neat 3-((chloro(diisopropylamino)phosphino)oxy)propanenitrile (0.35 mL, 1.57 mmol). The reaction mixture was stirred at RT for 2 hrs, and then quenched by the addition of sat. aq.NaHCO$_3$ (0.3 mL) and H$_2$O (1 mL). The resulting mixture was concentrated under reduced pressure and purified directly by RP-MPLC (25-100% ACN/H$_2$O containing 0.1% NH$_4$CO$_3$) to give Intermediate 54 (0.19 g, 52%) as a white solid. LCMS m/z (M+H+OH-N, N-diisopropylamino)$^+$ 640.3. $^1$H NMR (CDCl$_3$) δ 8.96 (s, 1H), 8.85 (s, 1H), 7.45 (app. d, J=7.3 Hz, 2H), 7.36 (app. d, J=8.8 Hz, 4H), 7.30 (app. t, J=7.5 Hz, 1H), 6.84 (app. d, J=8.8 Hz, 4H), 4.42 (s, 2H), 4.21 (dt, J=17.2, 8.6 Hz, 2H), 4.05 (dd, J=14.8, 7.1 Hz, 1H), 3.85 (m, 2H), 3.77 (s, 6H), 3.37 (dt, J=17.6, 8.7 Hz, 2H), 2.65 (m, 4H), 2.00 (app hept, J=6.8 Hz, 2H), 1.20 (s, 6H), 1.18 (d, 6H). $^{31}$P NMR (CDCl$_3$) δ 145.86.

Example 35
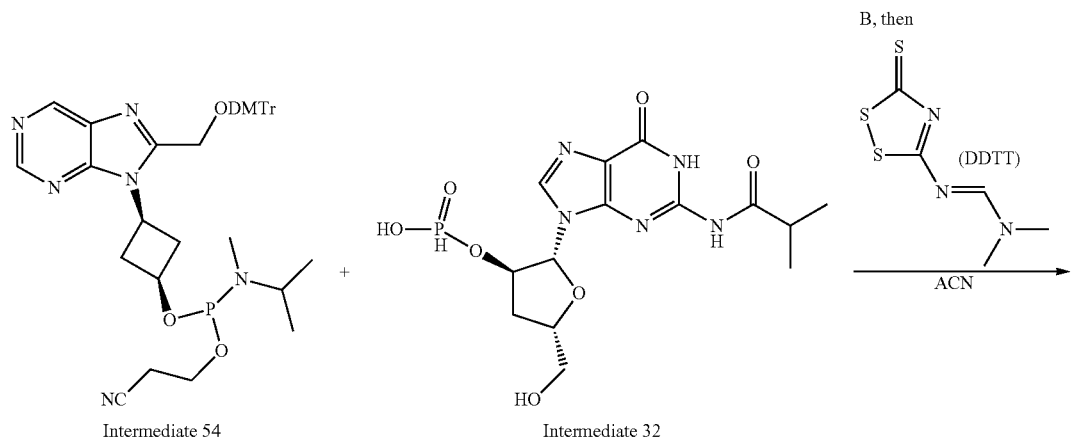
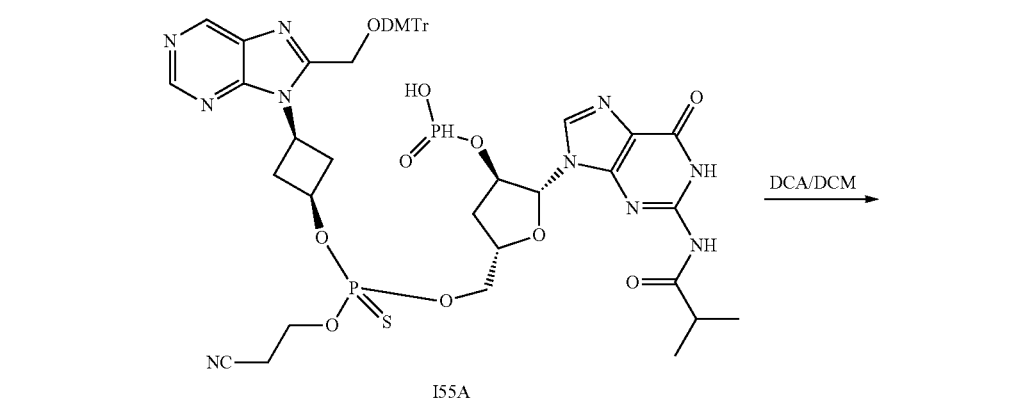
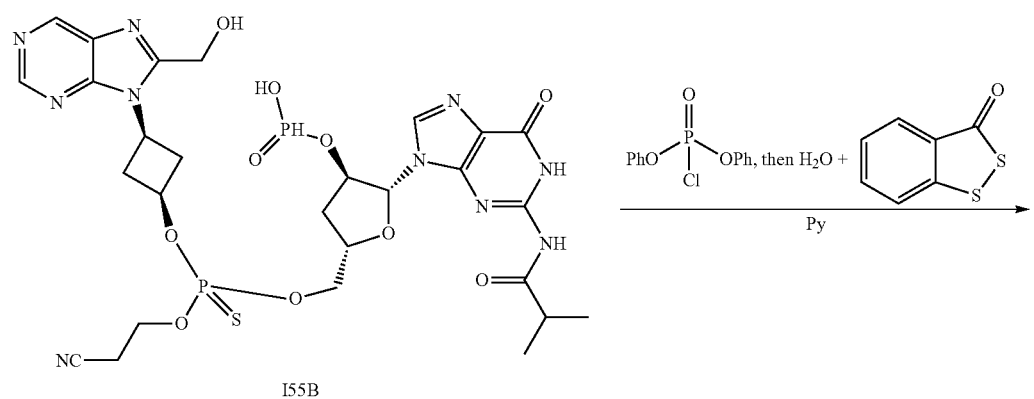
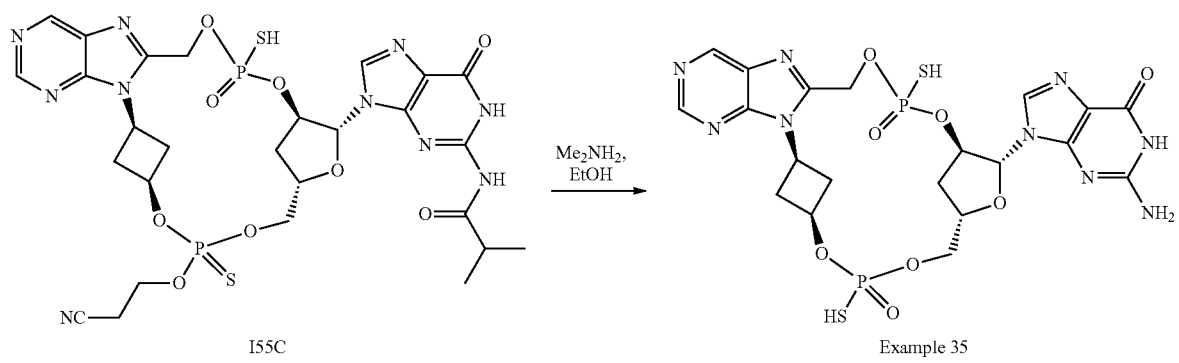

Example 35 diastereomers (Diastereomers A-D) were prepared according to procedures analogous to those outlined in Example 27.

(2R,3R,5S)-5-(((((1S,3R)-3-(8-((Bis(4-methoxyphenyl)(phenyl)methoxy)methyl)-9H-purin-9-yl)cyclobutoxy)(2-cyanoethoxy)phosphorothioyl)oxy)methyl)-2-(2-isobutyramido-6-oxo-1H-purin-9(6H)-yl)tetrahydrofuran-3-yl hydrogen phosphonate (I55A)

LCMS ($T_R$=1.24 min) m/z 1053.3 (M–H)$^-$. $^{31}$P NMR (CD$_3$OD) δ 66.14, 65.99, 2.60, 2.59.

(2R,3R,5S)-5-((((2-Cyanoethoxy)((1S,3R)-3-(8-(hydroxymethyl)-9H-purin-9-yl)cyclobutoxy)phosphorothioyl)oxy)methyl)-2-(2-isobutyramido-6-oxo-1H-purin-9(6H)-yl)tetrahydrofuran-3-yl hydrogen phosphonate (I55B)

LCMS ($T_R$=0.75 min) m/z 751.3 (M–H)$^-$. $^{31}$P NMR (CD$_3$OD) δ 66.12, 65.95, 2.63, 2.62.

N-{9-[(1S,22R,23R)-4-(2-Cyanoethoxy)-20-oxo-20-sulfanyl-4-sulfanylidene-3,5,19,21,24-pentaoxa-9,11,13,16-tetraaza-4lambda5,20lambda5-diphosphapentacyclo[20.2.1.16,8.09,17.010,15]hexacosa-10,12,14,16-tetraen-23-yl]-6-oxo-6,9-dihydro-1H-purin-2-yl}-2-meth ylpropanamide (155C)

LCMS (Method C $T_R$=1.26, 1.28, and 1.32 min) m/z 765.2 (M–H)$^-$. $^{31}$P NMR (CD$_3$OD) δ 67.11, 66.26, 64.55, 64.01, 58.87, 58.17, 56.39, 56.17.

(1S,6S,8S,22R,23R)-23-(2-Amino-6-oxo-6,9-dihydro-1H-purin-9-yl)-4,20-disulfanyl-3,5,19,21,24-pentaoxa-9,11,13,16-tetraaza-4lambda5,20lambda5-diphosphapentacyclo[20.2.1.16,8.09,17.010,15] hexacosa-10,12,14,16-tetraene-4,20-dione (Example 35)

A solution of 155C (0.17 g, 0.29 mmol, a mixture of diastereomers) in MeNH$_2$/EtOH (33%, 5.2 mL) was stirred at RT for 2 hrs, and then concentrated under reduced pressure. The residue was purified by RP—HPLC (Waters, X Bridge C18, 5 jam, 19×150 mm column eluting with 4-8% [33 min] ACN/H$_2$O containing 0.04% NH$_4$HCO$_3$, Flow rate=10 mL/min) to give four pure diastereomers (Diastereomer A: $T_R$=15.78 min, 16.9 mg; Diastereomer B: $T_R$=23.18 min, 25.9 mg; Diastereomer C: $T_R$=27.18 min, 11.5 mg; Diastereomer D: $T_R$=27.80 min, 27.4 mg; Total: 0.0817 g, 48% for two steps) of Example 35C (Diastereomer C): LCMS (Method D, $T_R$=1.27 min) m/z 642.1.0 (M–H)$^-$. $^1$H NMR (D$_2$O) δ 8.89 (s, 1H), 8.73 (s, 1H), 7.91 (s, 1H), 5.76 (d, J=6.4 Hz, 1H), 4.89-4.81 (m, 1H), 4.77 (dd, J=11.5, 3.6 Hz, 1H), 4.61-4.55 (m, 1H), 4.49 (dd, J=11.5, 2.9 Hz, 1H), 4.29 (dt, J=16.2, 8.2 Hz, 1H), 4.10-3.69 (m, 1H), 3.83 (dd, J=11.1, 4.3 Hz, 1H), 3.37 (dt, J=12.6, 6.5 Hz, 1H), 3.27 (td, J=13.1, 6.6 Hz, 1H), 2.94 (dd, J=20.0, 8.6 Hz, 1H), 2.55 (dd, J=12.5, 7.8 Hz, 1H), 2.48-2.31 (m, 2H), 1.83 (dd, J=18.9, 8.3 Hz, 1H). $^{31}$P NMR (D$_2$O) δ 54.18, 53.89. Example 35D (Diastereomer D): LCMS (Method D, $T_R$=1.28 min) m/z 642.2 (M–H)$^-$. $^1$H NMR (D$_2$O) δ 8.88 (s, 1H), 8.73 (s, 1H), 7.94 (s, 1H), 5.74 (d, J=6.5 Hz, 1H), 5.14-4.98 (m, 1H), 4.81 (dd, J=11.8, 4.7 Hz, 1H), 4.71 (dd, J=11.9, 4.8 Hz, 1H), 4.60-4.53 (m, 1H), 4.44 (dt, J=16.1, 8.1 Hz, 1H), 4.02 (ddd, J=11.1, 4.2, 2.5 Hz, 1H), 3.87 (dd, J=10.9, 5.4 Hz, 1H), 3.26 (dt, J=12.7, 6.5 Hz, 1H), 3.15 (dt, J=17.3, 6.4 Hz, 1H), 2.92 (dd, J=19.8, 8.5 Hz, 1H), 2.48-2.37 (m, 3H), 2.24 (dd, J=19.1, 8.3 Hz, 1H). $^{31}$P NMR (D$_2$O) δ 55.65, 54.23.

Intermediate 56

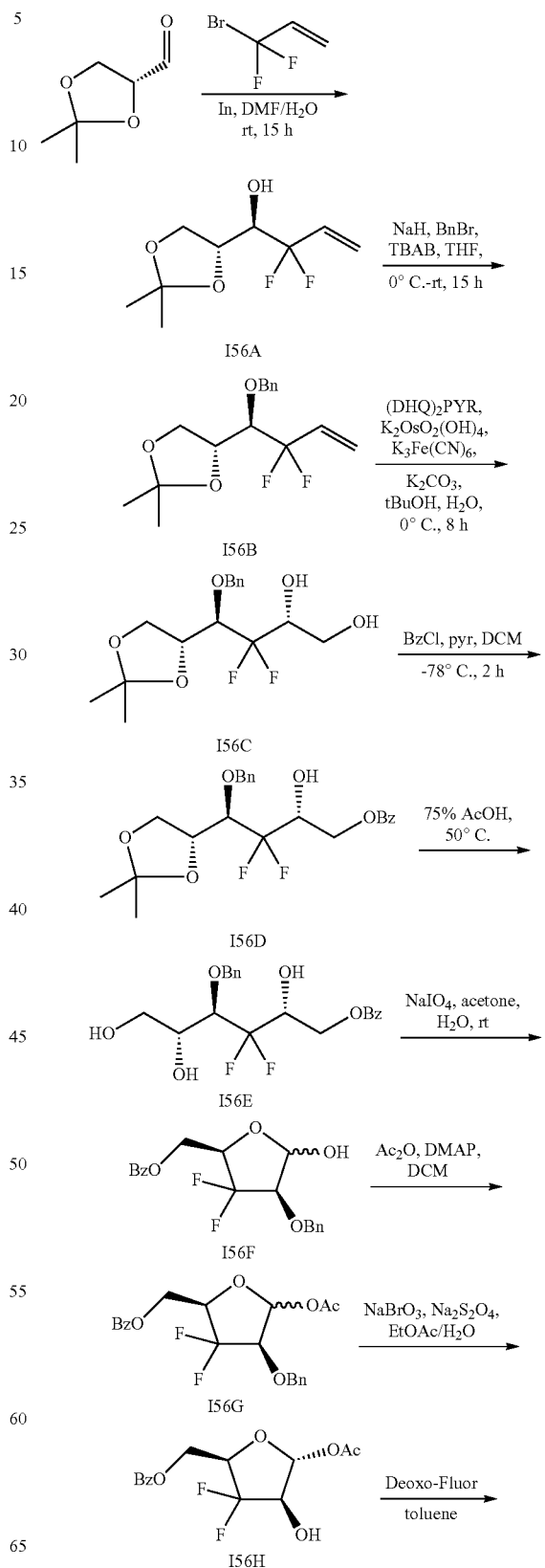

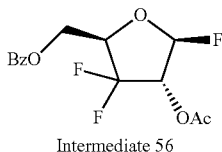

Intermediate 56

(R)-1-((R)-2,2-Dimethyl-1,3-dioxolan-4-yl)-2,2-difluorobut-3-en-1-ol (I56A)

To a stirred mixture of (R)-2,2-dimethyl-1,3-dioxolane-4-carbaldehyde (20 g, 0.15 mol) in DMF (300 mL) was added 3-bromo-3,3-difluoroprop-1-ene (24 g, 0.15 mol) in portions at 25° C. After stirring at 25° C. for 2 hrs, the reaction was diluted with EtOAc (500 mL). The resulting mixture was washed with $H_2O$ (500 mL×3), brine (2×500 mL). The organic layer was dried over $Na_2SO_4$. After filtration, the filtrate was concentrated under reduced pressure. The residue was purified by silica gel chromatography eluted (EtOAc/PE=6:1) to give compound I56A (24 g, 75%) which was used in the step without further analysis.

(R)-4-((R)-1-(Benzyloxy)-2,2-difluorobut-3-en-1-yl)-2,2-dimethyl-1,3-dioxolane (I56B)

To a stirred mixture of NaH (3.7 g, 0.92 mol, 60%) and TBAB (3.7 g, 0.12 mol) in THF (300 mL) at 0° C. was added I56A (24 g, 0.12 mol) in THF (30 mL) dropwise. After stirring at 0° C. for 30 min, the reaction mixture was allowed to warm to RT and stirred for 30 min. The resulting reaction mixture was cooled to 0° C., treated with benzyl bromide (14.2 mL) and stirred at RT overnight. The reaction was diluted with EtOAc (500 mL) and washed with $H_2O$ (3×500 mL), brine (2×500 mL). The organic layer dried over $Na_2SO_4$, filtered and concentrated under reduced pressure. The residue was purified by silica gel chromatography (EtOAc/PE=50:1) to give I56B (31 g, 91%) which was used in the step without further analysis.

(2R,4R)-4-(Benzyloxy)-4-((R)-2,2-dimethyl-1,3-dioxolan-4-yl)-3,3-difluorobutane-1,2-diol (I56C)

To a stirred mixture of $(DHQ)_2PYR$ (5.0 g, 5.7 mmol), $K_2OsO_2(OH)_4$ (781 mg, 2.1 mmol), $K_3Fe(CN)_6$ (105 g, 0.32 mol) and $K_2CO_3$ (43.8 g, 0.32 mol) in t-BuOH/$H_2O$ (1200 mL, 1:1) at 0° C. was added I56B (31 g, 0.11 mol) in portions. After stirring at 0° C. for 24 hrs, sat. aq. $NaHSO_3$ was added slowly and stirred for 30 min. The reaction was diluted with EtOAc (500 mL) and washed with $H_2O$ (500 mL×3) and brine (500 mL×2). The organic layer was dried over $Na_2SO_4$, filtered and concentrated under reduced pressure. The residue was purified by silica gel chromatography (EtOAc/PE=15:1) to give I56C (28 g, 75%) as a white solid. $^1H$ NMR ($CDCl_3$) δ 7.40-7.27 (m, 5H), 4.92 (d, J=12.0 Hz, 1H), 4.79 (d, J=12.0 Hz, 1H), 4.50-4.42 (m, 1H), 4.33-4.29 (m, 0.5H), 4.28-4.22 (m, 0.5H), 4.14-4.00 (m, 3H), 3.79 (d, J=4.0 Hz, 2H), 1.44 (s, 3H), 1.38 (s, 3H).

(2R,4R)-4-(Benzyloxy)-4-((R)-2,2-dimethyl-1,3-dioxolan-4-yl)-3,3-difluoro-2-hydroxybutyl benzoate (I56D)

To a stirred mixture of compound I56C (28 g, 84.3 mmol) in DCM/pyridine (400 mL, 1:1) was added BzCl (11.8 g, 84.3 mmol) in portions at −70° C. After stirring at −70° C. for 2 hrs, MeOH was added and the mixture was stirred for 30 min. The reaction was diluted with EtOAc (500 mL). The resulting mixture was washed with 1 N HCl (500 mL×3) and sat. aq. $NaHCO_3$ (500 mL×2). The organic layer was dried over $Na_2SO_4$, filtered and concentrated under reduced pressure. The residue was purified by silica gel chromatography (EtOAc/PE=10:1) to give compound I56D (25 g, 68%) as a white solid. $^1H$ NMR ($CDCl_3$) δ 8.05-7.98 (m, 2H), 7.58-7.51 (m, 1H), 7.45-7.25 (m, 7H), 4.94 (d, J=8.0 Hz, 1H), 4.81 (d, J=12.0 Hz, 1H), 4.62-4.46 (m, 3H), 4.41-4.27 (m, 2H), 4.16-4.02 (m, 2H), 3.21 (d, J=8.0 Hz, 1H), 1.44 (s, 3H), 1.38 (s, 3H).

(2R,4R,5R)-4-(Benzyloxy)-3,3-difluoro-2,5,6-trihydroxyhexyl benzoate (I56E)

I56D (25 g, 35.5 mmol, 1 eq.) was stirred in 75% aq. AcOH (220 mL) at 50° C. for 1.5 hrs. The mixture was concentrated under reduced pressure and the crude I56E was used in the next reaction directly.

((2R,4R)-4-(Benzyloxy)-3,3-difluoro-5-hydroxytetrahydrofuran-2-yl)methyl benzoate (I56F)

I56E was dissolved in acetone and treated with a solution of $NaIO_4$ (18.4 g, 53.3 mmol) in water and stirred at 25° C. for 1.5 hrs. After filtration, the filtrate was concentrated under reduced pressure. The residue was diluted with DCM (500 mL) and washed with water (500 mL×3) and brine (500 mL×2). The organic layer was dried over $Na_2SO_4$, filtered and concentrated under reduced pressure. The residue was purified by silica gel chromatography (EtOAc/PE=15:1) to give I56F (16 g, 77%) as a white solid which was used in the step without further analysis.

((2R,4R)-5-Acetoxy-4-(benzyloxy)-3,3-difluorotetrahydrofuran-2-yl)methyl benzoate (I56G)

To a stirred mixture of compound I56F (16 g, 43.9 mmol) in DCM (300 mL) was added DMAP (535 mg, 4.38 mmol) and $Ac_2O$ (4.56 mL, 4.83 mmol) in portions at 25° C. After stirring at 25° C. for 16 hrs the reaction mixture was diluted with DCM (500 mL) and washed with $H_2O$ (500 mL×3) and brine (500 mL×2). The organic layer was dried over $Na_2SO_4$, filtered and concentrated under reduced pressure. The residue was purified by silica gel chromatography (EtOAc/PE=15:1) to give I56G (15 g, 81%) which was used in the step without further analysis.

((2R,4R,5R)-5-Acetoxy-3,3-difluoro-4-hydroxytetrahydrofuran-2-yl)methyl benzoate (I56H)

To a stirred mixture of I56G (15 g, 37 mmol) in EtOAc (330 mL) was added $NaBrO_3$ (36.7 g, 244 mmol) at 25° C. To the well stirred two-phase system was added dropwise a solution of $Na_2S_2O_4$ (42.4 g, 244 mmol in 300 mL water) over 1 h at 25° C. After stirring at 25° C. for 5 hrs the reaction was diluted with EtOAc (500 mL) and washed with $H_2O$ (500 mL×3) and brine (500 mL×2). The organic layer was dried over $Na_2SO_4$, filtered and concentrated under reduced pressure. The residue was purified by silica gel chromatography (EtOAc/PE=5:1) to give I56H (12.1 g, 90%) as a white solid which was used in the step without further analysis.

((2R,4S,5S)-4-Acetoxy-3,3,5-trifluorotetrahydrofuran-2-yl)methyl benzoate (Intermediate 56)

To a stirred mixture of I56H (12 g, 31 mmol) in DCM (300 mL) was added Deoxo-Fluor (17 mL, 71 mmol) in portions at 25° C. After stirring at 120° C. for 16 hrs the mixture was concentrated under reduced pressure. The residue was purified by silica gel chromatography (EtOAc/PE=15:1) to give Intermediate 56 (5.3 g, 45%) as a yellow oil. MS: m/z=299 [M-F]$^+$ $^1H$ NMR ($CDCl_3$) δ 8.07-8.02 (m, 2H), 7.59-7.53 (m, 1H), 7.47-7.39 (m, 2H), 5.73 (dd, J=60.0, 2.8 Hz), 5.38 (dd, J=9.8, 6.1 Hz), 4.75-4.60 (m, 2H), 4.61-4.51 (m, 1H), 2.18 (s, 3H). $^{19}$F NMR (CDCl$_3$) δ −116.18 (dd, J=256.1, 8.2 Hz, 1F), −118.84 (dd, J=8.2, 2.2 Hz, 1F), −120.51 (dd, J=256.1, 2.3 Hz, 1F).
Intermediate 57
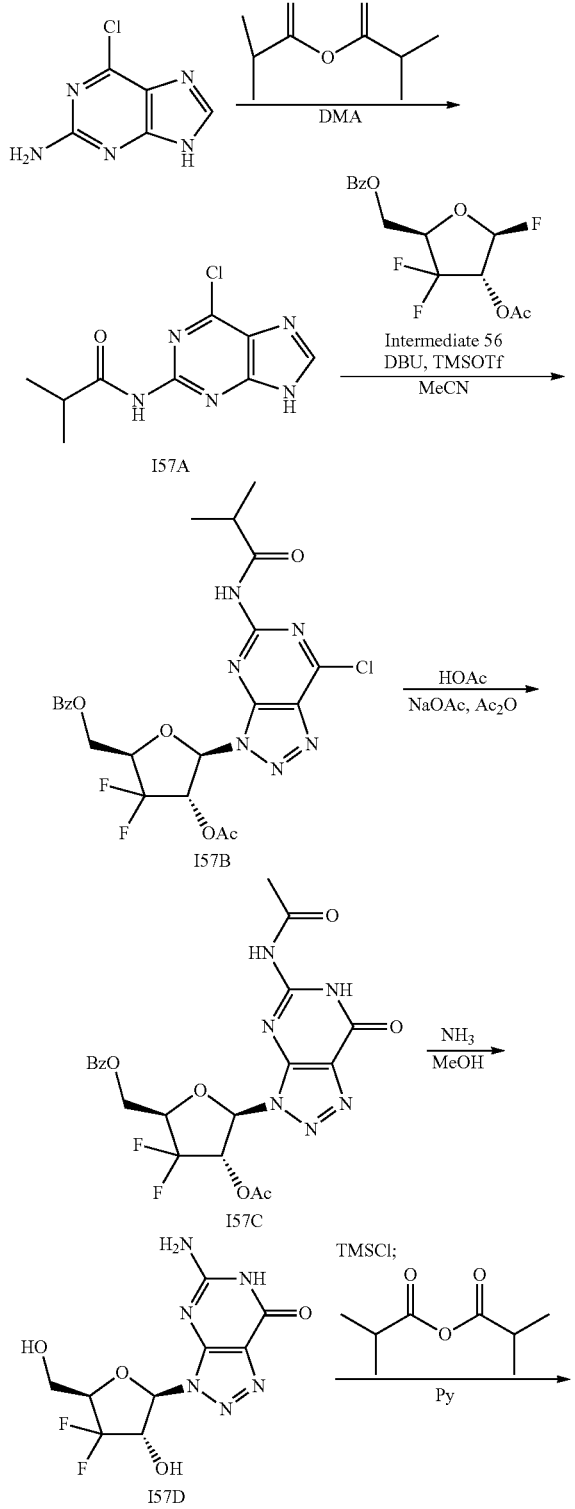
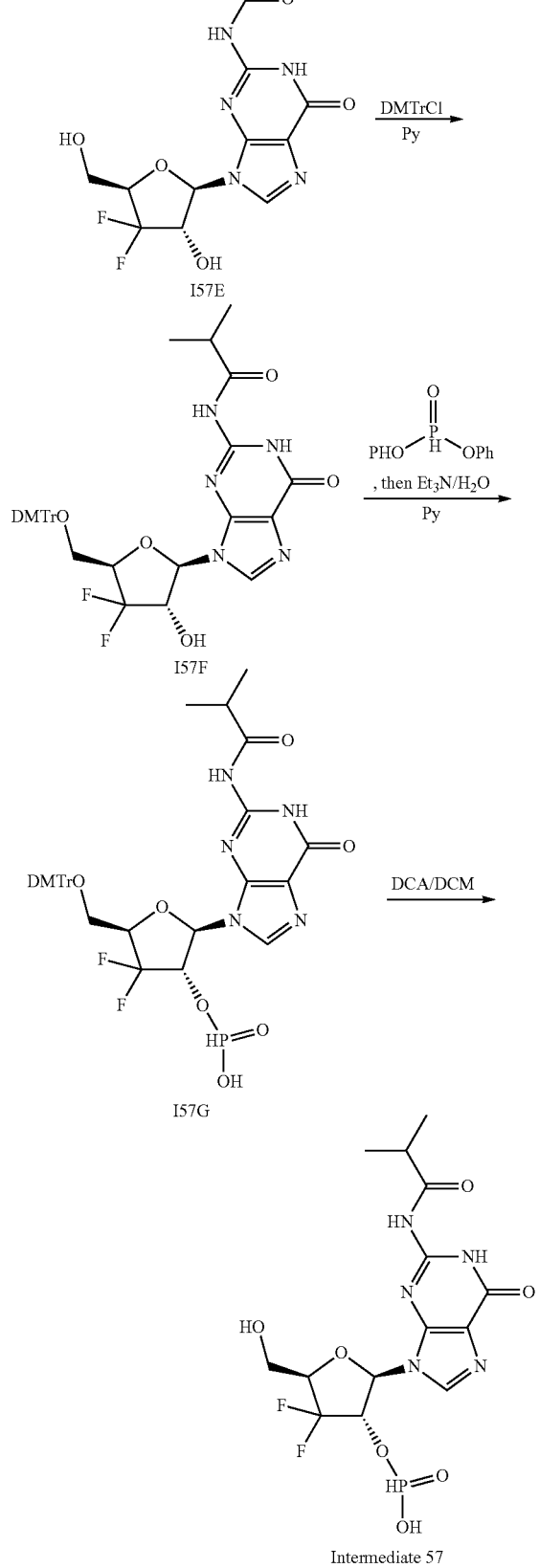

N-(6-Chloro-9H-purin-2-yl)isobutyramide (I57A)

To a solution of 6-chloro-9H-purin-2-amine (5.07 g, 29.3 mmol) in DMA (40 mL, previously dried over 3 Å MS) at RT was added isobutyric anhydride (13.4 mL, 80.8 mmol) slowly and then heated to 140° C. for 4 hrs. After cooling the mixture was diluted in EtOAc (200 mL) and water added; an emulsion formed with a precipitate which was filtered off. The filtrate was washed with water (6×25 mL), brine (4×25 mL), dried over $Na_2SO_4$, filtered and concentrated. The precipitate and residue were separately purified by silica gel chromatography (4-6% MeOH/DCM) to give I57A (4.05 g, 58%) as a white solid. LCMS m/z 565.1 $(M+H)^+$. $^1H$ NMR ($CDCl_3$, drop of $CD_3OD$) δ 8.32 (s, 1H), 2.62 (dt, J=13.7, 6.8 Hz, 1H), 1.25 (s, 3H), 1.23 (s, 3H).

((2R,4S,5R)-4-Acetoxy-5-(7-chloro-5-isobutyramido-3H-[1,2,3]triazolo[4,5-d]pyrimidin-3-yl)-3,3-difluorotetrahydrofuran-2-yl)methyl benzoate (I57B)

To Intermediate 56 (0.20 g, 0.60 mmol) in MeCN (3 mL) was added I57A (0.19 g, 0.79 mmol) and cooled to 0° C. To this was added DBU (0.34 mL, 1.79 mmol) and the mixture stirred for 30 min whereupon TMSOTf (0.66 mL, 3.65 mmol) was added dropwise. The mixture was stirred for an additional 30 min at 0° C. and then heated at 80° C. overnight. After cooling to RT, water (15 mL) and EtOAc (10 mL) was added and mixture extracted with EtOAc (3×15 mL). Combined organics were washed with sat. aq. $NaHCO_3$ (2×10 mL), brine (2×10 mL), dried over $Na_2SO_4$, filtered, concentrated and purified by silica gel chromatography (30-80% EtOAc/Hexane) to give I57B (0.17 g, 52%) as a white solid. LCMS m/z 538.2 $(M+H)^+$. $^1H$ NMR ($CDCl_3$) δ 8.33 (s, 1H), 8.12 (s, 1H), 7.99 (dd, J=8.4, 1.3 Hz, 2H), 7.54 (m, 1H), 7.41 (app t, J=7.8 Hz, 2H), 6.23 (d, J=5.2 Hz, 1H), 5.93 (m, 1H), 4.76 (dd, J=12.2, 4.4 Hz, 1H), 4.67 (dd, J=12.4, 5.6 Hz, 1H), 4.60 (m, 1H), 2.92 (m, 1H), 2.16 (s, 3H), 1.25 (s, 3H), 1.23 (s, 3H). $^{19}F$ NMR ($CDCl_3$) δ −116.49 (d, J=247.3 Hz, 1F), −118.06 (d, J=247.3 Hz, 1F).

((2R,4S,5R)-5-(5-Acetamido-7-oxo-6,7-dihydro-3H-[1,2,3]triazolo[4,5-d]pyrimidin-3-yl)-4-acetoxy-3,3-difluorotetrahydrofuran-2-yl)methyl benzoate (I57C)

To a solution of I57B (0.17, 0.32 mmol) in HOAc (2.7 mL, 47 mmol) at RT was added NaOAc (0.14 g, 1.7 mmol) and then acetic anhydride (2.7 mL, 29 mmol) slowly and then heated to 125° C. for 2.5 hrs. After cooling, MeOH (5 mL) was added and the mixture concentrated under reduced pressure; this procedure was repeated with EtOH (5 mL) twice more. The mixture was taken up in DCM (15 mL) and then washed with water and sat. aq. $NaHCO_3$ (2×10 mL), dried over $Na_2SO_4$, filtered and concentrated. The residue, a mixture of acetamide I57C and the isopropyl amide congener (0.16 g), was used in the next reaction without further purification.

5-Amino-3-((2R,3S,5R)-4,4-difluoro-3-hydroxy-5-(hydroxymethyl)tetrahydrofuran-2-yl)-3H-[1,2,3]triazolo[4,5-d]pyrimidin-7(6H)-one (I57D)

To I57C (0.16 g, ~0.32 mmol) was added ammonia in MeOH (8 mL, 7 M, 8 mmol) at RT which was stirred for 3 days. The mixture was concentrated under reduced pressure and purified by RP-MPLC (0-50% $ACN/H_2O$ containing 0.04% $NH_4HCO_3$ to give I57D (0.04 g, 44% for two steps) as a white solid. LCMS m/z 304.1 $(M+H)^+$. $^1H$ NMR (DMSO-$d_6$) δ 8.50 (br s, 1H), 7.97 (s, 1H), 6.55 (br s, 2H), 6.51 (d, J=6.0 Hz, 1H), 5.65 (d, J=7.9 Hz, 1H), 5.35 (t, J=5.0 Hz, 1H), 4.86 (m, 1H), 4.18 (ddd, J=11.6, 7.6, 3.4 Hz, 1H), 3.65 (m, 2H). $^{19}F$ NMR (DMSO-$d_6$) δ −113.10 (d, J=234.7 Hz, 1F), −121.77 (d, J=234.6 Hz, 1F).

N-(9-((2R,3S,5R)-4,4-Difluoro-3-hydroxy-5-(hydroxymethyl)tetrahydrofuran-2-yl)-6-oxo-6,9-dihydro-1H-purin-2-yl)isobutyramide (I57E)

To a solution of I57D (42.0 mg, 0.138 mmol) in pyridine (2 mL) at −5° C. was added TMSCl (0.10 mL, 0.79 mmol) in a dropwise fashion. The bath was removed and the reaction mixture was allowed to stir at RT for 4 hrs, whereupon isobutyric anhydride (0.08 mL, 0.47 mmol) was added in a dropwise fashion. The reaction was stirred at RT for 2 hrs, and then quenched by the addition of MeOH (1 mL). After stirring at RT for 5 min, conc. aq. ammonium hydroxide (1.8 mL) was added in a dropwise fashion with intermittent cooling using a RT water bath. The mixture was capped and placed in a freezer overnight, and then stirred at 30° C. for 1 hr and then concentrated to dryness under reduced pressure. To the residue was added MeOH (5 mL), and silica gel (1 g), and the mixture was concentrated under reduced pressure. The residue was purified by silica gel chromatography (5-20% MeOH/DCM) to give I57E (39.4 mg, 76%) as a white solid. LCMS m/z 374.2 $(M+H)^+$. $^1H$ NMR (DMSO-$d_6$) δ 12.13 (br s, 1H), 11.70 (br s, 1H), 8.30 (s, 1H), 6.59 (d, J=6.2 Hz, 1H), 5.75 (d, J=7.8 Hz, 1H), 5.35 (t, J=5.2 Hz, 1H), 4.91 (m, 1H), 4.23 (ddd, J=12.1, 7.9, 3.8 Hz, 1H), 3.67 (m, 2H), 2.76 (hept, J=6.8 Hz, 1H), 1.12 (s, H), 1.10 (s, H). $^{19}F$ NMR (DMSO-$d_6$) δ −113.45 (d, J=235.0 Hz, 1F), −121.98 (d, J=234.9 Hz, 1F).

N-(9-((2R,3S,5R)-5-((Bis(4-methoxyphenyl)(phenyl)methoxy)methyl)-4,4-difluoro-3-hydroxytetrahydrofuran-2-yl)-6-oxo-6,9-dihydro-1H-purin-2-yl)isobutyramide (I57F)

To a solution of I57E (0.47 g, 1.25 mmol) in pyridine (15 mL) at −5° C. was added DMTrCl (0.79 g, 2.22 mmol) in one portion. The resulting mixture was stirred at RT for 5 hrs, and then concentrated under reduced pressure. The residue was purified by silica gel chromatography (0.5-10% MeOH/DCM) to give I57F (0.54 g, 63%) as an off-white solid. LCMS m/z 676.3 $(M+H)^+$. $^1H$ NMR ($CDCl_3$) δ 12.00 (br s, 1H), 7.59 (s, 1H), 7.47 (app. d, J=7.2 Hz, 2H), 7.34 (m, 4H), 7.22 (m, 2H), 7.13 (m, 1H), 6.78 (t, J=10.2, 9.0 Hz, 4H), 5.75 (d, J=7.3 Hz, 1H), 5.29 (m, 1H), 4.30 (m, 1H), 3.74 (s, 3H), 3.73 (s, 3H), 3.43 (dd, J=10.9, 3.0 Hz, 1H), 3.31 (dd, J=10.9, 4.5 Hz, 1H), 2.01 (dt, J=13.4, 6.5 Hz, 1H), 1.03 (d, J=6.8 Hz, 3H), 0.86 (d, J=6.9 Hz, 3H). $^{19}F$ NMR ($CDCl_3$) δ −113.12 (d, J=240.1 Hz, 1F), −119.68 (d, J=238.7 Hz, 1F).

(2R,3S,5R)-5-((Bis(4-methoxyphenyl)(phenyl)methoxy)methyl)-4,4-difluoro-2-(2-isobutyramido-6-oxo-1H-purin-9(6H)-yl)tetrahydrofuran-3-yl hydrogen phosphonate (I57G)

To a solution of I57F (0.75 g, 1.11 mmol) in pyridine (8 mL) was added diphenyl phosphite (0.70 mL, 3.66 mmol). The reaction mixture was stirred at RT for 30 min, and then cooled in an ice/acetone bath, whereupon TEA (1.1 mL) and then $H_2O$ (1.1 mL) were added in a dropwise fashion. The bath was removed and the reaction mixture was stirred at RT for 1 hr. The mixture was concentrated under reduced pressure and the residue was purified by RP-MPLC (35-100% ACN/H₂O) to provide I57G (0.35 g as a triethyl amine salt, 88% product by weight assigned by ¹H NMR, 38% yield) as a white solid. This material was used "as is" in subsequent transformations. LCMS m/z 740.3 (M+H)⁺.

(2R,3S,5R)-4,4-Difluoro-5-(hydroxymethyl)-2-(2-isobutyramido-6-oxo-1H-purin-9(6H)-yl)tetrahydrofuran-3-yl hydrogen phosphonate (Intermediate 57)

To a suspension of I57G (0.35 g, 0.42 mmol) in DCM (4 mL) was added H₂O (0.08 mL, 4.44 mmol) followed by a solution of DCA (0.31 mL, 3.76 mmol) in DCM (4 mL). The reaction mixture was stirred for 30 min at RT, and then TES (3.5 mL) was added. After stirring for an additional 2 hrs, pyridine (0.60 mL) was added. The mixture was concentrated under reduced pressure and the residue was purified by silica gel chromatography (5-70% MeOH/DCM) to give Intermediate 57 (0.15 g as a salt; 11% triethyl amine by weight, 3% pyridine by weight, 86% product by weight assigned by ¹H NMR, 71% yield) as a white solid. LCMS (Method A: $T_R$=0.65 min, m/z 438.2 (M+H)⁺. ¹H NMR (CD₃OD) δ 8.31 (s, 1H), 6.44 (d, J=322.4 Hz, 1H), 6.11 (d, J=6.3 Hz, 1H), 5.56 (ddd, J=20.5, 10.6, 6.5 Hz, 1H), 4.34 (dtd, J=10.8, 7.1, 3.6 Hz, 1H), 3.19 (d, J=3.5 Hz, 2H), 2.72 (hept, J=6.8 Hz, 1H), 1.22 (d, J=6.9 Hz, 6H) [pyridine, 2CH 8.75 (d, J=4.9 Hz, 0.40H), CH 8.38 (t, J=7.8 Hz, 0.23H), 2CH 8.02 (dd, J=7.6, 6.3 Hz, 0.40H)][triethyl amine, 3CH₂ 3.19 (q, J=7.3 Hz, 3.27H), 3CH₃ 1.29 (t, J=7.3 Hz, 4.84H)]. ¹⁹F NMR (CD₃OD) δ −115.88 (d, J=240.8 Hz, 1F), −122.64 (d, J=240.9 Hz, 1F). ³¹P NMR (CD₃OD) δ 1.88.

Example 36

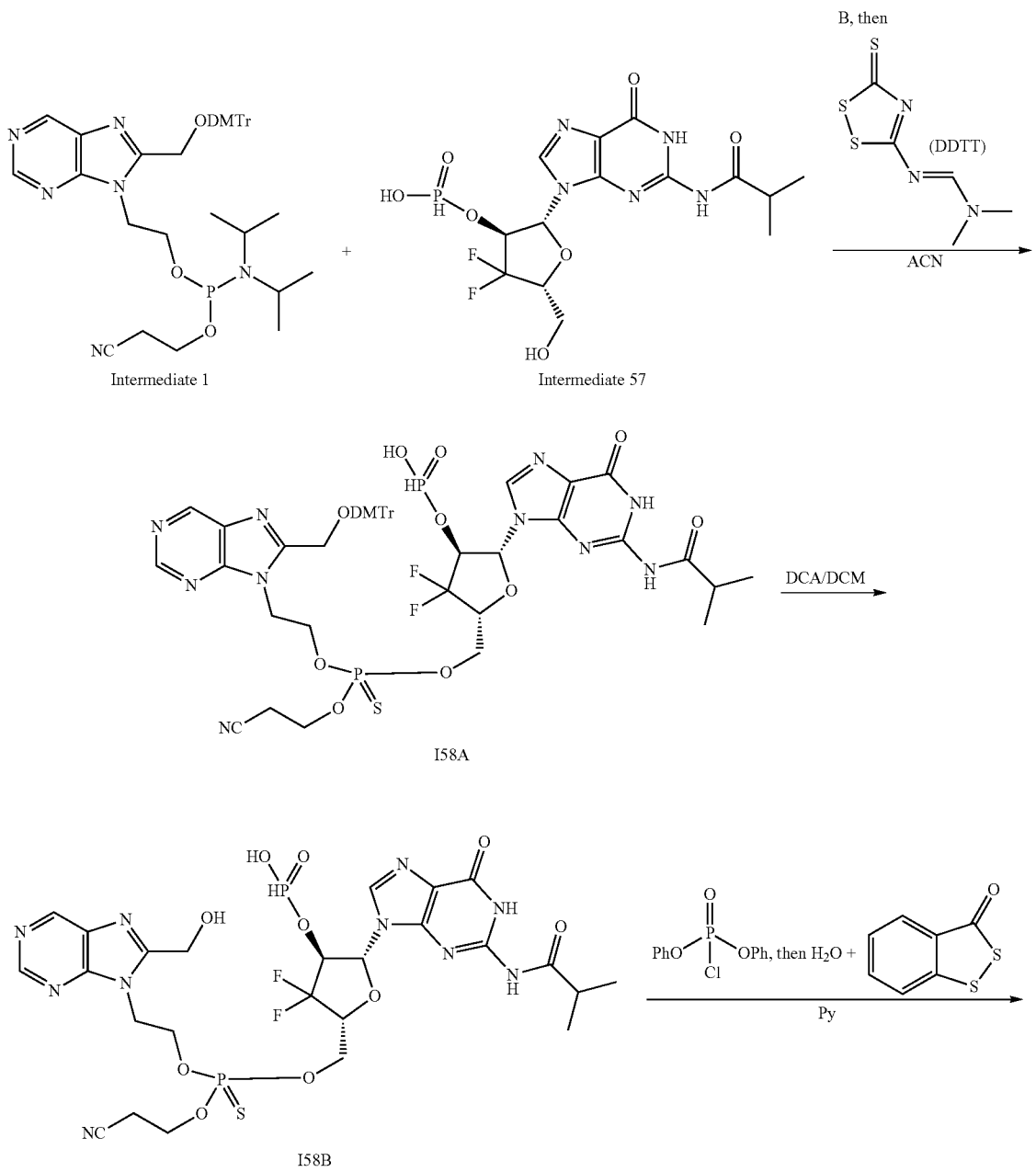

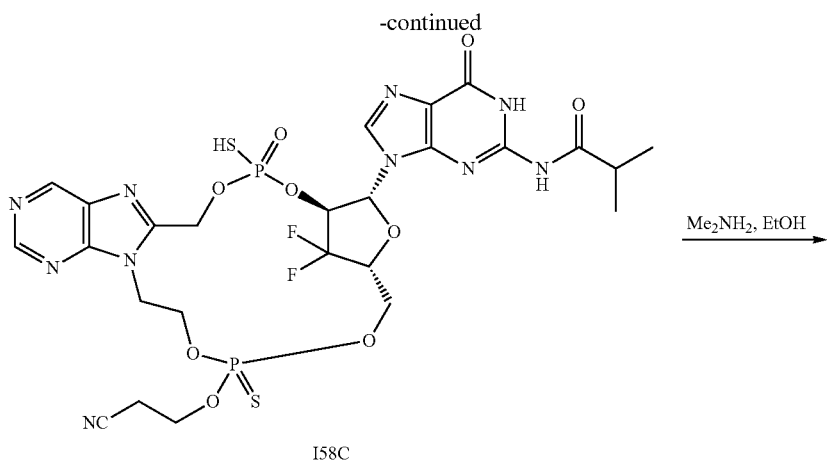

I58C

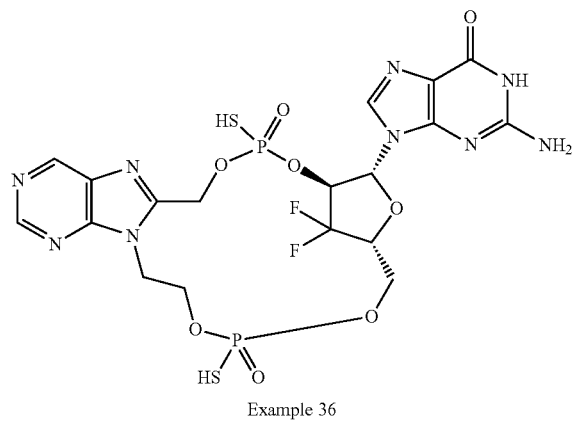 [SMILES: Nc1nc2c(ncn2[C@@H]2O[C@@H]3COP(=O)(S)OCCn4c(nc5cncnc54)COP(=O)(S)O[C@@H]2C3(F)F)c(=O)[nH]1]

Example 36

Example 36 diastereomers (Diastereomers A-D) were prepared according to procedures analogous to those outlined in Example 27.

(2R,3S,5R)-5-((((2-(8-((Bis(4-methoxyphenyl)(phenyl)methoxy)methyl)-9H-purin-9-yl)ethoxy)(2-cyanoethoxy)phosphorothioyl)oxy)methyl)-4,4-difluoro-2-(2-isobutyramido-6-oxo-1H-purin-9(6H)-yl)tetrahydrofuran-3-yl hydrogen phosphonate (I58A)

LCMS ($T_R$=1.38 min) m/z 1063.4 (M−H)⁻.

(2R,3S,5R)-5-((((2-Cyanoethoxy)(2-(8-(hydroxymethyl)-9H-purin-9-yl)ethoxy)phosphorothioyl)oxy)methyl)-4,4-difluoro-2-(2-isobutyramido-6-oxo-1H-purin-9(6H)-yl)tetrahydrofuran-3-yl hydrogen phosphonate (I58B)

LCMS ($T_R$=0.76 min) m/z 761.2 (M−H)⁻. ³¹P NMR (CD₃OD) δ 68.14, 68.03, 1.84. ¹⁹F NMR (CD₃OD) δ −115.35 (d, J=52.4 Hz, 1F), −116.00 (d, 52.5 Hz, 1F), −120.79 (d, J=23.9 Hz, 1F), −121.43(d, J=24.0 Hz, 1F).

N-{9-[(1S',21R,23R)-18-(2-Cyanoethoxy)-24,24-difluoro-3-oxo-3-sulfanyl-18-sulfanylidene-2,4,17,19,22-pentaoxa-7,10,12,14-tetraaza-3 lambda5,18lambda5-diphosphatetracyclo[19.2.1.0⁶,¹⁴.0⁸,¹³]tetracosa-6,8,10,12-tetraen-23-yl]-6-oxo-6,9-dihydro-1H-purin-2-yl}-2-methylpropanamide (I58C)

LCMS ($T_R$=0.88, 0.90 and 0.95 min) m/z 775.2 (M−H)⁻. ³¹P NMR (CD₃OD) δ 68.50, 68.22, 64.20, 64.16, 60.80, 59.72, 59.31, 58.01.

(1S,21R,23R)-23-(2-Amino-6-oxo-6,9-dihydro-1H-purin-9-yl)-24,24-difluoro-3,18-disulfanyl-2, 4,17, 19,22-pentaoxa-7,10,12,14-tetraaza-3lambda5, 18lambda5-diphosphatetracyclo[19.2.1.0⁶,¹⁴.0⁸,¹³]tetracosa-6,8,10,12-tetraene-3,18-dione (Example 36)

A solution of I58C (0.13 g, 0.29 mmol, a mixture of diastereomers) in MeNH₂/EtOH (33%, 10 mL) was stirred at RT for 2.5 hrs, and then concentrated under reduced pressure. The residue was purified by preparative-HPLC (Waters, X Bridge C18, 5 μm, 19×150 mm column eluting with 4-7% [33 min] ACN/H₂O containing 0.04% NH₄HCO₃, Flow rate=10 mL/min) to give two pure diastereomers (Diastereomer C: $T_R$=13.82 min, 11.3 mg; Diastereomer D: $T_R$=21.12 min, 12.5 mg; Total: 0.0238 g, 13% for two steps) of Example 36. Example 36D (Diastereomer D): LCMS (Method D, $T_R$=1.23 min) m/z 652.1 (M−H)⁻. ¹H NMR (D₂O) δ 8.94 (s, 1H), 8.80 (s, 1H), 7.75 (s, 1H), 5.85 (d, J=7.9 Hz, 1H), 5.20 (dd, J=12.6, 7.0 Hz, 1H), 5.08 (ddd, J=18.6, 13.2, 6.7 Hz, 1H), 4.72 (dd, 7=12.8, 3.7 Hz, 1H), 4.59-4.45 (m, 2H), 4.38 (dt, J=15.0, 5.3 Hz, 1H), 4.32-4.20 (m, 1H), 4.15-4.03 (m, 2H), 3.98-3.90 (m, 1H). ¹⁹F NMR (D₂O) δ −115.03 (d, J=237.6 Hz, 1F), −121.78 (d, 237.4 Hz, 1F). ³¹P NMR (D₂O) δ 56.37, 55.03.

Intermediate 59

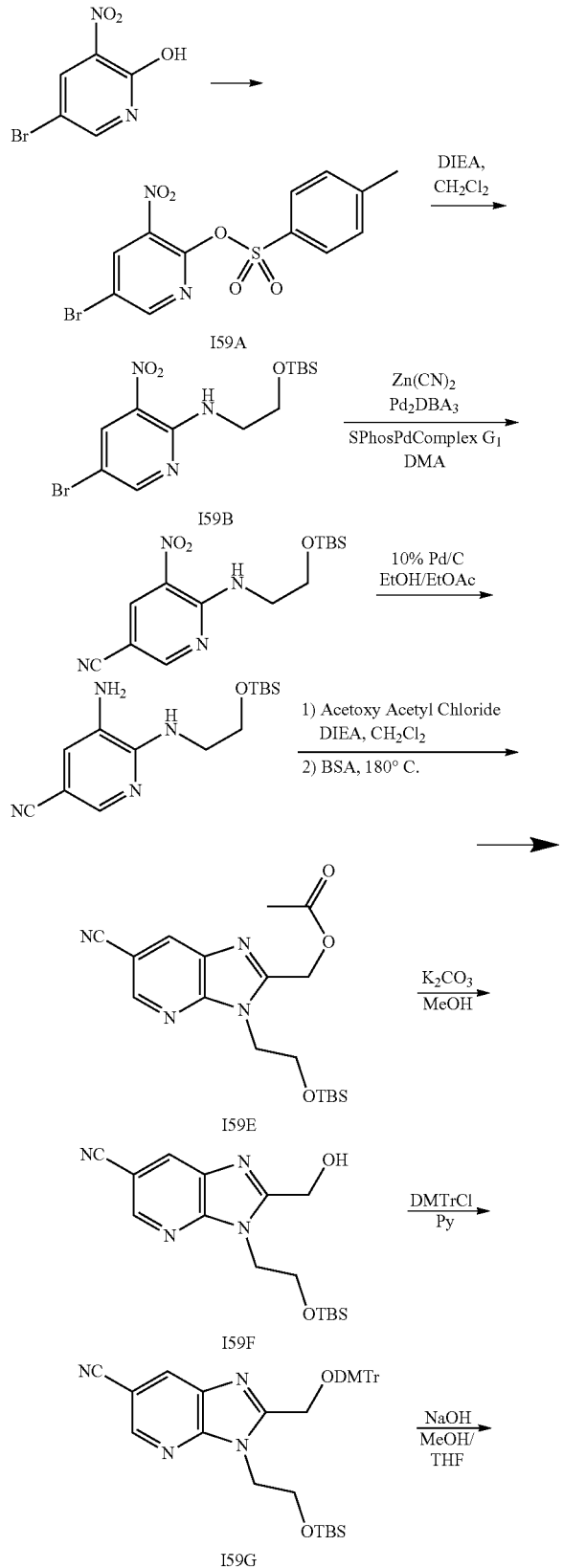

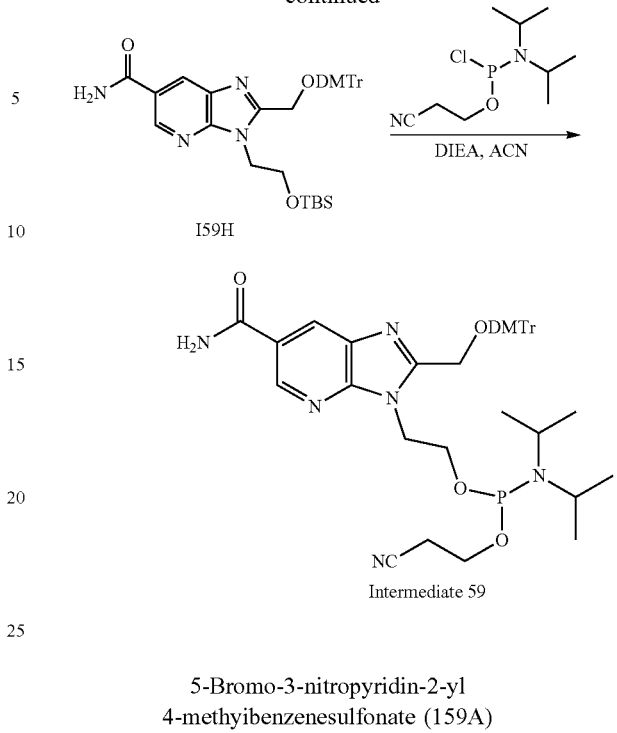

5-Bromo-3-nitropyridin-2-yl 4-methyibenzenesulfonate (159A)

5-Bromo-3-nitropyridin-2-ol (3.0 g, 13.7 mmol) and p-toluenesulfonyl chloride (3.01 g, 15.8 mmol) were suspended in DCM (100 mL). After dropwise of DIEA (4.77 mL, 27.4 mmol) a portion of DMAP (0.335 g, 2.74 mmol) was added. After stirring at RT for 16 hrs the mixture was diluted with DCM (500 mL) then washed with 1M HCl (aq) (2×500 mL) and brine (500 mL). The aqueous layer was extracted with DCM (200 mL) and the combined organic layers dried over $Na_2SO_4$, and concentrated in vacuo. The crude material was purified by silica gel chromatography (50% EtOAc/Hexane) to give I59A as an oil. Crystallization from 50% EtOAc/Hexane gave 3.84 g (74%) of a yellow solid which was used directly in the next step.

5-Bromo-N-(2-((tert-butyldimethylsilyl)oxy)ethyl)-3-nitropyridin-2-amine (I59B)

To a mixture of 159A and DIEA in ACN and was added at RT a portion of IIA (2.09 g, 11.96 mmol, 1.8 eq). The mixture was heated to reflux for 5 hrs. Solvent was removed under reduced pressure and the crude product was purified by silica gel chromatography (0-35% EtOAc/Hexane) to give I59B. LCMS (Method E): $T_R$=1.86 min, m/z=378.2 $(M+H)^+$. $^1H$ NMR ($CDCl_3$) δ 8.54 (d, J=2.2 Hz, 1H), 8.48 (br s, 1H), 8.41 (d, J=2.3 Hz, 1H), 3.83 (t, J=5.4 Hz, 2H), 3.74 (q, J=5.4 Hz, 2H), 0.91 (s, 9H), 0.06 (s, 6H).

6-((2-((tert-Butyldimethylsilyl)oxy)ethyl)amino)-5-nitronicotinonitrile (I59C)

A portion of I59B (600 mg, 1.59 mmol) and $Zn(CN)_2$ (0.206 g, 1.75 mmol, 1.1 eq) were dissolved in DMA (15 mL) in a microwave vial. The solution was purged using Argon for 15 min through the solution then SPhos Pd G1

(Aldrich, 0.107 g, 0.16 mmol) was added before heating in a microwave reactor for 30 min at 150° C. The mixture was diluted with EtOAc and washed with $H_2O$ (3×). The organic layer was dried, solvent removed and the residue purified by silica gel chromatography (0-30% EtOAc/Hexane) to give I59C (0.386 g, 74%). LCMS (Method E): $T_R$=1.59; m/z=323.3 (M+H)$^+$. $^1$H NMR (CDCl$_3$) δ 8.90 (br s, 1H), 8.66 (d, J=2 Hz, 1H), 8.58 (d, J=2.0 Hz, 1H), 3.84 (m, 4H), 0.91 (s, 9H), 0.08 (s, 6H).

5-Amino-6-((2-((tert-butyldimethylsilyl)oxy)ethyl)amino)picolinonitrile (I59D)

A portion of I59C (0.600 g, 1.59 mmol) was dissolved in EtOH (120 mL) and EtOAc (40 mL). The flask was evacuated and flushed with nitrogen and 10% Pd/C (0.08 g) was added. The flask was again evacuated and flushed with hydrogen three times. The mixture was then stirred overnight under an atmosphere of hydrogen. The material was filtered through a plug of Celite and the solvent removed to provide I59D (0.342 g, 73%). LCMS (Method E): $T_R$=1.24 min) m/z=293.3 (M+H)$^+$. $^1$H NMR (CDCl$_3$) δ 8.04 (d, J=1.6 Hz, 1H), 6.96 (d, J=1.2 Hz, 1H), 3.83 (t, J=5.2 Hz, 2H), 3.60 (q, J=5.2 Hz, 2H), 3.26 (br s, 2H), 0.90 (s, 9H), 0.06 (s, 6H).

(3-(2-((tert-Butyldimethylsilyl)oxy)ethyl)-6-cyano-3H-imidazo[4,5-b]pyridin-2-yl)methyl acetate (I59E)

To a solution of I59D (0.460 g, 1.57 mmol) in THF (10 mL) was added DIEA (0.84 mL, 4.72 mmol) followed by dropwise addition of acetoxyacetyl chloride (0.21 mL, 1.97 mmol). The solution was stirred for 2 hrs at RT, diluted with EtOAc, and washed with 0.1N HCl. The organic layer was dried (MgSO$_4$) and the solvent removed in vaccuo. The material was dissolved in BSA (3.0 mL) and heated to 180° C. overnight. After cooling to RT DCM and MeOH were added. Solvents were removed under reduced pressure and the residue was purified by silica gel chromatography (0-60% EtOAC/Hexane) to provide I59E (0.301 g, 51%). LCMS (Method E): $T_R$=1.32 min; m/z=447.4 (M+H)$^+$. $^1$H NMR (CDCl$_3$) δ 8.63 (d, J=1.8 Hz, 1H), 8.30 (d, J=1.8 Hz, 1H), 5.46 (s, 2H), 4.53 (t, J=5.0 Hz, 2H), 3.97 (t, J=5.0 Hz, 2H), 2.17 (s, 3H), 0.74 (s, 9H), −0.18 (s, 6H).

3-(2-((tert-Butyldimethylsilyl)oxy)ethyl)-2-(hydroxymethyl)-3H-imidazo[4,5-b]pyridine-6-carbonitrile (I59F)

To a solution of I59E (1.58 g, 4.22 mmol) in MeOH (60 mL) was added K$_2$CO$_3$ (0.058 g, 0.42 mmol). The mixture was stirred at RT for 30 min. The solvent was removed under reduced pressure and the mixture purified by silica gel chromatography (0-60% EtOAc in Hexane) to provide 159F (1.42 g, 98%) which was used in the next step without further purification.

2-((Bis(4-methoxyphenyl)(phenyl)methoxy)methyl)-3-(2-((tert-butyldimethylsilyl)oxy)ethyl)-3H-imidazo[4,5-b]pyridine-6-carbonitrile (159G)

To a solution of 159F (1.42 g, 4.27 mmol) in pyridine (20 mL) was added DMTrCl (2.17 g, 6.41 mmol) at 0° C. The mixture was stirred overnight, concentrated and partioned between EtOAc and H$_2$O. The organic layer was dried (MgSO$_4$), solvent removed under reduced pressure and purified by silica gel chromatography (0-50% EtOAC/Hexane) to provide 159G (2.01 g, 74%). LCMS (Method E): $T_R$=1.89 min; m/z=635.6 (M+H)$^+$. $^1$H NMR (CDCl$_3$) δ 8.62 (d, J=1.8 Hz, 1H), 8.27 (d, J=1.8 Hz, 1H), 7.48 (d, J=7.0 Hz, 2H), 7.39 (dt, J=9.0 and 2.2 Hz, 4H), 7.31 (t, J=7.8 Hz, 2H), 7.22 (tt, J=8.5 and 4 Hz, 1H), 6.85 (dt, J=8.8 and 2.0 Hz, 4H), 4.52 (s, 2H), 4.40 (t, J=5.5 Hz, 2H), 3.78 (m, 8H), 0.58 (s, 9H), −0.38 (s, 6H).

2-((Bis(4-methoxyphenyl)(phenyl)methoxy)methyl)-3-(2-hydroxyethyl)-3H-imidazo[4,5-b]pyridine-6-carboxamide (159H)

To a solution of 159G (2.01 g, 3.17 mmol) in 1:1 THF/MeOH (50 mL) was added a solution of 1N NaOH (15.83 mL, 15.83 mmol). The mixture was heated to reflux for 30 min. After cooling to RT the mixture was diluted with DCM and washed with H$_2$O. The organic layer was dried (MgSO$_4$) and the solvent removed under reduced pressure. The residue was purified by silica gel chromatography (0-10% MeOH/DCM) to yield 159H (1.1 g, 65%). LCMS (Method E, $T_R$=1.01 min) m/z=539.5 (M+H)$^+$. $^1$H NMR (CDCl$_3$) δ 8.77 (d, J=2 Hz, 1H), 8.30 (d, J=2 Hz, 1H), 7.46 (d, J=7.0 Hz, 2H), 7.36 (dt, J=9.0 and 2.2 Hz, 4H), 7.29 (t, J=7.8 Hz, 2H), 7.22 (tt, J=7.0 and 2.0 Hz, 1H),6.85 (dt, J=9 and 3 Hz, 4H),6.71 (bs, 1H), 5.92 (br s, 1H), 4.48 (s, 2H), 4.28 (t, J=4.8 Hz, 2H), 4.25 (d, J=6 Hz, 1H), 3.89 (q, J=4.2 Hz, 2H), 3.77 (s, 6H).

2-(2-((Bis(4-methoxyphenyl)(phenyl)methoxy)methyl)-6-carbamoyl-3H-imidazo[4,5-b]pyridin-3-yl)ethyl (2-cyanoethyl) diisopropylphosphoramidite (Intermediate 59)

To a solution of I59H (1.10 g, 2.04 mmol) and DIEA (0.396 g, 0.53 mL, 3.06 mmol, 1.5 eq) in DCM (15 mL) was added dropwise a solution of 2-cyanoethyl N,N-diisopropylchlorophosphoramidite (0.628 g, 0.66 mL, 2.66 mmol, 1.3 eq) in DCM (15 mL). After 1 hr the mixture was diluted with DCM and washed with a 1% aq. NaHCO$_3$ solution. The organic layer was dried (MgSO$_4$), and the solvent removed under reduced pressure. After 1 h the mixture was diluted with DCM and washed with a 1% aq. NaHCO$_3$. The organic layer was dried (MgSO$_4$), and the solvent removed under reduced pressure. The residue was purified by RP-MPLC (0-100% ACN/H$_2$O) to provide Intermediate 59 (0.851 g, 56%). $^1$H NMR (CDCl$_3$) δ 8.87 (d, J=1.8 Hz, 1H), 8.44 (d, J=1.8 Hz, 1H), 7.48 (d, J=7.3 Hz, 2H), 7.39 (dt, J=8.8 and 2.0 Hz, 4H), 7.31 (t, J=7.3H, 2H), 7.23 (tt, J=7.3 and 1.3 Hz, 1H), 6.85 (dt, J=8.8 and 3 Hz, 4H),6.34 (bs, 1H), 5.76 (br s, 1H), 4.53 (m, 4H), 3.88-3.72 (comp, 7H), 3.42 (m, 2H), 3.29 (m, 2H), 2.38 (t, J=6.5 Hz, 2H), 1.02 (d, J=6.8 Hz, 6H), 0.86 (d, J=6.8 Hz, 6H). $^{31}$P NMR (CDCl$_3$) δ 174.77.

Intermediate 60C and Intermediate 61C
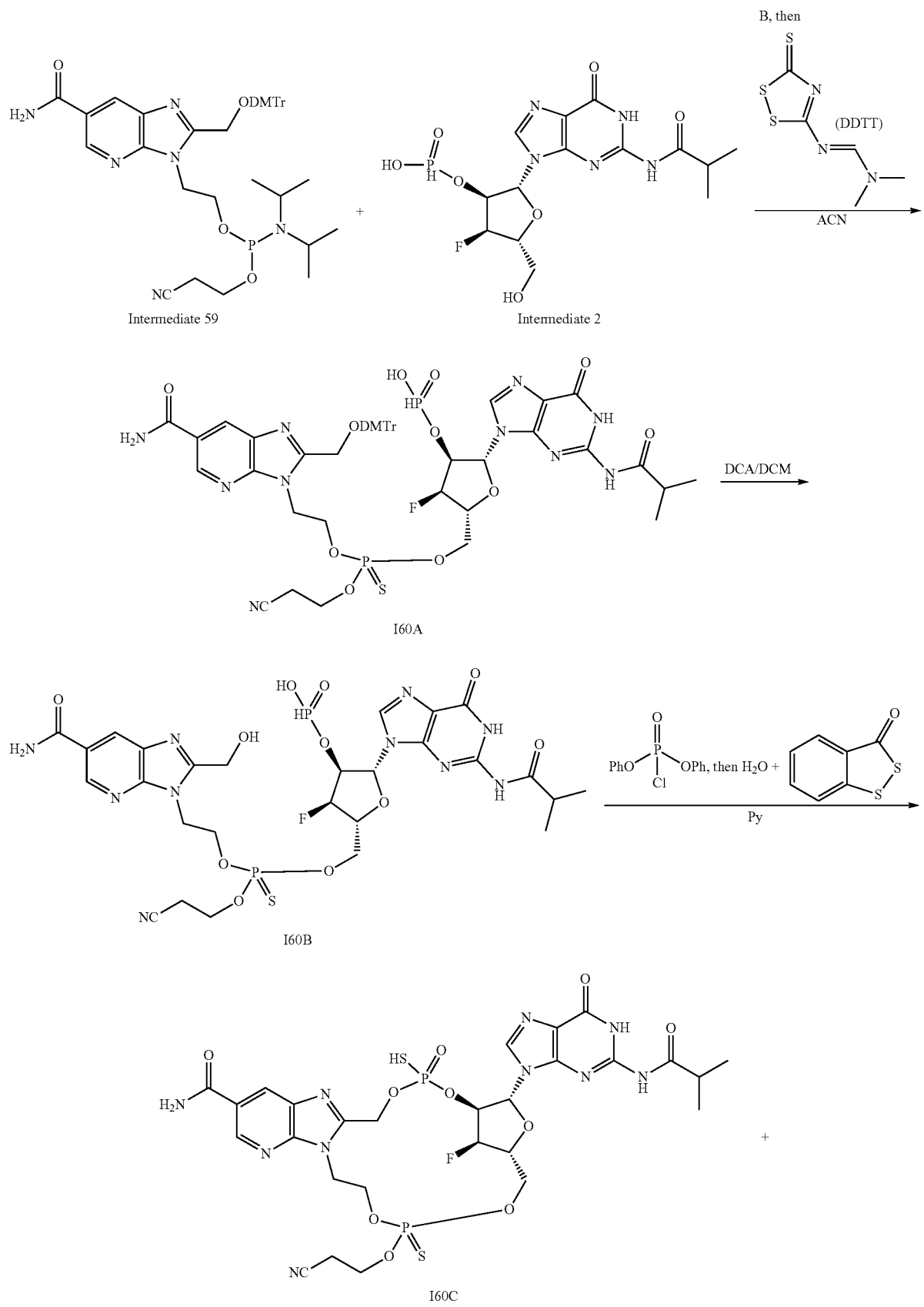

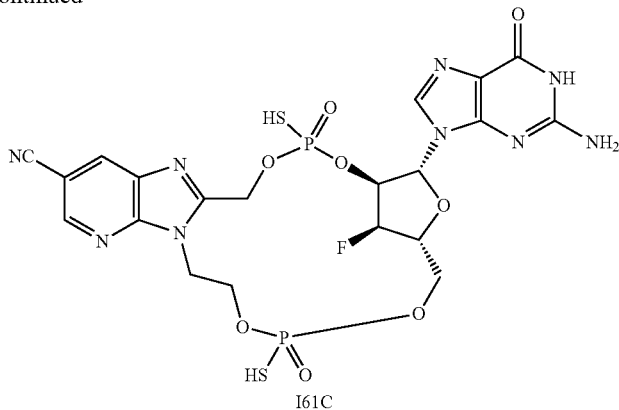
I61C (2R,3S,4R,5R)-5-((((2-(2-((Bis(4-methoxyphenyl)
(phenyl)methoxy)methyl)-6-carbamoyl-3H-imidazo
[4,5-b]pyridin-3-yl)ethoxy)(2-cyanoethoxy)phospho-
rothioyl)oxy)methyl)-4-fluoro-2-(2-isobutyramido-6-
oxo-1H-purin-9(6H)-yl)tetrahydrofuran-3-yl
hydrogen phosphonate (I60A)

To a solution of Intermediate 2 (0.440 g, 1.05 mmol) in ACN (20 mL) was added ethylthiatetrazole (0.273 g, 2.10 mmol). The solution was stirred for 2 hrs with activated 3 Å MS. In a separate flask Intermediate 59 (0.853 g, 1.15 mmol) was dissolved in ACN (20 mL) and stirred with activated 3 Å MS for 2h. The solution of Intermediate 59 was then added dropwise over 20 min to the solution of Intermediate 2 and ethylthiatetrazole. After 30 min DDTT (0.302 g, 1.47 mmol) was added and stirring was continued for an additional 15 min. The mixture was filtered and the remaining sieves were washed with additional ACN. The solvent was removed under reduced pressure and the residue purified via RP-MPLC (0-60% ACN/H$_2$O with 0.04% NH$_4$HCO$_3$) to provide I60A (0.588 g, 52%). This was used directly in the next step without further characterization.

(2R,3S,4R,5R)-5-((((2-(6-Carbamoyl-2-(hydroxym-
ethyl)-3H-imidazo[4,5-b]pyridin-3-yl)ethoxy)(2-
cyanoethoxy)phosphorothioyl)oxy)methyl)-4-fluoro-
2-(2-isobutyramido-6-oxo-1H-purin-9(6H)-yl)
tetrahydrofuran-3-yl hydrogen phosphonate (I60B)

To I60A (0.588 g, 0.54 mmol) in DCM (6.5 mL) at RT was added water (0.10 mL) and a solution of DCA (0.63 g, 4.86 mmol) in DCM (6.5 mL). After 15 min triethylsilane (9.0 mL) was added and the solution stirred for 2h. Pyridine (6.35 mL) was added and the solvent removed under reduced pressure. The residue was purified via RP-MPLC (0-50% ACN/H$_2$O with 0.04% NH$_4$HCO$_3$) to give I60B (0.383 g, 90%) as a ~1:1 mixture of diastereomers confirmed by both $^{31}$P NMR and $^{19}$F NMR. LCMS (Method A): T$_R$=0.69, min m/z=785.3 (M–H)$^-$. $^{31}$P NMR (D$_2$O) δ 68.12 (0.52P), 67.96 (0.48 P), 2.59P (1.0 P). $^{19}$F NMR (D$_2$O) δ-202.13 (0.53F), –202.18 (0.47F).

(1S,21R,23R,24R)-18-(2-Cyanoethoxy)-24-fluoro-
23-[2-(2-methylpropanamido)-6-oxo-6,9-dihydro-
1H-purin-9-yl]-3-oxo-3-sulfanyl-18-sulfanylidene-2,
4,17,19,22-pentaoxa-7,12,14-triaza-3lambda5,
18lambda5-diphosphatetracyclo[19.2.1.0⁶,¹⁴.0⁸,¹³]
tetracosa-6,8,10,12-tetraene-10-carboxamide (I60C)
and N-{9-[(1S,21R,23R,24R)-10-Cyano-18-(2-cya-
noethoxy)-24-fluoro-3-oxo-3-sulfanyl-18-sulfa-
nylidene-2,4,17,19,22-pentaoxa-7,12,14-triaza-
3lambda5,18lambda5-diphosphatetracyclo
[19.2.1.0⁶,¹⁴.0⁸,¹³]tetracosa-6,8,10,12-tetraen-23-
yl]-6-oxo-6,9-dihydro-1H-purin-2-yl}-2-
methylpropanamide (I61C)

A portion of I60B (0.383 g, 0.487 mmol) was co-evaporated with pyridine (3×15 mL) and and then dissolved in pyridine (50 mL). This solution was added dropwise over 30 min to a solution of diphenylphosphoryl chloride (2.52 mL, 12.17 mmol) in pyridine (50 mL) cooled to –40° C. under argon. The resulting mixture was stirred at –40° C. for 20 min and then 3H-benzo[c][1,2]dithiol-3-one (0.123 g, 0.73 mmol) was added followed by H$_2$O (0.32 mL, 17.5 mmol). The solution was warmed to RT, stirred for 1 hr and quenched with a solution of Na$_2$S$_2$O$_3$ (0.20 g) in H$_2$O (12.7 mL). The mixture was concentrated and purified via RP-MPLC (0-100% ACN/H$_2$O with 0.04% NH$_4$HCO$_3$) to provide I60C (0.40 g, 11%) and I61C (0.226 g, 59%). I60C: LCMS (Method D): T$_R$=1.23 min, m/z 801.5 (M+H)$^+$. I61C: LCMS (Method D): T$_R$=1.40 min, m/z 781.2 (M–H)$^-$.

Example 37

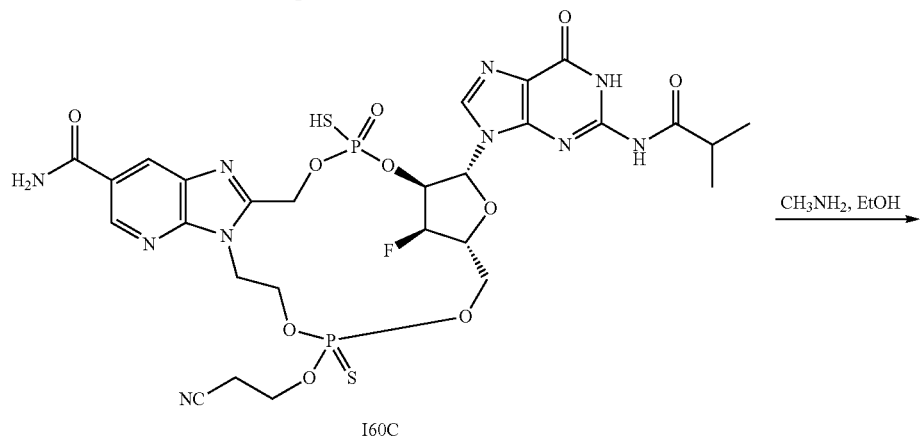

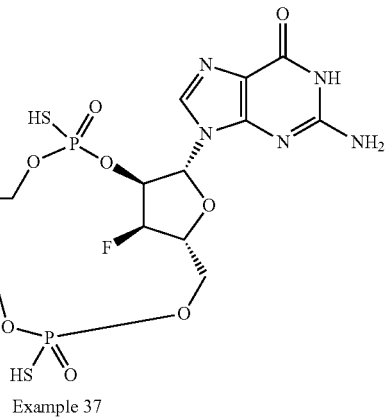

Example 37

(1S,21R,23R,24R)-23-(2-Amino-6-oxo-6,9-dihydro-1H-purin-9-yl)-24-fluoro-3,18-dioxo-3,18-disulfanyl-2,4,17,19,22-pentaoxa-7,12,14-triaza-3lambda,5,18lambda5-diphosphater To I60C (0.04 g, 0.05 mmol) was added a 33% solution of methyl amine in EtOH (5.0 mL) at RT. After 3 hrs the solvent was removed under reduced pressure and the residue purified via prep. RP—HPLC. Example 37A (2:1 mixture of isomers) major vs minor calculated by $^{31}$P NMR and confirmed via both 19F NMR and $^1$H NMR): LCMS (Method D, T$_R$=0.70 min) m/z=676.1 (M–H)–. $^1$H NMR (D$_2$O) δ 8.85 (m, 1H), 8.42 (m, 1H), 8.07 (s, 0.3H), 7.86 (s, 0.7H), 6.03 (d, J=8.0 Hz, 1H), 5.62 (d, J=3 Hz, 0.355) 5.5-5.4 (comp, 1H), 5.29-5.18 (comp, 0.7), 5.06 (m, 0.3H), 4.99- 4.84 (comp, 2H, 4.74-4.34 (comp, 5H), 4.29-3.93 (comp, 3H). $^{31}$P NMR (D$_2$O) δ 57.10 (0.34P), 55.52 (0.33 P), 55.41 (0.67 P), 55.33 (0.68 P). 19F NMR (D$_2$O) δ –196.78 (0.31 F), –198.51 (0.71 F). Example 37B (Diasteomer B) (single isomer confirmed by $^{31}$P, $^{19}$F, an $^1$H NMR): LCMS (Method D, T$_R$=0.74 min) m/z=676.2 (M–H)–. $^1$H NMR (D$_2$O) δ 8.84 (d, J=1.8 Hz, 1H), 8.45 (d, J=1.8 Hz, 1H), 7.64 (s, 1H), 6.06 (d, J=8.0 Hz, 1H), 5.54 (dd, J=52.7 and 3.8 Hz, 1H), 5.40 (dd, J=12.8 and 8.3 Hz, 1H), 5.02-4.90 (comp, 1H), 4.87 (dd, J=12.8 and 3.4 Hz 1H), 4.57-4.35 (comp, 3H), 4.23 (dd, J=11.1 and 4.5 Hz, 1H), 4.00 (dd, J=11.5 and 1.8, 1H). $^{31}$P NMR (D$_2$O) δ 54.83 (s, 1P), 54.46 (s, 1P). $^{19}$F NMR (D$_2$O) δ –198.4 (S, 1F).

Example 38

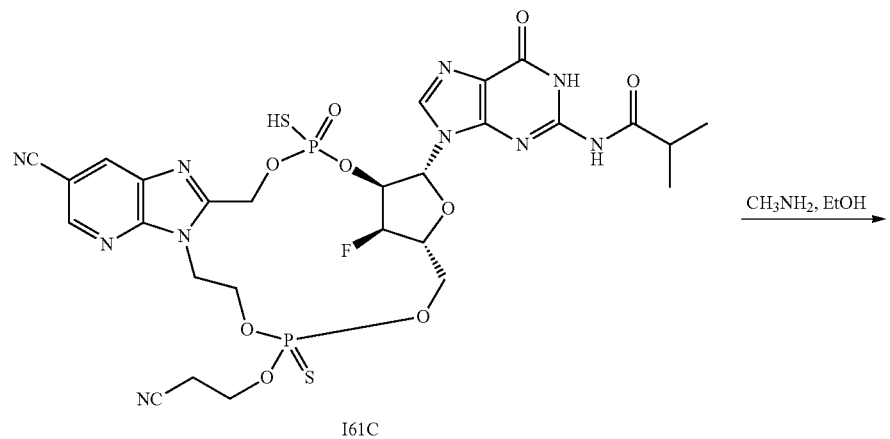

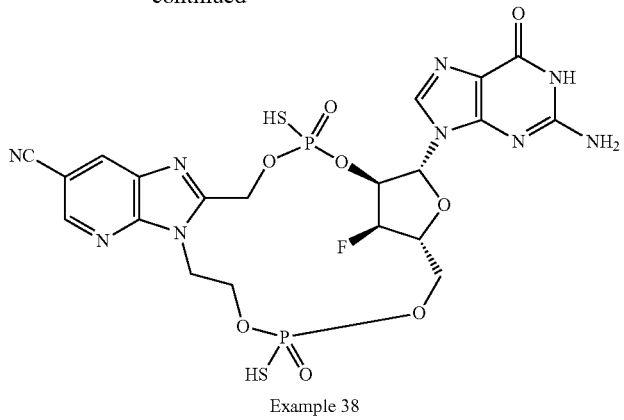

Example 38

(1S,21R,23R,24R)-23-(2-Amino-6-oxo-6,9-dihydro-1H-purin-9-yl)-24-fluoro-3,18-dioxo-3,18-disulfanyl-2,4,17,19,22-pentaoxa-7,12,14-triaza-3lambda5,18lambda5-diphosphatetracyclo[19.2.1.06,14.08,13]tetracosa-6,8,10,12-tetraene-10-carbonitrile (Example 38)

To I61C (0.050 g, 0.062 mmol) was added a 33% solution of methyl amine in EtOH (5.0 mL) at RT. After 3 hrs the solvent was removed and the product purified via prep. RP—HPLC. Example 38A (Diastereomer A): LCMS (Method D): $T_R$=0.76 min; m/z=658.1 (M−H)−. 1HNMR (D$_2$O) δ 8.72 (d, J=1.8 Hz, 1H), 8.42 (d, J=1.8 Hz, 1H), 7.91 (s, 1H), 6.00 (d, J=8.0 Hz, 1H), 5.48 (dd, J=52.7 and 3.8 Hz, 1H), 5.37 (dd, J=13.8 and 7.8 Hz, 1H), 4.96-4.80 (comp, 2H), 4.71-4.61 (comp, 2H), 4.52-4.44 (comp, 1H), 4.43-4.34 (comp, 1H), 4.26-4.17 (comp, 1H), 4.12 (m, 1H), 4.04 (bd, J=11.8 Hz, 1H). 31P NMR (D$_2$O) δ 55.49 (s, 1P), 55.39 (s, 1P). 19F NMR (D$_2$O) 8-198.56 (s, 1F). Example 38B (Diastereomer B): LCMS (Method D: $T_R$=0.76 min, m/z=658.1 (M−H)−. 1HNMR (D$_2$O) δ 8.75 (d, J=1.8 Hz, 1H), 8.44 (d, J=1.5 Hz, 1H), 8.20 (s, 1H), 6.04 (d, J=7.8 Hz, 1H), 5.29-5.02 (comp, 6H), 4.73-4.56 (comp, 4H), 4.46-4.30 (comp, 3H), 4.14 (m, 1H), 3.97 (dd, J=11.1 and 4.3 Hz, 1H). 31P NMR (D$_2$O) δ 57.22 (s, 1P), 55.56 (s, 1P). 19F NMR (D$_2$O) 8-196.83 (s, 1F). Example 38C (Diastereomer C): LCMS (Method D): $T_R$=0.85 min), m/z=658.1 (M−H)−. 1H NMR (D$_2$O) δ 8.77 (d, J=1.8 Hz, 1H), 8.48 (d, J=1.8 Hz, 1H), 7.76 (s, 1H), 6.03 (d, J=8.0 Hz, 1H), 5.52 (dd, J=53 and 3.8 Hz, 1H), 5.40 (dd, J=12.8 and 8 Hz, 1H), 5.01-4.82 (comp, 3H), 4.76-4.67 (comp, 1H), 4.57-4.34 (comp, 3H), 4.22 (dd, J=11.6 and 4.8 Hz, 1H), 4.02 (dd, J=11.7 and 1.8 Hz, 1H). 31P NMR (D$_2$O) δ 54.94 (s, 1P), 54.55 (s, 1P). 19F NMR (D$_2$O) δ −198.51 (s 1F) Example 38D (Diastereomer C): LCMS (Method D): $T_R$=0.87 min, m/z=658.1 (M−H)−. 1H NMR (D$_2$O) δ 8.68 (d, J=1.8 Hz, 1H), 8.35 (d, J=1.5 Hz, 1H), 7.80 (s, 1H), 5.95 (d, J=7.5 Hz, 1H), 5.2-4.95 (comp, 4H), 4.62-4.47 (comp, 2H), 4.35 (m, 2H), 4.16 (dd, J=11.6 and 7.5, 1H), 3.96 (dd, J=11.8 and 1.3 Hz, 1H). 31P NMR (D$_2$O) δ 56.81 (s, 1P), 55.44 (s, 1P). 19F NMR (D2O) δ −197.08 s, 1F).

Example 39

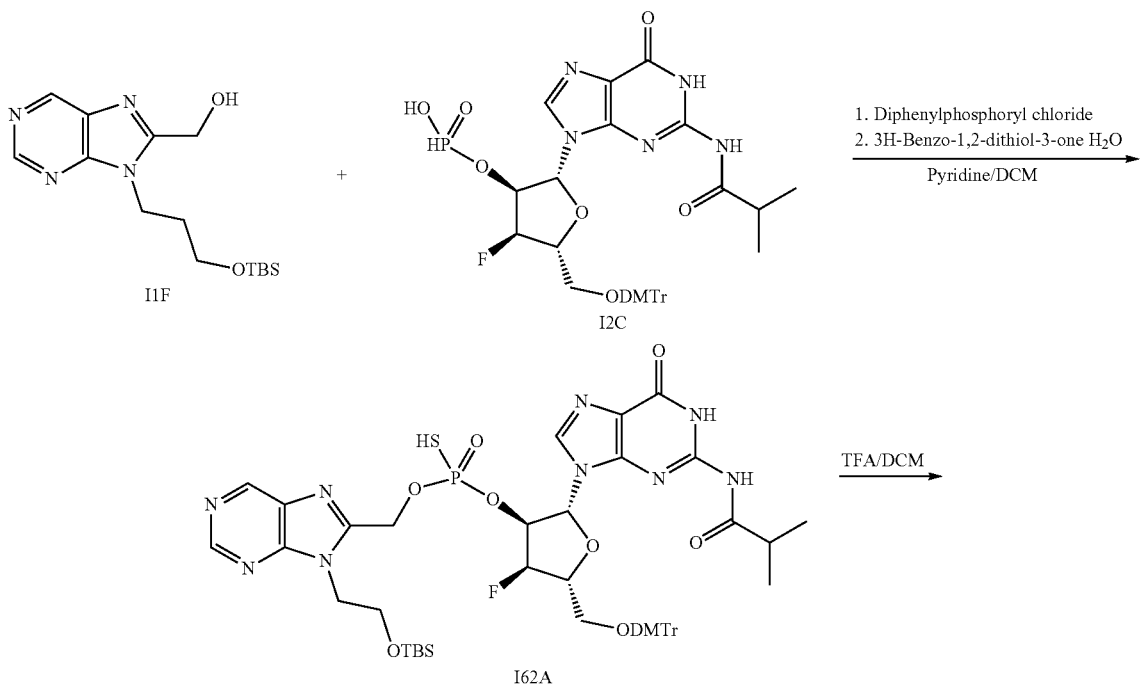

317

-continued

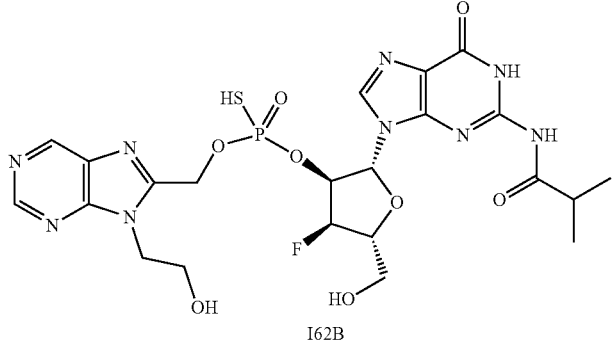

I62B

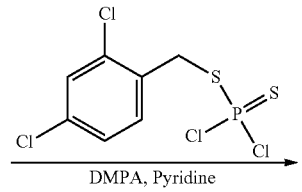

DMPA, Pyridine

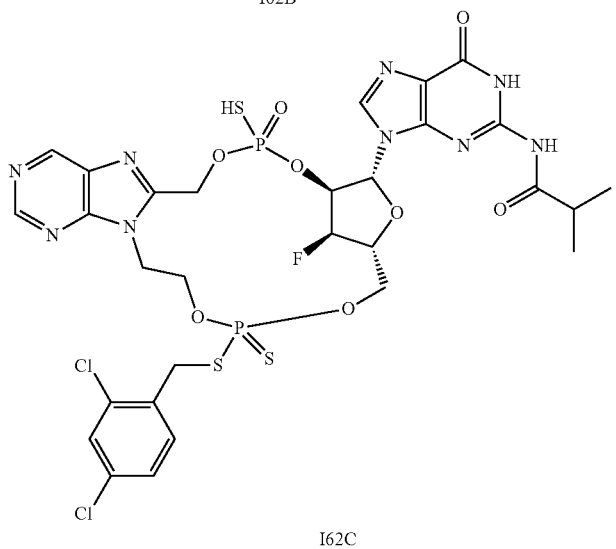

I62C

318

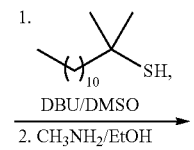

DBU/DMSO

2. CH₃NH₂/EtOH

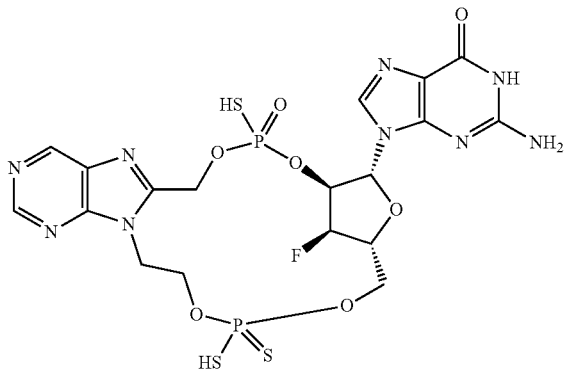

Example 39

O-((2R,3S,4R,5R)-5-((Bis(4-methoxyphenyl)(phenyl)methoxy)methyl)-4-fluoro-2-(2-isobutyramido-6-oxo-1H-purin-9(6H)-yl)tetrahydrofuran-3-yl)-O-((9-(2-((tert-butyldimethylsilyl)oxy)ethyl)-9H-purin-8-yl)methyl)S-hydrogen phosphorothioate (I62A)

To a mixture of I2C (160 mg, 0.22 mmol) and I1F (69 mg, 0.22 mmol) in pyridine (4.0 mL) and DCM (1.5 mL) at −40° C. under N₂ was added diphenylphosphoryl chloride (0.92 mL, 4.43 mmol) over 10 min and the resulting mixture was continued stirring for 45 min. 3H-benzo[c][1,2]dithiol-3-one (56 mg, 0.333 mmol) and H₂O (0.1 mL) were added and the cold bath was replaced with a RT water bath. The mixture was stirred for 1 hr, then concentrated and used in the next step without further purification.

O-((2R,3S,4R,5R)-4-Fluoro-5-(hydroxymethyl)-2-(2-isobutyramido-6-oxo-1H-purin-9(6H)-yl)tetrahydrofuran-3-yl)O-((9-(2-hydroxyethyl)-9H-purin-8-yl)methyl)S-hydrogen phosphorothioate (I62B)

A solution of I62A in DCM (5 mL) was treated with TFA (0.15 mL) at RT for 2 hrs. Additional DCM (5 mL) and TFA (0.15 mL) were added and the mixture was stirred for 1 hr. Then TFA was added until a red color persisted and the mixture was continued stirring for 1 hr. Et₃SiH (4.0 mL) was added and the mixture was stirred for 1 hr. Pyridine (2 mL) was added and the mixture was stirred for 5 min, then concentrated and purified by RP-MPLC (C18, 0-100% ACN/H₂O containing 0.04% NH₄HCO₃) to give I62B (75 mg, 54%). LCMS m/z 626.2 (M−H)⁻.

N-{9-[(1S,21R,23R,24R)-18-{[(2,4-Dichlorophenyl)methyl]sulfanyl}-24-fluoro-3-oxo-3-sulfanyl-18-sulfanylidene-2,4,17,19,22-pentaoxa-7,10,12,14-tetraaza-3lambda5,8lambda5-diphosphatetracyclo[19.2.1.0⁶,¹⁴.0⁸,¹³]tetracosa-6,8(13),9,11-tetraen-23-yl]-6-oxo-6,9-dihydro-1H-purin-2-yl}-2-methylpropanamide (162C)

To a solution of 162B (25 mg, 0.04 mmol) in pyridine (5.0 mL) was added a small crystal of DMAP followed by a solution of 2,4-dichlorobenzyl phosphorodichloridodithioate (7.0 mg, 0.02 mmol) in DCM (0.125 mL). The mixture was stirred for 15 min, then additional 4-dichlorobenzyl phosphorodichloridodithioate (7 mg, 0.02 mmol) in DCM (0.125 mL) was added and the mixture was stirred for 2 hrs. Additional 4-dichlorobenzyl phosphorodichloridodithioate (28 mg, 0.08 mmol) in DCM (0.5 mL) was added and the mixture was stirred at RT for 3 days. The mixture was concentrated and the residue was purified by RP-MPLC (C18, 0-100% ACN/H₂O containing 0.04% NH₄HCO₃) to give 162C (4.0 mg, 11%). LCMS m/z 878.2 (M−H)⁻.

(1S,21R,23R,24R)-23-(2-Amino-6-oxo-6,9-dihydro-1H-purin-9-yl)-24-fluoro-3,18-disulfanyl-18-sulfanylidene-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),9,11-tetraen-3-one (Example 39)

A solution of 162C (4.0 mg, 0.0045 mmol) in DMSO (1.0 mL) was treated with DBU (4.1 µL, 0.027 mmol) and tert-tetradecanethiol (4.8 µL, 0.018 mmol) for 3 hrs. Additional DBU (1 drop) and tert-tetradecanethiol (1 drop) were added and the mixture was stirred at RT overnight. A solution of methylamine (33% in EtOH, 1 mL) was added and the mixture was stirred for 3 hrs, and then concentrated under reduced pressure. The residue was purified by prep. RP—HPLC (XBridge Prep C18, OBD 5 µm, 19×150 mm column eluting with 0-30% ACN/H₂O containing 0.4% NH₄HCO₃, Flow rate=10 mL/min) to give a 50:50 mixture of two diastereomers of Example 39 ((Diastereomer A+B: T$_R$=13.5 min, 0.16 mg, 5.3%): LCMS (Method D, T$_R$=1.40 min), m/z 650.1 (M−H)⁻. ¹H NMR (D₂O) δ 9.04 (s, 0.5H), 9.00 (s, 0.5H), 8.93 (s, 0.5H), 8.92 (s, 0.5H), 7.96 (s, 0.5H), 7.77 (s, 0.5H), 6.02 (d, J=8.4 Hz, 1H), 5.64-5.37 (comp, 1H), 5.23-5.17 (comp, 1H), 5.08-5.05 (comp, 0.5H), 4.88-4.87 (comp, 0.5H), 4.85-4.82 (m, 0.5H), 4.68-4.62 (comp, 1H), 4.61-4.51 (comp, 1H), 4.51-4.42 (comp, 2H), 4.41-4.35 (m, 0.5H), 4.18-4.10 (comp, 1.5H), 4.09-4.03 (comp, 0.5H), 3.70-3.61 (comp, 0.5H), 3.49-3.42 (m, 0.5H). ¹⁹F NMR (D₂O) δ −197.13, −198.49. ³¹P NMR (D₂O) δ 113.82, 113.03, 56.91, 55.15.

Example 40

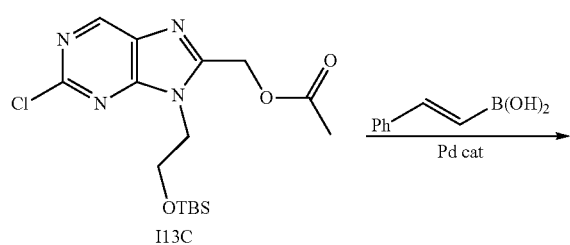

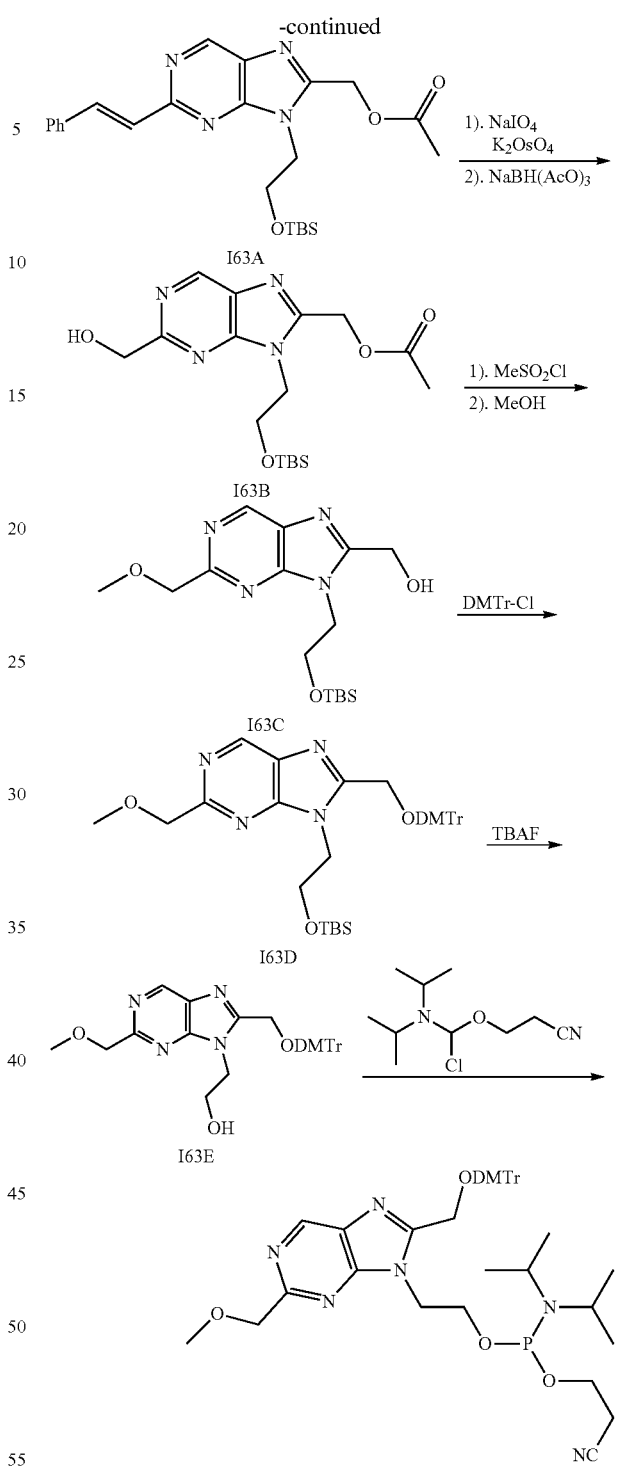

Intermediate 63

(E)-(9-(2-((tert-Butyldimethylsilyl)oxy)ethyl)-2-styryl-9H-purin-8-yl)methyl acetate (I63A)

To a solution of I13C (4.0 g, 10.4 mmol) in toluene (100 mL) was added trans-2-phenylvinylboronic acid (2.2 g, 15.0 mmol) and an aq. solution of K₃PO₄ (2.0 M, 6.5 mL). To this solution was added a portion of Pd(PPh₃)₄ (600 mg, 0.52 mmol) under an inert atmosphere and the mixture was heated to 100° C. for 4 hrs. The reaction mixture was allowed to cool to RT, then was washed with water (20 mL×3), sat. aq. NaHCO$_3$, brine and dried (Na$_2$SO$_4$). Volatiles were removed under reduced pressure and the residue was purified by silica gel chromatography (0-100% EtOAc/Hexane) to give I63A as a yellow solid (2.6 g, 56%). LCMS m/z 453.4 (M+H)$^+$. $^1$H-NMR (CDCl$_3$) δ 9.20 (s, 1H); 8.14 (d, J=16.0 Hz, 1H); 7.76 (d, J=7.6 Hz, 2H); 7.49 (m, 4H); 5.58 (s, 2H); 4.61 (t, J=5.2 Hz, 2H); 4.13 (t, J=5.2 Hz, 2H); 2.29 (s, 3H); 0.89 (s, 9H); 0.01 (s, 6H).

(9-(2-((tert-Butyldimethylsilyl)oxy)ethyl)-2-(hydroxymethyl)-9H-purin-8-yl)methyl acetate (I63B)

To a suspension of I63A (2.54 g, 5.62 mmol), sodium periodate (7.22 g, 33.7 mmol) and 2,6-lutidine (1.3 mL, 11.24 mmol) in THF (40 mL) and water (20 mL) was added potassium osmate dihydrate (46 mg, 0.14 mmol) and the mixture was stirred at RT overnight. To the reaction mixture was then added EtOAc (200 mL) and the organic layer was washed with water (50 mL×3), brine and dried (Na$_2$SO$_4$). Removal of volatiles under reduced pressure was followed by addition of DCM (90 mL) and sodium triacetoxyborohydride (14.3 g, 6.74 mmol). The resulting mixture was stirred at RT overnight, and then washed with sat. aq. NaHCO$_3$ (20 mL×3), brine and dried (Na$_2$SO$_4$). After removal of volatiles under reduced pressure the residue was purified by silica gel chromatography (0-100% EtOAc/Hexane) to give compound I63B (332 mg, 16%) as a white solid. LCMS m/z 381.4 (M+H)$^+$. $^1$H-NMR (CDCl$_3$) δ 9.21 (s, 1H); 5.60 (s, 2H); 5.06 (d, J=4.8 Hz, 2H); 4.63 (t, J=4.8 Hz, 2H); 4.10 (t, J=5.2 Hz, 2H); 3.97 (t, J=4.8 Hz, 1H); 2.31 (s, 3H); 0.90 (s, 9H); 0.01 (s, 6H).

(9-(2-((tert-Butyldimethylsilyl)oxy)ethyl)-2-(methoxymethyl)-9H-purin-8-yl)methanol (I63C)

To a solution of compound I63B (275 mg, 0.72 mmol) in DCM (10 mL) was added TEA (0.40 mL, 2.9 mmol) followed by methanesulfonyl chloride (0.12 mL, 1.45 mmol). The reaction mixture was stirred at RT for 2 hrs, and then DCM (100 mL) was added. The mixture was washed with 0.5% aq. acetic acid (50 mL×3), water, sat. aq. NaHCO$_3$ and brine. The solution was then dried (Na$_2$SO$_4$.) and concentrated under reduced pressure. The residue was dissolved in MeOH (10 mL), potassium carbonate (500 mg, 3.62 mmol) was added and the resulting solution was stirred at RT overnight. Volatiles were then removed in vacuo and the residue was dissolved in EtOAc (100 mL). The organic layer was washed with water, sat. aq. NaHCO$_3$, brine and dried (Na$_2$SO$_4$) to give I63C (187 mg, 73%) as a yellow oil which was used in the next step without further purification. LCMS m/z 352.4 (M+H)$^+$. $^1$H-NMR (CDCl$_3$,) δ 9.17 (s, 1H); 5.15 (s, 2H); 4.92 (s, 2H); 4.66 (t, J=4.8 Hz, 2H); 4.16 (t, J=4.8 Hz, 2H); 3.68 (s, 3H); 0.90 (s, 9H); 0.04 (s, 6H).

8-((Bis(4-methoxyphenyl)(phenyl)methoxy)methyl)-9-(2-((tert-butyldimethylsilyl)oxy)ethyl)-2-(methoxymethyl)-9H-purine (I63D)

To solution of compound I63C (187 mg, 0.53 mmol) in pyridine (5 mL) at 0° C. was added DMTrCl (198 mg, 0.58 mmol) and the resulting mixture was stirred at RT overnight. After removal of volatiles in vacuo the residue was dissolved in EtOAc (100 mL) and then washed with water, sat. aq. NaHCO$_3$, brine and dried (Na$_2$SO$_4$). Volatiles were removed under reduced pressure and the residue was purified by silica gel chromatography (0-100 EtOAc/Hexane) to to give I63D (183 mg, 53%) as a white solid. LCMS m/z 654.4 (M+1)$^+$. $^1$H-NMR (CDCl$_3$) δ 9.29 (s, 1H); 7.71 (d, J=7.2 Hz, 2H); 7.60 (d, J=8.8 Hz, 4H); 7.52 (t, J=7.2 Hz, 2H); 7.45 (t, J=7.2 Hz, 1H); 7.06 (d, J=8.8 Hz, 4H); 4.98 (s, 2H); 4.71 (s, 2H); 4.58 (t, J=5.2 Hz, 2H); 3.99 (s, 6H); 3.98 (t, J=4.8 Hz, 2H); 3.75 (s, 3H); 0.80 (s, 9H); −0.15 (s, 6H).

2-(8-((Bis(4-methoxyphenyl)(phenyl)methoxy)methyl)-2-(methoxymethyl)-9H-purin-9-yl)ethanol (I63E)

To a solution of compound I63D (183 mg, 0.28 mmol) in THF (5 mL) was added a solution of TBAF in THF (1.0 M, 0.3 mL) and stirring was continued for 1 hr. After removal of volatiles under reduced pressure the residue was dissolved in EtOAc (100 mL) and washed with water, sat. aq. NaHCO$_3$, brine and then dried (Na$_2$SO$_4$). The solution was then concentrated in vacuo and the residue purified by silica gel chromatography (0-100% EtOAc/Hexane) to give I63E (150 mg, 99%) as a white solid. LCMS 541.4 (M+H)$^+$. $^1$H-NMR (CDCl$_3$) δ 9.09 (s, 1H); 7.49 (d, J=7.2 Hz, 2H); 7.40 (d, J=9.2 Hz, 4H); 7.36 (t, J=7.2 Hz, 2H); 7.26 (t, J=7.2 Hz, 1H); 6.88 (d, J=9.2 Hz, 4H); 4.78 (s, 2H); 4.50 (s, 2H); 4.28 (t, J=4.8 Hz, 2H); 3.92 (q, J=4 Hz, 2H); 3.85 (t, J=5.6 Hz, 1H); 3.81 (s, 6H); 3.56 (s, 3H).

2-(8-((Bis(4-methoxyphenyl)(phenyl)methoxy)methyl)-2-(methoxymethyl)-9H-purin-9-yl)ethyl-(2-cyanoethyl)-diisopropylphosphoramidite (Intermediate 63)

A portion of I63E (150 mg, 0.28 mmol) was evaporated from toluene (10 mL×3), and then dissolved in DCM (10 mL) and cooled to 0° C. under an inert atmosphere. To this solution was added DIEA (146 μL, 0.84 mmol) followed by 3-((chloro(diisopropylamino)phosphino)oxy)propanenitrile (75 μL, 0.34 mmol), and the resulting solution was continued stirring at 0° C. for 1 hr. To the mixtures was then added DCM (100 mL) and the resulting solution was washed with sat. aq. NaHCO$_3$ and brine. After removal of volatiles the residue was purified by RP-MPLC (0-100% ACN/H$_2$O) to give Intermediate 63 (160 mg, 77%) as a white solid. LCMS 658.4 (M−83+1)$^+$. $^1$H-NMR (CDCl$_3$) δ 8.94 (s, 1H); 7.37 (d, 2H); 7.37 (d, J=7.2 Hz, 2H); 7.27 (d, J=9.2 Hz, 4H); 7.19 (t, J=6.8 Hz, 2H); 7.11 (t, J=7.2 Hz, 1H); 6.73 (d, J=8.8 Hz, 4H); 4.64 (s, 2H); 4.41 (q, J=5.2 Hz, 2H); 4.36 (m, 2H); 3.70 (m, 2H); 3.66 (s, 6H); 3.43 (s, 3H); 3.34 (q, J=6.4 Hz, 2H); 3.21 (m, 2H); 2.27 (t, J=6.0 Hz, 2H); 0.92 (d, J=6.8 Hz, 6H); 0.74 (d, J=6.8 Hz, 6H). $^{31}$P-NMR (CDCl$_3$) δ 148.02 ppm.

Example 40
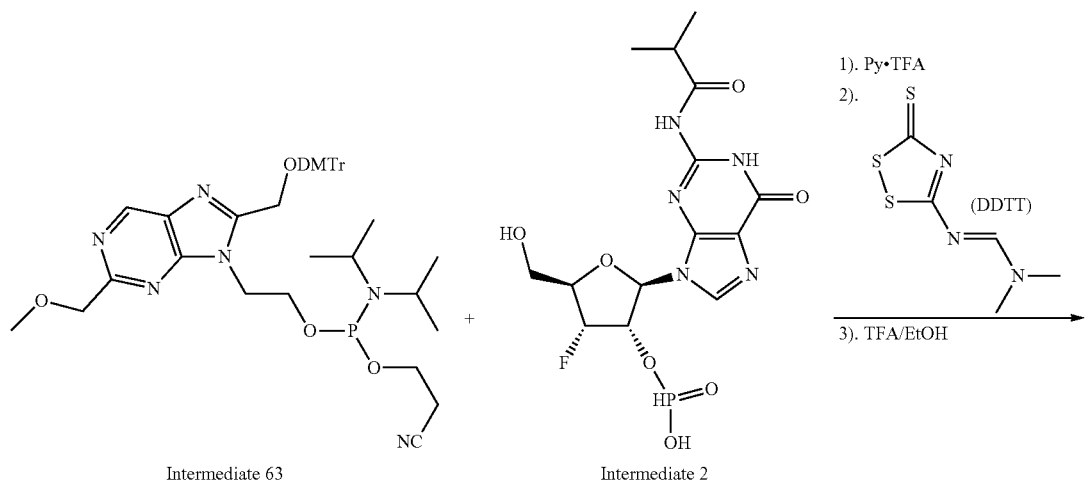
Intermediate 63 + Intermediate 2
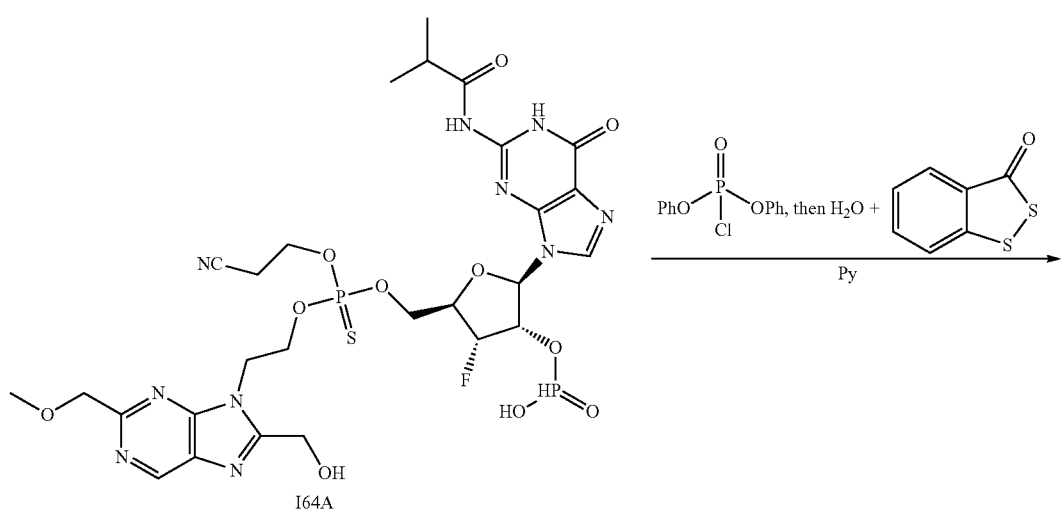
I64A
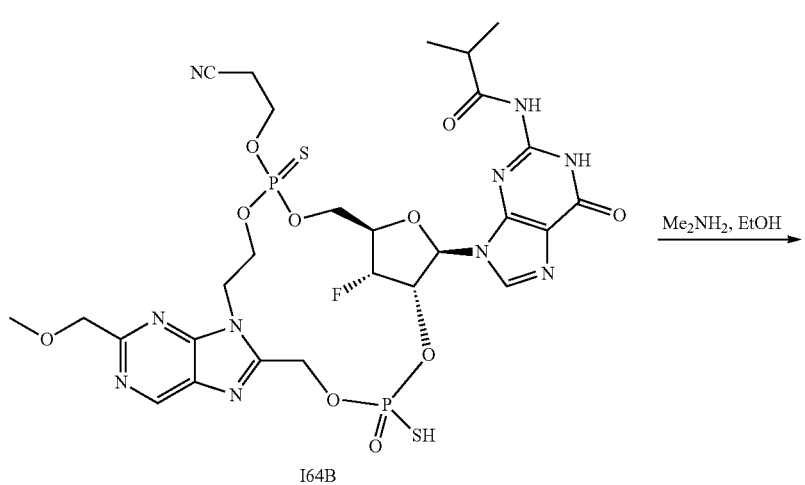
I64B

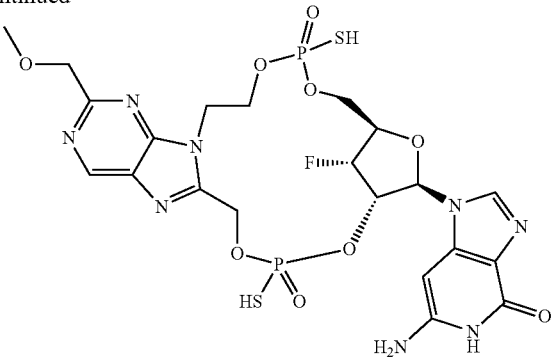

Example 40

Example 40 diastereomers (Diastereomers A-D) were prepared according to procedures analogous to those outlined in Example 1.

(2R,3S,4R,5R)-5-((((2-Cyanoethoxy) (2-(8-(hydroxymethyl)-2-(methoxymethyl)-9H-purin-9-yl) ethoxy)phosphorothioyl)oxy)methyl)-4-fluoro-2-(2-isobutyramido-6-oxo-1H-purin-9(6H)-yl) tetrahydrofuran-3-yl hydrogen phosphonate (164A)

LC/MS m/z 787.5 (M−H)⁻. $^{31}$P-NMR (CD$_3$OD) δ 68.12; 67.75; 2.55. $^{19}$F-NMR (CD$_3$OD) δ −201.85; −202.04.

N-{9-[(1S,21R,23R,24R)-18-(2-Cyanoethoxy)-24-fluoro-11-(methoxymethyl)-3-oxo-3-sulfanyl-18-sulfanylidene-2,4,17,19,22-pentaoxa-7,10,12,14-tetraaza-3lambda5,8lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (164B)

LCMS m/z 801.5 (M−1)⁻. $^{19}$F-NMR (CD$_3$OD) δ −196.9; −197.5; −198.84; −199.52. $^{31}$P NMR (CD$_3$OD) δ 69.03; 67.81; 65.43; 65.25; 60.72; 60.21; 57.61; 56.66.

(1S,21R,23R,24R)-23-(2-Amino-6-oxo-6,9-dihydro-H-purin-9-yl)-24-fluoro-11-(methoxy methyl)-3,18-disulfanyl-2,4,17,19,22-pentaoxa-7,10,12,14-tetraaza-3lambda5,18lambda5-diphosphatetracyclo[19.2.1.06,14.08,13]tetracosa-6,8,10,12-tetraene-3,18-dione Example 40

Example 40 diastereomers (Diastereomers A-D) were purified by prep. RP—HPLC (XBridge Prep C18 OBD 5 μm, 19×150 mm column) using aq. NH$_4$HCO$_3$ (50 mM) (A) and ACN (B) as eluents. Gradient: 0-2.0 min—Isocratic—100% A; 2.1-20.0 min—Linear gradient 0%-13% B. Flow rate: 10 mL/min. Example 40C (Diastereomer C): Prep. RP—HPLC: T$_R$=20.0 min; LCMS (Method D, T$_R$=1.29 min) m/z 678.2 (M−H)⁻. $^1$H-NMR (D$_2$O) δ 9.15 (s, 1H); 7.85 (s, 1H); 6.06 (d, J=7.6 Hz, 1H); 5.50 (dd, J=54.8 Hz, 2.8 Hz, 1H); 5.41 (dd, J=13.2 Hz, 8.0 Hz, 1H); 4.84 (m, 5H); 4.73 (m, 1H); 4.42 (m, 3H); 4.20 (dd, J=4.8 Hz, 6.4 Hz, 1H); 4.01 (dd, J=9.6 Hz, 2.0 Hz, 1H); 3.57 (s, 3H). $^{19}$F-NMR (D$_2$O) δ −199.52. $^{31}$P-NMR (D$_2$O) δ 55.19; 54.93.

Examples 41 to 103 set forth in table 1 are prepared in a similar manner to the synthesis described in Examples 1 to 40.

BIOLOGY

The term "STING agonist" or "STING Protein Agonist" denotes an agonist which binds to STING and activates the STING pathway promoting IKK-related kinase TANK-binding kinase 1 (TBK1) signaling and activates nuclear factor-kappa B (NF-kB) and interferon regulatory factor 3 (IRF3) in immune cells in the tumor microenvironment. Typically, STING activity is increased in a dose dependent manner by at least 10%, at least 20%, at least 30%, at least 40%, at least 50%, at least 60%, at least 70%, at least 80%, at least 90%, or at least 100% compared to such activity in a control cell. The control cell is a cell that has not been treated with the compound. STING pathway activity is determined by any standard method in the art, including those described herein.

It is desirable to find compounds with advantageous and improved characteristics compared with known STING agonists, in one or more of the following categories that are given as examples, and are not intended to be limiting: (a) pharmacokinetic properties, including oral bioavailability, half-life, and clearance; (b) pharmaceutical properties; (c) dosage requirements; (d) factors that increase the concentration of active drug at the receptor; (e) factors that decrease the liability for clinical drug-drug interactions; (f) factors that decrease the potential for adverse side-effects, including selectivity versus other biological targets; and (g) factors that improve manufacturing costs or feasibility.

As STING protein agonists, it is believed that the compounds of Formula I or Formula I', and the examples are useful in methods for treating or preventing a viral infection, disease, a syndrome, a condition or a disorder in a subject, including an animal, a mammal and a human in which the viral infection, disease, the syndrome, the condition or the disorder is affected by the modulation, including agonism, of the STING protein. Such methods comprise, consist of and/or consist essentially of administering to a subject, including an animal, a mammal, and a human, in need of such treatment or prevention, a therapeutically effective amount of a compound, salt or solvate of Formula I or Formula I'.

In one embodiment, the present invention is directed to a compound of Formula I or Formula I', or a stereoisomer, a tautomer, a salt, a solvate or a prodrug form thereof, for the use in the treatment of cancer, and cancer diseases and conditions, or a viral infection. Examples of cancer diseases and conditions for which compounds of Formula I or Formula I', or a stereoisomer, a tautomer, a salt, a solvate or a prodrug form thereof, may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In another embodiment, the present invention is directed to a compound of Formula I or Formula I', or a stereoisomer, a tautomer, a salt, a solvate or a prodrug form thereof, for use in the treatment of a disorder affected by the agonism of STING selected from the group consisting of melanoma, colon cancer, breast cancer, prostate cancer, lung cancer, fibrosarcoma, and hepatitis B. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is melanoma. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is colon cancer. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is breast cancer. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is prostate cancer. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is lung cancer. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is fibrosarcoma. In another embodiment, the present invention is directed to a compound of Formula I or Formula I', or a stereoisomer, a tautomer, a salt, a solvate or a prodrug form thereof, for use in the treatment of a disorder affected by the agonism of STING, wherein the disorder is hepatitis B.

In another embodiment, the present invention is directed to a compound of Formula I or Formula I', or a stereoisomer, a tautomer, a salt, a solvate or a prodrug form thereof, for use in the treatment of a disorder affected by the agonism of STING wherein the disorder is bladder cancer.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy,* 20th Edition, Mack Publishing Co., Easton, Pa. (2000).

The invention includes administering to a subject a pharmaceutical composition that includes a compound that modulates STING (referred to herein as a "STING agonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, intravesical, subcutaneous, or intramuscular form, and all using dosage forms well known to those of ordinary skill in the pharmaceutical arts. They can be administered alone, but generally will be administered with a pharmaceutical carrier selected on the basis of the chosen route of administration and standard pharmaceutical practice.

The therapeutically effective dose of the STING agonist is a biologically active dose. A biologically active dose is a dose that will modulate the STING protein and have an appropriate effect. For example, the dose includes a dose range from about 0.0005 mg to about 3000 mg, from about 0.0005 mg to about 1000 mg, from about 0.0005 mg to about 250 mg or from about 0.0005 mg to about 200 mg inclusive of any particular amount or range therein, of active ingredient in a regimen of about 1 to about 4 times per day for an average (70 kg) human. In a specific embodiment, the dose ranges from about 0.01 mg to about 100 mg or or from about 1 mg to about 100 mg inclusive of any particular amount or range therein. It is apparent to one skilled in the art that the therapeutically effective amount for a compound of Formula I or Formula I' will vary with the diseases, syndromes, conditions, and disorders being treated.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

Compounds of this invention can be administered in intravesical form via a solution that is run through a tube (instilled through a catheter) into the particular organ, for example, the bladder, to treat the cancer.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of this invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of this invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams (mg), inclusive, i.e., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21, mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg of active ingredient per dosage unit. In these pharmaceutical compositions the active ingredient will ordinarily be present in an amount of about 0.5-95%, inclusive, by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hrs. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I or Formula I', for example, a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated in vivo after administration of the prodrug of that compound. In one embodiment, a compound may be useful as a metabolite by being useful for treating disorders as described herein.

The disclosed compounds of Formula I or Formula I' may be useful in combination with one or more additional therapeutic agents. The additional therapeutic agent may be, e.g., a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNa2, GM-CSF), and cells transfected with genes encoding immune stimulating cytokines such as but not limited to GM-CSF).

The additional therapeutic agent(s) may be administered in a single dosage form with at least one compound of the present invention, or the additional therapeutic agent(s) may be administered in separate dosage form(s) from the dosage form containing the compound of the present invention.

The compound of the present invention disclosed herein may be used in combination with one or more other therapeutic agents, including but not limited to, other anti-cancer agents that are used in the prevention, treatment, control, amelioration, or reduction of risk of a particular disease or condition. In one embodiment, a compound disclosed herein is combined with one or more other anti-cancer agents for use in the prevention, treatment, control amelioration, or reduction of risk of a particular disease or condition for which the compounds disclosed herein are useful. Such other therapeutic agents may be administered, by a route and in an amount commonly used therefor, contemporaneously or sequentially with a compound of the present disclosure.

The additional therapeutic agent(s) may be one or more agents selected from the group consisting of another STING agonist, anti-viral compounds, antigens, adjuvants, anti-cancer agents, CTLA-4, LAG-3, PD-1 pathway antagonists, PD-L1 antibodies, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the STING agonist, and one or more additional therapeutic agents will be determined based on the individual patient needs.

When the compound disclosed herein is used contemporaneously with one or more other therapeutic agents, the compound may be administered either simultaneously with, or before or after, one or more other therapeutic agent(s).

The weight ratio of the compound of the present invention may be varied and will depend upon the therapeutically effective dose of each agent. Generally, a therapeutically effective dose of each will be used. Combinations including at least one compound of the present invention, and other therapeutic agents will generally include a therapeutically effective dose of each active agent. In such combinations, the compound of the present invention disclosed herein and other therapeutic agents may be administered separately or in conjunction. In addition, the administration of one element may be prior to, concurrent with, or subsequent to the administration of other agent(s).

In one embodiment, this disclosure provides at least one compound of the present invention, and at least one other therapeutic agent as a combined preparation for simultaneous, separate or sequential use in therapy. In one embodiment, the therapy is the treatment of a disorder affected by the agonism of STING, such as cancer.

The disclosure also provides the use of a compound of Formula I or Formula I' for treating a disorder affected by agonism of STING, where the patient has previously (e.g., within 24 hrs) been treated with another therapeutic agent.

Anti-viral compounds that may be used in combination with the compounds disclosed herein include hepatitis B virus (HBV) inhibitors, hepatitis C virus (HCV) protease inhibitors, HCV polymerase inhibitors, HCV NS4A inhibitors, HCV NSSA inhibitors, HCV NSSb inhibitors, and human immunodeficiency virus (HIV) inhibitors.

Antigens and adjuvants that may be used in combination with the compounds disclosed herein include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, lipopolysaccharide (LPS), monophosphoryllipid A, lipoteichoic acid, imiquimod, resiquimod, and in addition retinoic acid-inducible gene I (RIG-I) agonists such as poly I:C, used separately or in combination are also potential adjuvants.

Examples of cytotoxic agents that may be used in combination with the compounds disclosed herein include, but are not limited to, arsenic trioxide, asparaginase, and Erwinia L-asparaginase.

Chemotherapeutic agents that may be used in combination with the compounds disclosed herein include abiraterone acetate, altretamine, anhydrovinblastine, auristatin, bexarotene, bicalutamide, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea and taxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine, and pharmaceutically acceptable salts thereof.

Examples of vascular endothelial growth factor (VEGF) receptor inhibitors include, but are not limited to, bevacizumab, Brivanib Alaninate, motesanib, pasireotide, and sorafenib.

Examples of topoisomerase II inhibitors, include but are not limited to, etoposide and teniposide.

Examples of hypomethylating agents and alkylating agents, include but are not limited to, 5-azacytidine, decitabine, temozolomide, dactinomycin, melphalan, phenylalanine mustard, altretamine, carmustine, bendamustine, busulfan, carboplatin, lomustine, cisplatin, chlorambucil, cyclophosphamide, dacarbazine, altretamine, ifosfamide, procarbazine, mechlorethamine, streptozocin, thiotepa, and pharmaceutically acceptable salts thereof.

Examples of anti-tumor antibiotics include, but are not limited to, doxorubicin, bleomycin, daunorubicin, daunorubicin liposomal, mitoxantrone, epirubicin, idarubicin, and mitomycin C.

Examples of anti-metabolites include, but are not limited to, claribine, 5-fluorouracil, 6-thioguanine, pemetrexed, cytarabine, cytarabine liposomal, decitabine, hydroxyurea fludarabine, floxuridine, cladribine, methotrexate, and pentostatin.

Examples of retinoids include, but are not limited to, alitretinoin, tretinoin, isotretinoin and bexarotene.

Examples of PD-1 antagonists include, but are not limited to, nivolumab, pembrolizumab, pidilizumab, and AMP-224.

Examples of PD-L1 antibodies include, but are not limited to, Atezolizumab, Avelumab, and Durvalumab.

An example of a CLT-4 antagonist is ipilimumab.

The disclosed compounds of Formula I or Formula I' may be useful in combination with radiation therapy.

The activity of the STING agonists of the present invention can be measured in a variety of in vitro assays. Exemplary assays are shown in the Examples below.

The Human AQ and WT STING Binding assay is an exemplary in vitro assay for measuring STING agonist binding to the human STING protein as shown in Example A The murine STING Binding assay is an exemplary in vitro assay for measuring STING agonist binding to the murine STING protein as shown in Example B The Human HAQ and WT Reporter Cellular Reporter assay is an exemplary in vitro assay for measuring the activity of the STING agonists of the present invention. In these assays, activation of the STING protein is induced in THP1 Dual (HAQ) human cells (Invivogen) by a STING agonist and luciferase activity is monitored. See, e.g., Example D.

The compounds of the current invention can be tested in vitro for their ability to activate the STING pathway as shown in Example E. In these assays, activation of the STING protein is induced in RAW-Dual™ cells by a STING agonist and luciferase secretion is monitored.

The natural ligands (2',2') cyclic guanosine monophosphate-adenosine monophosphate (2',2'-cGAMP) and (2',3') cyclic guanosine monophosphate-adenosine monophosphate (2',3'-cGAMP) are known STING agonists. As shown in Examples F and K below, 2',3'-cGAMP was validated as a STING agonist in the Human IFN-β Secretion assay. 2',3'-cGAMP can be synthesized using methods well known to those of skill in the art. In addition, several STING agonists are currently being investigated in clinical studies for the treatment of various types of cancer. For example, ADU-S100 is a STING agonist currently being investigated by Aduro Biotech for the treatment of various types of cancers (see U.S. Pat. No. 9,724,408 B1 and "Activation of STING with Synthetic Cyclic Dinucleotides and Synergy with Checkpoint Inhibition", Sarah McWhirter, Ph.D., Director STING Program, ICI Boston 2017 Presentation).

Example C is a protein thermal shift assay. Protein thermal shift assays are used to assess the binding of a compound to a protein. The assay involves measuring the unfolding of a protein with increasing temperature. Unfolding is measured by the increase in fluorescent signal coming from a dye (e.g. SYPRO Orange) that binds to hydrophobic regions of a protein that become exposed to solvent as the protein melts. The temperature at the midpoint of the fluorescent signal increase is defined as the melting temperature (Tm). The Tm of a protein will increase when it binds specifically to a binding partner (i.e. ligand). The Tm shift increases with how tightly the protein binds the ligand—the tighter the binding, the larger the Tm shift. (Huynh K, Partch C L. Current Protocols in Protein Science: Analysis of protein stability and ligand interactions by thermal shift assay. Current protocols in protein science/editorial board, John E Coligan. [et al]. 2015; 79:28.9.1-28.9.14. doi: 10.1002/0471140864.ps2809s79.). Thermal shift assays are used to assess ligand binging to STING variants (Ouyang S, Song X, Wang Y, et al. Structural and Functional Analysis of STING Sheds New Light on Cyclic di-GMP Mediated Immune Signaling Mechanism. Immunity. 2012; 36(6): 10.1016/j.immuni.2012.03.019. doi: 10.1016/j.immuni.2012.03.019). Thermal shift analysis was performed to show binding of compounds to the three most prevalent STING variants, in particular, the STING(R232H) variant.

Figure 2:
FIG. 2 is a biochemical analysis using Western Blot analysis of STING pathway activation in THP1 (HAQ) Dual reporter cells.

Example G is a Western Blot analysis of STING signaling pathway activation. The ability of a selective STING agonist of the present invention, namely, the Example 1C compound to activate the STING pathway was measured using a standard Western Blot analysis. STING pathway activation by the Example 1C compound in comparison to known STING agonists 2',3'-cGAMP and ADU-S100 is shown in FIG. 2.

Example H is a Human IFN-α/β induction and secretion assay. Genetically engineered human type-1 Interferons (IFN-α/β) sensor cells-HEK Blue™ IFNα/β cells (Invivogen) were employed to measure the type-1 IFNs produced by THP1 cells that are treated with activators of STING. The human embryonic (HEK) Blue™ cells are specially designed to monitor the activation of JAK/STAT pathway induced by type 1 IFNs. Briefly, THP1 cells are treated with compounds for 5 hrs. In the second step, supernatants of THP1 cells are transferred to HEK Blue™ IFNα/β reporter cells and incubated for 24 hrs. The secreted embryonic alkaline phosphatase (SEAP) activity in the supernatants of HEK blue IFNα/β reporter cells is measured and used to determine the quantities of IFNs. Type 1 Interferons play key role in mounting efficient immune responses by eliciting innate immunity and cytotoxic T cell responses. Activation of STING pathway leads to robust induction of type 1 IFNs and strong anti-tumor immunity. In the present invention we measured the potency of the compounds for their ability to activate STING pathway and induce IFNs production. Analysis of compound dose responses in THP1 (monocyte) cells for type-1 IFNs production confirm that compounds of the present invention lead to induction of IFN production (Table 8).

Example I is an assay that measures Mouse IFN-β. Mouse Interferon-β (IFN-β) in the supernatants of murine macrophages treated with STING activators was quantified using sandwich enzyme linked immunosorbent assay (ELISA). Briefly, IFN-β binds to plates coated with antibody and detection is accomplished using a detection antibody followed by streptavidin conjugated to horseradish peroxidase. Tetramethyl-benzidine is used as the substrate in this kit (PBL Assay Science). INF-β is one of the major targets of STING pathway and is a critical factor in building proficient immune responses downstream to STING activation. Additionally, its role in antitumor immunity has been very well established in several pre-clinical mouse models. In this invention, mouse IFN-β ELISA is used to determine the potency of compound on STING pathway activation in mouse macrophages. In this assay, Example 1C appears to robustly induce IFN-β (Table 9).

Figure 4:
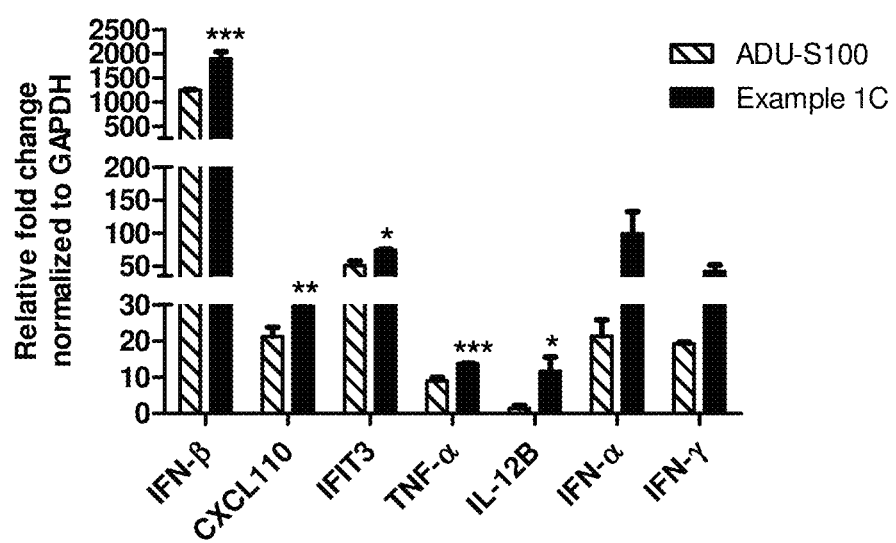
FIG. 4 is a graphical representation of the activation by Example 1C of Type I and II interferons and interferon stimulated (ISG) genes in human PBMCs.

Example J is a qRT-PCR assay. qRT-PCR assay was used to determines the changes in mRNA in genes involved in immune regulation. The ability of Example 1C to activate the STING pathway leading to an activation of genes in an immunological response was assessed. Activation of Type I and II interferons and interferon stimulated (ISG) genes in human peripheral blood mononuclear cells (PBMCs) by the Example 1C compound in comparison to known STING agonists 2',3'-cGAMP and ADU-S100 is shown in FIG. 4.

Example L is qRT-PCR assays showing that treatment of mouse bone marrow derived dendritic cells with the Example 1C compound leads to activation of ISG genes.

Example M is a Western blot analysis showing STING Pathway activation upon treatment of primary human bladder epithelial cells with the Example 1C compound. The efficacy of the STING agonists of the present invention can also be measured in a variety of in vivo assays. Exemplary mammals that can provide models to test the effectiveness of the STING agonists of the present invention as anticancer agents include, but are not limited to, mice. Models of tumor growth and other tumor measurements can be used to assess the effectiveness of the anticancer agents described in the current invention. Example N describes an in vivo model of tumor growth in BALB/cAnNTac mice. Compounds of the present invention can be tested in this model for their ability to inhibit growth of tumors. Examples O through S describe additional models in which the Example 1C compound can be used to inhibit growth of tumors. Demonstration of efficacy in these models support the utility of STING agonists of the present invention for treatment of oncological diseases.

Assays

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

Example A

Human AQ and WT STING Binding Assay

A human STING [³H] 2',3'-cGAMP scintillation proximity competition binding assay was utilized to detect binding of compounds to STING protein. The competition binding assay was conducted with either a wild-type (WT, SEQ ID NO: 1) or an AQ variant (SEQ ID NO: 2) of truncated human STING protein that lacks the N-terminal four transmembrane domains and contains amino acids 155-379. The protein encoding plasmid contained a HIS tag, followed by an Avi tag and then a SUMO tag, which were followed by the STING coding sequence within the pET-28a (+) vector. The plasmid was transfected into a BL21 (DE3)/BirA *E. coli* co-expression strain. Protein was purified from the bacterial lysate using a cobalt-affinity column. The purified protein was dialyzed against PBS and then 20% glycerol was added prior to storage at −80° C.

The assay was conducted in a 384-well plate containing final concentration of 25 nM biotin-STING protein and 17.5 nM [$^3$H] 2',3'-cGAMP in assay buffer (50 mM Tris pH 7.5, 100 mM NaCl, 0.1% Fatty Acid Free BSA). Test compounds (2.5 µL) were added to the plate first followed by a 25 µL mixture of STING protein, streptavidin PVT SPA beads (Perkin Elmer) and 10 µL [$^3$H] 2',3'-cGAMP. Plates were incubated at room temperature for 18 hrs and read on a Wallac MicroBeta TriLux (Perkin Elmer). 2',2'-cGAMP was used as a reference compound and had an IC$_{50}$ of 0.562 µM using the WT STING protein and 0.098 M using the AQ STING protein.

Example B

Murine STING Binding Assay

The murine STING [$^3$H] 2',3'-cGAMP scintillation proximity competition binding assay was performed in the same manner as the human STING competition binding assay (described above) with the exception that murine STING protein (amino acids 154-378, SEQ ID NO: 3) was utilized. 2',2'-cGAMP was used as a reference compound and had an IC$_{50}$ of 0.055 µM.

Compounds of the present invention were tested in the Human AQ and WT STING Binding and Murine Binding assays described immediately above and the results shown in Table 6 below were obtained.

TABLE 6

| Example | Human WT Binding IC$_{50}$ (µM) | Human AQ Binding IC$_{50}$ (µM) | Murine Binding IC$_{50}$ (µM) |
|---|---|---|---|
| 1A | B | A | A |
| 1B | C | C | C |
| 1C | A | A | A |
| 1D | B | A | A |
| 2 | C | C | |
| 3B | C | C | B |
| 3C | B | B | A |
| 3D | C | C | B |
| 4 | C | B | A |
| 5A | B | A | A |
| 5B | C | C | B |
| 6A | B | B | A |
| 6B | A | A | A |
| 7A | C | B | A |
| 7B | C | B | A |
| 7C | A | A | A |
| 7D | B | A | A |
| 8 | C | C | B |
| 9 (Diast C/D) | C | B | B |
| 10 | C | B | A |
| 18C | B | B | A |
| 18D | C | C | C |
| 15A | B | A | A |
| 15C | B | B | A |
| 15D | A | A | A |
| 19A | C | C | C |
| 19B | C | C | C |
| 19C | C | B | C |
| 19D | B | A | A |
| 17C | C | B | A |
| 25B | C | B | B |
| 25C | C | B | B |
| 25D | A | A | A |
| 33B | C | C | B |
| 33C | C | C | C |
| 33D | B | A | A |
| 20D | C | C | C |
| 13A | B | B | A |
| 13B | C | C | B |
| 11A | C | B | B |
| 11C | A | A | A |
| 11D | B | A | A |
| 14A | C | B | A |
| 14C | A | A | A |
| 14D | C | B | A |
| 16A | C | B | A |
| 16C | A | A | A |
| 16D | B | A | A |
| 24A | C | B | A |
| 24B | C | C | C |
| 24C | A | A | A |
| 24D | B | A | A |
| 21B | C | B | B |
| 21C | B | A | A |
| 21D | C | B | B |
| 27B | C | B | A |
| 27C | A | A | A |
| 27D | B | A | A |
| 23B | C | C | B |
| 23D | C | C | C |
| 29A | C | B | B |
| 29B | A | A | A |
| 22A | C | B | B |
| 22B | C | C | B |
| 22C | B | A | A |
| 22D | A | A | A |
| 12C | C | B | A |
| 12D | C | C | B |
| 34B | C | C | B |
| 34C | B | A | A |
| 34D | C | C | B |
| 36D | C | B | A |
| 35C | C | B | B |
| 35D | C | C | C |
| 37A | A | A | A |
| 37B | A | A | A |
| 38A | B | B | A |
| 38B | C | B | B |
| 38C | A | A | A |
| 38D | B | A | A |
| 39 | A | A | A |
| 40C | C | B | A |

A: IC$_{50}$ < 1.00 µM;
B: IC$_{50}$ = 1.00 µM-9.99 µM;
C: IC$_{50}$ = 10.0 µM-100 µM

Example C

Thermal Shift Binding Assays

Binding of compounds to four STING variants (cytosolic domain, amino acids 155-379), human STING (WT, SEQ ID NO:1), human STING (G230A-R293Q, SEQ ID NO: 2), human STING (R232H, SEQ ID NO: 4) and mouse STING (SEQ ID NO: 3) were measured by protein thermal shift assays (Huynh K, Partch C L. Current Protocols in Protein Science: Analysis of protein stability and ligand interactions by thermal shift assay. *Current protocols in protein science/ editorial board*, John E Coligan. [et al]. 2015; 79:28.9.1-28.9.14. doi: 10.1002/0471140864.ps2809s79.). The protein encoding plasmid contained a HIS tag, followed by an Avi tag and then a SUMO tag, which were followed by the STING coding sequence within the pET-28a (+) vector (Genscript). The plasmid was transfected into a BL21 (DE3)/BirA *E. coli* co-expression strain. Protein was purified from the bacterial lysate using a cobalt-affinity column. The purified protein was dialyzed against PBS and then 20% glycerol was added prior to storage at −80° C.

The assay was conducted in 96-well PCR plates containing 5 μM STING protein, 100 μM compound, 1 mM Tris(2-carboxyethyl)phosphine hydrochloride, and 1:5000 dilution of stock SYPRO Orange dye (Sigma) in phosphate buffered saline. Plates were sealed and analyzed in a qRT-PCR machine (Mx3005P, Strategene). The results are shown in Table 7. Example 1C binds to human STING (R232H), human STING(AQ), human STING(WT) and mouse STING with affinities equal to or better than ADU-S100.

TABLE 7

| EXAMPLE | Human STING(WT) $T_m$ Shift | Human STING(AQ) $T_m$ Shift | Human STING(R232H) $T_m$ Shift | Mouse STING $T_m$ Shift |
|---|---|---|---|---|
| 2',3'-cGAMP | B | A | C | ND |
| ADU-S100 | B | B | C | B |
| EXAMPLE 1C | B | A | C | A |

A: $T_m > 20°$ C.;
B: $T_m = 20°$ C.-10.1° C.
C: $T_m = 10$-5° C.
ND: Not Determined

Example D

Human HAQ and WT Cellular Reporter Assay

Activation of the STING pathway within cells was determined using THP1 Dual™ cells that have endogenous HAQ STING protein (referred to as THP1 Dual (HAQ) human cells, Catalogue #thpd-nfis, Invivogen); or THP1-Dual™ KI-hSTING-R232 Cells that have wildtype (WT) STING protein (referred to as THP1 Dual (WT) human cells, Catalogue #thpd-r232, Invivogen). THP1-Dual™ cells are human monocyte cell lines that have stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of STING will lead to enhanced luciferase secretion. 2',3'-cGAMP was used as a reference compound and had an $EC_{50}$ of 14.5 μM.

This assay was conducted in 384-well low volume plates containing 2 μL of test compound. Cells were added to the plate (10,000 cells in 3 μL). The cells were prepared in RPMI 1640 (Corning). The assay was incubated for 5 hrs at 37° C. in 5% $CO_2$. The luciferase detection reagent, QUANTI-Luc™ (Invivogen) was added (3 μL). The plate was then read using a ViewLUX (Perkin Elmer).

Example E

Murine Cellular Reporter Assay

Activation of the STING pathway within murine cells was determined using the RAW-Dual™ Reporter cell line (Catalogue #rawd-ismip, Invivogen); which is derived from the RAW 264.7 macrophage cell line that has and added stable integration of an ISRE Lucia reporter gene. The assay was performed in the same manner as the human cellular reporter assay (described above) with the exception that the cells were prepared for addition to the assay plate in DMEM (Corning) supplemented with 10% heat-inactivated fetal bovine serum (Corning). 2',3'cGAMP was used as a reference compound and had an $EC_{50}$ of 11.5 μM.

Compounds of the present invention were tested in the Human HAQ and WT Cellular Reporter Assay and Murine Cellular Reporter Assay described in Examples D and E set forth above and the results shown in Table 8 below were obtained.

TABLE 8

| Example | Human HAQ Agonist $EC_{50}$ (μM) | Human HAQ Agonist Efficacy (%) | Human WT Agonist $EC_{50}$ (μM) | Human WT Agonist Efficacy (%) | Murine Agonist $EC_{50}$ (μM) | Murine Agonist Efficacy (%) |
|---|---|---|---|---|---|---|
| 1A | B | >100 | B | <100 | A | >100 |
| 1B | B | <100 | | | B | >100 |
| 1C | A | >100 | A | >100 | A | >100 |
| 1D | A | >100 | B | <100 | A | >100 |
| 2 | C | >100 | | | | |
| 3B | B | <100 | D | <100 | A | >100 |
| 3C | A | <100 | D | <100 | A | >100 |
| 3D | B | <100 | D | <100 | B | <100 |
| 4 | B | <100 | C | >100 | B | >200 |
| 5A | B | <100 | B | <100 | A | >100 |
| 5B | B | <100 | C | <100 | B | >100 |
| 6A | B | <100 | C | <100 | B | >100 |
| 6B | A | <100 | B | <100 | A | >100 |
| 7A | A | >100 | C | <100 | A | >100 |
| 7B | A | >100 | C | <100 | B | >100 |
| 7C | A | >100 | A | >100 | A | >100 |
| 7D | A | >100 | B | <100 | A | >100 |
| 8 | B | <100 | C | <100 | C | <100 |
| 9 (Diast C/D) | B | >100 | C | <100 | B | <100 |
| 10 | B | >200 | C | <100 | B | >100 |
| 18C | A | >100 | B | >100 | A | >100 |
| 18D | B | >100 | C | <100 | C | <100 |
| 15A | B | >100 | B | <100 | A | >100 |
| 15C | B | >100 | C | <100 | B | >100 |
| 15D | A | >100 | A | <100 | A | >100 |
| 19A | C | <100 | C | <100 | C | <100 |
| 19B | B | <100 | C | <100 | C | <100 |
| 19C | A | >100 | C | <100 | C | <100 |
| 19D | A | >100 | A | >100 | A | >100 |
| 17C | A | >100 | B | <100 | A | <100 |
| 25B | C | <100 | C | <100 | C | <100 |
| 25C | A | >100 | C | <100 | B | <100 |
| 25D | A | <100 | A | >100 | A | <100 |
| 33B | B | >100 | C | <100 | C | <100 |
| 33C | B | <100 | C | <100 | C | <100 |
| 33D | A | <100 | B | <100 | A | <100 |
| 20D | B | >100 | C | <100 | B | <100 |
| 13A | A | >100 | B | <100 | A | >100 |
| 13B | B | <100 | D | <100 | B | >100 |
| 11A | B | >100 | C | <100 | B | >100 |
| 11C | A | >100 | A | >100 | A | >100 |
| 11D | A | >100 | B | <100 | A | >100 |
| 14A | A | >100 | B | <100 | A | >100 |
| 14C | A | >100 | A | >100 | A | >100 |
| 14D | A | >100 | B | <100 | A | >100 |
| 16A | A | >100 | C | <100 | A | >100 |
| 16C | A | >100 | A | >100 | A | >100 |
| 16D | A | >100 | B | <100 | A | >100 |
| 24A | A | >100 | B | <100 | A | <100 |
| 24B | B | <100 | D | <100 | B | <100 |
| 24C | A | >100 | A | >100 | A | <100 |
| 24D | A | >100 | B | <100 | A | >100 |
| 21B | A | >100 | B | <100 | B | >100 |
| 21C | A | <100 | B | <100 | A | >100 |
| 21D | A | <100 | D | <100 | B | >100 |
| 27B | A | <100 | C | <100 | B | >100 |
| 27C | A | >100 | A | <100 | B | <100 |
| 27D | A | >100 | B | <100 | A | >100 |
| 23B | A | >100 | C | <100 | B | <100 |
| 23D | B | >100 | D | <100 | B | >100 |
| 29A | A | >100 | B | <100 | B | >100 |
| 29B | A | >100 | A | >100 | A | >100 |
| 22A | A | >100 | C | <100 | B | >100 |

TABLE 8-continued

| Example | Human HAQ Agonist EC$_{50}$ (μM) | Human HAQ Agonist Efficacy (%) | Human WT Agonist EC$_{50}$ (μM) | Human WT Agonist Efficacy (%) | Murine Agonist EC$_{50}$ (μM) | Murine Agonist Efficacy (%) |
|---|---|---|---|---|---|---|
| 22B | A | <100 | C | <100 | B | <100 |
| 22C | A | >100 | C | <100 | B | <100 |
| 22D | A | >100 | B | >100 | A | >100 |
| 12C | B | <100 | C | <100 | A | <100 |
| 12D | B | <100 | D | <100 | B | >100 |
| 34B | B | <100 | D | <100 | C | <100 |
| 34C | A | >100 | B | >100 | A | >100 |
| 34D | B | <100 | D | <100 | B | <100 |
| 36D | A | >100 | B | <100 | A | <100 |
| 35C | B | >100 | C | <100 | B | >100 |
| 35D | B | >100 | C | <100 | C | <100 |
| 37A | A | >100 | A | <100 | A | >100 |
| 37B | A | >100 | A | >100 | A | >100 |
| 38A | A | >100 | B | <100 | A | >100 |
| 38B | B | >100 | C | <100 | B | >100 |
| 38C | A | >100 | A | >100 | A | >100 |
| 38D | A | >100 | B | >100 | A | >100 |
| 39 | A | <100 | A | >100 | A | >100 |

A: EC$_{50}$ < 10.0 μM;
B: EC$_{50}$ = 10.0 μM-99.9 μM;
C: EC$_{50}$ = 100 μM-999 μM;
D: EC$_{50}$ > 1000 μM

Example F

Human IFN-β Secretion Assay

Human THP1 Dual (HAQ) human cells (Invivogen) were used to determine the amount of IFN-β secretion in response to STING pathway activation. Secreted IFN-β protein was detected using the human IFN-β AlphaLISA Detection Kit (Perkin Elmer). This assay was conducted in 384-well plates containing 3 μL of test compound. Cells were added to the plate (64,000 cells in 75 μL). The cells were prepared in RPMI 1640 without phenol red (Corning) supplemented with 10% heat-inactivated fetal bovine serum. The assay was incubated for 20 hrs at 37° C. in 5% CO$_2$. Following the incubation, 5 μL of the cell/compound mixture was transferred to a 384-well plate. Then, 10 μL of anti-IFN-β acceptor beads were added and incubated at room temperature for 30 minutes. 10 μL of biotinylated anti-IFN-β antibody was then added and incubated at room temperature for an additional 60 minutes. Then, 25 μL of streptavidin-donor beads were added and incubated for an additional 30 minutes at room temperature. The assay was read on an EnVision plate reader (Perkin Elmer). In this assay 2',3'-cGAMP was used as a reference compound, which had an EC$_{50}$ of 12.6 μM. Secretion of IFN-β by 2',3'-cGAMP, ADU-S100, and the Example 1C compound is shown in FIG. 1.

Example G

Western Blot Analysis of STING Signaling Pathway Activation

Figure 3:
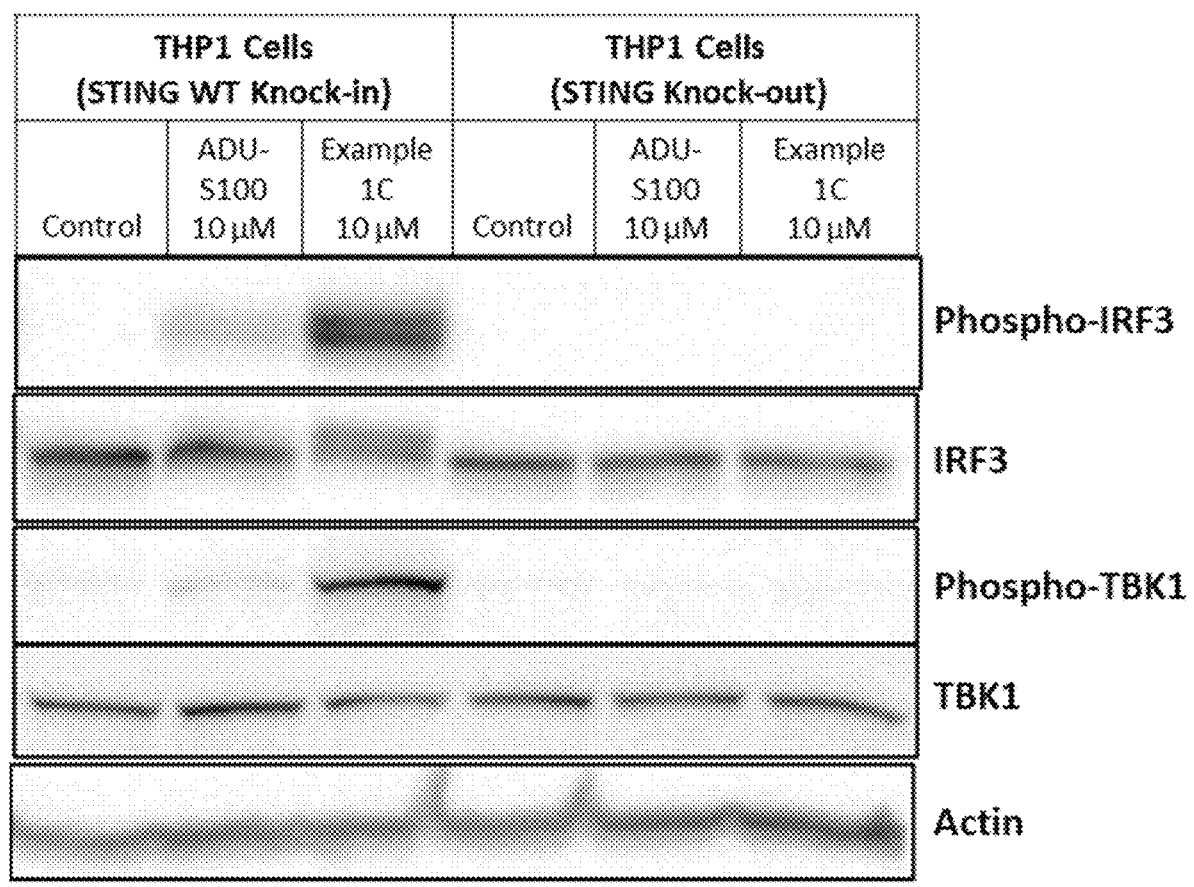
FIG. 3 is Western Blot analysis of Example 1C that demonstrates activity is STING dependent.

STING Pathway activation was measured in THP1 Dual (HAQ) human cells (Invivogen) by performing Western Blot analysis of phosphoIRF3 (S386) and phosphoTBK1 (S172) on cell lysates treated with compounds of the present invention. Briefly, 2 million cells were treated with test compounds for 4 hrs at 37° C., in a 5% CO$_2$ tissue culture incubator. Cell lysates were prepared by lysing cells in RIPA lysis buffer followed by sonication. Equal amounts of cell lysates from control and treated samples were mixed with SDS-PAGE loading buffer, boiled at 95° C. for 5 minutes. Boiled samples were then run on SDS-PAGE gels and Western blotted on PVDF membrane. Blots were probed with antibodies against IRF3 (phospho-IRF3 and total IRF3) and TBK1 (phospho-TBK1 and total TBK1). Antibodies for protein detection were purchased from the following commercial sources: IRF3 (Cell Signaling Technology), phosphoIRF3 (Abcam), TBK1 (Cell Signaling Technology), phosphoTBK1 (Cell Signaling Technology), and Actin (Abcam). FIG. 2 shows the analysis of STING pathway activation in THP1 Dual (HAQ) human cells (Invivogen) by 2',3'-cGAMP, ADU-S100 and Example 1C of the present invention. FIG. 3 is the genetic analysis that demonstrates activity of Example 1C is dependent upon the STING pathway.

Example H

Human IFN-α/β Induction Assay

HEK-Blue IFN-α/β reporter cells (Invivogen) were used to measure the secretion of IFN-α/β into culture supernatants of THP1 cells following STING pathway activation. In the first step, THP1 cells were cultured in presence of STING activators for 5 hrs at 37° C., in a 5% CO$_2$ tissue culture incubator, which facilitates the release of IFN-α/β into the supernatants. In the second step, cell supernatants from THP1 cells were transferred to HEK-Blue IFN-α/β reporter cells and incubated at 37° C., in a 5% CO$_2$ incubator for 24 hrs. HEK-Blue IFN-α/β reporter cells are specifically designed to monitor the activation of JAK-STAT pathway activation by type 1 IFNs. These cells express a secreted embryonic alkaline phosphatase (SEAP) reporter gene under the control of ISG54 promoter, which is a well-known interferon stimulatory gene activated by type 1 IFNs. Upon IFN-α/β stimulation, HEK-Blue IFN-α/β reporter cells activate the JAK-STAT pathway and subsequently the expression of the reporter gene. SEAP which is secreted in the supernatant is easily detectable using alkaline phosphatase detection medium (Quanti-Blue reagent from Invivogen).

These assays were run by adding 2 μL of compound stock solution to tissue culture treated 384-well plates with electronic pipettes. Compounds were diluted in autoclaved sterile water, initially spotted on the intermediate dilution plate and then to the assay plate. 10,000 cells in 18 μL were dispensed into each well of the 384-well plate. Plates were incubated for 5 hrs at 37° C., in a 5% CO$_2$ incubator. After the incubation time, plates were centrifuged at 240×g for 5 minutes and 10 μL of supernatant were transferred to a new 384-well plate that contained HEK-Blue IFN-α/β reporter cells at a concentration of 10,000 cells/well in 50 μL media. Cells were incubated at 37° C., in a 5% CO$_2$ incubator for 24 hours. After final incubation, 70 μL of Quanti Blue (SEAP detection reagent) was added to each well in a new 384 plate and 10 μL of the cell supernatant was added from the assay plate. Plates were incubated at 370C for 30 minutes and the absorbance was measured at 655 nm on Envision plate reader.

Compounds of the present invention along with 2',3'-cGAMP and ADU-S100 were tested in the Human IFN-α/β induction assay described immediately above and the results shown in Table 9 below were obtained.

TABLE 9

| Compound | EC$_{50}$ (μM) |
| --- | --- |
| 2',3'-cGAMP | >10 |
| ADU-S100 | >10 |
| Example 1C | <5 |
| Example 1D | <5 |

Example I

Measurement of Mouse IFN-β

Murine macrophage derived cell line RAW-Dual reporter cells (Invivogen) were used to measure the IFN-β produced by STING signaling activation. Briefly, 20,000 cells in 27 μL were seeded into tissue culture treated 384-well plate that contained 3 μL of test compound. Cells were incubated at 37° C., in a 5% CO$_2$ incubator for 5.5 hours. Supernatants from treated cells were diluted 20-fold and prior to measurement of IFN-β levels using ELISA kit (PBL Assay Science). 100 μL of diluted sample was added to ELISA plate. Plates were incubated at RT for 1 hour with shaking at 650 rpm. Post incubation, samples were aspirated from wells and the wells were washed 4 times. Diluted antibody (50 μL) was added to plates and incubated at RT for 30 minutes with shaking, followed by aspiration of antibody and 4× washes. Diluted HRP (horseradish peroxidase) solution (50 μL) was added and incubated for 10 minutes, followed by aspiration of the solution and 4× wash steps. After the final wash steps, plates were incubated with 100 μL of TMB (tetramethyl benzidine) substrate for 10 minutes, followed by addition of 100 μL of stop solution and plates were read on Envision plate reader for optical density.

Compounds of the present invention along with 2',3'-cGAMP and ADU-S100 were tested to measure mouse IFN-β in the assay described immediately above and the results shown in Table 10 below were obtained.

TABLE 10

| Compound | EC$_{50}$ (μM) |
| --- | --- |
| 2',3'-cGAMP | >25 |
| ADU-S100 | >5 |
| Example 1C | <5 |
| Example 1D | >5 |

Example J qRT-PCR Assay

Human PBMCs, THP1 Dual (HAQ) human cells (Invivogen)), THP1 Dual (WT) human cells (Invivogen), and RAW-Dual murine macrophage reporter cells (Invivogen) were treated with test compounds. Cells were harvested by centrifugation and washed with phosphate buffer saline. Total RNA was isolated using Qiagen RNeasy mini kit. Genomic DNA was degraded using Thermo Scientific DNase 1 kit. Total RNA was quantified using Nanodrop spectrophotometer. Using equal amounts of RNA, cDNA was synthesized using Invitrogen Superstrand III First Strand synthesis kit. Target and reference gene expression levels were determined by real-time qRT-PCR using Taqman gene expression assay and Stratagene QPCR system (all reagents were from Taqman). Data was analyzed by the Comparative C$_T$ method. GAPDH was used for normalization. Target genes included interferon responsive genes (IFN-β, CXCL10, IFIT1, IFIT3, ISG15) and NF-κB dependent pro-inflammatory cytokines (IL-6 and TNFα). In PBMCs, Th1-associated cytokines (IFNγ and IL-12) were also determined. Activation of Type I and II interferons and interferon stimulated (ISG) genes in human PBMCs by the Example 1C compound in comparison to known STING agonists 2',3'-cGAMP and ADU-S100 is shown in FIG. 4.

Example 1C induced IFN-β and its target genes CXCL10, IFIT3 and TNFα, significantly higher than endogenous STING agonist and ADU-S100 at 6 hours. Example 1C also induced Th1-associated cytokines, such as IFNγ and IL-12 compared to 2',3'-cGAMP and ADU-S100, suggesting that Example 1C induces a robust innate immune response and a T-cell mediated response. Example 1C induced both type I and type II interferons to produce an effective immunological response in STING$^{WT/WT}$ human PBMC. The results set forth in FIG. 4 indicate that Example 1C is a potent activator of the STING pathway in the immune compartment.

In THP1 Dual (HAQ) human cells (Invivogen) treatment with the Example 1C compound, was increased IFN-β mRNA by 4000 fold compared to Control and 30-fold compared to ADU-S100. ISG genes such as CXCL10, IFIT1, IFIT3 and ISG15 were also increased. A 1000 fold increase in CXCL10 was observed in THP1 Dual (HAQ) human cells (Invivogen). by treatment with the Example 1C compound. Larger increases in pro-inflammatory genes such as IL-6 and TNFα were also observed in cells treated with the Example 1C compound as compared to ADU-S100 and 2',3'-cGAMP (see Table 11). A 300 fold increase in IL-6 was observed in response to the Example 1C compound compared to Control, suggesting a potent immune response. Similar results were observed in THP1 Dual (WT) human cells (Invivogen) (see Table 12). We demonstrate that Example 1C is a potent activator of the STING pathway in more than one allele of the human STING protein.

TABLE 11

THP1 Dual (HAQ) human cells, 4 h, 10 μM test compound, Relative Fold Change Compared to Unstimulated

| Human | Control | 2'3'-cGAMP | ADU-S100 | Example 1C |
| --- | --- | --- | --- | --- |
| IFN-β | 1 | 129 | 273 | 623 |
| CXCL10 | 1 | 96 | 895 | 1347 |
| IFIT1 | 1 | 30 | 114 | 171 |
| IFIT3 | 1 | 49 | 127 | 213 |
| ISG15 | 1 | 10 | 19 | 31 |
| IL-6 | 1 | 26 | 323 | 680 |

TABLE 12

THP1 Dual (WT) human cells, 4 h, 10 μM test compound Relative Fold Change Compared to Unstimulated

| Human | Control | ADU-S100 | Example 1C |
| --- | --- | --- | --- |
| IFN-β | 1 | 8 | 26 |
| CXCL10 | 1 | 13 | 28 |
| IFIT1 | 1 | 42 | 107 |
| IFIT3 | 1 | 32 | 88 |
| ISG15 | 1 | 7 | 14 |

Consistent with previous results, in murine RAW-Dual macrophages the Example IC compound further activated STING pathway genes such as IFN-β and TNFα compared to ADU-S100 and control (see Table 13). These results demonstrate that Example 1C is a potent activator of the STING pathway in murine immune cells which translates into in vivo studies (see in vivo data).

TABLE 13

RAW Murine Macrophage Reporter Cells, 4 hr, 10 µM Test Compounds Relative Fold Change Compared to Unstimulated

| Murine Gene | Control | 2',3'-cGAMP | ADU-S100 | Example 1C |
|---|---|---|---|---|
| IFN-β | 1 | 135 | 1736 | 3806 |
| TNFα | 1 | 1.4 | 2 | 3.8 |

Example K

IFN-β Secretion by Human Peripheral Blood Mononuclear Cells

Figure 5:
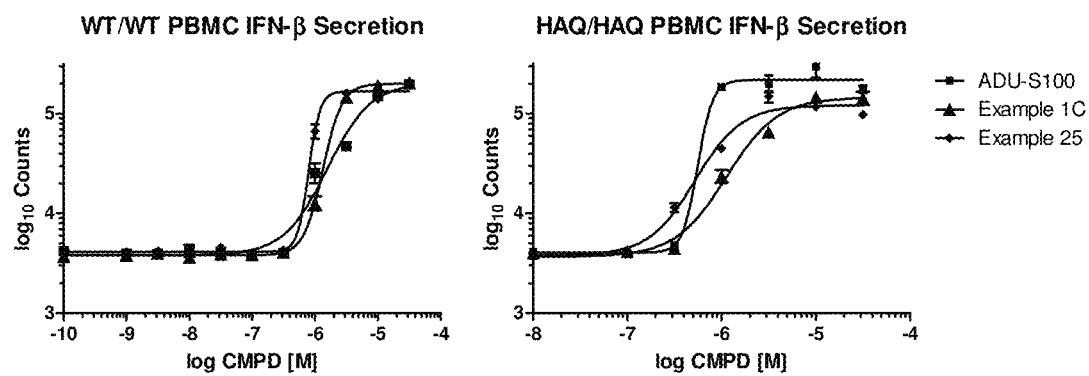
FIG. 5 is a graph which shows a dose response of Example 1C in stimulating IFN-β secretion by human PBMC.

Human peripheral blood mononuclear cells (PBMC) were used to determine the amount of IFN-β secretion in response to STING pathway activation. Secreted IFN-β protein was detected using the human IFN-β AlphaLISA Detection Kit (Perkin Elmer). This assay was conducted in 384-well plates containing 5 µL of test compound. Cells were added to the plate (150,000 cells in 45 µL). The cells were prepared in RPMI 1640 without phenol red (Corning) supplemented with 10% heat-inactivated fetal bovine serum. The assay was incubated for 20 hours at 37° C. in 5% $CO_2$. Following the incubation, 5 µL of the cell/compound mixture was transferred to a 384-well plate. Then, 10 µL of anti-IFN-β acceptor beads were added and incubated at room temperature for 30 minutes. 10 µL of biotinylated anti-IFN-β antibody was then added and incubated at room temperature for an additional 60 minutes. Then, 25 µL of streptavidin-donor beads were added and incubated for an additional 30 minutes at room temperature. The assay was read on an EnVision plate reader (Perkin Elmer). Secretion of IFN-β induced by compound is shown in FIG. 5.

Example L

STING Pathway Activation in Mouse Bone Marrow-Derived Dendritic Cells

Bone marrow-derived dendritic cells (BMDCs) from wild type mice femurs were prepared and cultured in tissue culture vessels according to published protocols. Cells were stimulated with either 10 µM of ADU-S100 or Example 1C for 4 hours. Expression of innate cytokines was measured by RT-qPCR. Total RNA was isolated using Qiagen RNeasy mini kit and genomic DNA in the sample was digested using Thermo Scientific DNase 1 kit. Using equal amounts of RNA, cDNA was synthesized using Invitrogen Superstrand III first strand synthesis kit. Target and reference gene expression levels were determined by real time RT-qPCR using Taqman gene expression assay and BioRad CFX Maestro system. Data was analyzed by the comparative $C_T$ method. GAPDH was used for normalization and fold change compacted to untreated was calculated (see Table 14).

TABLE 14

Example 1C Activates STING Pathway in Mouse Bon Marrow-Derived Dendritic Cells

| BMDC | Control | ADU-S100 | Example 1C |
|---|---|---|---|
| IFN-β | 1 | 17506 | 51271 |
| IFIT1 | 1 | 1777 | 5032 |
| IFNα | 1 | 428 | 50 |
| IFNγ | 1 | 3258 | 148 |
| TNFα | 1 | 7285 | 513 |
| IL-6 | 1 | 58 | 148 |

Example M

STING Pathway Activation in Primary Bladder Epithelial Cells

STING Pathway activation was measured in primary bladder epithelial cells by performing Western Blot analysis of phosphoIRF3 (S386) cell lysates treated with compounds. Briefly, 0.5 million cells were treated with test compounds for 2 hours at 37° C., 5% $CO_2$ tissue culture incubator. Cell lysates were prepared by lysing cells in RIPA lysis buffer followed by sonication. Equal amount of cell lysates from control and treated samples were mixed with SDS-PAGE loading buffer, boiled at 95° C. for 5 minutes. Boiled samples were then run on SDS-PAGE gels and Western Blotted on PVDF membrane. Blots were probed with antibodies against IRF3 (phospho-IRF3 and total IRF3). See FIG. 6.

Example N

CT-26 Tumor Bearing Mice Treated with Example 1C

Eight week old female BALB/cAnNTac mice were purchased from Taconic (Germantown, N.Y.). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, N.J.) were available ad libitum.

CT-26 cells were maintained in vitro as a monolayer culture in RPMI 1640+10% heat-inactivated FBS and harvested at passage 7. Mice were inoculated subcutaneously with $0.3 \times 10^6$ CT-26 tumor cells in 100 µl serum free DMEM on the lower right flank. Tumors were measured in two dimensions using calipers. Tumor volumes were calculated using the formula: volume (mm3)=(length×width2)/2. Animals were euthanized when the tumor volume reached 2000 $mm^3$.

Figure 7:
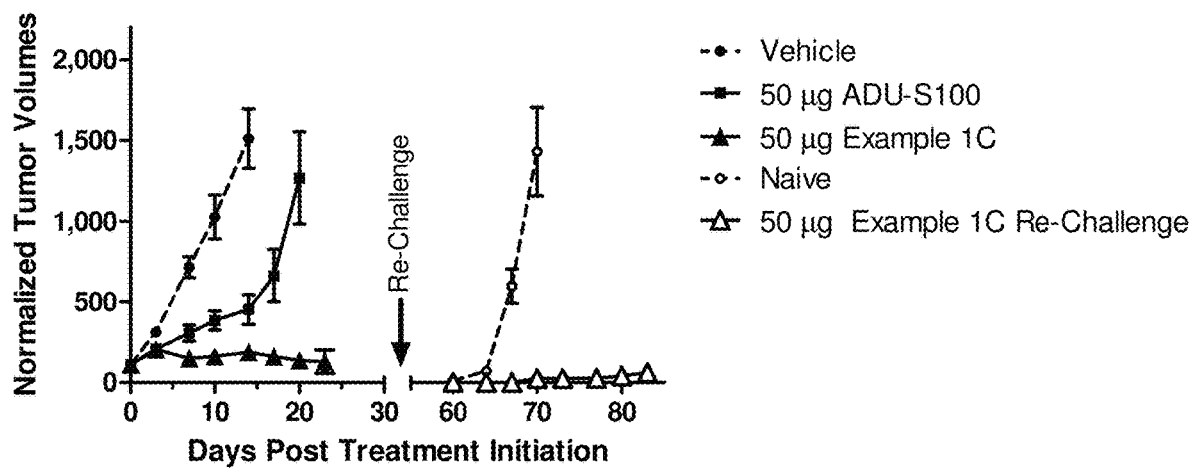
FIG. 7 is CT-26 tumor bearing mice treated with Example 1C.

Tumors grew for 10 days to an average size of 110 $mm^3$. Animals were randomized by tumor volume and body weight into groups of ten mice per treatment group on Day 0. Mice were treated by intra-tumoral injection of 50 µg of Example 1C, ADU-S100 in 30 µL of PBS or with PBS alone. Mice were given three injections on Days 0, 3 and 7. Tumor volumes ($T_{vol}$) were normalized to the initial tumor ($T_{init}$)

volume using the formula $((T_{vol}-T_{init})/(T_{init}))*100$. All vehicle treated animals were alive until Day 14. Complete regression of the tumors was observed in 8 out of 10 animals in the 50 µg Example 1C treatment group by Day 30. None of the 50 µg ADU-S100 treated mice demonstrated complete regression of the tumors. These data are shown in FIG. 7. Survival of the three groups from Day 0 through Day 35 is shown in Table 15. Example 1C induces a strong and durable anti-tumor immune response.

TABLE 15

Number of surviving mice from Day 0 through Day 35 in the initial study.

| Treatment Day | Vehicle | 50 µg Example 1C | 50 µg ADU-S100 |
|---|---|---|---|
| 0 | 10/10 | 10/10 | 10/10 |
| 3 | 10/10 | 10/10 | 10/10 |
| 7 | 10/10 | 10/10 | 10/10 |
| 10 | 10/10 | 10/10 | 10/10 |
| 14 | 10/10 | 10/10 | 10/10 |
| 17 | 8/10 | 10/10 | 10/10 |
| 20 | 6/10 | 10/10 | 10/10 |
| 23 | 1/10 | 10/10 | 7/10 |
| 35 | 0/10 | 8/10 | 1/10 |

Figure 6:
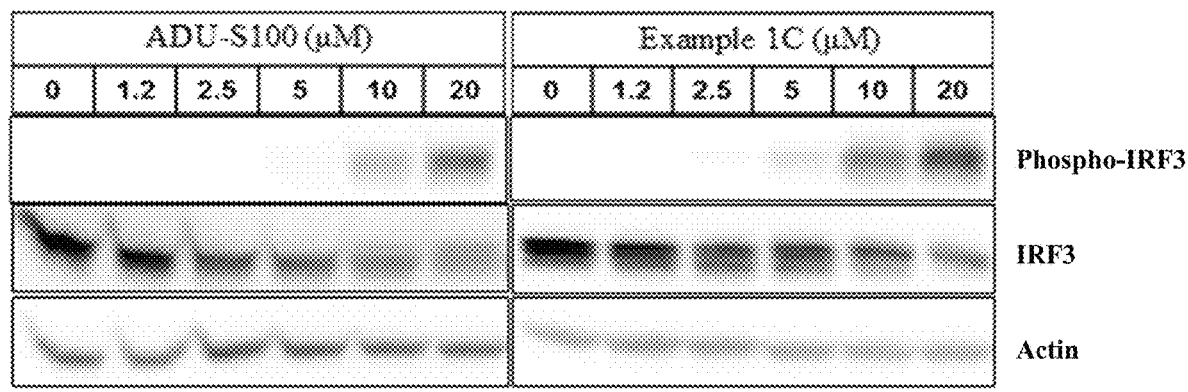
FIG. 6 is a graphical representation of Example 1C leading to STING pathway activation in primary human bladder epithelial cells.

The 8 animals with complete regression of the initial tumors treated with 50-g Example 1C were re-challenged with CT-26 cells and a naïve control group was inoculated in parallel on Day 53 (re-challenge Day 0). No animals received any further treatment. By Day 27 of the re-challenge all naïve animals were euthanized due to the tumor volumes reaching 2000 mm³. In the group that was treated with Example 1C in the initial phase (8 animals from Table 14 above), 2 out of 8 animals showed signs of tumor growth by re-challenge Day 30; 6 out of 8 mice showed no signs of tumor growth 33 days after the re-challenge. The re-challenge data are shown in FIG. 6. The number of surviving mice in the naïve and Example IC pre-treated groups are shown in Table 16.

TABLE 16

Number of surviving mice from Day 0 through Day 33 in the re-challenge.

| Rechallenge Day | Naïve | 50 µg Example 1C |
|---|---|---|
| 0 | 10/10 | 8/8 |
| 7 | 10/10 | 8/8 |
| 11 | 10/10 | 8/8 |
| 14 | 10/10 | 8/8 |
| 17 | 10/10 | 8/8 |
| 20 | 7/10 | 8/8 |
| 24 | 4/10 | 8/8 |
| 27 | 0/10 | 8/8 |
| 30 | 0/10 | 8/8 |
| 33 | 0/10 | 8/8 |

Example O

MC-38 Tumor Bearing Mice Treated with Example 1C and Anti-PD-1

Eight week old female C57BL/6J mice were purchased from the Jackson Laboratory West (Sacramento, Calif.). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, N.J.) were available ad libitum.

MC-38 cells were maintained in vitro as a monolayer culture in DMEM+10% heat-inactivated FBS and harvested at passage 5. Mice were inoculated subcutaneously with $1\times10^6$ MC-38 tumor cells in 100 l phenol free DMEM on the lower right flank. Tumors were measured in two dimensions using calipers. Tumor volumes were calculated using the formula: volume $(mm^3)=(length\times width2)/2$. Animals were euthanized when the tumor volume reached 2000 mm³.

Tumors grew for 8 days to an average size of 150 mm³. Animals were randomized by tumor volume and body weight into groups of ten mice per treatment group on Day 0. Mice were treated by intra-tumoral injection of 5 µg of Example 1C in 30 µL of PBS or with PBS alone on Days 0, 3 and 7. Mice were treated with injections of 10 mg/kg anti-PD-1 antibody (Clone RMP1-14; Catalogue #BE0146) or an isotype control (Clone 2A3; Catalogue #BE0089) purchased from BioXcell (West Lebanon, N.H.) two times a week for three weeks. Tumor volumes ($T_{vol}$) were normalized to the initial tumor ($T_{init}$) volume using the formula $((T_{vol}-T_{init})/(T_{init}))*100$. The study was terminated when the tumor size in the vehicle treated group reached 2,000 mm³. Animals with complete tumor regression were retained for a re-challenge study. The re-challenge study was initiated 21 days after complete tumor regression was observed.

All vehicle treated animals were alive until Day 17. By Day 30 complete regression of the tumors was observed in 7 out of 10 animals in the 5 µg Example 1C+anti-PD-1 treatment group, and 1 out of 10 animals in the 5 µg Example 1C monotherapy group. None of the anti-PD-1 monotherapy treated mice demonstrated complete regression of the tumors. Survival of the three groups from Day 0 through Day 34 is shown in Table 17.

TABLE 17

Number of surviving mice from Day 0 through Day 34 in the initial study.

| | Treatment | | | |
|---|---|---|---|---|
| Day | 10 mg/kg Isotype Control | 10 mg/kg Anti-PD-1 | 5 µg Example 1C | 5 µg Example 1C + 10 mg/kg Anti-PD-1 |
| 0 | 10/10 | 10/10 | 10/10 | 10/10 |
| 3 | 10/10 | 10/10 | 10/10 | 10/10 |
| 6 | 10/10 | 10/10 | 10/10 | 10/10 |
| 10 | 10/10 | 10/10 | 10/10 | 10/10 |
| 14 | 10/10 | 10/10 | 10/10 | 10/10 |
| 17 | 10/10 | 10/10 | 10/10 | 10/10 |
| 21 | 2/10 | 9/10 | 10/10 | 10/10 |
| 24 | 0/10 | 6/10 | 10/10 | 10/10 |
| 27 | 0/10 | 0/10 | 7/10 | 9/10 |
| 30 | 0/10 | 0/10 | 3/10 | 8/10 |
| 34 | 0/10 | 0/10 | 1/10 | 7/10 |

Figure 8:
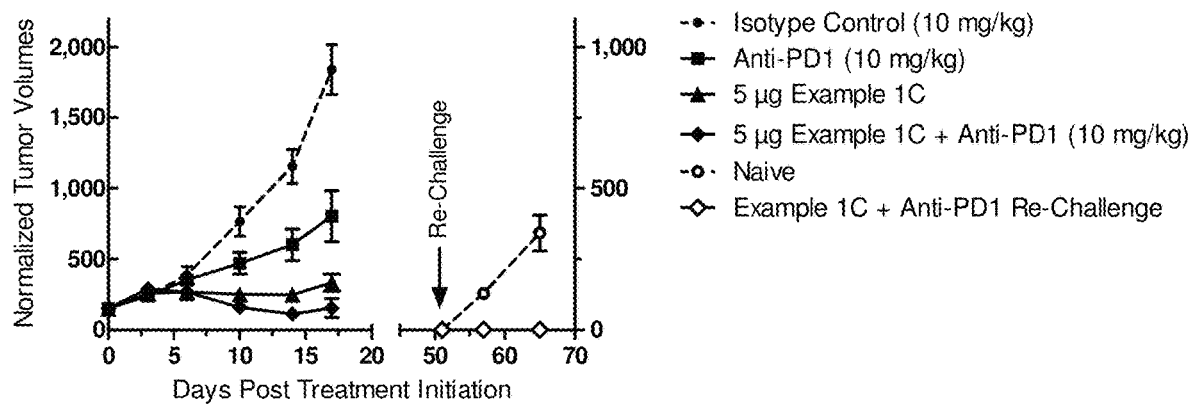
FIG. 8 is MC38 tumor bearing mice treated with Example 1C and PD-1.

The 7 animals with complete regression of the initial tumors treated with 5 µg Example 1C and 10 mg/kg anti-PD-1 and one animal treated with Example 1C alone were re-challenged with MC-38 cells and a naïve control group was inoculated in parallel on Day 51 (re-challenge Day 0). No animals received any further treatment. By Day 14 of the re-challenge all naïve animals had measurable tumors. In the groups that were treated with Example 1C as a monotherapy or in combination with anti-PD-1 in the initial phase (8 animals from Table 14 above), 8 out of 8 animals showed no signs of tumor growth by re-challenge Day 14. The re-challenge data are shown in FIG. 8.

Example P

MB49-Luc Tumor Bearing Mice Treated with Example 1C

Ten week old female C57BL/6J mice were purchased from Jackson Laboratory (www.jax.org). During the study, the care and use of animals was conducted in accordance with the regulations of the Association for Assessment and Accreditation of Laboratory Animal Care (AAALAC). The protocol and any amendment(s) or procedures involving the care and use of animals in the study was reviewed and approved by the Institutional Animal Care and Use Committee (IACUC) of Invivotek prior the initiation of the study. Mice were acclimated for 72 hours before orthotopic implantation of cells. Mice were group housed (n=5/cage) and maintained on a 12 hour light: dark schedule. Reverse osmosis chlorinated water and irradiated food Purina rodent diet #5053 (Fisher Feeds, Bound Brook, N.J.) were available ad libitum.

MB49-luc cells were maintained in vitro as a monolayer culture in DMEM+10% heat-inactivated FBS and harvested at passage 10. MB49-luc cells were surgically implanted into the bladder wall. Bioluminescent imaging (BLI) was used to monitor tumor growth in the orthotopic location (bladder) and metastases in the chest area (lungs).

Figure 9:
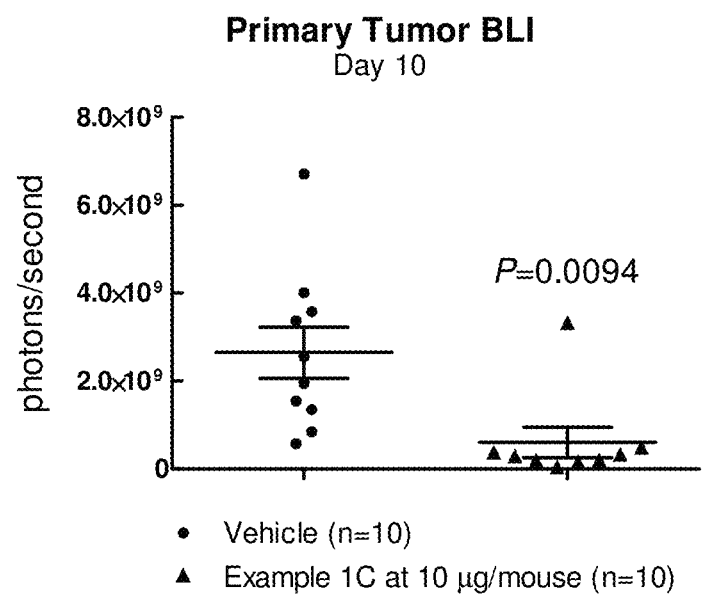
FIG. 9 is Example 1C in the orthotopic MB-49 tumor model showing Bio-Lumenescence imaging (BLI) data.
Figure 9:
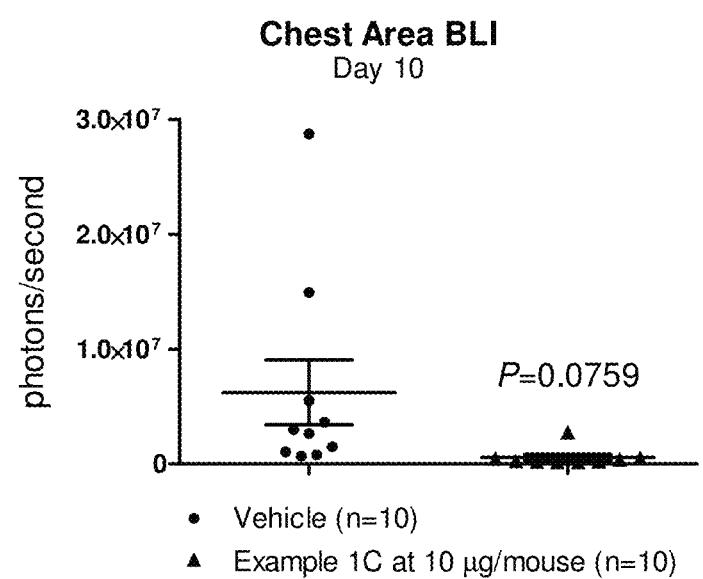
Figure 10:
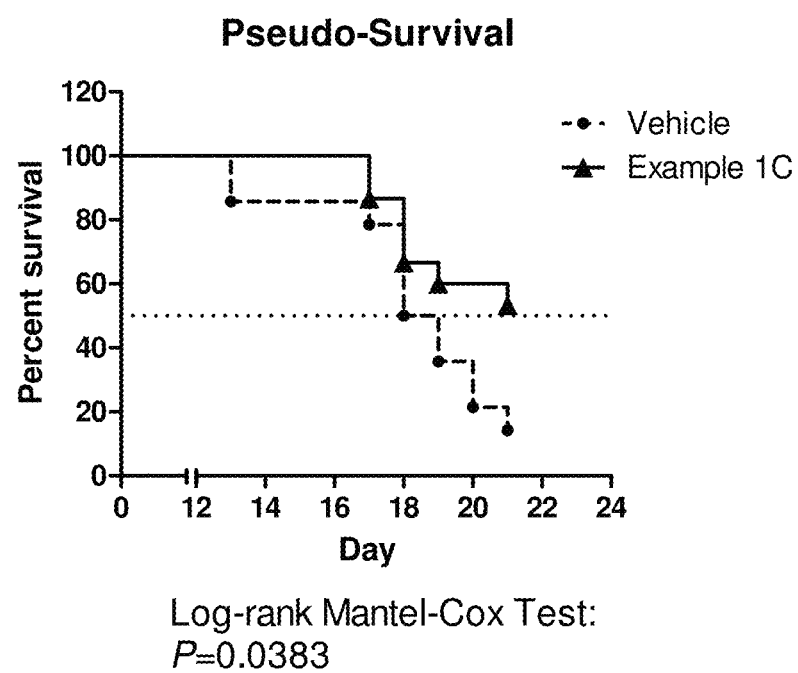
FIG. 10 is pseudo-survival of mice treated with Example 1C in the orthotopic MB-49 tumor model.

The study consisted of an imaging arm and a pseudo-survival arm. Seven days after orthotopic implantation of the MB49-luc cells, animals were randomized by tumor load values, as determined by BLI, into groups of ten mice per treatment group on Day 0 for the imaging arm and fifteen mice per group for the pseudo survival arm. Mice were treated by intra-tumoral injection of 10 µg of Example 1C in 30 µL of PBS or with PBS alone. Mice were given five injections on Days 0, 3, 7, 10, and 14. Imaging of the primary tumor showed a statistically significant reduction of the bladder tumor in the 10 µg/mouse of Example 1C treatment group by Day 10 (FIG. 9). Additionally, imaging showed a trend towards significant reduction of the tumor load in the chest areas in the 10 µg/mouse of Example 1C treatment group by Day 10. Treatment with Example 1C significantly extended the survival time compared with the vehicle treated controls (FIG. 10).

Example Q

MC-38 Tumor Bearing Mice Treated with Example 1C, and Anti-PD-1, Anti-PD-L1, Anti-CTLA4

Eight week old female C57BL/6J mice were purchased from the Jackson Laboratory (www.jax.org). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, N.J.) were available ad libitum.

MC-38 cells were maintained in vitro as a monolayer culture in DMEM+10% 15 heat-inactivated FBS and harvested at passage 5. Mice were inoculated subcutaneously with $1 \times 10^6$ MC-38 tumor cells in 100 µL phenol free DMEM on the lower right flank. Tumors were measured in two dimensions using calipers. Tumor volumes were calculated using the formula: volume $(mm^3)=(length \times width^2)/2$. Animals were euthanized when the tumor volume reached 2,000 $mm^3$.

Tumors grew for 8 days to an average size of 100 $mm^3$. Animals were randomized by tumor volume and body weight into groups of ten mice per treatment group on Day 0. Mice were treated by intra-tumoral injection of 5 µg of Example 1C in 30 µL of PBS or with PBS alone on Days 0, 3, 7, and 14. Mice were treated with injections of a combination of 5 mg/kg anti-PD-1 antibody (Clone RMP1-14; Catalogue 5 # BE0146)+5 mg/kg anti-PD-L1 antibody (Clone 10F.9G2; Catalogue #BE0101), or a combination of 5 mg/kg anti-PD-L1 antibody (Clone 10F.9G2; Catalogue #BE0101)+5 mg/kg of anti-CTLA4 antibody, or an isotype control (Clone 2A3; Catalogue #BE0089) purchased from BioXcell (West Lebanon, N.H.) two times a week for three weeks. The animals were terminated when the tumor size reached 2,000 $mm^3$.

All vehicle treated animals achieved 2,000 $mm^3$ tumor size and were euthanized 10 by Day 26. By Day 26, complete regression of the tumors was observed in 8 out of 10 animals in the 5 µg Example 1C+anti-PD-1+anti-PD-L1 treatment group, 6 out of 10 animals in the 5 µg Example 1C+anti-PD-L1+anti-CTLA4 treatment group, and 2 out of 10 animals in the 5 µg Example 1C monotherapy group. None of the anti-PD-1+anti-PD-L1 therapy treated mice demonstrated complete regression of the tumors. (see Table 17).

The 12 animals with complete regression of the initial tumors treated with 5 µg Example 1C and combinations of either 5 mg/kg anti-PD-1+5 mg/kg anti-PD-L1 or 5 mg/kg anti_P-L1+5 mg/kg anti-CTLA4, and the one animal treated with Example 1C alone were re-challenged with MC-38 cells and a naïve control group was inoculated in parallel on Day 65 (re-challenge Day 0). No animals received any further treatment. By Day 27 of the rechallenge all naïve animals had exited the study due to excessive tumor burden. By Day 27 of the rechallenge 5 out of 8 mice that were treated with Example 1C in combination with anti-PD-1+anti-PD-L1 were tumor free, 6 out of 6 mice that were treated with Example 1C in combination with anti-PD-L1+anti-CTLA4 were tumor free, and 1 out of 2 mice treated with Example 1c as monotherapy were tumor free (see Table 18)

TABLE 18

Tumor free mice following the primary and re-challenge

| Group | Animals/Group | Treatment | #Tumor Free Mice after Treatment/ #Tumor Free Mice after Re-challenge |
|---|---|---|---|
| 1 | 10 | Iso Ab (10 mg/kg) + Vehicle | 0/0 |
| 2 | 10 | Iso Ab (10 mg/kg) + 5 µg Example 1C | 2/1 |
| 3 | 10 | PD1 + PD-L1 (5 + 5 mg/kg) + Vehicle | 0/0 |

TABLE 18-continued

Tumor free mice following the primary and re-challenge

| Group | Animals/ Group | Treatment | #Tumor Free Mice after Treatment/ #Tumor Free Mice after Re-challenge |
|---|---|---|---|
| 4 | 10 | PD1 + PD-L1 (5 + 5 mg/kg) + 5 µg Example 1C | 8/5 |
| 5 | 10 | CTLA4 + PD-L1(5 + 5 mg/kg) + Vehicle | 0/0 |
| 6 | 10 | CTLA4 + PD-L1(5 + 5 mg/kg) + 5 µg Example 1C | 6/6 |

Example R

Treatment of MC-38 Tumors with Example 1C and Radiotherapy

Eight week old female C57BL/6J mice were purchased from the Jackson Laboratory West (Sacramento, Calif.). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, N.J.) were available ad libitum.

MC-38 cells (murine colon adenocarcinoma) were maintained in vitro as a monolayer culture in DMEM+10% heat-inactivated FBS and harvested at passage 5. Mice were inoculated subcutaneously with $1\times10^6$ MC-38 tumor cells in 100 µl phenol free DMEM on the lower right flank. Tumors were measured in two dimensions using calipers. Tumor volumes were calculated using the formula: volume (mm$^3$) =(length×width2)/2. Animals were euthanized when the tumor volume reached 2000 mm$^3$.

Tumors grew for 7 days to an average size of 100 mm$^3$. Animals were randomized by tumor volume and body weight into groups of ten mice per treatment group on Day −2. On Days −2, −1 and 0 received 5 Gy of radiation targeted to the tumor using the Small Animal Radiation Research Platform (SARRP) manufactured by Xstrahl Inc. Radiotherapy treatments were given according to the outline in Table 18. Mice were treated by intra-tumoral injection of 5 ag of Example 1C in 30 µL of PBS or with PBS alone on Days 0, 3, 7 and 14. Radiotherapy treatments were given according to the outline in Table 19.

TABLE 19

Example R Experimental Design

| Group | Animals/ group | Day-2 RT | Day-1 RT | Day 0 RT (before Example C) | IT Example 1C (5 µg/30 µl) | IT Vehicle |
|---|---|---|---|---|---|---|
| 1 | 10 | 5 Gy | 5 Gy | 5 Gy | Day 0, 3, 7, 14 | N/A |
| 2 | 10 | N/A | 5 Gy | 5 Gy | Day 0, 3, 7, 14 | N/A |
| 3 | 10 | N/A | N/A | N/A | Day 0, 3, 7, 14 | N/A |
| 4 | 10 | 5 Gy | 5 Gy | 5 Gy | N/A | N/A |
| 5 | 10 | N/A | N/A | N/A | N/A | Day 0, 3, 7, 14 |

The last vehicle treated animals were alive until Day 26. The re-challenge study was initiated 39 days after complete tumor regression was observed. The results of animals with complete tumor regression following the primary challenge and were tumor free after the re-challenge are shown in Table 20.

TABLE 20

Tumor free mice following the primary and re-challenge

| Group | Animals/ Group | Treatment | #Tumor Free Mice after Treatment/ #Tumor Free Mice after Re-challenge |
|---|---|---|---|
| 1 | 10 | RT Day −2, −1, 0/Example 1C IT Day 0, 3, 7, 14 | 8/7 |
| 2 | 10 | RT Day −1, 0/Example 1C IT Day 0, 3, 7, 14 | 4/3 |
| 3 | 10 | Example 1C IT Day 0, 3, 7, 14 | 0/0 |
| 4 | 10 | RT Day −2, −1, 0 | 0/0 |
| 5 | 10 | Vehicle IT Day 0, 3, 7, 14 | 0/0 |

Example S

Treatment of Orthotopically Implanted MB49-Luc Tumor Bearing Mice with Example 1C Eleven to twelve week old female C57BL/6 mice were purchased from the Jackson Laboratory West (Sacramento, Calif.). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=4 to 5/cage) and maintained on a 12 hour light and dark schedule. Reverse osmosis chlorinated water and irradiated food Purina rodent diet #5053 (Fisher Feeds, Bound Brook, N.J.) were available ad libitum.

MB49-luc cells (MB49 mouse bladder carcinoma cell line, Millipore) were maintained as monolayer culture in DMEM supplemented with 10% heat inactivated fetal bovine serum at 37° C. and harvested at passage 10. Each mouse was inoculated with a single cell suspension of 95% viable MB49-luc tumor cells via intravesical injection into the bladder lumen ($1.5\times10^5$ cells in 100 µl of PBS). Mice were kept under isoflurane anesthesia for 45 minutes with the catheter maintained in place to retain the tumor cells into the bladder. The experimental groups are shown in Table 1. The growth of orthotopically implanted MB49-luc tumor cells was monitored with the Perkin Elmer In Vivo Imaging System (IVIS). Before commencement of treatment, all animals were weighed and assigned to treatment groups using a randomization procedure based on BLI levels on Day 3 post tumor inoculation. Animals were treated by intravescular instillation into the bladder for 2 hours with vehicle or Example 1C on Days 4, 7 and 11). BLI data and body weights were acquired and animals were euthanized if body weight loss≥ to 20% of the initial body weight was observed. The experimental treatment groups are shown in Table 21.

TABLE 21

Treatment Groups

| Group # | Treatment | Animals/ group | MB49-luc inoculation | Treatment 1 (Day 4) | Treatment 2 (Day 7) | Treatment 3 (Day 11) |
|---|---|---|---|---|---|---|
| 1 | Vehicle | 9 | 1.5 × 10⁵ cells/ mouse | Vehicle | Vehicle | Vehicle |
| 2 | 100 μg Example 1C | 10 | | 100 μg Example 1C | 100 μg Example 1C | 100 μg Example 1C |
| 3 | 50 μg Example 1C | 10 | | 50 μg Example 1C | 50 μg Example 1C | 50 μg Example 1C |
| 4 | 25 μg Example 1C | 10 | | 25 μg Example 1C | 25 μg Example 1C | 25 μg Example 1C |

Figure 11:
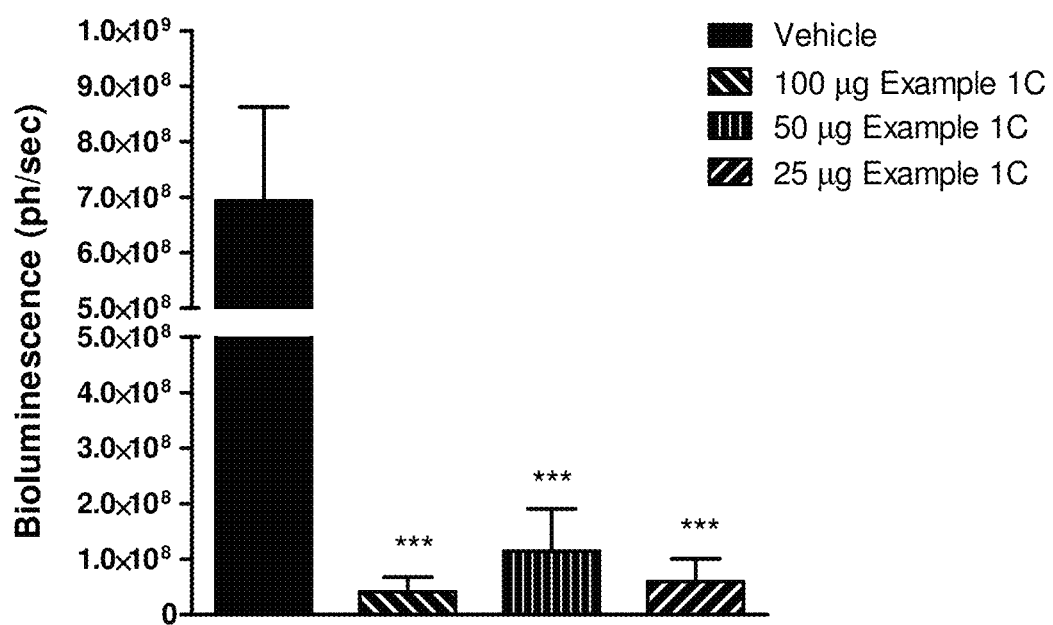
FIG. 11 is a graph showing MB-49 mouse tumor Bio-Luminescence imaging (BLI) on Day 14 after treatment with Example 1C.

FIG. 11 shows BLI values measured on Day 14, three days after the last treatment. The effect of treatment was significant (P<0.001, denoted as *** FIG. 11) when analyzed using a one-way ANOVA. Dunnett's post-hoc shows each treatment group compared to the vehicle treated controls.

Figure 12:
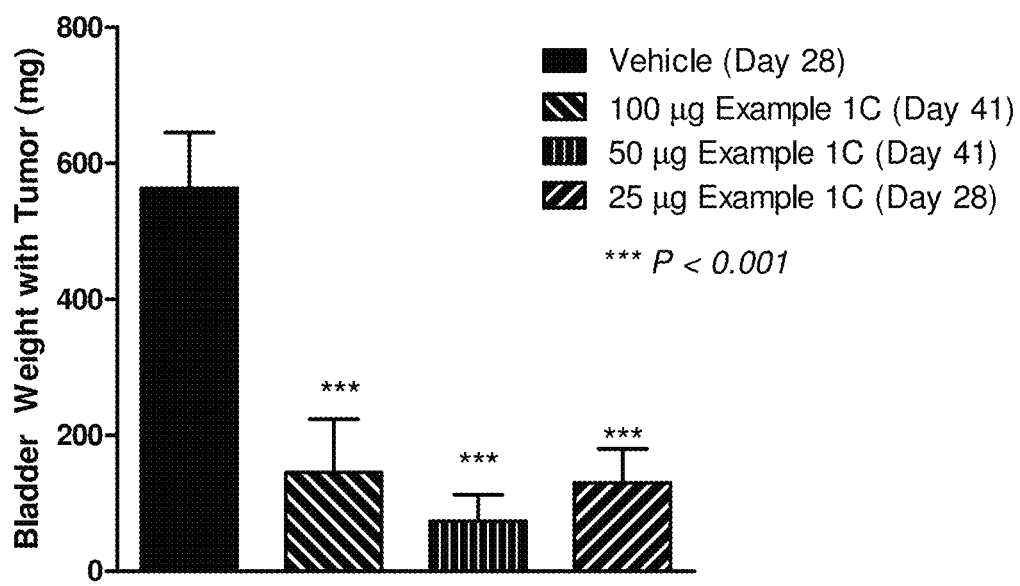
FIG. 12 is a graph of the MB-49 mouse bladder weight at the experimental end point.
Figure 13:
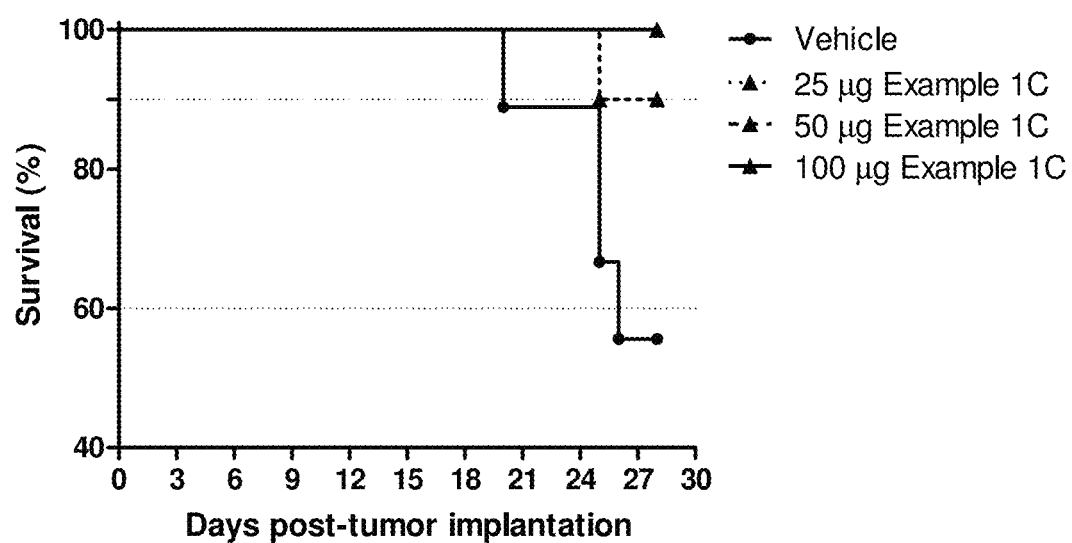
FIG. 13 is a graph showing pseudo survival of mice at Day 28 when treated with Example 1C.

On Day 28 the vehicle and 25 μg treatment groups were euthanized and bladder weights were recorded. The 50 μg and 100 μg treatment groups were sacrificed on Day 41 and bladder weights were recorded. These data are presented in FIG. 12. During the course of the study dates were recorded when animals were euthanized due to body weight loss or found dead; these data are depicted by survival curves in FIG. 13. The effect of treatment on survival was significant using the Mantel-Cox log-rank test.

Example T

HSV1 antiviral activity of STING agonists will be evaluated in mouse fibroblasts (Cer6n S. et al., The STING agonist 5,6-dimethylxanthenone-4-acetic acid (DMXAA) stimulates an antiviral state and protects mice against herpes simplex virus induced neurological disease. Virology, 2019: 529:23-28.) Fibroblasts will be harvested from the pinnae of adult mice after being digested in 1000 U/ml collagenase type II (Invitrogen) and 0.05% trypsin (Cellgo). Triturated cell suspensions will be plated in 6-well plates in Dulbecco's modified Eagle medium (DMEM) (HyClone) supplemented with 2% fetal bovine serum (HyClone), 1% nonessential amino acid (Lonza) and 1% penicillin-streptomycin (HyClone). Cells will be passaged at least one time prior to experimental usage. HSV KOS will be used as described (Wang et al., HSV-1 strain McKrae is more neuroinvasive than HSV-1 KOS after corneal or vaginal inoculation in mice. Virus Res. 2013; 173:436-440). Vero cells will be used to titer virus (Rader et al. In vivo characterization of site-directed mutations in the promoter of the herpes simplex virus type 1 latency-associated transcripts. J. Gen. Virol. 1993; 74 (Pt 9):1859-1869). $C_{57}BL/6$ fibroblasts will be cultured in 24 well plates. Cells will be treated with STING agonist at 0.1 mg/mL supplemented in the media 18 h prior to infection with HSV-1 KOS at a MOI of 1. Fibroblasts will be washed three times with PBS before being replenished with fresh media containing STING agonist. Supernatants will be collected at 24 h post infection and will be used to calculate viral titers as described in Rader et al.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:
1. A compound having the structure:

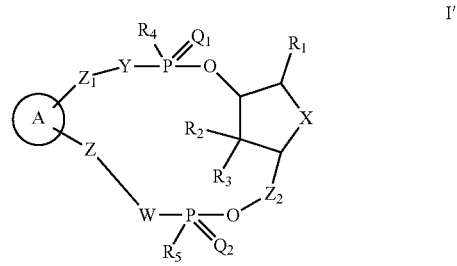

or a pharmaceutically acceptable salt thereof, wherein:
V is CH or N;
$Q_1$ and $Q_2$ are each independently O or S;
Ⓐ is a 5- to 6-membered monocyclic heteroaryl or a 7- to 12-membered bicyclic heteroaryl; both of which are optionally substituted with $R_{10}$ and Rn and wherein the 7- to 12-membered bicyclic heteroaryl contains at least two N atoms;
Z is selected from $C_1$-$C_6$ alkyl, halo-$C_1$-$C_6$-alkyl and $C_3$-$C_6$ cycloalkyl;
$R_2$ is selected from H, halo, $C_1$-$C_4$ alkyl, $C_1$-$C_4$ alkoxy, halo-$C_1$-$C_4$ alkyl, halo-$C_1$-$C_4$ alkoxy, CN, —$NR_8R_9$; $C_3$-$C_4$ cycloalkyl and OH;
$R_3$ is selected from H, halo, $C_1$-$C_4$ alkyl, $C_1$-$C_4$ alkoxy, halo-$C_1$-$C_4$ alkyl, halo-$C_1$-$C_4$ alkoxy, CN, and OH;
or $R_2$ and $R_3$ can be taken together with the carbon to which they are attached to form a $C_3$-$C_4$ cycloalkyl ring;
$R_4$ is selected from OH, SH, $C_1$-$C_6$ alkoxy-carbonyloxy-$C_1$-$C_6$ alkoxy, $C_1$-$C_6$ alkoxy-carbonyloxy-$C_1$-$C_6$ alkylthio, and $BH_3$;
$R_5$ is selected from OH, SH, $C_1$-$C_6$ alkoxy-carbonyloxy-$C_1$-$C_6$ alkoxy, $C_1$-$C_6$ alkoxy-carbonyl oxy-$C_1$-$C_6$ alkylthio, and $BH_3$;
$R_8$ is selected from H, $C_1$-$C_4$ alkyl, $C_1$-$C_4$ alkoxy, halo-$C_1$-$C_4$-alkyl, —C(=O)$R_{15}$ and —$SO_2R_{15}$;
$R_9$ is selected from H, $C_1$-$C_4$ alkyl, $C_1$-$C_4$ alkoxy, and halo-$C_1$-$C_4$-alkyl;
$R_{10}$ is selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}C(=O)R_{15}$, —C(=O) $NR_{14}R_{15}$, a $C_6$-$C_{10}$ aryl, a 5- to 10-membered heteroaryl, a 4- to 6-membered heterocycloalkyl, a $C_3$-$C_{10}$ cycloalkyl, $SR_{18}$ and OH; wherein the $C_1$-$C_4$ alkyl, $C_1$-$C_4$ alkoxy, halo-$C_1$-$C_4$ alkyl, halo-$C_1$-$C_4$ alkoxy, $C_6$-$C_{10}$ aryl, the 5- to 10-membered heteroaryl and the $C_3$-$C_6$ cycloalkyl are each optionally substituted with OH, 1 to 3 halo, CN, —$NR_{14}R_{15}$, —C(=O)$NR_{14}R_{15}$, $C_1$-$C_4$ alkyl, $C_1$-$C_4$ alkoxy, halo-$C_1$-$C_4$ alkyl and halo-$C_1$-$C_4$ alkoxy;

$R_{11}$ is selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, —C(=O)$NR_{14}R_{15}$, a $C_6$-$C_{10}$ aryl, a 5- to 10-membered heteroaryl, a 4- to 6-membered heterocycloalkyl, a C3-C6 cycloalkyl, $SR_{18}$ and OH; wherein the $C_1$-$C_4$ alkyl, $C_1$-$C_4$ alkoxy, halo-$C_1$-$C_4$ alkyl, halo-$C_1$-$C_4$ alkoxy, $C_6$-$C_{10}$ aryl, the 5- to 10-membered heteroaryl and the $C_3$-$C_6$ cycloalkyl are optionally substituted with OH, 1 to 3 halo, CN, —$NR_{14}R_{15}$, —C(=O)$NR_{14}R_{15}$, $C_1$-$C_4$ alkyl, $C_1$-$C_4$ alkoxy, halo-$C_1$-$C_4$ alkyl and halo-$C_1$-$C_4$ alkoxy;

$R_{12}$ is independently selected from H and $NH_2$;

$R_{14}$ at each occurrence, is independently selected from H, $C_1$-$C_4$ alkyl, $C_1$-$C_4$ alkoxy, halo-$C_1$-$C_4$-alkyl, —C(=O)$R_{15}$ and —$SO_2R_{15}$;

$R_{15}$, at each occurrence, is independently selected from H, $C_1$-$C_4$ alkyl, $C_1$-$C_4$ alkoxy, halo-$C_1$-$C_4$-alkyl, a $C_6$-$C_{10}$ aryl and a 5- to 10-membered heteroaryl;

$R_{18}$ is selected from H and $C_1$-$C_4$ alkyl.

2. The compound of claim 1, or a pharmaceutically acceptable salt thereof, wherein:

$R_4$ is selected from OH and SH, $R_5$ is selected from OH and SH, $R_{10}$ is selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, —C(=O)$NR_{14}R_{15}$, a $C_6$-$C_{10}$ aryl, a 5- to 10-membered heteroaryl and OH;

$R_{11}$ is selected from H, =O, halo, $C_1$-$C_4$ alkyl, $C_1$-$C_4$ alkoxy, halo-$C_1$-$C_4$ alkyl, halo-$C_1$-$C_4$ alkoxy, CN, —$NR_{14}R_{15}$, —$NR_{14}$C(=O)$R_{15}$, —C(=O)$NR_{14}R_{15}$, a $C_6$-$C_{10}$ aryl, a 5- to 10-membered heteroaryl and OH;

$R_{14}$, at each occurrence, is independently selected from H, $C_1$-$C_4$ alkyl, $C_1$-$C_4$ alkoxy, halo-$C_1$-$C_4$-alkyl, —C(=O)$R_{15}$ and —$SO_2R_{15}$; and $R_{15}$, at each occurrence, is independently selected from H, $C_1$-$C_4$ alkyl, $C_1$-$C_4$ alkoxy, halo-$C_1$-$C_4$-alkyl, a $C_6$-$C_{10}$ aryl and a 5- to 10-membered heteroaryl.

3. The compound or the pharmaceutically acceptable salt thereof of claim 1 or 2, wherein:

Ⓐ is a 7- to 10-membered bicyclic heteroaryl ring containing at least three N atoms; which is optionally substituted with $R_{10}$ and $R_{11}$;

$R_2$ is selected from H, halo, $C_1$-$C_4$ alkyl, $C_1$-$C_4$ alkoxy, halo-$C_1$-$C_4$ alkyl, halo-$C_1$-$C_4$ alkoxy, —$NR_8R_9$ and OH;

$R_3$ is independently selected from H, halo, $C_1$-$C_4$ alkyl, $C_1$-$C_4$ alkoxy, halo-$C_1$-$C_4$ alkyl, halo-$C_1$-$C_4$ alkoxy, and OH;

$R_8$ is selected from H, $C_1$-$C_4$ alkyl, and halo-$C_1$-$C_4$-alkyl;

$R_9$ is selected from H, $C_1$-$C_4$ alkyl, and halo-$C_1$-$C_4$-alkyl;

$R_{10}$ is selected fom H, =O, halo, $C_1$-$C_4$ alkyl, $C_1$-$C_4$ alkoxy, halo-$C_1$-$C_4$ alkyl, halo-$C_1$-$C_4$ alkoxy, $R_{14}R_{15}$, C(=O)$NR_{14}R_{15}$, and OH;

$R_{11}$ is selected from H, =O, halo, $C_1$-$C_4$ alkyl, $C_1$-$C_4$ alkoxy, halo-$C_1$-$C_4$ alkyl, halo-$C_1$-$C_4$ alkoxy, —$NR_{14}R_{15}$, —C(=O)$NR_{14}R_{15}$, and OH;

$R_{14}$, at each occurrence, is independently selected from H, $C_1$-$C_4$ alkyl, and halo-$C_1$-$C_4$-alkyl; and $R_{15}$, at each occurrence, is independently selected from H, $C_1$-$C_4$ alkyl, and halo-$C_1$-$C_4$-alkyl.

4. The compound or the pharmaceutically acceptable salt thereof of claim 1, wherein:

Ⓐ is selected from purinyl, dihydropurinyl, dihydroimidazopyridazinyl, dihydropyrrolopyrimidinyl, imidazopyridinyl, imidazopyrazinyl, and pyrrolopyrimidinyl; all of which are optionally substituted with $R_{10}$ and $R_{11}$;

$R_2$ is selected from H, halo, $C_1$-$C_4$ alkyl, $C_1$-$C_4$ alkoxy, halo-$C_1$-$C_4$ alkyl, —$NR_8R_9$ and OH;

$R_3$ is selected from H, halo, $C_1$-$C_4$ alkyl, $C_1$-$C_4$ alkoxy, halo-$C_1$-$C_4$ alkyl, and OH;

$R_4$ is selected from OH, SH, and $C_1$-$C_6$ alkoxy-carbonyloxy-$C_1$-$C_6$ alkoxy;

$R_5$ is selected from OH, SH, and $C_1$-$C_6$ alkoxy-carbonyloxy-$C_1$-$C_6$ alkoxyl;

$R_8$ is selected from H, $C_1$-$C_4$ alkyl, and halo-$C_1$-$C_4$-alkyl;

$R_9$ is selected from H, $C_1$-$C_4$ alkyl, and halo-$C_1$-$C_4$-alkyl;

$R_{10}$ is selected from H, =O, halo, $C_1$-$C_4$ alkyl, $C_1$-$C_4$ alkoxy, halo-$C_1$-$C_4$ alkyl, —CN, —$NR_{14}R_{15}$, —C(=O)$NR_{14}R_{15}$, and OH;

$R_{11}$ is selected from H, =O, halo, $C_1$-$C_4$ alkyl, $C_1$-$C_4$ alkoxy, halo-$C_1$-$C_4$ alkyl, —$NR_{14}R_{15}$, —C(=O)$NR_{14}R_{15}$, and OH;

$R_{14}$, at each occurrence, is independently selected from H, $C_1$-$C_4$ alkyl, and halo-$C_1$-$C_4$-alkyl; and $R_{15}$, at each occurrence, is independently selected from H, $C_1$-$C_4$ alkyl, and halo-$C_1$-$C_4$-alkyl.

5. The compound or the pharmaceutically acceptable salt thereof of claim 1 or 2, wherein:

Ⓐ is selected from

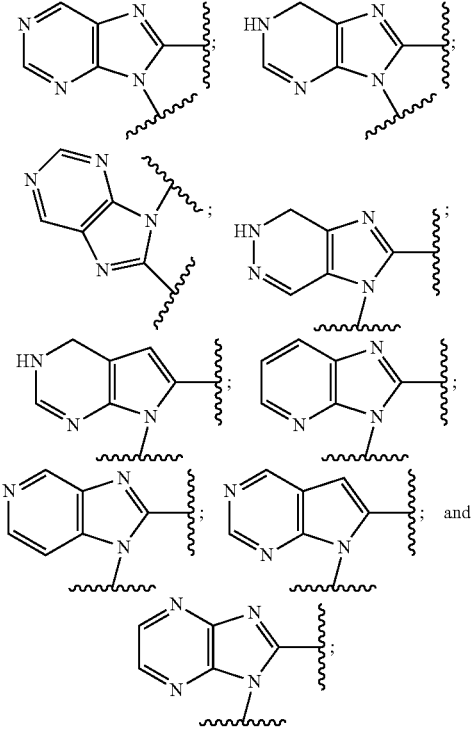

all of which are optionally substituted with $R_{10}$ and $R_{11}$;

$R_2$ is selected from H, halo, $C_1$-$C_4$ alkyl, $C_1$-$C_4$ alkoxy, —$NR_8R_9$ and OH;

R$_3$ is selected from H, halo, C$_1$-C$_4$ alkyl, C$_1$-C$_4$ alkoxy, and OH;
R$_8$ is independently selected from H, C$_1$-C$_4$ alkyl, and halo-C$_1$-C$_4$-alkyl;
R$_9$ is selected from H, C$_1$-C$_4$ alkyl, and halo-C$_1$-C$_4$-alkyl;
R$_{10}$ is selected from H, =O, halo, C$_1$-C$_4$ alkyl, C$_1$-C$_4$ alkoxy —NR$_{14}$R$_{15}$, —C(=O)NR$_{14}$R$_{15}$ and OH;
R$_{11}$ is selected from H, =O, halo, C$_1$-C$_4$ alkyl, C$_1$-C$_4$ alkoxy, halo C$_1$-C$_4$alkoxy, —NR$_{14}$R$_{15}$, —CN, —C(=O)NR$_{14}$R$_{15}$ and OH;
R$_{14}$, at each occurrence, is independently selected from H, C$_1$-C$_4$ alkyl, and halo-C$_1$-C$_4$-alkyl; and
R$_{15}$, at each occurrence, is independently selected from H, C$_1$-C$_4$ alkyl, and halo-C$_1$-C$_4$-alkyl.

6. The compound or the pharmaceutically acceptable salt thereof of claim 1, wherein:
Ⓐ is selected from

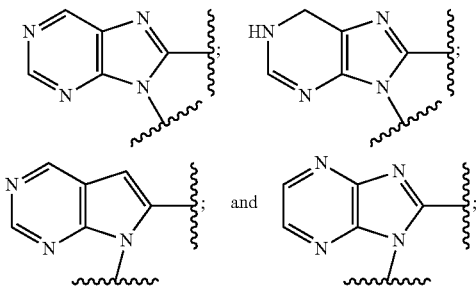

all of which are optionally substituted with R$_{10}$ and R$_{11}$;
R$_2$ is selected from H, halo, C$_1$-C$_4$ alkoxy, —NR$_8$R$_9$; and OH;
R$_3$ is selected from H, halo, C$_1$-C$_4$ alkoxy, and OH;
R$_4$ is selected from OH, SH, and C$_1$-C$_6$ alkoxy-carbonyloxy-C$_1$-C$_6$ alkoxy;
R$_5$ is selected from OH, SH, and C$_1$-C$_6$ alkoxy-carbonyloxy-C$_1$-C$_6$ alkoxy;
R$_8$ is selected from H, C$_1$-C$_4$ alkyl, and halo-C$_1$-C$_4$-alkyl;
R$_9$ is selected from H, C$_1$-C$_4$ alkyl, and halo-C$_1$-C$_4$-alkyl;
R$_{10}$ is selected from H, =O, halo, C$_1$-C$_4$ alkyl, C$_1$-C$_4$ alkoxy, —NR$_{14}$R$_{15}$ and OH;
R$_{11}$ is selected from H, =O, halo, C$_1$-C$_4$ alkyl, C$_1$-C$_4$ alkoxy, —NR$_{14}$R$_{15}$ and OH;
R$_{14}$, at each occurrence, is independently selected from H, C$_1$-C$_4$ alkyl, and halo-C$_1$-C$_4$-alkyl; and
R$_{15}$, at each occurrence, is independently selected from H, C$_1$-C$_4$ alkyl, and halo-C$_1$-C$_4$-alkyl.

7. The compound or the pharmaceutically acceptable salt thereof of claim 1 or 2, wherein
Ⓐ is selected from

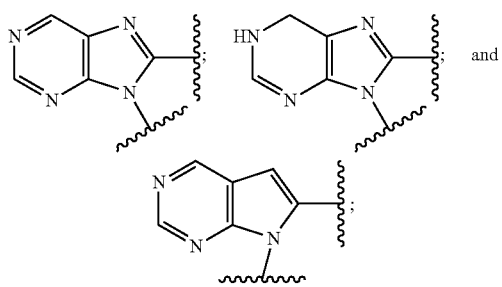

all of which are optionally substituted with R$_{10}$ and R$_{11}$;
R$_2$ is selected from H, halo, C$_1$-C$_4$ alkoxy, —NR$_8$R$_9$ and OH;

R$_3$ is selected from H, halo, and OH;
R$_4$ is selected from OH and SH;
R$_5$ is selected from OH and SH;
R$_8$ is independently selected from H, C$_1$-C$_4$ alkyl, and halo-C$_1$-C$_4$-alkyl;
R$_9$ is independently selected from H, C$_1$-C$_4$ alkyl, and halo-C$_1$-C$_4$-alkyl;
R$_{10}$ is independently selected from H, =O, halo, C$_1$-C$_4$ alkyl, —NR$_{14}$R$_{15}$, —CN, —C(=O)NR$_{14}$R$_{15}$, and OH;
R$_{11}$ is selected from H, =O, halo, C$_1$-C$_4$ alkyl, —NR$_{14}$R$_{15}$, —CN, —C(=O)NR$_{14}$R$_{15}$, and OH;
R$_{14}$, at each occurrence, is independently selected from H, and C$_1$-C$_4$ alkyl; and
R$_{15}$, at each occurrence, is independently selected from H, and C$_1$-C$_4$ alkyl.

8. The compound or the pharmaceutically acceptable salt thereof of claim 1 or 2, wherein:
Ⓐ is selected from

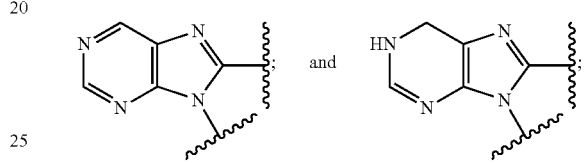

all of which are optionally substituted with R$_{10}$ and R$_{11}$;
Z is C$_1$-C$_6$ alkyl;
R$_2$ is selected from H, halo, C$_1$-C$_4$ alkoxy, —NR$_8$R$_9$ and OH;
R$_3$ is selected from H and halo;
R$_4$ is selected from OH and SH;
R$_5$ is selected from OH and SH;
R$_8$ is selected from H and C$_1$-C$_4$ alkyl;
R$_9$ is selected from H and C$_1$-C$_4$ alkyl;
R$_{10}$ is selected from H, =O, halo, C$_1$-C$_4$ alkyl, —CN, —C(=O)NR$_{14}$R$_{15}$, and —NR$_{14}$R$_{15}$;
R$_{11}$ is selected from H, =O, halo, C$_1$-C$_4$ alkyl, —CN, —C(=O)NR$_{14}$R$_{15}$, and —NR$_{14}$R$_{15}$;
R$_{14}$, at each occurrence, is independently selected from H and C$_1$-C$_4$ alkyl; and
R$_{15}$, at each occurrence, is independently selected from H and C$_1$-C$_4$ alkyl.

9. The compound or the pharmaceutically acceptable salt thereof of either of claim 1 or 2, wherein Ⓐ is a 5- or 6-membered monocyclic heteroaryl group in which substituents R$_{10}$ and R$_{11}$ on Ⓐ are selected from any one of the following:

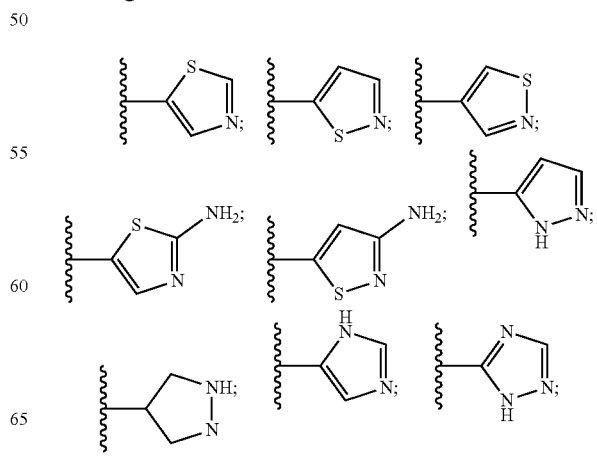

-continued

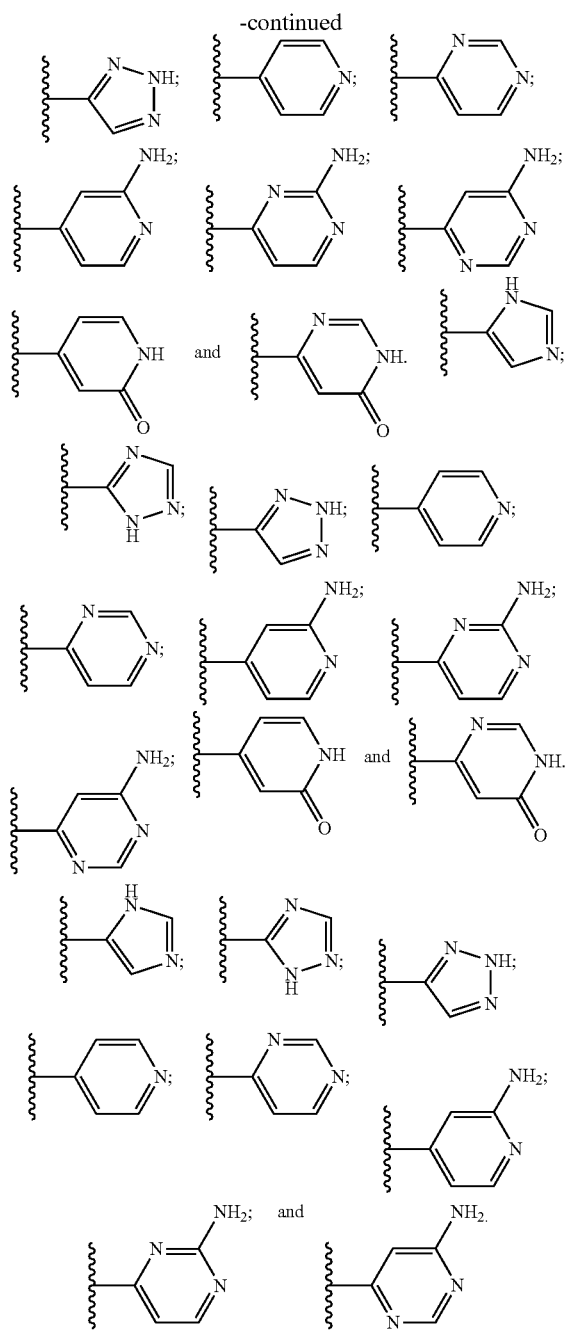

10. The compound or the pharmaceutically acceptable salt thereof of claim 1 or 2, wherein:

Z is selected from —CH$_2$CH$_2$—, —CH(CH$_3$)CH$_2$—, —CH$_2$CH(CH$_3$)—, —CH$_2$CH$_2$CH$_2$—, —CH$_2$CF$_2$CH$_2$—, —CH$_2$CH(CH$_3$)CH$_2$—, and cyclobutyl, R$_2$ is selected from H, F, OH, —OCH$_3$ and —NH$_2$, R$_3$ is selected from H and F;

R$_4$ is selected from SH and OH,

R$_5$ is selected from SH, OH and BH$_3$;

R$_{10}$ is selected from H, —NH$_2$, —Cl, —C(=O)NH$_2$, —CN, —CH$_3$, cyclopropyl, thiazolyl, pyridyl, and 2-aminothiazol-5-yl; and R$_{11}$ is H.

11. The compound or the pharmaceutically acceptable salt thereof of claim 1, wherein the compound is represented by any one of the following formulae:

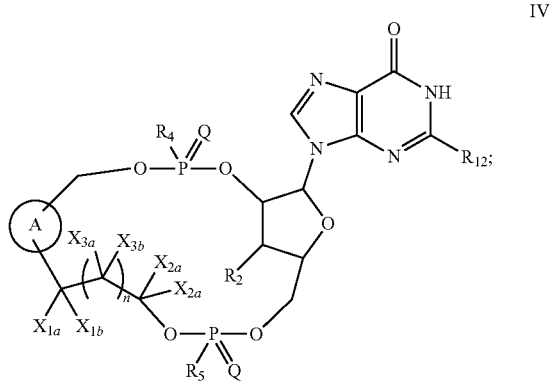
IV

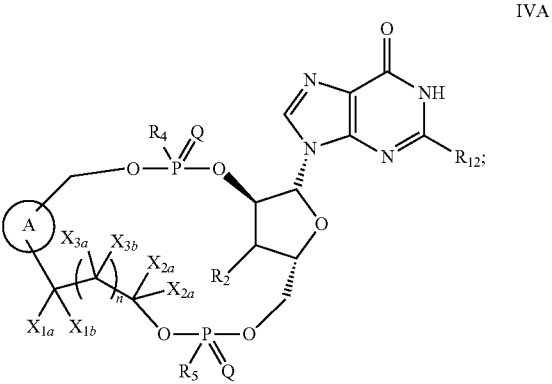
IVA

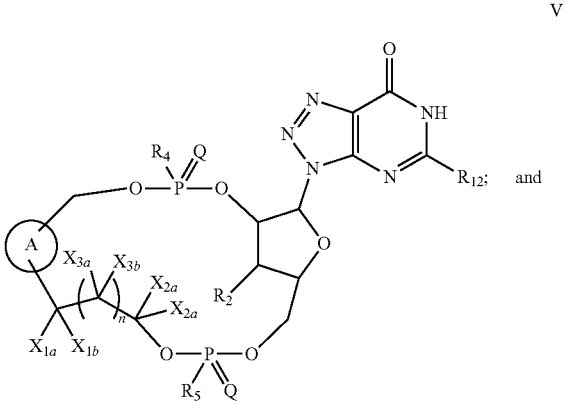
V

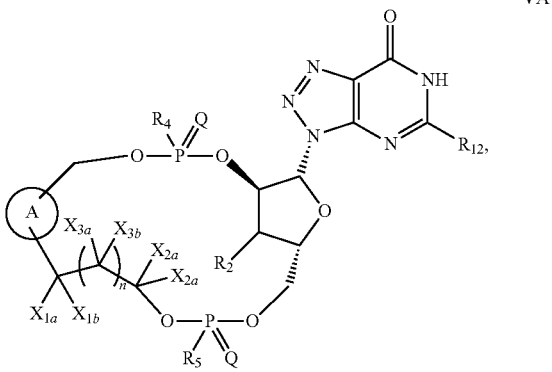
VA wherein:

X$_{1a}$ and X$_{1b}$ are each independently selected from H, halo and C$_{1-4}$ alkyl;

X$_{2a}$ and X$_{2b}$ are each independently selected from H, halo and C$_{1-4}$ alkyl;

X$_{3a}$ and X$_{3b}$ are each independently selected from H, halo, and C$_{1-4}$ alkyl;

Ring A is selected from

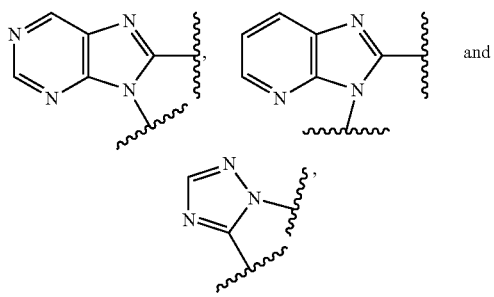

and each of which is optionally substituted with R$_{10}$ and R$_{11}$;

R$_2$ is selected from H, halo, C$_1$-C$_4$ alkoxy and OH;

R$_{10}$ is selected from H, halo, —C(=O)NH$_2$, —CN, C$_1$-C$_4$ alkyl, C$_1$-C$_4$ alkoxy-n-C$_1$-C$_4$ alkyl, —NH$_2$, and 5- to 6-membered monocyclic heteroaryl having one to two heteroatoms independently selected from N, O and S;

R$_{11}$ is H;

R$_{12}$ is NH$_2$; or and n is 0 or 1.

12. The compound or the pharmaceutically acceptable salt thereof of claim 11, wherein:

X$_{1a}$ and X$_{1b}$ are both H;

X$_{2a}$ and X$_{2b}$ are each independently selected form H, halo and C$_{1-4}$ alkyl; and n is 0.

13. The compound or the pharmaceutically acceptable salt thereof of claim 11, wherein:

R$_{10}$ is selected from H, Cl, —C(=O)NH$_2$, —CN, —CH$_3$, —CH$_2$—O—CH$_3$, —NH$_2$, pyridyl, and thiazolyl;

X$_{1a}$ and X$_{1b}$ are both H;

X$_{2a}$ and X$_{2b}$ are independently selected from H, F and methyl;

R$_4$ and R$_5$ are independently selected from —OH and SH;

R$_2$ is selected from H, F, —OCH$_3$ and OH; and (i) n is 0; or (ii) n is 1; and X$_{3a}$ and X$_{3b}$ are F.

14. The compound or pharmaceutically acceptable salt of claim 1, wherein the compound is selected from any one of the following compounds Example 1

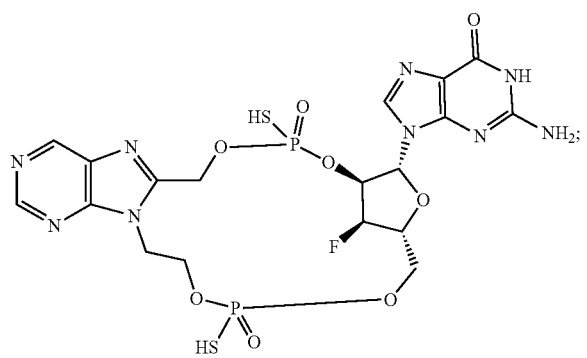

Example 2

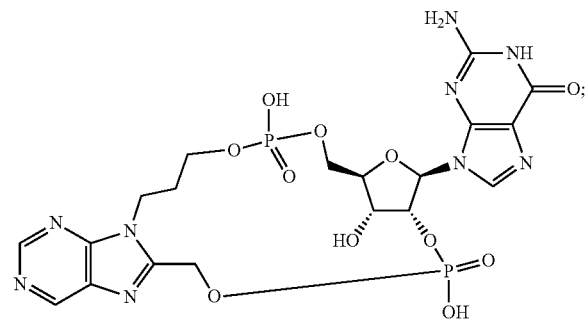

Example 3

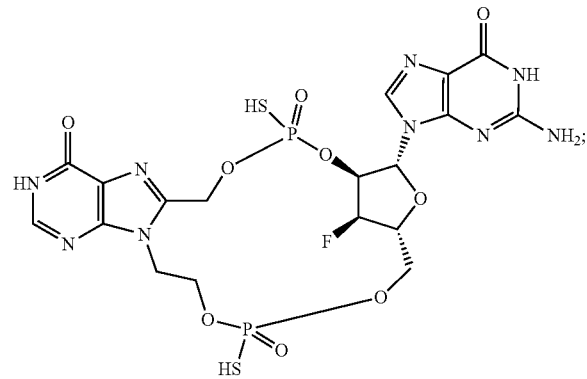

Example 4

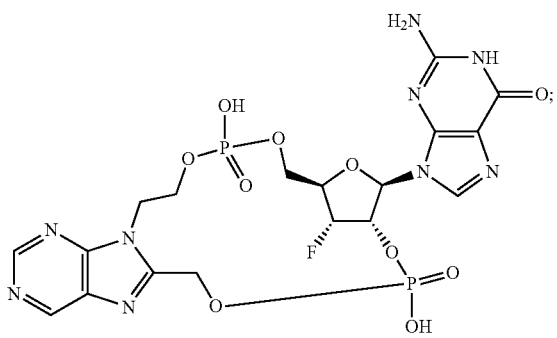

Example 5

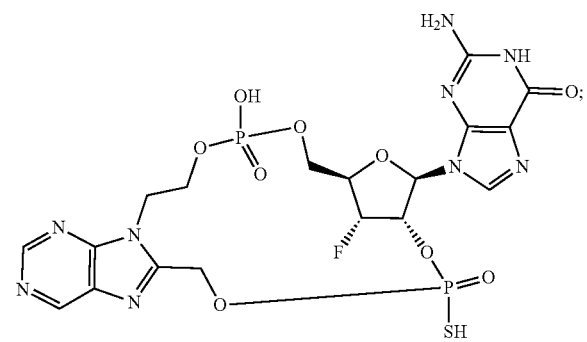

Example 6
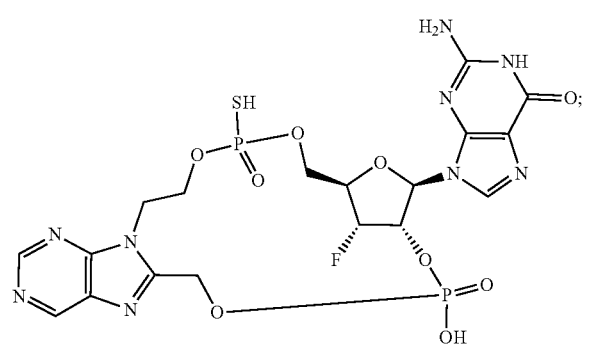
Example 12
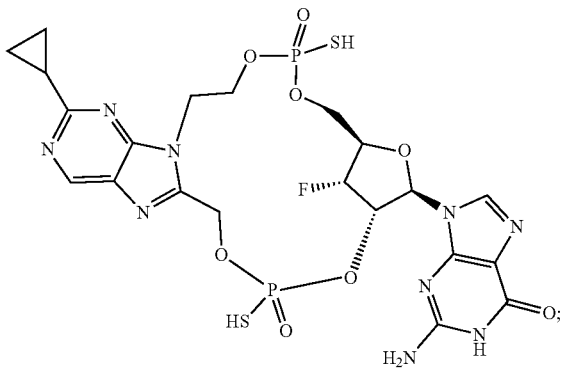
Example 7
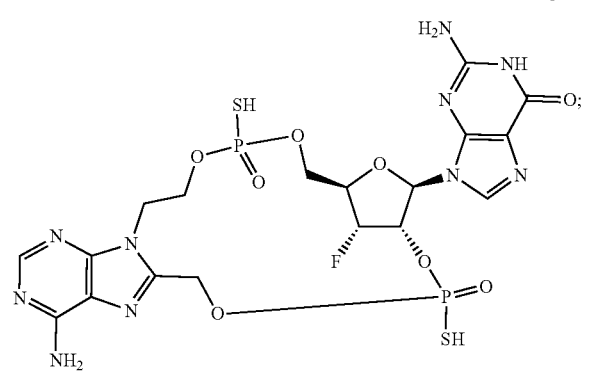
Example 11
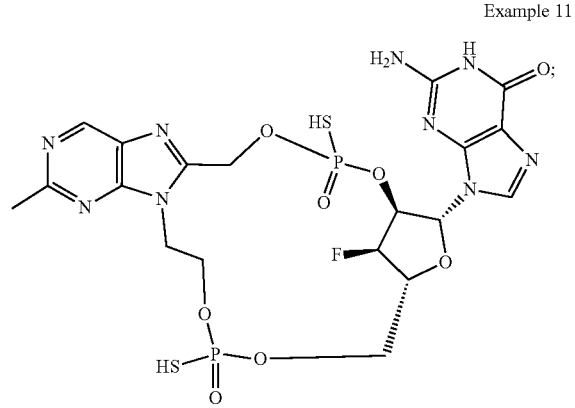
Example 10
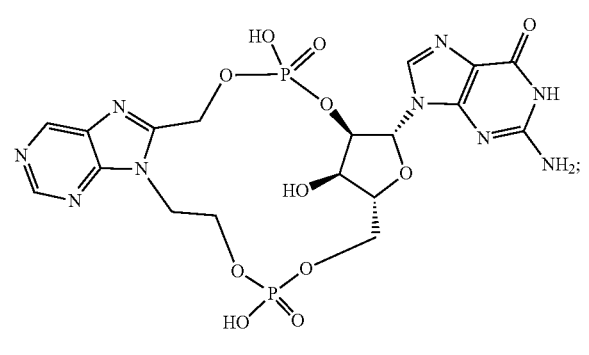
Example 16
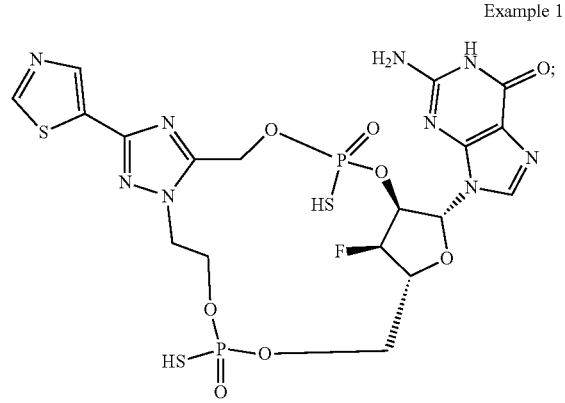
Example 9
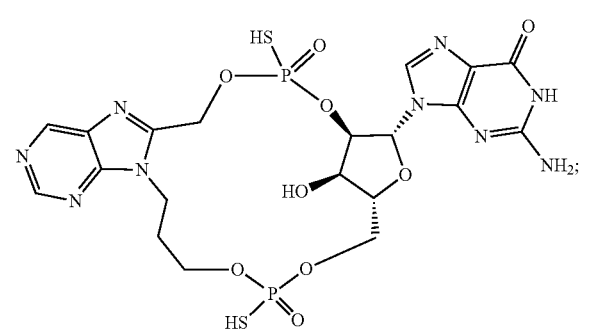
Example 14
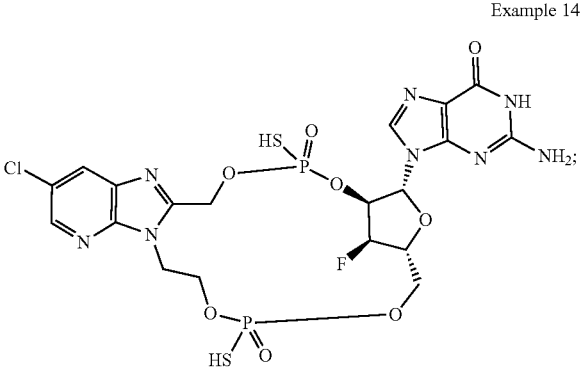

365
-continued
Example 18
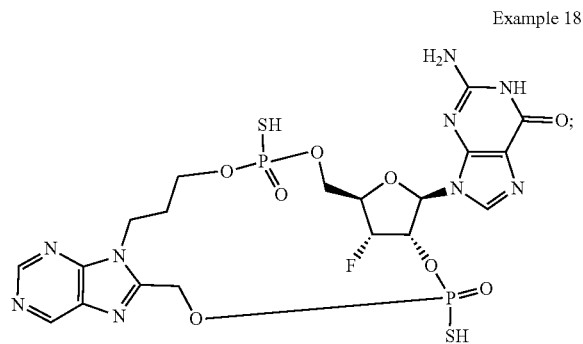
Example 15
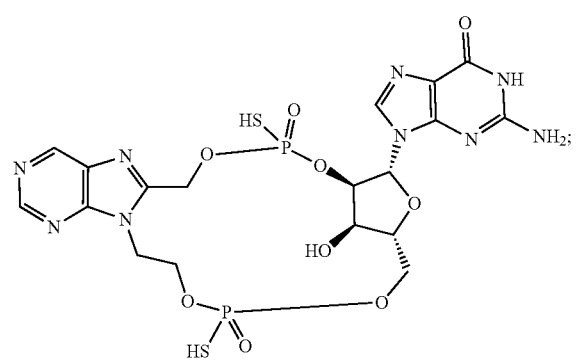
366
-continued
Example 17
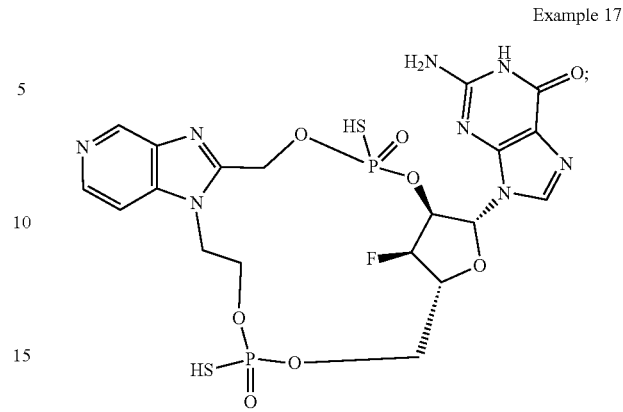
Example 22
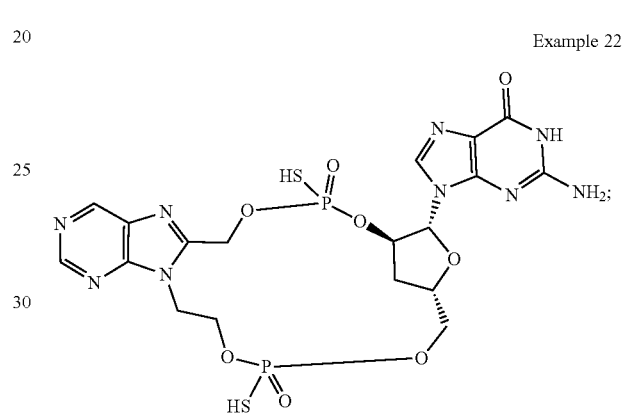

367
-continued
Example 21
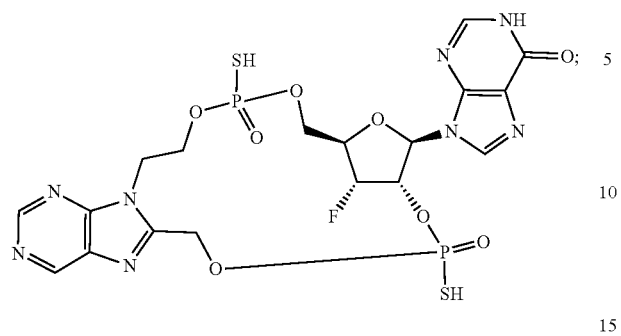
Example 34
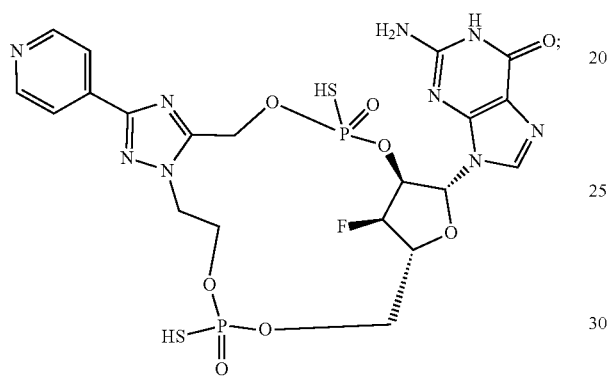
Example 25
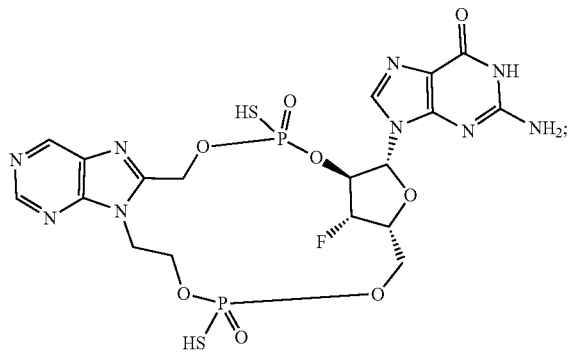
Example 36
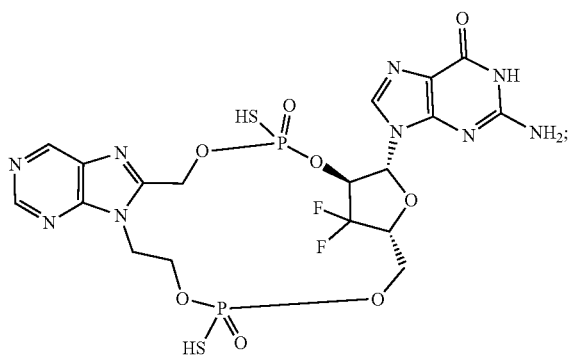
368
-continued
Example 27
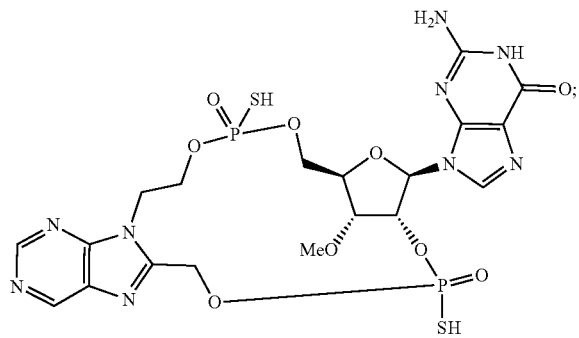
Example 38
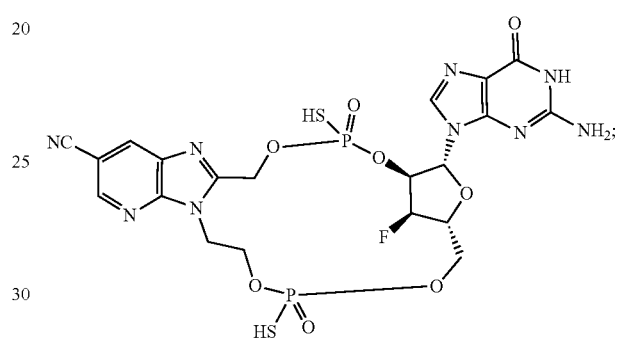
Example 29
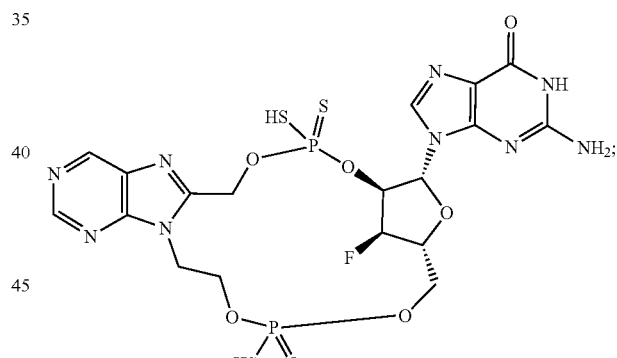
Example 40
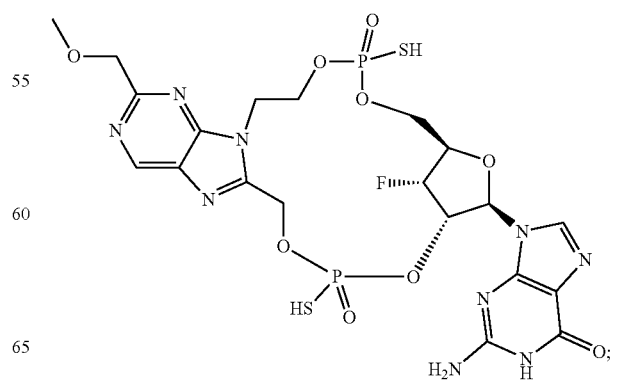

Example 33
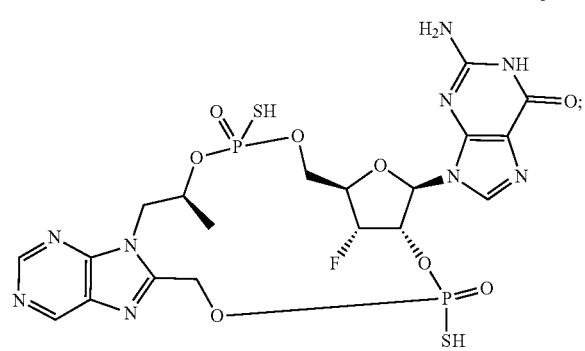
Example 37
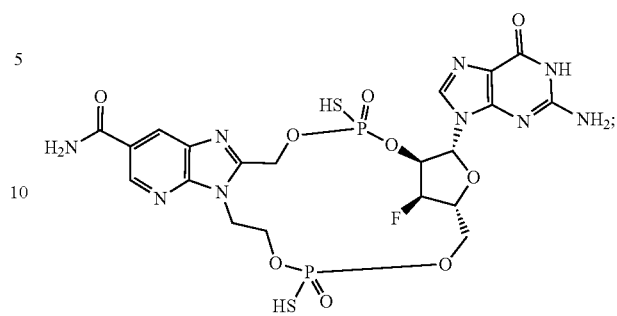
Example 44
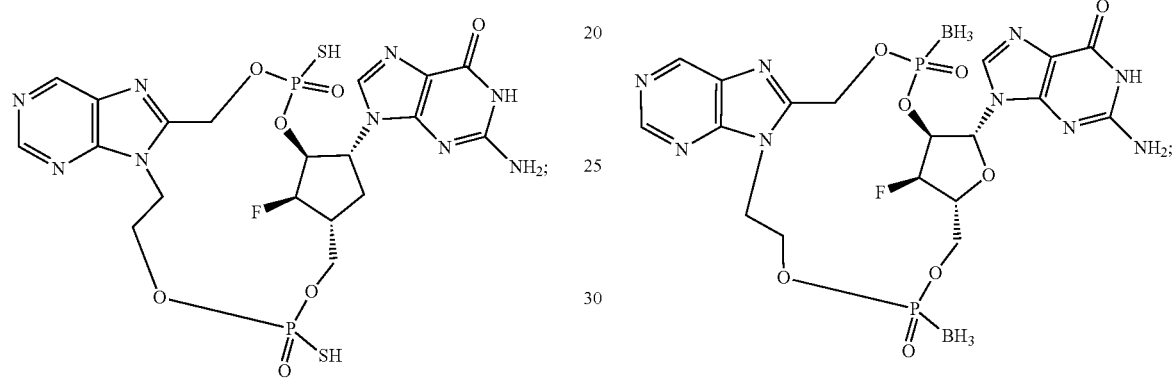
Example 50
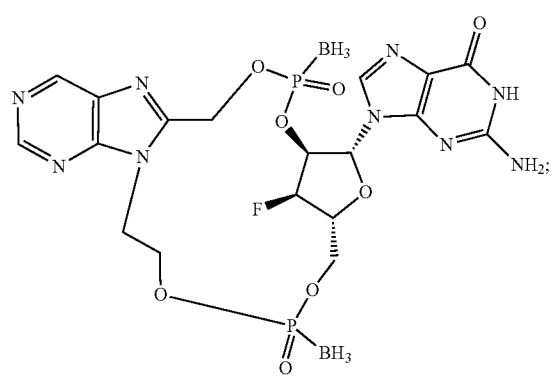
Example 35
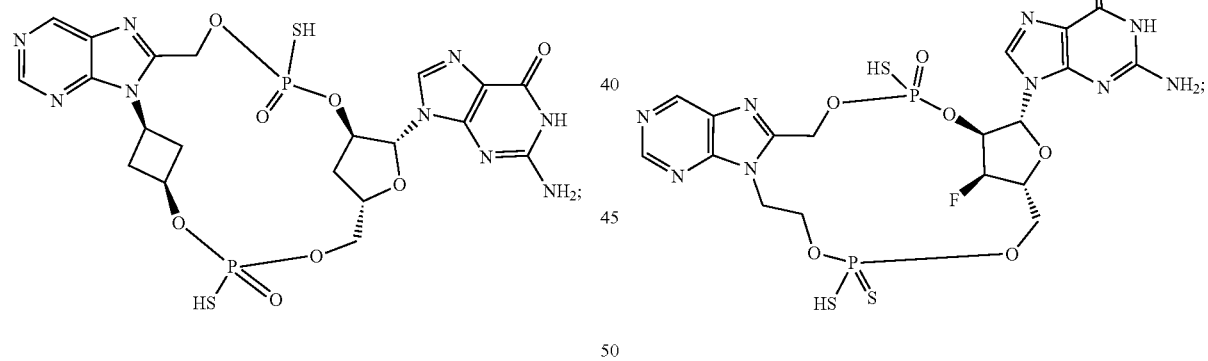
Example 39
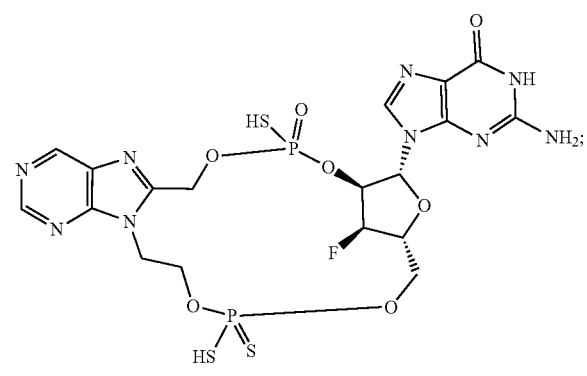
Example 46
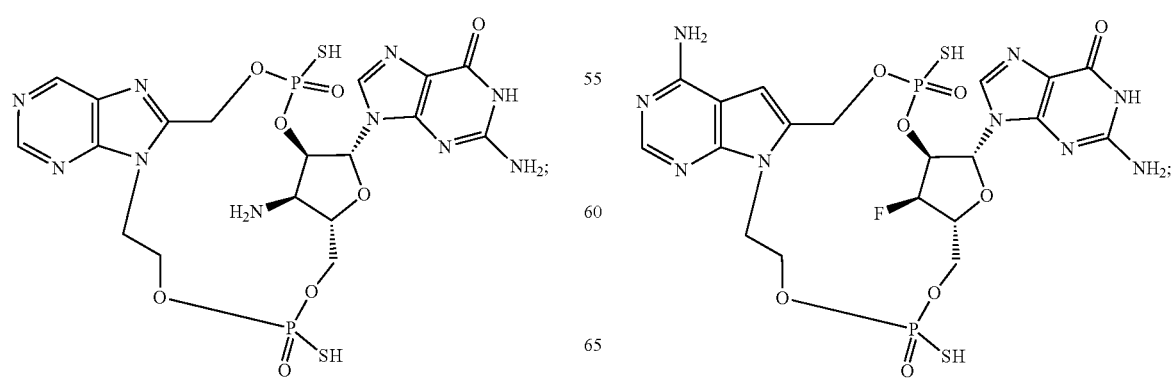
Example 52
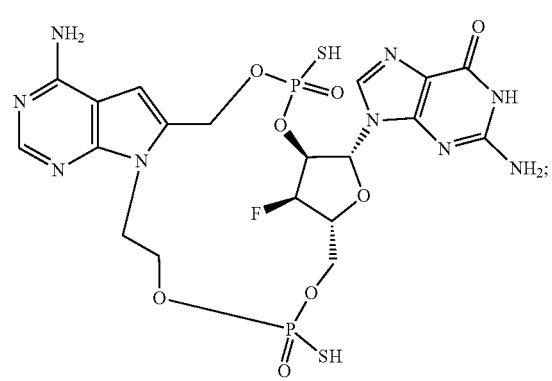

Example 54
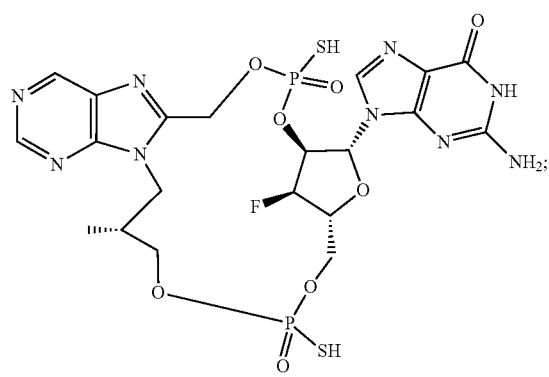
Example 58
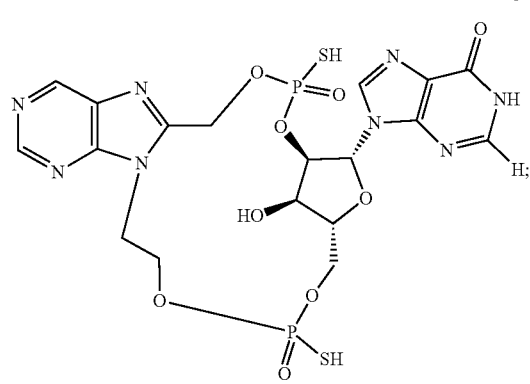
Example 45
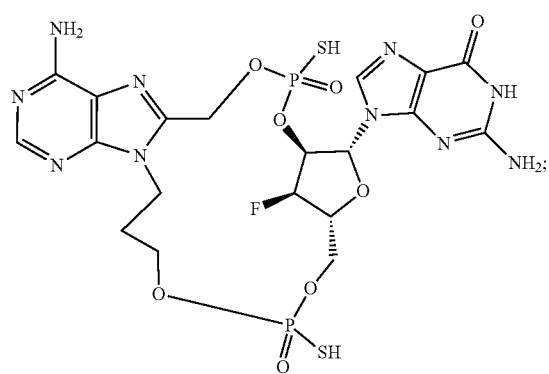
Example 51
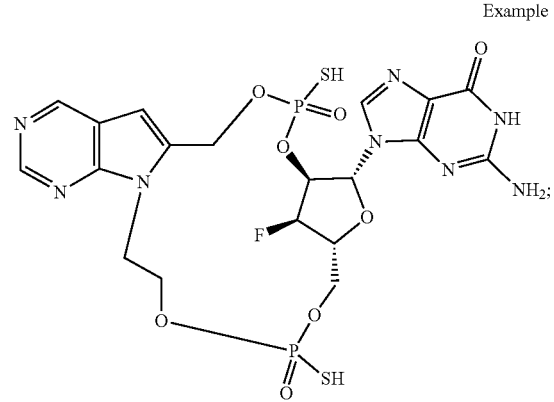
Example 56
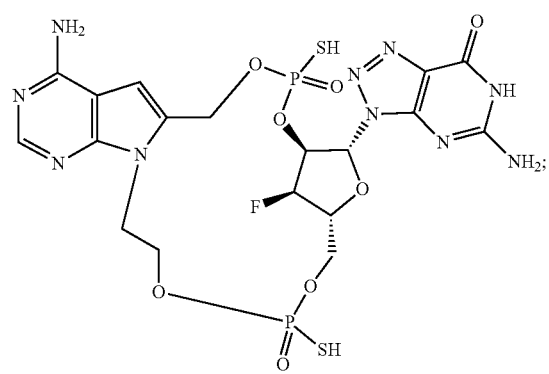
Example 60
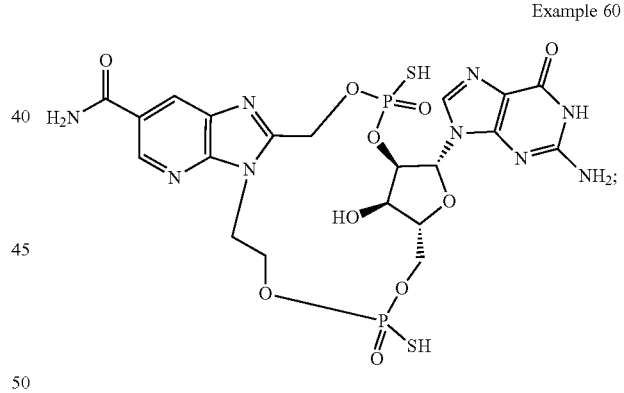
Example 49
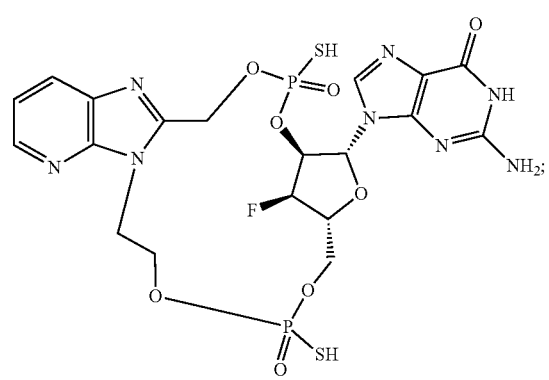
Example 53
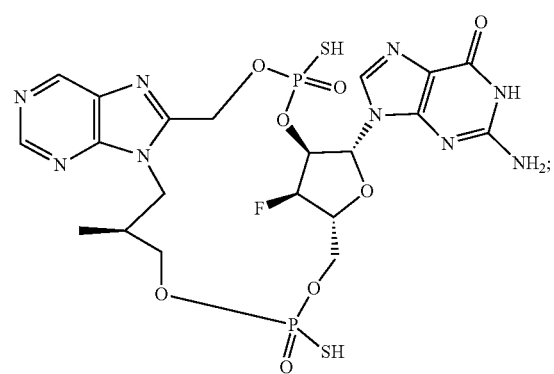

Example 62
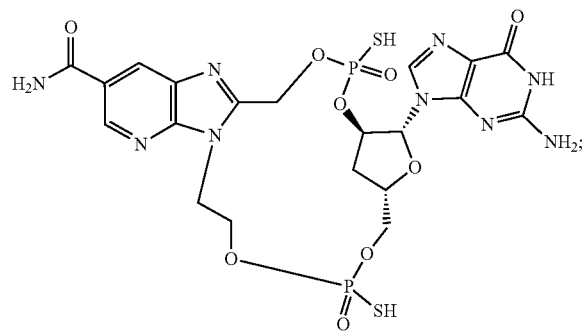
Example 55
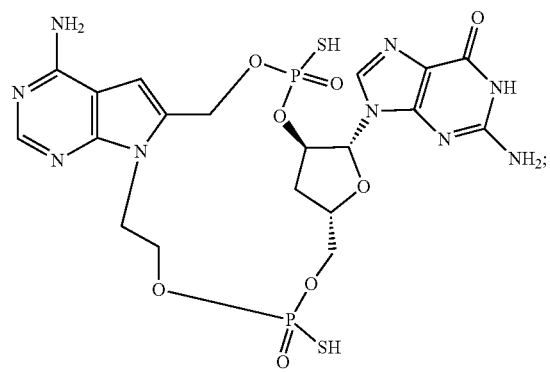
Example 64
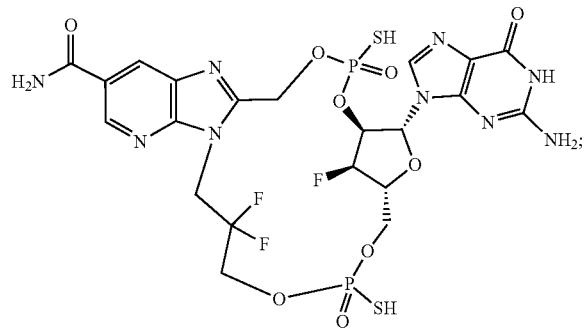
Example 59
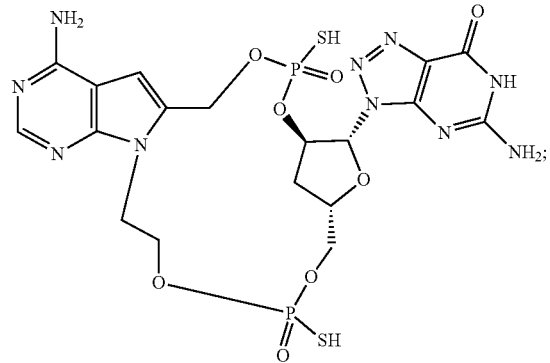
Example 66
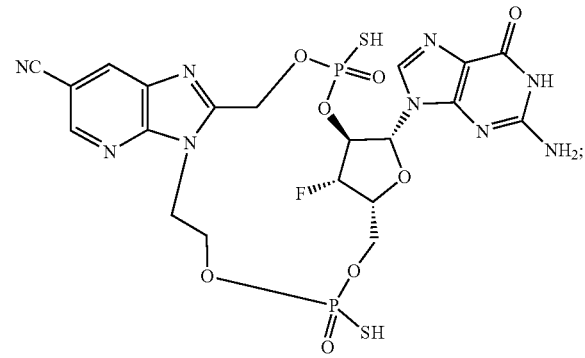
Example 61
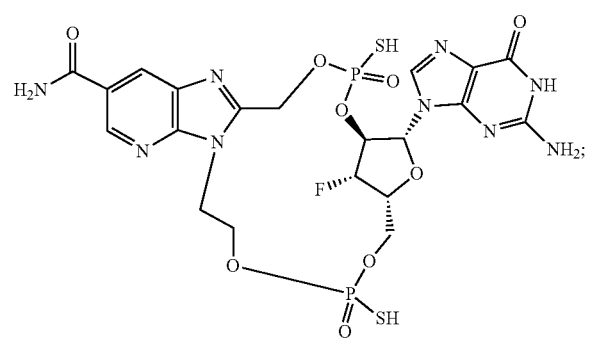
Example 68
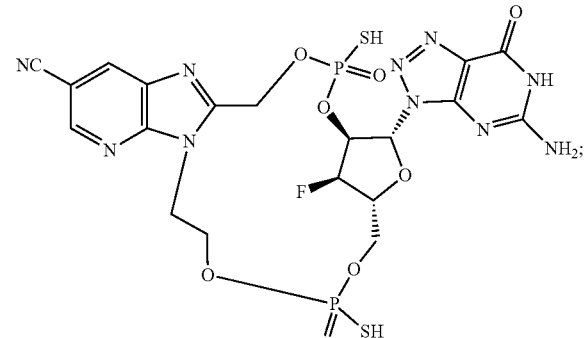
Example 63
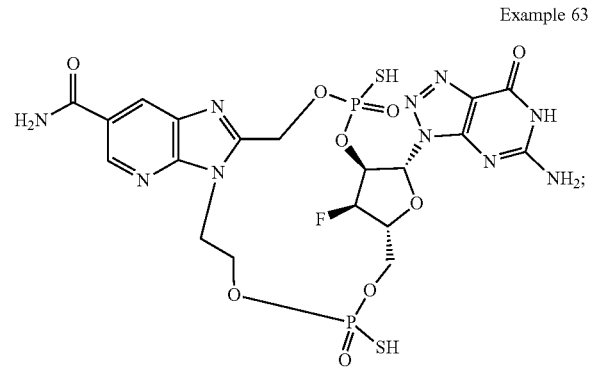

-continued
Example 70
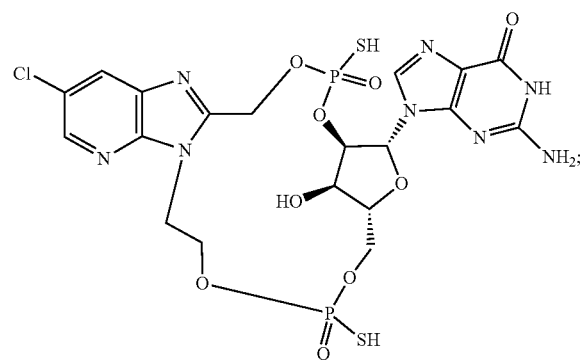
Example 65
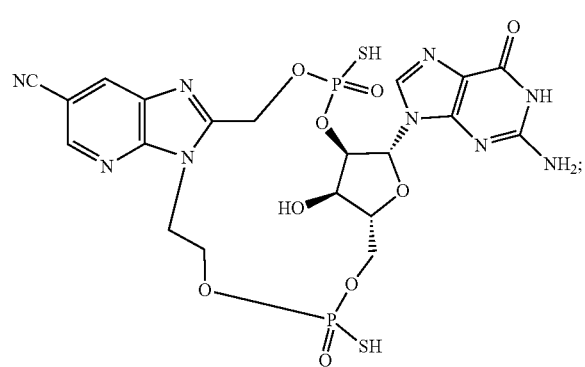
Example 72
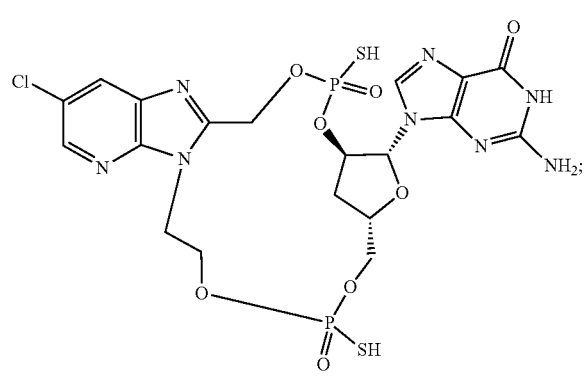
Example 67
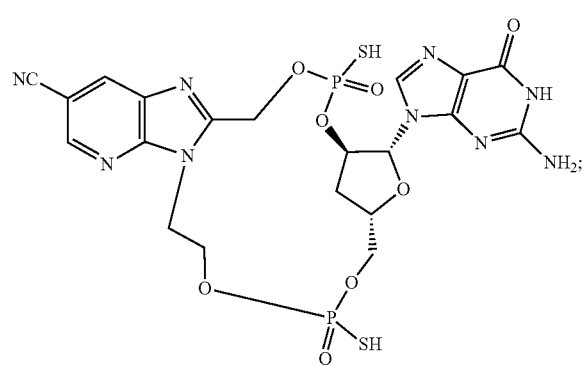
-continued
Example 74
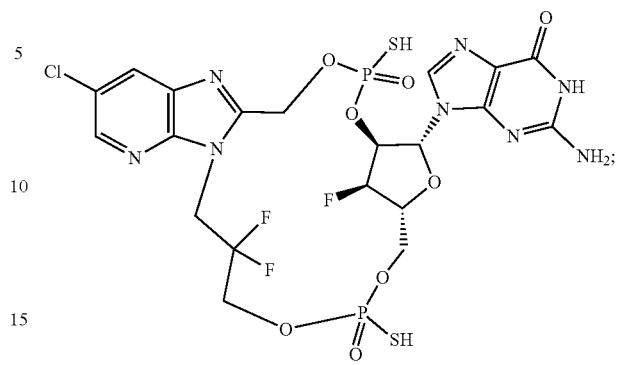
Example 69
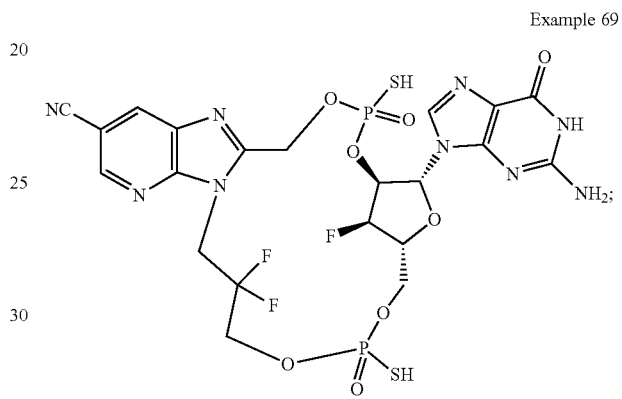
Example 76
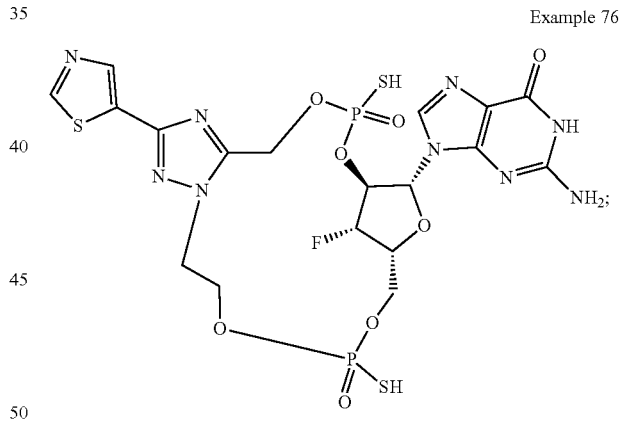
Example 71
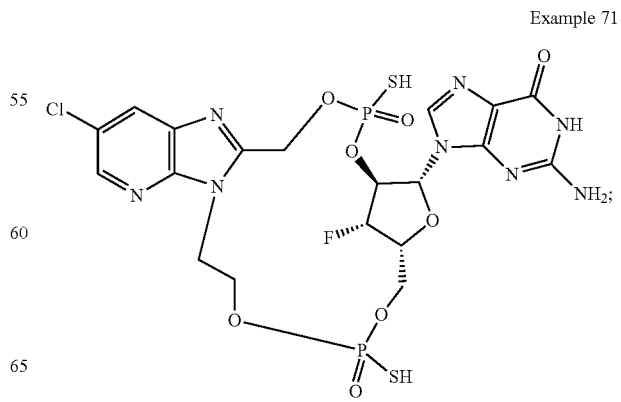

Example 78
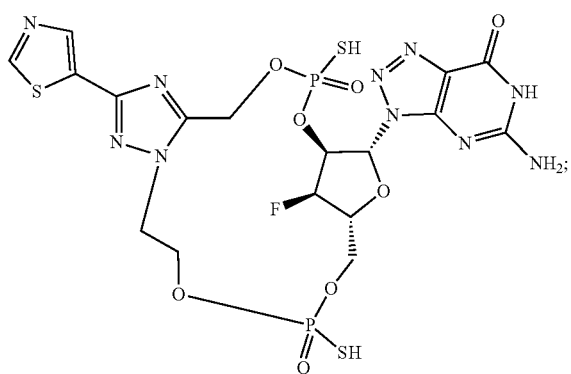
Example 73
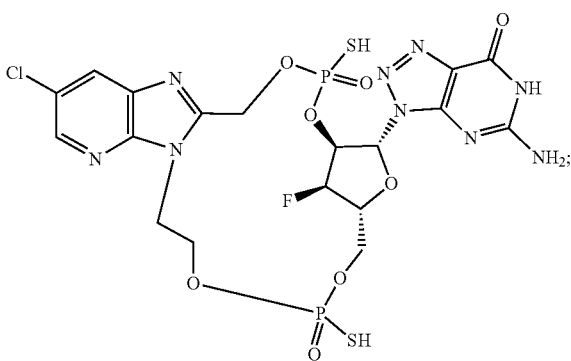
Example 80
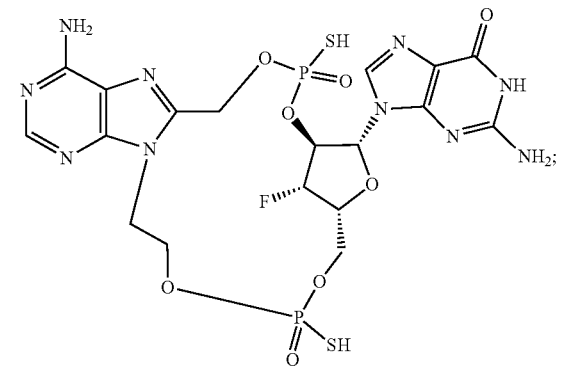
Example 75
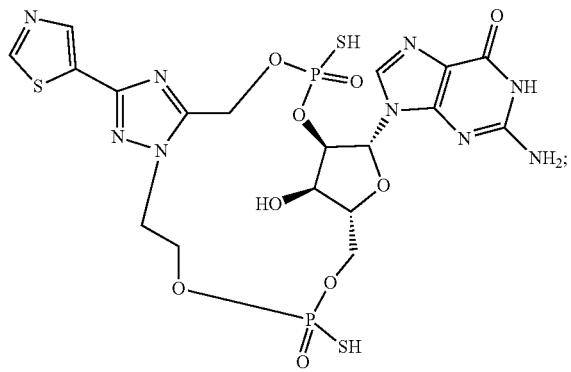
Example 82
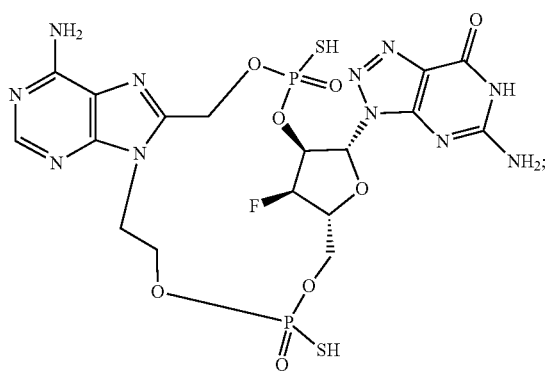
Example 77
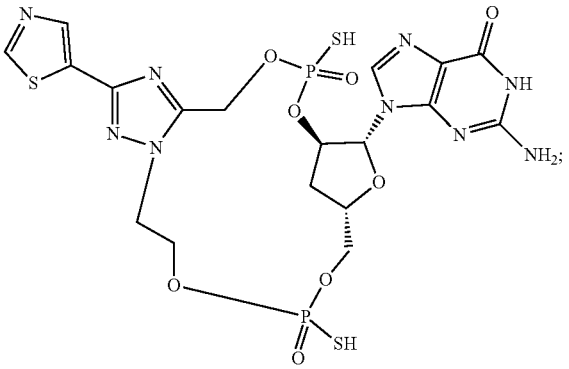
Example 84
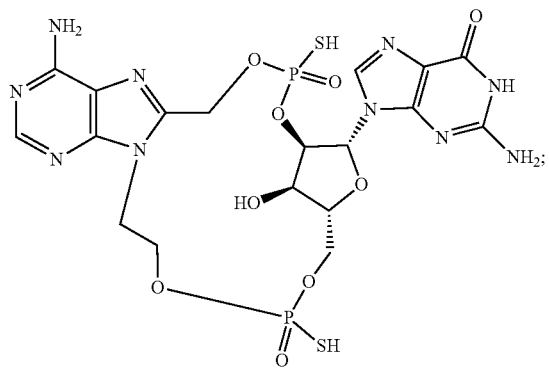
Example 79
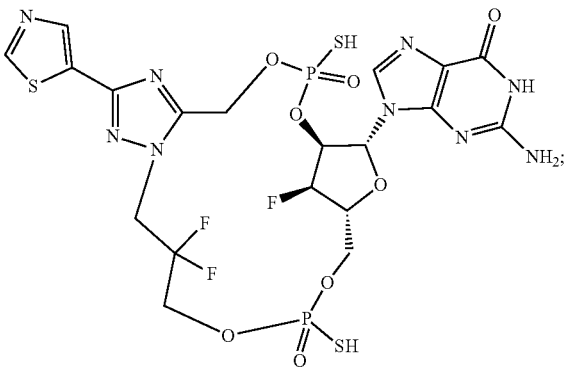

379
-continued
Example 86
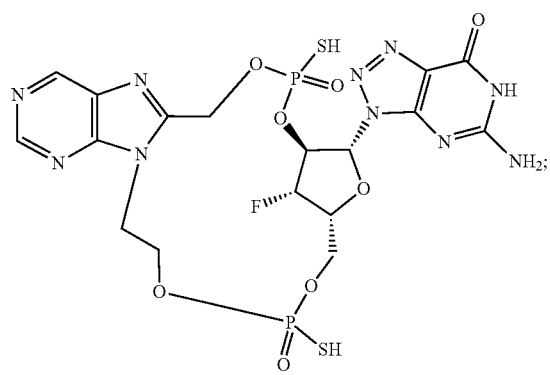
Example 81
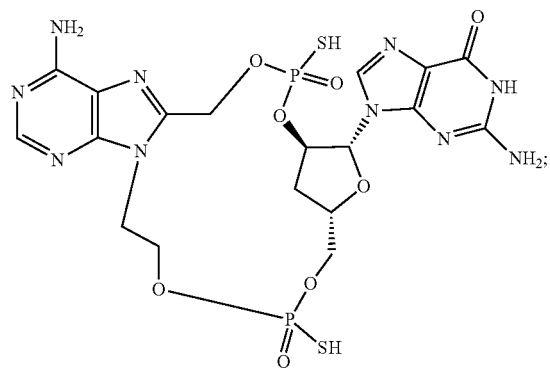
Example 88
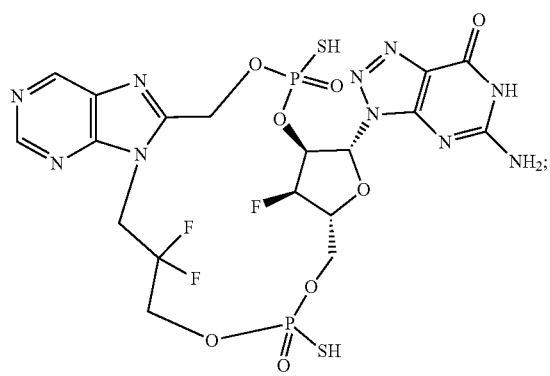
Example 83
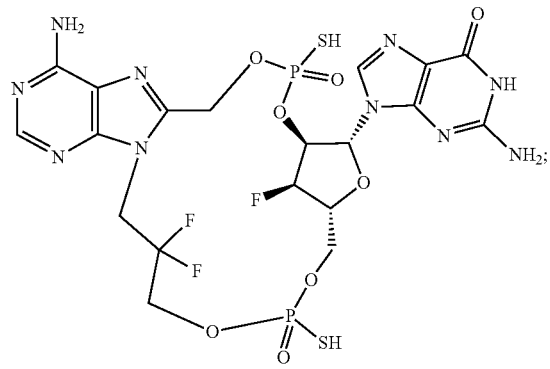
380
-continued
Example 90
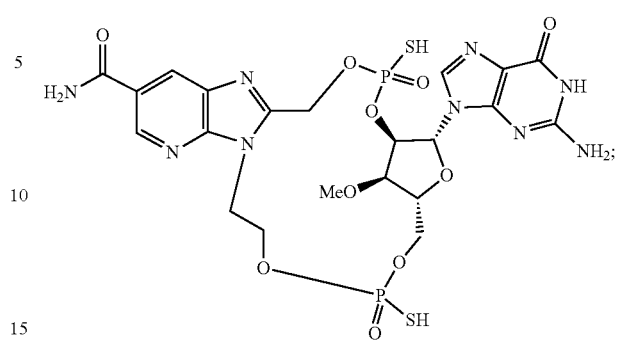
Example 85
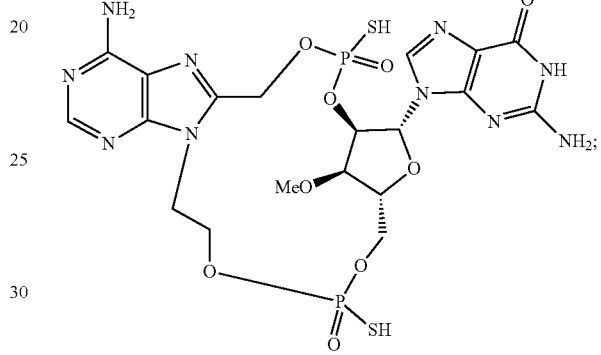
Example 92
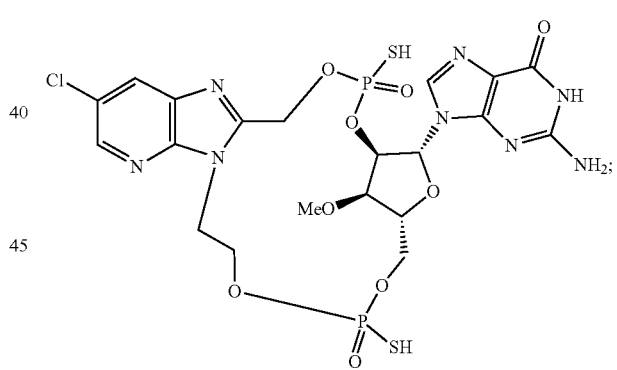
Example 87
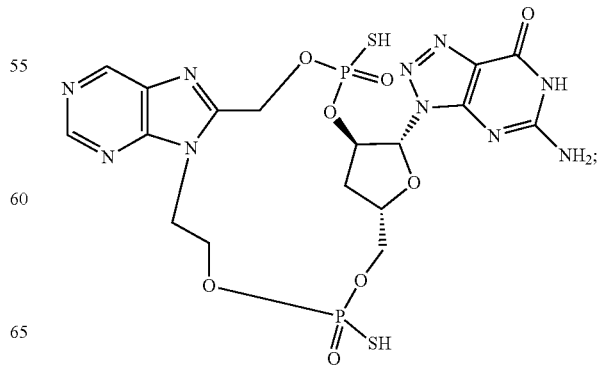

Example 94
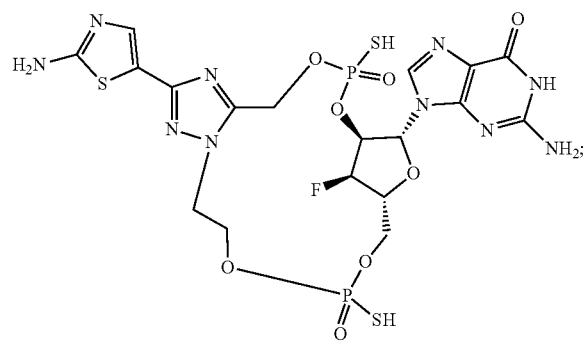
Example 98
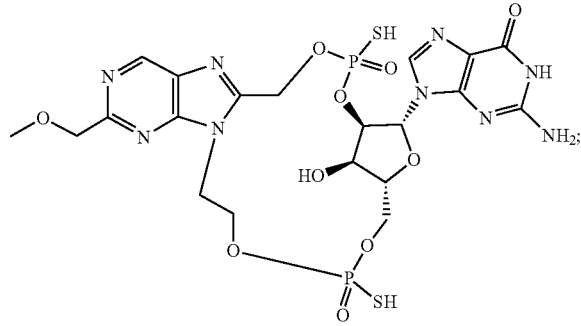
Example 89
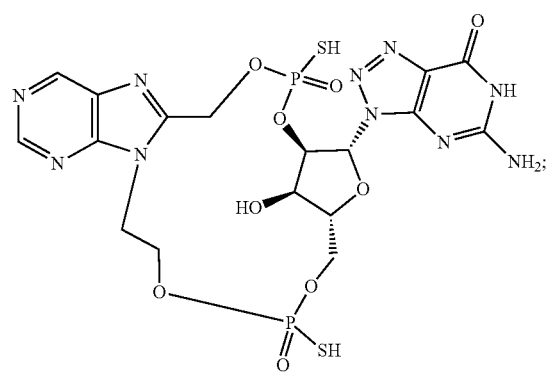
Example 93
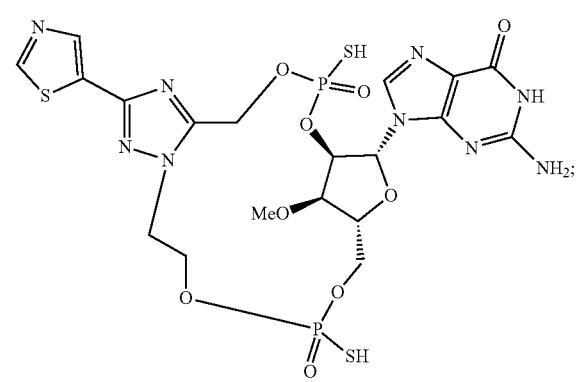
Example 96
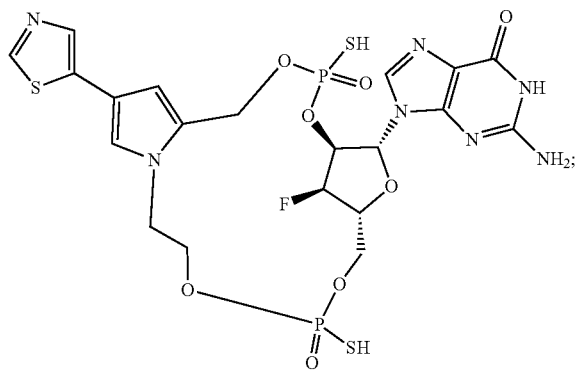
Example 100
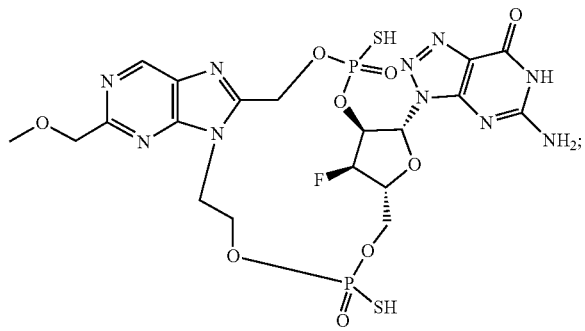
Example 91
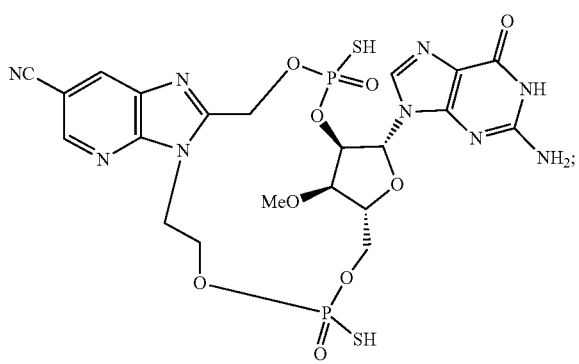
Example 95
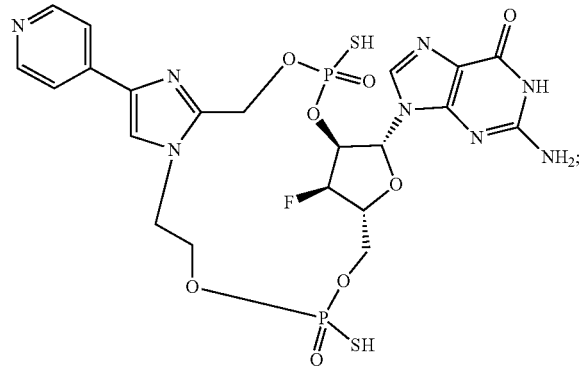

Example 102

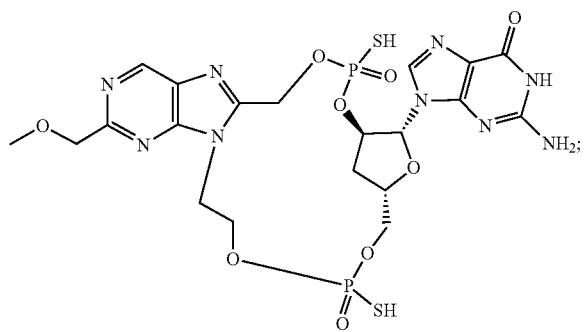

Example 97

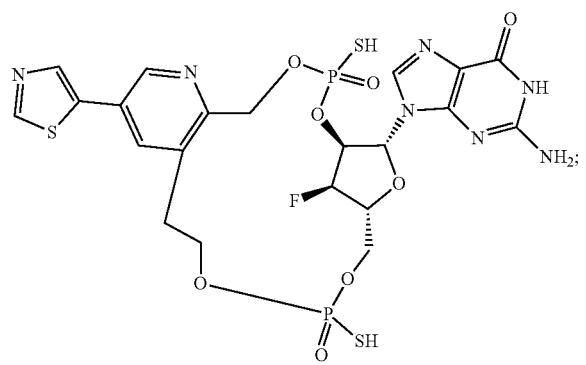

Example 99

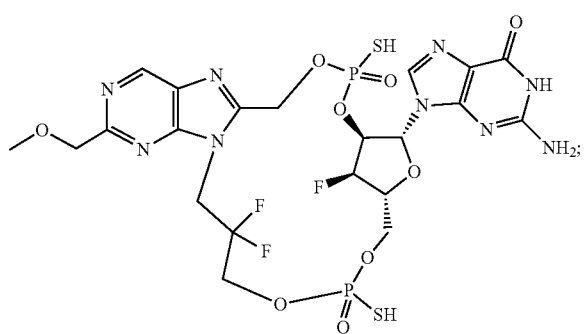

Example 101

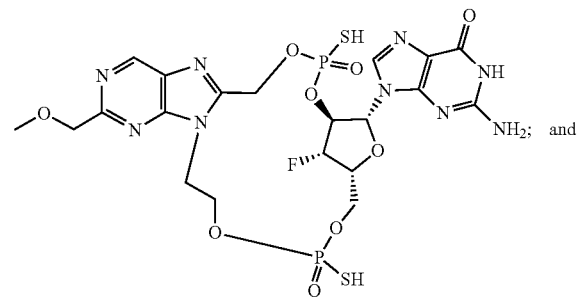

Example 103

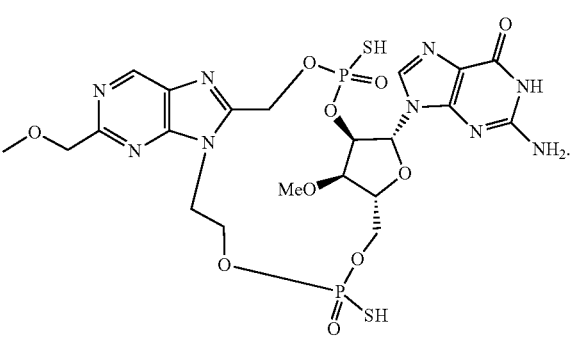

15. A pharmaceutical composition comprising a pharmaceutically acceptable carrier and a compound as defined in any one of claims 1, 2 or 14, or pharmaceutically acceptable salts thereof, alone or in combination with another therapeutic agent.

16. The pharmaceutical composition of claim 15, wherein the other therapeutic agent is selected from the group consisting of an anti-cancer agent, an anti-viral compound, an antigen, an adjuvant, a lipid, a liposome, a peptide, a cytotoxic agent, a chemotherapeutic agent, an immunomodulatory cell line, a checkpoint inhibitor, a biotherapeutic agent, an immunogenic agent, and cells transfected with genes encoding immune stimulating cytokines.

17. A method of treating bladder cancer comprising administering to a subject in need thereof a therapeutically effective amount of the compound, or pharmaceutically acceptable salt thereof, of any one of claims 1, 2 or 14.

18. A compound according to claim 1, or pharmaceutically acceptable salt thereof, of formula

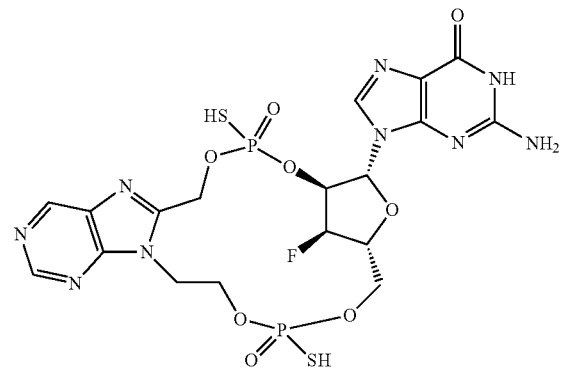 [SMILES: Nc1nc2c(ncn2[C@@H]2O[C@@H]3COP(=O)(S)OCCn4c(nc5cncnc54)COP(=O)(S)O[C@@H]2[C@@H]3F)c(=O)[nH]1]

* * * * *

UNITED STATES PATENT AND TRADEMARK OFFICE
CERTIFICATE OF CORRECTION

PATENT NO. : 11,161,864 B2
APPLICATION NO. : 16/662980
DATED : November 2, 2021
INVENTOR(S) : Diller et al.

Page 1 of 1

It is certified that error appears in the above-identified patent and that said Letters Patent is hereby corrected as shown below:

In the Claims

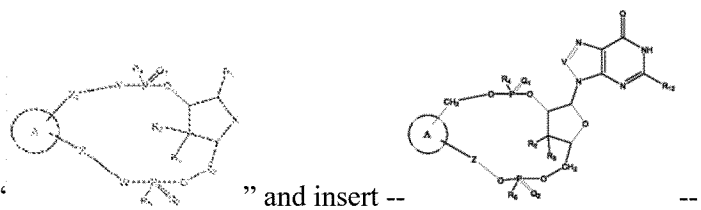

Column 354, Line 25: Claim 1, Delete " " and insert -- --

Column 354, Line 38: Claim 1, Delete "substituted with $R_{10}$ and Rn and" and insert -- substituted with $R_{10}$ and $R_{11}$ and --

Column 354, Line 66: Claim 1, Delete "4- to 6-membered heterocycloalkyl, a C3-C10 cycloalkyl," and insert -- 4- to 6-membered heterocycloalkyl, a C3-C6 cycloalkyl, --

Column 357, Line 7: Claim 5, Delete "$NR_{14}R_{15}$, – C(=O)$NR_{14}R_{15}$, and OH" and insert -- $NR_{14}R_{15}$, -CN, – C(=O)$NR_{14}R_{15}$, and OH --

Column 357, Line 9: Claim 5, Delete "halo, $C_1$-$C_4$ alkyl, $C_1$-$C_4$ alkoxy, halo $C_1$-$C_4$ alkoxy, –$NR_{14}R_{15}$," and insert -- halo, $C_1$-$C_4$ alkyl, $C_1$-$C_4$ alkoxy, –$NR_{14}R_{15}$, --

Column 357, Line 60: Claim 7, Insert -- 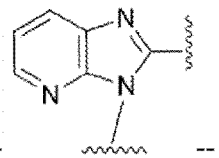 --

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*